(12) United States Patent
Schaefer et al.

(10) Patent No.: US 11,174,258 B2
(45) Date of Patent: Nov. 16, 2021

(54) BENZIMIDAZOLO[1,2-A]BENZIMIDAZOLE DERIVATIVES FOR ORGANIC LIGHT EMITTING DIODES

(71) Applicant: Idemitsu Kosan Co., Ltd., Chiyoda-ku (JP)

(72) Inventors: Thomas Schaefer, Liestal (CH);
Jean-Charles Flores, Rixheim (FR);
Hideaki Nagashima, Basel (CH)

(73) Assignee: Idemitsu Kosan Co., Ltd., Chiyoda-ku (JP)

( * ) Notice: Subject to any disclaimer, the term of this patent is extended or adjusted under 35 U.S.C. 154(b) by 398 days.

(21) Appl. No.: 15/780,688

(22) PCT Filed: Dec. 2, 2016

(86) PCT No.: PCT/IB2016/057299
§ 371 (c)(1),
(2) Date: Jun. 1, 2018

(87) PCT Pub. No.: WO2017/093958
PCT Pub. Date: Jun. 8, 2017

(65) Prior Publication Data
US 2019/0002469 A1    Jan. 3, 2019

(30) Foreign Application Priority Data

Dec. 4, 2015  (EP) ..................................... 15198034

(51) Int. Cl.
| | | |
|---|---|---|
| *C07D 487/04* | (2006.01) | |
| *C07D 487/14* | (2006.01) | |
| *C07D 403/14* | (2006.01) | |
| *C07D 487/22* | (2006.01) | |
| *C07D 235/26* | (2006.01) | |
| *C07D 405/14* | (2006.01) | |
| *C07D 403/10* | (2006.01) | |
| *C09K 11/06* | (2006.01) | |
| *H05B 33/14* | (2006.01) | |

(52) U.S. Cl.
CPC ......... *C07D 487/04* (2013.01); *C07D 235/26* (2013.01); *C07D 403/10* (2013.01);
(Continued)

(58) Field of Classification Search
CPC .. C07D 235/26; C07D 403/10; C07D 403/14; C07D 405/14; C07D 487/14;
(Continued)

(56) References Cited

U.S. PATENT DOCUMENTS 10,069,085 B2 *  9/2018  Lee ..................... H01L 51/0077
2013/0092922 A1   4/2013  Stoessel et al.
2016/0260911 A1   9/2016  Stoessel et al.

FOREIGN PATENT DOCUMENTS

EP    3 034 506 A1    6/2016
EP    3 034 507 A1    6/2016
(Continued)

OTHER PUBLICATIONS

STN Structure search for U.S. Appl. No. 15/780,688 conducted by the Examiner, All Pages, 2020. (Year: 2020).*
(Continued)

*Primary Examiner* — Daniel P Malley, Jr.
(74) *Attorney, Agent, or Firm* — Oblon, McClelland, Maier, Neustadt, L.L.P.

(57) ABSTRACT

Compounds of formula (I) and their use in electronic devices, especially electroluminescent devices: (I) wherein at least two of the substituents $R^1$ and $R^2$, $R^2$ and $R^3$, $R^3$ and $R^4$, $R^5$ and $R^6$, $R^6$ and $R^7$, or $R^7$ and $R^8$ form together one of the following ring systems (IIa), (IIb) (IIc). When used as charge transport material, charge blocker material and/or host material in electroluminescent devices, the compounds of formula (I) may provide improved efficiency, stability, manufacturability, or spectral characteristics of electroluminescent devices and reduced driving voltage of electroluminescent devices.

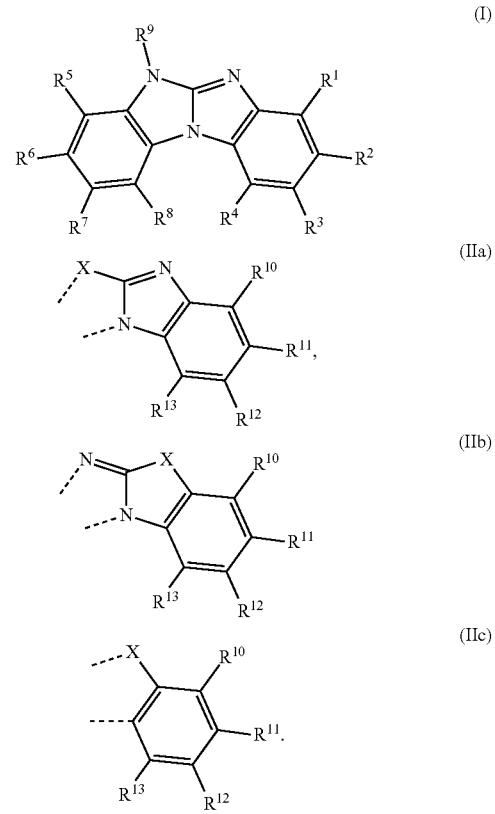

23 Claims, No Drawings

(52) U.S. Cl.
CPC ......... *C07D 403/14* (2013.01); *C07D 405/14* (2013.01); *C07D 487/14* (2013.01); *C07D 487/22* (2013.01); *C09K 11/06* (2013.01); *H05B 33/14* (2013.01); *C09K 2211/183* (2013.01)

(58) Field of Classification Search
CPC .................. C07D 487/22; C09K 11/06; C09K 2211/183; H05B 33/14
See application file for complete search history.

(56) References Cited

FOREIGN PATENT DOCUMENTS

| WO | WO 2011/160757 | A1 | | 12/2011 | |
|---|---|---|---|---|---|
| WO | WO 2012/130709 | A1 | | 10/2012 | |
| WO | WO-2012130709 | A1 | * | 10/2012 | ........... C07D 519/00 |
| WO | WO 2014/009317 | A1 | | 1/2014 | |
| WO | WO 2014/044722 | A1 | | 3/2014 | |
| WO | WO 2015/014791 | A1 | | 2/2015 | |

OTHER PUBLICATIONS

STN structure search conducted by the Examiner, Jan. 26, 2021, All Pages. (Year: 2021).*
STN structure search for U.S. Appl. No. 15/780,688 conducted by the Examiner Jun. 15, 2021. All Pages. (Year: 2021).*
International Search Report dated Feb. 13, 2017 in PCT/IB2016/057299, 2 pages.
Misbahul Ain Khan, et al. "Tetracydic Heteroaromatic Systems. Part-II. Benzimidazo [1, 2-a] Benzimidazoles" Journal of Scientific and Industrial Research, vol. 43, No. 3, 2000, p. 168-170.
Pedro Molina, et al. "Synthetic Applications of C,C-Bis(Iminophosphoranes): Preparation of [5+5] Rigid Bicyclic Guanidines and 1,3,6-Benzothiadiazepino[3,2,—a] Benzimidazole Derivatives" Tetrahedron, vol. 50, No. 33, 1994, pp. 10029-10036.
I. V. Kolesnikova, et al. "Reaction of N-Pentafluorophenylcarbonimidoyl Dichloride with Primary Amines" Zhurnal Organicheskoi Khimii, vol. 25, No. 8, 1989, pp. 1689-1695 (with cover page, submitting English translation only).
Reddouane Achour, et al. "Syntheses Des Benzimidazolo [1,2—a] Benzimidazoles A Partir Des Benzodiazepine—1, 5Ones-2" Bulletin des Sodetes Chimiques Beiges, vol. 96, No. 10, 1987, pp. 787-792 (with English Abstract).
André J. Hubert, et al. "Thermolyse and Photolyse von Benzotriazolyl-(1)-Derivaten" Chemische Berichte, vol. 103, 1970, pp. 2828-2835 (with English Abstract).
Xiaoqiang Wang, et al. "Copper-Catalyzed Aerobic Oxidative Intramolecular C—H Amination Leading to Imidazobenzimidazole Derivatives" Organic Letters, vol. 14, No. 2, 2012, pp. 452-455.
Parthasarathi Subramanian, et al. "A Unified Strategy Towards N-Aryl Heterocycles by a One-Pot Copper-Catalyzed Oxidative C—H Amination of Azoles" European Journal of Organic Chemistry, 2014, pp. 5986-5997.
Guodong Yuan, et al. "An Efficient and Facile Synthesis of Benzimidazo [1,2—a] Benzimidazoles Via Copper-Catalyzed Domino Addition/Double Cyclization", RSC Advances, vol. 4, 2014, pp. 21904-21908.

* cited by examiner

BENZIMIDAZOLO[1,2-A]BENZIMIDAZOLE DERIVATIVES FOR ORGANIC LIGHT EMITTING DIODES

The present invention relates to compounds of formula (I) and their use in electronic devices, especially electroluminescent devices. When used as charge transport material, charge blocker material and/or host material in electroluminescent devices, the compounds of formula (I) may provide improved efficiency, stability, manufacturability, or spectral characteristics of electroluminescent devices and reduced driving voltage of electroluminescent devices.

Khan, Misbahul Ain; Ribeiro, Vera Lucia Teixeira, Pakistan Journal of Scientific and Industrial Research 43 (2000) 168-170 describes the synthesis of benzimidazo[1,2-a]benzimadozoles

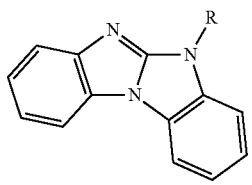

(R=H, Me, Et) by trialkyl phosphite-induced deoxygenation and thermolysis of 1-(o-nitrophenyl)- and 1-(o-azidophenyl)benzimidazoles.

Pedro Molina et al. Tetrahedron (1994) 10029-10036 reports that aza Wittig-type reaction of bis(iminophosphoranes), derived from bis(2-aminophenyl)amine with two equivalents of isocyanate directly provided benzimidazo[1,2-a]benzimidazole derivatives.

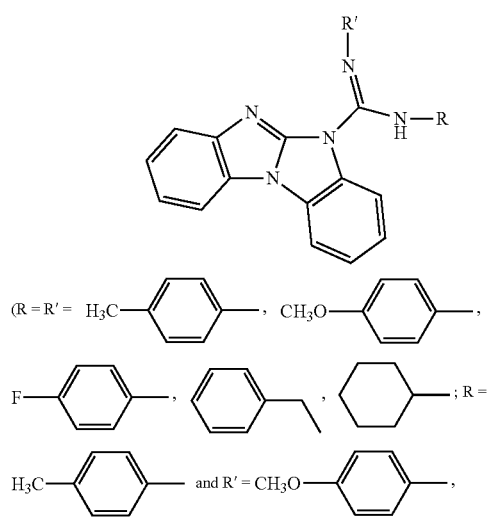

(R = R′ = H$_3$C—⟨⟩—, CH$_3$O—⟨⟩—, F—⟨⟩—, ⟨⟩—CH$_2$—, ⟨⟩— ; R = H$_3$C—⟨⟩— and R′ = CH$_3$O—⟨⟩—, R=iso-propyl and R′=ethyl)

Kolesnikova, I. V.; Zhurnal Organicheskoi Khimii 25 (1989) 1689-95 describes the synthesis of 5H-benzimidazo[1,2-a]benzimidazole 1,2,3,4,7,8,9,10-octafluoro-5-(2,3,4,5,6-pentafluorophenyl).

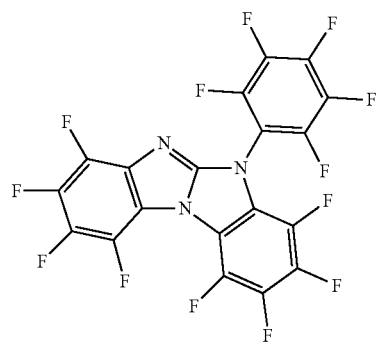 [SMILES: Fc1c(F)c(F)c(-n2c3c(F)c(F)c(F)c(F)c3n3c4c(F)c(F)c(F)c(F)c4nc23)c(F)c1F]

Achour, Reddouane; Zniber, Rachid, Bulletin des Societes Chimiques Belges 96 (1987) 787-92 describes the synthesis of benzimidazobenzimidazoles

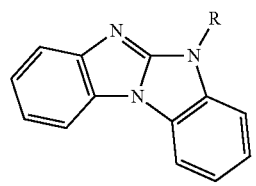

(R=H, —CH(CH$_3$)$_2$) which were prepared from benzimidazolinone derivatives.

Hubert, Andre J.; Reimlinger, Hans, Chemische Berichte 103 (1970) 2828-35 describes the synthesis of benzimidazobenzimidazoles

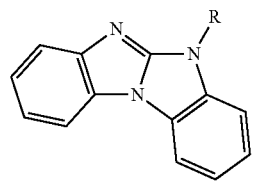

(R=H, CH$_3$,

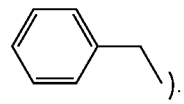

).

X. Wang et al. Org. Lett. 2012, 14, 452-455 discloses a highly efficient copper-catalyzed synthesis for compounds of formula

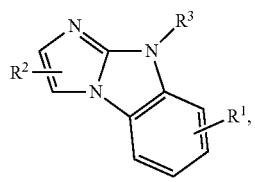

wherein compounds of formula

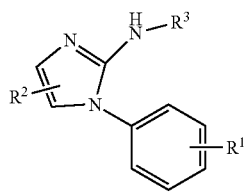

are reacted in the presence of copper acetate (Cu(OAc)$_2$)/ PPh$_3$/1,10-phenathroline/sodium acetate and oxygen in m-xylene (1 atm) at elevated temperature. Among others the following compounds can be prepared by the described synthesis method:

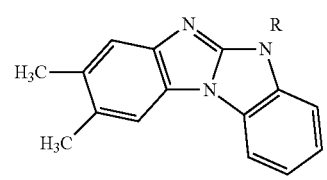

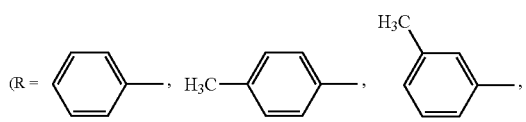

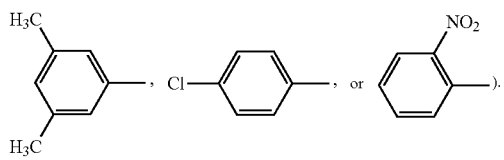

In *Eur. J. Org. Chem.* 2014, 5986-5997 a new synthesis of benzimidazolo[1,2-a]benzimidazole is described.

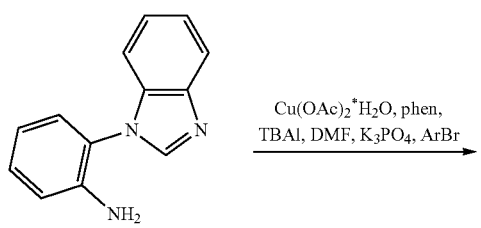

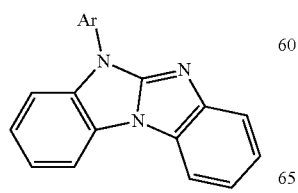

In *RSC Advances* 2014, 4, 21904-21908 a new synthesis of benzimidazolo[1,2-a]benzimidazole is described.

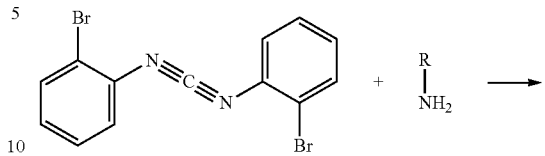

It is mentioned—as a general statement—that these polycyclic molecules have—besides other applications—also attracted great interest in the field of electroluminescent devices.

WO2011/160757 relates to an electronic device comprising an anode, cathode and at least one organic layer which contains a compound of formulae

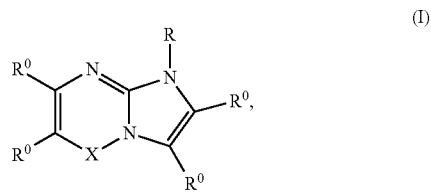 (I)

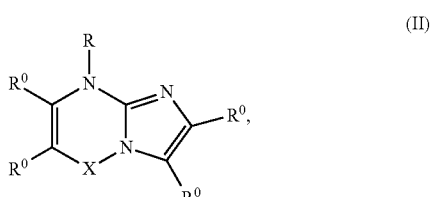 (II)

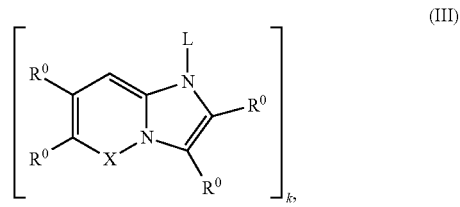 (III)

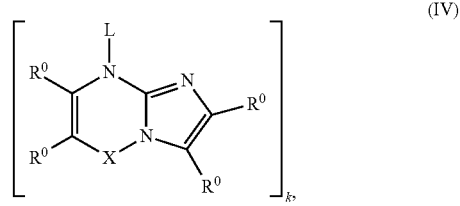 (IV)

wherein X may be a single bond and L may be a divalent group. The following 4H-Imidazo[1,2-a]imidazole compounds are explicitly disclosed:
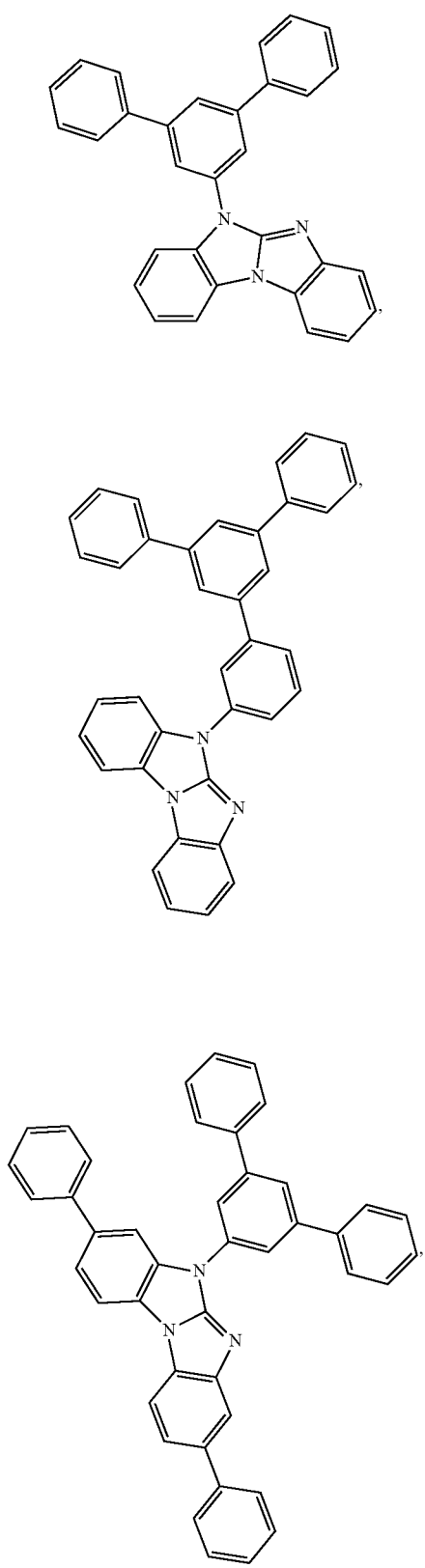
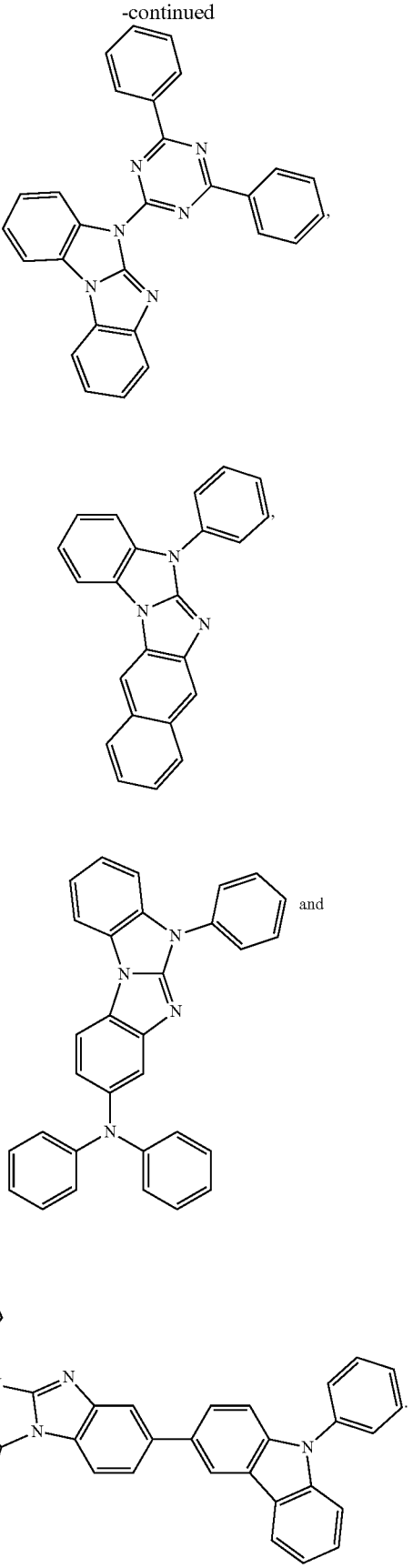

WO2012/130709 relates to 4H-Imidazo[1,2-a]imidazoles
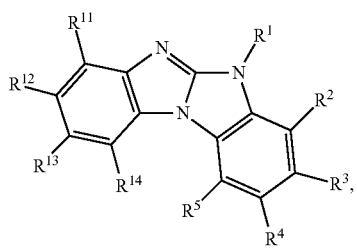
such as, for example,
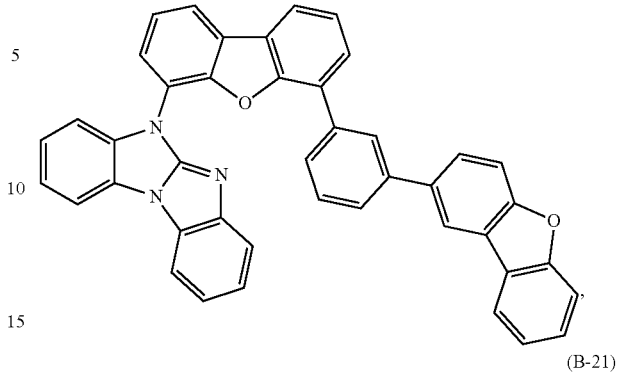
(A-1)
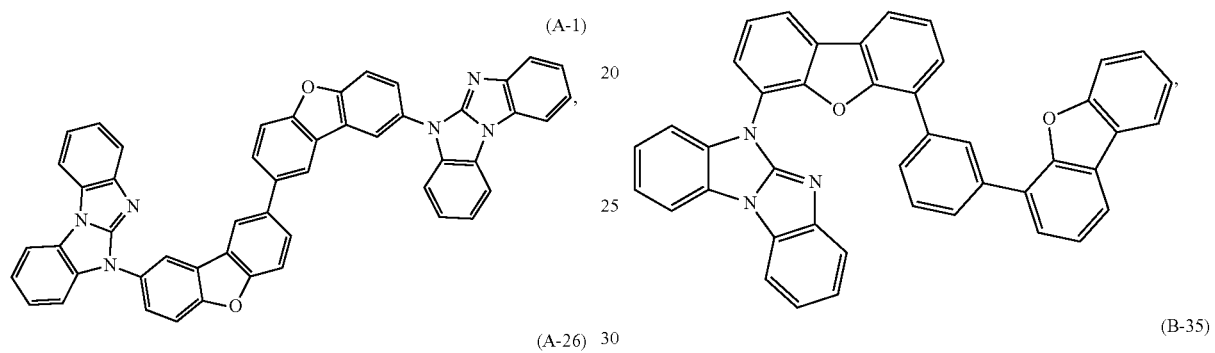
(A-26)
(B-12)
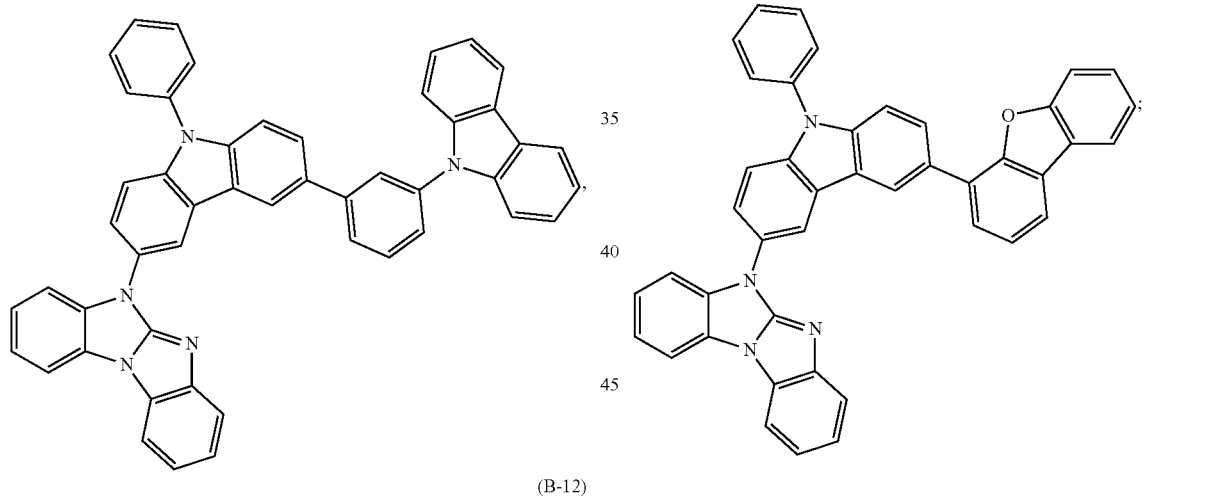
(B-20)
(B-21)
(B-35)
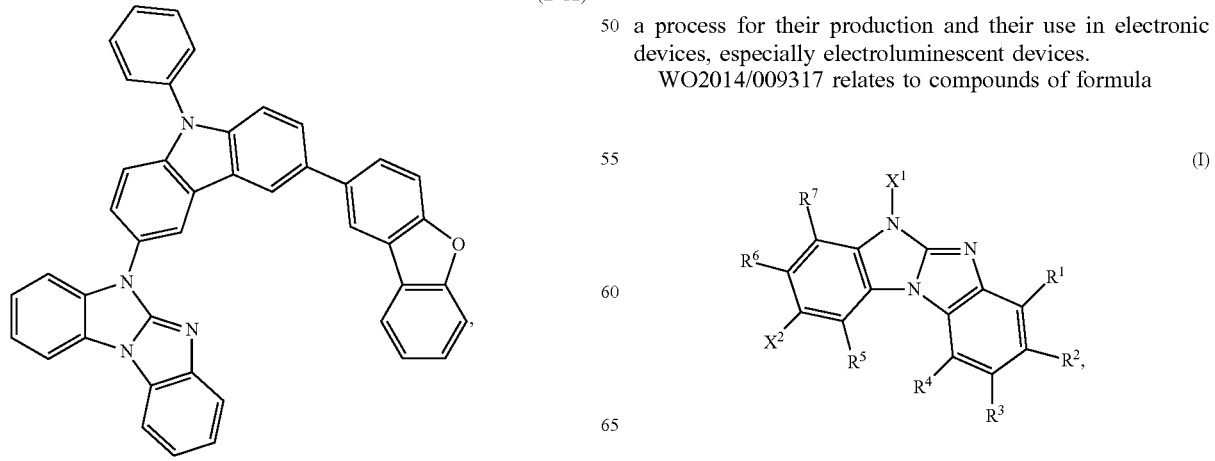
a process for their production and their use in electronic devices, especially electroluminescent devices.
WO2014/009317 relates to compounds of formula
(I)
especially compounds of formula

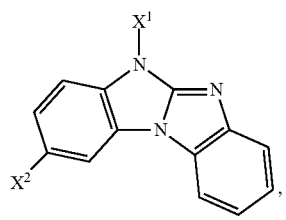

such as, for example,

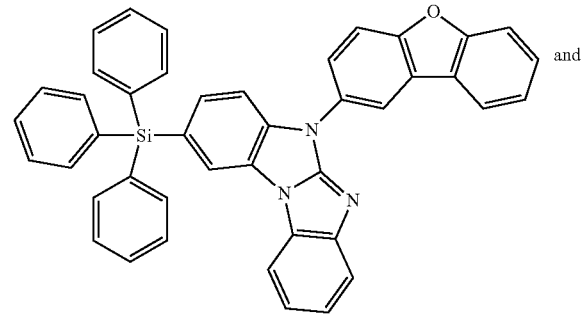

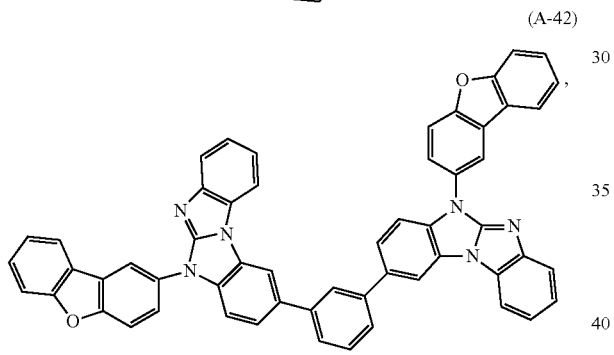

a process for their production and their use in electronic devices, especially electroluminescent devices. The 2,5-disubstituted benzimidazo[1,2-a]benzimidazole derivatives are suitable hole transporting materials, or host materials for phosphorescent emitters.

Notwithstanding these developments, there remains a need for organic light emitting devices comprising new materials, especially host (=matrix) materials, charge transport materials, especially hole transport materials, and/or charge blocker materials, especially electron/exciton blocker materials, to provide long lifetimes, improved efficiency, stability, manufacturability, driving voltage and/or spectral characteristics of electroluminescent devices.

Accordingly, it is an object of the present invention, with respect to the aforementioned relevant art, to provide further materials suitable for use in OLEDs and further applications in organic electronics. More particularly, it should be possible to provide charge transport materials, especially hole transport materials, charge blocker materials, especially electron/exciton blocker materials and host (=matrix) materials for use in OLEDs. The materials should be suitable especially for OLEDs which comprise at least one emitter, which is preferably a phosphorescence emitter, for example at least one green, red or yellow emitter, especially at least one green emitter or at least one red emitter.

Furthermore, the materials should be suitable for providing OLEDs which ensure good efficiencies, good operative lifetimes and a high stability to thermal stress, and a low use and operating voltage of the OLEDs.

Said object is solved by a compound of formula (I)

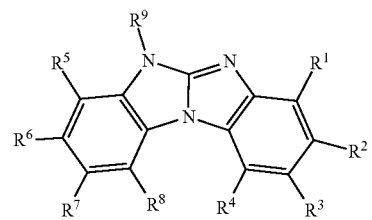

wherein at least two of the substituents $R^1$ and $R^2$, $R^2$ and $R^3$, $R^3$ and $R^4$, $R^5$ and $R^6$, $R^6$ and $R^7$, or $R^7$ and $R^8$ form together one of the following ring systems

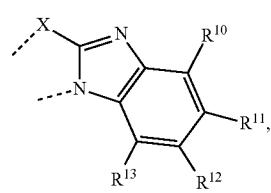

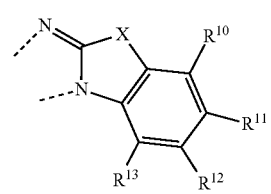

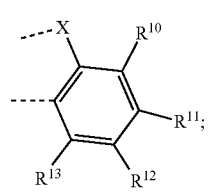

preferably a ring system of formula IIa or IIb, more preferably a ring system of formula IIb;

X is $NR^{19}$, O, S, $C(R^{28})_2$, or $Si(R^{28})_2$;

$R^9$ and $R^{19}$ are independently of each other group of formula $-(A^1)_o-(A^2)_p-(A^3)_q-(A^4)_r-R^{20}$; preferably, $R^9$ and $R^{19}$ are identical; in a further preferred embodiment, especially in the case that at least two of the substituents $R^1$ and $R^2$, $R^2$ and $R^3$, $R^3$ and $R^4$, $R^5$ and $R^6$, $R^6$ and $R^7$, or $R^7$ and $R^8$ together form a ring system (IIc), $R^9$ and $R^{19}$ are different;

$R^1$, $R^2$, $R^3$, $R^4$, $R^5$, $R^6$, $R^7$, $R^8$, which are not forming together a ring system of formula IIa, IIb or IIc are independently of each other H or group of formula $-(A^{1'})_o-(A^{2'})_p-(A^{3'})_q-(A^{4'})_r-R^{20'}$ or a group E; or adjacent groups $R^1$ and $R^2$, $R^2$ and $R^3$, $R^3$ and $R^4$, $R^5$ and $R^6$, $R^6$ and $R^7$, and/or $R^7$ and $R^8$ can from together a ring;

$R^{10}$, $R^{11}$, $R^{12}$, $R^{13}$ are independently of each other H, CN or group of formula $-(A^{1'})_o-(A^{2'})_p-(A^{3'})_q-(A^{4'})_r-R^{20'}$ or a group E; or adjacent groups $R^{10}$ and $R^{11}$, $R^{11}$ and $R^{12}$ and/or $R^{12}$ and $R^{13}$ can from together a ring;

o is 0, or 1, p is 0, or 1, q is 0, or 1, r is 0, or 1, preferably o is 0, or 1, p is 0, or 1, q is 0 and r is 0;

o' is 0, or 1, p' is 0, or 1, q' is 0, or 1, r' is 0, or 1, $A^1$, $A^2$, $A^3$, $A^4$ are independently of each other a $C_6$-$C_{24}$ arylene group which is unsubstituted or substituted by G, $C_2$-$C_{24}$ heteroarylene group which is unsubstituted or substituted by G; $R^{20}$ is a $C_6$-$C_{30}$ aryl group which is unsubstituted or substituted by G, $C_2$-$C_{60}$ heteroaryl group which is unsubstituted or substituted by G, a $C_1$-$C_{25}$alkyl group, which can optionally be substituted by E and or interrupted by D; or, in the case that at last one of o, p, q and r is 1, $R^{20}$ is CN; $A^{1'}$, $A^{2'}$, $A^{3'}$, $A^{4'}$ are independently of each other a $C_6$-$C_{24}$ arylene group which is unsubstituted or substituted by G, $C_2$-$C_{24}$ heteroarylene group which is unsubstituted or substituted by G;

$R^{20'}$ is H, CN, a $C_6$-$C_{30}$ aryl group which is unsubstituted or substituted by G, $C_2$-$C_{60}$ heteroaryl group which is unsubstituted or substituted by G, a $C_1$-$C_{25}$alkyl group, which can optionally be substituted by E and or interrupted by D;

$R^{28}$ is independently of each other $C_6$-$C_{18}$aryl which is unsubstituted or substituted by $C_1$-$C_{18}$alkyl or $C_1$-$C_{18}$alkoxy; or $C_1$-$C_{18}$alkyl which is interrupted by —O—, which is unsubstituted or substituted by E; or two residues $R^{28}$ can together with the carbon atom or Si atom to which they are bonded form a ring;

D is —CO—, —COO—, —S—, —SO—, —SO$_2$—, —O—, —CR$^{63}$=CR$^{64}$—, —NR$^{65}$—, —SiR$^{70}$R$^{71}$—, —POR$^{72}$—, or —C≡C—, preferably —O—, —NR$^{65}$—, —SiR$^{70}$R$^{71}$—;

E is —OR$^{69}$, —SR$^{69}$, —NR$^{65}$R$^{66}$, —COR$^{68}$, —COOR$^{67}$, —CONR$^{65}$R$^{66}$, —CN, —Si(R$^{70}$)$_3$ or halogen, preferably —NR$^{65}$R$^{66}$, —CN, —Si(R$^{70}$)$_3$ G is E, or a $C_1$-$C_{24}$alkyl group, a $C_6$-$C_{24}$aryl group, a $C_6$-$C_{24}$aryl group, which is substituted by F, $C_1$-$C_{24}$alkyl, $C_1$-$C_{24}$alkyl which is interrupted by O, a $C_2$-$C_{30}$heteroaryl group, or a $C_2$-$C_{30}$heteroaryl group, which is substituted by F, $C_1$-$C_{24}$alkyl, $C_1$-$C_{24}$alkyl which is interrupted by O; preferably E;

$R^{63}$ and $R^{64}$ are independently of each other $C_6$-$C_{18}$aryl; $C_6$-$C_{18}$aryl which is substituted by $C_1$-$C_{18}$alkyl or $C_1$-$C_{18}$alkoxy; $C_1$-$C_{18}$alkyl; or $C_1$-$C_{18}$alkyl which is interrupted by —O—;

$R^{65}$ and $R^{66}$ are independently of each other a $C_6$-$C_{18}$aryl group; a $C_6$-$C_{18}$aryl which is substituted by $C_1$-$C_{18}$alkyl or $C_1$-$C_{18}$alkoxy; a $C_1$-$C_{18}$alkyl group; or a $C_1$-$C_{18}$alkyl group, which is interrupted by —O—; or $R^{65}$ and $R^{66}$ together form a five or six membered ring, $R^{67}$ is a $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—;

$R^{68}$ is H; a $C_6$-$C_{18}$aryl group; a $C_6$-$C_{18}$aryl group, which is substituted by $C_1$-$C_{18}$alkyl or $C_1$-$C_{18}$alkoxy; a $C_1$-$C_{18}$alkyl group; or a $C_1$-$C_{18}$alkyl group, which is interrupted by —O—;

$R^{69}$ is a $C_6$-$C_{18}$aryl; a $C_6$-$C_{18}$aryl, which is substituted by $C_1$-$C_{18}$alkyl or $C_1$-$C_{18}$alkoxy; a $C_1$-$C_{18}$alkyl group; or a $C_1$-$C_{18}$alkyl group, which is interrupted by —O—;

$R^{70}$ and $R^{71}$ are independently of each other a $C_1$-$C_{18}$alkyl group, a $C_6$-$C_{18}$aryl group, or a $C_6$-$C_{18}$aryl group, which is substituted by $C_1$-$C_{18}$alkyl; and $R^{72}$ is a $C_1$-$C_{18}$alkyl group, a $C_6$-$C_{18}$aryl group, or a $C_6$-$C_{18}$aryl group, which is substituted by $C_1$-$C_{18}$alkyl.

The combination of the benzimidazo[1,2-a]benzimidazole structure with a ring system of formula (IIa), (IIb) or (IIc) gives rise to materials that are highly suitable in devices that emit green, red or yellow light, preferably green or red light, more preferably green light. Devices are achieved resulting in low voltages and high external quantum efficiencies (EQE's) and/or long lifetimes.

The compounds of the present invention may be used for electrophotographic photoreceptors, photoelectric converters, organic solar cells (organic photovoltaics), switching elements, such as organic transistors, for example, organic FETs and organic TFTs, organic light emitting field effect transistors (OLEFETs), image sensors, dye lasers and electroluminescent devices, such as, for example, organic light-emitting diodes (OLEDs).

Accordingly, a further subject of the present invention is directed to an electronic device, comprising a compound according to the present invention. The electronic device is preferably an electroluminescent device, such as an organic light-emitting diode (OLED).

The compounds of formula (I) can in principal be used in any layer of an EL device, but are preferably used as host, charge transport (i.e. hole transport or electron transport) material, especially hole transport and/or charge/exciton blocking (i.e. hole/exciton blocking or electron exciton blocking) material, especially electron/exciton blocking material. Particularly, the compounds of formula (I) are used as host material for green, red and yellow, preferably green and red, more preferably green light emitting, preferably phosphorescent, emitters.

Hence, a further subject of the present invention is directed to a charge transport layer, especially a hole transport layer, comprising a compound of formula (I) according to the present invention.

A further subject of the present invention is directed to an emitting layer, comprising a compound of formula (I) according to the present invention. In said embodiment a compound of formula (I) is preferably used as host material or as co-host material together with one or more, preferably one, further host materials. More preferably, a combination of a compound of formula (I) and optionally a co-host material together with a phosphorescent emitter is used.

A further subject of the present invention is directed to a charge/exciton blocking layer, especially an electron/exciton blocking layer, comprising a compound of formula (I) according to the present invention.

The terms halogen, alkyl, alkoxy, cycloalkyl, aryl, aryloxy, aralkyl, heteroaryl, arylene, heteroarylene generally have the following meaning, if said groups are not further specified in specific embodiments mentioned below:

Halogen is fluorine, chlorine, bromine and iodine, preferably fluorine.

$C_1$-$C_{25}$alkyl, preferably $C_1$-$C_{24}$alkyl and more preferably $C_1$-$C_{18}$alkyl are typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, iso-heptyl, 1,1,3,3-tetramethylbutyl, 1-methylheptyl, 3-methyl-heptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, or octadecyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

The alkyl groups mentioned above can optionally be substituted by E and/or interrupted by D. Preferably, the alkyl groups mentioned above are unsubstituted or can optionally be substituted by E.

$C_1$-$C_{25}$alkoxy groups and preferably $C_1$-$C_{18}$alkoxy groups are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, un-decyloxy, dodecyloxy, tetradecyloxy, pentadecyloxy, hexa-decyloxy, heptadecyloxy and octade-cyloxy. Examples of $C_1$-$C_8$alkoxy are methoxy, ethoxy, n-propoxy, isopropoxy, n-butoxy, sec.-butoxy, isobutoxy, tert.-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy, preferably $C_1$-$C_4$alkoxy such as typically methoxy, ethoxy, n-propoxy, isopropoxy, n-butoxy, sec.-butoxy, isobutoxy, tert.-butoxy.

The term "cycloalkyl group" is preferably $C_5$-$C_{12}$cycloalkyl, such as cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted by G.

$C_6$-$C_{30}$aryl, preferably $C_6$-$C_{24}$aryl and more preferably $C_6$-$C_{18}$aryl, which is unsubstituted or optionally can be substituted by G, is most preferably phenyl, 4-methylphenyl, 4-methoxyphenyl, naphthyl, especially 1-naphthyl, or 2-naphthyl, biphenylyl, triphenylyl, fluoranthenyl, terphenylyl, pyrenyl, 2- or 9-fluorenyl, phenanthryl, or anthryl, which may be unsubstituted or substituted by G. Phenyl, 1-naphthyl and 2-naphthyl are examples of a $C_6$-$C_{10}$aryl group.

$C_2$-$C_{60}$heteroaryl, preferably $C_2$-$C_{30}$heteroaryl, more preferably $C_2$-$C_{24}$ heteroaryl, most preferably $C_2$-$C_{18}$ heteroaryl, further most preferably $C_2$-$C_{13}$ heteroaryl represents a ring with five, six or seven ring atoms or a condensed ring system, wherein nitrogen, oxygen or sulfur are the possible heteroatoms, and is typically a heterocyclic group with five to 60 atoms, preferably with five to 30 atoms, more preferably with five to 24 atoms, most preferably with five to 18 atoms, further most preferably with five to 13 atoms having at least six conjugated t-electrons such as thienyl, benzothiophenyl, dibenzothiophenyl, thianthrenyl, furyl, furfuryl, 2H-pyranyl, benzofuranyl, iso-benzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quin-olizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl, 4-imidazo[1,2-a]benzimidazoyl, 5-benzimidazo[1,2-a]benzimidazoyl, benzimidazolo[2,1-b][1,3]benzothiazolyl, carbazolyl, azatriphenylyl, azadibenzofuryl, azadibenzothiophenyl, azacarbazolyl, quinolonyl, isoquinolinyl, quinoxalinyl, quinazolinyl, phenanthrolinyl, phenanthridinyl, benzo[h]quinolonyl, benz[h]isoquinolinyl, benzo[f]isoquinolinyl, benzo[f]quinolinyl, benzo[h]quinazolinyl, benzo[f]quinazolinyl, dibenzo[f,h]quinolonyl, dibenzo[f,h]isoquinolonyl, dibenzo[f,h]quinoxalinyl, dibenzo[f,h]quinazolinyl or phenoxazinyl, which can be unsubstituted or substituted by G. Benzimidazo[1,2-a]benzimidazo-5-yl, benzimidazo[1,2-a]benzimidazo-2-yl, carbazolyl and dibenzofuranyl are examples of a $C_2$-$C_{14}$heteroaryl group.

The group $C_2$-$C_{60}$heteroaryl, preferably $C_2$-$C_{30}$heteroaryl, more preferably $C_2$-$C_{24}$heteroaryl, most preferably $C_2$-$C_{18}$heteroaryl, further most preferably $C_2$-$C_{13}$ heteroaryl, may be unsubstituted or substituted by G.

A $C_2$-$C_3$heteroaryl group is for example, in addition to the groups mentioned above, benzimidazo[1,2-a]benzimidazo-5-yl

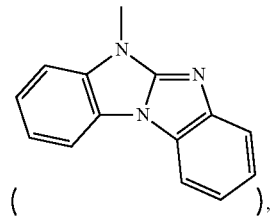

benzimidazo[1,2-a]benzimidazo-2-yl

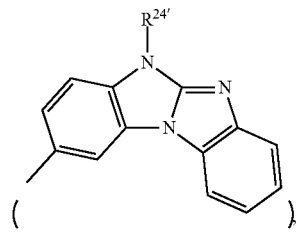

benzimidazolo[2,1-b][1,3]benzothiazolyl, benzimidazolo[2,1-b][1,3]benzoxazole, carbazolyl, dibenzofuranyl, or dibenzothiophenyl, which can be unsubstituted or substituted by G, especially by $C_6$-$C_{10}$aryl, or $C_6$-$C_{10}$aryl, which is substituted by $C_1$-$C_4$alkyl; or $C_2$-$C_{13}$heteroaryl.

$C_2$-$C_{60}$heteroaryl, preferably $C_2$-$C_{30}$heteroaryl, more preferably $C_2$-$C_{24}$heteroaryl, most preferably $C_2$-$C_{18}$ heteroaryl, further most preferably $C_2$-$C_{13}$ heteroaryl means that the heteroaryl residue comprises at least 2 carbon atoms and at most 60 carbon atoms in the base skeleton (without substituents). The further atoms in the heteroaryl base skeleton are heteroatoms (N, O and/or S).

$R^{24'}$ is in each case independently $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, tolyl, naphthyl, phenanthronyl, triphenylenyl, fluoranthenyl or biphenylyl.

$C_1$-$C_{24}$heterocyclic group, preferably $C_1$-$C_{13}$heterocyclic group, more preferably $C_2$-$C_{13}$ heterocyclic group represents a ring with five, six or seven ring atoms or a condensed ring system, wherein nitrogen, oxygen or sulfur are the possible heteroatoms, and is typically a heterocyclic group with five to 24 atoms, preferably with five to 13 atoms. The heterocyclic group may be a $C_1$-$C_{24}$heteroaryl group as defined above or a $C_1$-$C_{24}$heterocycloalkyl group which may be unsubstituted or substituted by G. Typical $C_1$-$C_{24}$heterocycloalkyl groups are oxetan, tetrahydrofuran, tetrahydropyran, oxepane, dioxane, azetidine, pyrrolidine, piperidine, hexahydroazepine, hexahydrodiazepin, tetrahydrothiophene, thietan, tetrahydrothiopyran, thiepan, morpholine as well as bridged heterocycloalkyl systems such as oxabicy-clo[4.4.0]decane and azabicyclo[2,2,1]undecane.

$C_6$-$C_{24}$arylene groups, preferably $C_6$-$C_{10}$arylene groups, which optionally can be substituted by G, preferably $C_6$-$C_{10}$arylene groups, which optionally can be substituted by G, are more preferably phenylene, 4-methylphenylene, 4-methoxyphenylene, naphthylene, especially 1-naphthylene, or 2-naphthylene, biphenylylene, triphenylylene, fluoranthenylene, terphenylylene, pyrenylene, 2- or 9-fluorenylene, phenanthrylene, or anthrylene, which may be unsubstituted or substituted by G. Preferred $C_6$-$C_{24}$arylen groups, preferably $C_6$-$C_{10}$arylene groups are 1,3-phenylene, 3,3'-biphenylylene, 3,3'-m-terphenylene, 2- or 9-fluorenylene, phenanthrylene, which may be unsubstituted or substituted by G.

$C_2$-$C_{30}$heteroarylene groups, preferably $C_2$-$C_{14}$heteroarylene groups, which are unsubstituted or optionally can be substituted by G, represent a ring with five to seven ring atoms or a condensed ring system, wherein nitrogen, oxygen or sulfur are the possible heteroatoms, and is typically a heterocyclic group with five to 30 atoms having at least six conjugated-electrons such as thienylene, benzothiophenylene, dibenzothiophenylene, thianthrenylene, furylene, furfu-rylene, 2H-pyranylene, benzofuranylene, isobenzofuranylene, dibenzofuranylene, phenoxy-thienylene, pyrrolylene, imidazolylene, pyrazolylene, pyridylene, bipyridylene, triazinylene, pyrimidinylene, pyrazinylene, pyridazinylene, indolizinylene, isoindolylene, indolylene, indazolylene, purinylene, quinolizinylene, chinolylene, isochinolylene, phthalazinylene, naphthyridinylene, quinoxalinylene, quinazolinylene, cinnolinylene, pteridinylene, carbolinylene, benzotriazolylene, benzoxazolylene, phenanthridinylene, acridinylene, pyrimidinylene, phenanthrolinylene, phenazinylene, isothiazolylene, phenothiazinylene, isoxazolylene, furazanylene, carbazolylene, benzimidazo[1,2-a]benzimidazo-2,5-ylene, or phenoxazinylene, which can be unsubstituted or substituted by G. Preferred $C_2$-$C_{30}$heteroarylen groups are pyridylene, triazinylene, pyrimidinylene, carbazolylene, dibenzofuranylene, azatriphenylylene, azadibenzofurylene, aza-dibenzothiophenylene, azacarbazolylene, quinolonylene, isoquinolinylene, quinoxalinylene, quinazolinylene, phenanthrolinylene, phenanthridinylene, benzo[h]quinolonylene, benz[h]isoquinolinylene, benzo[f]isoquinolinylene, benzo[f]quinolinylene, benzo[h]quinazolinylene, benzo[f]quinazolinylene, dibenzo[f,h]quinolonylene, dibenzo[f,h]isoquinolonylene, dibenzo[f,h]quinoxalinylene, dibenzo[f,h]quinazolinylene and benzimidazo[1,2-a]benzimidazo-2,5-ylene

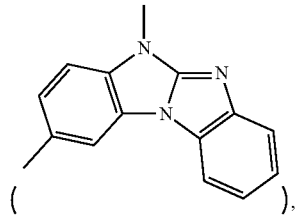

which can be unsubstituted or substituted by G, preferably substituted by $C_6$-$C_{10}$aryl, $C_6$-$C_{10}$aryl which is substituted by $C_1$-$C_4$alkyl; or $C_2$-$C_{13}$heteroaryl.

If a substituent occurs more than one time in a group, it can be different in each occurrence.

The wording "substituted by G" means that one, or more, especially one, two or three substituents G might be present. Preferred substituents G are mentioned below.

The wording "substituted by E" means that one, or more, especially one, two or three substituents E might be present. Preferred substituents E are mentioned below.

As described above, the aforementioned alkyl groups may be substituted by E and/or, if de-sired, interrupted by D. Interruptions are of course possible only in the case of groups containing at least 2 carbon atoms connected to one another by single bonds; $C_6$-$C_{18}$aryl is not interrupted; interrupted arylalkyl contains the unit D in the alkyl moiety. $C_1$-$C_{18}$alkyl substituted by one or more E and/or interrupted by one or more units D is, for example, $(CH_2CH_2O)_{1\text{-}9}$—$R^x$, where $R^x$ is H or $C_1$-$C_{10}$alkyl or $C_2$-$C_{10}$alkanoyl (e.g. CO—CH($C_2H_5$)$C_4H_9$), $CH_2$—CH($OR^{y'}$)—$CH_2$—O—$R^y$, where $R^y$ is $C_1$-$C_{18}$alkyl, $C_5$-$C_{12}$cycloalkyl, phenyl, $C_7$-$C_{15}$phenylalkyl, and $R^{y'}$ embraces the same definitions as $R^y$ or is H.

Halo-$C_1$-$C_8$alkyl is an alkyl group (as defined above) where at least one of the hydrogen atoms is replaced by a halogen atom. Examples are —$CF_3$, —$CF_2CF_3$, —$CF_2CF_2CF_3$, —$CF(CF_3)_2$, —$(CF_2)_3CF_3$, and —$C(CF_3)_3$.

This means, that an alkyl group substituted by E is, for example, an alkyl group where at least one of the hydrogen atoms is replaced by F. Examples are —$CF_3$, —$CF_2CF_3$, —$CF_2CF_2CF_3$, —$CF(CF_3)_2$, —$(CF_2)_3CF_3$, and —$C(CF_3)_3$. D is —CO—, —COO—, —S—, —SO—, —$SO_2$—, —O—, —$NR^{65}$—, —$SiR^{70}R^{71}$—, —$POR^{72}$, —$CR^{63}$=$CR^{64}$— or —C≡C. Suitable residues $R^{63}$, $R^{64}$, $R^{65}$, $R^{70}$ $R^{71}$ and $R^{72}$ are mentioned above. D is preferably —CO—, —COO—, —S—, —SO—, —$SO_2$—, —O—, —$NR^{65}$—, wherein $R^{65}$ is preferably $C_1$-$C_{18}$alkyl, such as methyl, ethyl, n-propyl, iso-propyl, n-butyl, isobutyl, or sec-butyl, or $C_6$-$C_{14}$aryl, such as phenyl, tolyl, naphthyl, triphenylyl or biphenylyl, or C_$C_{30}$heteroaryl, such as, for example, benzimidazo[1,2-a]benzimidazo-2-yl

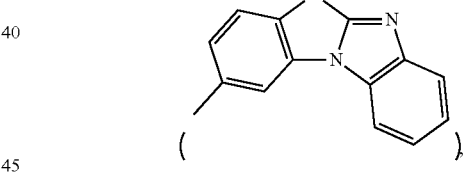

carbazolyl, dibenzofuranyl, which can be unsubstituted or substituted especially by $C_6$-$C_{10}$aryl, or $C_6$-$C_{10}$aryl, which is substituted by $C_1$-$C_4$alkyl; or $C_2$-$C_{13}$heteroaryl.

$R^{24'}$ is $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, tolyl, naphthyl, phenanthronyl, triphenylenyl, fluoranthenyl or biphenylyl.

E is —$OR^{69}$, —$SR^{69}$, —$NR^{65}R^{66}$, —$COR^{68}$, —$COOR^{67}$, —$CONR^{65}R^{66}$, —CN, —$Si(R^{70})_3$ or halogen. E is preferably —$OR^{69}$; —$SR^{69}$; —$NR^{65}R^{66}$; —$COR^{68}$; —$COOR^{67}$; —$CON^{65}R^{66}$; F or —CN; wherein $R^{65}$, $R^{66}$, $R^{67}$, $R^{68}$ and $R^{69}$ are preferably independently of each other $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, tolyl, naphthyl, triphenylyl or biphenylyl.

G is E, or a $C_1$-$C_{24}$alkyl group, an unsubstituted $C_6$-$C_{30}$aryl group or a $C_6$-$C_{30}$aryl group, which is substituted by G, whereby G is preferably F, $C_1$-$C_{24}$alkyl, or $C_1$-$C_{24}$alkyl which is interrupted by O; an unsubstituted $C_2$-$C_{60}$heteroaryl group or a $C_2$-$C_{60}$heteroaryl group, which is substituted by G, whereby G is preferably F, $C_1$-$C_{18}$alkyl, or $C_1$-$C_{18}$alkyl which is interrupted by O. G is preferably —$OR^{69}$, —$SR^{69}$, —$NR^{65}R^{66}$; a $C_1$-$C_{18}$alkyl group, an unsubstituted $C_6$-$C_{18}$aryl group, a $C_6$-$C_{18}$aryl group, which is substituted by F, or $C_1$-$C_{18}$alkyl; an unsubstituted $C_2$-$C_{24}$heteroaryl group, or a $C_2$-$C_{24}$heteroaryl group, which is substituted by F, or $C_1$-$C_{18}$alkyl; wherein $R^{65}$, $R^{66}$ and $R^{69}$ are independently of each other $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, tolyl, naphthyl, or biphenylyl. More preferably, G is a $C_6$-$C_{18}$aryl group like phenyl, tolyl, triphenylyl or biphenylyl, or a $C_6$-$C_{24}$heteroaryl group like dibenzothiophenylyl, dibenzofuranyl, pyridyl, triazinyl, pyrimidinyl, azatriphenylyl, azadibenzofuryl, azadibenzothiophenyl, azacarbazolyl, quinolonyl, isoquinolinyl, quinoxalinyl, quinazolinyl, phenanthrolinyl, phenanthridinyl, benzo[h]quinolonyl, benz[h]isoquinolinyl, benzo[f]isoquinolinyl, benzo[f]quinolinyl, benzo[h]quinazolinyl, benzo[f]quinazolinyl, dibenzo[f,h]quinolonyl, dibenzo[f,h]isoquinolonyl, dibenzo[f,h]quinoxalinyl or dibenzo[f,h]quinazolinyl.

Compound of Formula (I)

In the compound of formula (I), at least two of the substituents $R^1$ and $R^2$, $R^2$ and $R^3$, $R^3$ and $R^4$, $R^5$ and $R^6$, $R^6$ and $R^7$, or $R^7$ and $R^8$, preferably at least two of the substituents $R^1$ and $R^2$, $R^2$ and $R^3$, $R^3$ and $R^4$, or $R^6$ and $R^7$, more preferably $R^2$ and $R^3$ or $R^6$ and $R^7$, form together one of the following ring systems

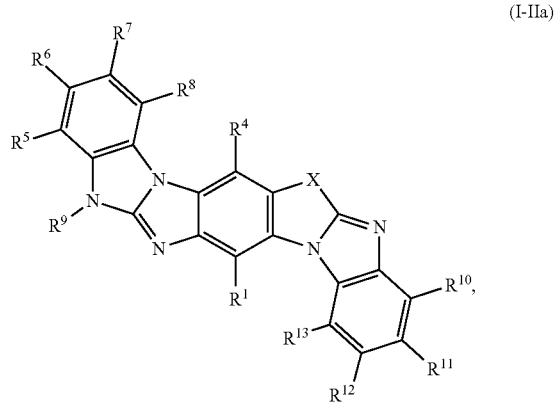

(IIa)

(IIb)

(IIc)

preferably a ring system of formula IIa or IIb, more preferably a ring system of formula IIb.

In a further embodiment, compounds of formula (I) are preferred, wherein at least two of the substituents $R^1$ and $R^2$, $R^2$ and $R^3$, $R^3$ and $R^4$, $R^5$ and $R^6$, $R^6$ and $R^7$, or $R^7$ and $R^8$, preferably at least two of the substituents $R^1$ and $R^2$, $R^2$ and $R^3$, $R^3$ and $R^4$, or $R^6$ and $R^7$, more preferably $R^2$ and $R^3$ or $R^5$ and $R^6$ or $R^6$ and $R^7$, form together a ring system of formula (IIc).

The residues $R^{10}$ to $R^{13}$ and the group X have been defined before and further preferred residues $R^{10}$ to $R^{13}$ and the group X are defined below. Preferably, X is $NR^{19}$ or $C(R^{28})_2$.

Preferably, two of the substituents $R^1$ and $R^2$, $R^2$ and $R^3$, $R^3$ and $R^4$, $R^5$ and $R^6$, $R^6$ and $R^7$, or $R^7$ and $R^8$, more preferably, two of the substituents $R^1$ and $R^2$, $R^2$ and $R^3$, $R^3$ and $R^4$, or $R^6$ and $R^7$, most preferably $R^2$ and $R^3$ or $R^6$ and $R^7$, form together a ring system of formula IIa, IIb or IIc, preferably $R^2$ and $R^3$ form together a ring system of formula IIa or IIb, more preferably a ring system of formula Ib. In a further preferred embodiment, $R^6$ and $R^7$, form together a ring system of formula IIc.

Most preferred compounds of formula (I) are compounds (I-IIa), (I-IIa'), (I-IIb), (I-IIb'), (I-IIc), (I-IIc'), (I'-II'a), (I'-II'a'), (I'-II'b), (I'-II'b'), (I'-II'c) and (I'-II'c'), as well as the compounds (I''-IIc), (I-IIc''), (I''-II''c), (I''-II''c''), (I'''-IIc), (I-IIc'''), (I'''-II'''c) and (I'''-II'''c'''):

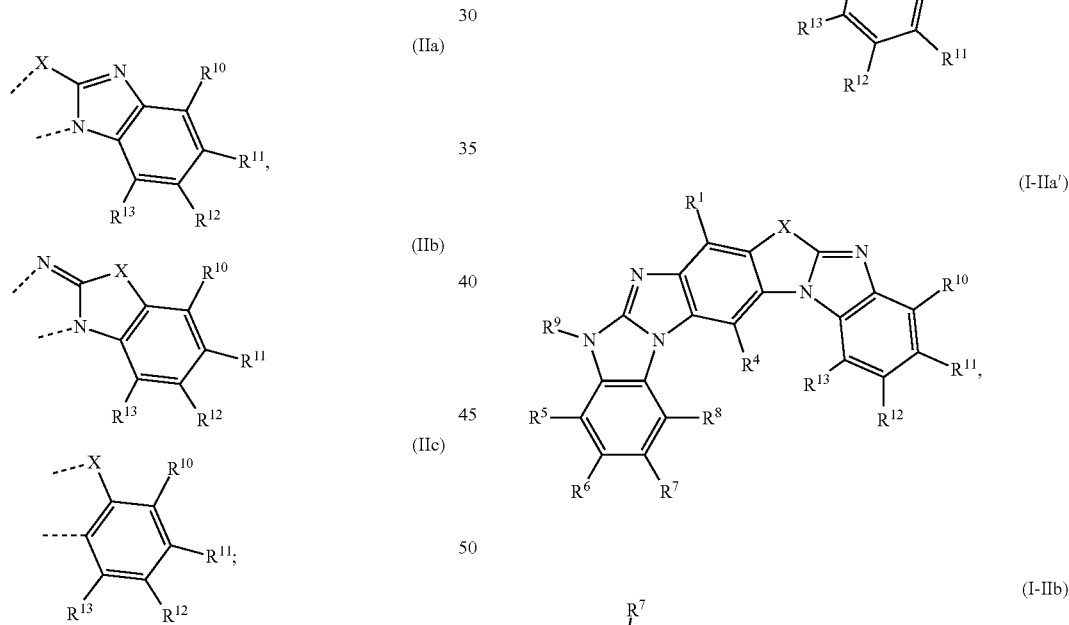

(I-IIa)

(I-IIa')

(I-IIb)

-continued
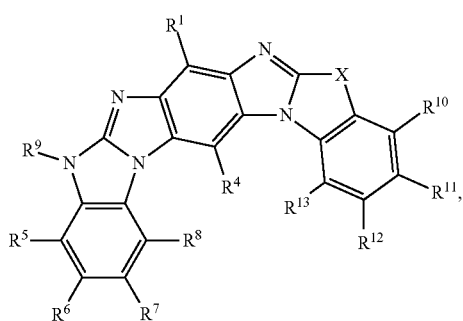
(I-IIb′)
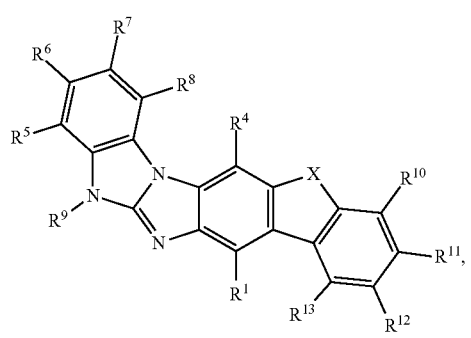
(I-IIc)
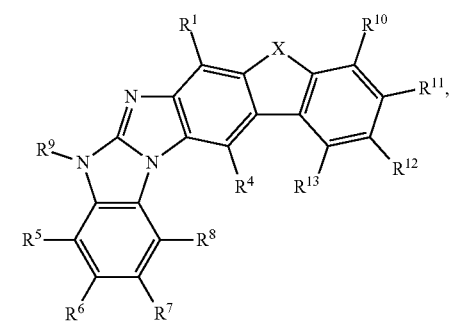
(I-IIc′)
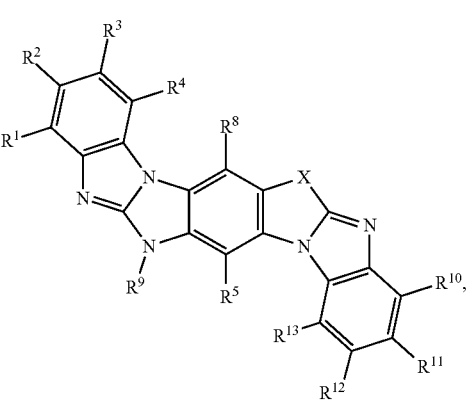
(I′-II′a)
-continued
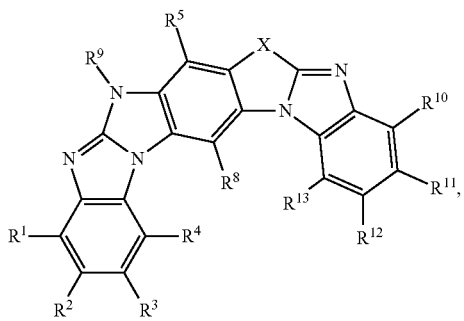
(I′-II′a′)
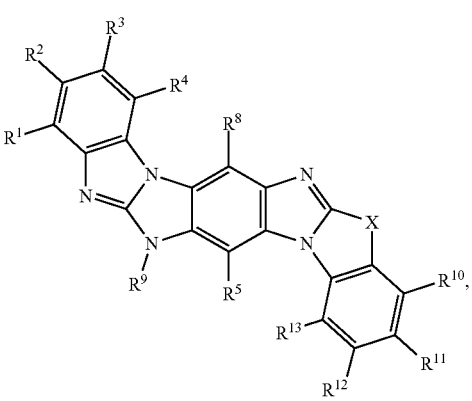
(I′-II′b)
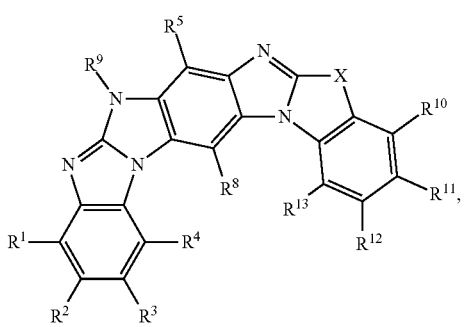
(I′-II′b′)
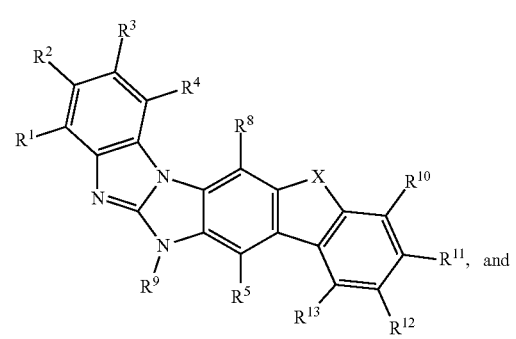
(I′-II′c)
and (I'-II'c')

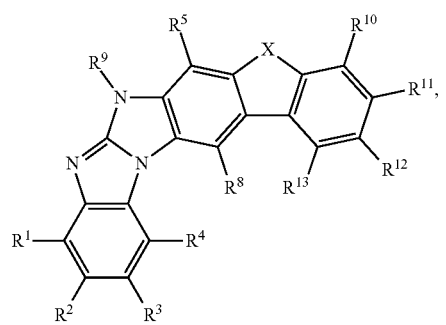

(I''-IIc)

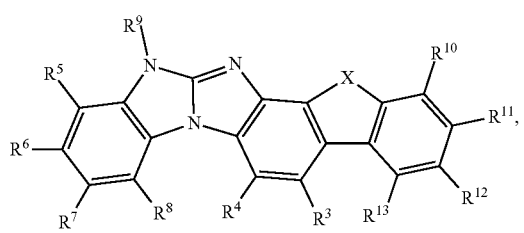

(I-IIc'')

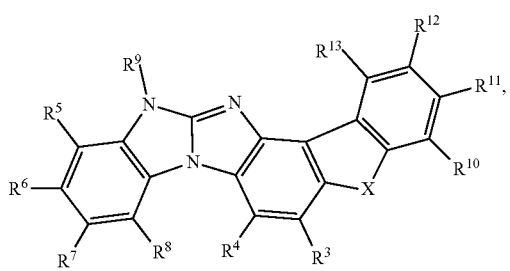

(I''-IIc'')

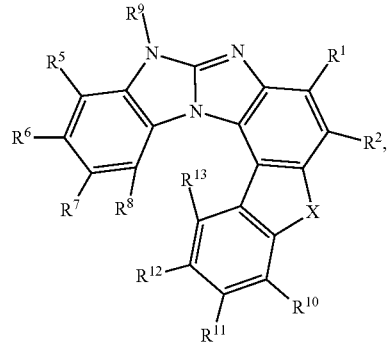

(I''-II''c'')

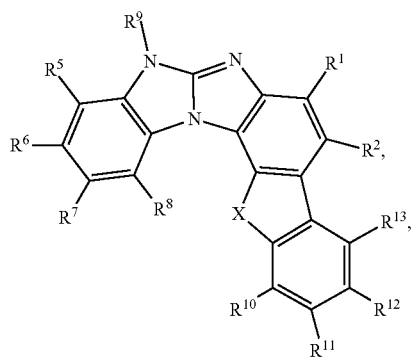

(I'''-IIc)

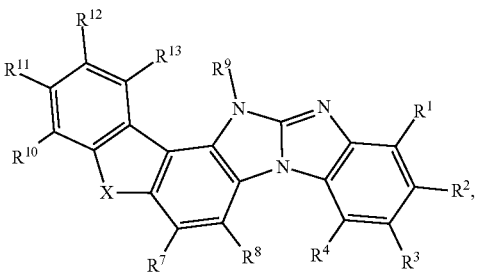

(I-IIc''')

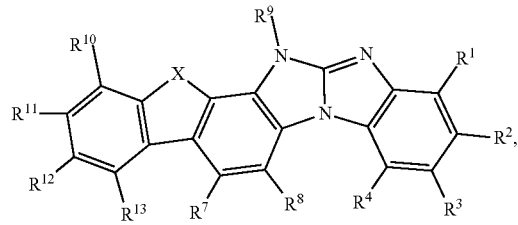

(I'''-IIc''')

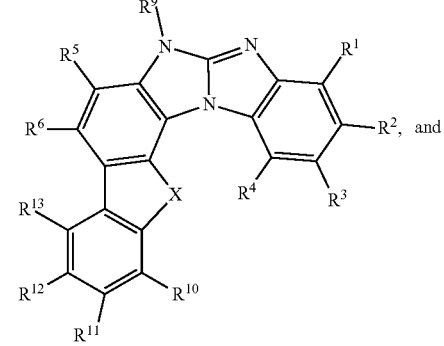

(I'''-II'''c''')

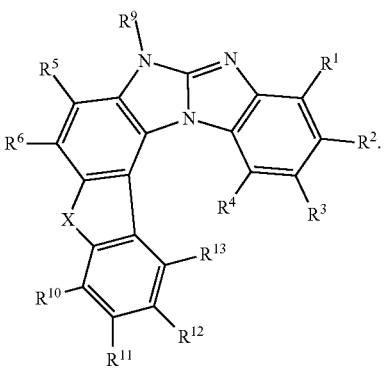

The residues $R^1$ to $R^{13}$ and the group X have been defined before and further preferred residues $R^1$ to $R^{13}$ and the group X are defined below. Preferably, X is $NR^{19}$ or $C(R^{28})_2$.

Of said compounds (I-IIa), (I-IIa'), (I-IIb), (I-IIb'), (I-IIc), (I-IIc'), (I'-II'a), (I'-II'a'), (I'-II'b), (I'-II'b'), (I'-II'c) and (I'-II'c'), the compounds (I-IIb') and (I-IIb), are especially preferred. Further, the compounds (I-IIc), (I-IIc'), (I'-II'c) and (I'-II'c') and the compounds (I''-IIc), (I-IIc''), (I''-II''c), (I''-II''c''), (I'''-IIc), (I-Ic'''), (I'''-II''c) and (I'''-II'''c''') are especially preferred.

In the compounds of formula (I), X is $NR^{19}$, O, S, $C(R^{28})_2$, or $Si(R^{28})_2$. Preferably, X is $NR^{19}$, O, S or $C(R^{28})_2$.

In the case that at least two of the substituents $R^1$ and $R^2$, $R^2$ and $R^3$, $R^3$ and $R^4$, $R^5$ and $R^6$, $R^6$ and $R^7$, or $R^7$ and $R^8$ form together a ring system of formula (IIa) or (IIb), preferably (IIb), X is more preferably, X is NR$^{19}$ or C(R$^{28}$)$_2$ and most preferably, X is NR$^{19}$.

In the case that at least two of the substituents R$^1$ and R$^2$, R$^2$ and R$^3$, R$^3$ and R$^4$, R$^5$ and R$^6$, R$^6$ and R$^7$, or R$^7$ and R$^8$ form together a ring system of formula (IIc), X is more preferably NR$^{19}$, O or C(R$^{28}$)$_2$. Further more preferably, X is in this case NR$^{19}$ or C(R$^{28}$)$_2$.

Therefore, especially preferred compounds are the compounds (I-IIa), (I-IIa'), (I-IIb), (I-IIb'), (I-IIc), (1-IIc'), (I'-II'a), (I'-II'a'), (I'-II'b), (I'-II'b'), (I'-II'c) and (I'-II'c'), wherein X is NR$^{19}$ or C(R$^{28}$)$_2$. Most preferably, X is NR$^{19}$. Further especially preferred are the compounds (I"-IIc"), (I-IIc"), (I"-II"c), (I"-II"c"), (I'"-IIc), (I-IIc'") , (I'"-II"'c) and (I'"-II"'c") wherein X is NR$^{19}$ or C(R$^{28}$)$_2$.

Most preferred compounds—in the case that X is NR$^{19}$—are compounds I-IIc, I-IIc''', I'-II'c' and I"-IIc.

Even more preferred compounds are—in one embodiment—the compounds (I-IIa), (I-IIa'), (I-IIb), (I-IIb'), (I'-II'a), (I'-II'a'), (I'-II'b) or (I'-II'b'), especially preferably compounds (I-IIa), (I-IIa'), (I-IIb) and (I-IIb'), even more preferred (I-IIb) and (I-IIb'), wherein X is NR$^{19}$.

Even more preferred compounds are—in a further embodiment—the compounds (I-IIc), (I-IIc'), (I'-II'c) and (I'-II'c'), wherein X is C(R$^{28}$)$_2$.

Also even more preferred compounds are—in a further embodiment—the compounds (I-IIc), (I-IIc'), (I'-II'c) and (I'-II'c'), wherein X is NR$^{19}$.

Also even more preferred compounds are—in a further embodiment—the compounds (I-IIc"), (I"-II"c), (I'"-IIc) and (I'"-II"'c") wherein X is C(R$^{28}$)$_2$.

Also even further more preferred compounds are—in a further embodiment—the compounds (I"-IIc), (I"-II"c"), (I-Ic'") and (I'"-II"'c) wherein X is NR$^{19}$.

The residues R$^1$ to R$^{13}$, R$^{19}$ and R$^{28}$ have been defined before and further preferred residues R$^1$ to R$^{13}$, R$^{19}$ and R$^{28}$ are defined below.

Most preferred are therefore the following compounds:

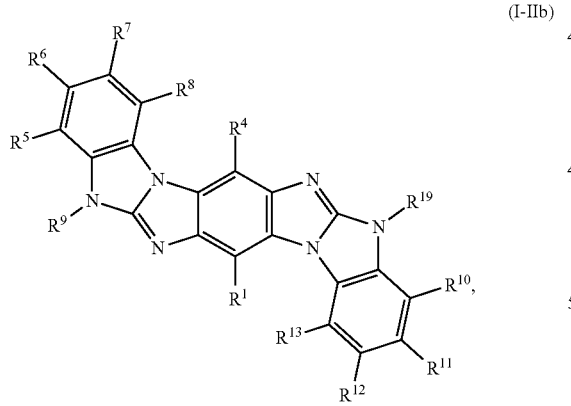
(I-IIb)

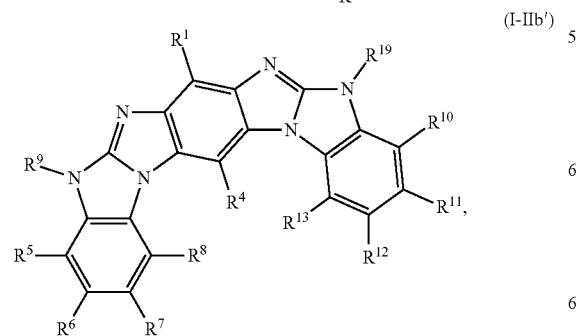
(I-IIb')

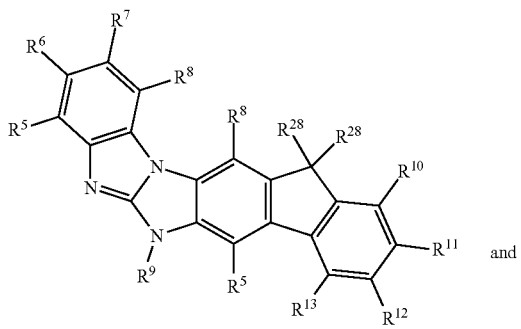
(I'-II'cb)

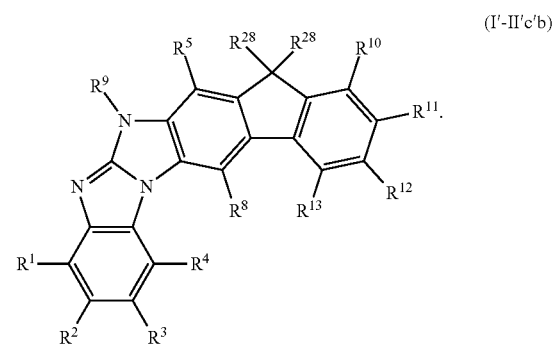
(I'-II'c'b)

and

Further most preferred compounds are:

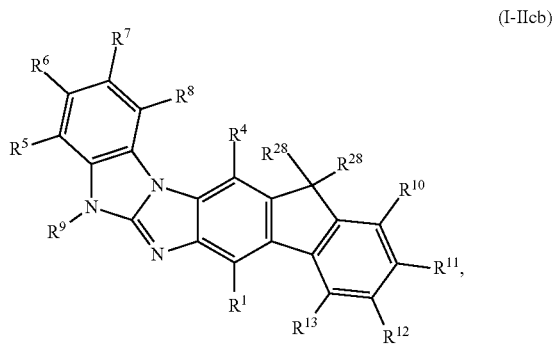
(I-IIcb)

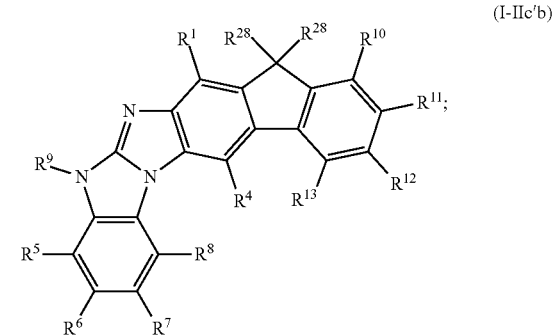
(I-IIc'b)

-continued
(I′-II′ca)
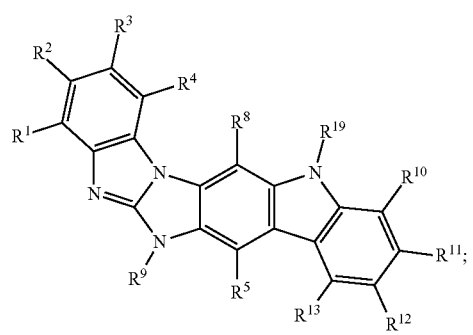
(I′-II′c′a)
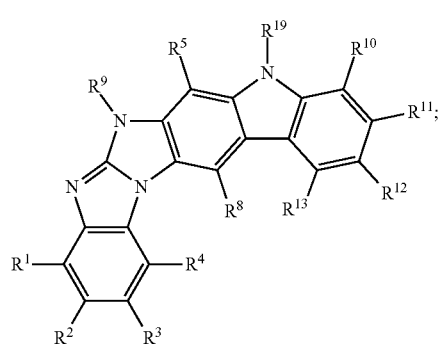
(I-IIca)
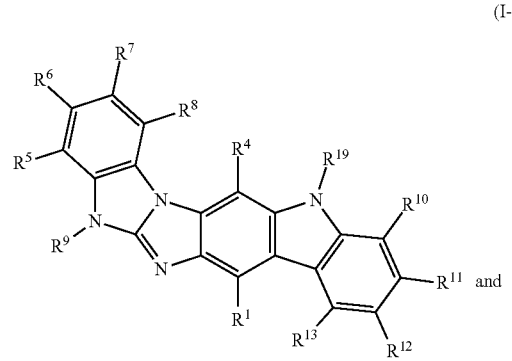
(I-IIc′a)
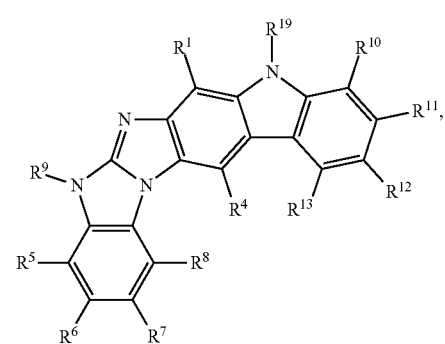
(I″-IIcb)
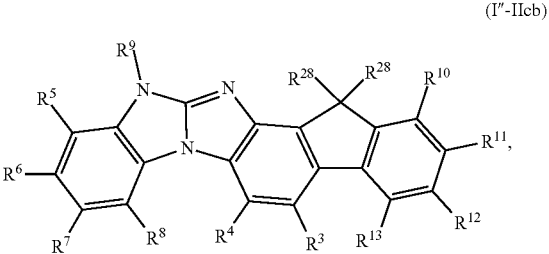
(I-IIc″b)
(I″-II″cb)
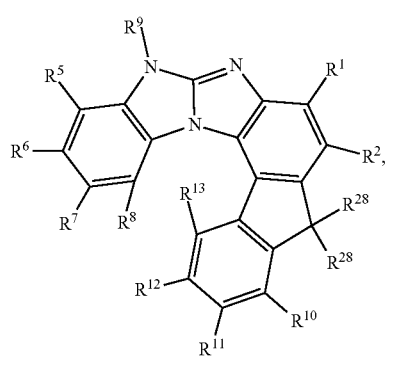
(I″-II″c″b)
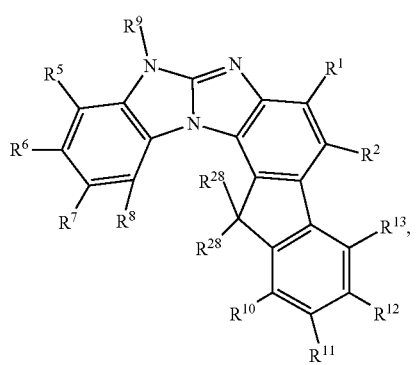
(I‴-IIcb)
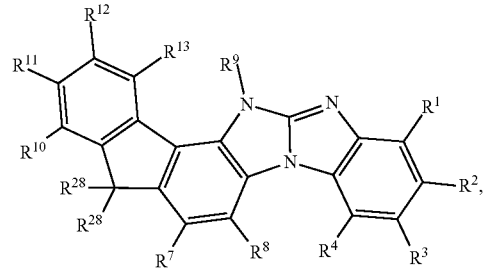
(I-IIc‴b)
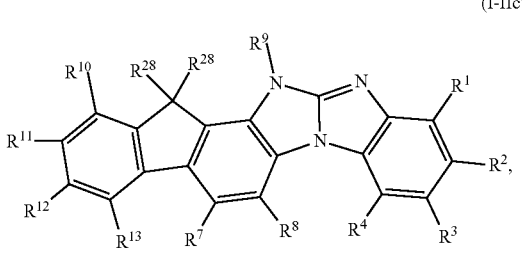

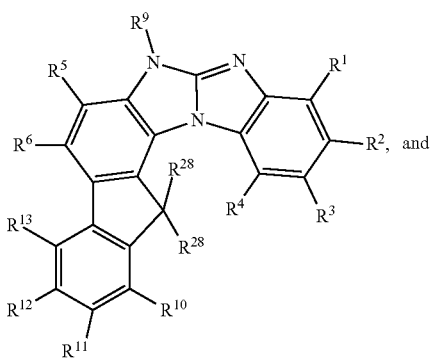
(I'''-IIc'''b)

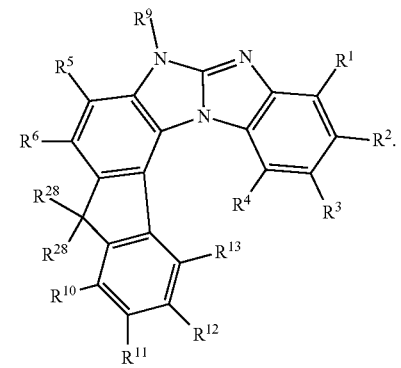
(I'''-II'''-c'''b)

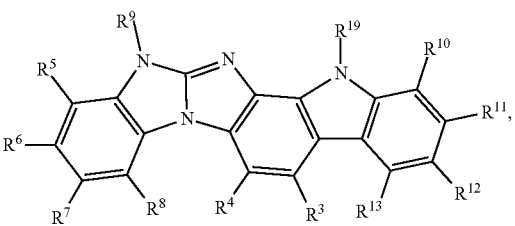
(I''-IIca)

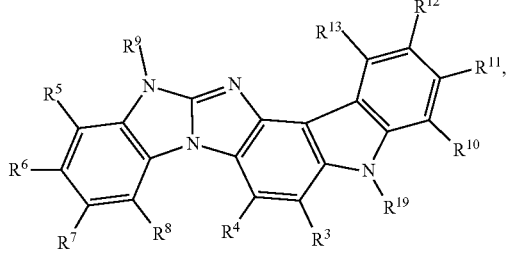
(I-IIc''a)

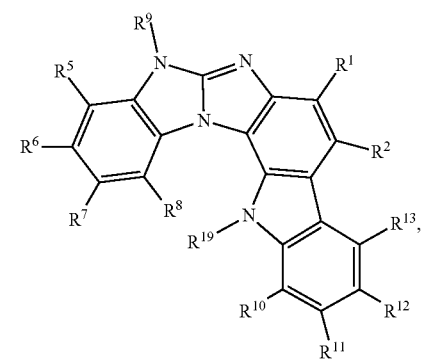
(I''-II''c''a)

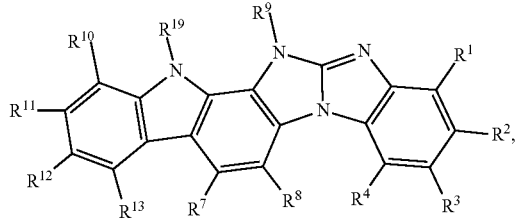
(I-IIc'''a)

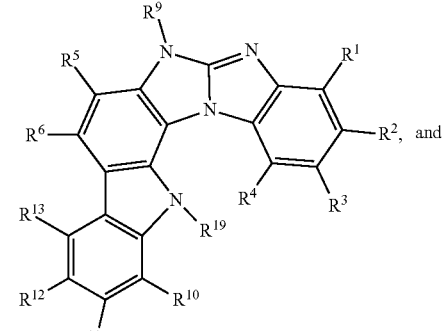
(I'''-IIca)

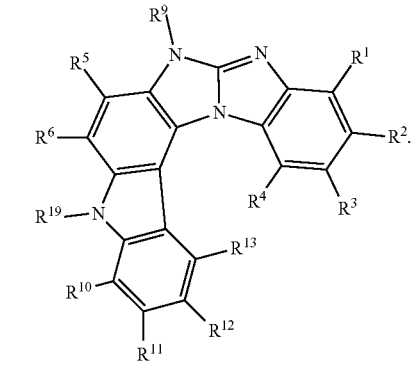
(I'''-IIc'''a)

The residues $R^1$ to $R^{13}$, $R^{19}$ and $R^{28}$ have been defined before and further preferred residues $R^1$ to $R^{13}$, $R^{19}$ and $R^{28}$ are defined below.

From the compounds mentioned above, compounds (I-IIb), (I-IIb'), (I'-II'cb), (I'-II'c'b), (I-IIcb), (I-IIc'b), (I'-II'ca), (I'-II'c'a), (I-IIca), (I-IIc'a), (I-IIc''b), (I''-II''cb), (I'''-IIcb), and (I'''-II'''c'''b), (I''-IIca), (I''-II''c''a), (I-IIc'''a) and (I'''-IIca), and (I'''-II'''c'''a) are more preferred.

Compounds (I'-II'c'b), (1-IIc'b), (I'-II'c'a), (1-IIca), (I''-IIca) and (I-IIc'''a) are even more preferred.

Compounds I-IIb and I-IIb' are even more most preferred.
$A^1$, $A^2$, $A^3$, $A^4$, $A^{1'}$, $A^{2'}$, $A^{3'}$ and $A^{4'}$ $A^1$, $A^2$, $A^3$, $A^4$, $A^{1'}$, $A^{2'}$, $A^{3'}$ and $A^{4'}$ are independently of each other a $C_6$-$C_{24}$ arylene group which is unsubstituted or substituted by G, $C_2$-$C_{24}$ heteroarylene group which is unsubstituted or substituted by G;

$A^1$, $A^2$, $A^3$, $A^4$, $A^{1'}$, $A^{2'}$, $A^{3'}$ and $A^{4'}$ are preferably independently of each other $C_6$-$C_{24}$arylene groups, which optionally can be substituted by G, selected from the group consisting of phenylene, naphthylene, especially 1-naphthylene, or 2-naphthylene, biphenylene, triphenylene, terphenylene, pyrenylene, 2- or 9-fluorenylene, phenanthrylene, or anthrylene, which may be unsubstituted or substituted by G; or $C_5$-$C_{24}$heteroarylene groups, and $C_2$-$C_{24}$heteroarylene groups, which optionally can be substituted by G, characterized by a ring with five to seven ring atoms or a condensed ring system, wherein nitrogen, oxygen or sulfur are the possible heteroatoms, and having at least six conju-gated-electrons, preferably selected from benzothiophenylene, thianthrenylene, furylene, furfu-rylene, 2H-pyranylene, benzofuranylene, isobenzofuranylene, dibenzofuranylene

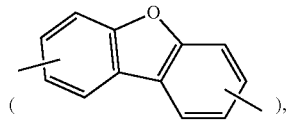

dibenzothiophenylene

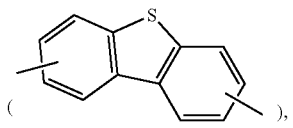

carbazolylene

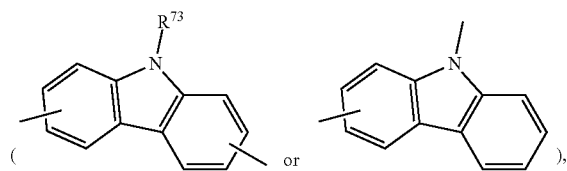

imidazolylene, pyrazolylene, pyridylene, bipyridylene, triazinylene, pyrimidinylene, pyrazinylene, pyridazinylene, indolizinylene, isoindolylene, indolylene, indazolylene, purinylene, quinolizinylene, chinolylene, isochinolylene, phthalazinylene, naphthyridinylene, chinoxalinylene, chinazolinylene, cinnolinylene, pteridinylene, carbolinylene, benzotriazolylene, benzoxazolylene, phenanthridinylene, pyrimidinylene, benzimidazo[1,2-a]benzimidazo-2,5-ylene, which can be unsubstituted or substituted by G; $R^{73}$ is a $C_6$-$C_{24}$aryl group, or a $C_2$-$C_{30}$heteroaryl group, which can optionally be substituted by G; wherein the lines are bonding sites;

preferably, $A^1$, $A^2$, $A^3$, $A^4$, $A^{1'}$, $A^{2'}$, $A^{3'}$ and $A^{4'}$ are

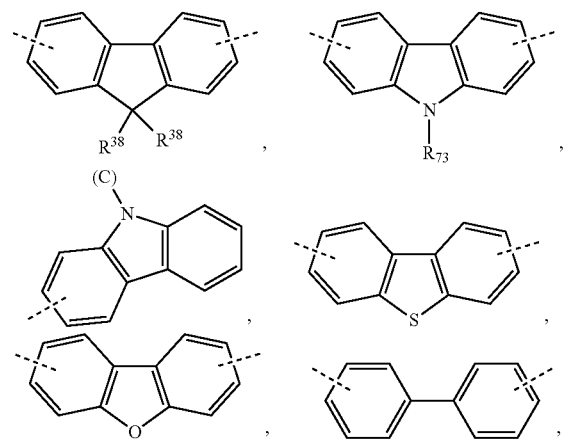

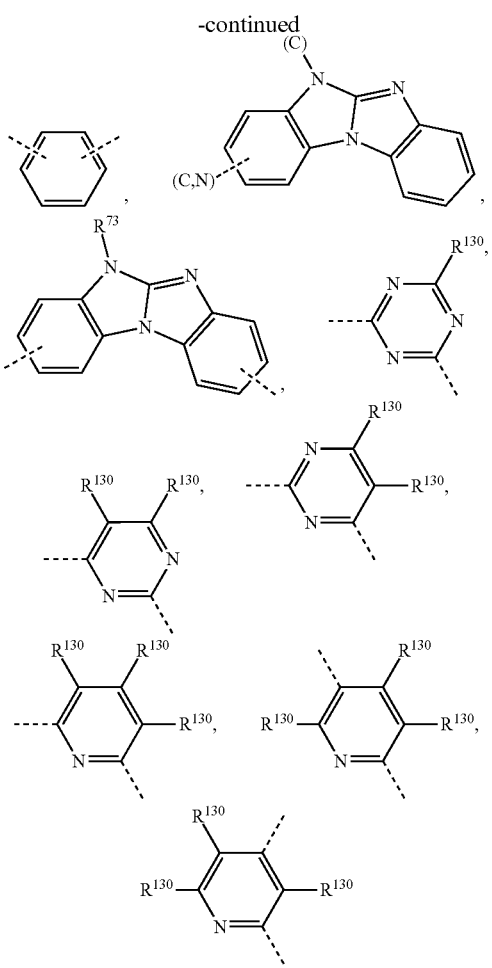

which can be unsubstituted or substituted by G, preferably unsubstituted or substituted by 1, 2, 3 or 4 groups G, more preferably unsubstituted or substituted by 1 or 2 groups G, most preferably unsubstituted; whereby G is defined above and is most preferably —$NR^{65}R^{66}$, —CN, —$Si(R^{70})_3$, a $C_1$-$C_{24}$alkyl group, an unsubstituted $C_6$-$C_{30}$aryl group or a $C_2$-$C_{30}$heteroaryl group; $R^{73}$ is a $C_6$-$C_{18}$aryl group; a $C_6$-$C_{18}$aryl which is substituted by $C_1$-$C_{18}$alkyl or $C_1$-$C_{18}$alkoxy; a $C_1$-$C_{18}$alkyl group; or a $C_1$-$C_{18}$alkyl group, which is interrupted by —O—, preferably $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, tolyl, naphthyl, or biphenylyl;

$R^{38}$ a $C_1$-$C_{25}$alkyl group, which can optionally be substituted by E and or interrupted by D; a $C_6$-$C_{24}$aryl group, which can optionally be substituted by G, or a $C_1$-$C_{24}$heteroaryl group, which can optionally be substituted by G; and/or two adjacent groups of the groups may form together with the atom to which they are bonded a ring structure, which can optionally be substituted by G; $R^{130}$ is independently in each occurrence H or $C_6$-$C_{24}$arylene group, which can optionally be substituted by G, or a $C_2$-$C_{30}$heteroarylene group, which can optionally be substituted by G; wherein G is as defined in above; wherein the dotted lines are bonding sites;

wherein (C)— has the meaning that the bonding site of the group $A^1$, $A^2$, $A^3$, $A^4$, $A^{1'}$, $A^{2'}$, $A^{3'}$ and $A^{4'}$ is linked to a C-atom, and (N)— has the meaning that the bonding site of the group $A^1$, $A^2$, $A^3$, $A^4$, $A^{1'}$, $A^{2'}$, $A^{3'}$ and $A^{4'}$ is linked to a N-atom, and (C,N) has the meaning that the bonding site of the group A¹, A², A³, A⁴, A¹', A²', A³' and A⁴' is linked to a C or N-atom.
A¹, A², A³, A⁴, A¹', A²', A³' and A⁴' are more preferably in each occurrence independently of each other a group of the formula:
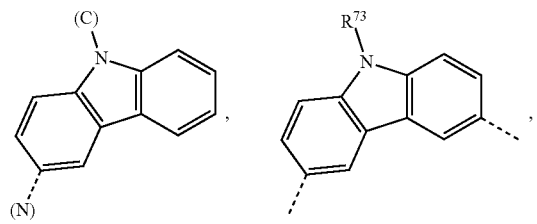
preferably
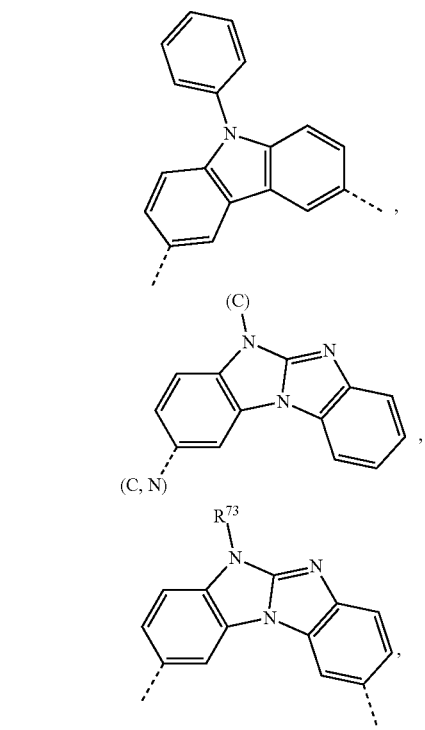
preferably
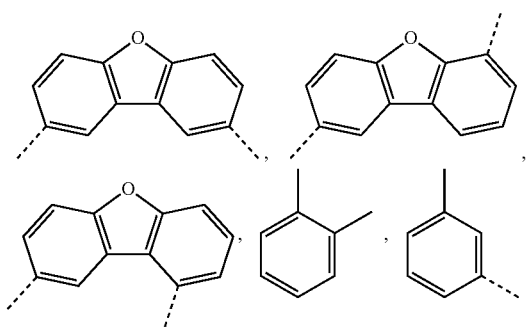
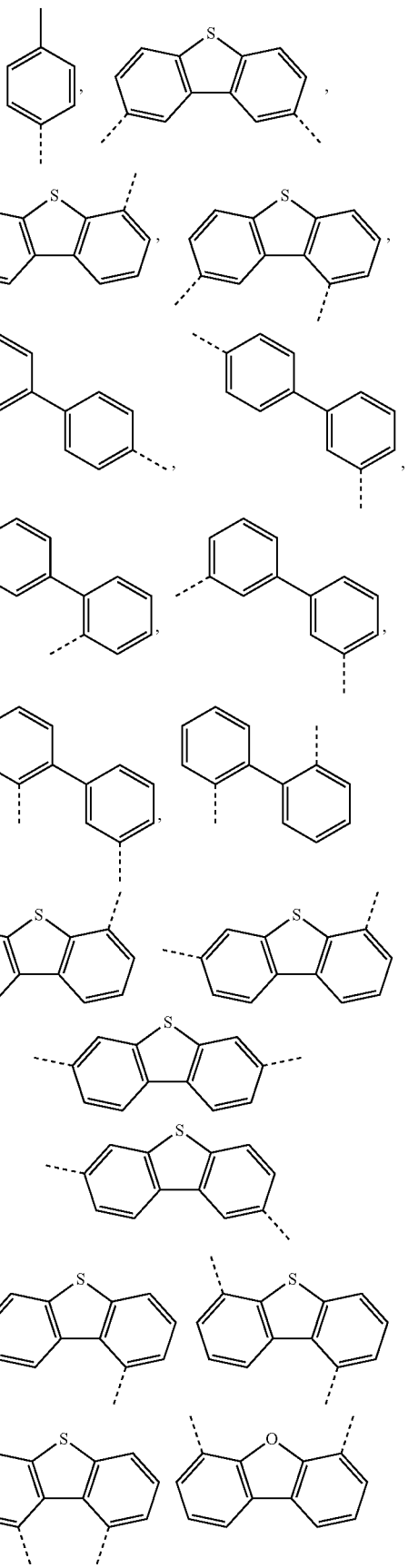

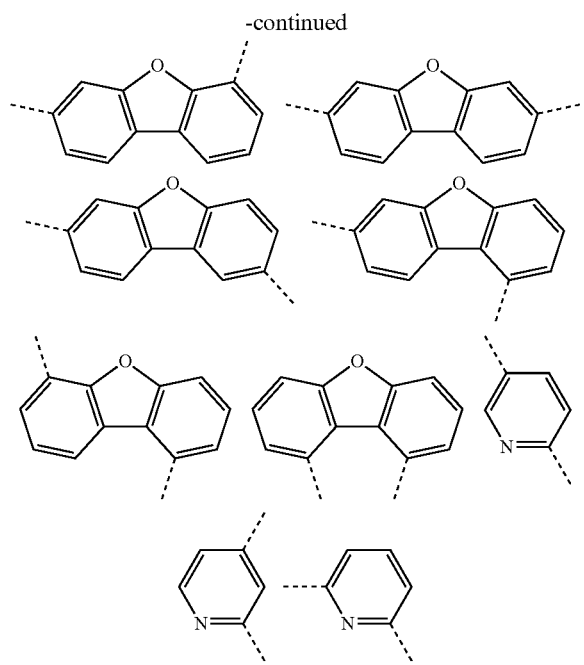

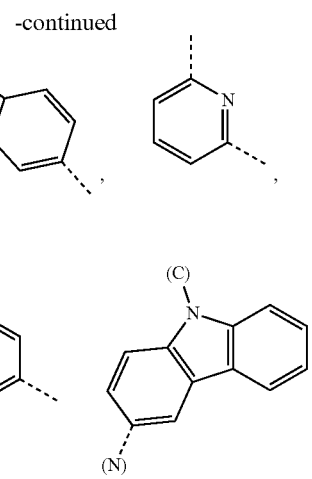

which can be unsubstituted or substituted by G, preferably unsubstituted or substituted by 1, 2, 3 or 4 groups G, more preferably unsubstituted or substituted by 1 or 2 groups G, most preferably unsubstituted; whereby G is defined above and is most preferably —NR$^{65}$R$^{66}$, —CN, —Si(R$^{70}$)$_3$, a C$_1$-C$_{24}$alkyl group, an unsubstituted C$_6$-C$_{30}$aryl group or a C$_2$-C$_{30}$heteroaryl group; R$^{73}$ is a C$_6$-C$_{18}$aryl group; a C$_6$-C$_{18}$aryl which is substituted by C$_1$-C$_{18}$alkyl or C$_1$-C$_{18}$alkoxy; a C$_1$-C$_{18}$alkyl group; or a C$_1$-C$_{18}$alkyl group, which is interrupted by —O—, preferably C$_1$-C$_{18}$alkyl, such as methyl, ethyl, n-propyl, iso-propyl, n-butyl, isobutyl, sec-butyl, hexyl, octyl, or 2-ethyl-hexyl, or C$_6$-C$_{14}$aryl, such as phenyl, tolyl, naphthyl, or biphenylyl;

wherein (C)— has the meaning that the bonding site of the group A$^1$, A$^2$, A$^3$, A$^4$, A$^{1'}$, A$^{2'}$, A$^{3'}$ and A$^{4'}$ is linked to a C-atom, and (N)— has the meaning that the bonding site of the group A$^1$, A$^2$, A$^3$, A$^4$, A$^{1'}$, A$^{2'}$, A$^{3'}$ and A$^{4'}$ is linked to a N-atom, and (C,N) has the meaning that the bonding site of the group A$^1$, A$^2$, A$^3$, A$^4$, A$^{1'}$, A$^{2'}$, A$^{3'}$ and A$^{4'}$ is linked to a C or N-atom; and the dotted lines are bonding sites.

A$^1$, A$^2$, A$^3$, A$^4$, A$^{1'}$, A$^{2'}$, A$^{3'}$ and A$^{4'}$ are most preferably in each occurrence independently of each other a group of the formula:

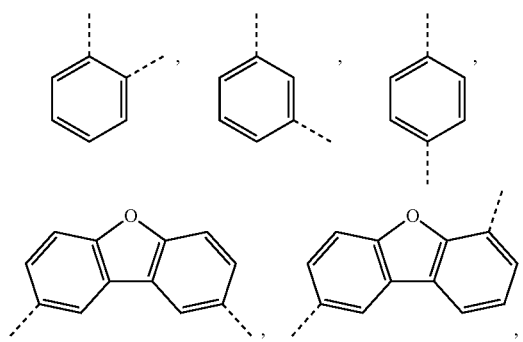

which can be unsubstituted or substituted by G, preferably unsubstituted or substituted by 1, 2, 3 or 4 groups G, more preferably unsubstituted or substituted by 1 or 2 groups G, most preferably unsubstituted; whereby G is defined above and is most preferably NR$^{65}$R$^{66}$, —CN, a C$_1$-C$_{24}$alkyl group, an unsubstituted C$_6$-C$_{30}$aryl group or a C$_2$-C$_{30}$heteroaryl group, wherein the dotted lines are bonding sites.

Further most preferably, A$^1$, A$^2$, A$^3$, A$^4$, A$^{1'}$, A$^{2'}$, A$^{3'}$ and A$^{4'}$ are in each occurrence independently of each other 1,3-phenylene, 1,4-phenylene,

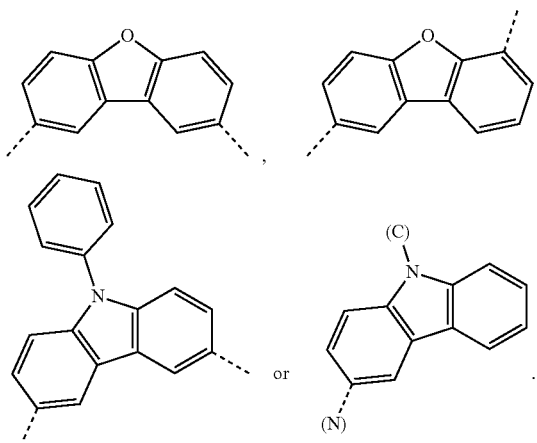

R$^{20}$ and R$^{20'}$

R$^{20}$ is a C$_6$-C$_{30}$ aryl group which is unsubstituted or substituted by G, C$_2$-C$_{60}$ heteroaryl group which is unsubstituted or substituted by G, a C$_1$-C$_{25}$alkyl group, which can optionally be substituted by E and or interrupted by D; or, in the case that at last one of o, p, q and r is 1, R$^{20}$ is CN;

R$^{20'}$ is H, CN, a C$_6$-C$_{30}$ aryl group which is unsubstituted or substituted by G, C$_2$-C$_{60}$ heteroaryl group which is unsubstituted or substituted by G, a C$_1$-C$_{25}$alkyl group, which can optionally be substituted by E and or interrupted by D.

The groups G, E and D are defined above.

Preferably, R$^{20'}$ is H, CN or has one of the definitions given for R$^{20}$ mentioned below.

Preferably, $R^{20}$ is

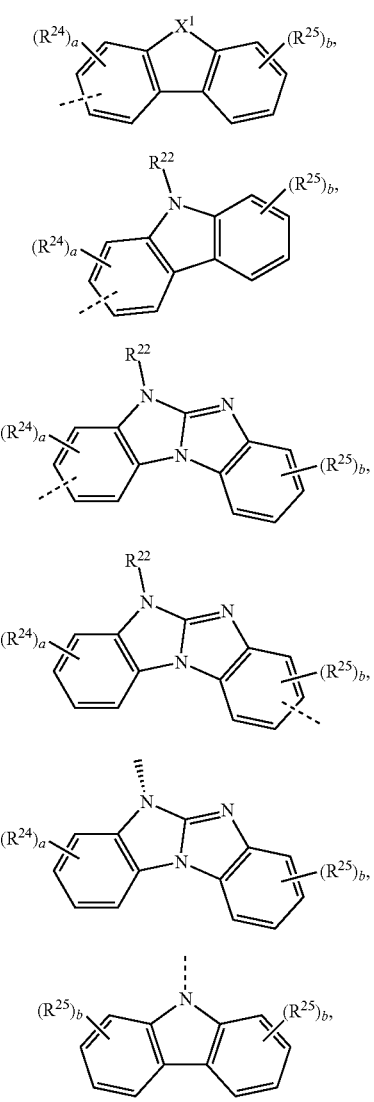

or, in the case that at last one of o, p, q and r is 1, CN;
wherein
$X^1$ is S, O, $C(R^{21})_2$, $NR^{23}$;
$R^{21}$ is a $C_1$-$C_{25}$alkyl group, which can optionally be substituted by E and or interrupted by D; a $C_6$-$C_{24}$aryl group, which can optionally be substituted by G, or a $C_1$-$C_{24}$heteroaryl group, which can optionally be substituted by G; and/or two adjacent groups of the groups $R^{21}$ may form together with the atom to which they are bonded a ring structure, which can optionally be substituted by G;
$R^{22}$ is a $C_6$-$C_{18}$ aryl group which is unsubstituted or substituted by G, $C_2$-$C_{18}$ heteroaryl group which is unsubstituted or substituted by G;
$R^{23}$ is a $C_6$-$C_{18}$ aryl group which is unsubstituted or substituted by G, $C_2$-$C_{18}$ heteroaryl group which is unsubstituted or substituted by G;
$R^{24}$ and $R^{25}$ are independently of each other H, a $C_6$-$C_{18}$ aryl group which is unsubstituted or substituted by G, $C_2$-$C_{18}$ heteroaryl group which is unsubstituted or substituted by G, a $C_1$-$C_{25}$alkyl group, which can optionally be substituted by E and or interrupted by D, or —CN;

a is 0, 1, 2 or 3, preferably 0, 1 or 2;
b is 0, 1, 2, 3 or 4, preferably 0, 1 or 2;
the dotted lines are bonding sites; or

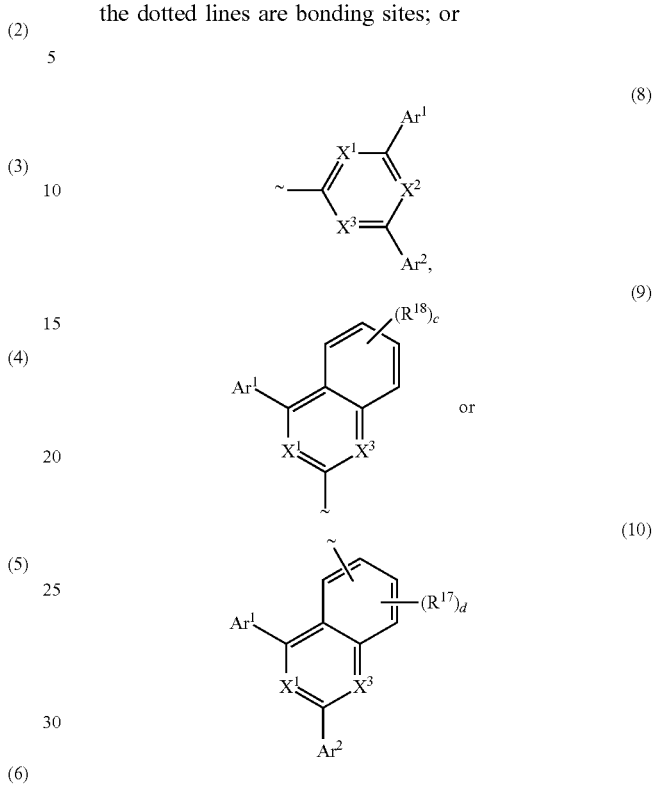

wherein
$X^1$, $X^2$ and $X^3$ are independently of each other $CR^{16}$ or N, wherein in formula (8) at least one of $X^1$ to $X^3$ is N, and wherein in formulae (9) and (10) at least one of $X^1$ and $X^3$ is N;
$Ar_1$ and $Ar_2$ are independently of each other a $C_6$-$C_{24}$ aryl group, which is optionally substituted by G, or a $C_1$-$C_{24}$ heteroaryl group, which is optionally substituted by G;
$R^{16}$, $R^{17}$ and $R^{18}$ are independently of each other H, a $C_6$-$C_{24}$ aryl group which can be substituted by G, a $C_1$-$C_{24}$ heteroaryl group which can be substituted by G or a $C_1$-$C_{25}$alkyl group, which can optionally be substituted by E and/or interrupted by D; preferably, H; or

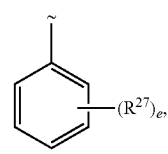

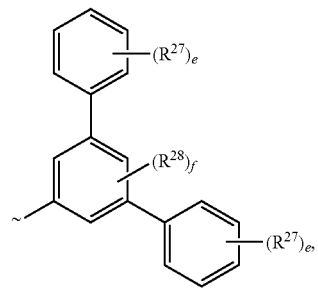

-continued (13a)
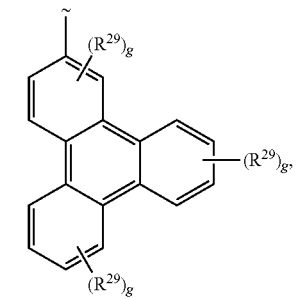

(13b)
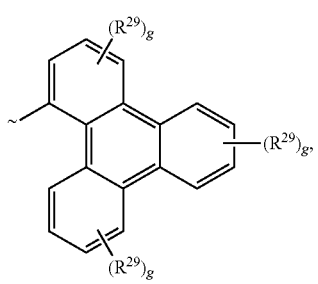

(14a)
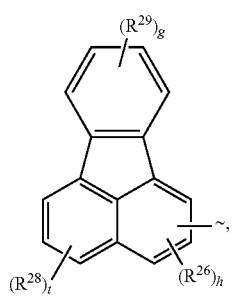

(14b)
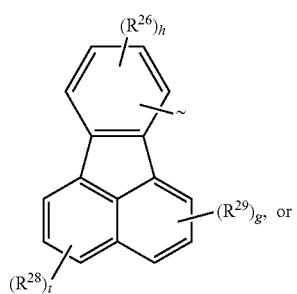

(15)
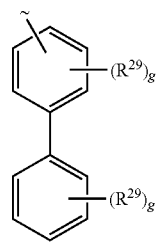

$R^{26}$, $R^{27}$, $R^{28}$ and $R^{29}$ are independently of each other H, a $C_6$-$C_{24}$ aryl group which can be substituted by G, a $C_1$-$C_{24}$ heteroaryl group which can be substituted by G or a $C_1$-$C_{25}$ alkyl group, which can optionally be substituted by E and/or interrupted by D; or a substituent E; preferably, H or CN, more preferably H;

e is 0, 1, 2, 3, 4 or 5; preferably 0, 1, 2 or 3; more preferably 0, 1 or 2;

f is 0, 1, 2 or 3; preferably 0, 1 or 2; more preferably 0;

g is 0, 1, 2, 3 or 4; preferably 0, 1 or 2; more preferably 0 or 1;

h is 0, 1 or 2, preferably 0 or 1; more preferably 0; or two adjacent groups $R^{26}$, $R^{27}$ $R^{28}$ or $R^{29}$ may form together with the atoms to which they are bonded a ring structure which may be substituted by G, wherein ~ is a bonding site.

Preferred groups (2), (3), (4), (5), (6) and (7) are:

(2′)
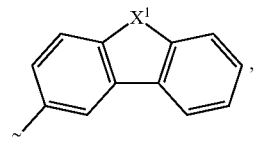

(2″)
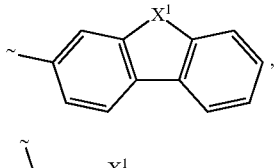

(2‴)
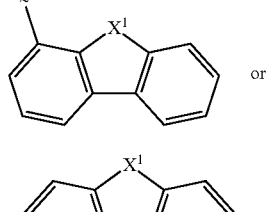

or (2″″)
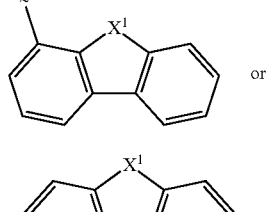

wherein $X^1$ is O or S;
wherein ~ is a bonding site.
Most preferred groups (2), (3), (4), (5), (6) and (7) are:

(2′a)
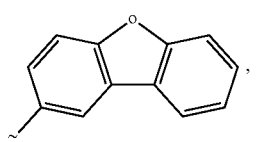

(2′b)
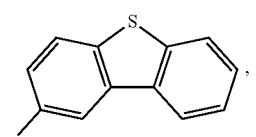

(2″a)
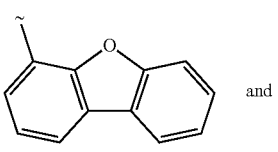

and (2‴b)
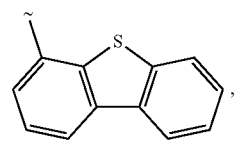

wherein ~ is a bonding site.

Preferred groups (8), (9) and (10) are:

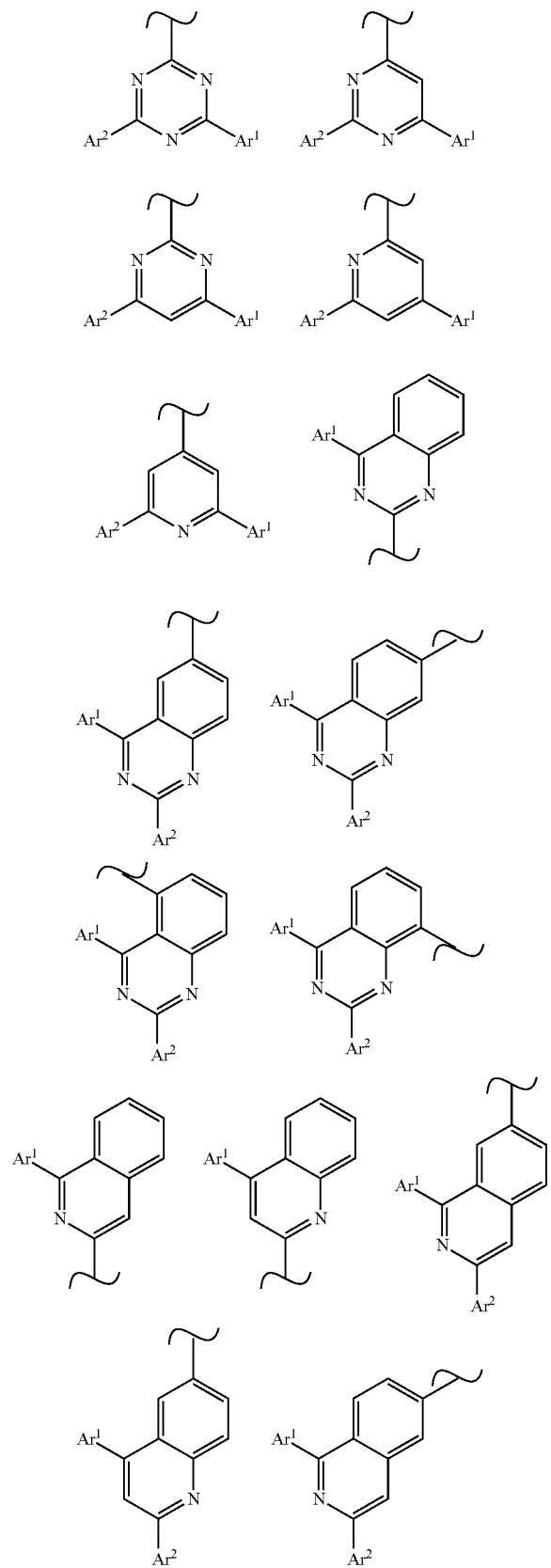

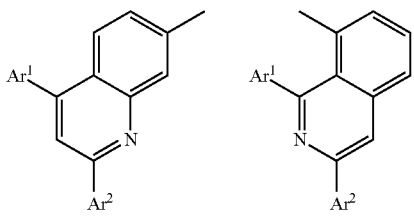

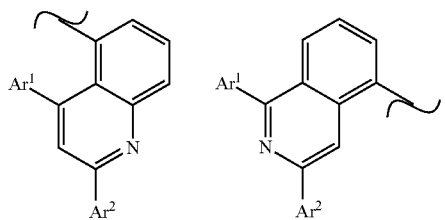

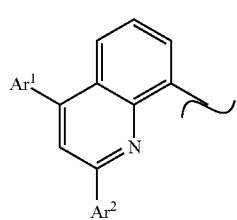

wherein $Ar_1$ and $Ar_2$ are independently of each other a $C_6$-$C_{24}$ aryl group, which is optionally substituted by G, or a $C_1$-$C_{24}$ heteroaryl group, which is optionally substituted by G;

~ are bonding sites to the neighboring groups.

The group G is described above.

Preferably, $Ar_1$ and $Ar_2$ are unsubstituted phenyl or a group of the following formula

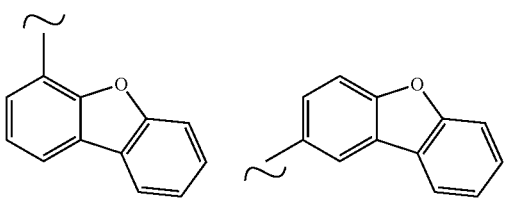

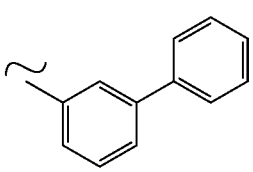

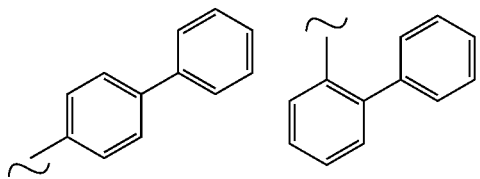

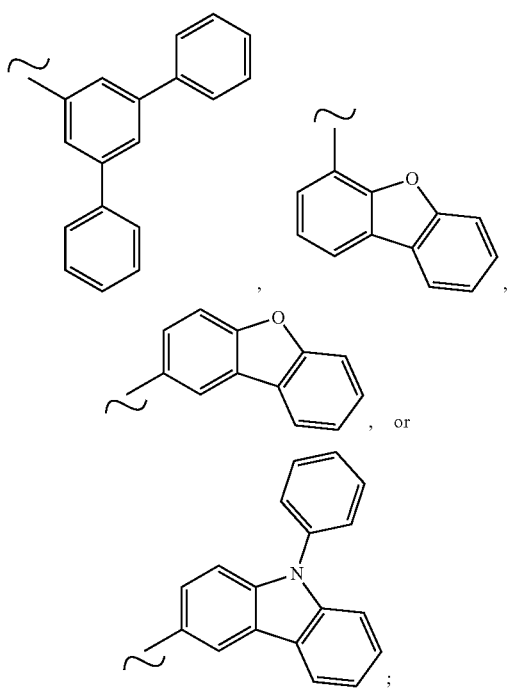
wherein
~ are bonding sites to the neighboring groups.
Most preferably, Ar₁ and Ar₂ are unsubstituted phenyl.
Most preferably, the groups (8), (9) and (10) are
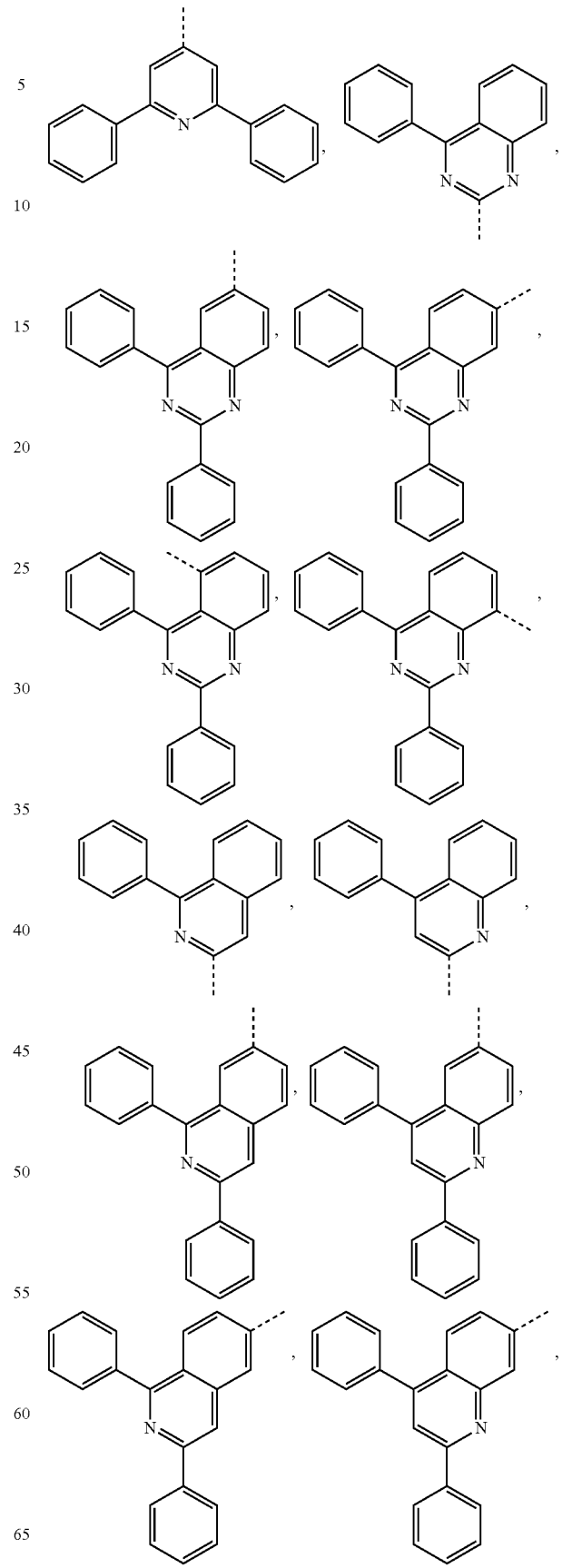

-continued
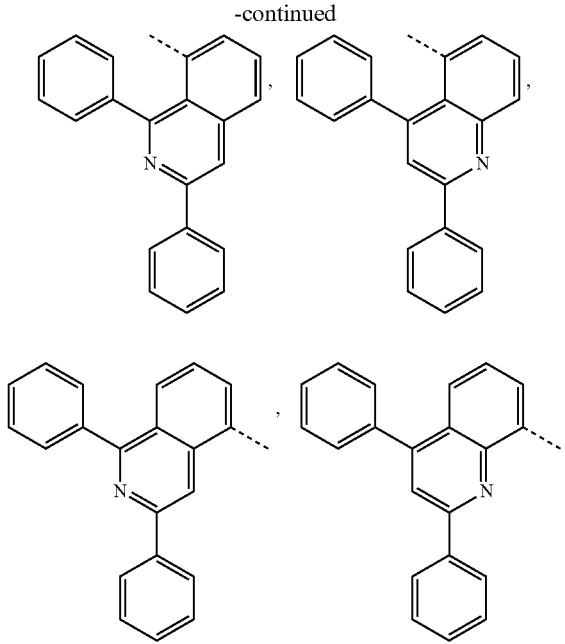
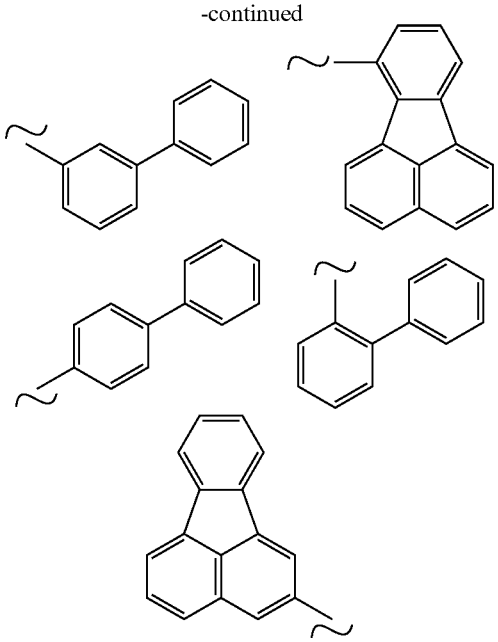
wherein
the dotted lines are bonding sites to the neighboring groups.
Preferred groups (11), (12), (13), (14) and (15) are
wherein
~ are bonding sites to the neighboring groups.
Most preferred groups (11), (12), (13), (14) and (15) are:
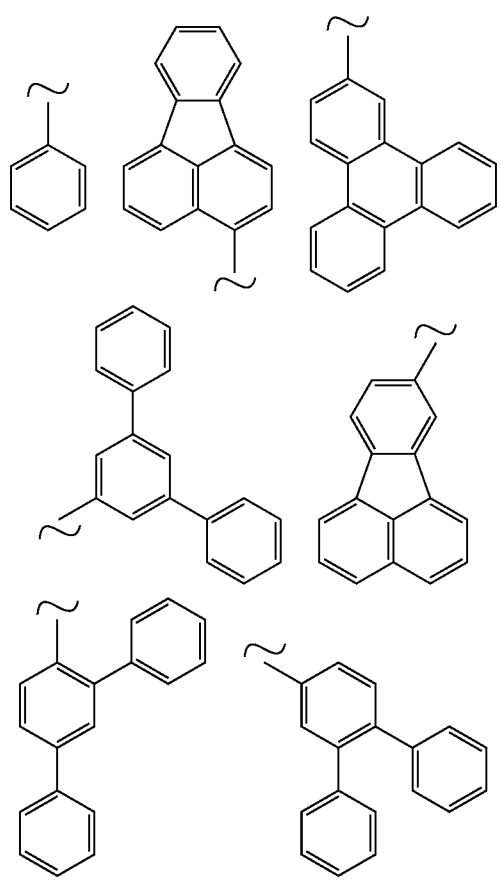
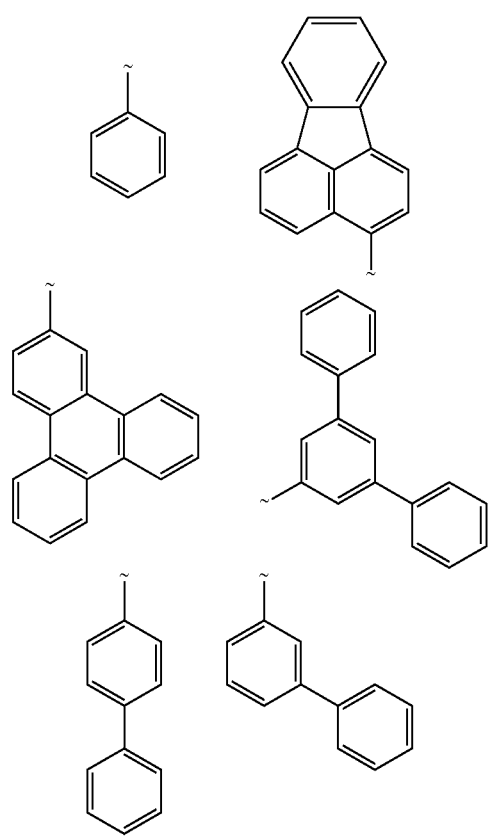
wherein
~ are bonding sites to the neighboring groups.

Most preferably, $R^{20'}$ is H, CN, or has one of the definitions for $R^{20}$ mentioned below: Most preferably, $R^{20}$ is
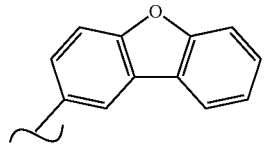 (2'a)
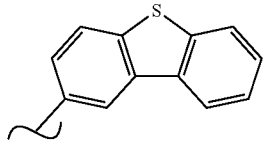 (2'b)
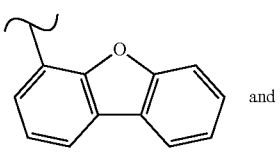 (2'''a)
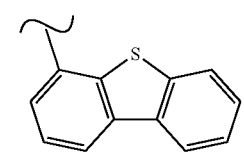 (2'''b) and
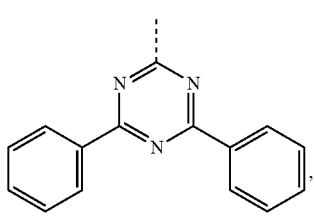
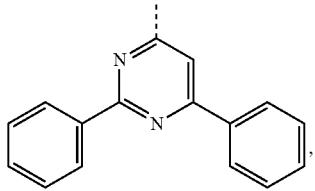
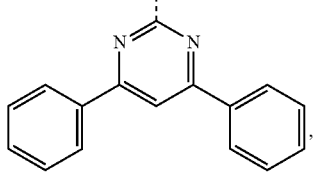
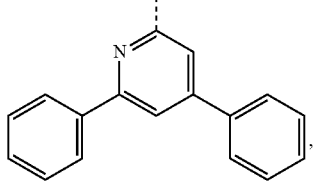
-continued
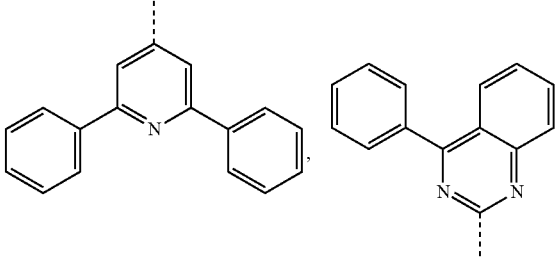
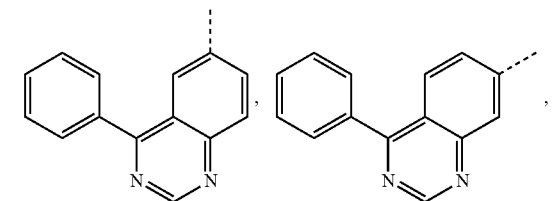
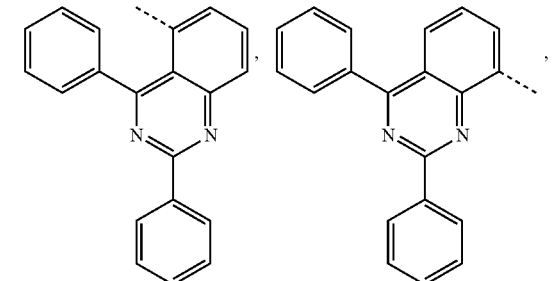
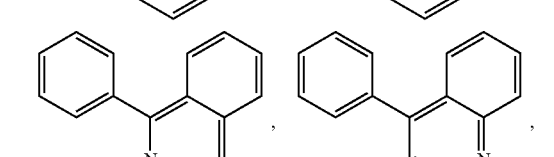
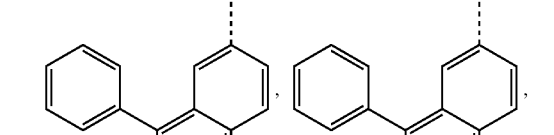
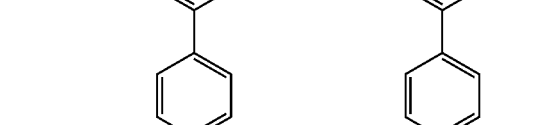
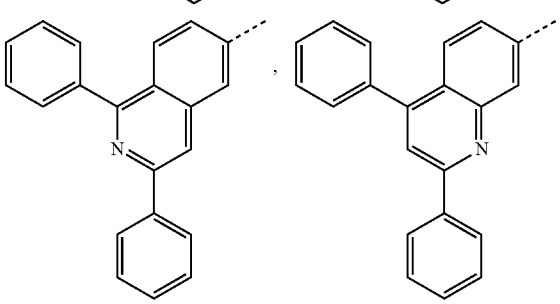

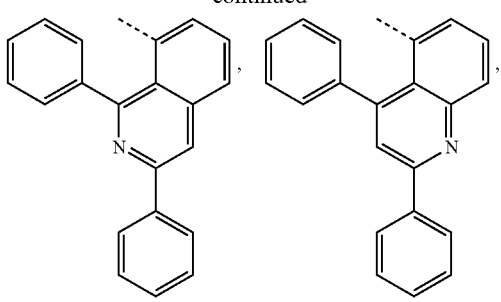

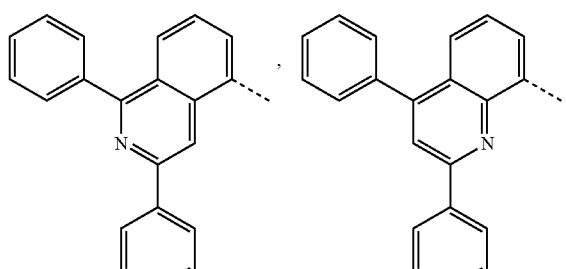

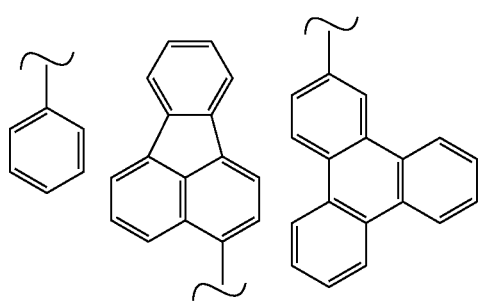

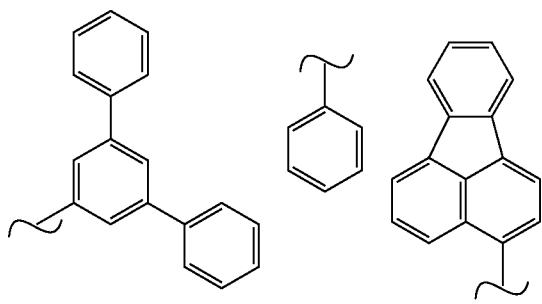

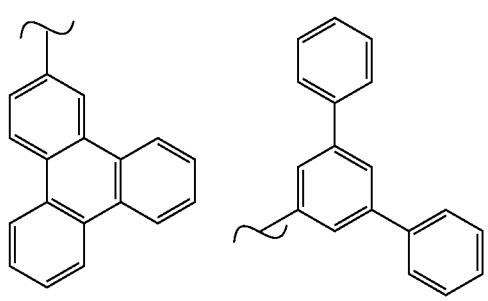

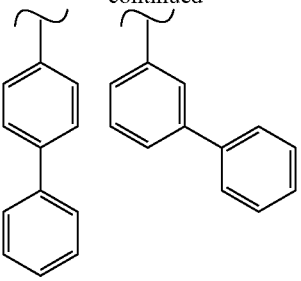

wherein

~ and the dotted lines are bonding sites to the neighboring groups.

o is 0 or 1, p is 0 or 1, q is 0 or 1, r is 0 or 1; preferably, o is 0 or 1, p is 0 or 1 and q and rare 0, more preferably, o is 0 or 1 and p, q and r are 0.

o' is 0 or 1, p' is 0 or 1, q' is 0 or 1, r' is 0 or 1; preferably, o' is 0 or 1, p' is 0 or 1 and q' and r' are 0, more preferably, o' is 0 or 1 and p', q' and r' are 0.

$R^9$ and $R^{19}$ $R^9$ and $R^{19}$ are independently of each other group of formula $-(A^1)_o-(A^2)_p-(A^3)_q-(A^4)_r-R^{20}$; preferably, $R^9$ and $R^{19}$ are identical.

In a further preferred embodiment, especially in the case that at least two of the substituents $R^1$ and $R^2$, $R^2$ and $R^3$, $R^3$ and $R^4$, $R^5$ and $R^6$, $R^6$ and $R^7$, or $R^7$ and $R^8$ together form a ring system (IIc), $R^9$ and $R^{19}$ are different.

The groups $A^1$, $A^2$, $A^3$ and $A^4$, the indices o, p, q and r and the residue $R^{20}$ are defined above and preferred specific combinations of groups $A^1$, $A^2$, $A^3$ and $A^4$, indices o, p, q and r and the residue $R^{20}$ are defined below.

Preferably, $R^9$ and $R^{19}$ are independently of each other a $-(A^1)_o-C_1-C_{25}$alkyl group, which can optionally be substituted by E; a $-(A^1)_o-C_6-C_{24}$aryl group, which can optionally be substituted by G, or a $-(A^1)_o-C_1-C_{24}$heteroaryl group, which can optionally be substituted by G, wherein $A^1$ and o are defined above, most preferably $A^1$ is 1,2-phenylene, 1,3-phenylene or 1,4-phenylene and o is 0 or 1;

more preferably, $R^9$ and $R^{19}$ are independently of each other (2-1)

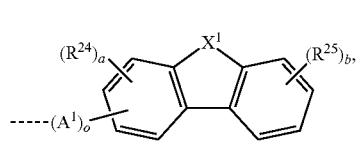

(3-1)

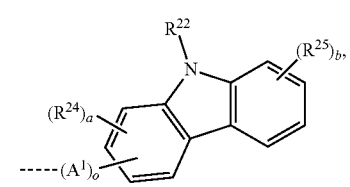

(4-1)

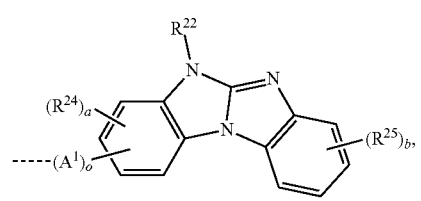

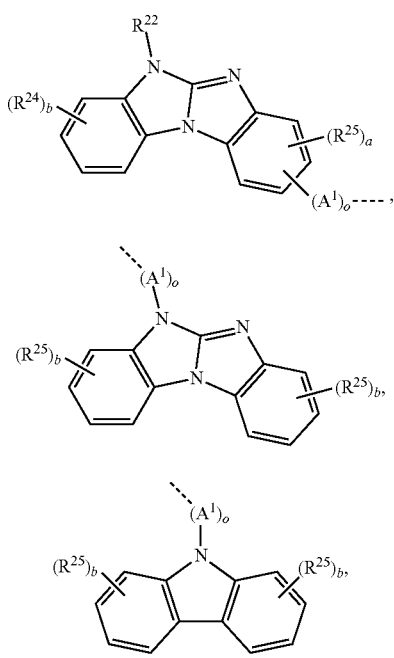

(5-1)

(6-1)

(7-1)

wherein

X$^1$ is S, O, C(R$^{21}$)$_2$, NR$^{23}$;

R$^{22}$ is a C$_6$-C$_{18}$ aryl group which is unsubstituted or substituted by G, C$_2$-C$_{18}$ heteroaryl group which is unsubstituted or substituted by G;

R$^{23}$ is H, a C$_6$-C$_{18}$ aryl group which is unsubstituted or substituted by G, C$_2$-C$_{18}$ heteroaryl group which is unsubstituted or substituted by G;

R$^{24}$ and R$^{25}$ are independently of each other H, a C$_6$-C$_{18}$ aryl group which is unsubstituted or substituted by G, C$_2$-C$_{18}$ heteroaryl group which is unsubstituted or substituted by G, a C$_1$-C$_{25}$alkyl group, which can optionally be substituted by E and or interrupted by D, or —CN;

a is 0, 1, 2 or 3, preferably 0, 1 or 2;

b is 0, 1, 2, 3 or 4, preferably 0, 1 or 2; or

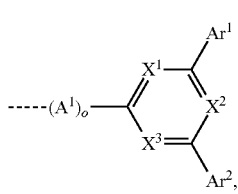
(8-1)

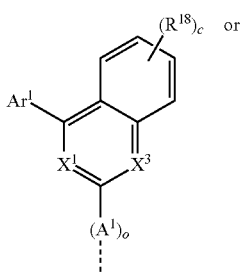
(9-1)

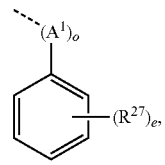
(10-1)

wherein

X$^1$, X$^2$ and X$^3$ are independently of each other CR$^{16}$ or N, wherein in formula (8) at least one of X$^1$ to X$^3$ is N, and wherein in formulae (9) and (10) at least one of X$^1$ and X$^3$ is N;

Ar$_1$ and Ar$_2$ are independently of each other a C$_6$-C$_{24}$ aryl group, which is optionally substituted by G, or a C$_1$-C$_{24}$ heteroaryl group, which is optionally substituted by G;

R$^{16}$, R$^{17}$ and R$^{18}$ are independently of each other H, a C$_6$-C$_{24}$ aryl group which can be substituted by G, a C$_1$-C$_{24}$ heteroaryl group which can be substituted by G or a C$_1$-C$_{25}$alkyl group, which can optionally be substituted by E and/or interrupted by D; preferably, H; or (11-1)

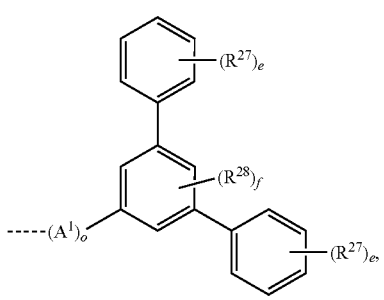
(12-1)

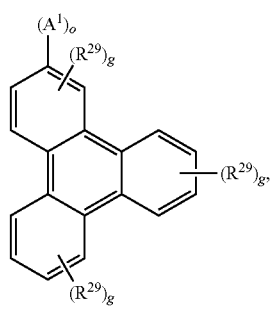
(13-1a)

-continued

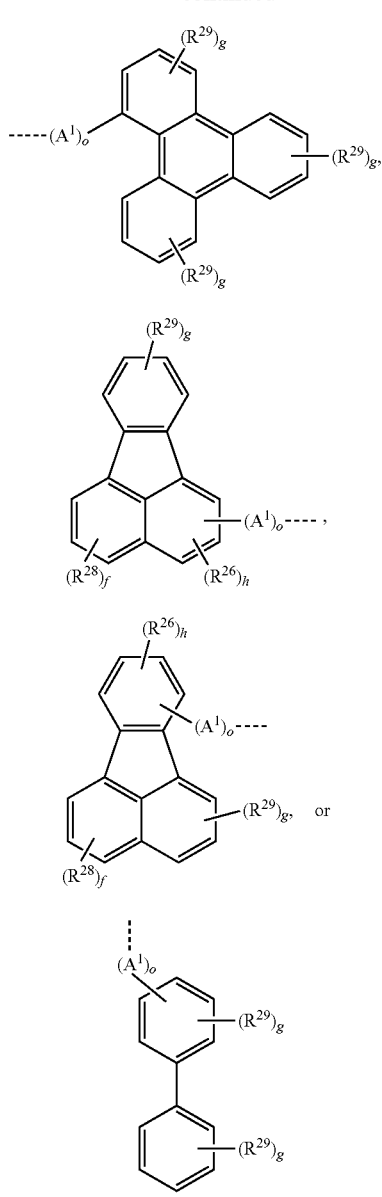

$R^{26}$, $R^{27}$, $R^{28}$ and $R^{29}$ are independently of each other H, a $C_6$-$C_{24}$ aryl group which can be substituted by G, a $C_1$-$C_{24}$ heteroaryl group which can be substituted by G or a $C_1$-$C_{25}$alkyl group, which can optionally be substituted by E and/or interrupted by D; or a substituent E; preferably, H or CN, more preferably H;

e is 0, 1, 2, 3, 4 or 5; preferably 0, 1, 2 or 3; more preferably 0, 1 or 2;

f is 0, 1, 2 or 3; preferably 0, 1 or 2; more preferably 0;

g is 0, 1, 2, 3 or 4; preferably 0, 1 or 2; more preferably 0 or 1;

h is 0, 1 or 2, preferably 0 or 1; more preferably 0;

or two adjacent groups $R^{26}$, $R^{27}$ $R^{28}$ or $R^{29}$ may form together with the atoms to which they are bonded a ring structure which may be substituted by G, wherein the dotted line is a bonding site, wherein the group -($A^1$)$_o$- is defined above and is preferably phenylene or a single bond, more preferably a single bond. Also more preferably 1,3-phenylene.

The groups G, E and D are defined above.

Preferred groups (2-1) to (15-1) are mentioned above in the definition of $R^{20}$, whereby the bonding site is replaced by a group -($A^1$)$_o$-, and preferred groups $A^1$ are also mentioned above. o is 0 or 1.

More preferred groups $R^9$ and $R^{19}$ are independently of each other:

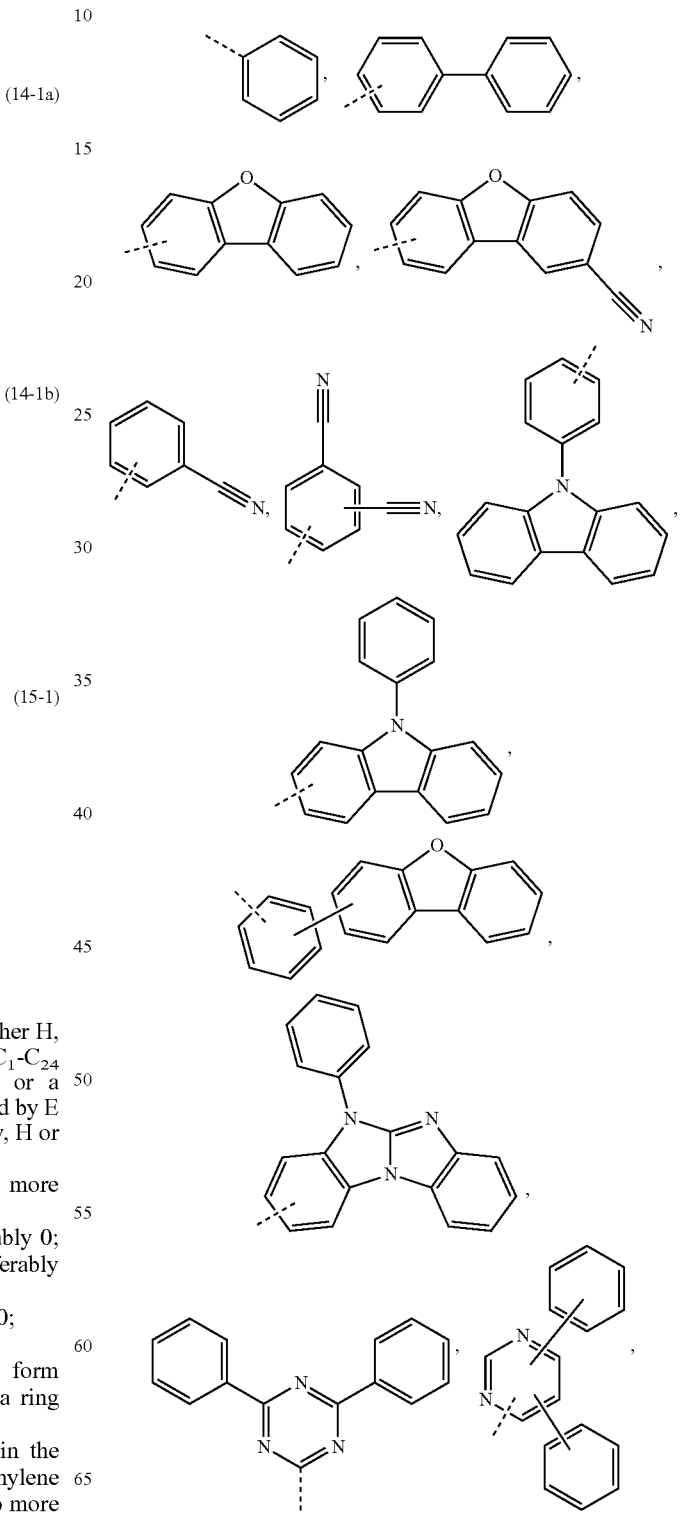

-continued
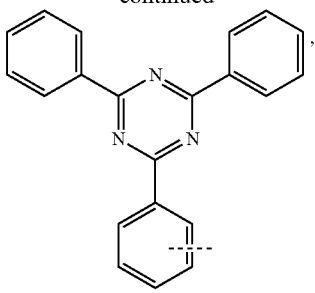
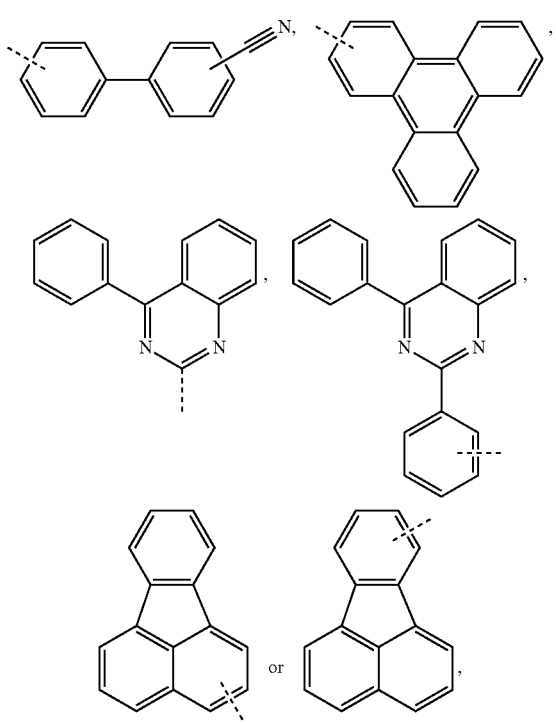
wherein the dotted lines are bonding sites.
In addition to the groups mentioned above, more preferred groups $R^9$ and $R^{19}$ are independently of each other
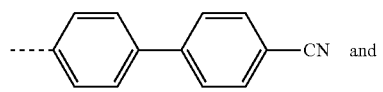 and
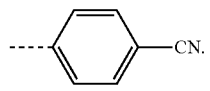
Most preferred groups $R^9$ and $R^{19}$ are independently of each other:

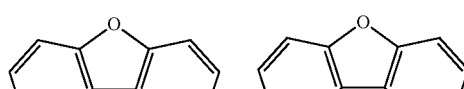
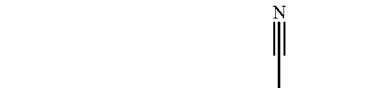
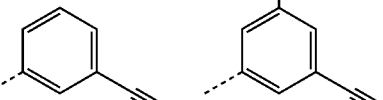
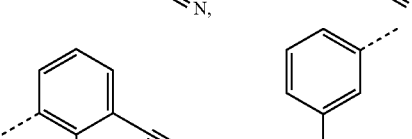
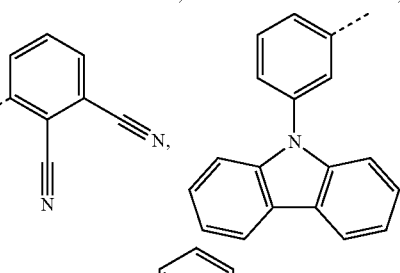
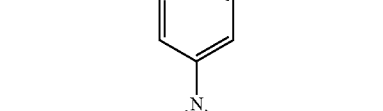
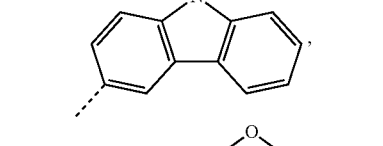

-continued

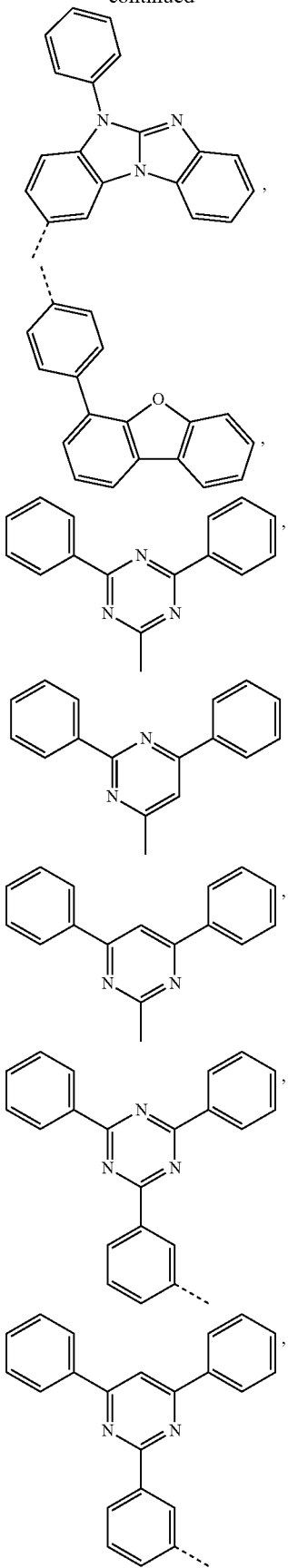

-continued

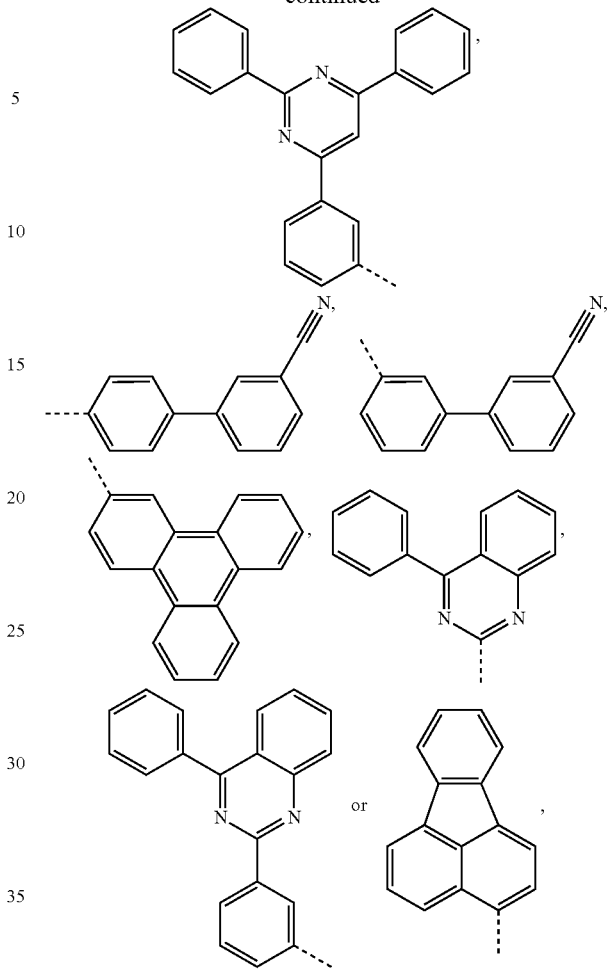

wherein the dotted lines are bonding sites.

R28

$R^{28}$ is independently of each other $C_6$-$C_{18}$aryl which is unsubstituted or substituted by $C_1$-$C_{18}$alkyl or $C_1$-$C_{18}$alkoxy; or $C_1$-$C_{18}$alkyl which is interrupted by —O—, which is unsubstituted or substituted by E; or two residues $R^{28}$ can together with the carbon atom or Si atom to which they are bonded form a ring. Preferably, two residues $R^{28}$ bonded to the same carbon atom or Si atom are identical.

The group E has been defined above.

In the case that two residues $R^{28}$ can together with the carbon atom or Si atom to which they are bonded form a ring, said ring is preferably a saturated aliphatic ring, an unsaturated aliphatic ring having one or two double bonds, an unsaturated heteroaliphatic ring having one or two double bonds and comprising one, two or three heteroatoms selected from N, O and S or an aromatic ring. More preferably, said ring comprises 5 to 10 ring atoms, even more preferably 5 to 7 ring atoms.

Preferably, $R^{28}$ is independently of each other $C_6$-$C_{18}$aryl which is unsubstituted or substituted by $C_1$-$C_{18}$alkyl or $C_1$-$C_{18}$alkoxy; or $C_1$-$C_{18}$alkyl which is interrupted by —O—, which is unsubstituted or substituted by E.

More preferably, $R^{28}$ is independently of each $C_1$-$C_{18}$alkyl, especially methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, or octadecyl, further more preferably $C_1$-$C_8$alkyl, especially methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl, and most preferably $C_1$-$C_4$alkyl, especially methyl, ethyl, n-propyl, isopropyl, n-butyl, sec.-butyl, isobutyl, tert.-butyl. Further most preferably, $R^{28}$ is in each case methyl.

$R^1$, $R^2$, $R^3$, $R^4$, $R^5$, $R^6$, $R^7$, $R^8$, which are not forming together a ring system of formula IIa, IIb or IIc and $R^{10}$, $R^{11}$, $R^{12}$, $R^{13}$ $R^1$, $R^2$, $R^3$, $R^4$, $R^5$, $R^6$, $R^7$, $R^8$, which are not forming together a ring system of formula IIa, IIb or IIc are independently of each other H, CN or group of formula -$(A^{1'})_{o'}$-$(A^{2'})_{p'}$-$(A^{3'})_{q'}$-$(A^{4'})_{r'}$-$R^{20'}$ or a group E; or adjacent groups $R^1$ and $R^2$, $R^2$ and $R^3$, $R^3$ and $R^4$, $R^5$ and $R^6$, $R^6$ and $R^7$, and/or $R^7$ and $R^8$ can from together a ring.

$R^{10}$, $R^{11}$, $R^{12}$, $R^{13}$ are independently of each other H, CN or group of formula -$(A^{1'})_{o'}$-$(A^{2'})_{p'}$-$(A^{3'})_{q'}$-$(A^{4'})_{r'}$-$R^{20'}$ or a group E; or adjacent groups $R^{10}$ and $R^{11}$, $R^{11}$ and $R^{12}$ and/or $R^{12}$ and $R^{13}$ can from together a ring.

The groups $A^{1'}$, $A^{2'}$, $A^{3'}$ and $A^{4'}$, the indices o', p', q' and r' and the residue $R^{20'}$ are defined above.

Preferably, $R^1$, $R^2$, $R^3$, $R^4$, $R^5$, $R^6$, $R^7$ and $R^8$, which are not forming together a ring system of formula IIa, IIb or IIc are independently of each other H, CN, a -$(A^{1'})_{o'}$-$C_6$-$C_{18}$ aryl group which is unsubstituted or substituted G, a -$(A^{1'})_{o'}$-$C_2$-$C_{18}$ heteroaryl group which is unsubstituted or substituted G or a -$(A^{1'})_{o'}$-$C_1$-$C_{25}$alkyl group, which can optionally be substituted by E and or interrupted by D, wherein $A^{1'}$ and o' are defined above, preferably $A^{1'}$ is 1,2-phenylene, 1,3-phenylene or 1,4-phenylene and o' is 0 or 1.

More preferably, $R^1$, $R^2$, $R^3$, $R^4$, $R^5$, $R^6$, $R^7$ and $R^8$, which are not forming together a ring system of formula IIa, IIb or IIc are independently of each other H, CN, a $C_6$-$C_{18}$ aryl group which is unsubstituted or substituted G, a $C_2$-$C_{18}$ heteroaryl group which is unsubstituted or substituted G or a $C_1$-$C_{25}$alkyl group, which can optionally be substituted by E and/or interrupted by D.

Most preferably, $R^1$, $R^2$, $R^3$, $R^4$, $R^5$, $R^6$, $R^7$ and $R^8$, which are not forming together a ring system of formula IIa, IIb or IIc are independently of each other H, CN or one of $R^5$, $R^6$, $R^7$ and $R^8$ is a $C_6$-$C_{18}$ aryl group which is unsubstituted or substituted G, a $C_2$-$C_{18}$ heteroaryl group which is unsubstituted or substituted G or a $C_1$-$C_{25}$alkyl group, which can optionally be substituted by E and/or interrupted by D, and all other $R^1$, $R^2$, $R^3$, $R^4$, $R^5$, $R^6$, $R^7$ and $R^8$ are H; or $R^1$, $R^2$, $R^3$, $R^4$, $R^5$, $R^6$, $R^7$ and $R^8$, which are not forming together a ring system of formula IIa, IIb or IIc are independently of each other H, CN or one of $R^1$, $R^2$, $R^3$ and $R^4$ is a $C_6$-$C_{18}$ aryl group which is unsubstituted or substituted G, a $C_2$-$C_{18}$ heteroaryl group which is unsubstituted or substituted G or a $C_1$-$C_{25}$alkyl group, which can optionally be substituted by E and/or interrupted by D, and all other $R^1$, $R^2$, $R^3$, $R^4$, $R^5$, $R^6$, $R^7$ and $R^8$ are H.

Further most preferably, $R^1$, $R^2$, $R^3$, $R^4$, $R^5$, $R^6$, $R^7$, $R^8$, which are not forming together a ring system of formula IIa, IIb or IIc are H.

The groups G, E and D have been defined before.

Preferably, $R^{10}$, $R^{11}$, $R^{12}$, $R^{13}$ are independently of each other H, CN, a -$(A^{1'})_{o'}$-$C_6$-$C_{18}$ aryl group which is unsubstituted or substituted G, a -$(A^{1'})_{o'}$-$C_2$-$C_{18}$ heteroaryl group which is unsubstituted or substituted G or a -$(A^{1'})_{o'}$-$C_1$-$C_{25}$alkyl group, which can optionally be substituted by E and or interrupted by D, wherein $A^{1'}$ and o' are defined above, preferably $A^{1'}$ is 1,2-phenylene, 1,3-phenylene or 1,4-phenylene and o' is 0 or 1

More preferably, $R^{10}$, $R^{11}$, $R^{12}$ and $R^{13}$ are independently of each other H, CN, a $C_6$-$C_{18}$ aryl group which is unsubstituted or substituted G, a $C_2$-$C_{18}$ heteroaryl group which is unsubstituted or substituted G or a $C_1$-$C_{25}$alkyl group, which can optionally be substituted by E and or interrupted by D.

Most preferably, $R^{10}$, $R^{11}$, $R^{12}$ and $R^{13}$ are independently of each other H, CN or one of $R^{10}$, $R^{11}$, $R^{12}$ and $R^{13}$ is a $C_6$-$C_{18}$ aryl group which is unsubstituted or substituted G, a $C_2$-$C_{18}$ heteroaryl group which is unsubstituted or substituted G or a $C_1$-$C_{25}$alkyl group, which can optionally be substituted by E and or interrupted by D, and all other $R^{10}$, $R^{11}$, $R^{12}$ and $R^{13}$ are H.

Most preferably, $R^{10}$, $R^{11}$, $R^{12}$ and $R^{13}$ are H.

The groups G, E and D have been defined before.

Most preferred compounds of formula (I) are therefore the following compounds: (I-IIaH), (I-IIa'H), (I-IIbH), (I-IIb'H), (I-IIcH), (I-IIc'H), (I'-II'aH), (I'-II'a'H), (I'-II'bH), (I'-II'b'H), (I'-II'cH) and (I'-II'c'H):

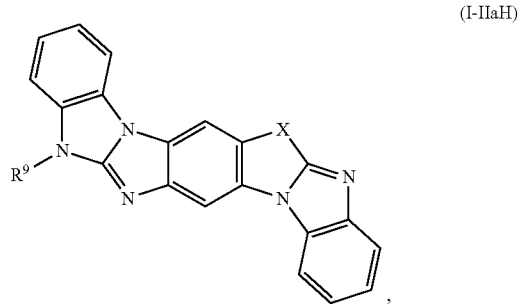

(I-IIaH)

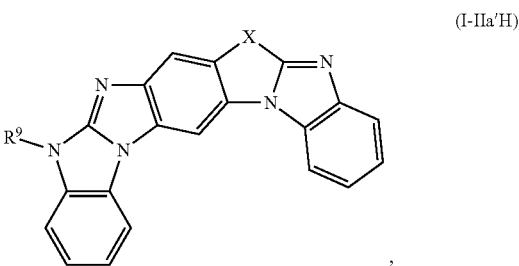

(I-IIa'H)

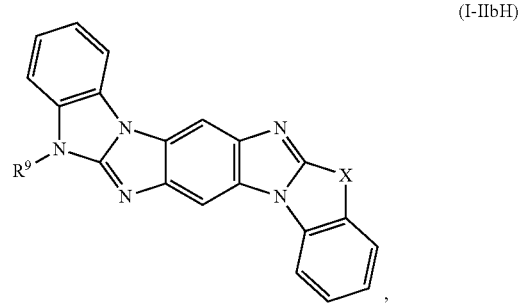

(I-IIbH)

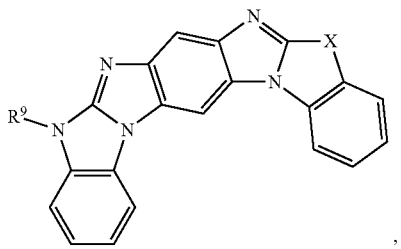
(I-IIb'H)

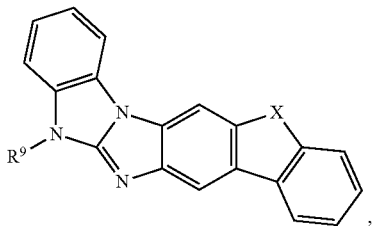
(I-IIcH)

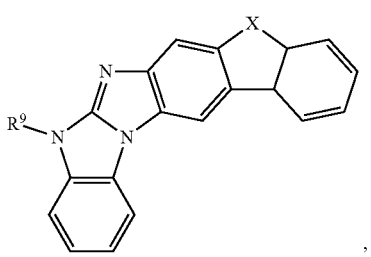
(I-IIc'H)

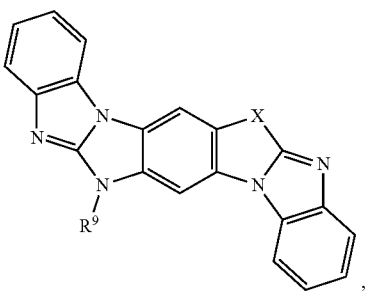
(I'-II'aH)

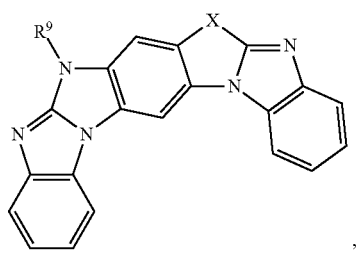
(I'-II'a'H)

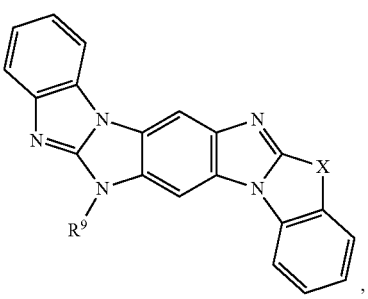
(I'-II'bH)

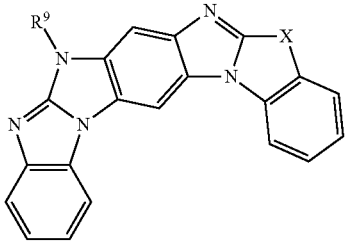
(I'-II'b'H)

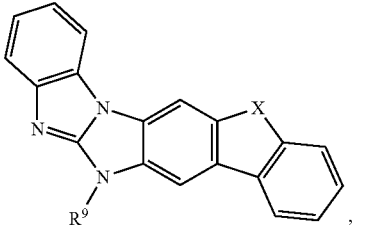
(I'-II'cH)

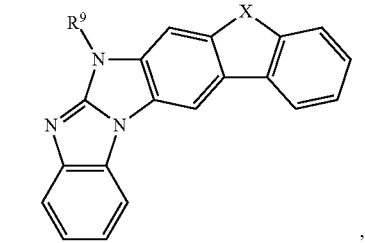
(I'-II'c'H)

and wherein X is NR$^{19}$ or C(R$^{28}$)$_2$, preferably NR$^{19}$, and R$^9$, R$^{19}$ and R$^{28}$ have been defined above.

Further most preferred compounds of formula (I) are the following compounds:

(I''-IIcH), (I-IIc''H), (I''-II''cH), (I''-II''c''H), (I'''-IIcH), (I-IIc'''H), (I'''-II'''cH), and (I'''-II'c'''H):

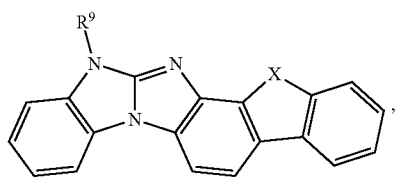
(I''-IIcH)

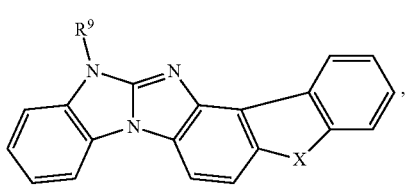
(I-IIc''H)

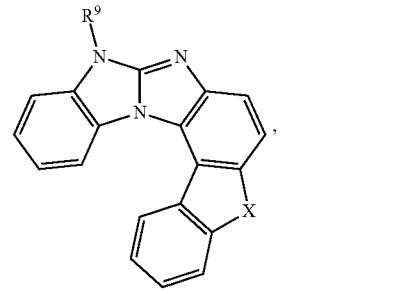
(I''-II''cH)

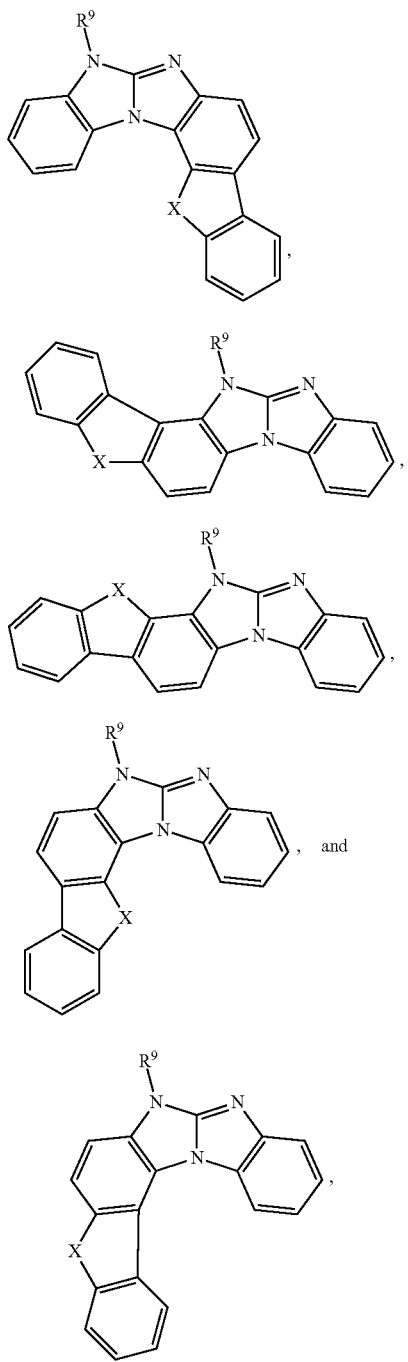

wherein X is NR$^{19}$ or (R$^{28}$)$_2$, and R$^9$, R$^9$ and R$^{28}$ have been defined above.

Of said compounds (I-IIaH), (I-IIa'H), (I-IIbH), (I-IIb'H), (I-IIcH), (I-IIc'H), (I'-II'aH), (I'-II'a'H), (I'-II'bH), (I'-II'b'H), (I'-II'cH) and (I'-II'c'H), the compounds (I-IIa'H) and (I-IIbH) are especially preferred.

Even more most preferred compounds are—in one embodiment—the compounds (I-IIaH), (I-IIa'H), (I-IIbH), (I-IIb'H), (I'-II'aH), (I'-II'a'H), (I'-II'bH) or (I'-II'b'H), especially preferably compounds (I-IIaH), (I-IIa'H), (I-IIbH) and (I-IIb'H), even more preferred (I-IIbH) and (I-IIb'H), wherein X is NR$^{19}$.

Further especially preferred compounds are the compounds (I-IIcH), (I'-II'c'H), (I''-IIcH), (I''-II''c''H), (I-IIc''H) and (I'''-II'''cH) in the case that X is NR$^{19}$.

Further especially preferred compounds are the compounds (I-IIc'H), (I'-II'c'H), (I-IIc''H), (I''-II''cH), (I'''-IIcH) and (I'''-II'''c'''H) in the case that X is C(R$^{28}$)$_2$.

Even more most preferred compounds are—in a further embodiment—the compounds (I-IIcH), (I-IIc'H), (I'-II'cH) and (I'-II'c'H), wherein X is C(R$^{28}$)$_2$.

Further even more most preferred compounds are—in a further embodiment—the compounds (I-IIcH), (I-IIc'H), (I'-II'cH), (I-IIc'''H) and (I'-II'c'H), wherein X is NR$^{19}$.

Also even more preferred compounds are—in a further embodiment—the compounds (I''-IIcH), (I''-II''c''H), (I-IIc''H) and (I'''-II'''cH) wherein X is NR$^{19}$.

Also even more preferred compounds are—in a further embodiment—the compounds (I'-II'c'H) and (I-IIc'H) wherein X is C(R$^{28}$)$_2$.

The residues R$^9$, R$^{19}$ and R$^{28}$ have been defined before.

Most preferred are therefore the following compounds:

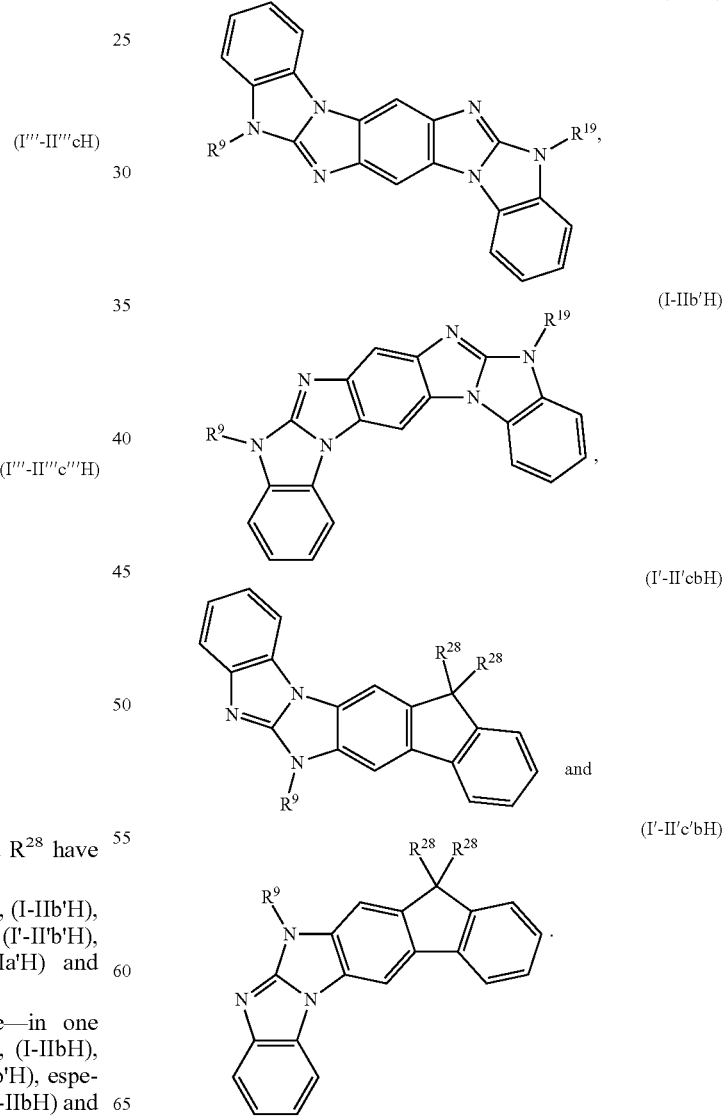

Further most preferred compounds are:
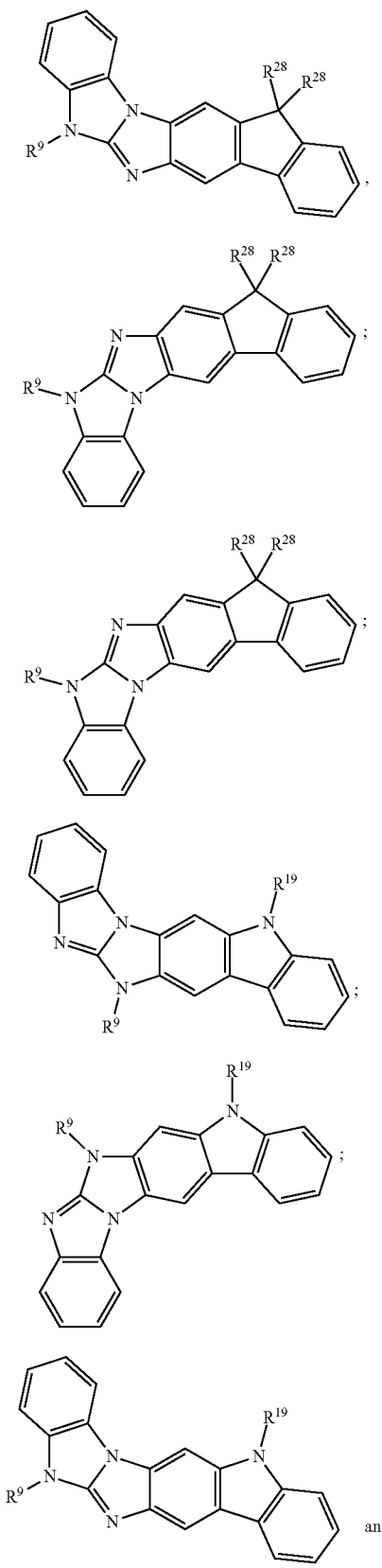
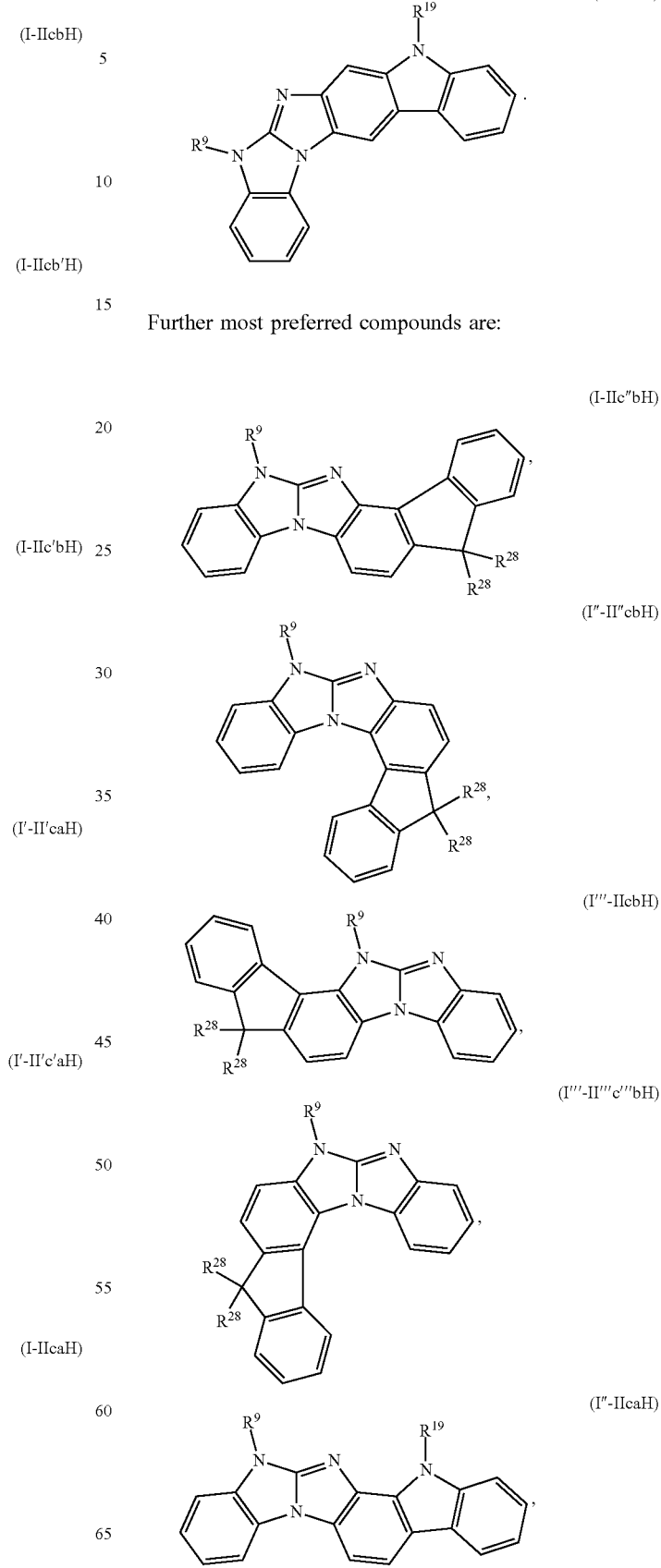

(I″-II″c″aH)

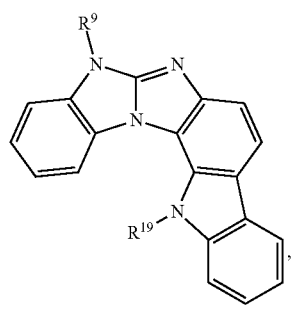

(I‴-II‴caH)

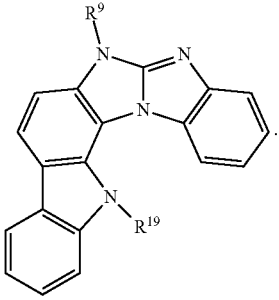

The residues R⁹, R¹⁹ and R²⁸ have been defined before.

Specific examples of the compounds represented by the formula (I) are given below. The compounds represented by the formula (I) are not limited to the following specific examples.

(I-IIc‴aH)

and (I-IIbH)

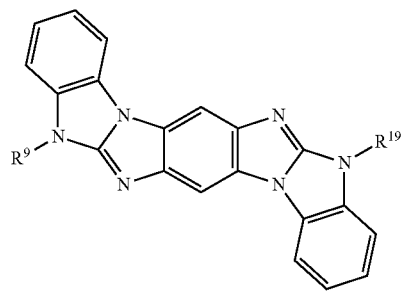

| | $R^9$ | $R^{19}$ |
|---|---|---|
| I-IIbH-1 | | |
| I-IIbH-2 | phenyl | phenyl |
| I-IIbH-3 | biphenyl | biphenyl |
| I-IIbH-4 | dibenzofuran | dibenzofuran |
| I-IIbH-5 | cyano-dibenzofuran | cyano-dibenzofuran |
| I-IIbH-6 | cyanophenyl | cyanophenyl |

-continued
| I-IIbH-1 | R⁹ | R¹⁹ |
|---|---|---|
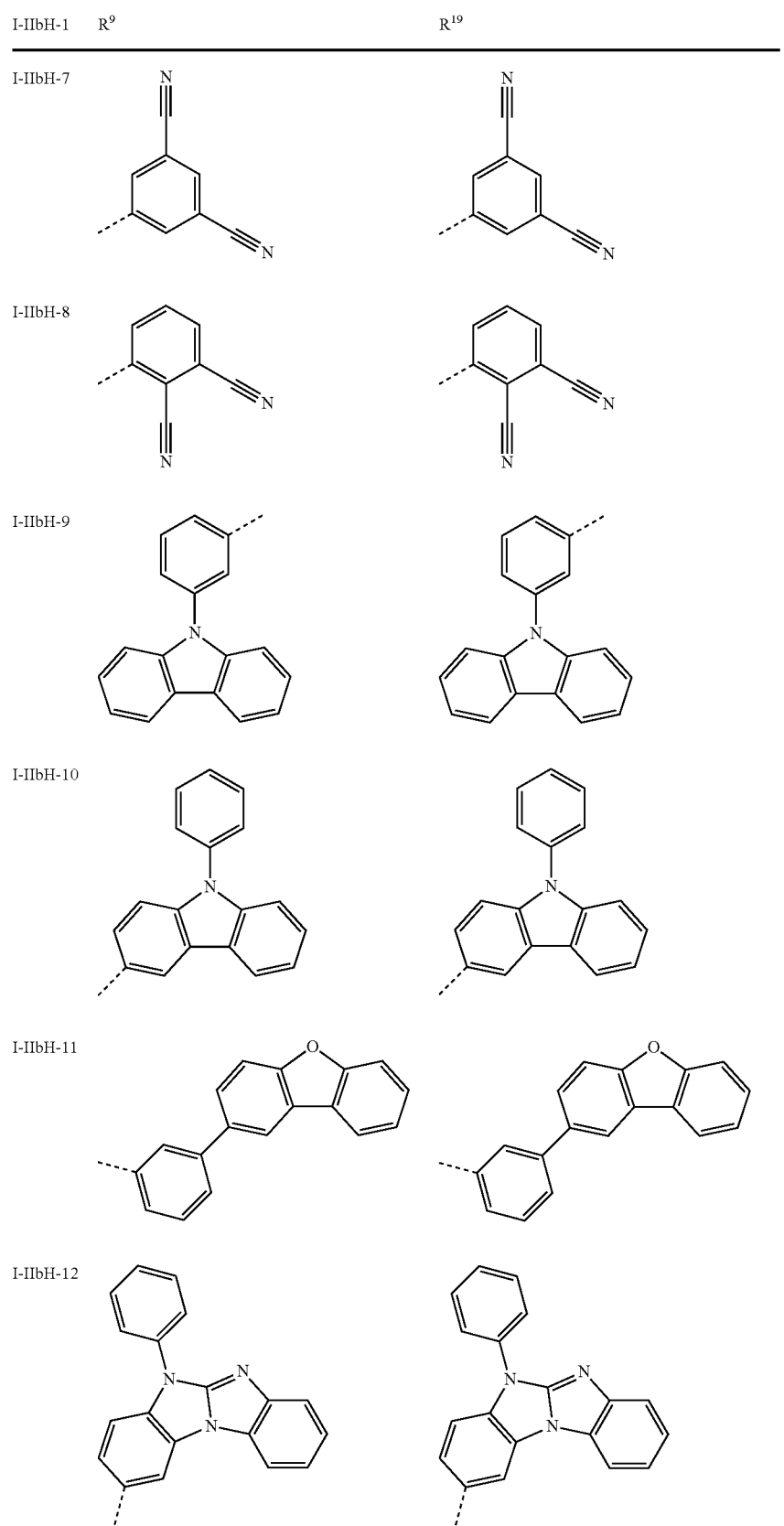

| I-IIbH-1 | $R^9$ | $R^{19}$ |
| --- | --- | --- |
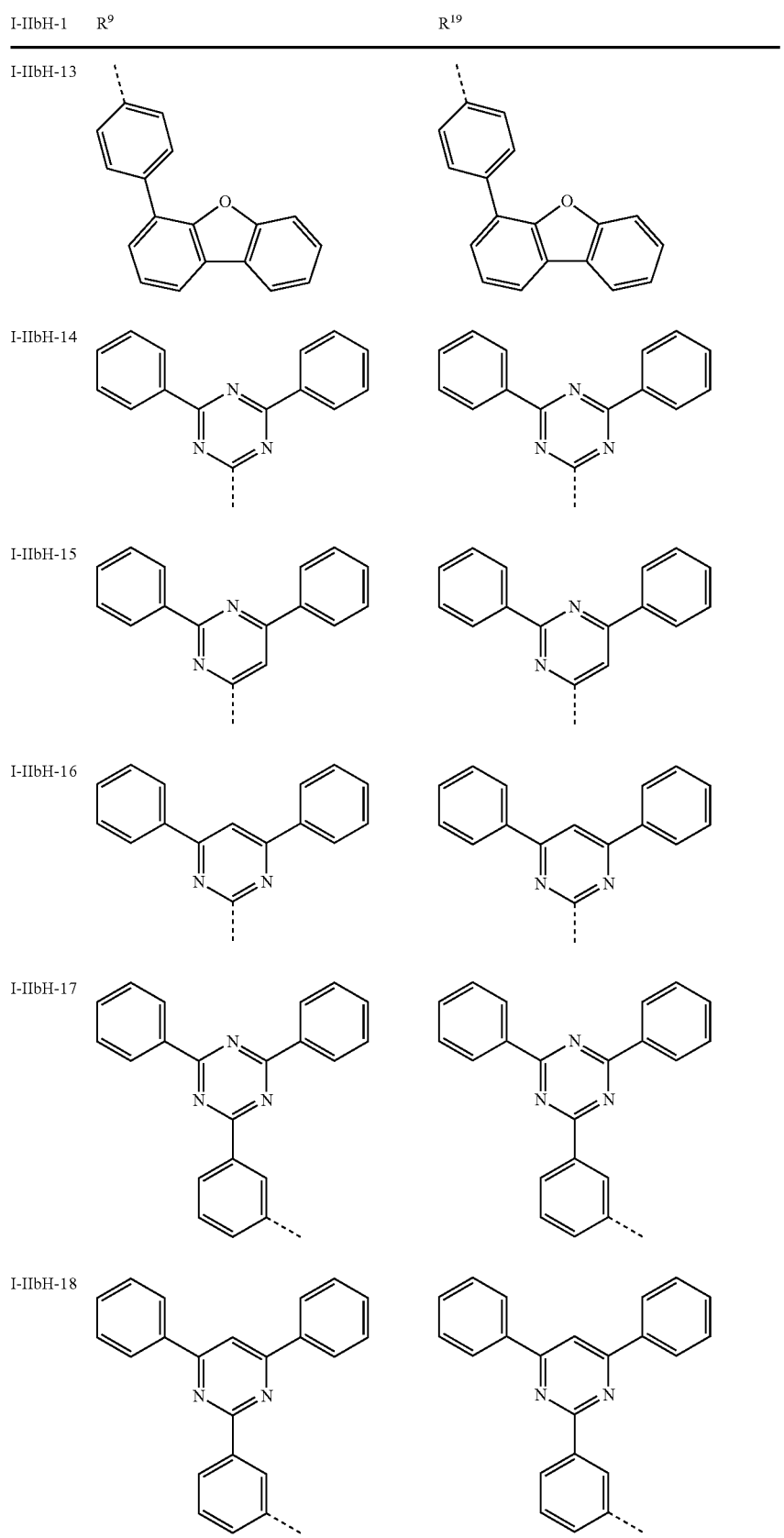

-continued
| I-IIbH-1 | $R^9$ | $R^{19}$ |
|---|---|---|
| I-IIbH-19 | 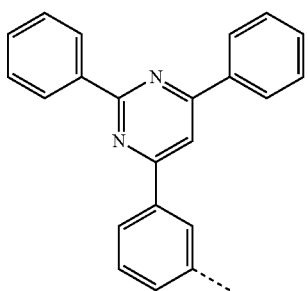 | 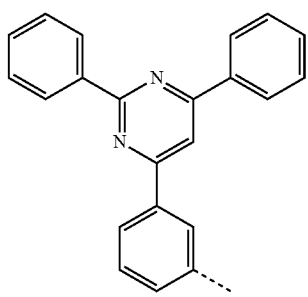 |
| I-IIbH-20 | 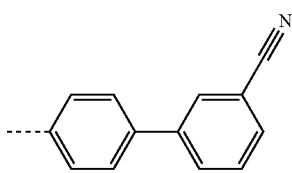 | 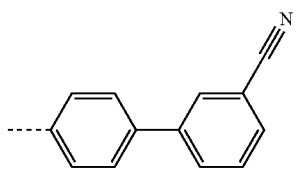 |
| I-IIbH-21 | 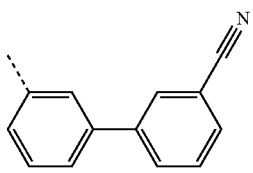 | 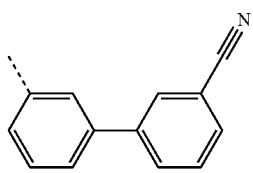 |
| I-IIbH-22 | 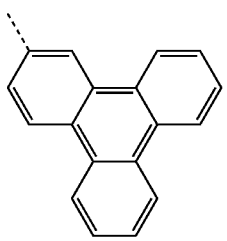 | 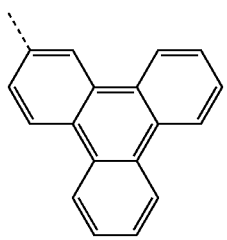 |
| I-IIbH-23 | 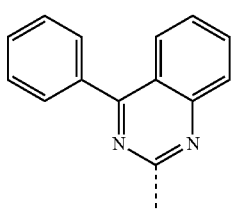 | 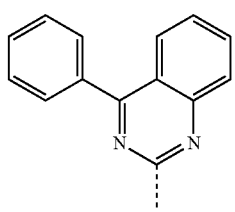 |
| I-IIbH-24 | 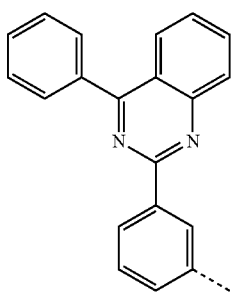 | 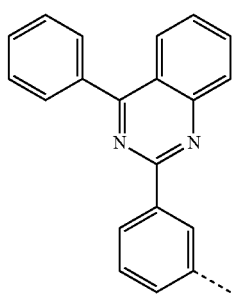 |

| I-IIbH-1 | $R^9$ | $R^{19}$ |
|---|---|---|
| I-IIbH-25 | 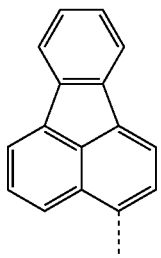 | 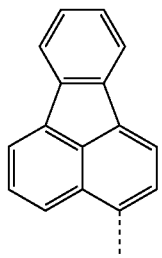 |
| I-IIbH-26 | 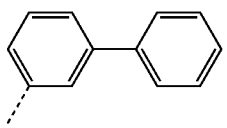 | 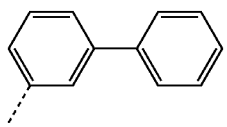 |
| I-IIbH-27 | 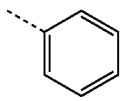 | 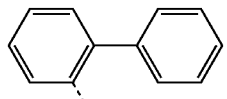 |
| I-IIbH-28 | 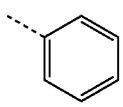 | 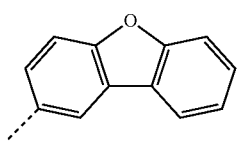 |
| I-IIbH-29 | 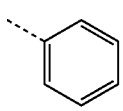 | 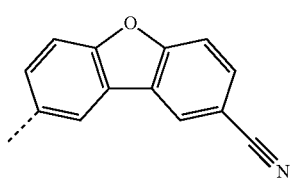 |
| I-IIbH-30 | 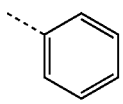 | 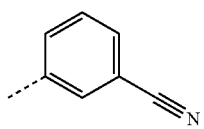 |
| I-IIbH-31 | 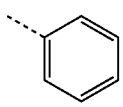 | 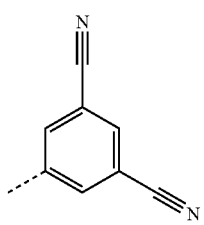 |
| I-IIbH-32 | 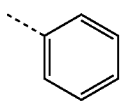 | 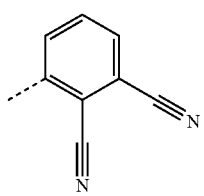 |

-continued
| I-IIbH-1 | $R^9$ | $R^{19}$ |
|---|---|---|
| I-IIbH-33 |  | 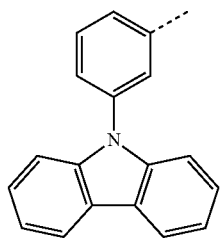 |
| I-IIbH-34 |  | 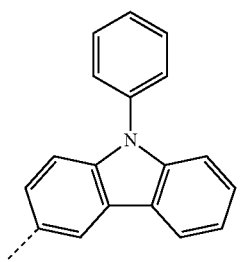 |
| I-IIbH-35 |  | 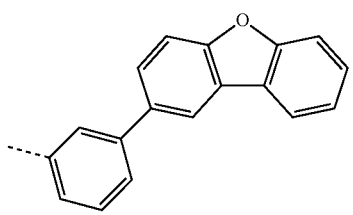 |
| I-IIbH-36 |  | 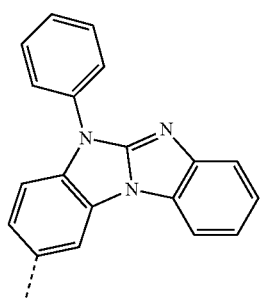 |
| I-IIbH-37 |  | 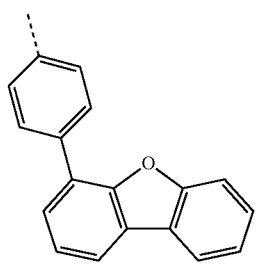 |
| I-IIbH-38 |  | 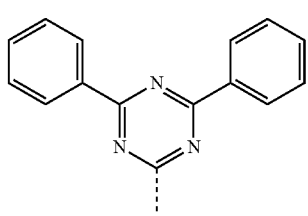 |

-continued
| I-IIbH-1 | R⁹ | R¹⁹ |
|---|---|---|
| I-IIbH-39 | 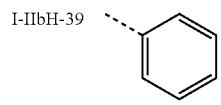 | 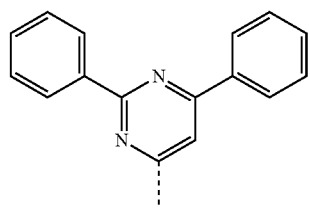 |
| I-IIbH-40 | 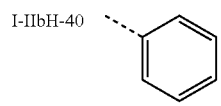 | 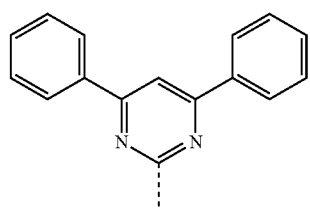 |
| I-IIbH-41 | 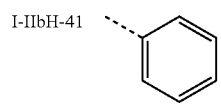 | 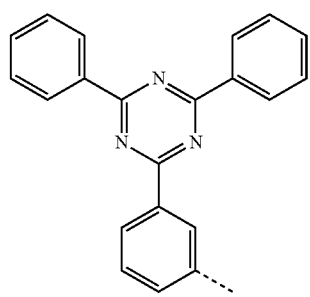 |
| I-IIbH-42 | 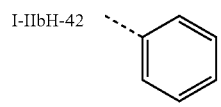 | 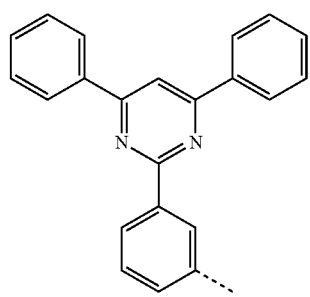 |
| I-IIbH-43 | 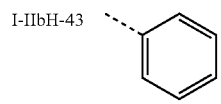 | 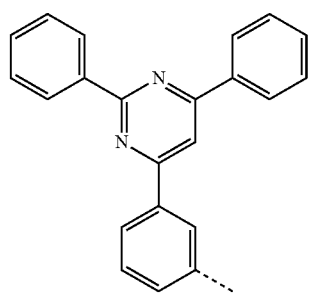 |
| I-IIbH-44 | 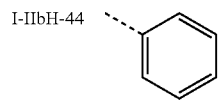 | 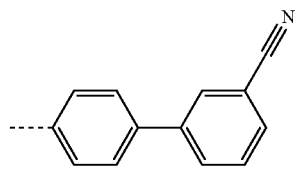 |

-continued
| I-IIbH-1 | R⁹ | R¹⁹ |
|---|---|---|
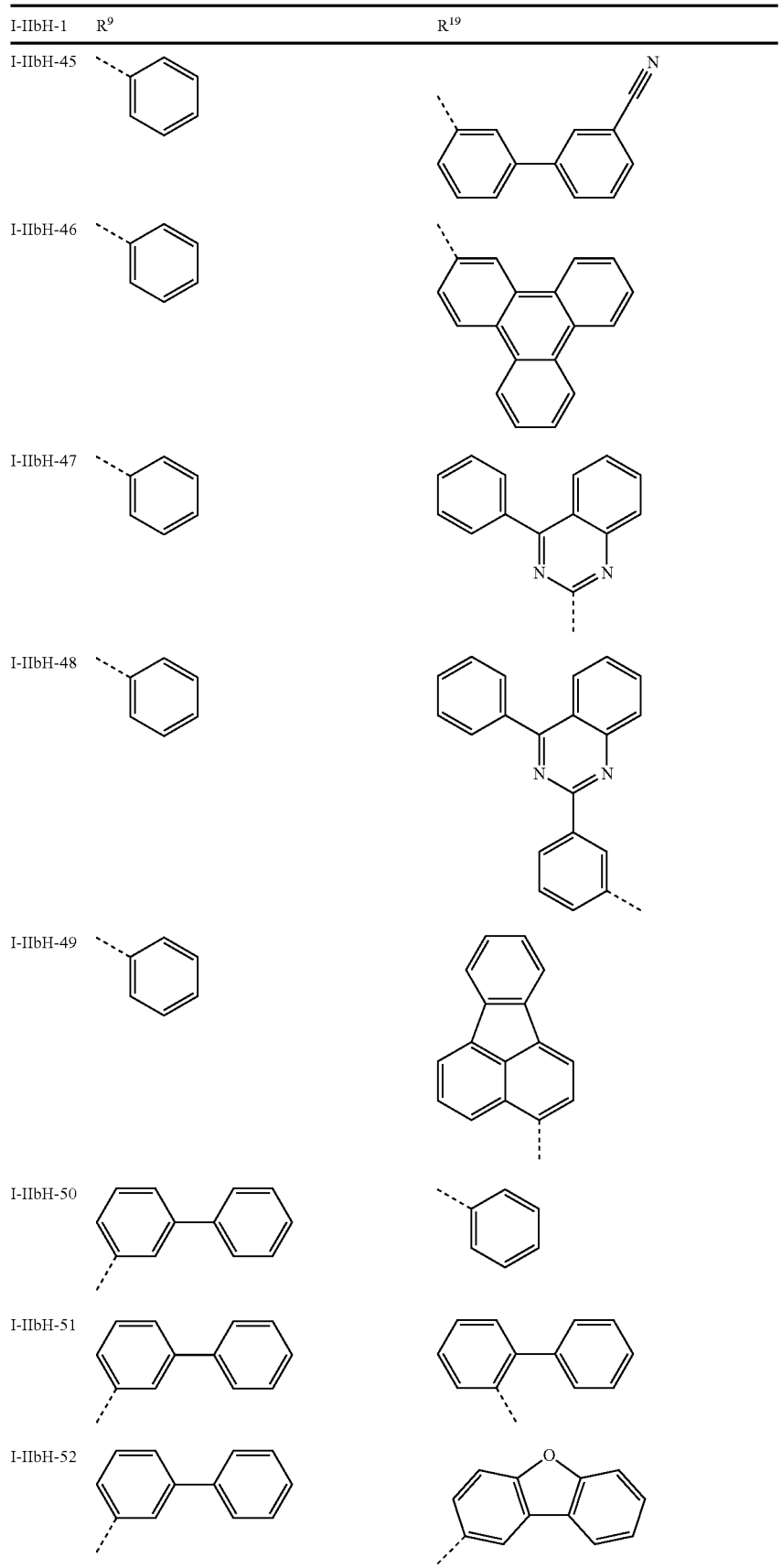

-continued
| I-IIbH-1 | R⁹ | R¹⁹ |
|---|---|---|
| I-IIbH-53 | 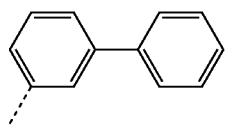 | 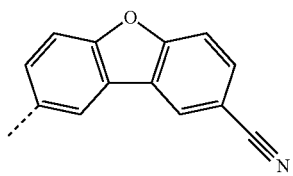 |
| I-IIbH-54 | 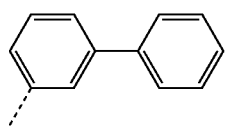 | 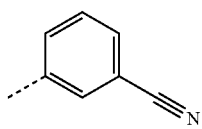 |
| I-IIbH-55 | 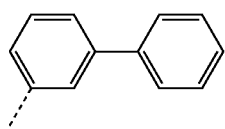 | 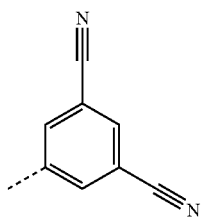 |
| I-IIbH-56 | 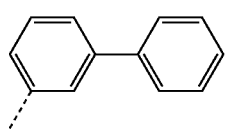 | 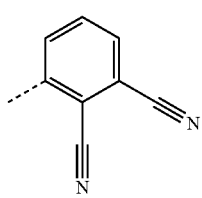 |
| I-IIbH-57 | 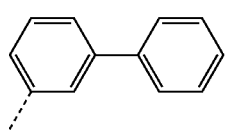 | 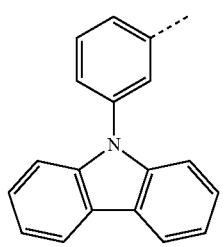 |
| I-IIbH-58 | 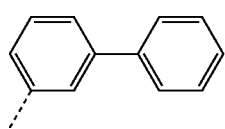 | 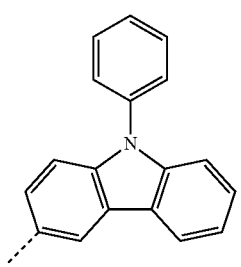 |
| I-IIbH-59 | 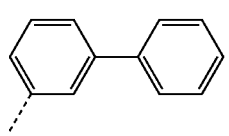 | 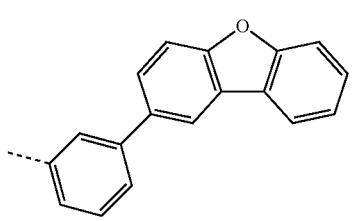 |

-continued
| I-IIbH-1 | R⁹ | R¹⁹ |
|---|---|---|
| I-IIbH-60 | 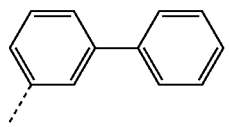 | 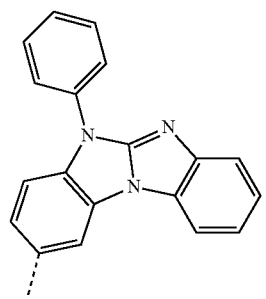 |
| I-IIbH-61 | 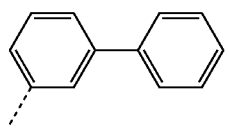 | 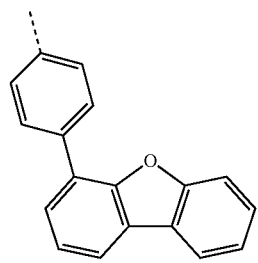 |
| I-IIbH-62 | 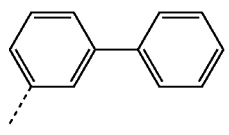 | 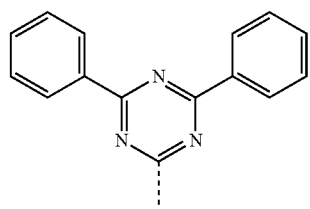 |
| I-IIbH-63 | 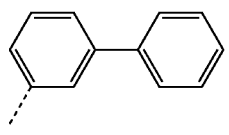 | 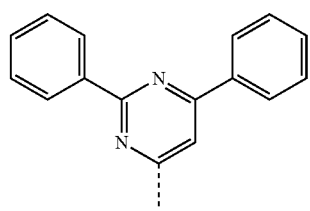 |
| I-IIbH-64 | 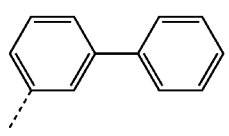 | 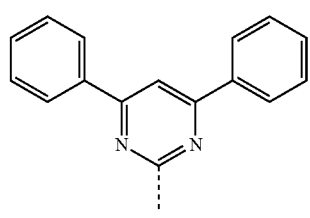 |
| I-IIbH-65 | 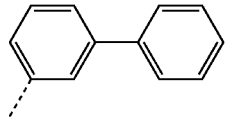 | 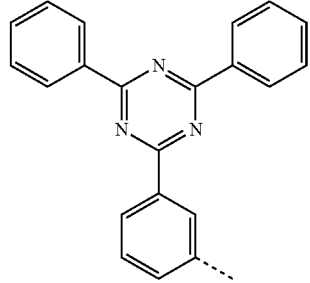 |

-continued
| I-IIbH-1 | R⁹ | R¹⁹ |
|---|---|---|
| I-IIbH-66 | 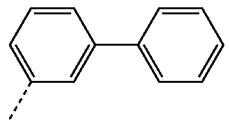 | 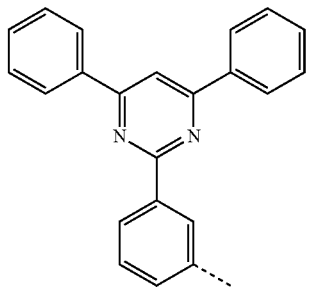 |
| I-IIbH-67 | 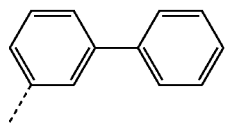 | 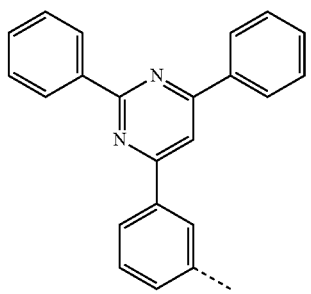 |
| I-IIbH-68 | 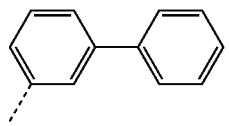 | 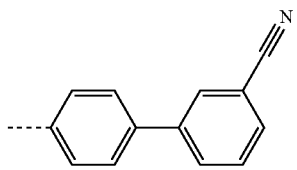 |
| I-IIbH-69 | 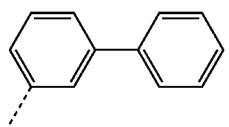 | 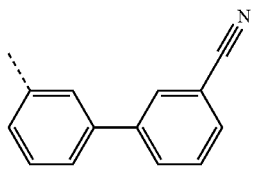 |
| I-IIbH-70 | 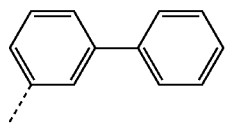 | 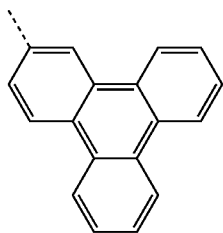 |
| I-IIbH-71 | 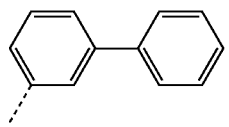 | 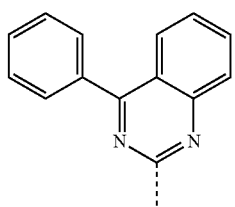 |

-continued
| I-IIbH-1 | R⁹ | R¹⁹ |
|---|---|---|
I-IIbH-72
I-IIbH-73
I-IIbH-74
I-IIbH-75
I-IIbH-76
I-IIbH-77
I-IIbH-78
I-IIbH-79
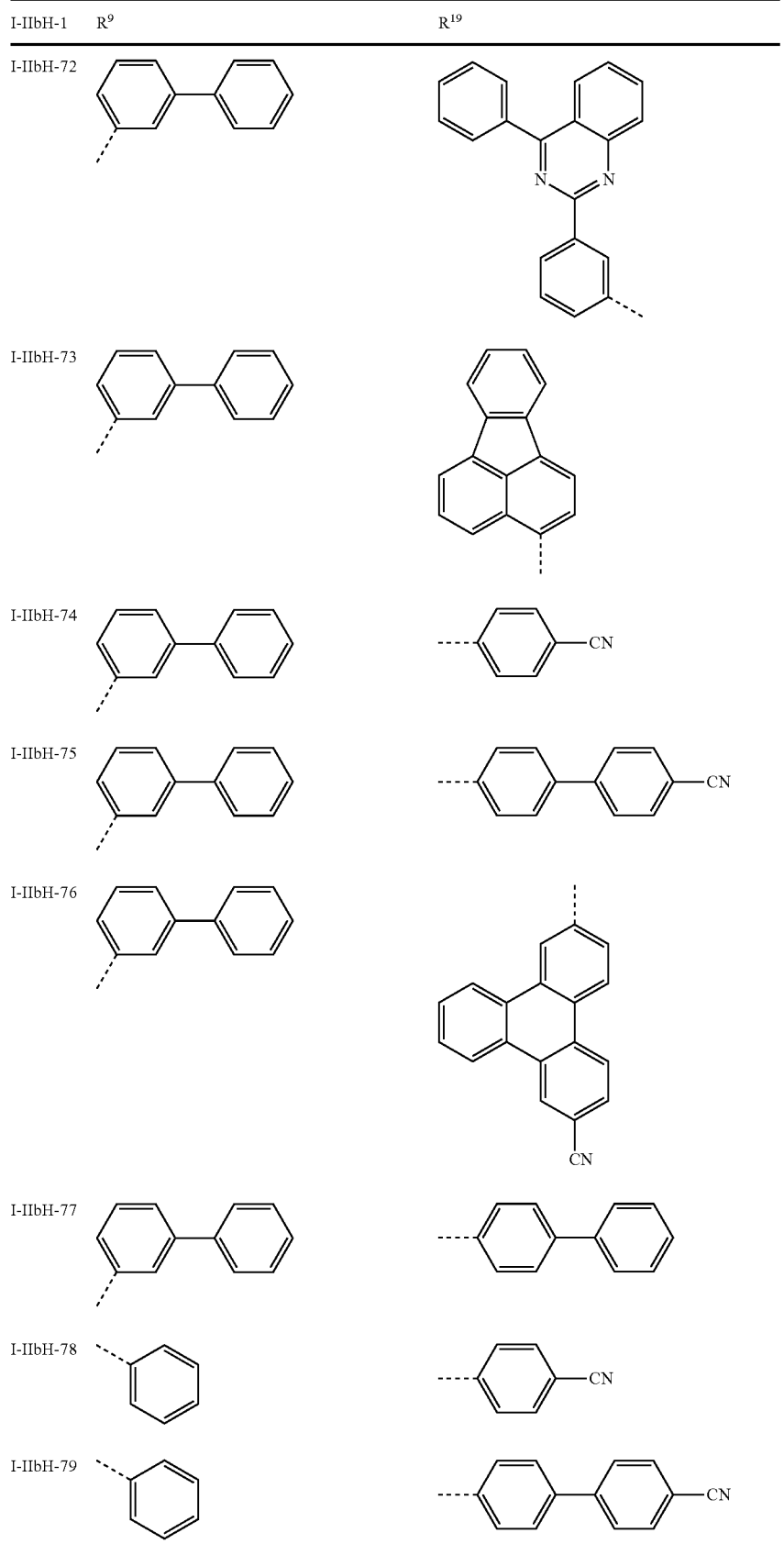

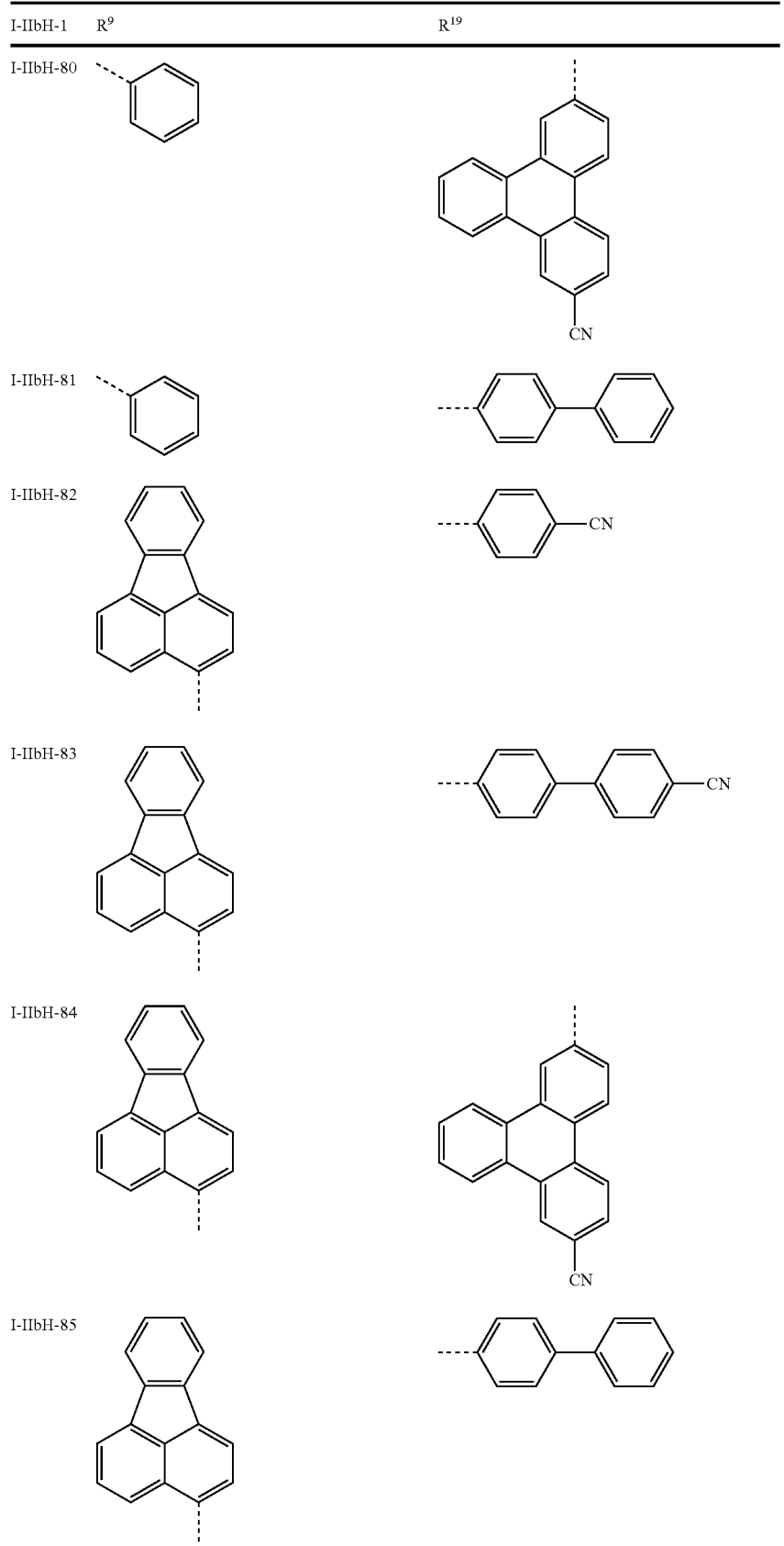

-continued
| I-IIbH-1 | R⁹ | R¹⁹ |
|---|---|---|
| I-IIbH-86 | 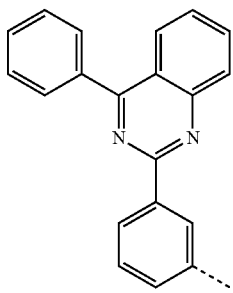 | 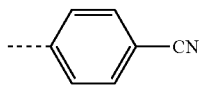 |
| I-IIbH-87 | 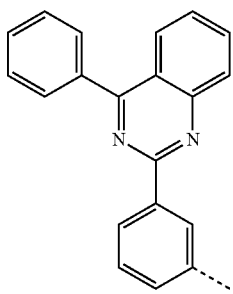 | 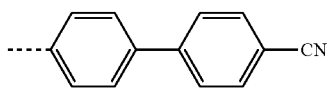 |
| I-IIbH-88 | 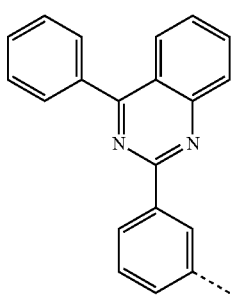 | 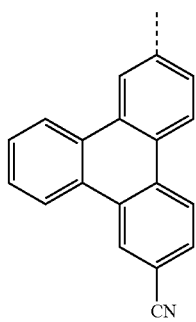 |
| I-IIbH-89 | 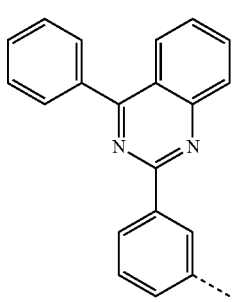 | 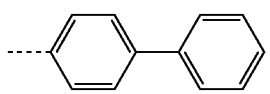 |
| I-IIbH-90 | 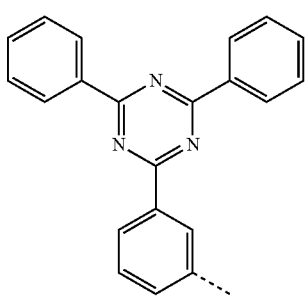 | 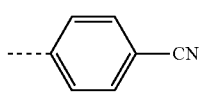 |

| I-IIbH-1 | R⁹ | R¹⁹ |
|---|---|---|
| I-IIbH-91 | | |
| I-IIbH-92 | | |
| I-IIbH-93 | | |
| I-IIbH-94 | | |
| I-IIbH-95 | | |
| I-IIbH-96 | | |
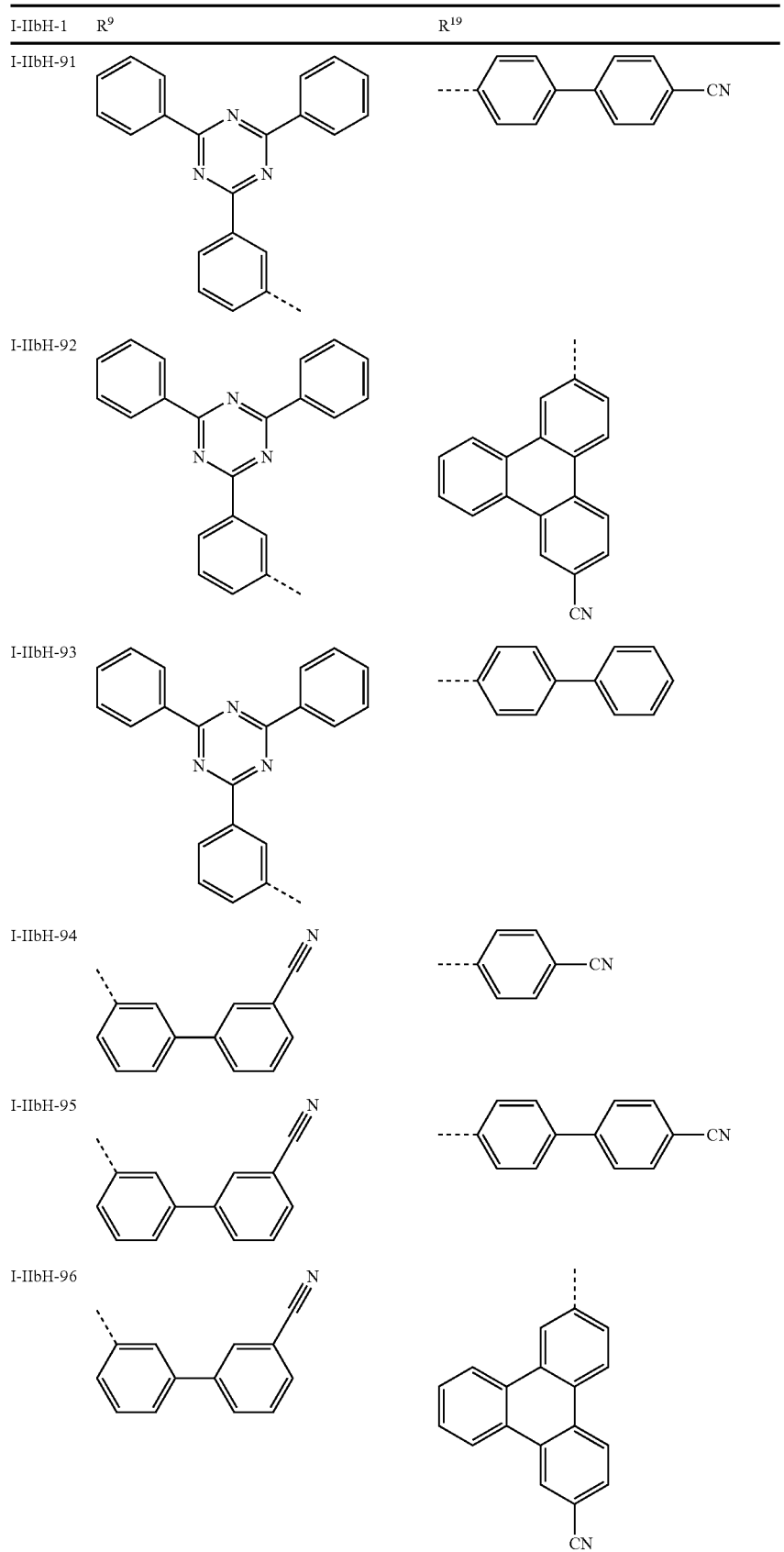

-continued
| I-IIbH-1 | R⁹ | R¹⁹ |
|---|---|---|
| I-IIbH-97 | 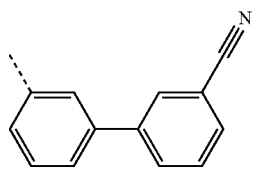 | 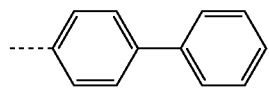 |
| I-IIbH-98 | 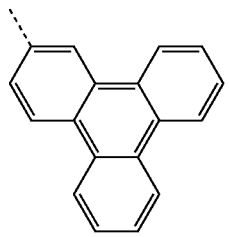 | 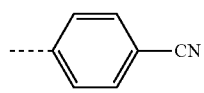 |
| I-IIbH-99 | 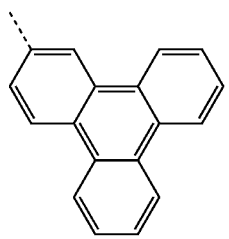 | 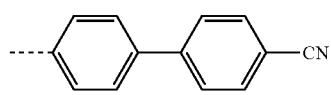 |
| I-IIbH-100 | 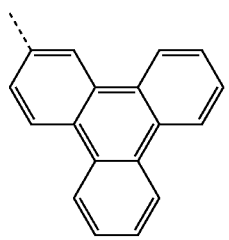 | 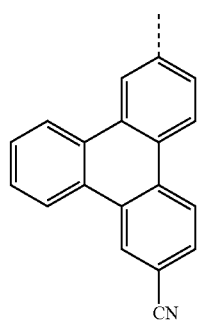 |
| I-IIbH-101 | 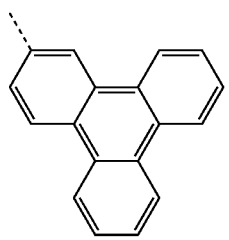 | 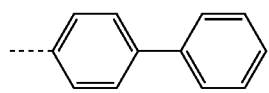 |
| I-IIbH-102 | 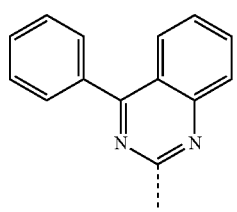 | 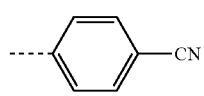 |

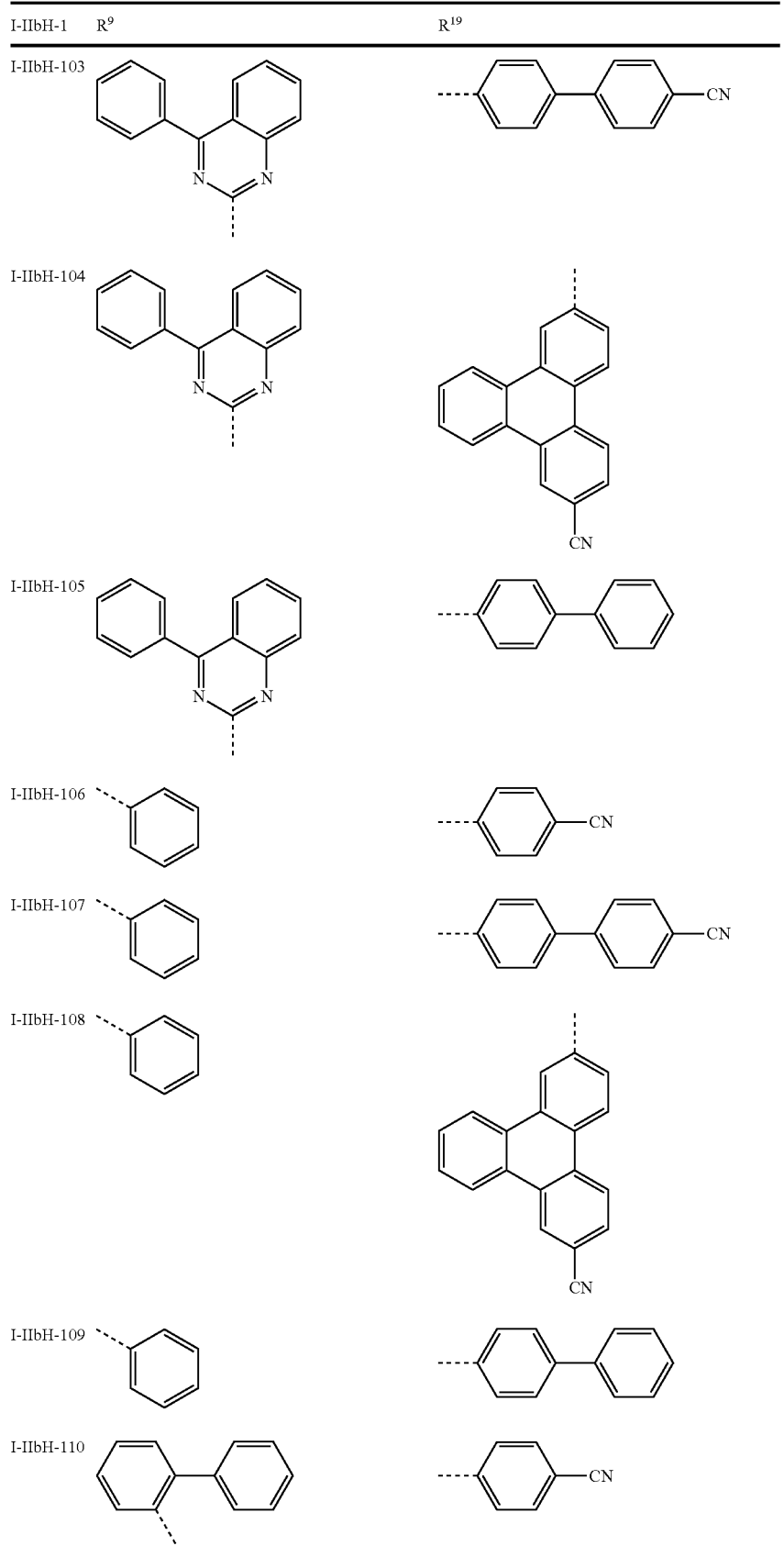

| I-IIbH-1 | $R^9$ | $R^{19}$ |
|---|---|---|
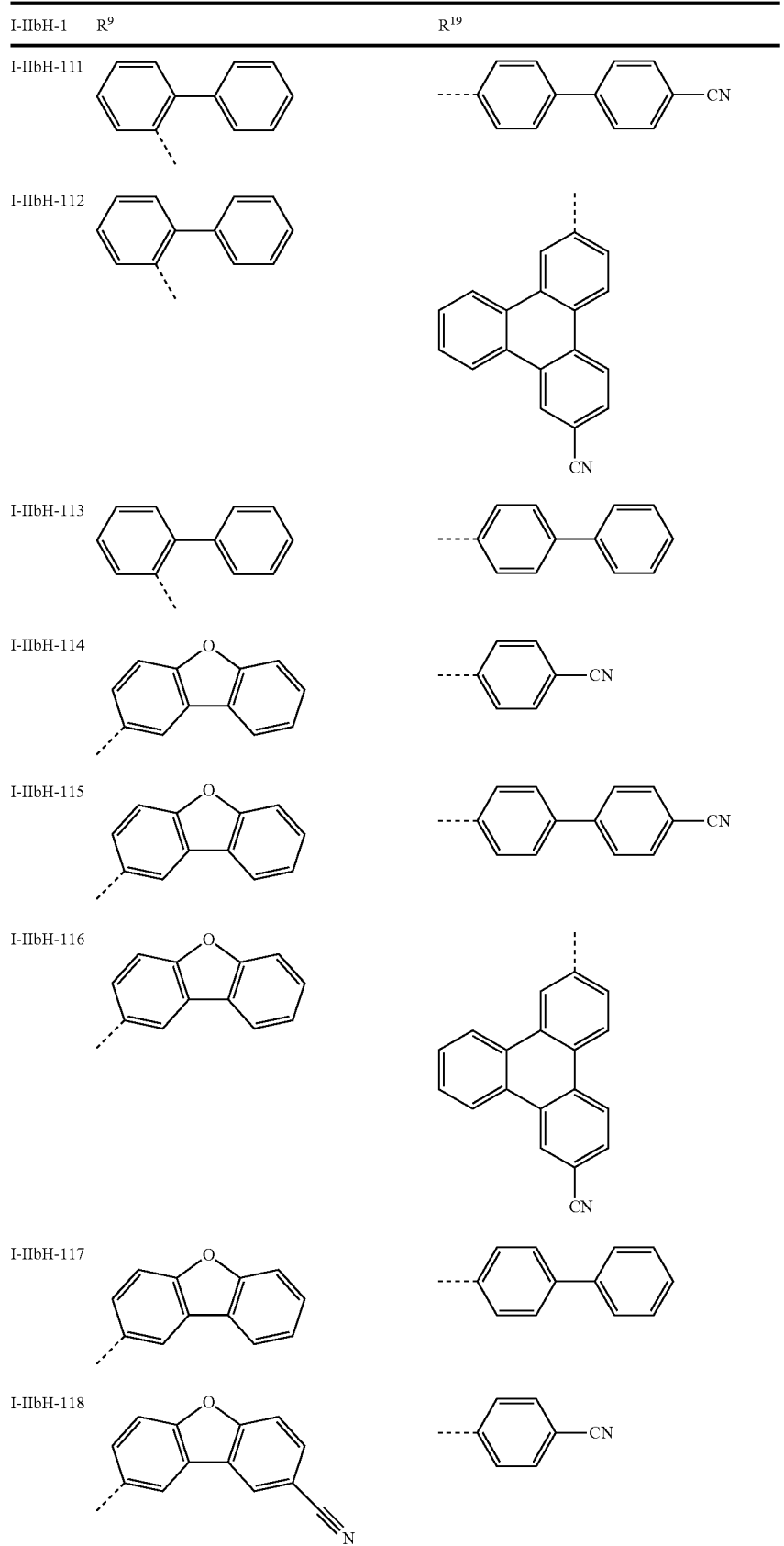

-continued
| I-IIbH-1 | R⁹ | R¹⁹ |
|---|---|---|
| I-IIbH-119 | 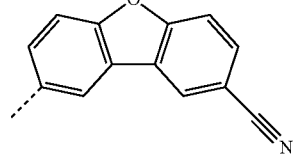 | 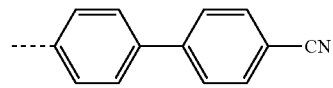 |
| I-IIbH-120 | 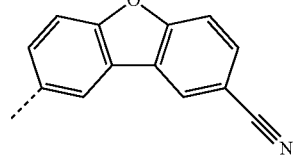 | 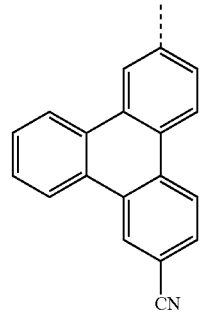 |
| I-IIbH-121 | 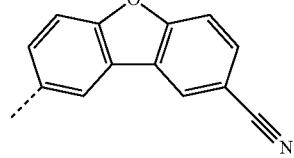 | 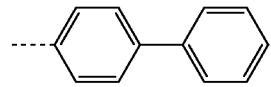 |
| I-IIbH-122 | 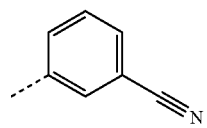 |  |
| I-IIbH-123 | 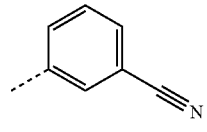 | 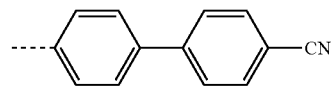 |
| I-IIbH-124 | 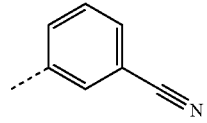 | 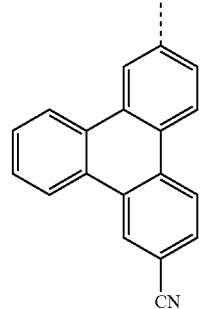 |
| I-IIbH-125 | 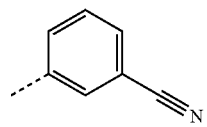 | 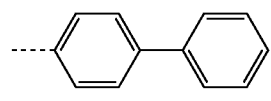 |

-continued
| I-IIbH-1 | R⁹ | R¹⁹ |
|---|---|---|
I-IIbH-126
I-IIbH-127
I-IIbH-128
I-IIbH-129
I-IIbH-130
I-IIbH-131
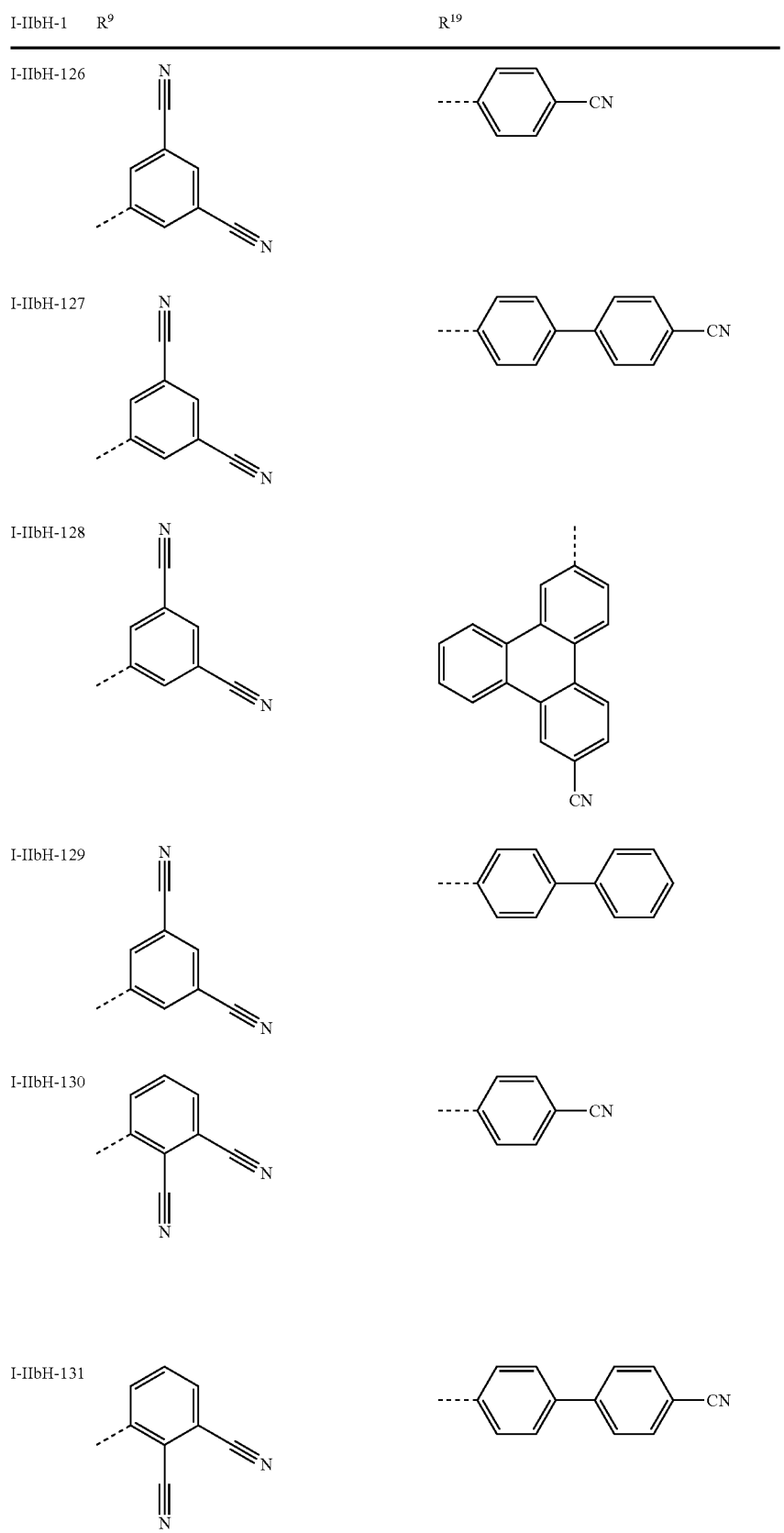

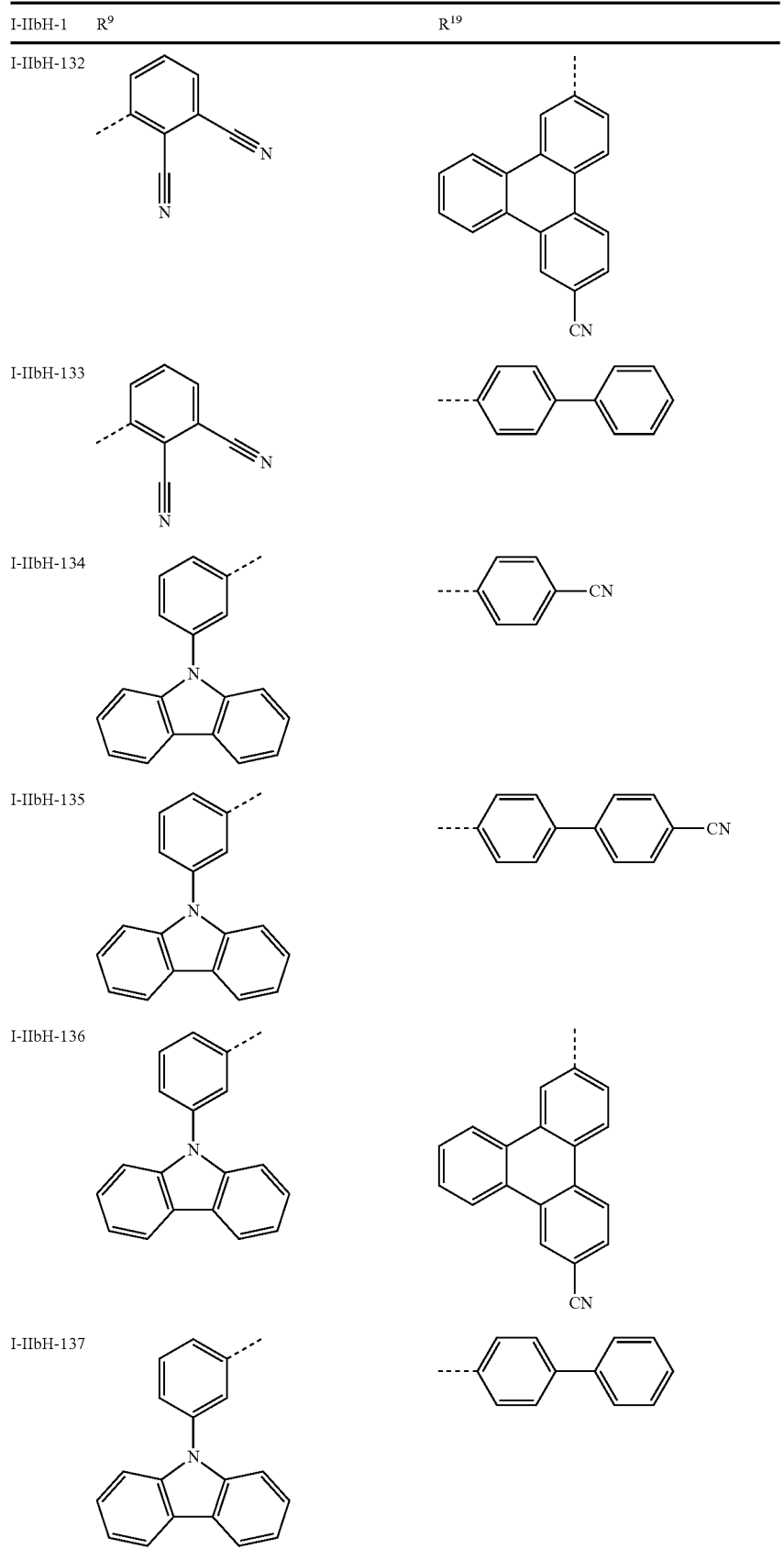

| I-IIbH-1 | R⁹ | R¹⁹ |
|---|---|---|
| I-IIbH-138 | | |
| I-IIbH-139 | | |
| I-IIbH-140 | | |
| I-IIbH-141 | | |
| I-IIbH-142 | | |
| I-IIbH-143 | | |
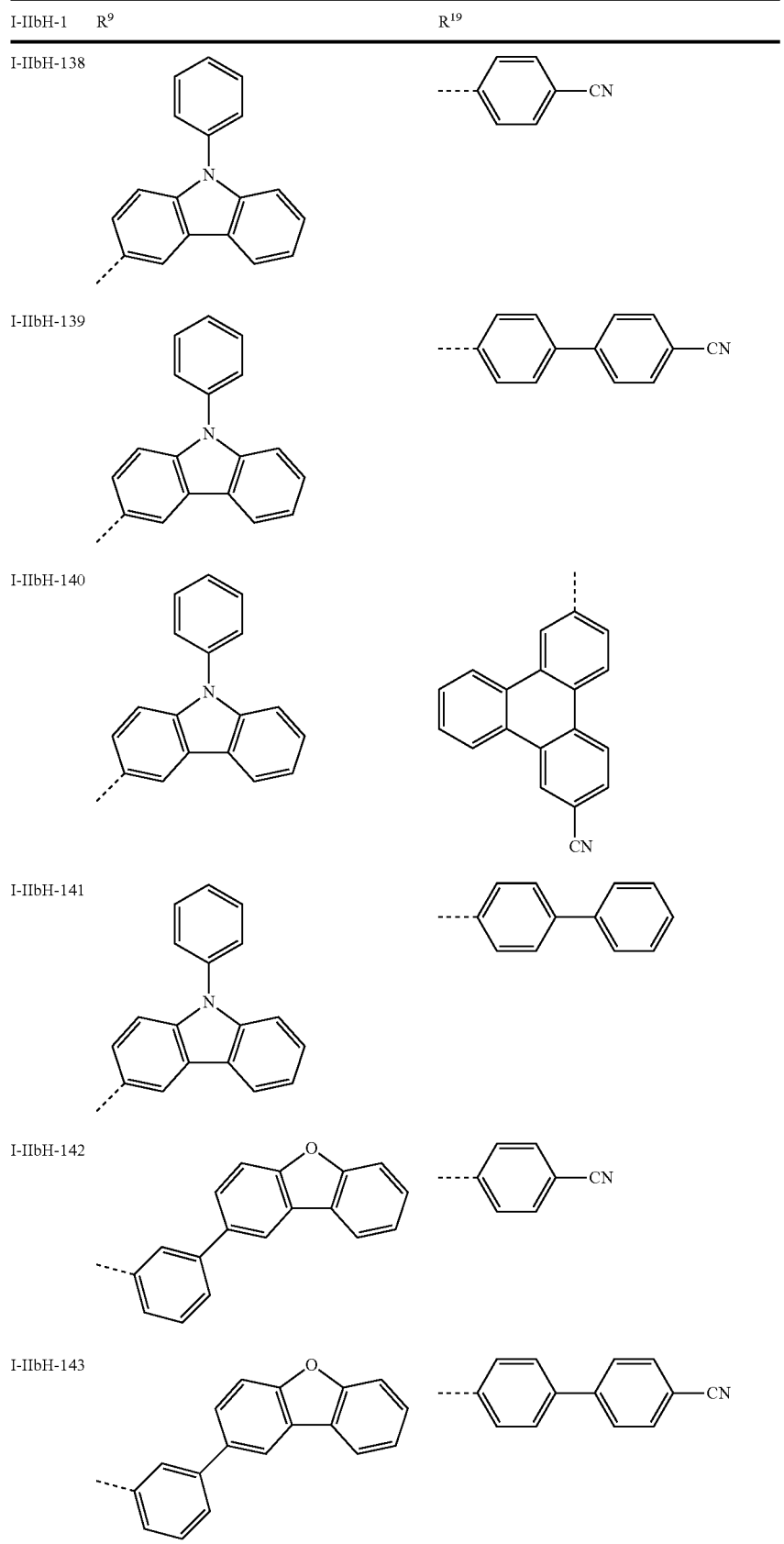

-continued
| I-IIbH-1 | R⁹ | R¹⁹ |
|---|---|---|
| I-IIbH-144 | 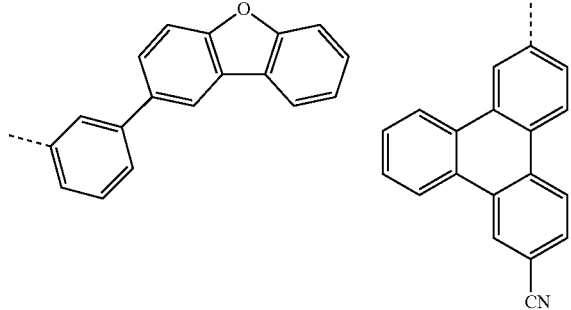 | |
| I-IIbH-145 | 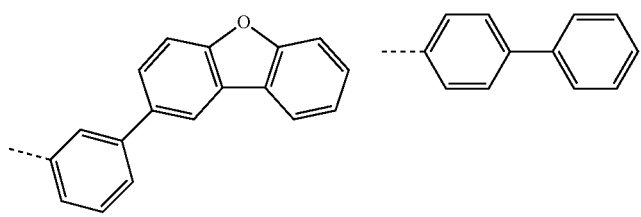 | |
| I-IIbH-146 | 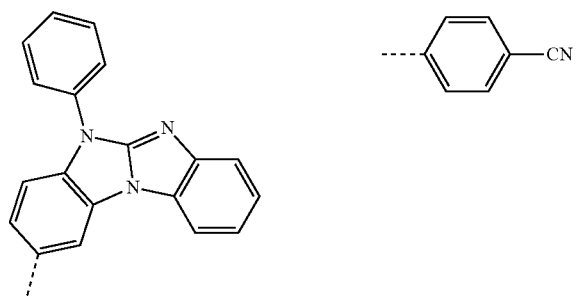 | |
| I-IIbH-147 | 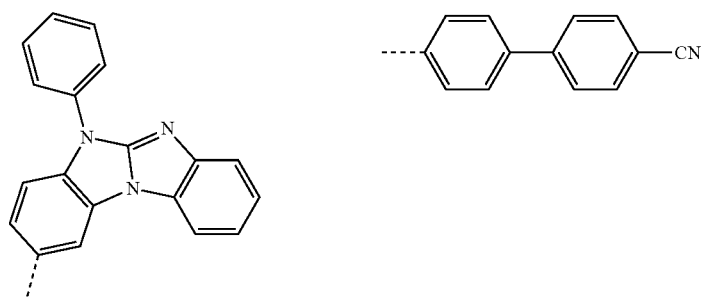 | |
| I-IIbH-148 | 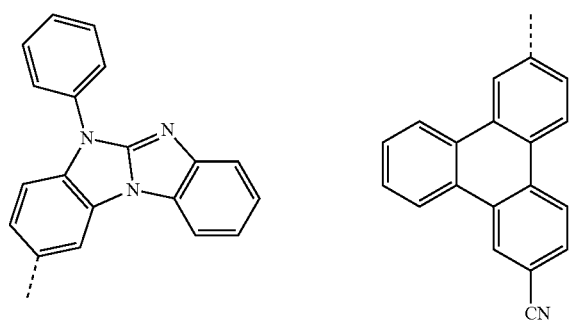 | |

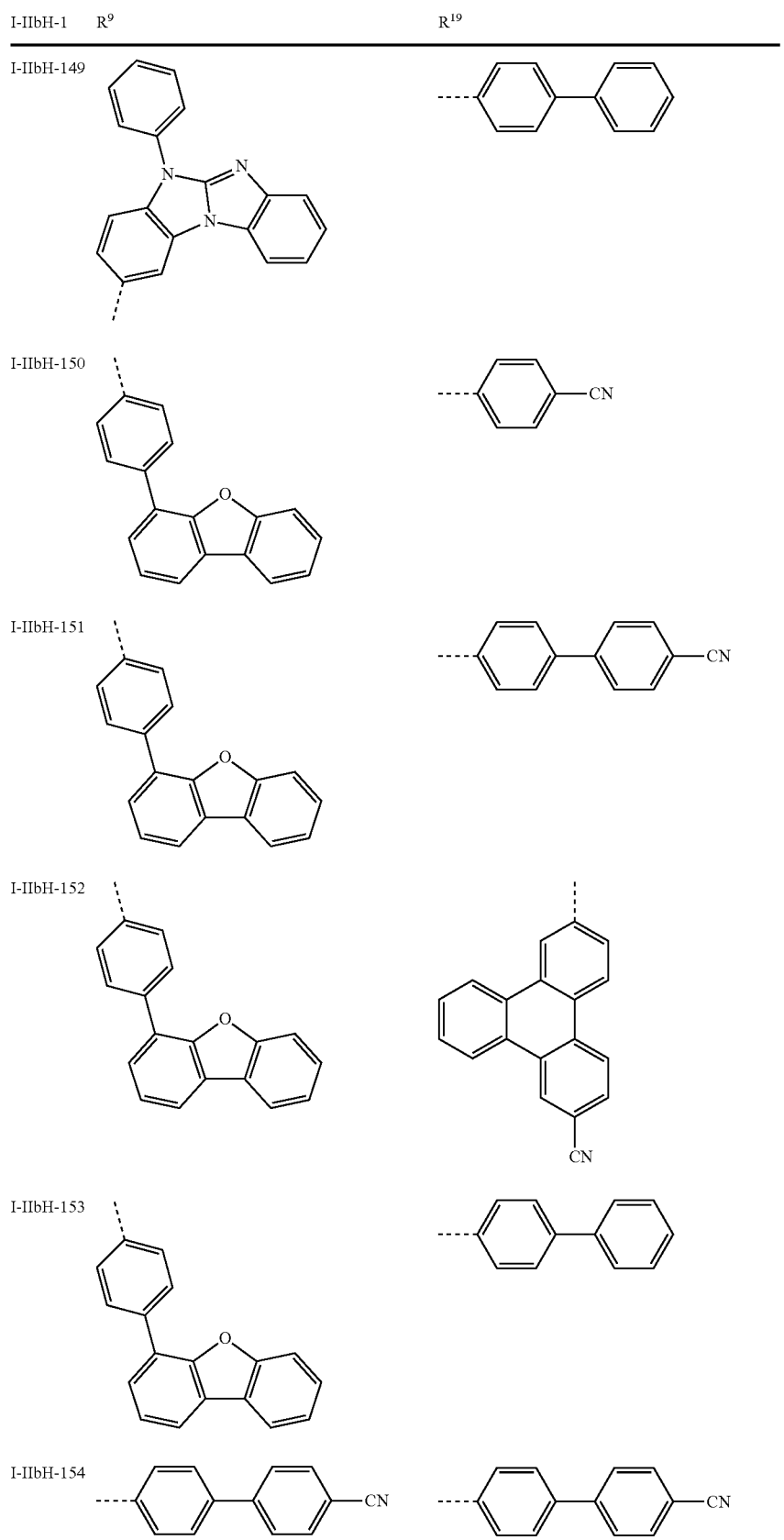

-continued
| I-IIbH-1 | R⁹ | R¹⁹ |
|---|---|---|
| I-IIbH-155 | | |
| I-IIbH-156 | | |
| I-IIbH-157 | | |
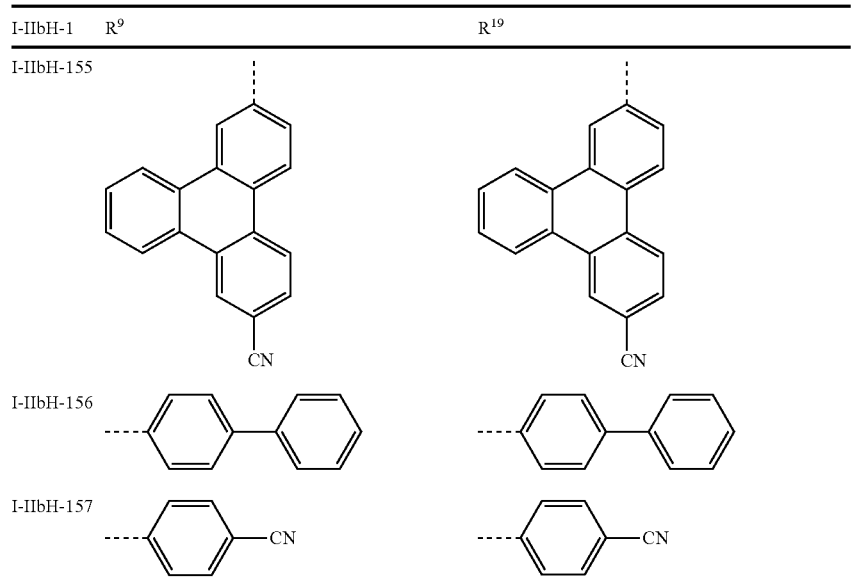
The dotted lines are bonding sites.
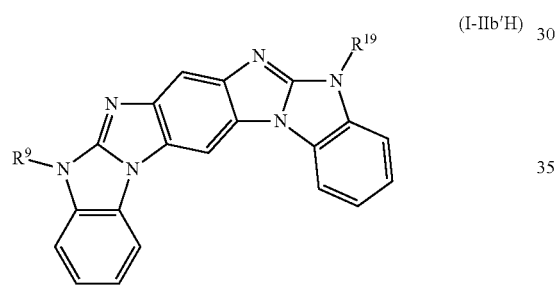
(I-IIb′H)
| I-IIb′H-1 | R⁹ | R¹⁹ |
|---|---|---|
| I-IIb′H-2 | | |
| I-IIb′H-3 | | |
| I-IIb′H-4 | | |
| I-IIb′H-5 | | |
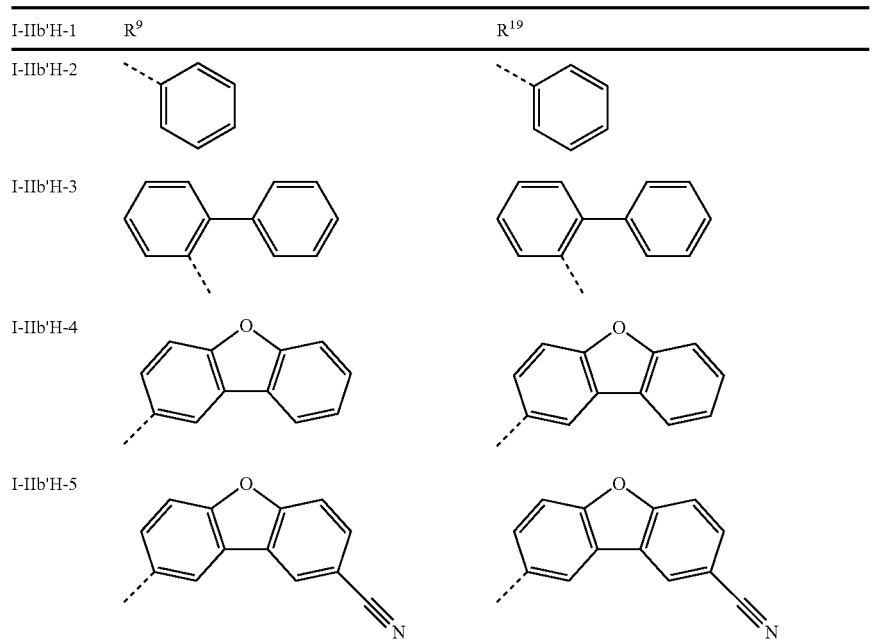

-continued
| I-IIb'H-1 | R⁹ | R¹⁹ |
|---|---|---|
| I-IIb'H-6 | 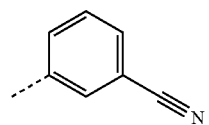 | 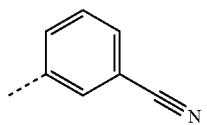 |
| I-IIb'H-7 | 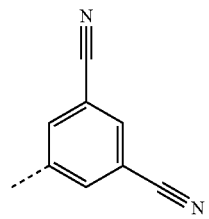 | 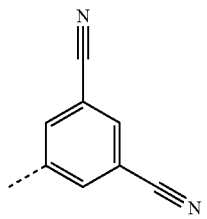 |
| I-IIb'H-8 | 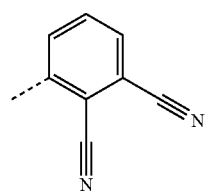 | 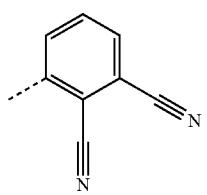 |
| I-IIb'H-9 | 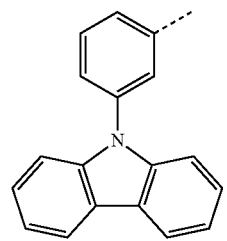 | 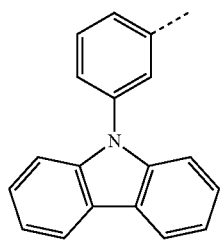 |
| I-IIb'H-10 | 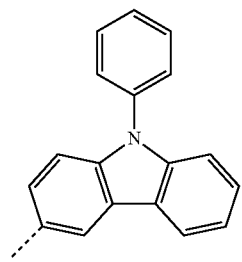 | 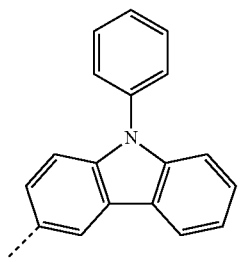 |
| I-IIb'H-11 | 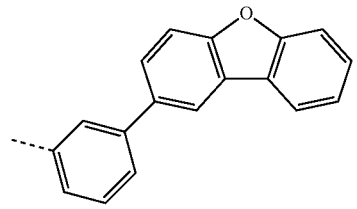 | 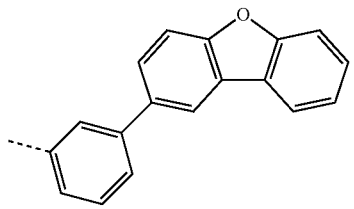 |
| I-IIb'H-12 | 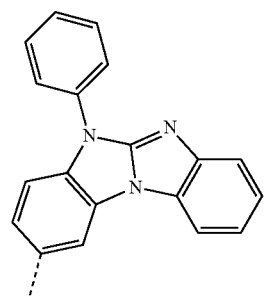 | 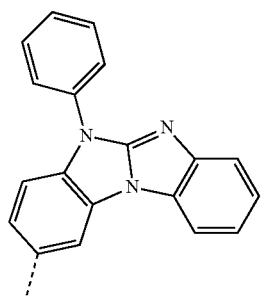 |

-continued
| I-IIb'H-1 | R⁹ | R¹⁹ |
|---|---|---|
| I-IIb'H-13 | 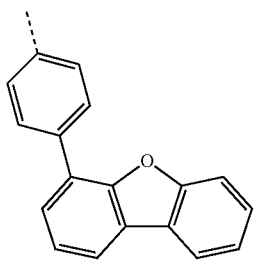 | 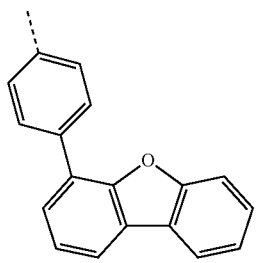 |
| I-IIb'H-14 | 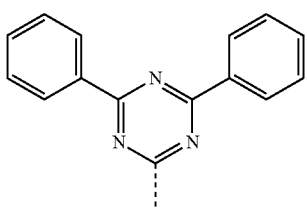 | 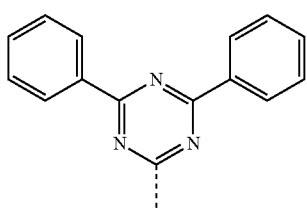 |
| I-IIb'H-15 | 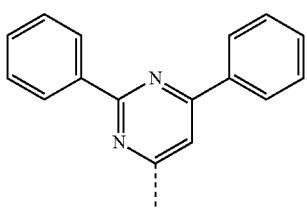 | 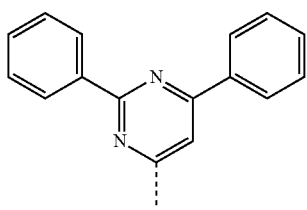 |
| I-IIb'H-16 | 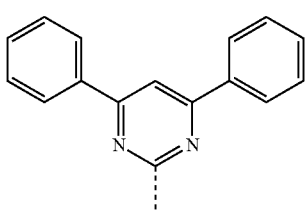 | 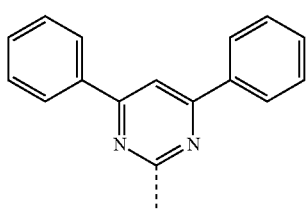 |
| I-IIb'H-17 | 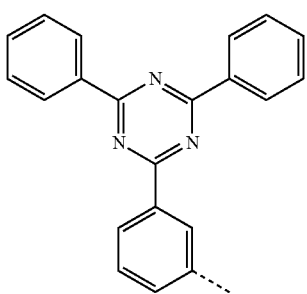 | 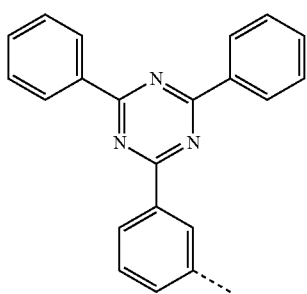 |
| I-IIb'H-18 | 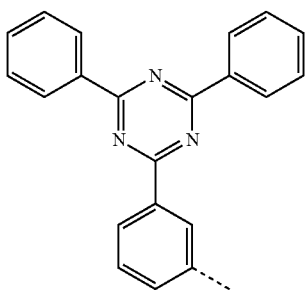 | 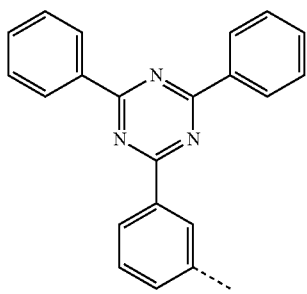 |

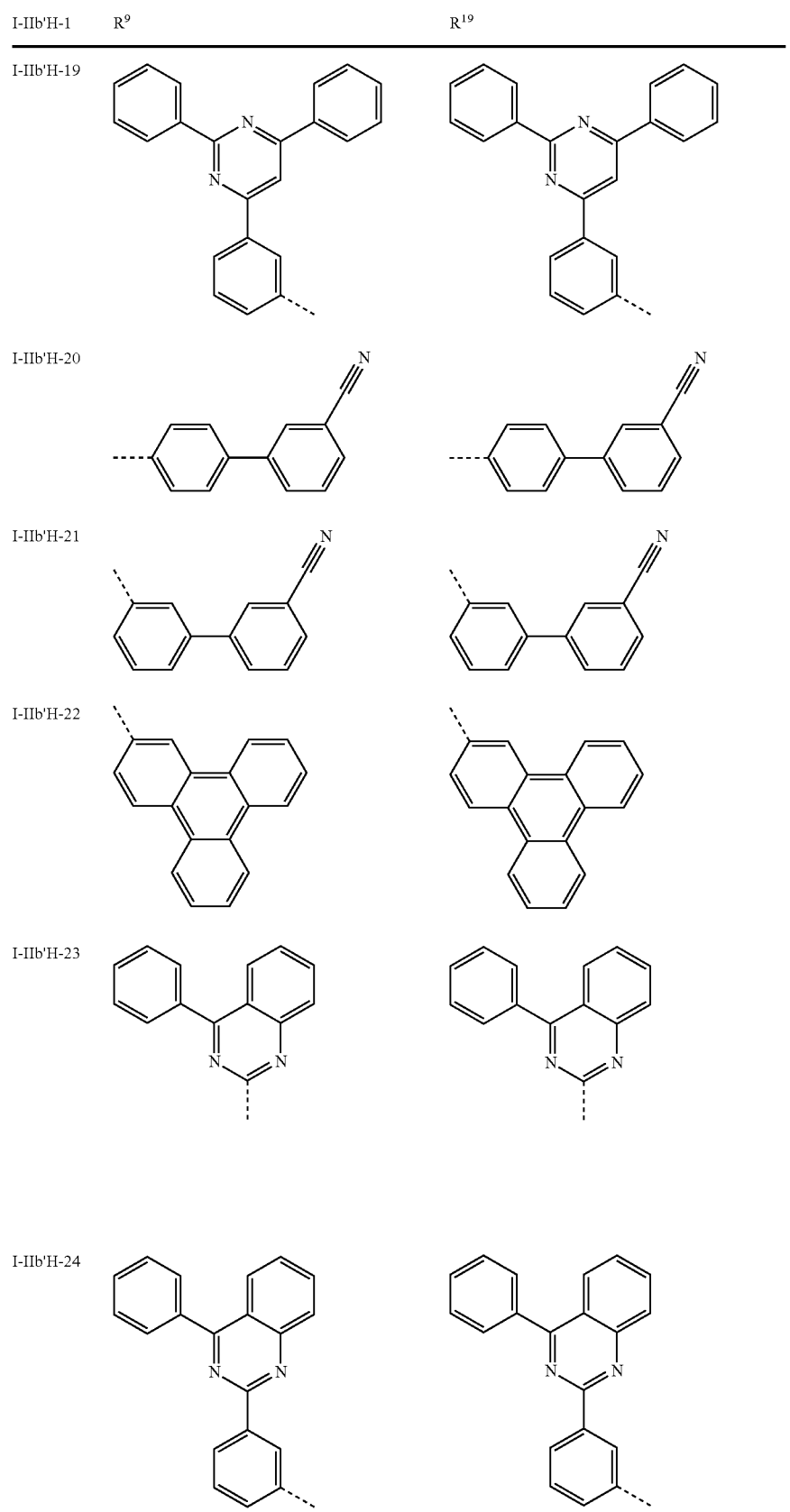

-continued
| I-IIb'H-1 | R⁹ | R¹⁹ |
|---|---|---|
| I-IIb'H-25 | 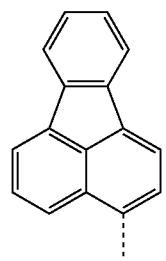 | 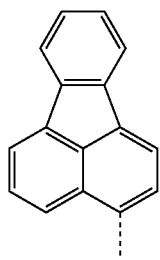 |
| I-IIb'H-26 | 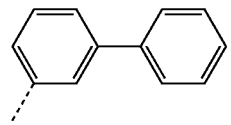 | 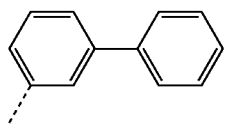 |
| I-IIb'H-27 | 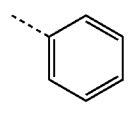 | 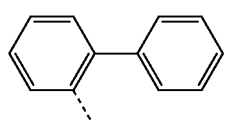 |
| I-IIb'H-28 | 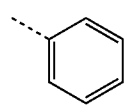 | 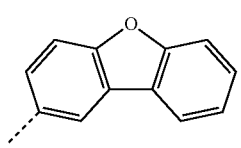 |
| I-IIb'H-29 | 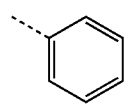 | 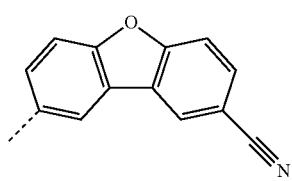 |
| I-IIb'H-30 | 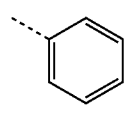 | 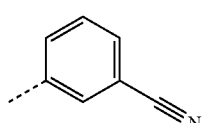 |
| I-IIb'H-31 | 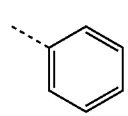 | 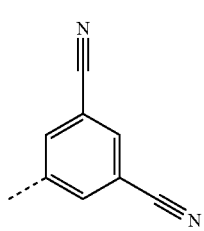 |
| I-IIb'H-32 | 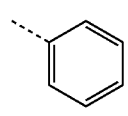 | 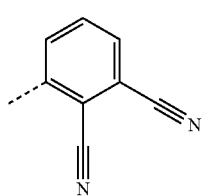 |

-continued
| I-IIb'H-1 | R⁹ | R¹⁹ |
|---|---|---|
| I-IIb'H-33 | | |
| I-IIb'H-34 | | |
| I-IIb'H-35 | | |
| I-IIb'H-36 | | |
| I-IIb'H-37 | | |
| I-IIb'H-38 | | |
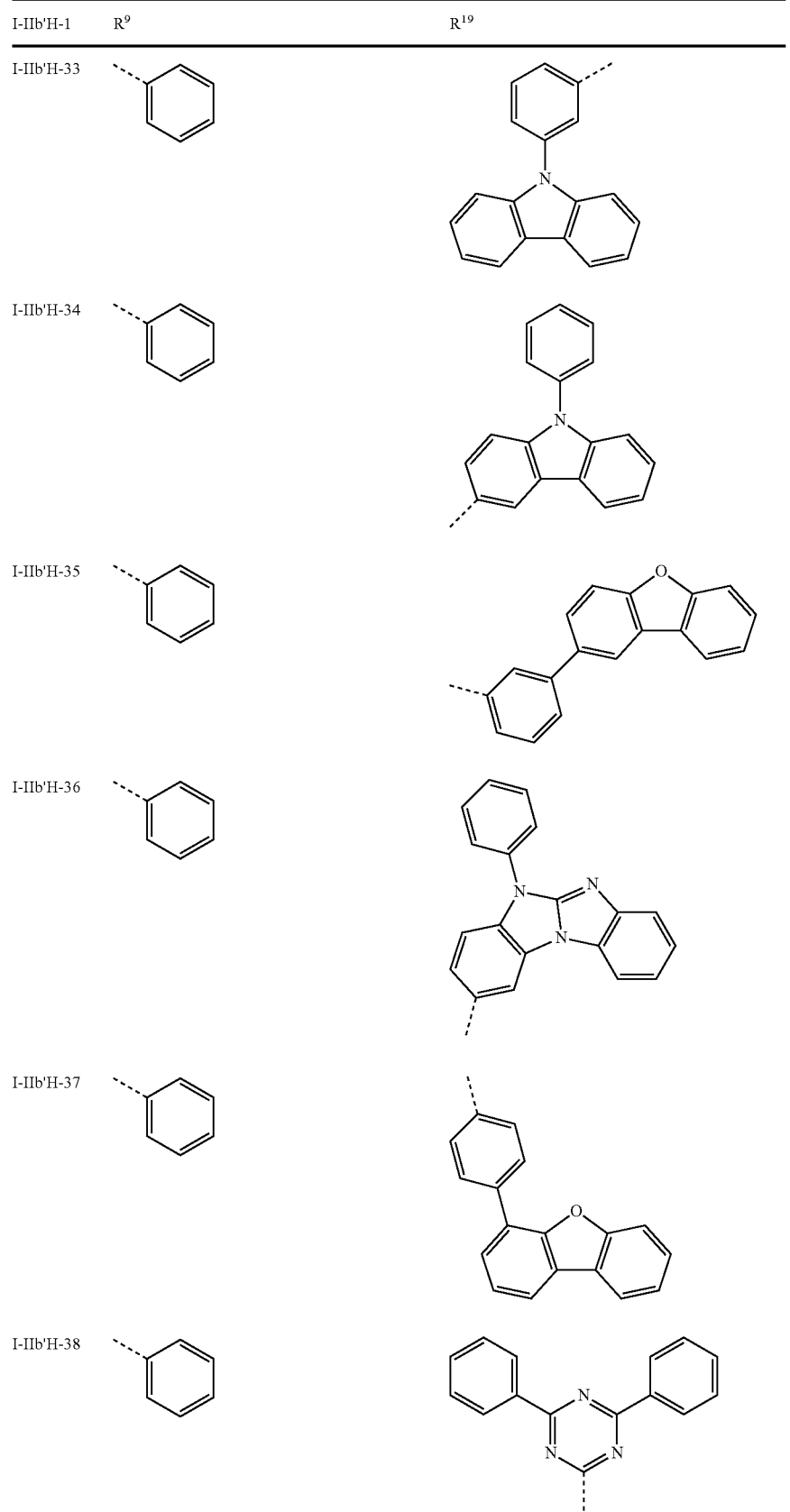

-continued
| I-IIb'H-1 | R⁹ | R¹⁹ |
|---|---|---|
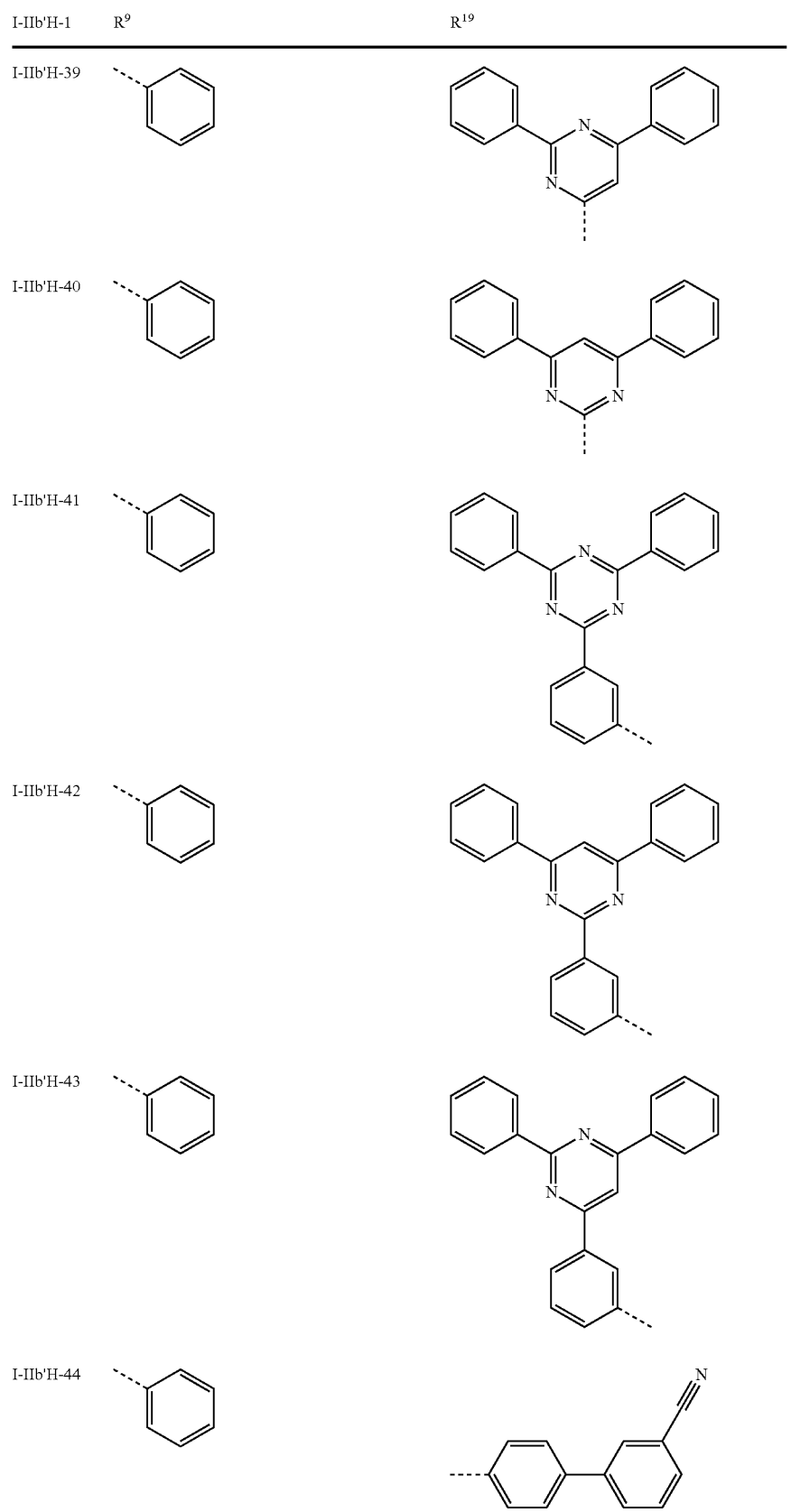

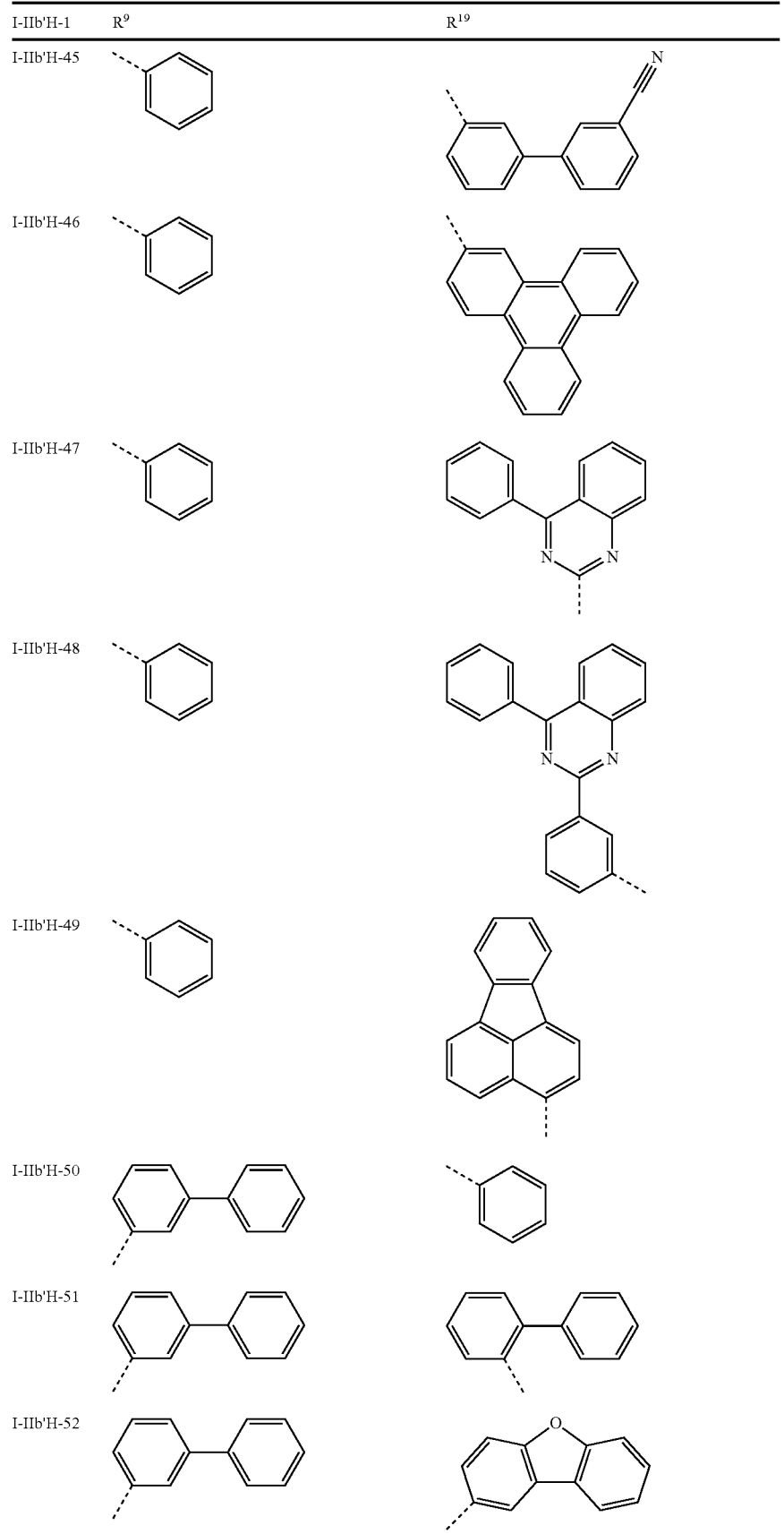

-continued
| I-IIb'H-1 | R⁹ | R¹⁹ |
|---|---|---|
| I-IIb'H-53 | 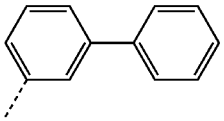 | 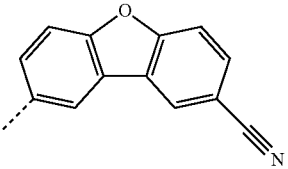 |
| I-IIb'H-54 | 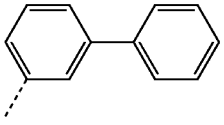 | 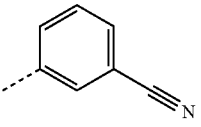 |
| I-IIb'H-55 | 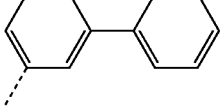 | 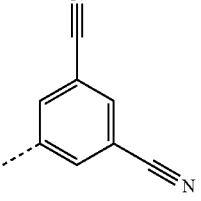 |
| I-IIb'H-56 | 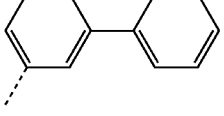 | 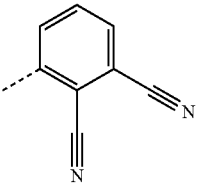 |
| I-IIb'H-57 | 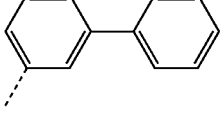 | 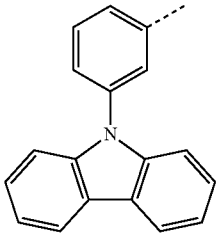 |
| I-IIb'H-58 | 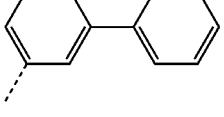 | 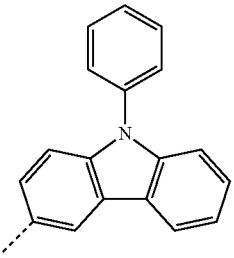 |
| I-IIb'H-59 | 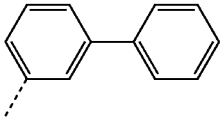 | 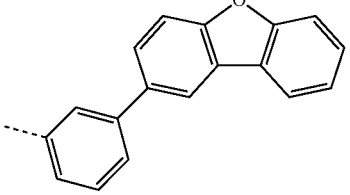 |

-continued
| I-IIb'H-1 | R⁹ | R¹⁹ |
|---|---|---|
| I-IIb'H-60 | 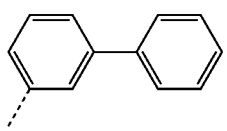 | 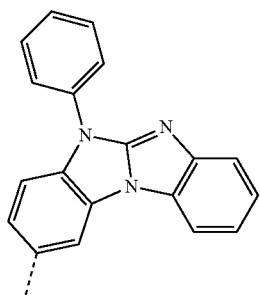 |
| I-IIb'H-61 | 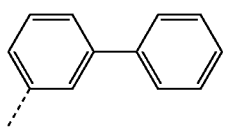 | 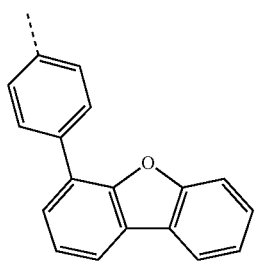 |
| I-IIb'H-62 | 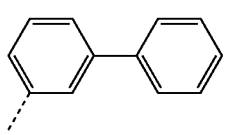 | 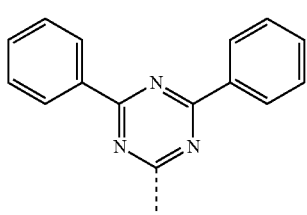 |
| I-IIb'H-63 | 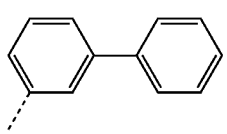 | 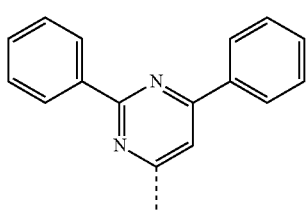 |
| I-IIb'H-64 | 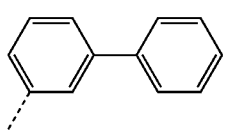 | 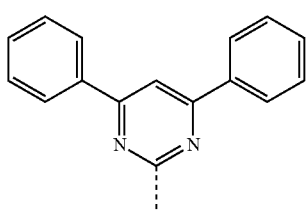 |
| I-IIb'H-65 | 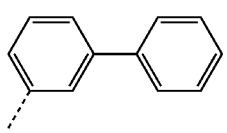 | 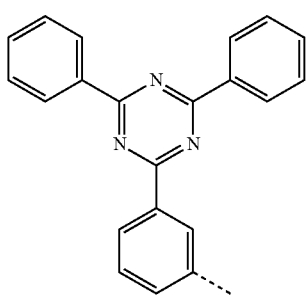 |

-continued

| I-IIb'H-1 | R⁹ | R¹⁹ |
|---|---|---|
| I-IIb'H-66 | 3-biphenyl | 2-(3-phenyl)-4,6-diphenylpyrimidine |
| I-IIb'H-67 | 3-biphenyl | 4-(3-phenyl)-2,6-diphenylpyrimidine |
| I-IIb'H-68 | 3-biphenyl | 3'-cyano-4-biphenyl |
| I-IIb'H-69 | 3-biphenyl | 3'-cyano-3-biphenyl |
| I-IIb'H-70 | 3-biphenyl | triphenylenyl |
| I-IIb'H-71 | 3-biphenyl | 4-phenylquinazolin-2-yl |

-continued
| I-IIb'H-1 | R⁹ | R¹⁹ |
|---|---|---|
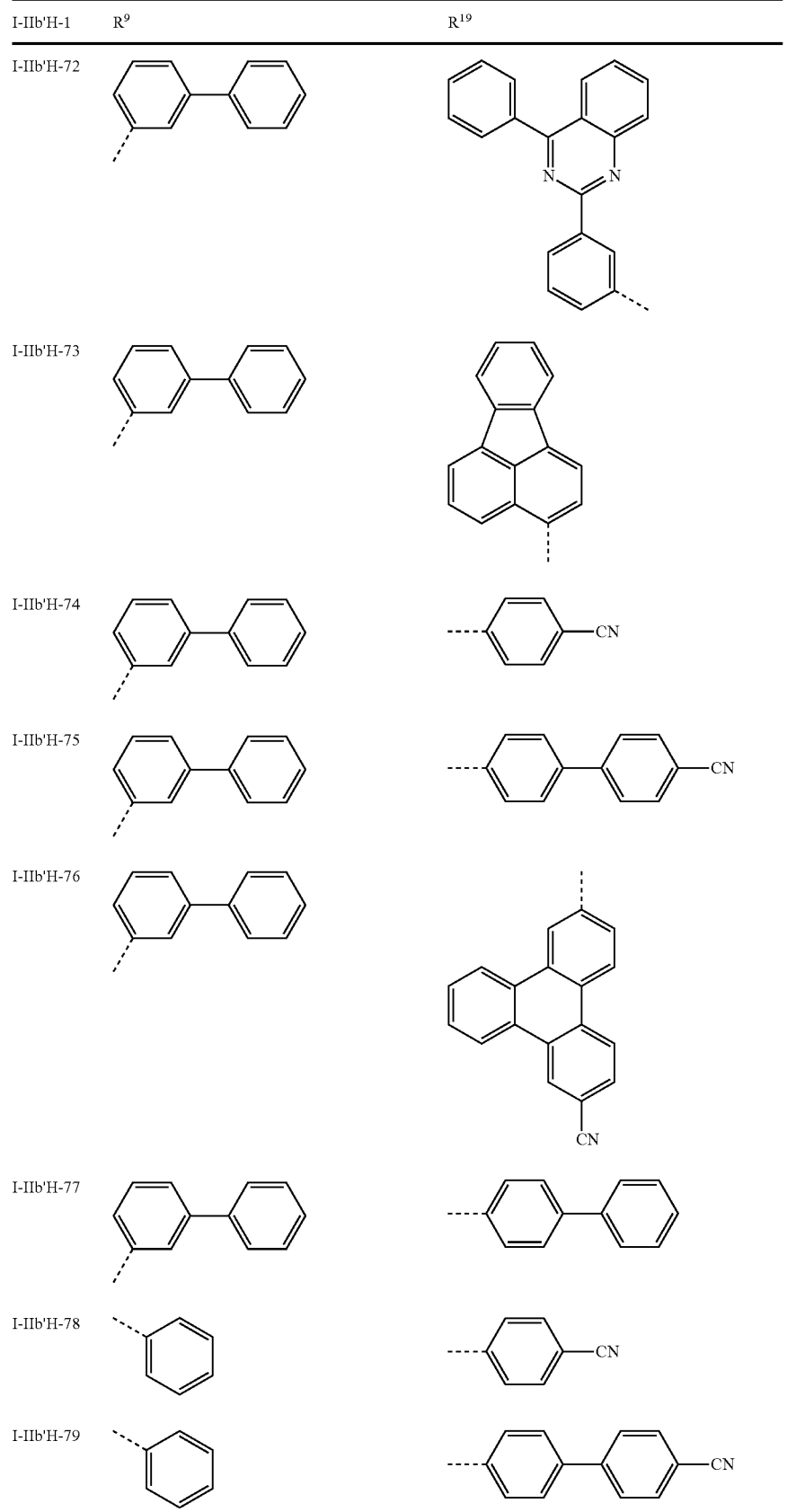

| I-IIb'H-1 | R⁹ | R¹⁹ |
|---|---|---|
| I-IIb'H-80 | phenyl | triphenylenyl-CN |
| I-IIb'H-81 | phenyl | biphenyl |
| I-IIb'H-82 | fluoranthenyl | 4-cyanophenyl |
| I-IIb'H-83 | fluoranthenyl | 4'-cyanobiphenyl |
| I-IIb'H-84 | fluoranthenyl | triphenylenyl-CN |
| I-IIb'H-85 | fluoranthenyl | biphenyl |

-continued
| I-IIb'H-1 | R⁹ | R¹⁹ |
|---|---|---|
| I-IIb'H-86 | 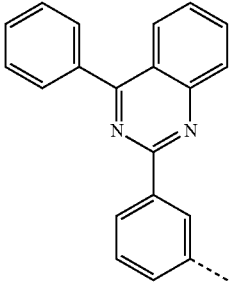 | 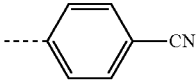 |
| I-IIb'H-87 | 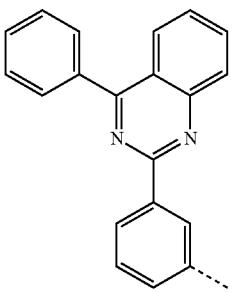 | 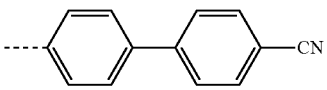 |
| I-IIb'H-88 | 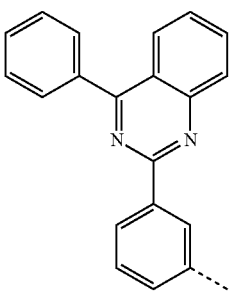 | 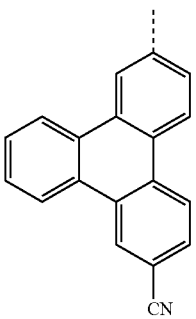 |
| I-IIb'H-89 | 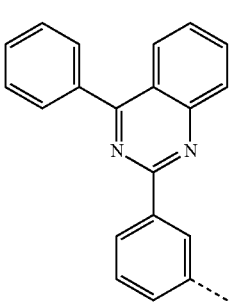 | 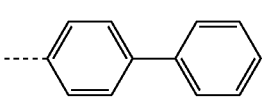 |
| I-IIb'H-90 | 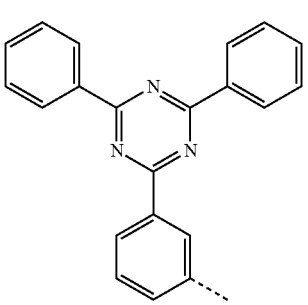 | 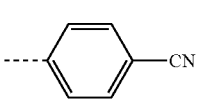 |

| I-IIb'H-1 | R⁹ | R¹⁹ |
|---|---|---|
| I-IIb'H-91 | 2,4-diphenyl-1,3,5-triazin-6-yl-(3-phenyl)- | 4'-cyano-biphenyl-4-yl |
| I-IIb'H-92 | 2,4-diphenyl-1,3,5-triazin-6-yl-(3-phenyl)- | cyano-triphenylenyl |
| I-IIb'H-93 | 2,4-diphenyl-1,3,5-triazin-6-yl-(3-phenyl)- | biphenyl-4-yl |
| I-IIb'H-94 | 3'-cyano-biphenyl-3-yl | 4-cyanophenyl |
| I-IIb'H-95 | 3'-cyano-biphenyl-3-yl | 4'-cyano-biphenyl-4-yl |
| I-IIb'H-96 | 3'-cyano-biphenyl-3-yl | cyano-triphenylenyl |

-continued
| I-IIb'H-1 | R⁹ | R¹⁹ |
|---|---|---|
| I-IIb'H-97 | 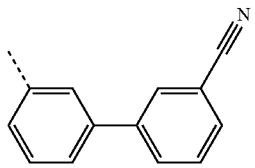 | 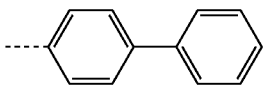 |
| I-IIb'H-98 | 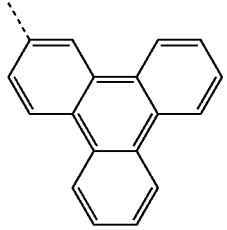 | 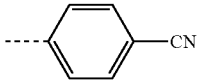 |
| I-IIb'H-99 | 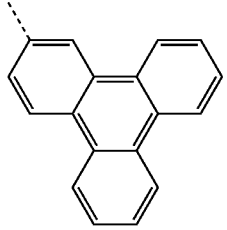 | 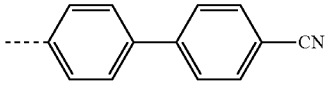 |
| I-IIb'H-100 | 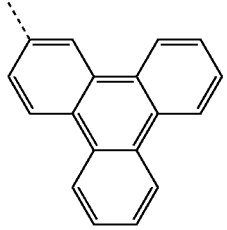 | 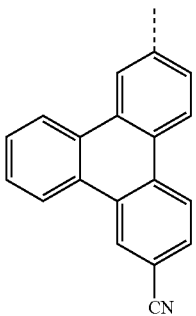 |
| I-IIb'H-101 | 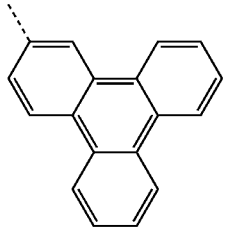 | 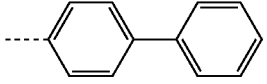 |
| I-IIb'H-102 | 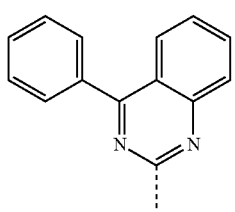 | 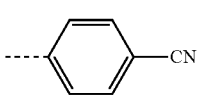 |

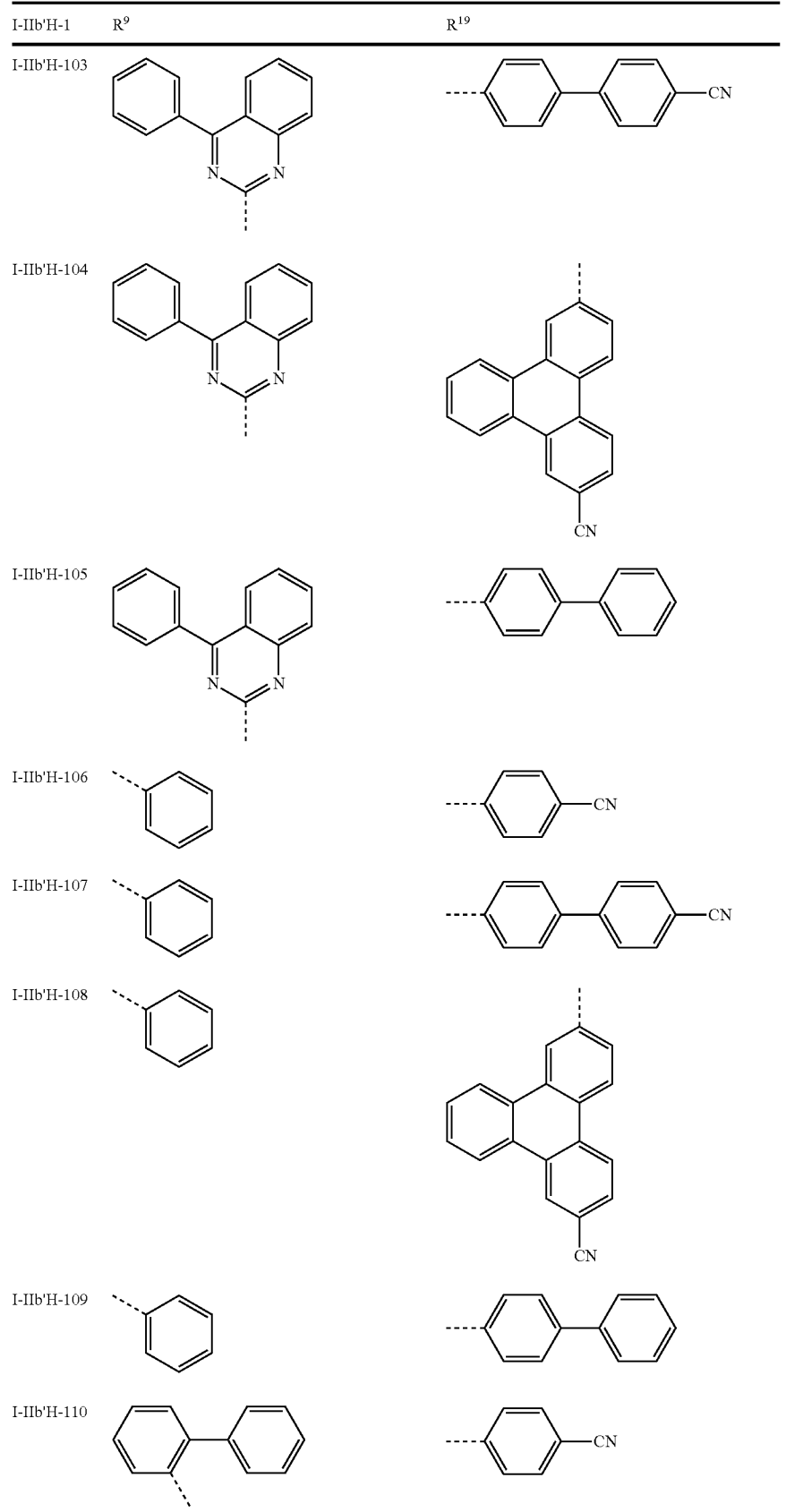

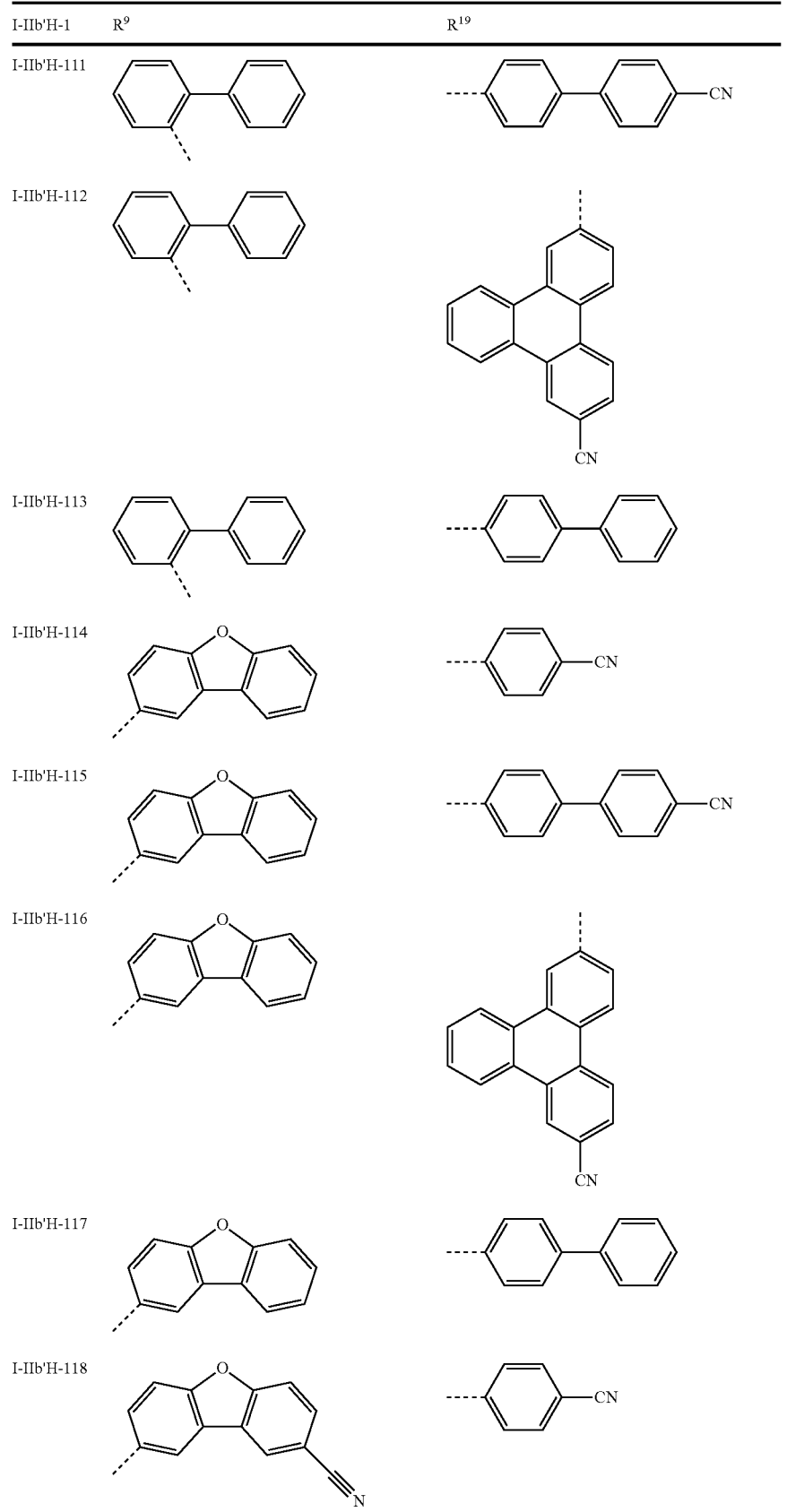

| I-IIb'H-1 | R⁹ | R¹⁹ |
|---|---|---|
| I-IIb'H-119 | dibenzofuran-CN | -biphenyl-CN |
| I-IIb'H-120 | dibenzofuran-CN | triphenylene-CN |
| I-IIb'H-121 | dibenzofuran-CN | -biphenyl |
| I-IIb'H-122 | 3-cyanophenyl | -phenyl-CN |
| I-IIb'H-123 | 3-cyanophenyl | -biphenyl-CN |
| I-IIb'H-124 | 3-cyanophenyl | triphenylene-CN |
| I-IIb'H-125 | 3-cyanophenyl | -biphenyl |

-continued

| I-IIb'H-1 | R⁹ | R¹⁹ |
|---|---|---|
| I-IIb'H-126 | 3,5-dicyanophenyl | 4-cyanophenyl |
| I-IIb'H-127 | 3,5-dicyanophenyl | 4'-cyano-biphenyl-4-yl |
| I-IIb'H-128 | 3,5-dicyanophenyl | cyano-triphenylenyl |
| I-IIb'H-129 | 3,5-dicyanophenyl | biphenyl-4-yl |
| I-IIb'H-130 | 2,3-dicyanophenyl | 4-cyanophenyl |
| I-IIb'H-131 | 2,3-dicyanophenyl | 4'-cyano-biphenyl-4-yl |

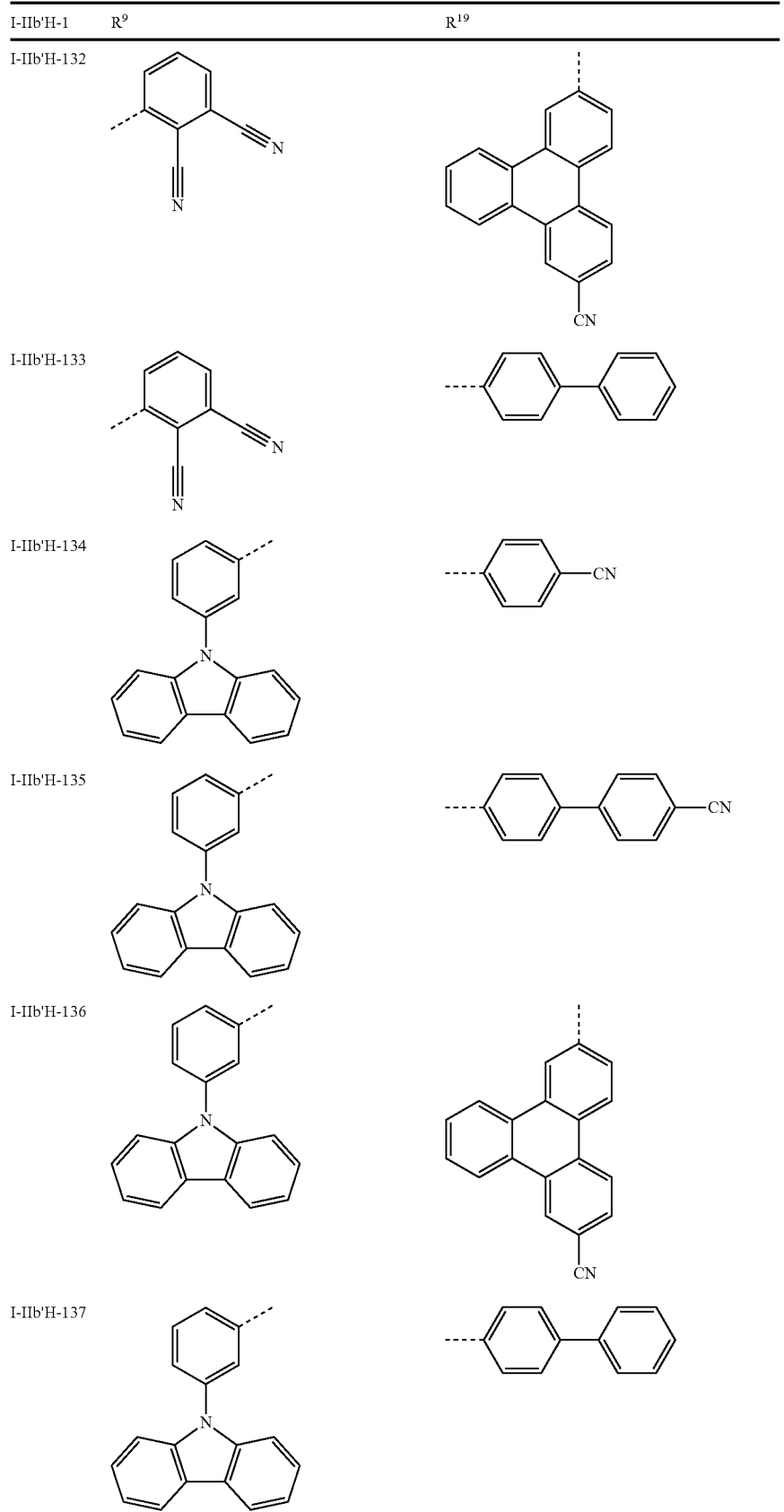

| I-IIb'H-1 | R⁹ | R¹⁹ |
|---|---|---|
| I-IIb'H-138 | | |
| I-IIb'H-139 | | |
| I-IIb'H-140 | | |
| I-IIb'H-141 | | |
| I-IIb'H-142 | | |
| I-IIb'H-143 | | |
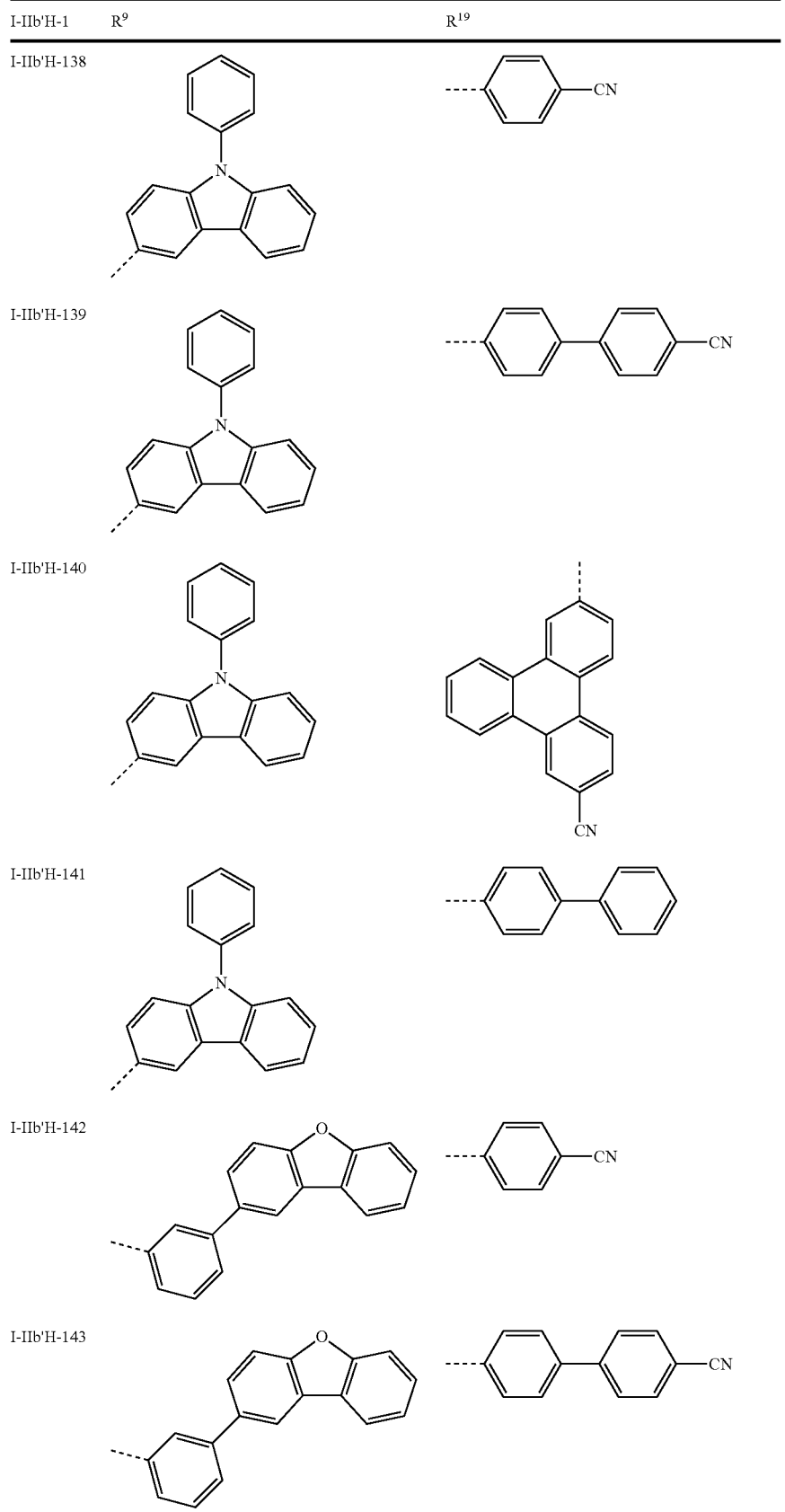

-continued
| I-IIb'H-1 | R⁹ | R¹⁹ |
|---|---|---|
I-IIb'H-144
I-IIb'H-145
I-IIb'H-146
I-IIb'H-147
I-IIb'H-148
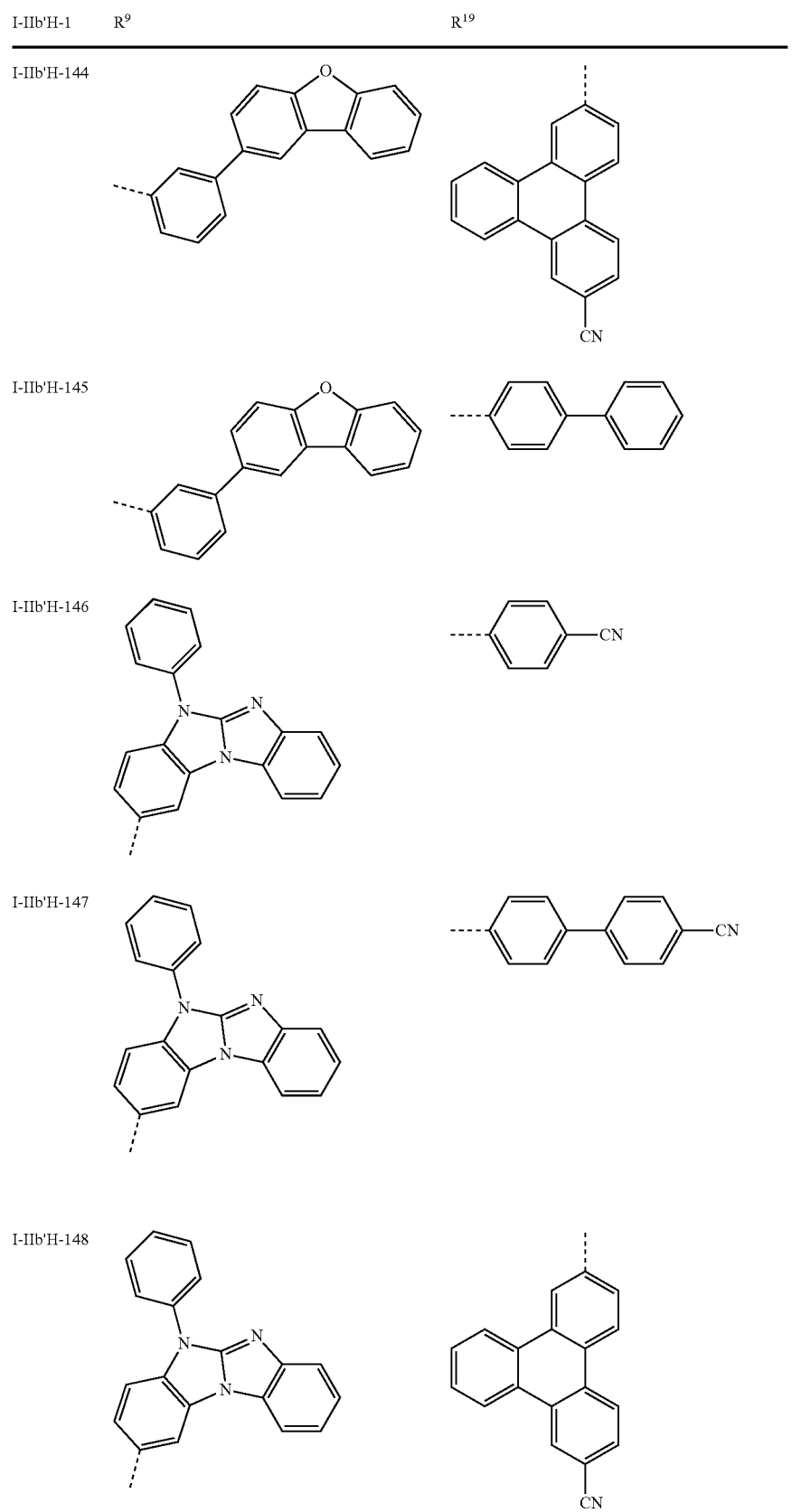

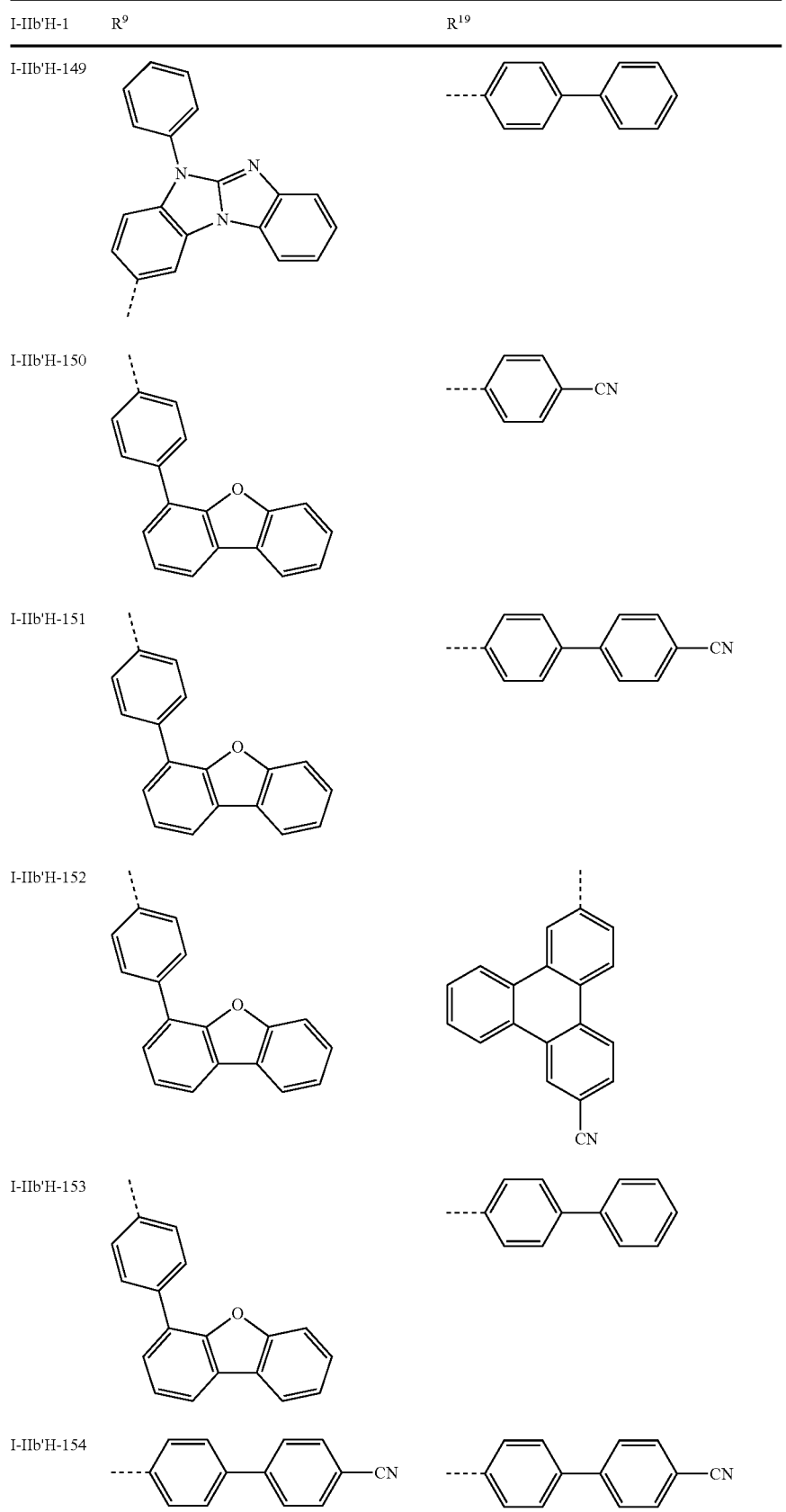

-continued
| I-IIb'H-1 | R⁹ | R¹⁹ |
|---|---|---|
| I-IIb'H-155 | | |
| I-IIb'H-156 | | |
| I-IIb'H-157 | | |
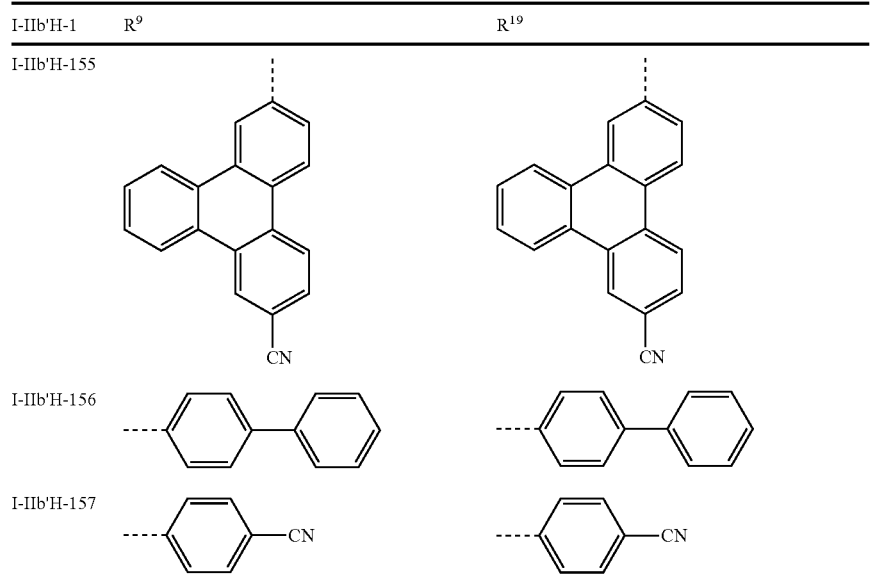
The dotted lines are bonding sites.
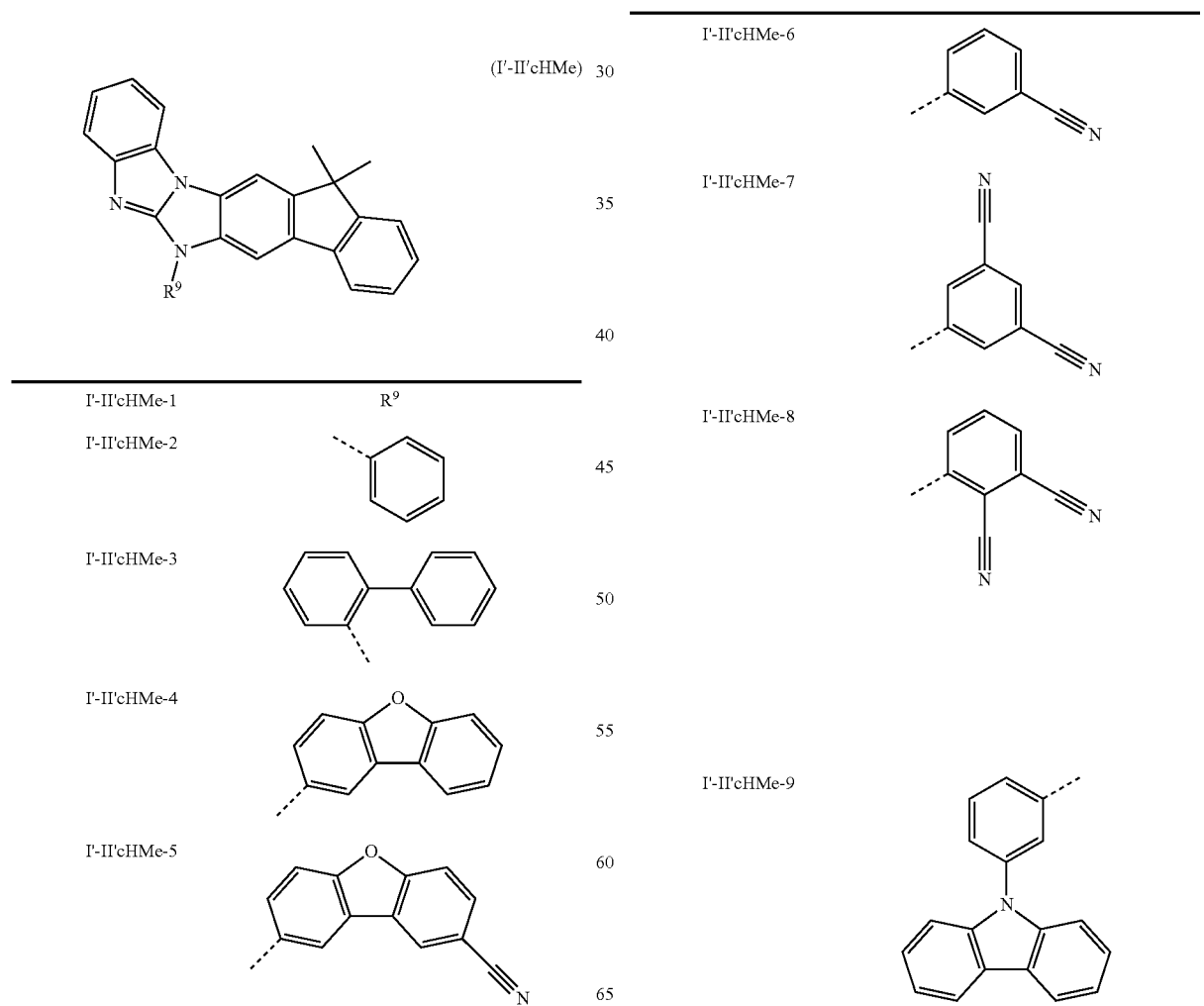

I'-II'cHMe-10 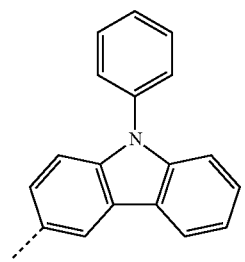
I'-II'cHMe-11 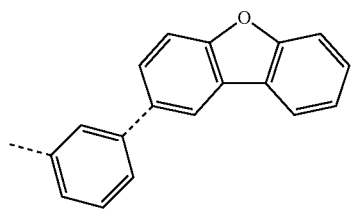
I'-II'cHMe-12 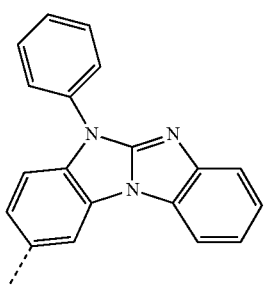
I'-II'cHMe-13 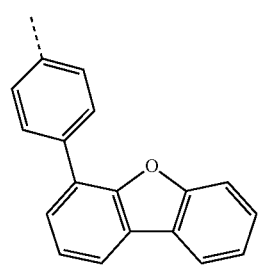
I'-II'cHMe-14 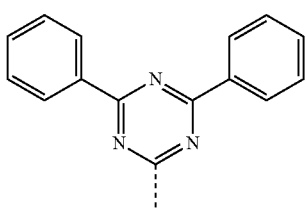
I'-II'cHMe-15 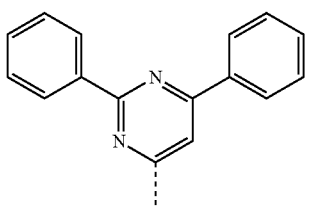
I'-II'cHMe-16 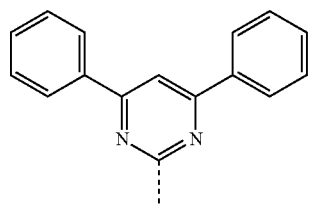
I'-II'cHMe-17 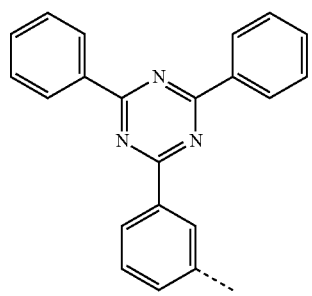
I'-II'cHMe-18 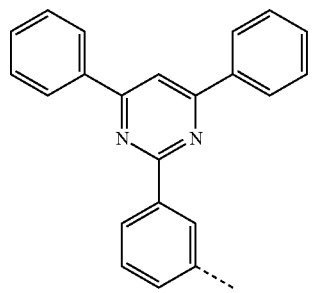
I'-II'cHMe-19 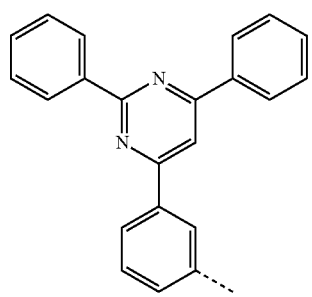
I'-II'cHMe-20 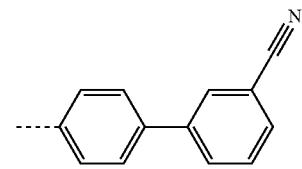
I'-II'cHMe-21 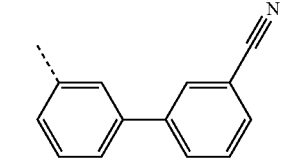

-continued
| | |
|---|---|
| I'-II'cHMe-22 | 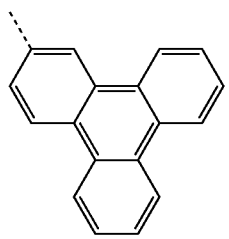 |
| I'-II'cHMe-23 | 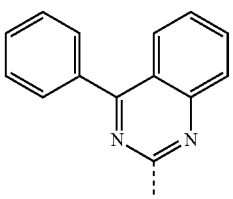 |
| I'-II'cHMe-24 | 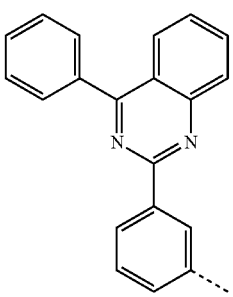 |
| I'-II'cHMe-25 | 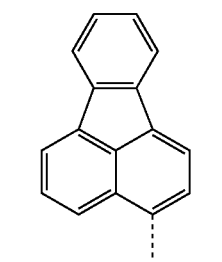 |
| I'-II'cHMe-26 | 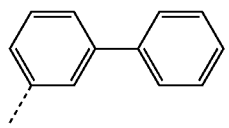 |
| I'-II'cHMe-27 |  |
| I'-II'cHMe-28 | 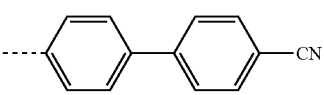 |
-continued
| | |
|---|---|
| I'-II'cHMe-29 | 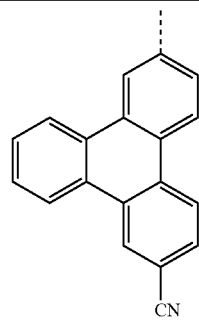 |
| I'-II'cHMe-30 | 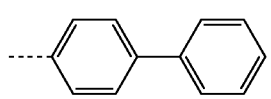 |
The dotted lines are bonding sites.
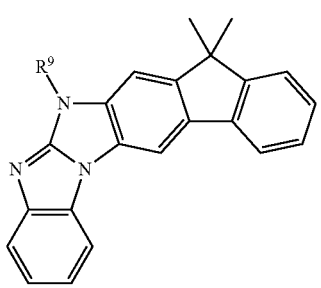
(I'-II'c'HMe)
| | R⁹ |
|---|---|
| I'-II'c'HMe-1 | |
| I'-II'c'HMe-2 | 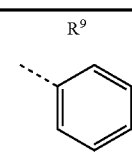 |
| I'-II'c'HMe-3 | 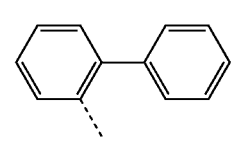 |
| I'-II'c'HMe-4 | 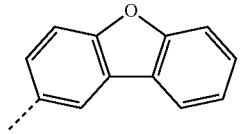 |
| I'-II'c'HMe-5 | 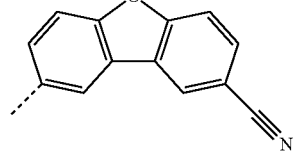 |
| I'-II'c'HMe-6 | 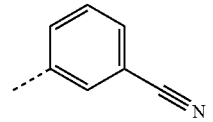 |

| | | | |
|---|---|---|---|
| I'-II'c'HMe-7 | 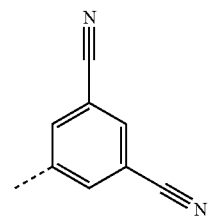 | I'-II'c'HMe-13 | 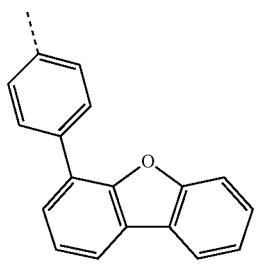 |
| I'-II'c'HMe-8 | 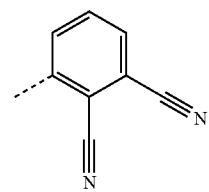 | I'-II'c'HMe-14 | 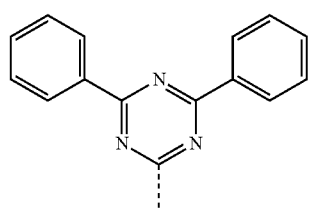 |
| I'-II'c'HMe-9 | 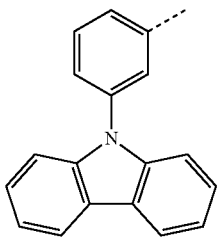 | I'-II'c'HMe-15 | 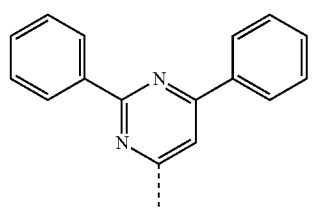 |
| I'-II'c'HMe-10 | 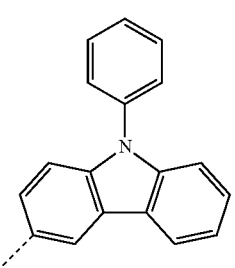 | I'-II'c'HMe-16 | 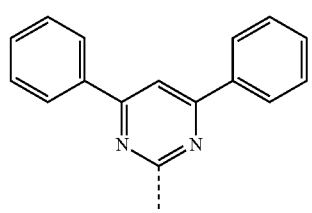 |
| I'-II'c'HMe-11 | 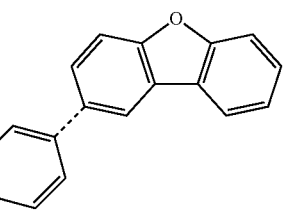 | I'-II'c'HMe-17 | 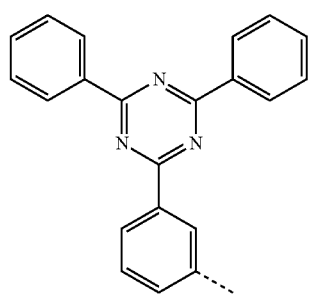 |
| I'-II'c'HMe-12 | 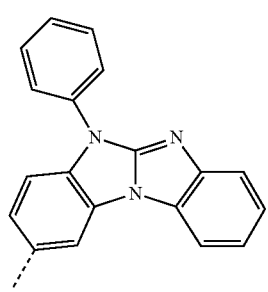 | I'-II'c'HMe-18 | 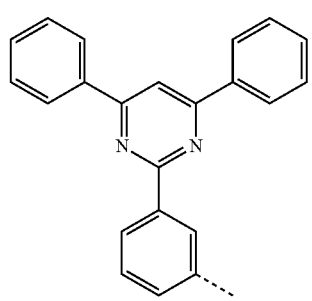 |

| | |
|---|---|
| I'-II'c'HMe-19 | 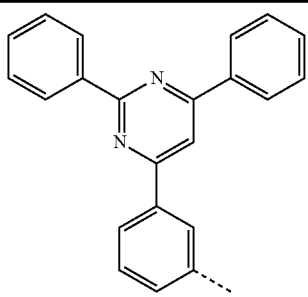 |
| I'-II'c'HMe-20 | 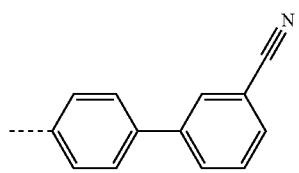 |
| I'-II'c'HMe-21 | 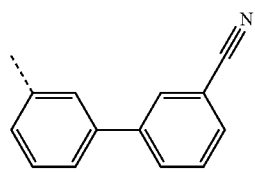 |
| I'-II'c'HMe-22 | 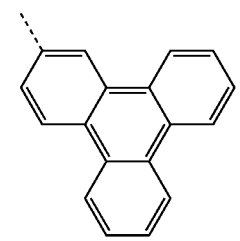 |
| I'-II'c'HMe-23 | 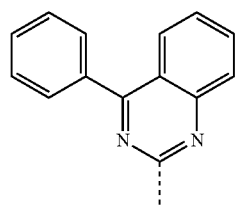 |
| I'-II'c'HMe-24 | 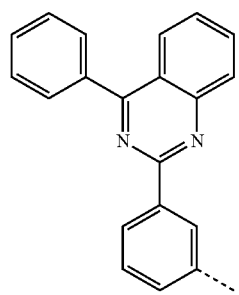 |
| I'-II'c'HMe-25 | 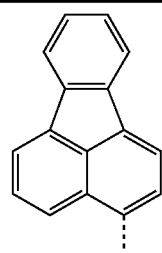 |
| I'-II'c'HMe-26 | 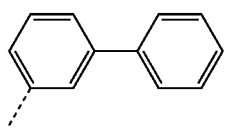 |
| I'-II'c'HMe-27 | 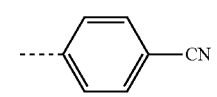 |
| I'-II'c'HMe-28 | 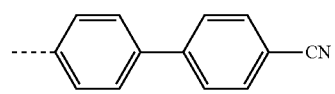 |
| I'-II'c'HMe-29 | 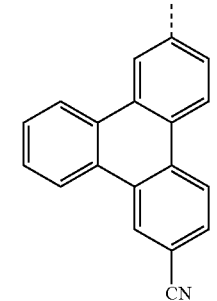 |
| I'-II'c'HMe-30 | 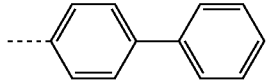 |
The dotted lines are bonding sites.
(I'-II'caH)
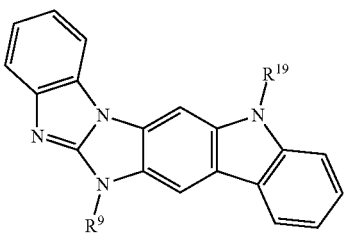
| | R⁹ | R¹⁹ |
|---|---|---|
| I'-II'caH-1 | 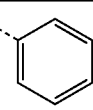 | 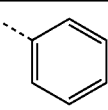 |

-continued
| | R⁹ | R¹⁹ |
|---|---|---|
| I'-II'caH-2 | | |
| I'-II'caH-3 | | |
| I'-II'caH-4 | | |
| I'-II'caH-5 | | |
| I'-II'caH-6 | | |
| I'-II'caH-7 | | |
| I'-II'caH-8 | | |
| I'-II'caH-9 | | |
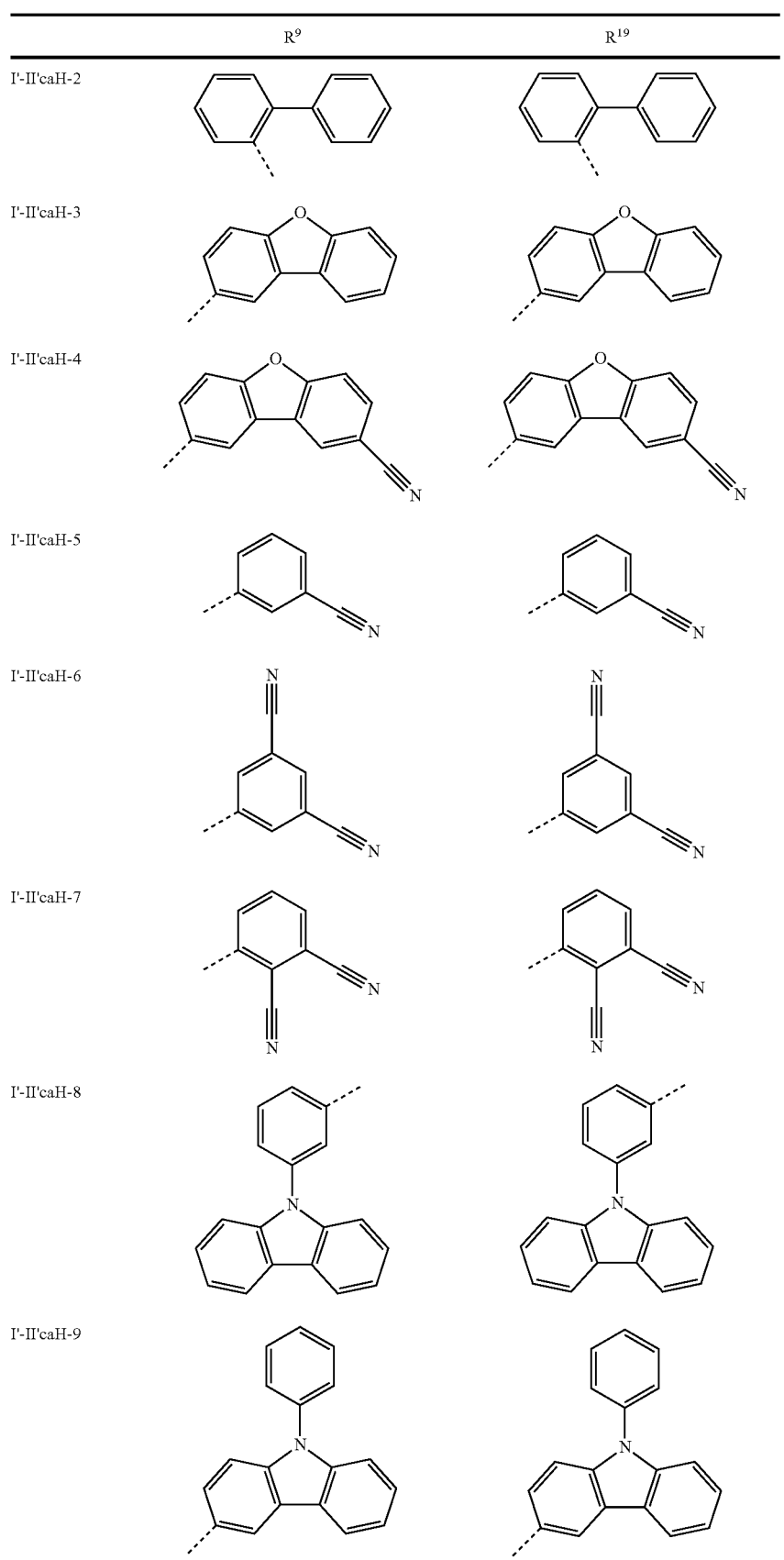

-continued
| | R⁹ | R¹⁹ |
|---|---|---|
| I'-II'caH-10 | | |
| I'-II'caH-11 | | |
| I'-II'caH-12 | | |
| I'-II'caH-13 | | |
| I'-II'caH-14 | | |
| I'-II'caH-15 | | |
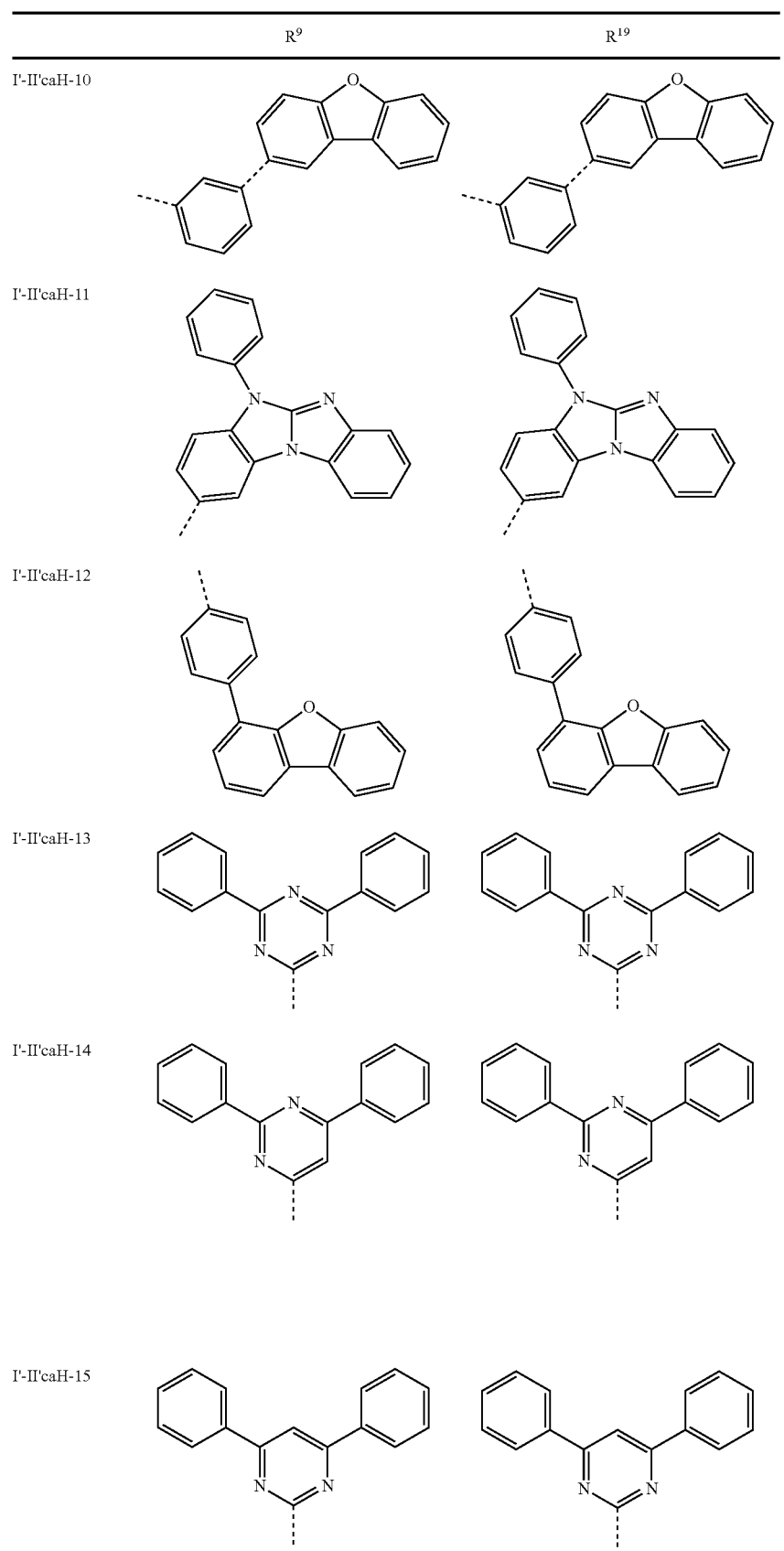

-continued
| | R⁹ | R¹⁹ |
|---|---|---|
| I'-II'caH-16 | | |
| I'-II'caH-17 | | |
| I'-II'caH-18 | | |
| I'-II'caH-19 | | |
| I'-II'caH-20 | | |
| I'-II'caH-21 | | |
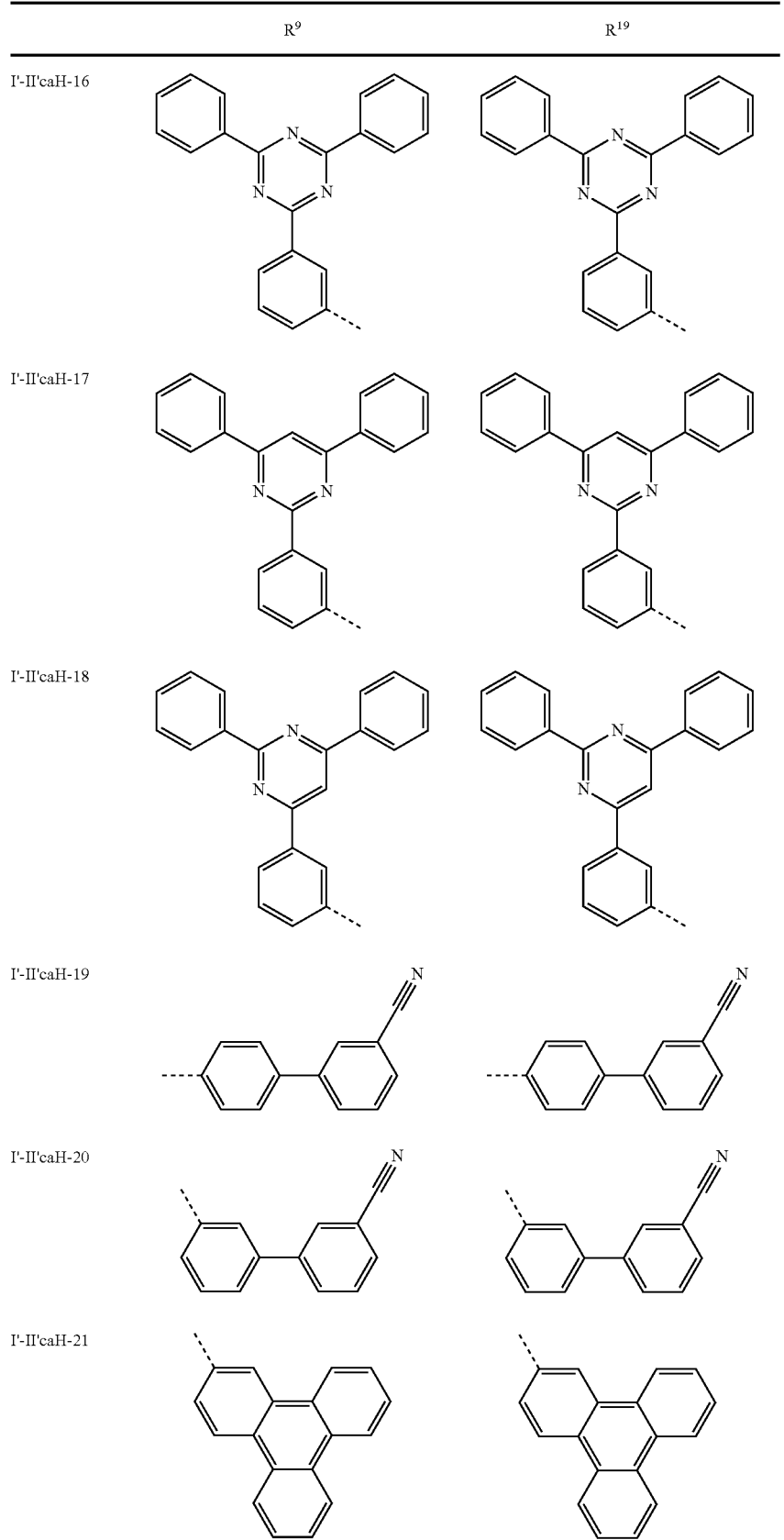

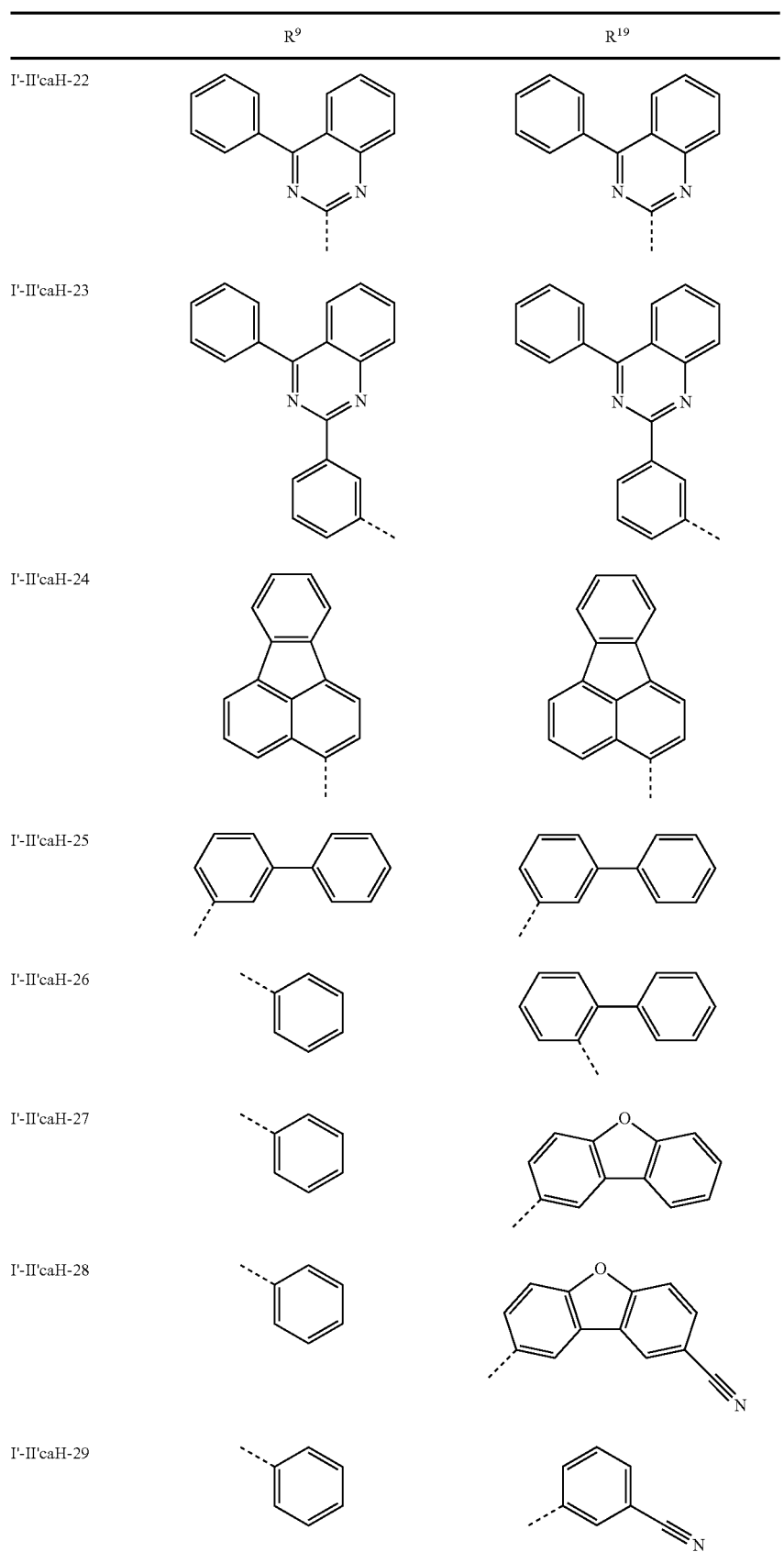

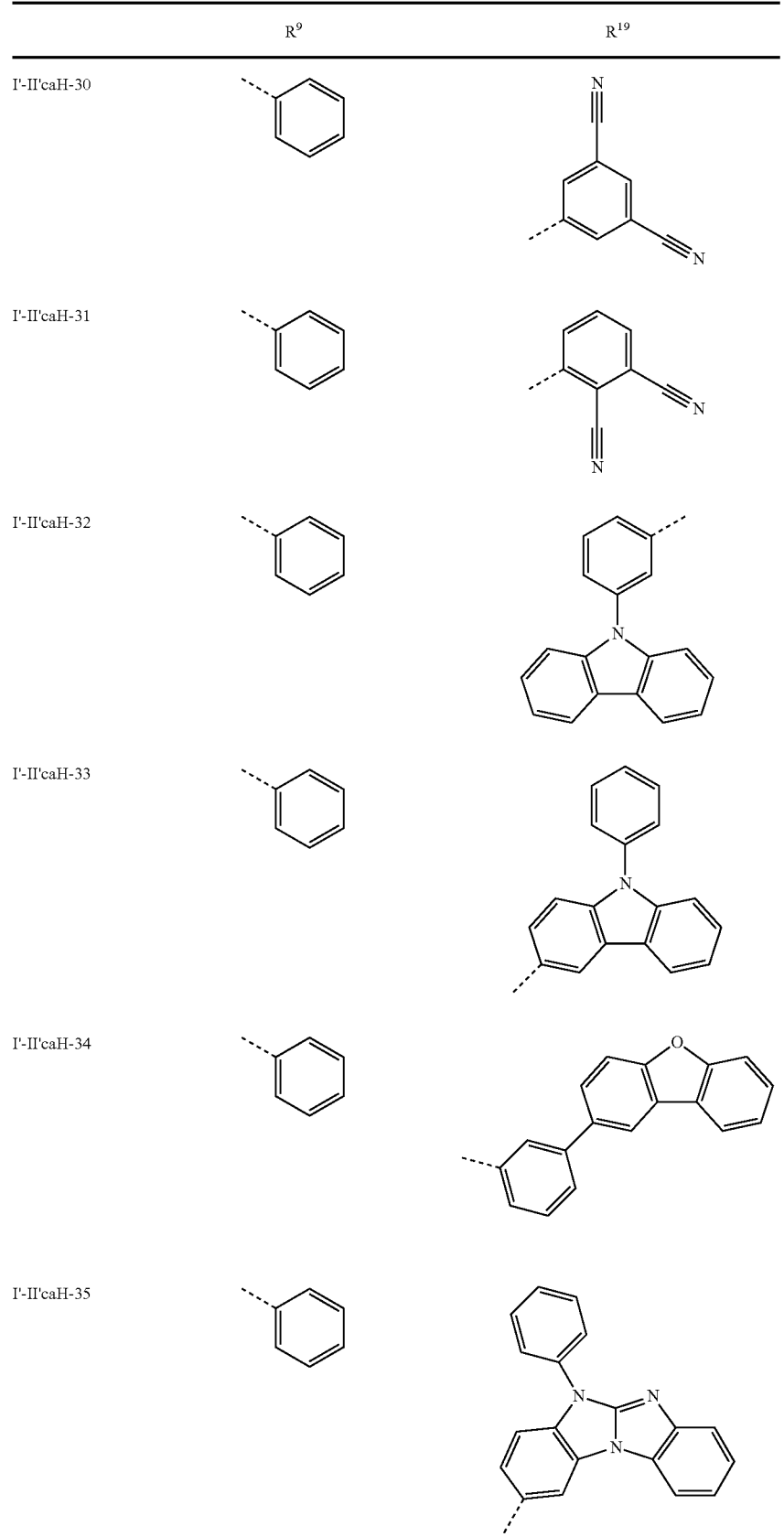

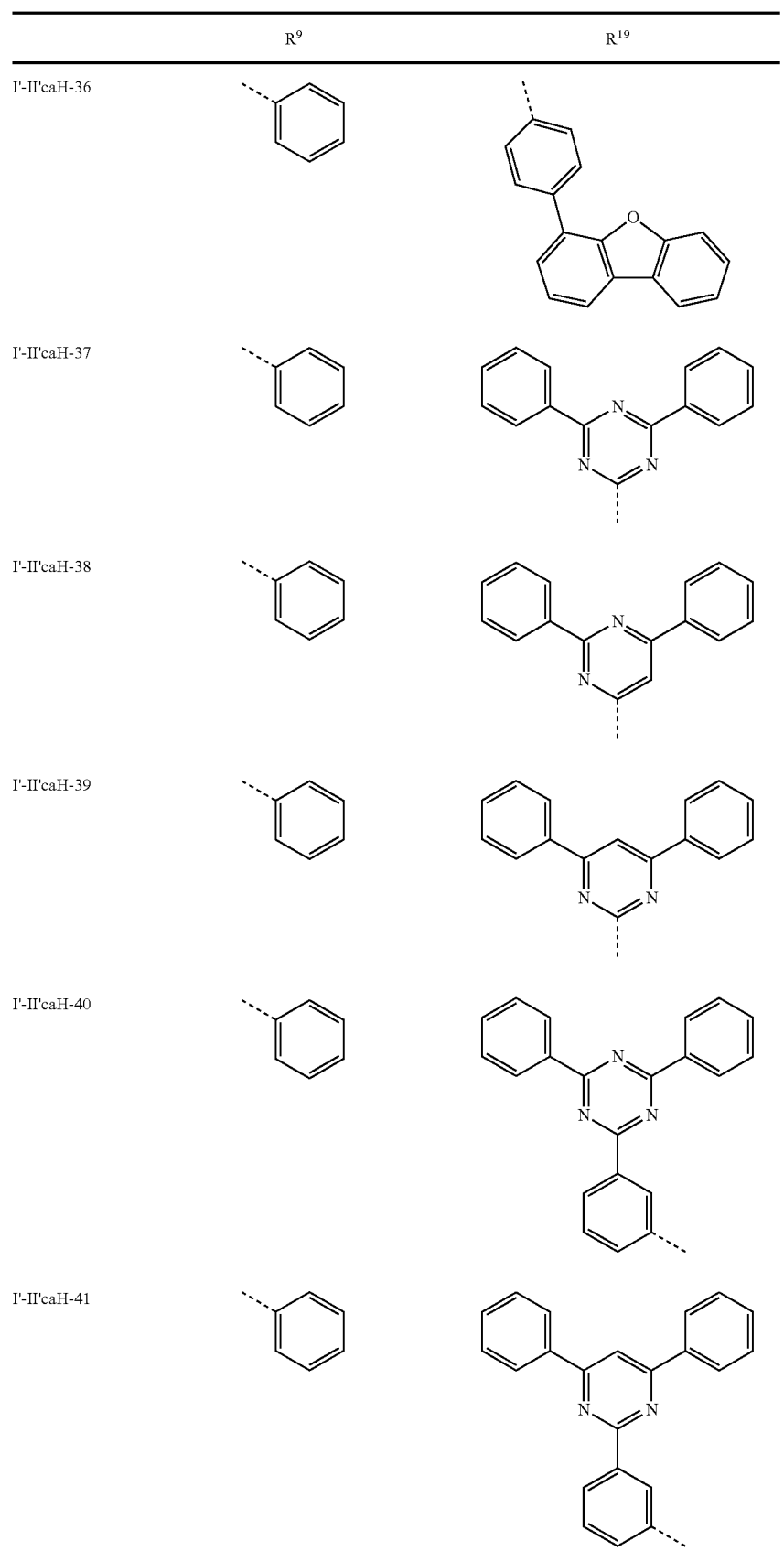

-continued
| | R⁹ | R¹⁹ |
|---|---|---|
| I'-II'caH-42 | | |
| I'-II'caH-43 | | |
| I'-II'caH-44 | | |
| I'-II'caH-45 | | |
| I'-II'caH-46 | | |
| I'-II'caH-47 | | |
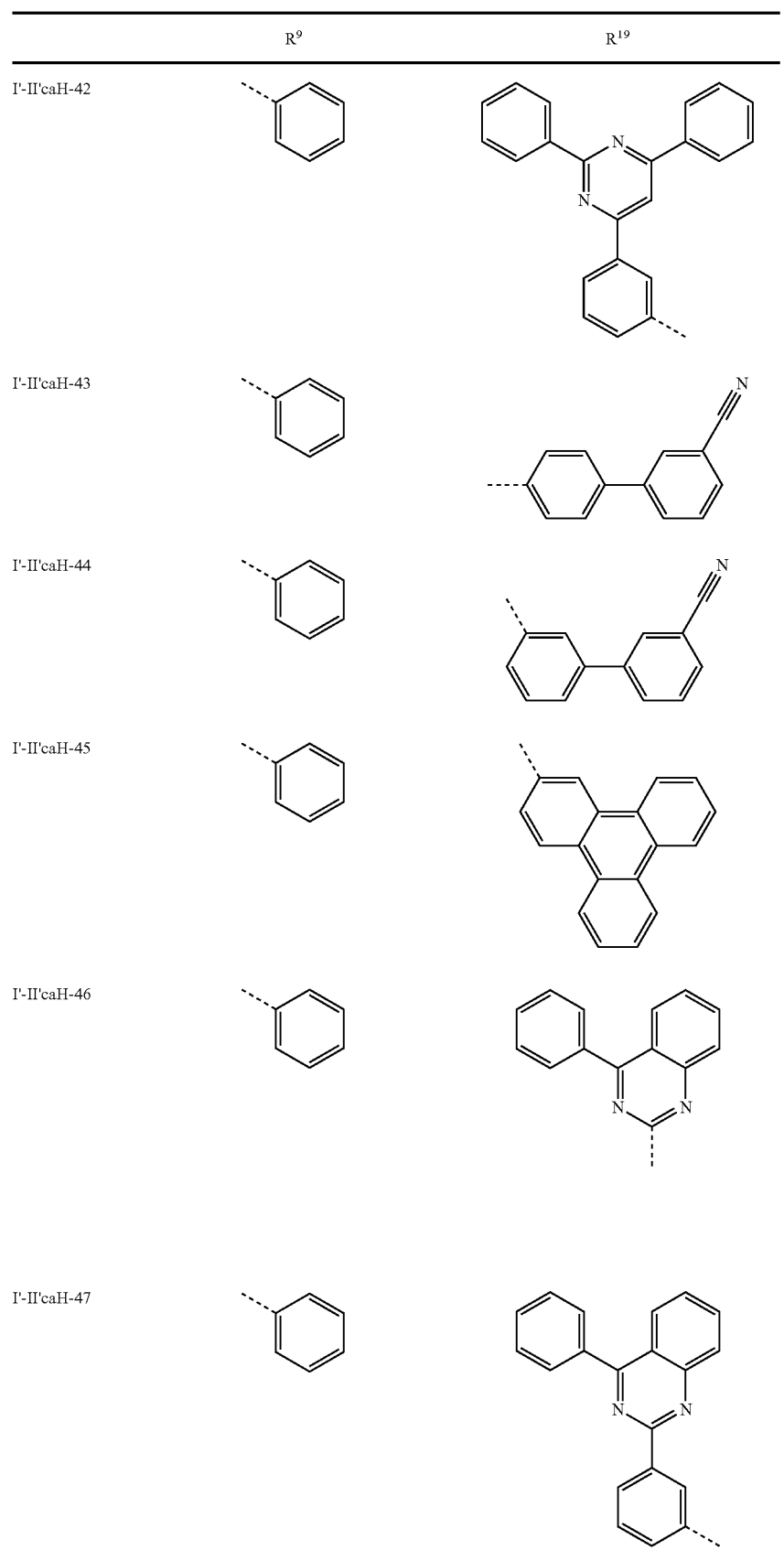

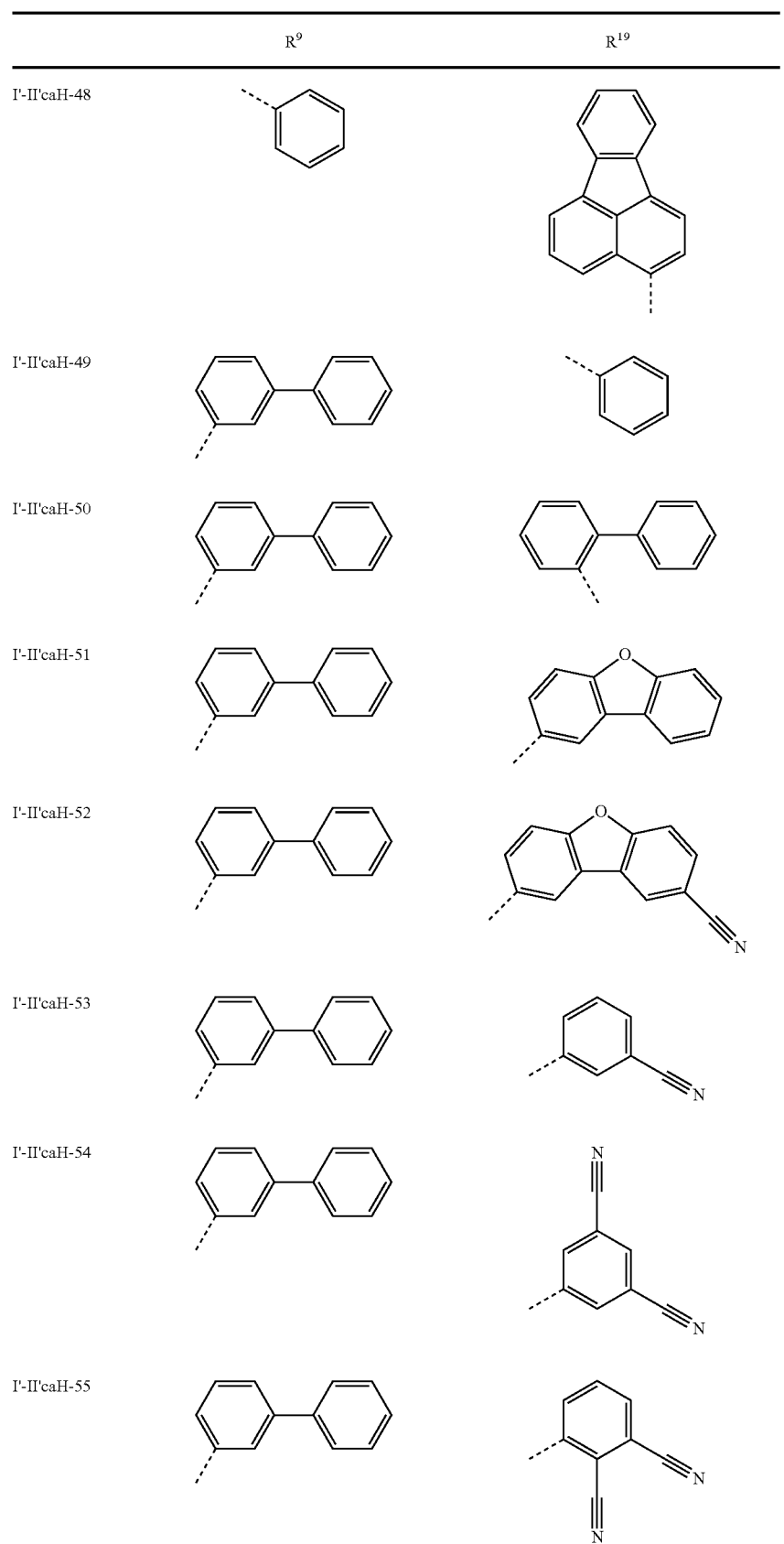

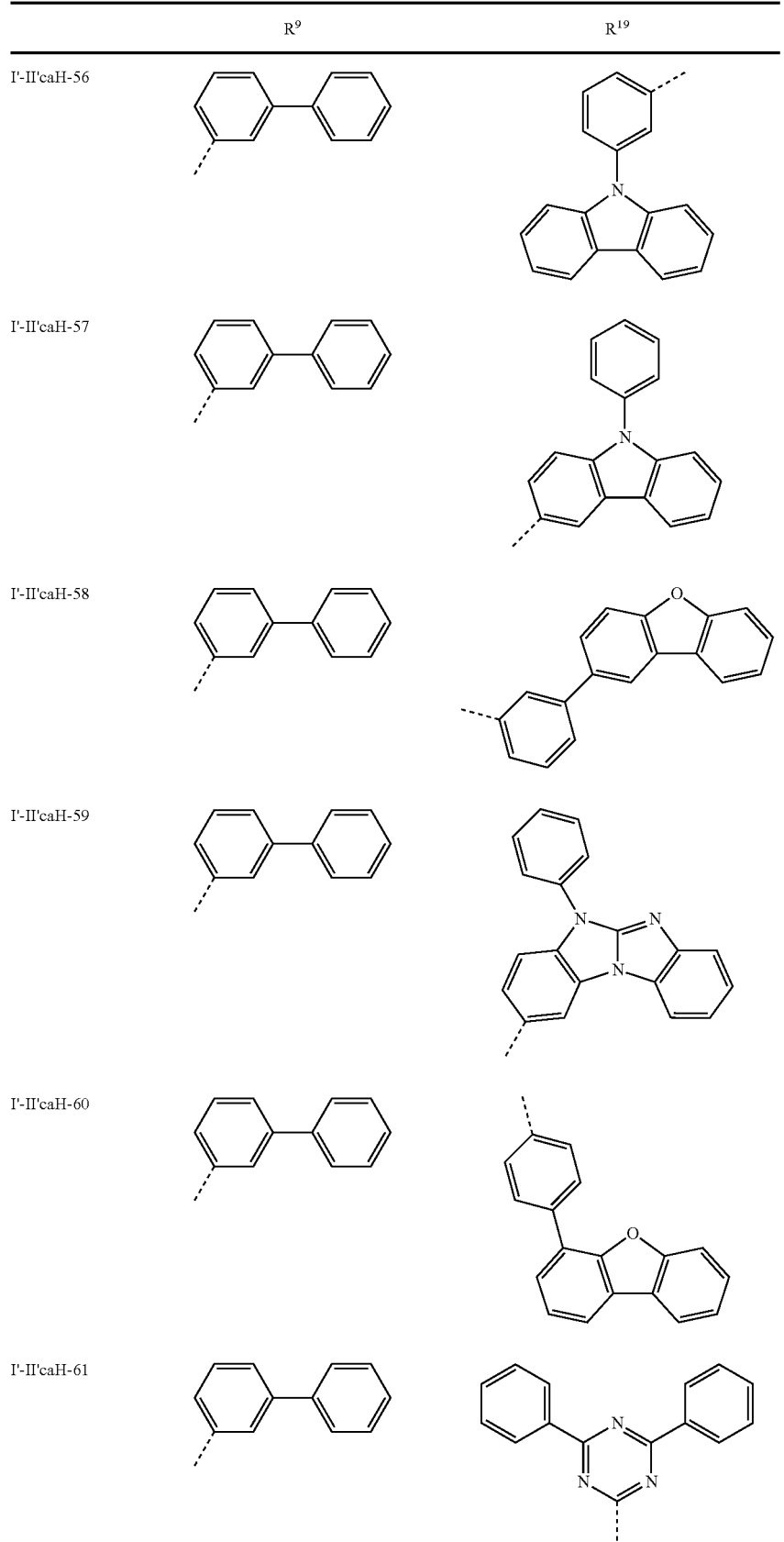

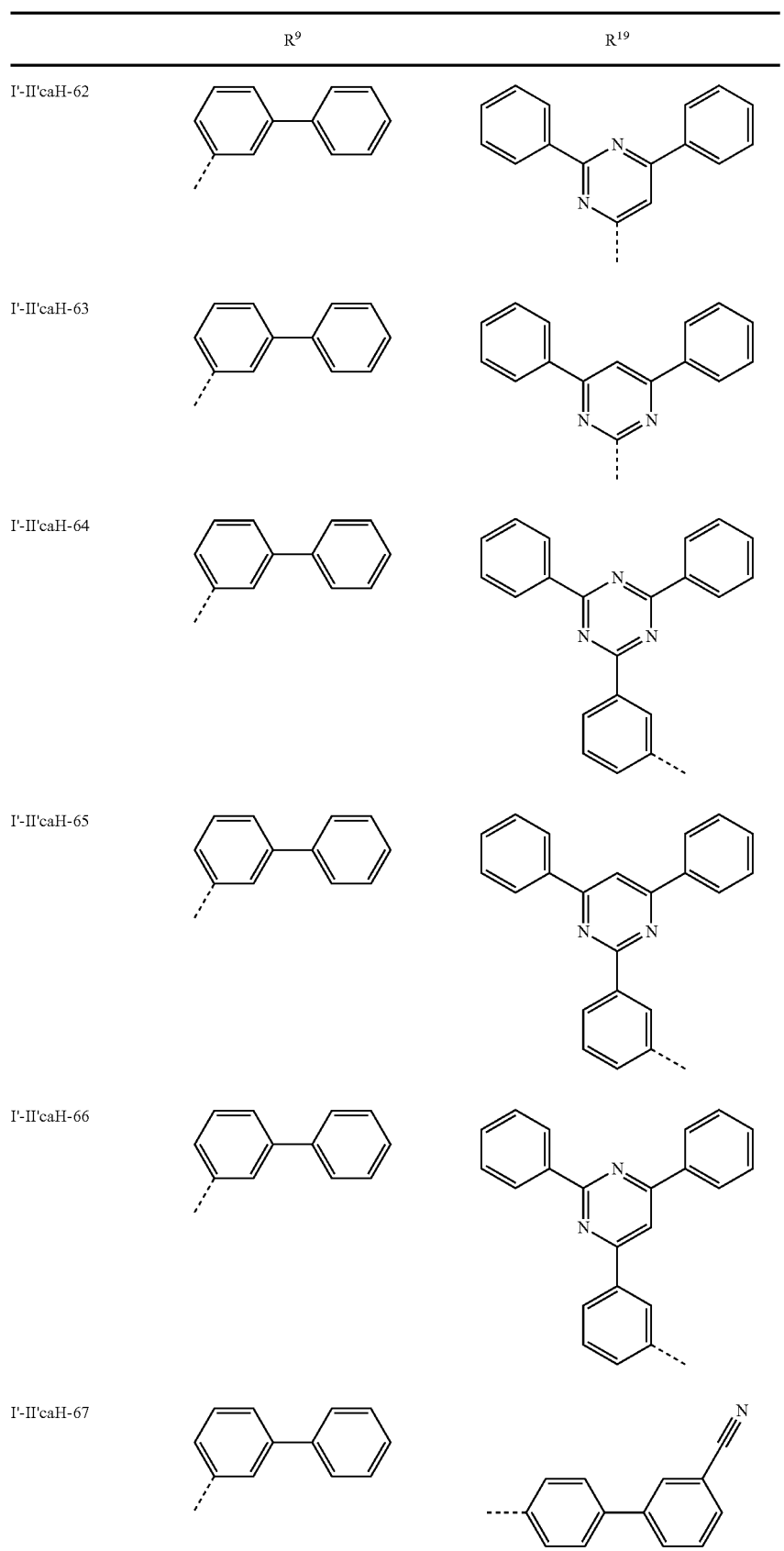

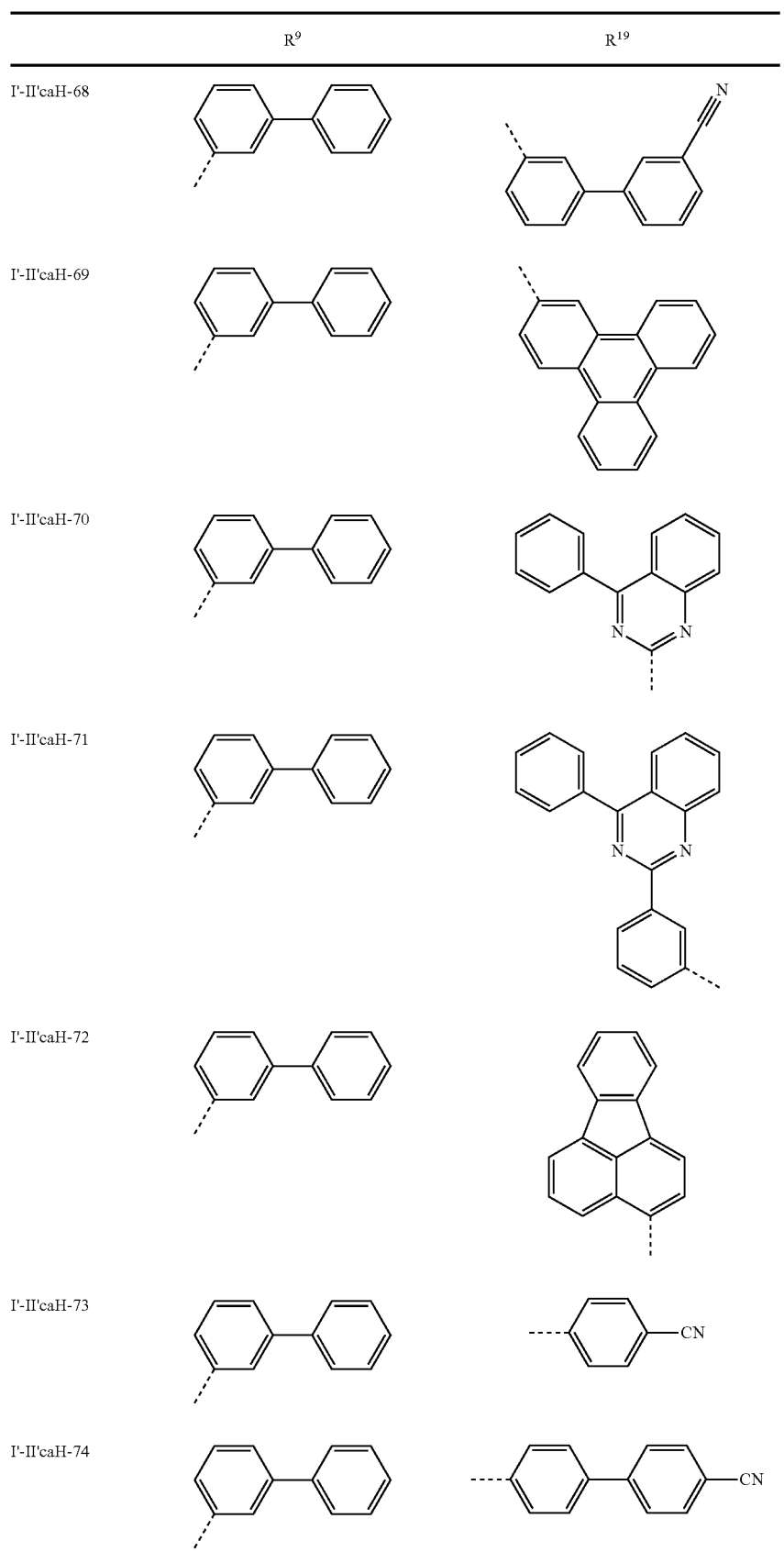

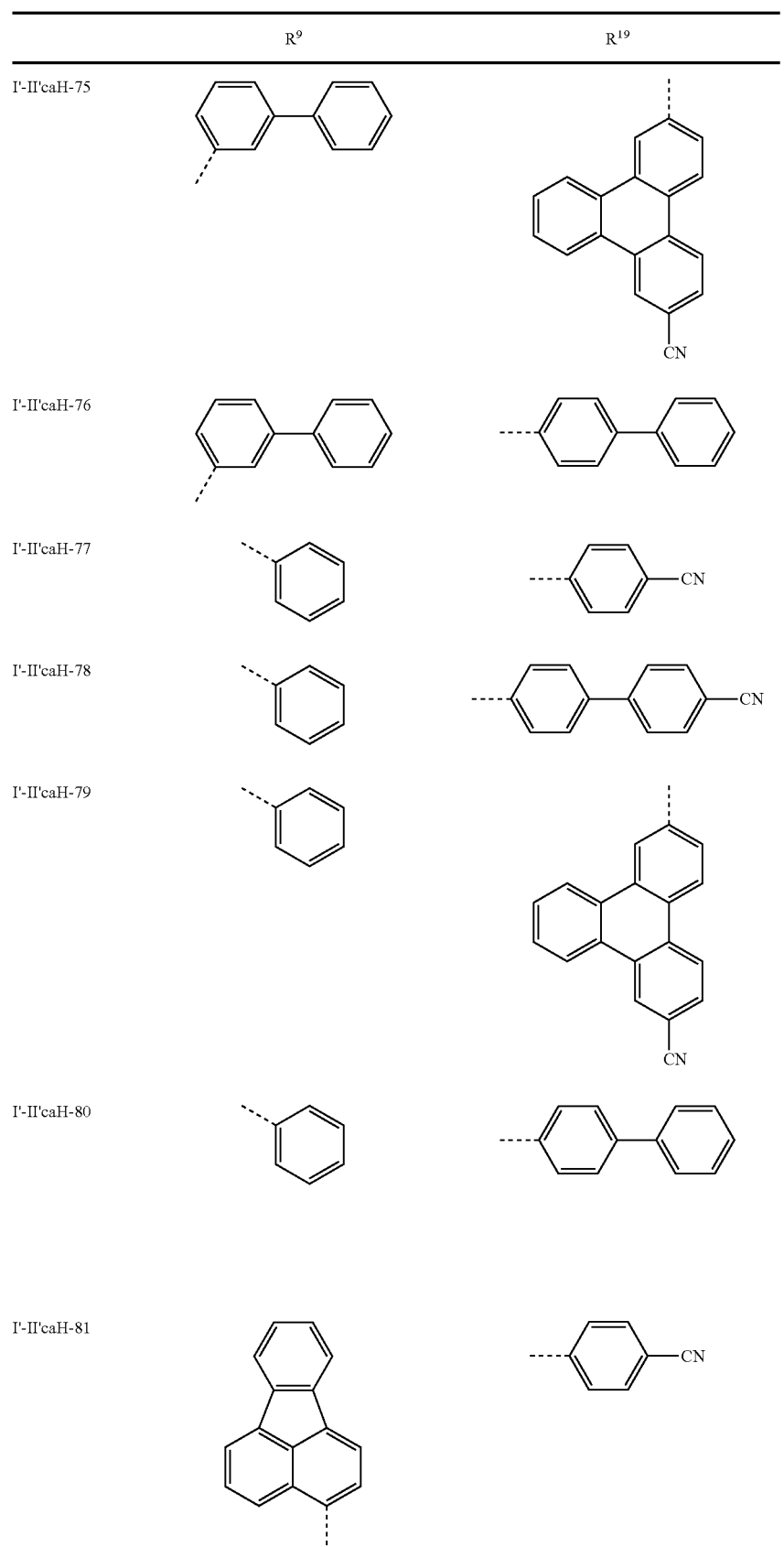

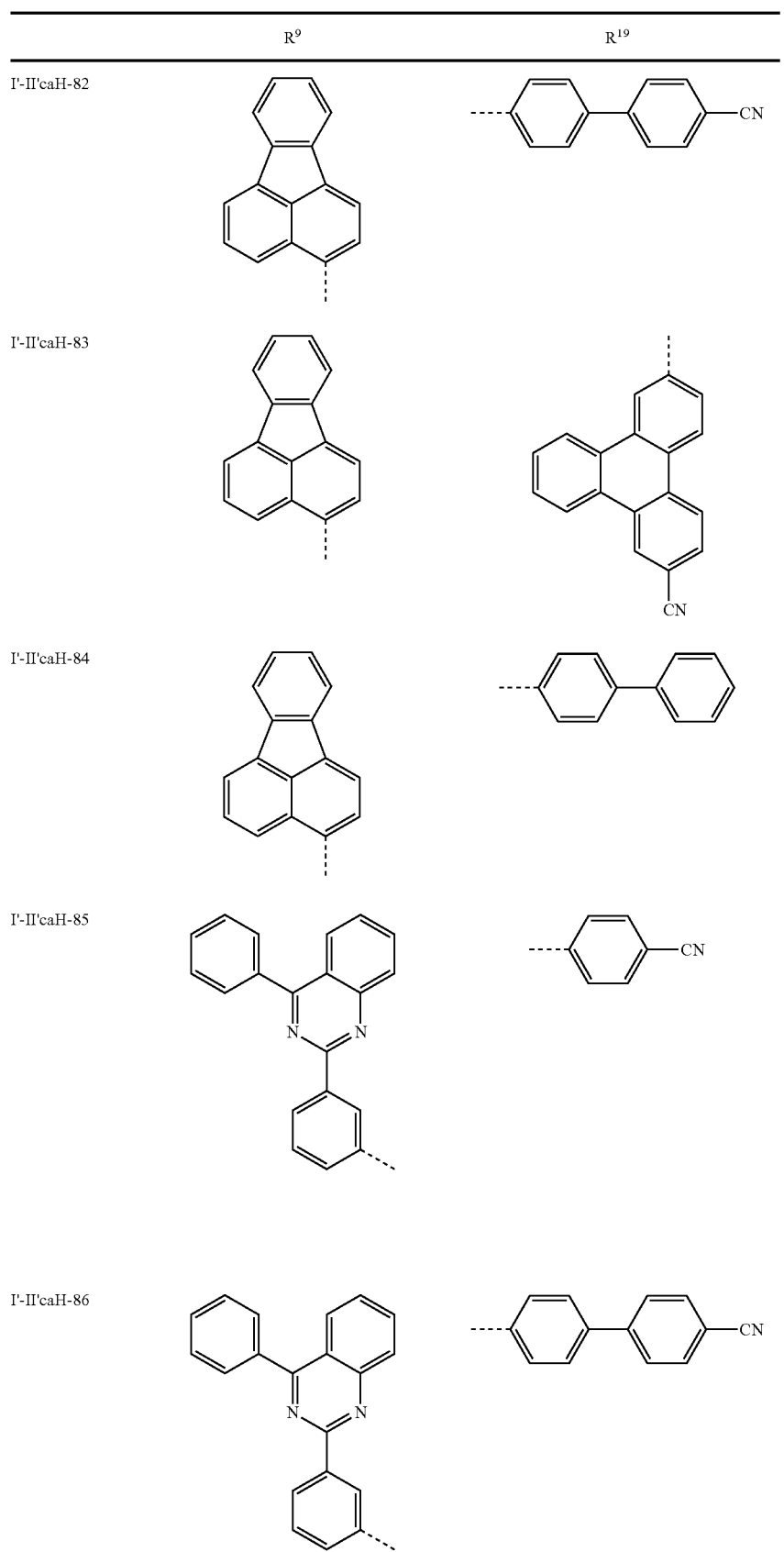

|  | R⁹ | R¹⁹ |
|---|---|---|
| I'-II'caH-87 | | |
| I'-II'caH-88 | | |
| I'-II'caH-89 | | |
| I'-II'caH-90 | | |
| I'-II'caH-91 | | |
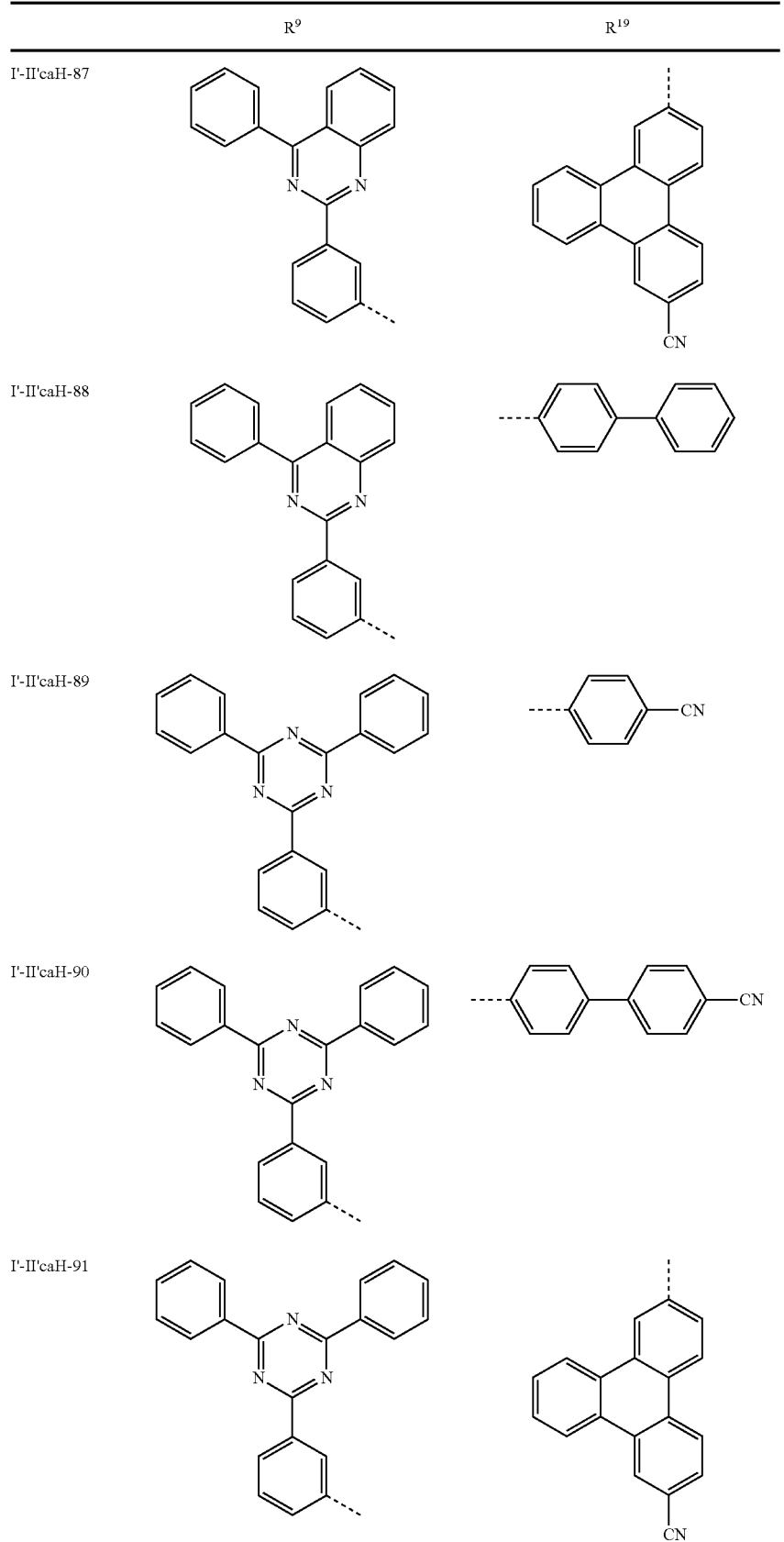

-continued
| | R⁹ | R¹⁹ |
|---|---|---|
| I'-II'caH-92 | 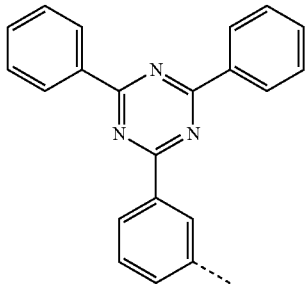 | 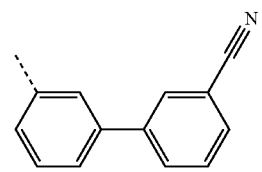 |
| I'-II'caH-93 | 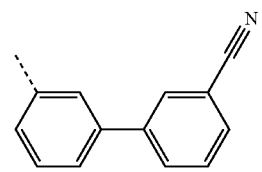 | 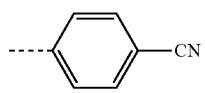 |
| I'-II'caH-94 | 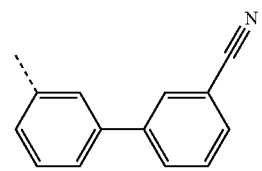 | 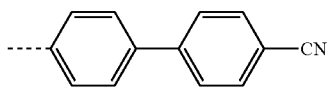 |
| I'-II'caH-95 | 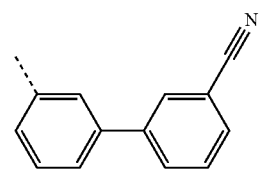 | 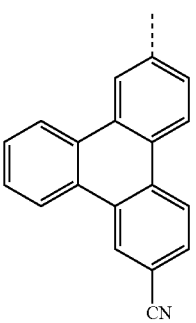 |
| I'-II'caH-96 | 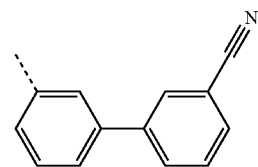 | 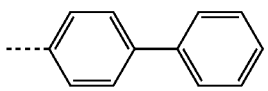 |
| I'-II'caH-97 | 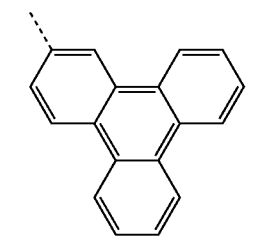 | 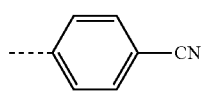 |

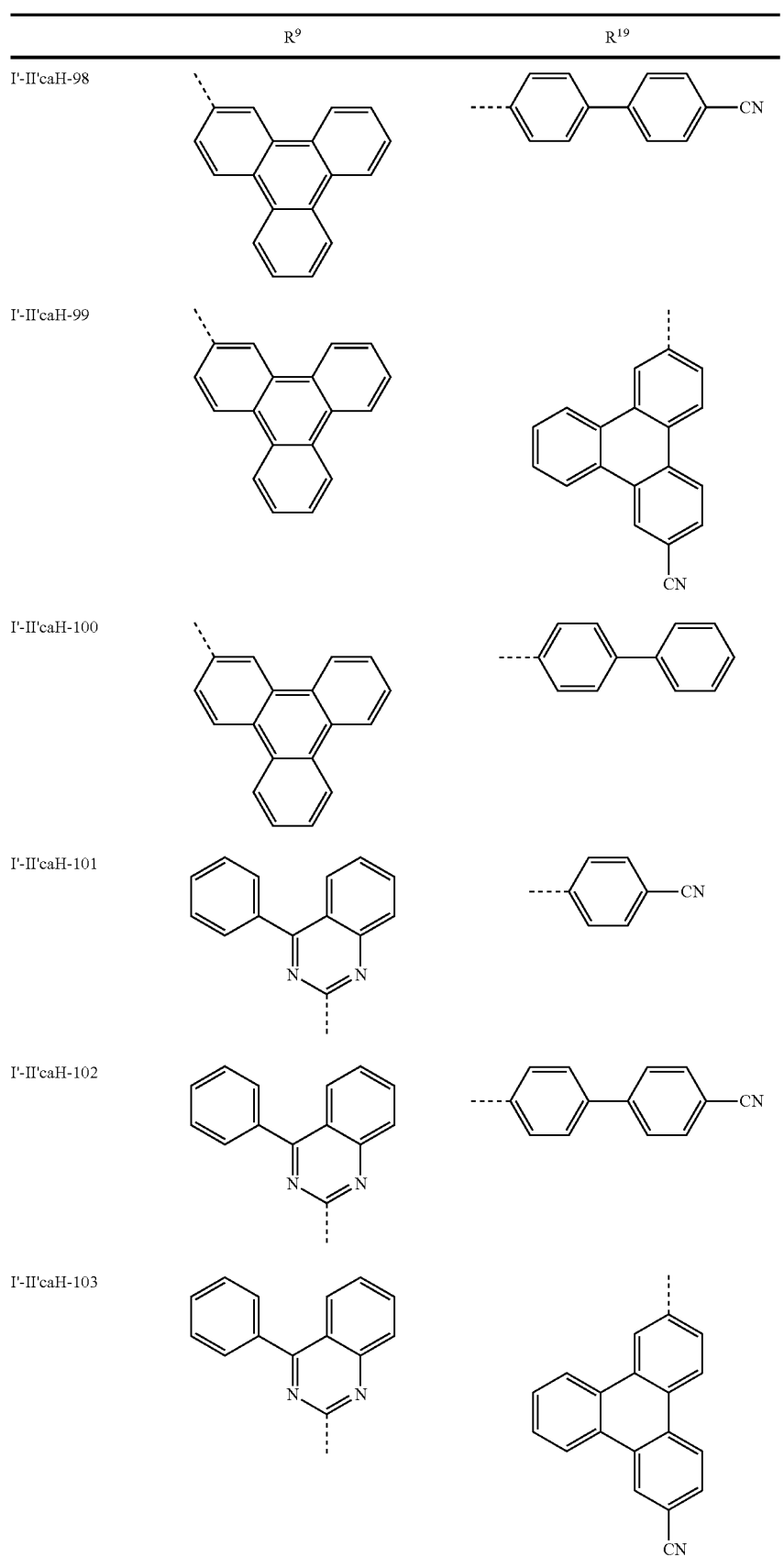

-continued
| | R⁹ | R¹⁹ |
|---|---|---|
| I'-II'caH-104 | | |
| I'-II'caH-105 | | |
| I'-II'caH-106 | | |
| I'-II'caH-107 | | |
| I'-II'caH-108 | | |
| I'-II'caH-109 | | |
| I'-II'caH-110 | | |
| I'-II'caH-111 | | |
| I'-II'caH-112 | | |
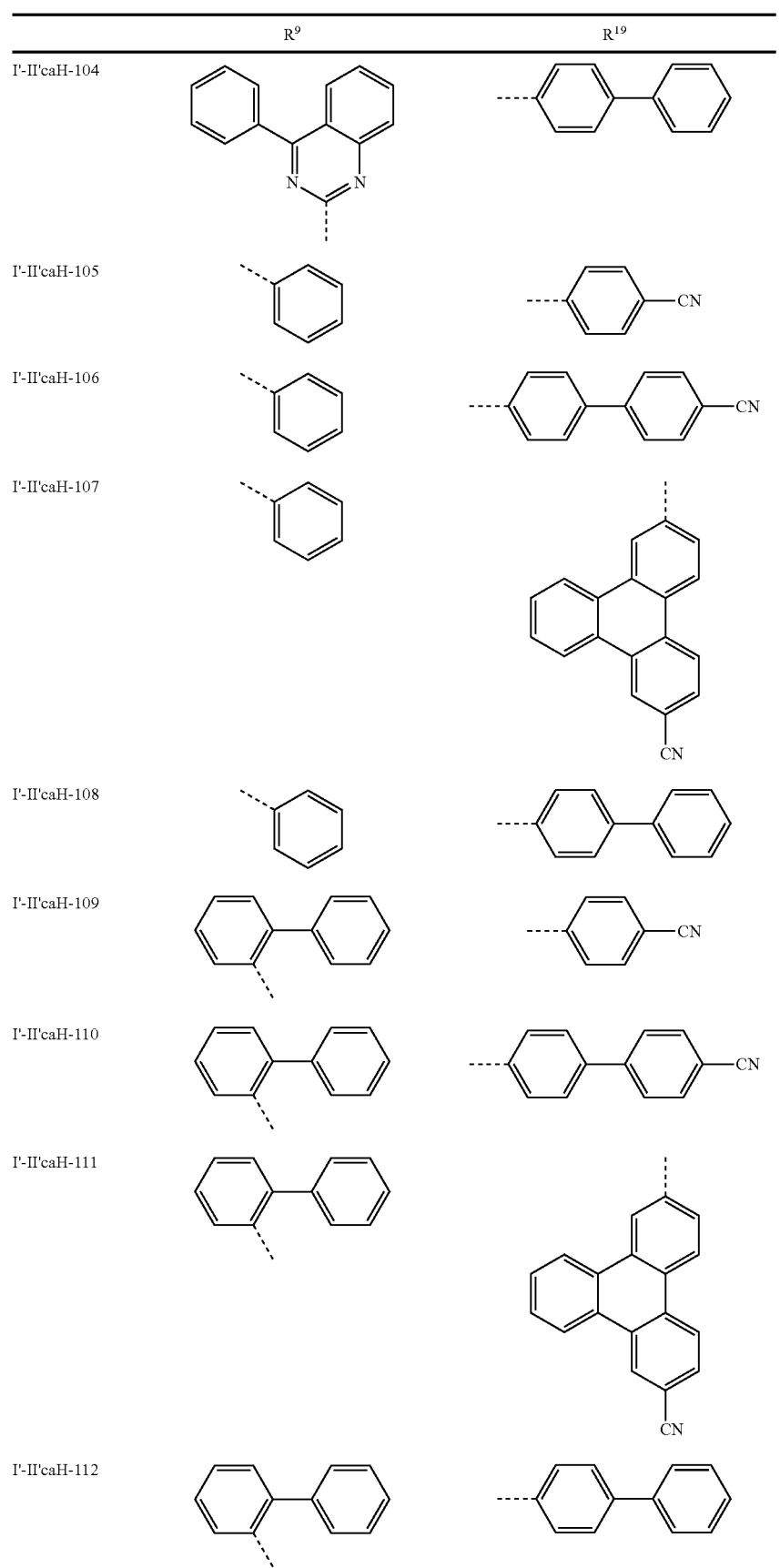

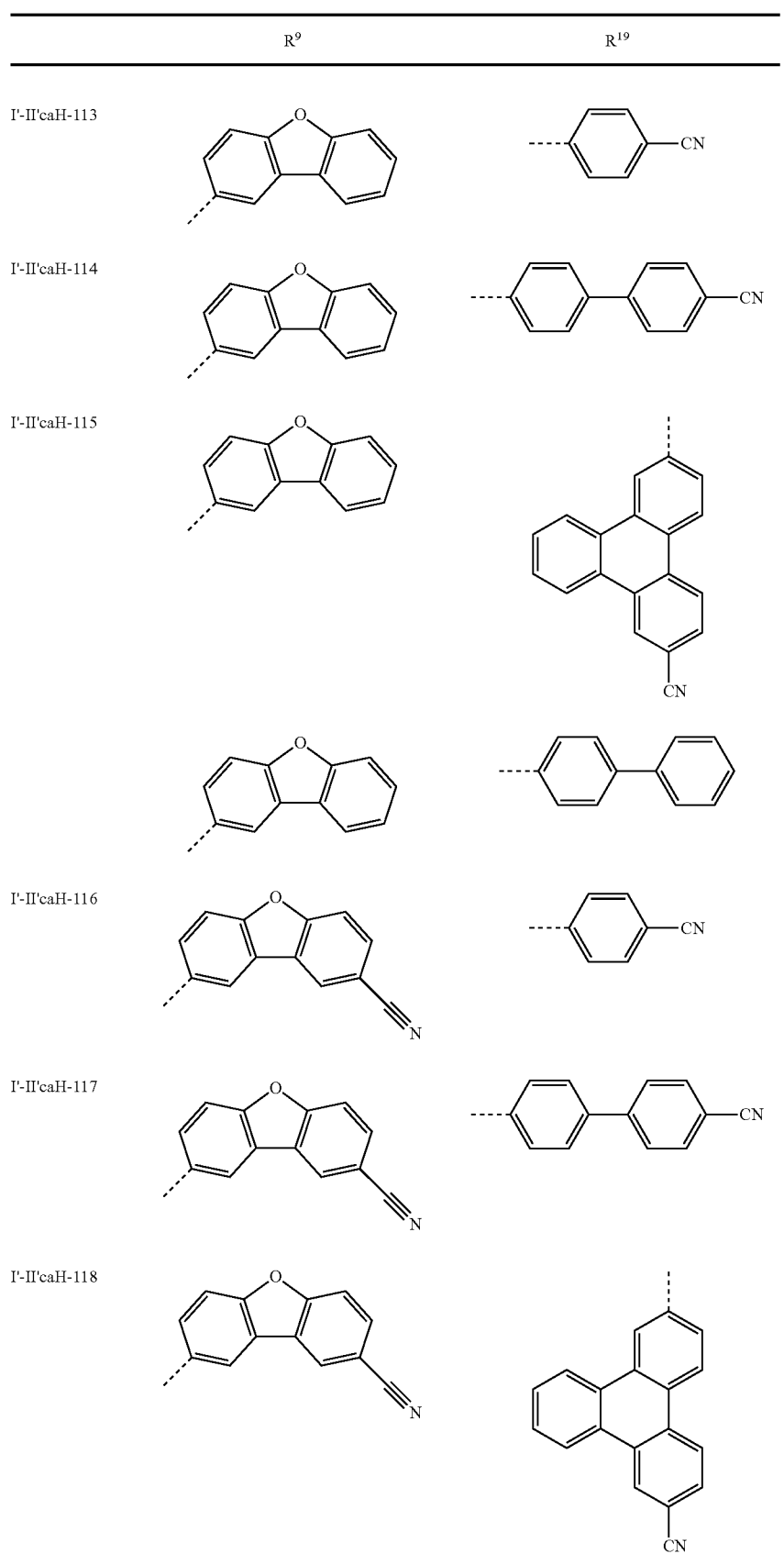

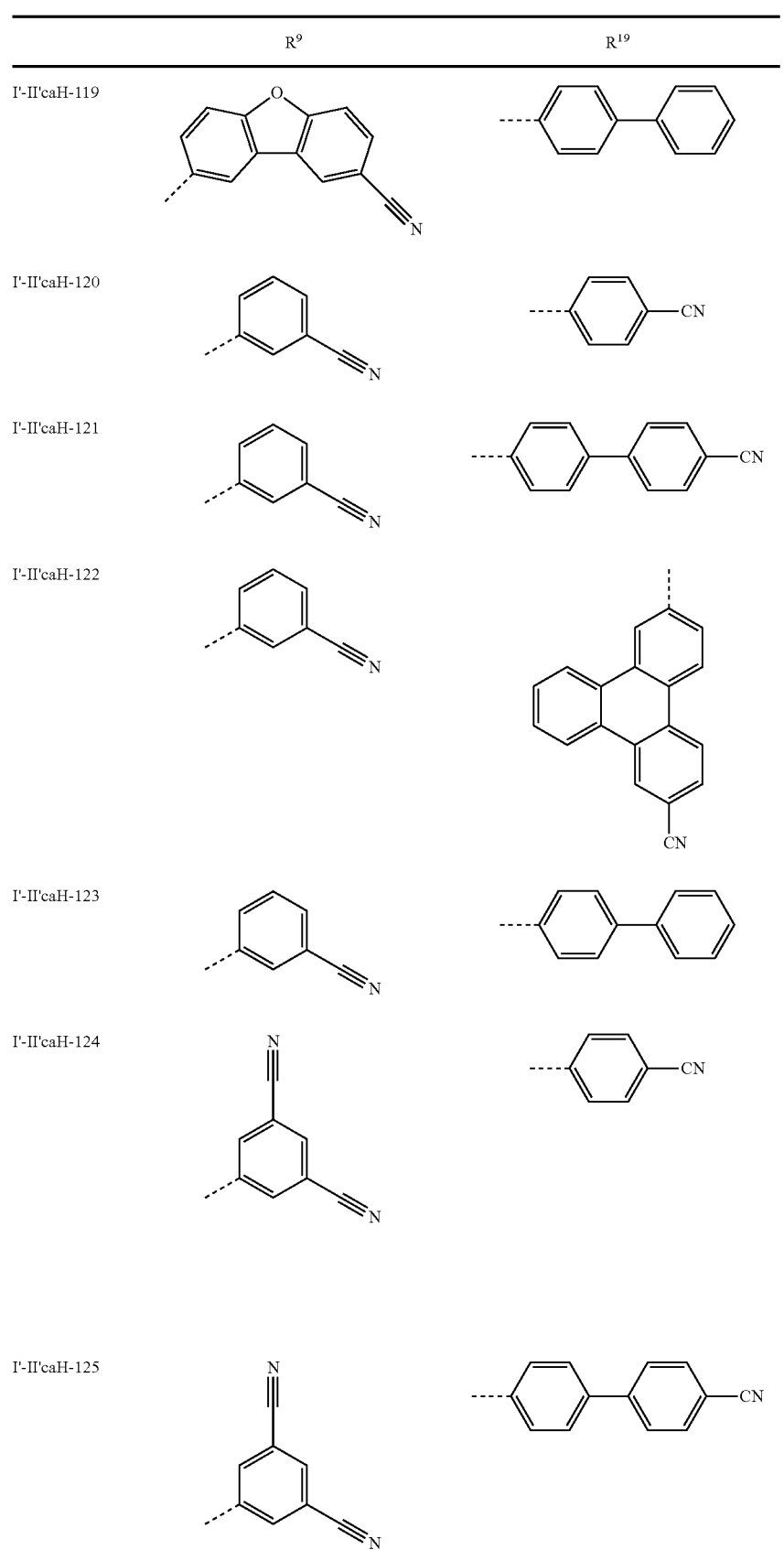

-continued
| | R⁹ | R¹⁹ |
|---|---|---|
| I'-II'caH-126 | | |
| I'-II'caH-127 | | |
| I'-II'caH-128 | | |
| I'-II'caH-129 | | |
| I'-II'caH-130 | | |
| I'-II'caH-131 | | |
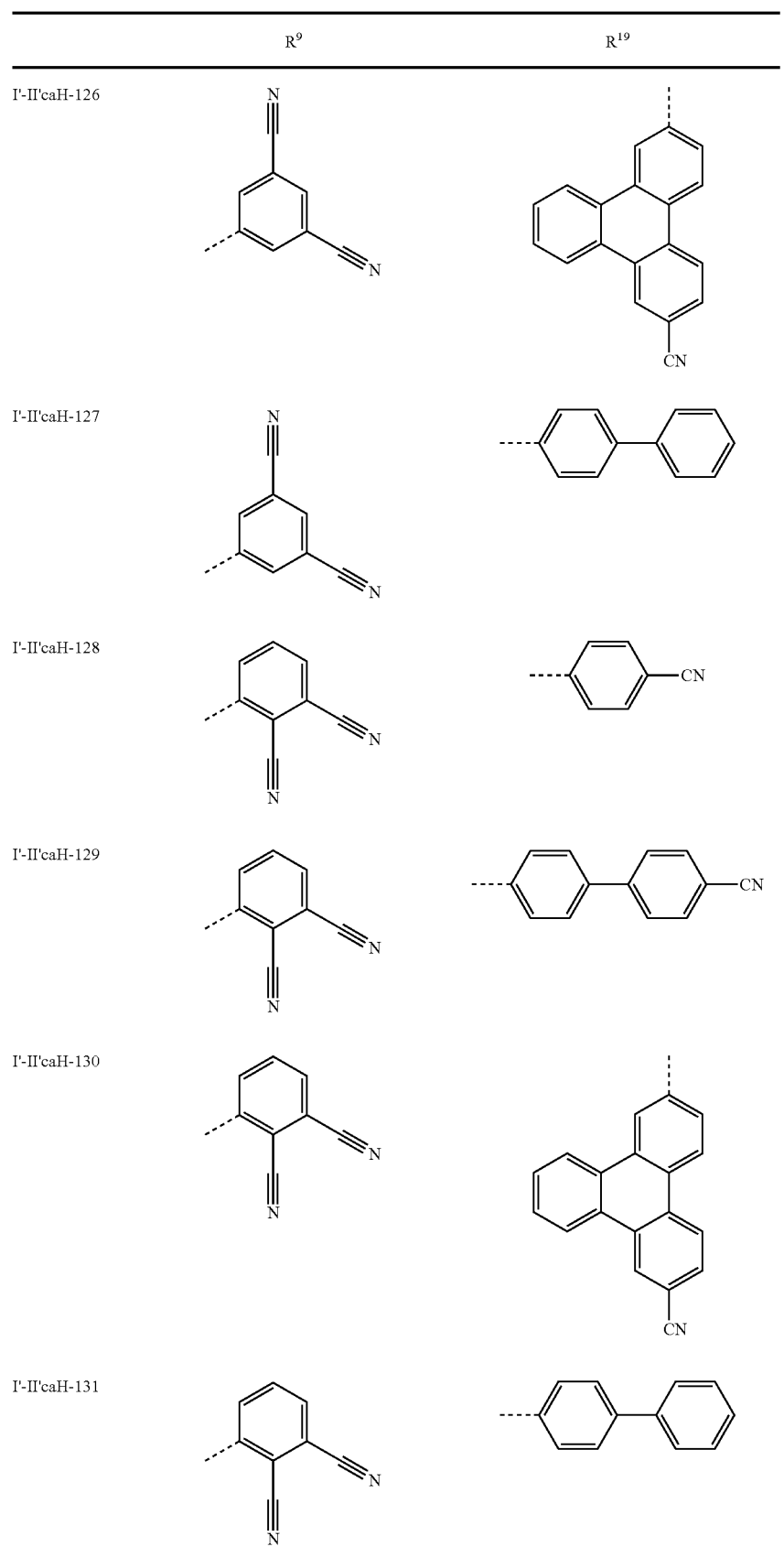

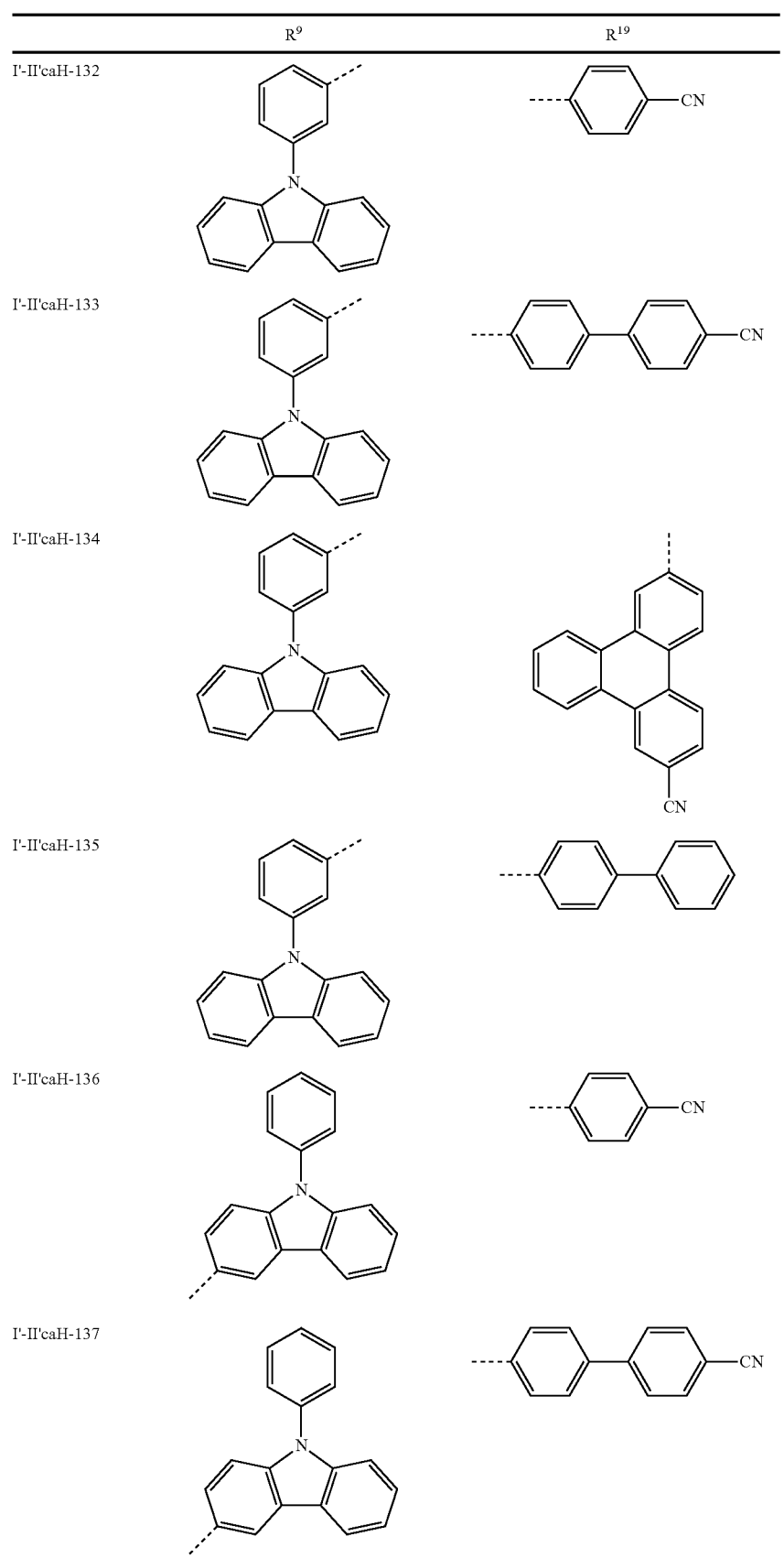

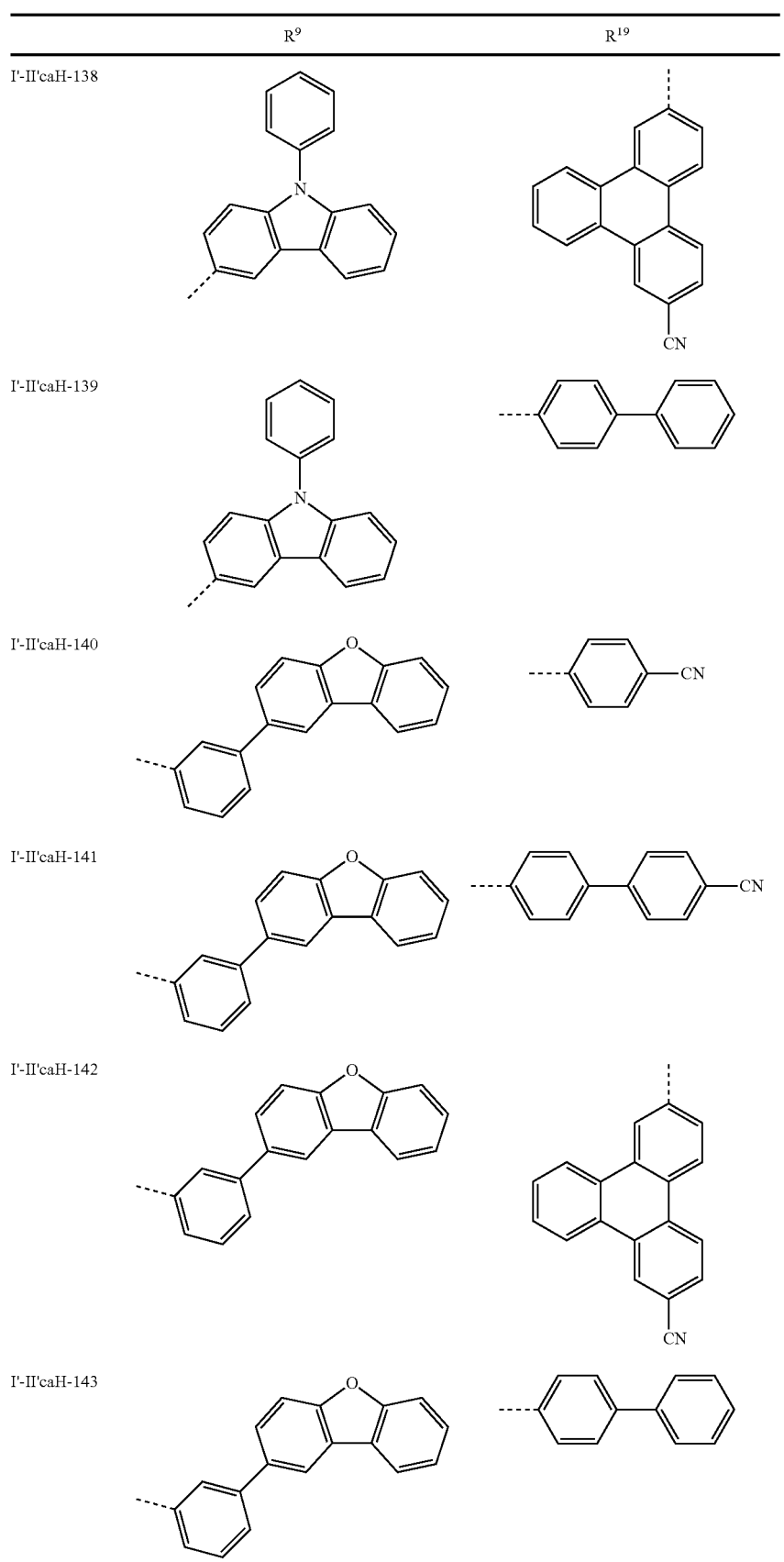

-continued
| | R⁹ | R¹⁹ |
|---|---|---|
| I'-II'caH-144 | | |
| I'-II'caH-145 | | |
| I'-II'caH-146 | | |
| I'-II'caH-147 | | |
| I'-II'caH-148 | | |
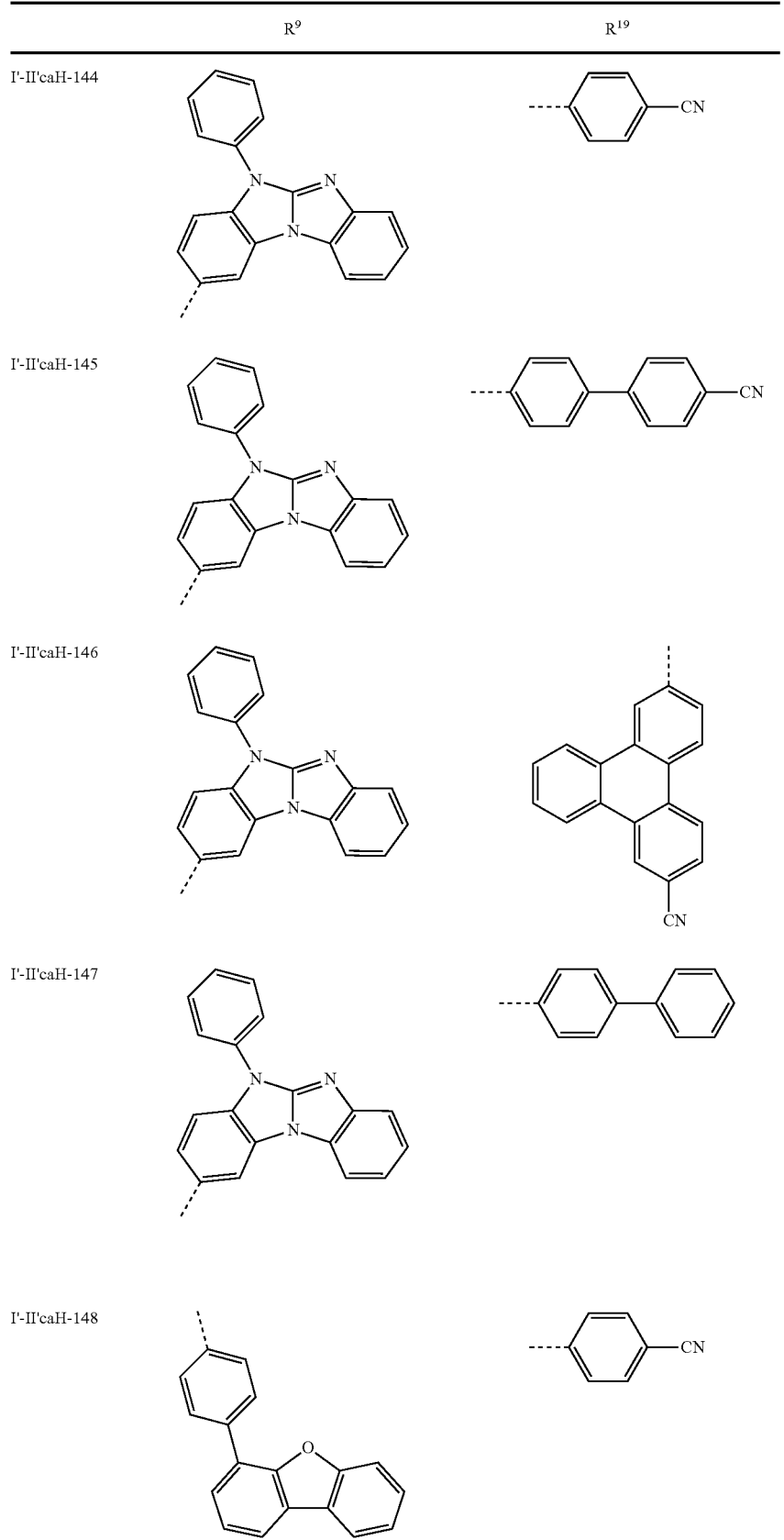

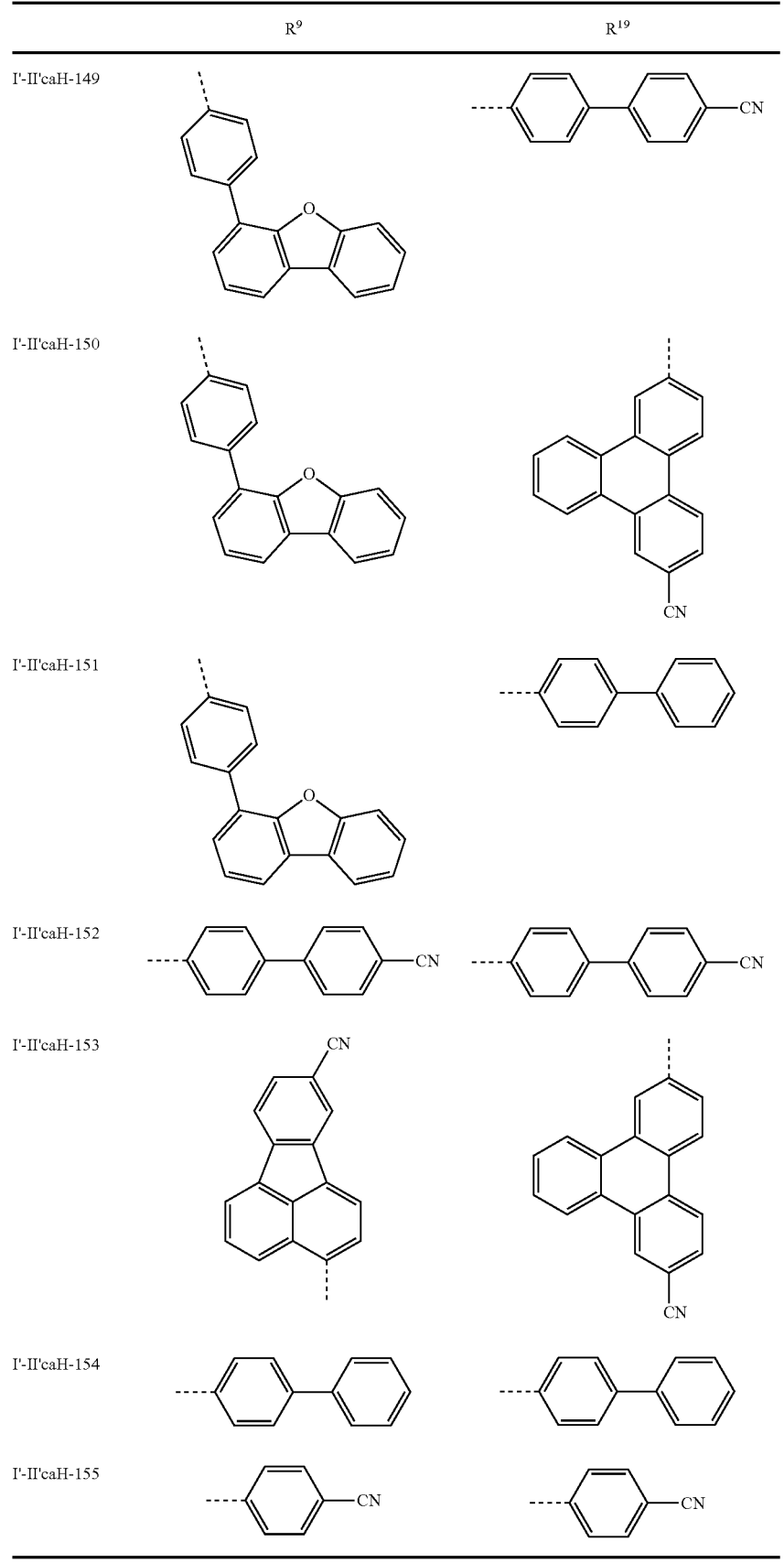

The dotted lines are bonding sites.
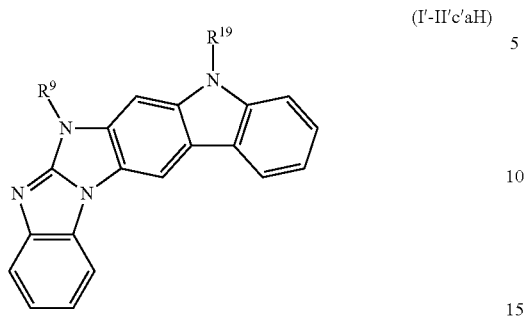
(I'-II'c'aH)
| | R⁹ | R¹⁹ |
|---|---|---|
| I'-II'c'aH-1 | | |
| I'-II'c'aH-2 | phenyl | phenyl |
| I'-II'c'aH-3 | 2-biphenyl | 2-biphenyl |
| I'-II'c'aH-4 | dibenzofuranyl | dibenzofuranyl |
| I'-II'c'aH-5 | cyano-dibenzofuranyl | cyano-dibenzofuranyl |
| I'-II'c'aH-6 | 3-cyanophenyl | 3-cyanophenyl |
| I'-II'c'aH-7 | 3,5-dicyanophenyl | 3,5-dicyanophenyl |
| I'-II'c'aH-8 | 2,3-dicyanophenyl | 2,3-dicyanophenyl |

-continued
I'-II'c'aH-9 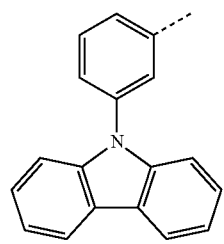 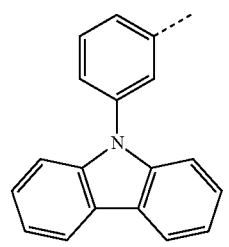
I'-II'c'aH-10 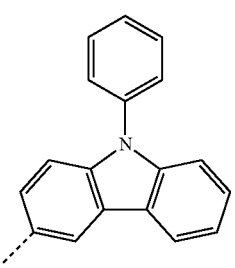 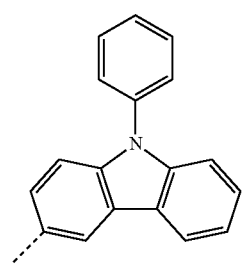
I'-II'c'aH-11 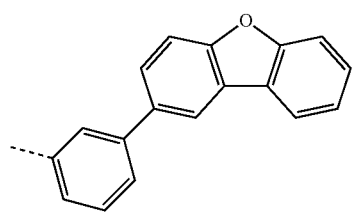 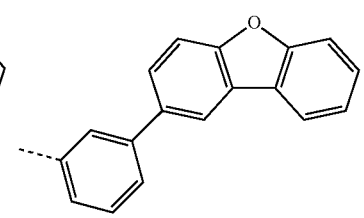
I'-II'c'aH-12 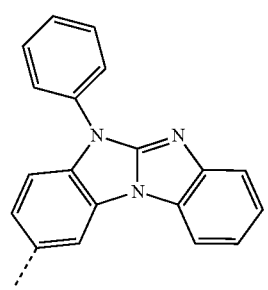 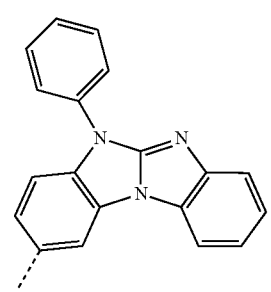
I'-II'c'aH-13 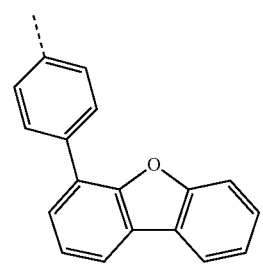 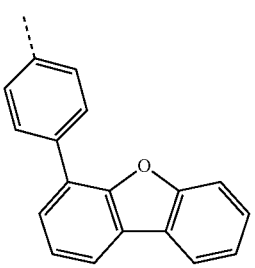
I'-II'c'aH-14 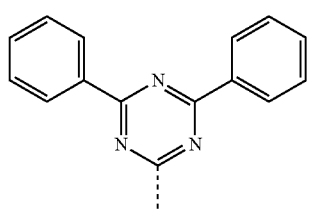 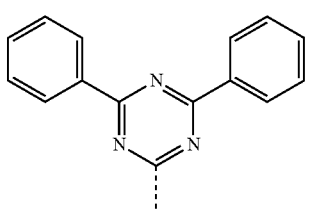

-continued
I'-II'c'aH-15 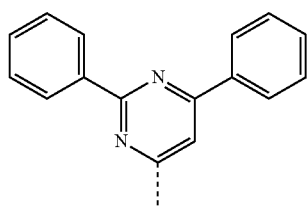 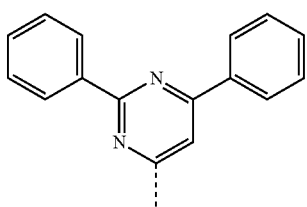
I'-II'c'aH-16 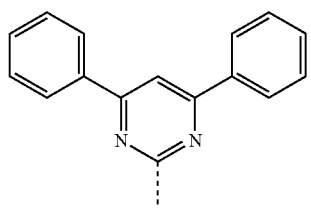 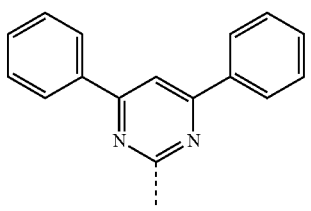
I'-II'c'aH-17 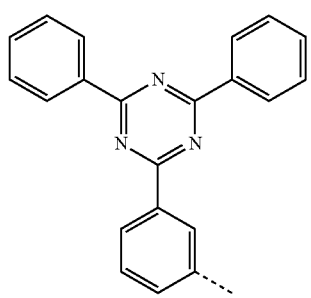 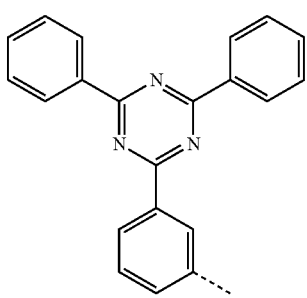
I'-II'c'aH-18 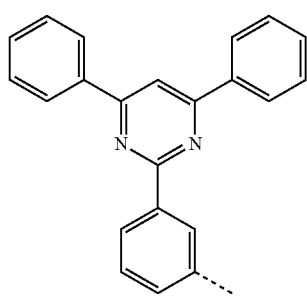 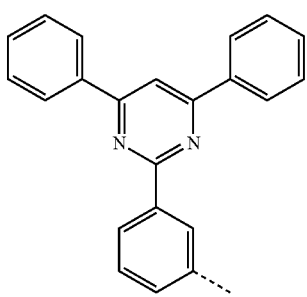
I'-II'c'aH-19 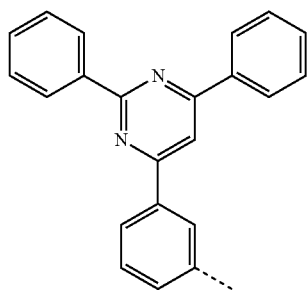 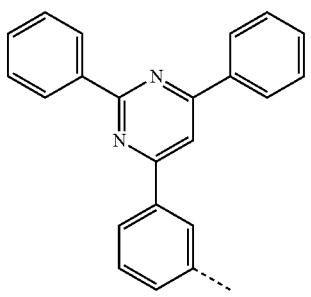
I'-II'c'aH-20 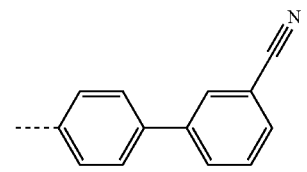 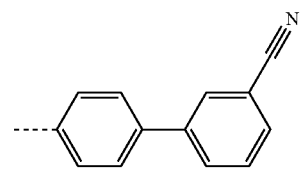

-continued
I'-II'c'aH-21 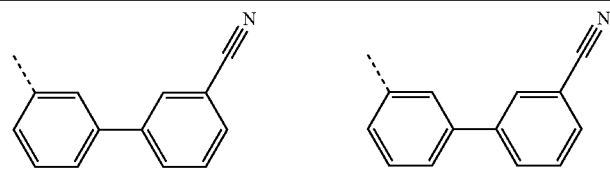
I'-II'c'aH-22 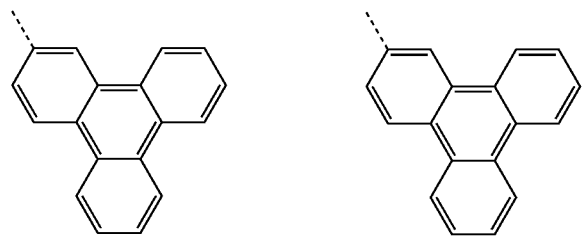
I'-II'c'aH-23 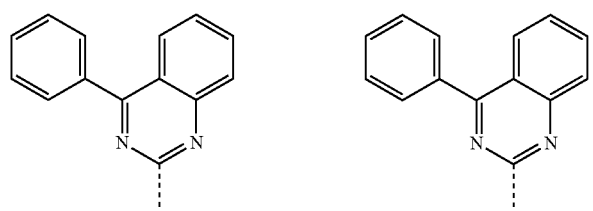
I'-II'c'aH-24 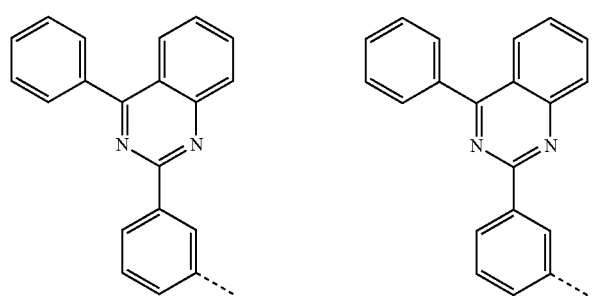
I'-II'c'aH-25 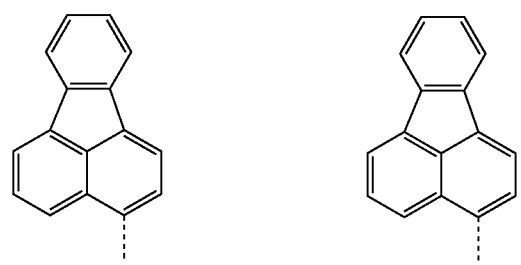
I'-II'c'aH-26 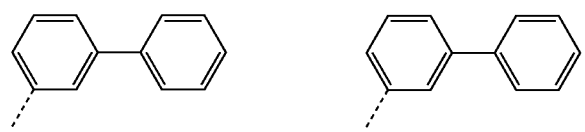
I'-II'c'aH-27 
I'-II'c'aH-28 

|  |  |  |
|---|---|---|
| I'-II'c'aH-29 | 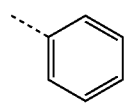 | 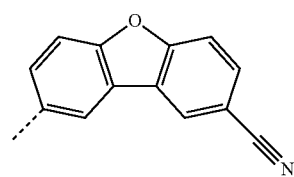 |
| I'-II'c'aH-30 | 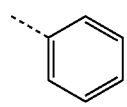 | 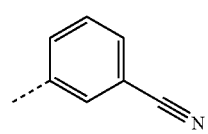 |
| I'-II'c'aH-31 | 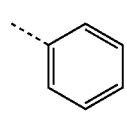 | 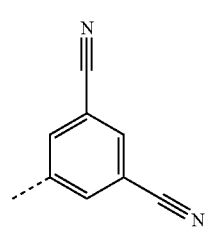 |
| I'-II'c'aH-32 | 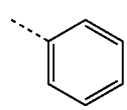 | 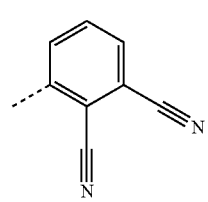 |
| I'-II'c'aH-33 | 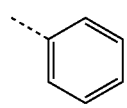 | 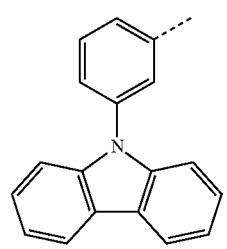 |
| I'-II'c'aH-34 | 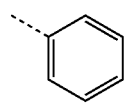 | 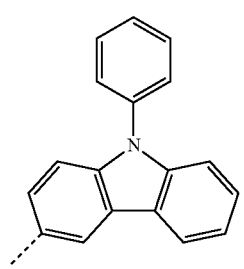 |
| I'-II'c'aH-35 | 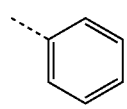 | 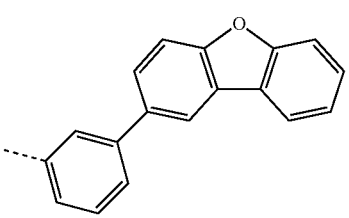 |

| | | |
|---|---|---|
| I'-II'c'aH-36 | 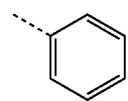 | 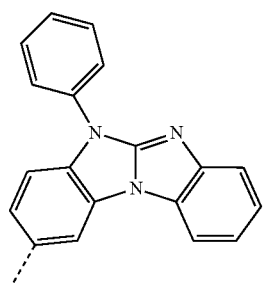 |
| I'-II'c'aH-37 | 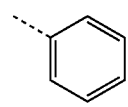 | 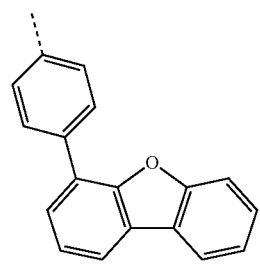 |
| I'-II'c'aH-38 | 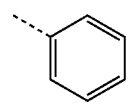 | 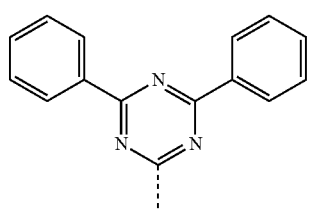 |
| I'-II'c'aH-39 | 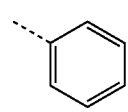 | 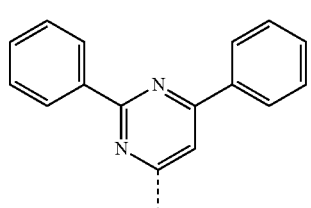 |
| I'-II'c'aH-40 | 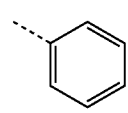 | 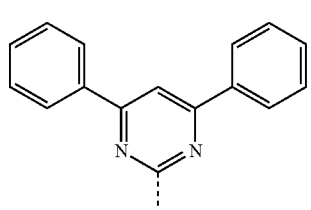 |
| I'-II'c'aH-41 | 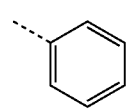 | 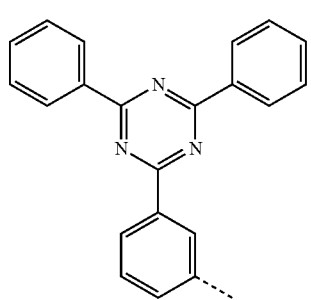 |

I'-II'c'aH-42 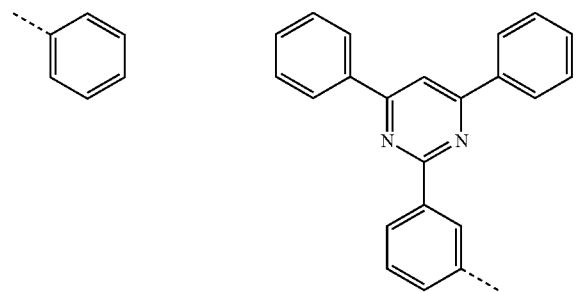
I'-II'c'aH-43 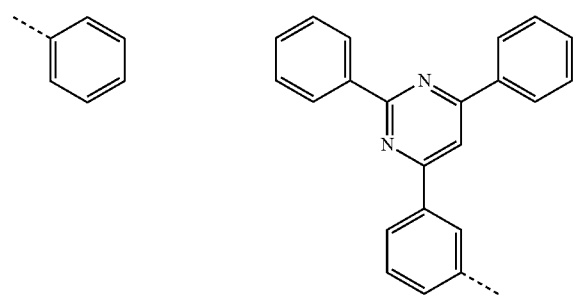
I'-II'c'aH-44 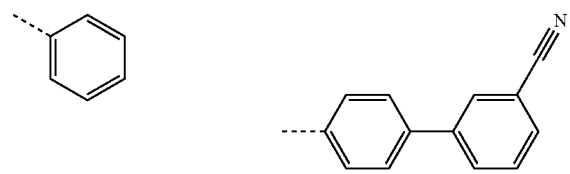
I'-II'c'aH-45 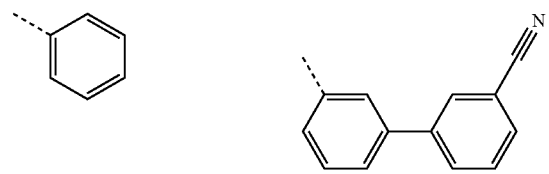
I'-II'c'aH-46 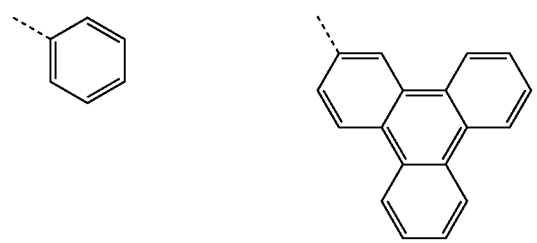
I'-II'c'aH-47 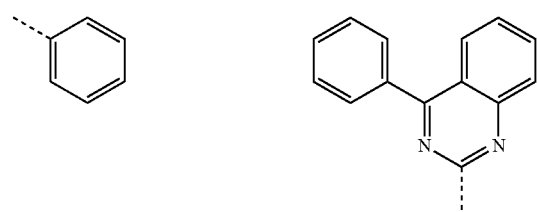

-continued
| | | |
|---|---|---|
| I'-II'c'aH-48 | 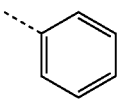 | 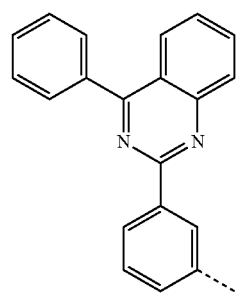 |
| I'-II'c'aH-49 | 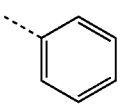 | 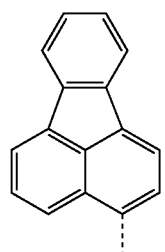 |
| I'-II'c'aH-50 | 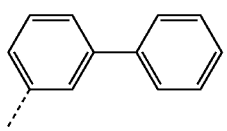 | 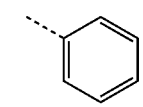 |
| I'-II'c'aH-51 | 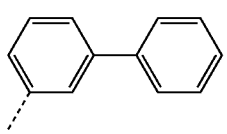 | 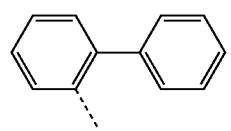 |
| I'-II'c'aH-52 | 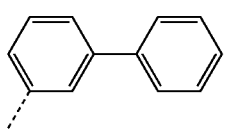 | 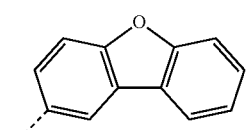 |
| I'-II'c'aH-53 | 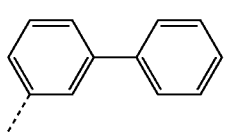 | 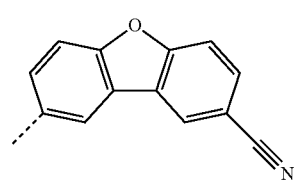 |
| I'-II'c'aH-54 | 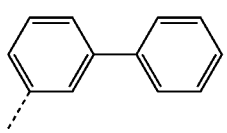 | 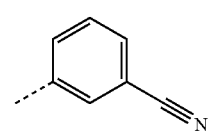 |
| I'-II'c'aH-55 | 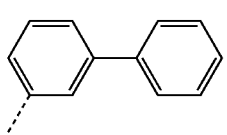 | 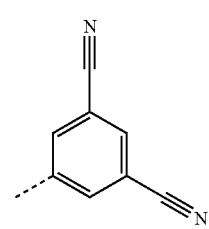 |

I'-II'c'aH-56 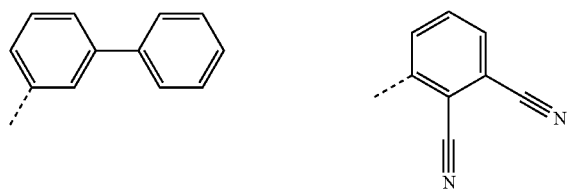
I'-II'c'aH-57 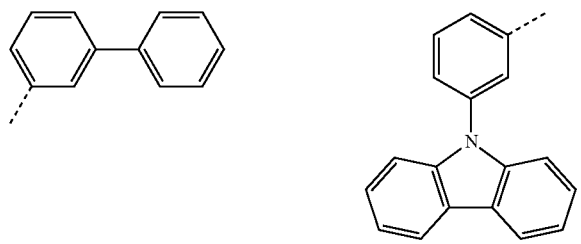
I'-II'c'aH-58 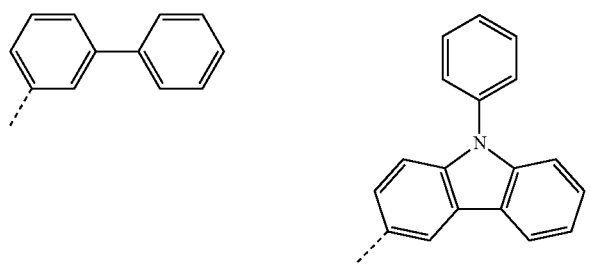
I'-II'c'aH-59 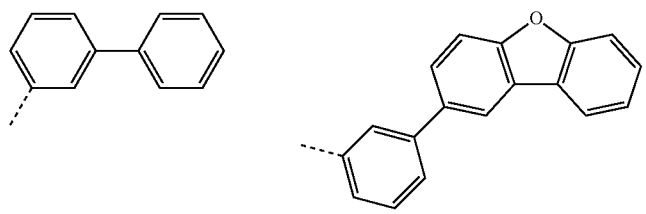
I'-II'c'aH-60 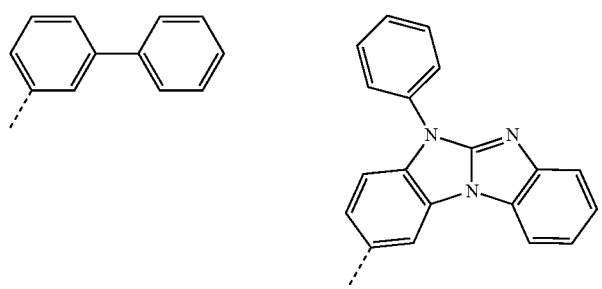
I'-II'c'aH-61 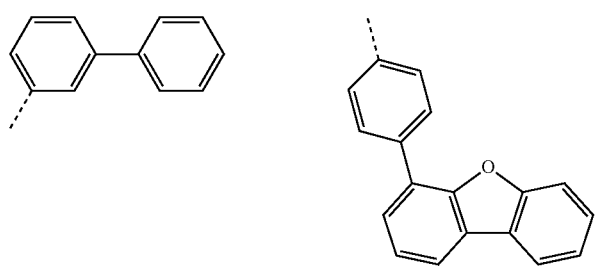

-continued
I'-II'c'aH-62 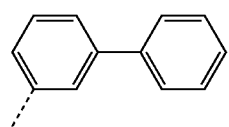 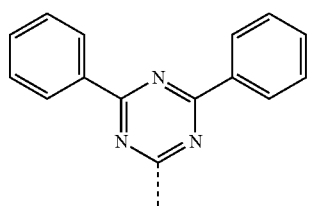
I'-II'c'aH-63 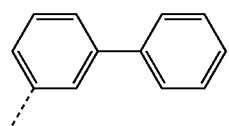 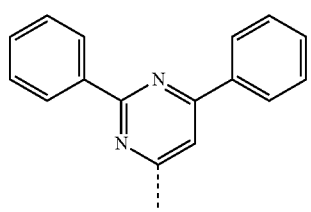
I'-II'c'aH-64 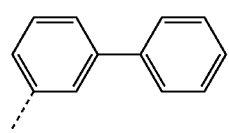 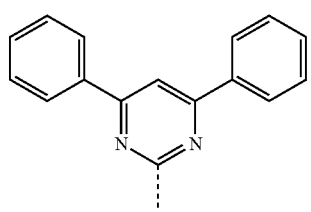
I'-II'c'aH-65 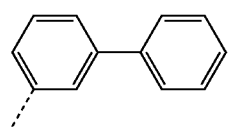 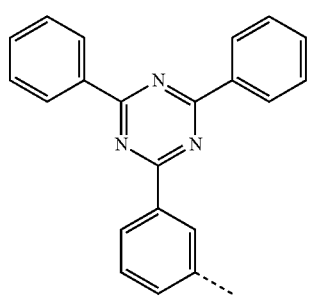
I'-II'c'aH-66 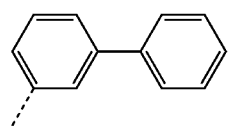 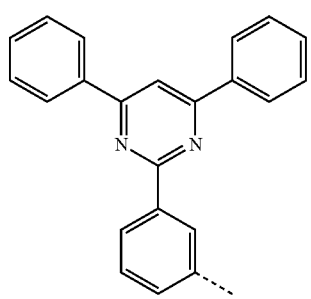
I'-II'c'aH-67 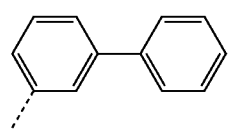 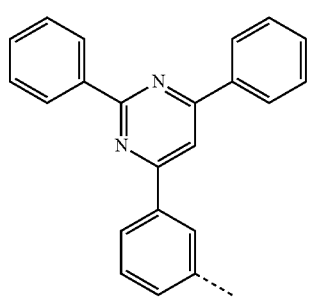

-continued
| | | |
|---|---|---|
| I'-II'c'aH-68 | 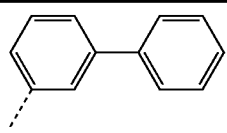 | 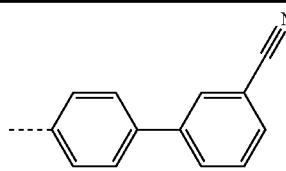 |
| I'-II'c'aH-69 | 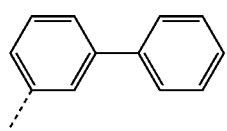 | 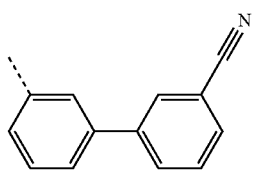 |
| I'-II'c'aH-70 | 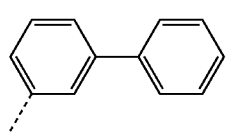 | 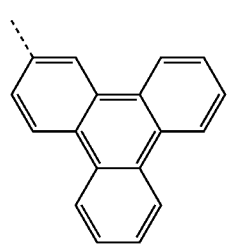 |
| I'-II'c'aH-71 | 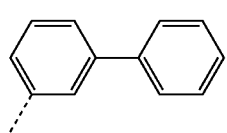 | 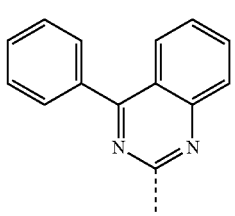 |
| I'-II'c'aH-72 | 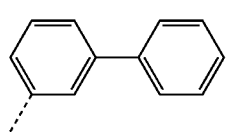 | 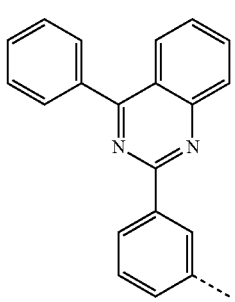 |
| I'-II'c'aH-73 | 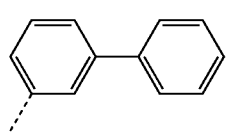 | 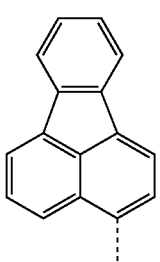 |
| I'-II'c'aH-74 | 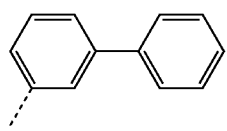 | 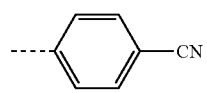 |
| I'-II'c'aH-75 | 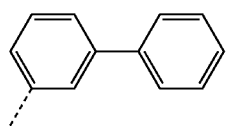 | 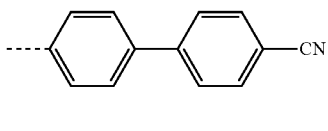 |

-continued
| | | |
|---|---|---|
| I'-II'c'aH-76 | 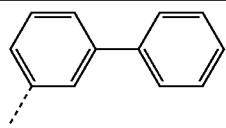 | 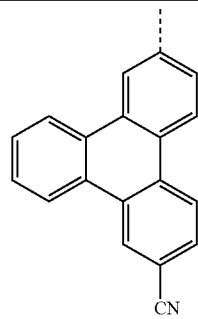 |
| I'-II'c'aH-77 | 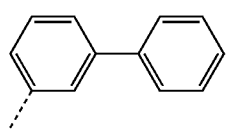 | 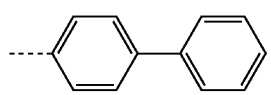 |
| I'-II'c'aH-78 | 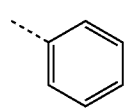 | 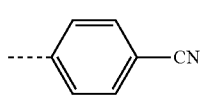 |
| I'-II'c'aH-79 | 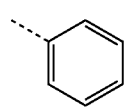 | 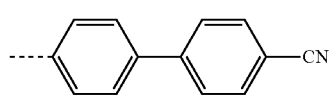 |
| I'-II'c'aH-80 | 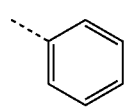 | 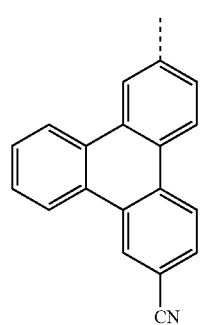 |
| I'-II'c'aH-81 | 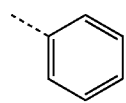 | 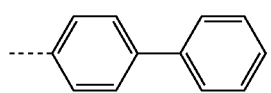 |
| I'-II'c'aH-82 | 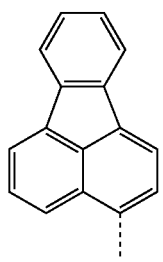 | 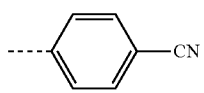 |
| I'-II'c'aH-83 | 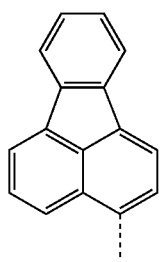 | 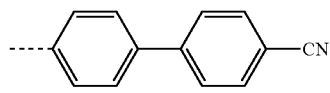 |

-continued
| | | |
|---|---|---|
| I'-II'c'aH-84 | 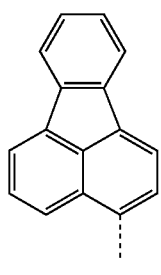 | 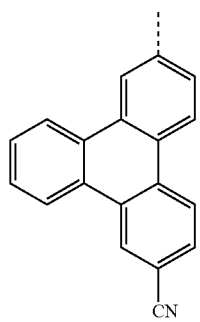 |
| I'-II'c'aH-85 | 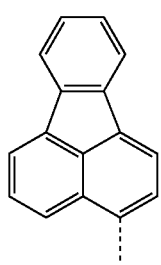 | 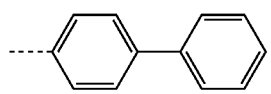 |
| I'-II'c'aH-86 | 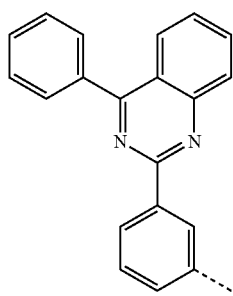 | 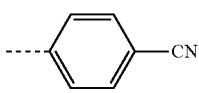 |
| I'-II'c'aH-87 | 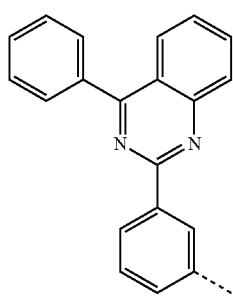 | 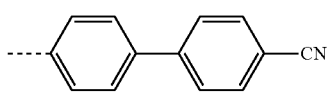 |
| I'-II'c'aH-88 | 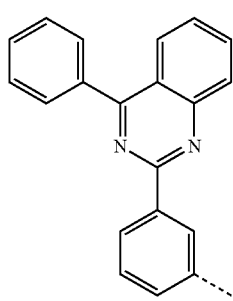 | 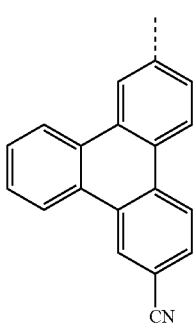 |

| | | |
|---|---|---|
| I'-II'c'aH-89 | 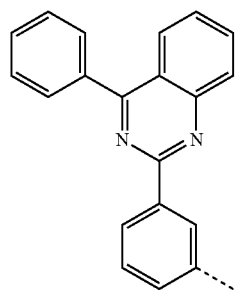 | 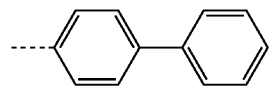 |
| I'-II'c'aH-90 | 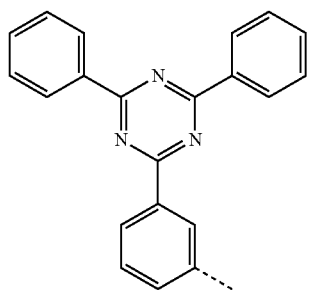 | 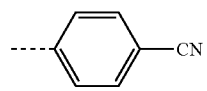 |
| I'-II'c'aH-91 | 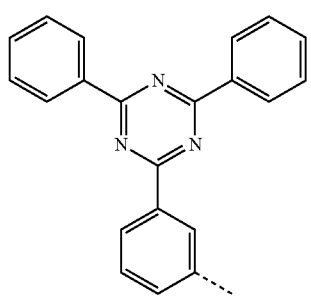 | 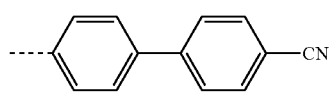 |
| I'-II'c'aH-92 | 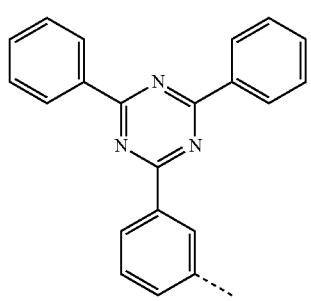 | 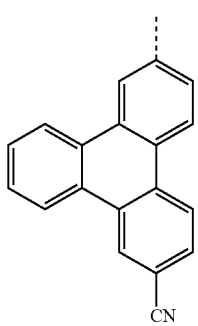 |
| I'-II'c'aH-93 | 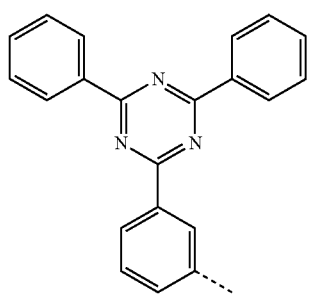 | 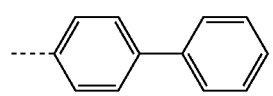 |

-continued
I'-II'c'aH-94 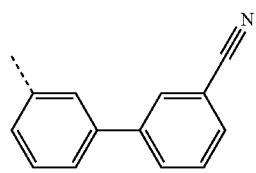 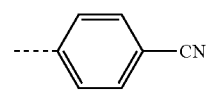
I'-II'c'aH-95 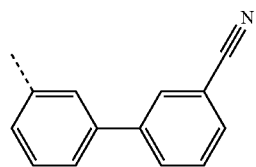 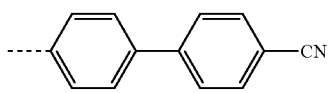
I'-II'c'aH-96 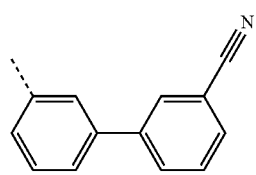 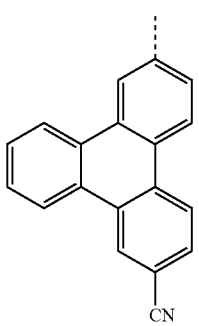
I'-II'c'aH-97 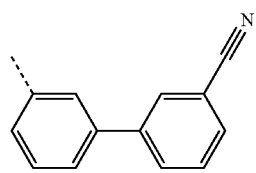 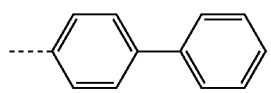
I'-II'c'aH-98 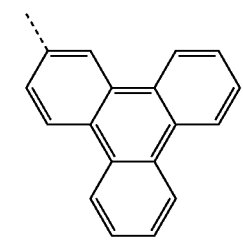 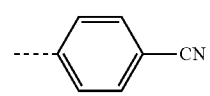
I'-II'c'aH-99 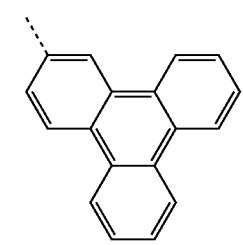 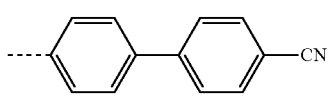

-continued
| | | |
|---|---|---|
| I'-II'c'aH-100 | 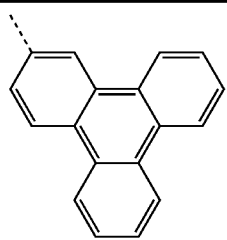 | 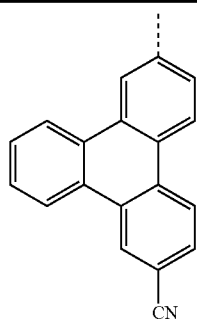 |
| I'-II'c'aH-101 | 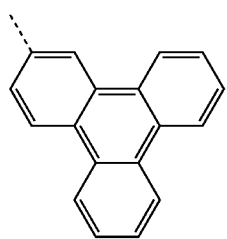 | 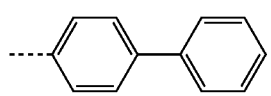 |
| I'-II'c'aH-102 | 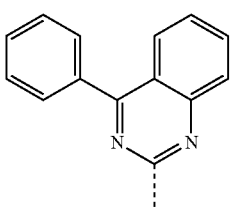 | 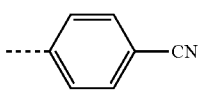 |
| I'-II'c'aH-103 | 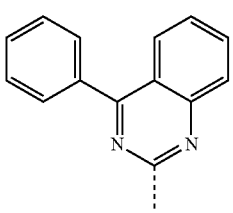 | 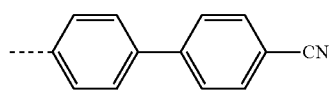 |
| I'-II'c'aH-104 | 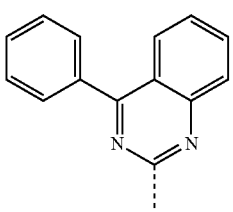 | 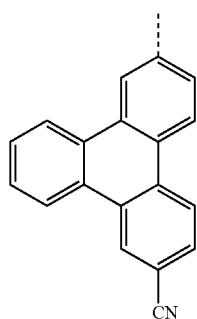 |
| I'-II'c'aH-105 | 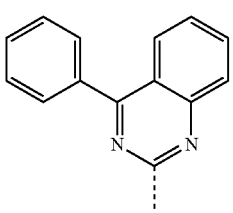 | 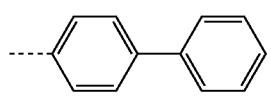 |
| I'-II'c'aH-106 | 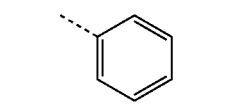 | 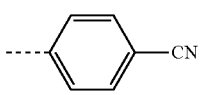 |

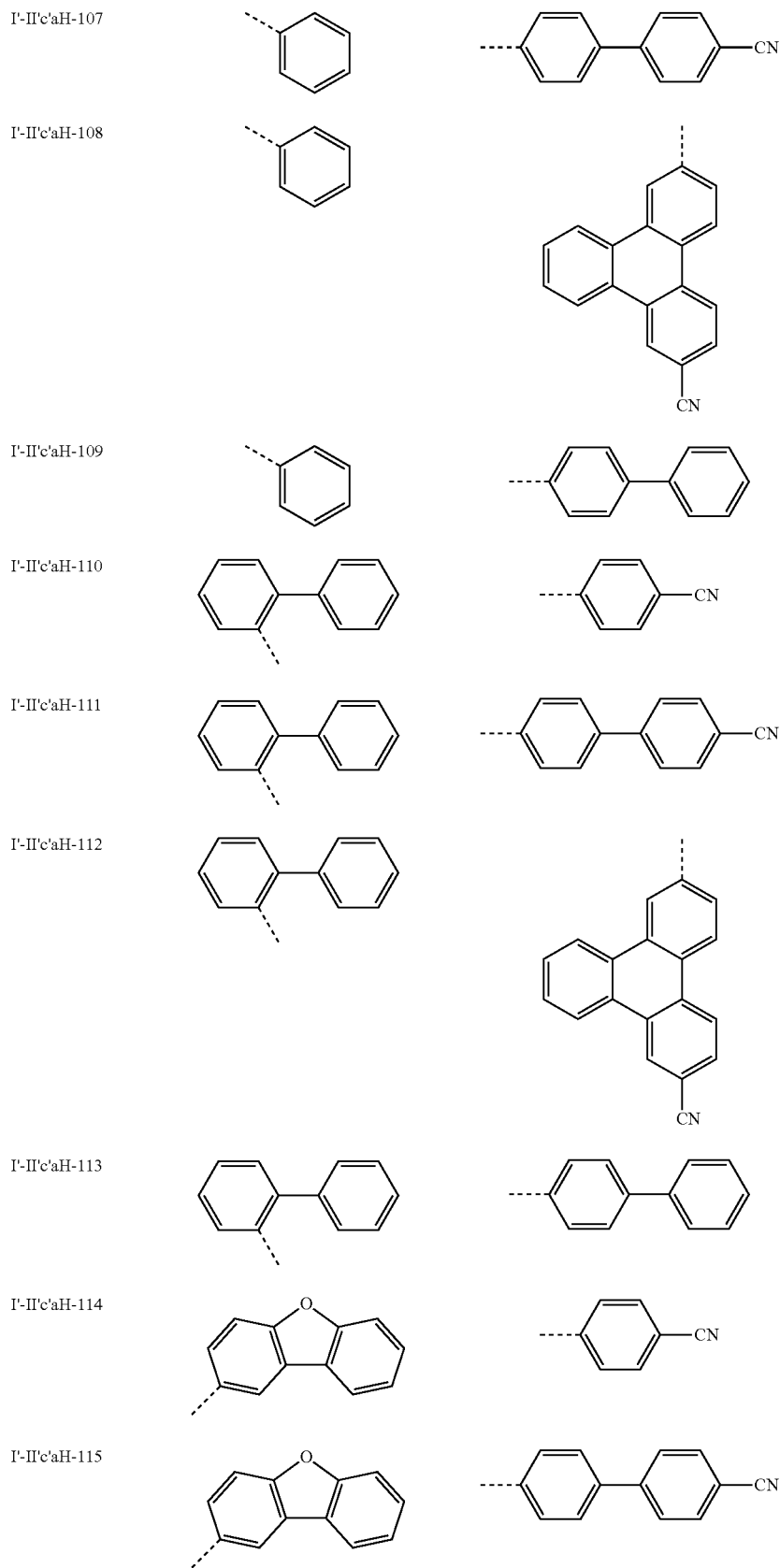

-continued
| | | |
|---|---|---|
| I'-II'c'aH-116 | 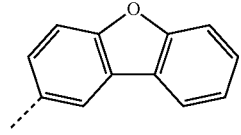 | 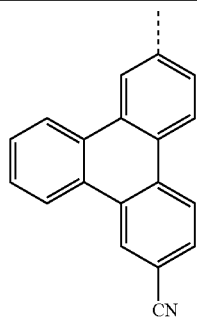 |
| I'-II'c'aH-117 | 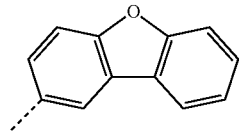 | 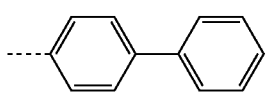 |
| I'-II'c'aH-118 | 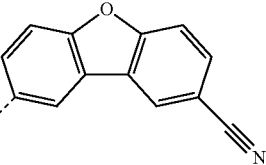 |  |
| I'-II'c'aH-119 | 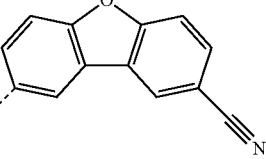 | 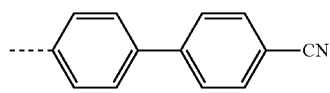 |
| I'-II'c'aH-120 | 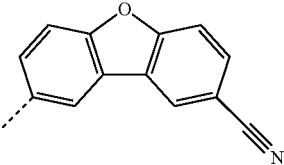 | 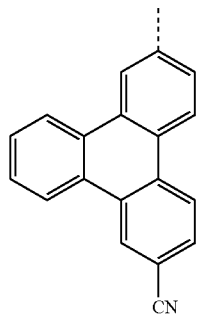 |
| I'-II'c'aH-121 | 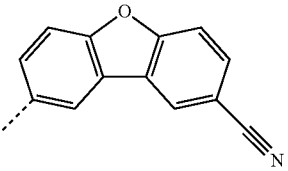 | 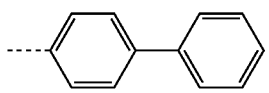 |
| I'-II'c'aH-122 | 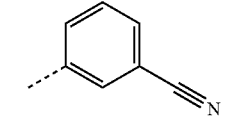 | 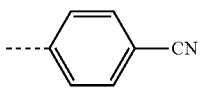 |
| I'-II'c'aH-123 | 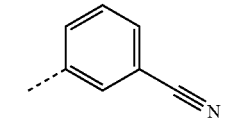 | 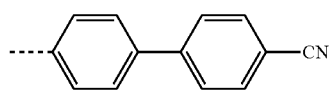 |

| | | |
|---|---|---|
| I'-II'c'aH-124 | 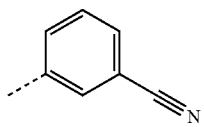 | 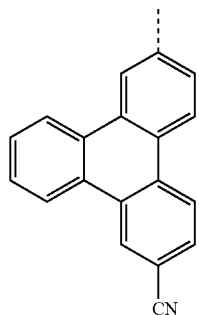 |
| I'-II'c'aH-125 | 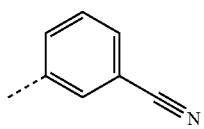 | 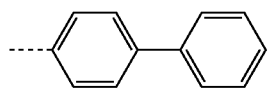 |
| I'-II'c'aH-126 | 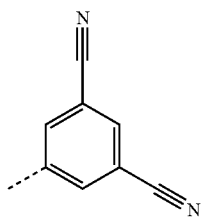 | 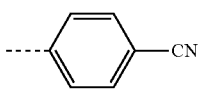 |
| I'-II'c'aH-127 | 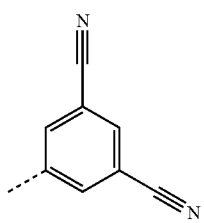 | 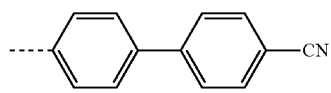 |
| I'-II'c'aH-128 | 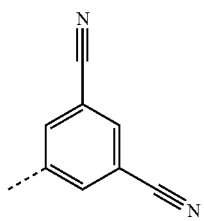 | 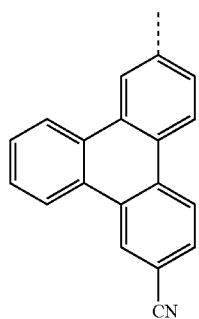 |
| I'-II'c'aH-129 | 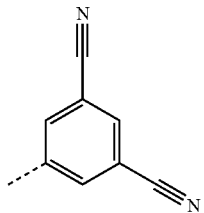 | 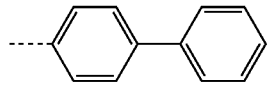 |
| I'-II'c'aH-130 | 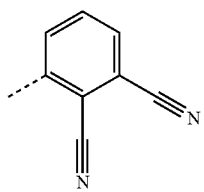 | 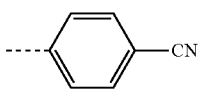 |

I'-II'c'aH-131 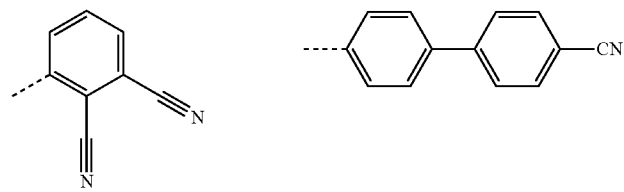
I'-II'c'aH-132 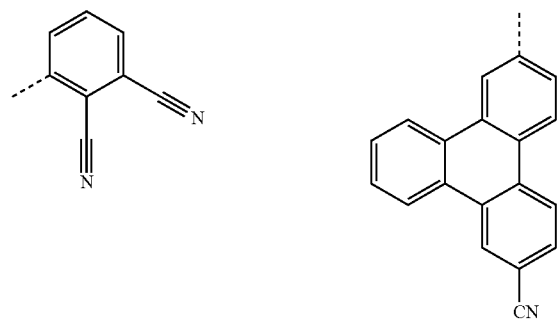
I'-II'c'aH-133 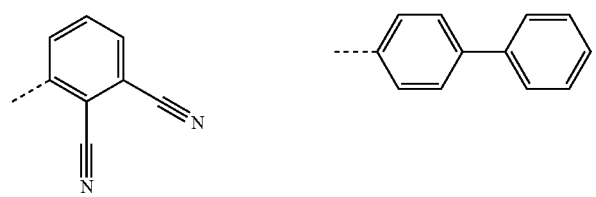
I'-II'c'aH-134 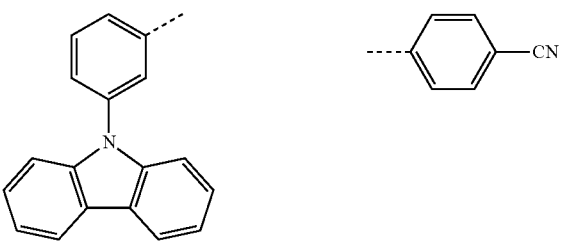
I'-II'c'aH-135 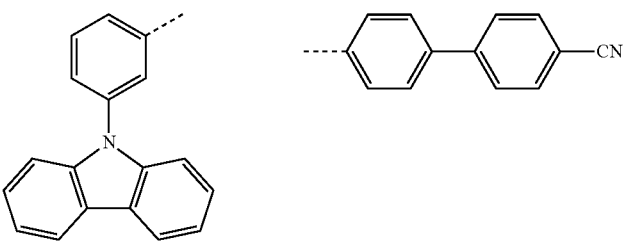
I'-II'c'aH-136 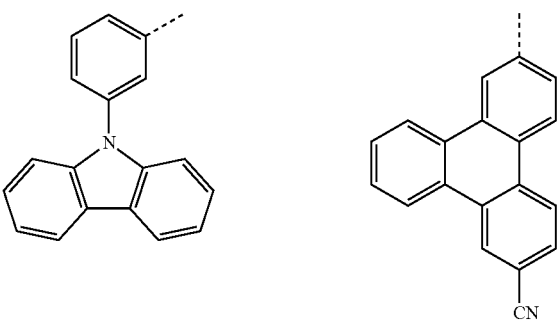

-continued
I'-II'c'aH-137 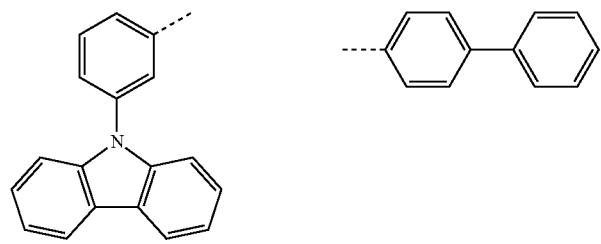
I'-II'c'aH-138 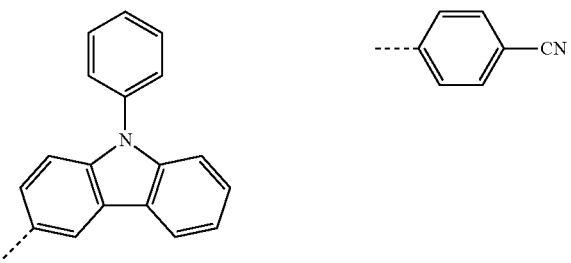
I'-II'c'aH-139 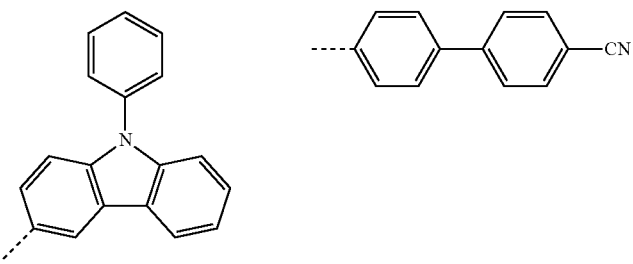
I'-II'c'aH-140 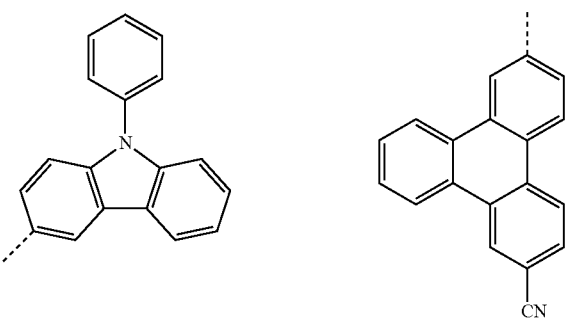
I'-II'c'aH-141 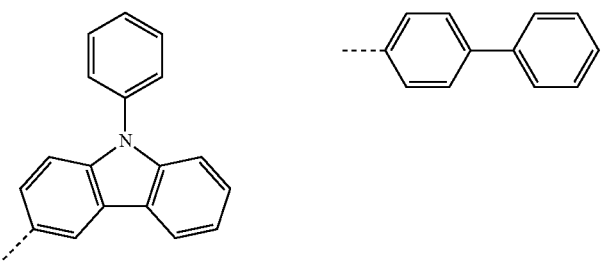
I'-II'c'aH-142 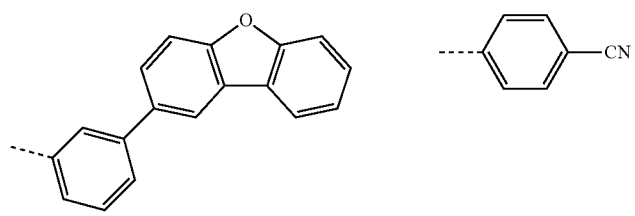

-continued
I'-II'c'aH-143 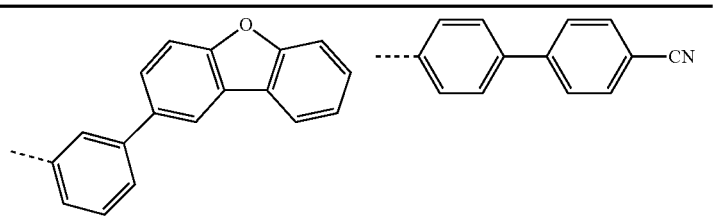
I'-II'c'aH-144 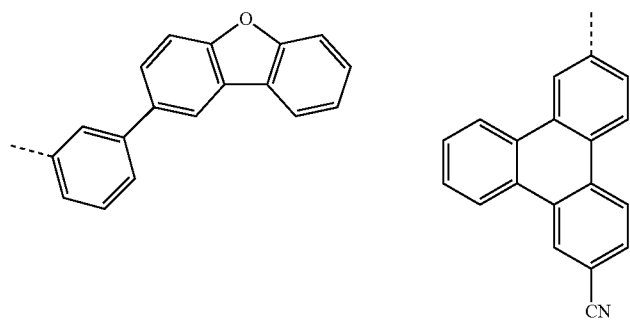
I'-II'c'aH-145 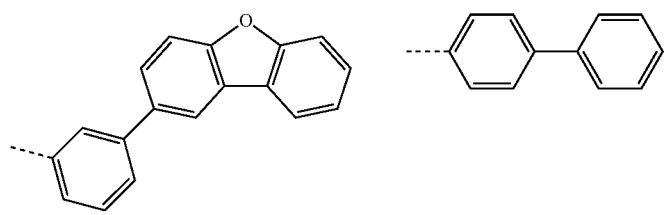
I'-II'c'aH-146 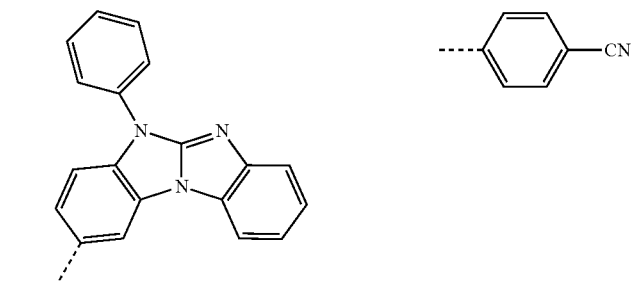
I'-II'c'aH-147 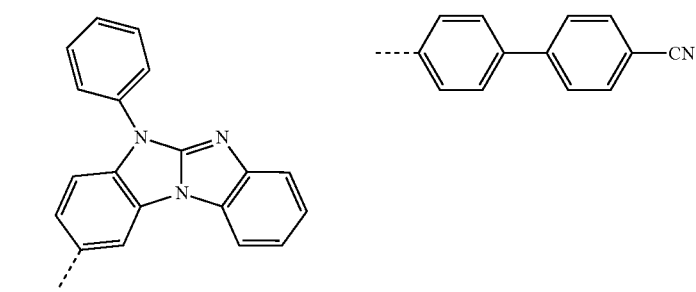
I'-II'c'aH-148 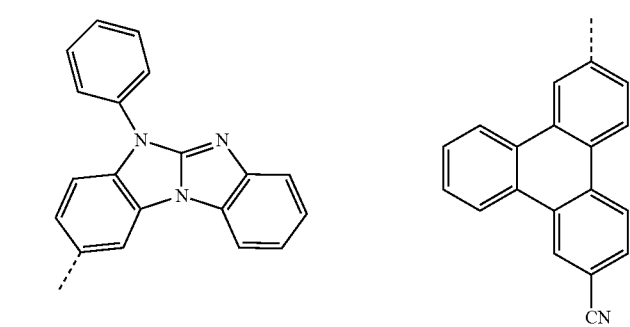

I'-II'c'aH-149 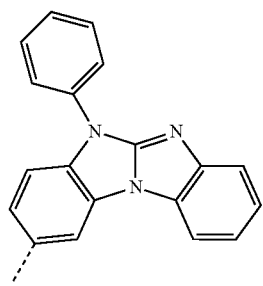 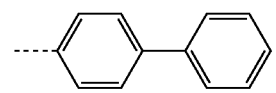
I'-II'c'aH-150 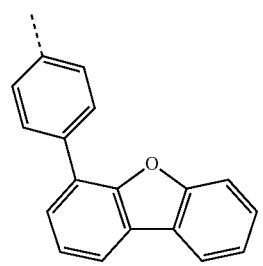 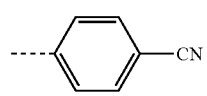
I'-II'c'aH-151 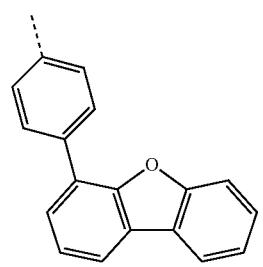 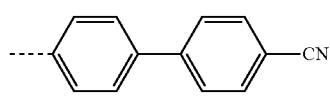
I'-II'c'aH-152 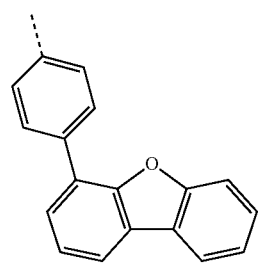 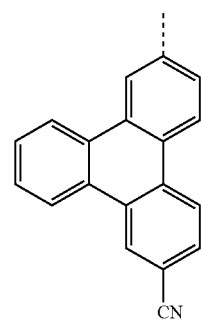
I'-II'c'aH-153 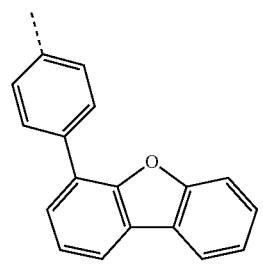 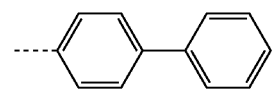
I'-II'c'aH-154 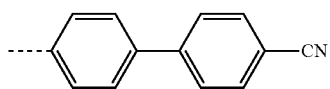 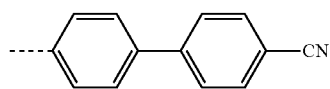

| | | |
|---|---|---|
| I'-II'c'aH-155 | 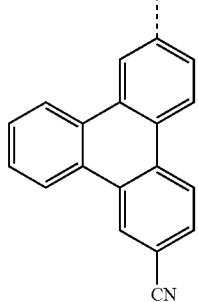 | 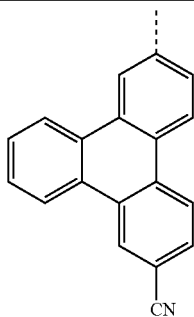 |
| I'-II'c'aH-156 | 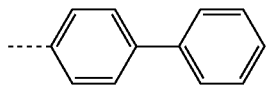 | 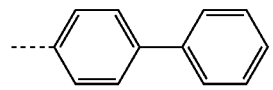 |
| I'-II'c'aH-157 | 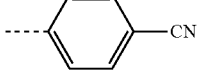 |  |
The dotted lines are bonding sites.
Very specific examples for compounds of formula (I) are:
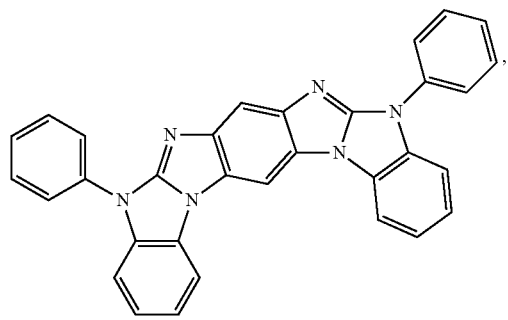
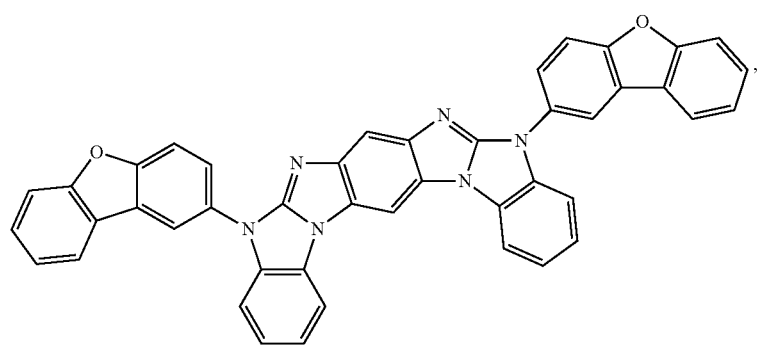

-continued
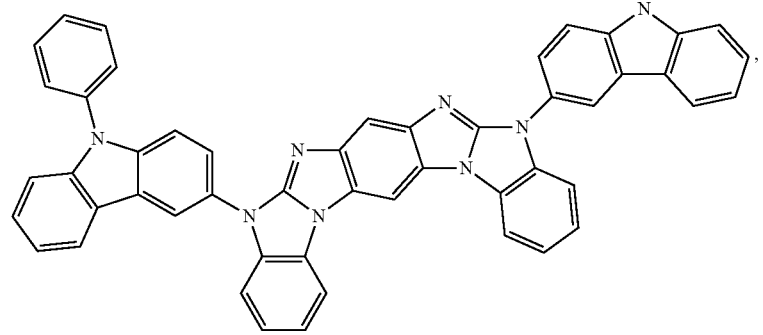
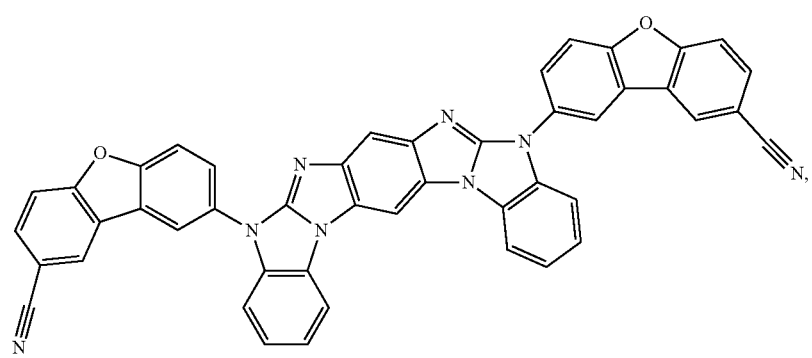
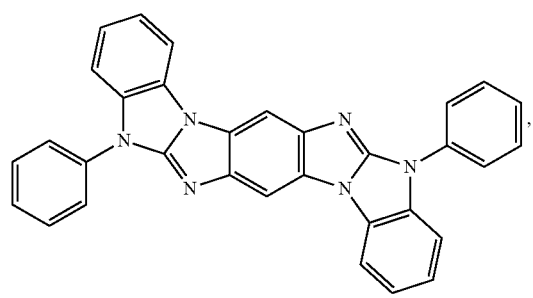
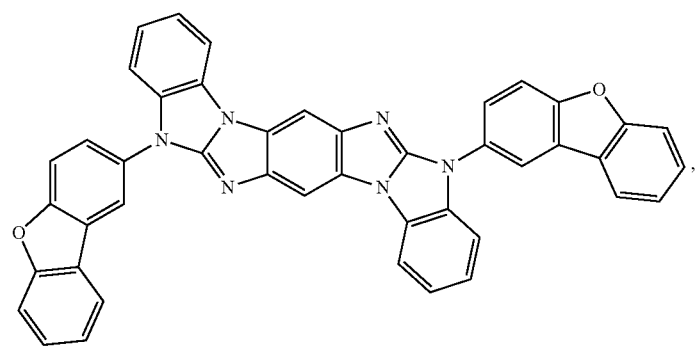

269 270
-continued
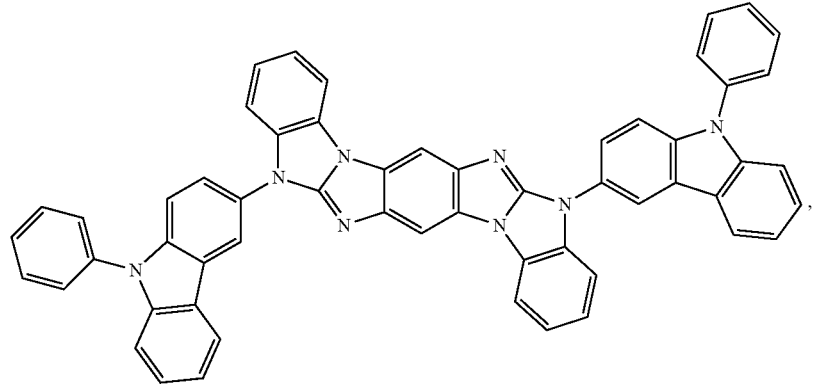
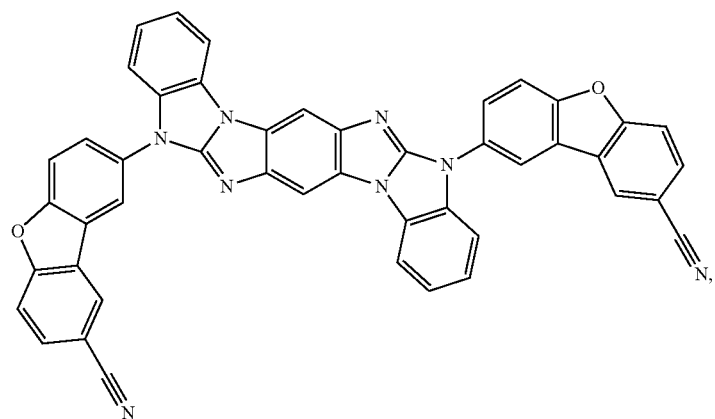
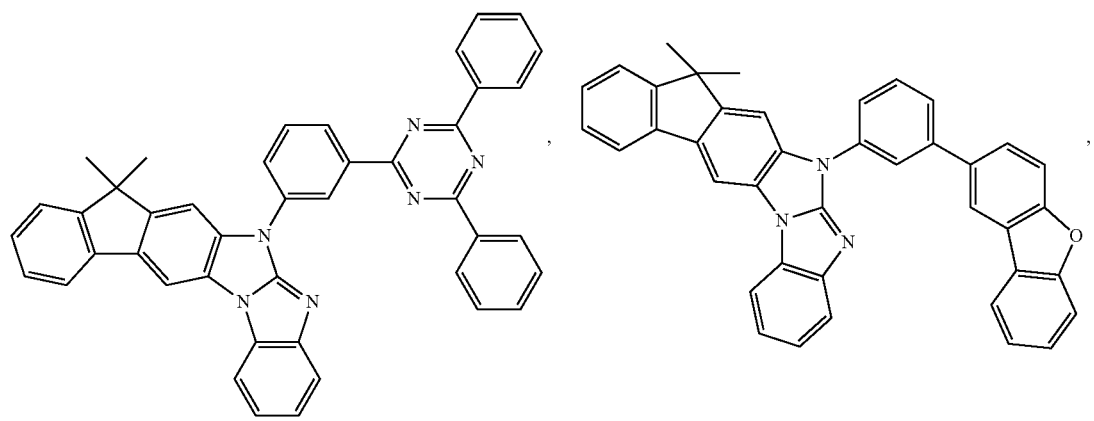
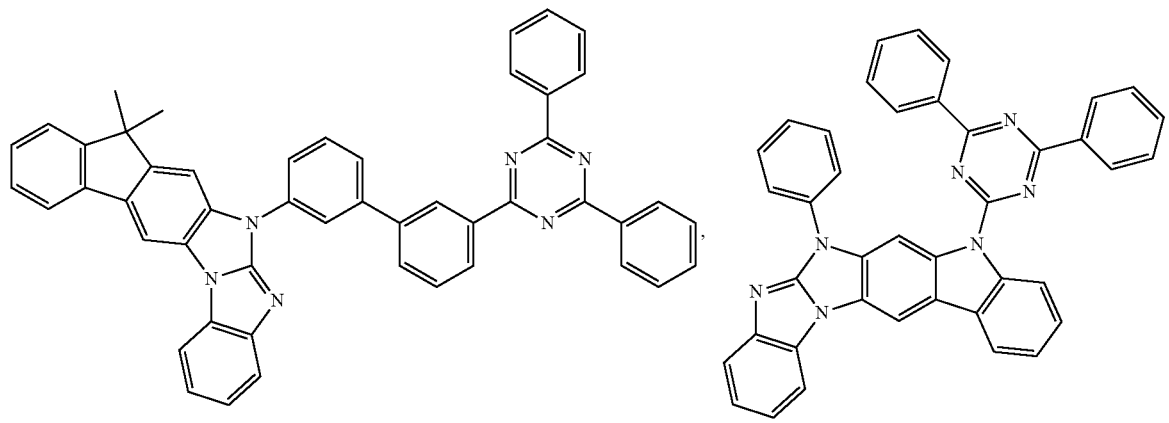

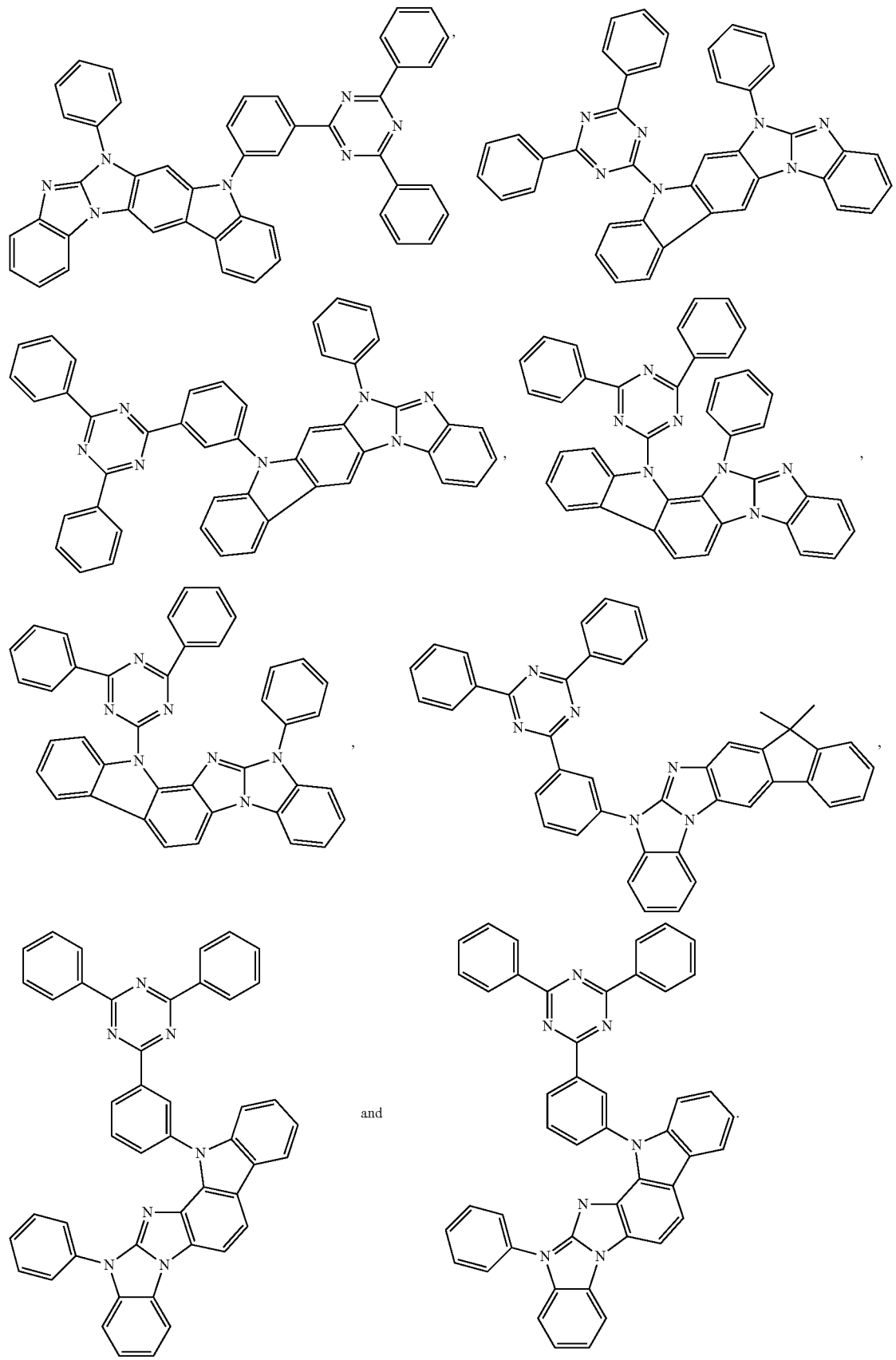

Synthesis of the Compounds of Formula (I)

Generally, the heterocyclic derivatives of formula (I) are prepared in analogy to the preparation processes described in the art, e.g. in WO2012/130709, WO2014/009317, WO2014/044722, European patent application no. 13191100.0, WO2015/014791, European patent application no. EP14197947.9 and European patent application no. EP14197952.6.

The present invention further relates to a process for the preparation of the heterocyclic derivatives of formula (I) comprising:

i) Preparation of a compound of formula (I), wherein $R^6$ and $R^7$ form together a ring system of formula IIa, comprising:
   ia) preparation of an intermediate of formula IIIa;

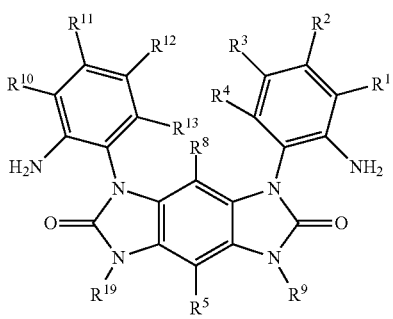

(IIIa)

ib) cyclization, whereby a compound of formula (I) is formed;

ii) Preparation of a compound of formula (I), wherein $R^2$ and $R^3$ form together a ring system of formula IIb, comprising:
   iia) preparation of an intermediate of formula IIIb or IIIb';

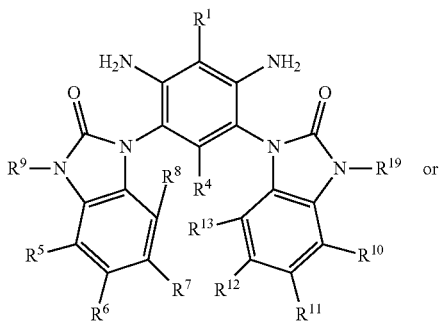

(IIIb)

(IIIb')

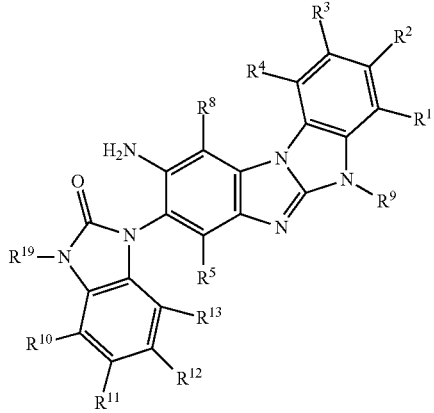

iib) cyclization, whereby a compound of formula (I) is formed;

iii) Preparation of a compound of formula (I), wherein $R^2$ and $R^3$ form together a ring system of formula IIc, comprising:

iiia) preparation of an intermediate of formula IIIc;

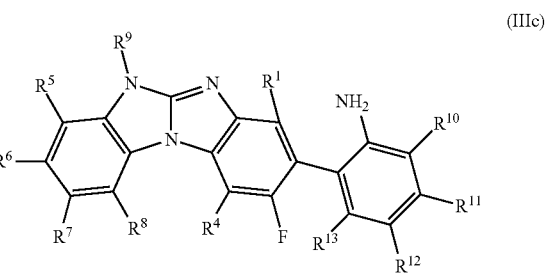

(IIIc)

iiib) cyclization, whereby a compound of formula (IIId) is formed;

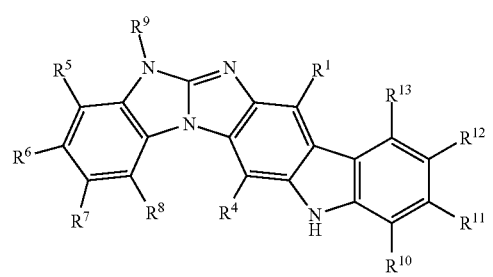

(IIId)

iiic) functionalization of the NH group, whereby a compound of formula (I) is formed;

iv) Preparation of a compound of formula (I), wherein $R^2$ and $R^3$ form together a ring system of formula IIc, comprising:

iva) preparation of an intermediate of formula IIIe;

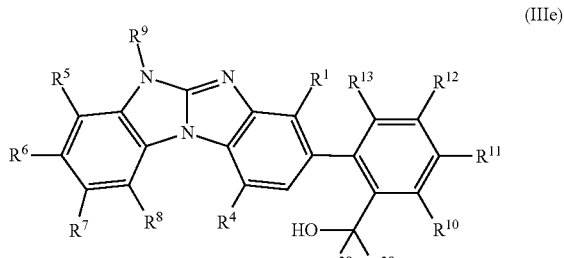

(IIIe)

ivb) cyclization, whereby a compound of formula (I) is formed;

v) Preparation of a compound of formula (I), wherein R⁶ and R⁷ form together a ring system of formula IIc, comprising:
va) preparation of an intermediate of formula IIIf;

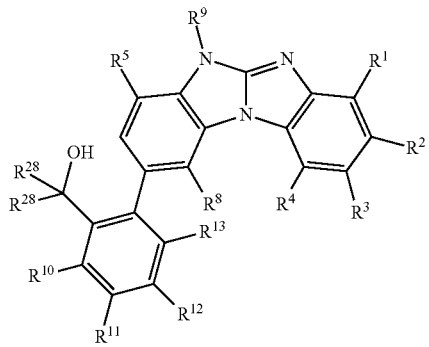

vb) cyclization, whereby a compound of formula (I) is formed;

vi) Preparation of a compound of formula (I), wherein R⁶ and R⁷ form together a ring system of formula IIIc, comprising:
via) preparation of an intermediate of formula IIIg;

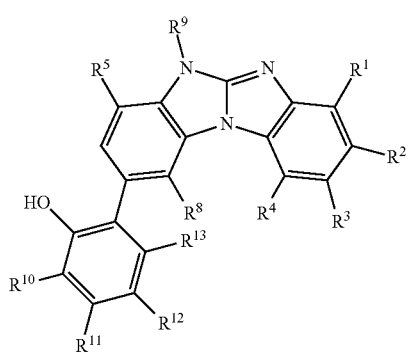

vib) cyclization, whereby a compound of formula (I) is formed;

vii) Preparation of a compound of formula (I), wherein R⁶ and R⁷ form together a ring system of formula IIc, comprising:
viia) preparation of an intermediate of formula IIIh;

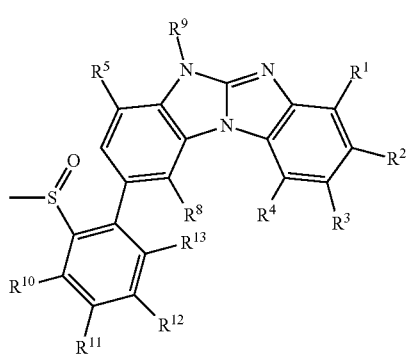

viib) cyclization, whereby a compound of formula (I) is formed;

viii) Preparation of a compound of formula (I), wherein R⁶ and R⁷ form together a ring system of formula IIc, comprising:
viiia) preparation of an intermediate of formula IIIi;

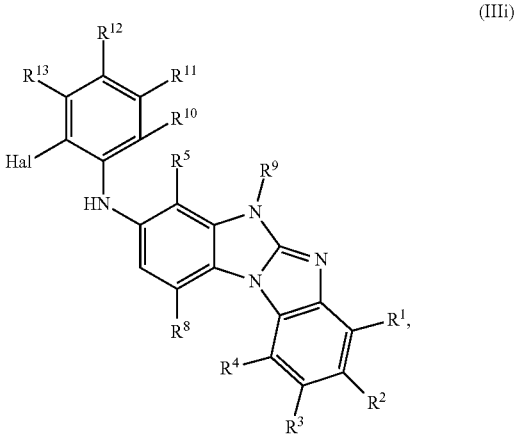

wherein Hal is halogen, preferably Br or Cl, more preferably $C_1$;
viiib) cyclization, whereby a compound of formula (IIIj) is formed;

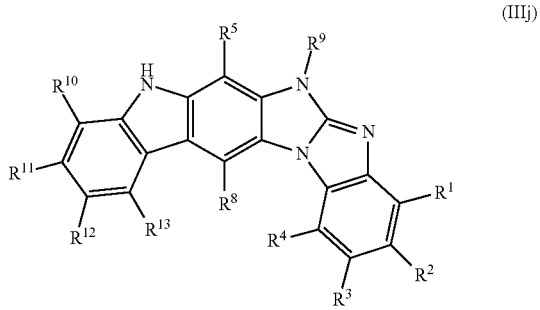

viiic) functionalization of the NH group, whereby a compound of formula (I) is formed;

ix) Preparation of a compound of formula (I), wherein R² and R³ form together a ring system of formula IIc, comprising:
ixa) preparation of an intermediate of formula IIIk;

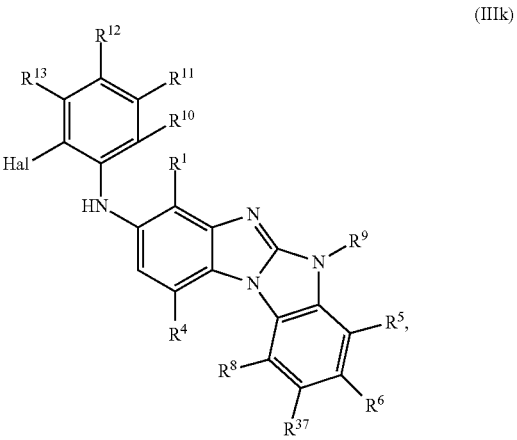

wherein Hal is halogen, preferably Br or Cl, more preferably Cl;

ixb) cyclization, whereby a compound of formula (IIIl) is formed;

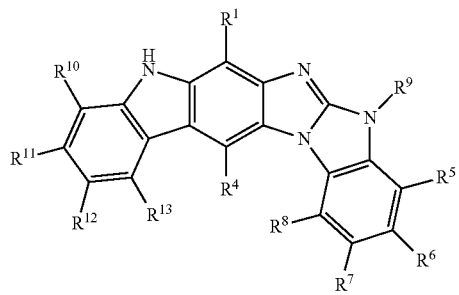

ixc) functionalization of the NH group, whereby a compound of formula (I) is formed;

wherein the residues $R^1$, $R^2$, $R^3$, $R^4$, $R^5$, $R^6$, $R^7$, $R^8$, $R^9$, $R^{10}$, $R^{11}$, $R^{12}$ and $R^{13}$ are described above.

Specific reaction conditions of the steps i) to vii) of the process according to the present invention are described below as well as in the example part of the present application.

i) Synthesis scheme with reaction conditions for the preparation of a compound of formula (I), wherein $R^6$ and $R^7$ form together a ring system of formula IIa:

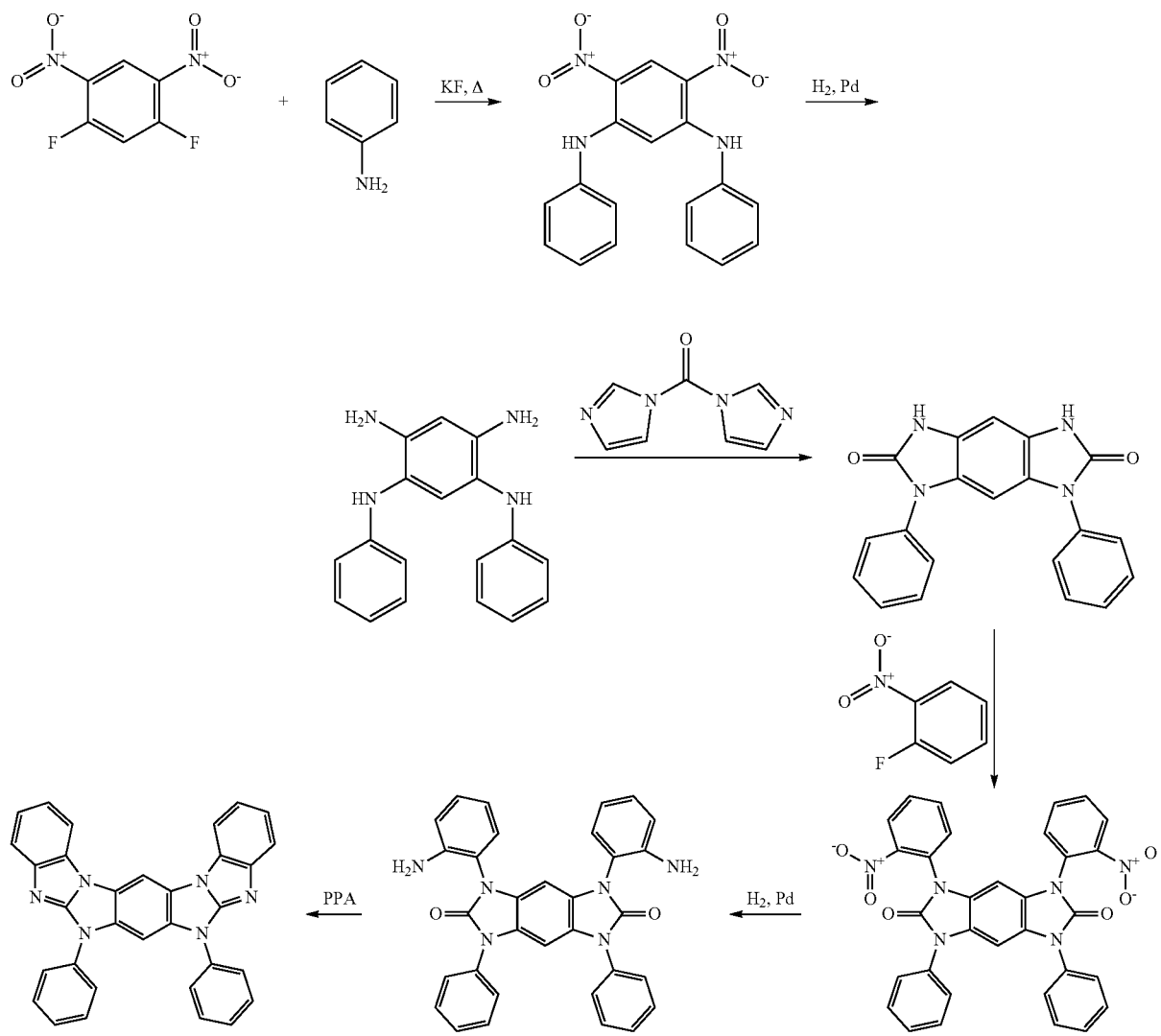

ii) Synthesis schemes with reaction conditions for the preparation of a compound of formula (I), wherein $R^2$ and $R^3$ form together a ring system of formula IIb:

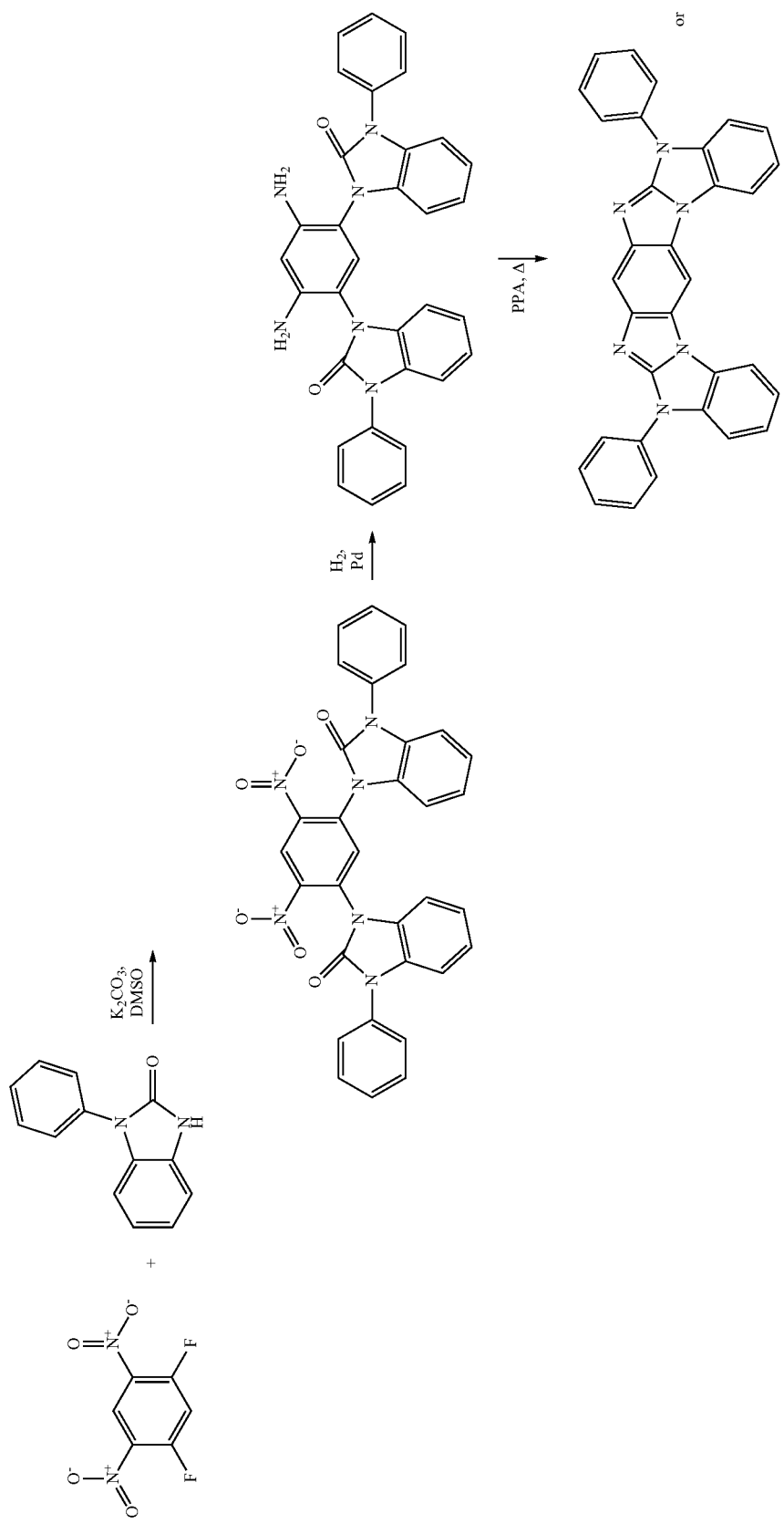

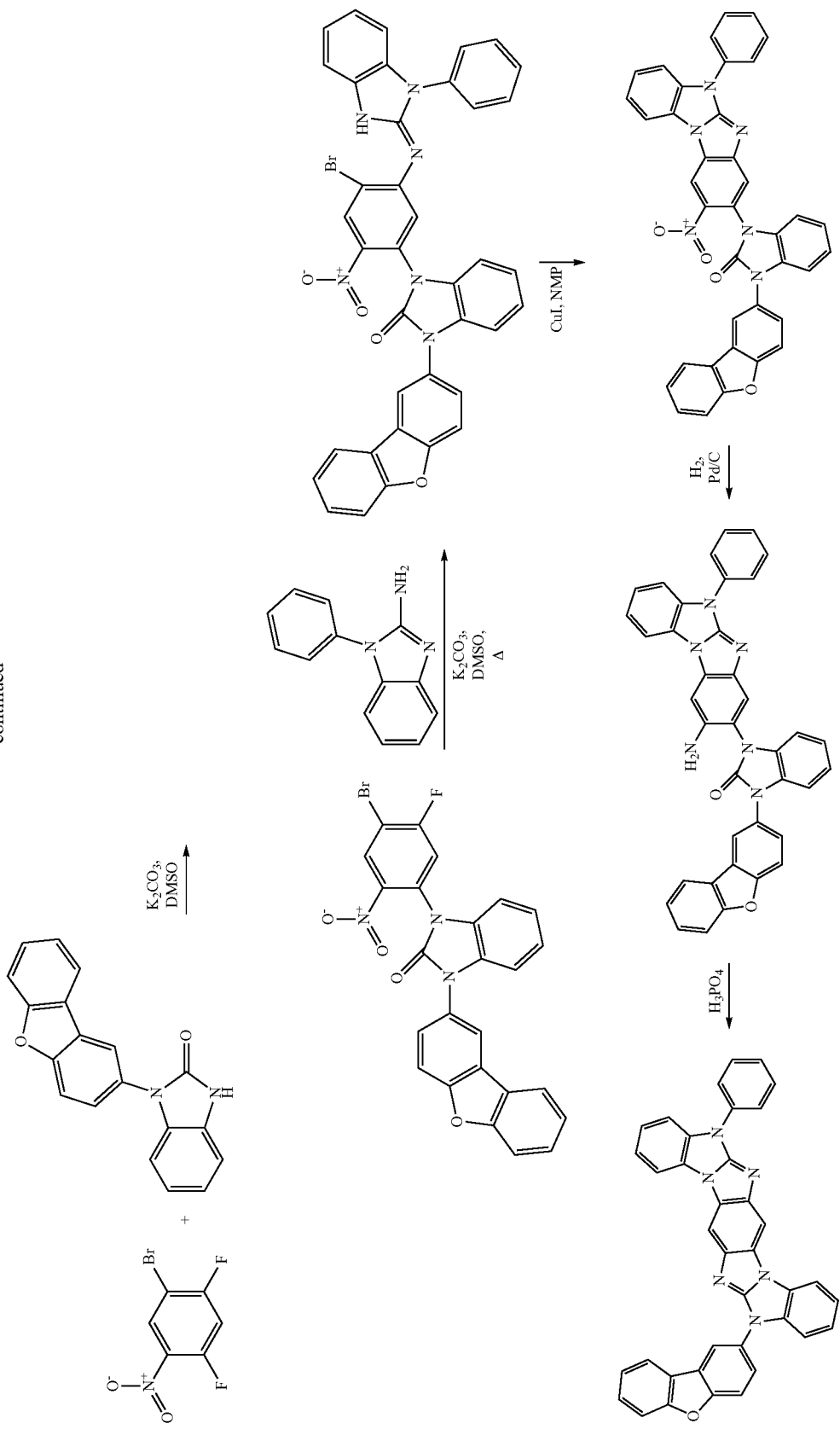

Specific conditions for the reaction steps shown in the schemes above are described for example in the example part and in Organic Letters, 14(6), 1432-1435; 2012, Organic Letters, 4(20), 3481-3484; 2002, Chemical Communications (Cambridge, United Kingdom), 50(85), 12911-12914; 2014, and Journal of Fluorine Chemistry, 40(2-3), 217-46; 1988.

iii) Synthesis scheme with reaction conditions for the preparation of a compound of formula (I), wherein $R^2$ and $R^3$ form together a ring system of formula IIc:

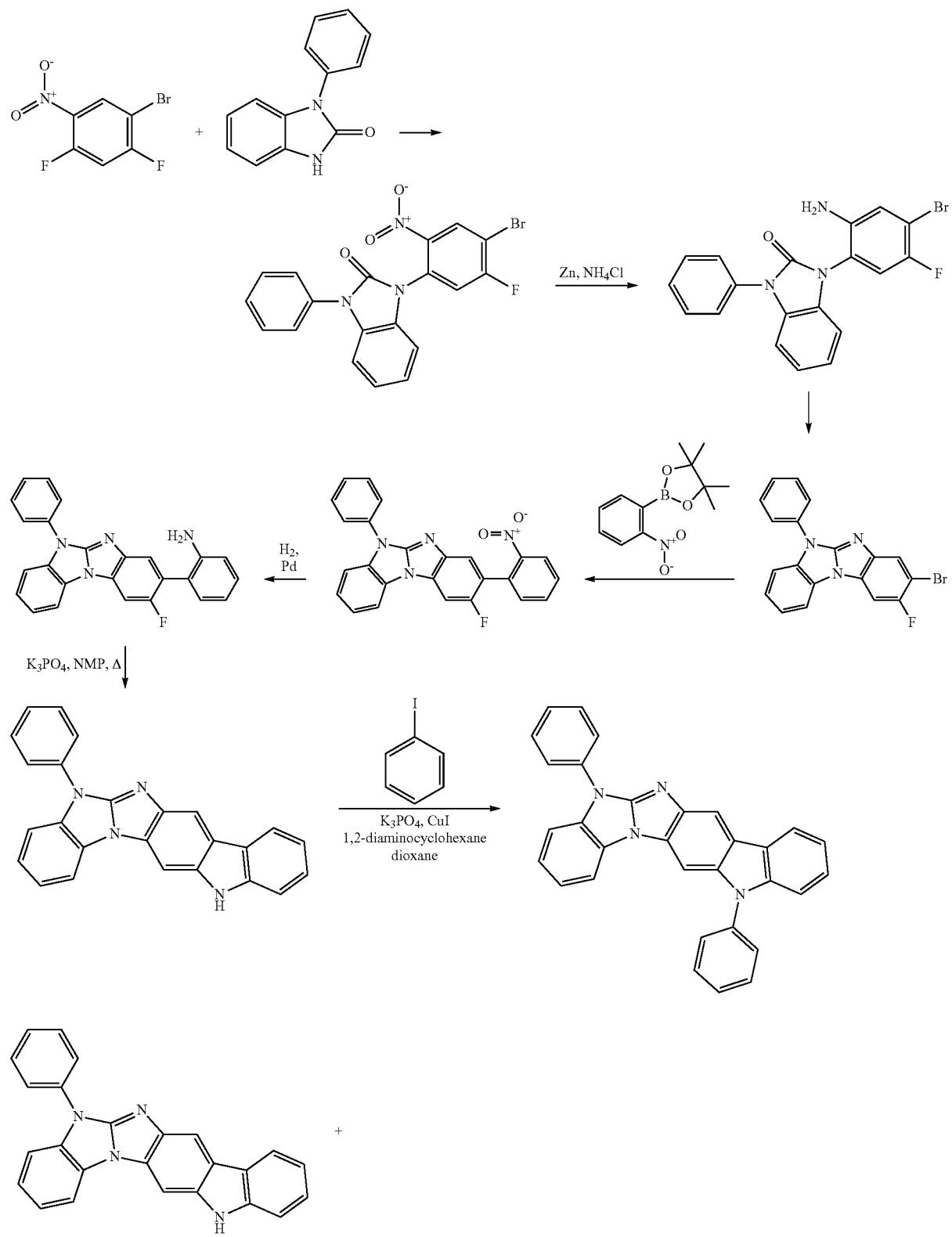

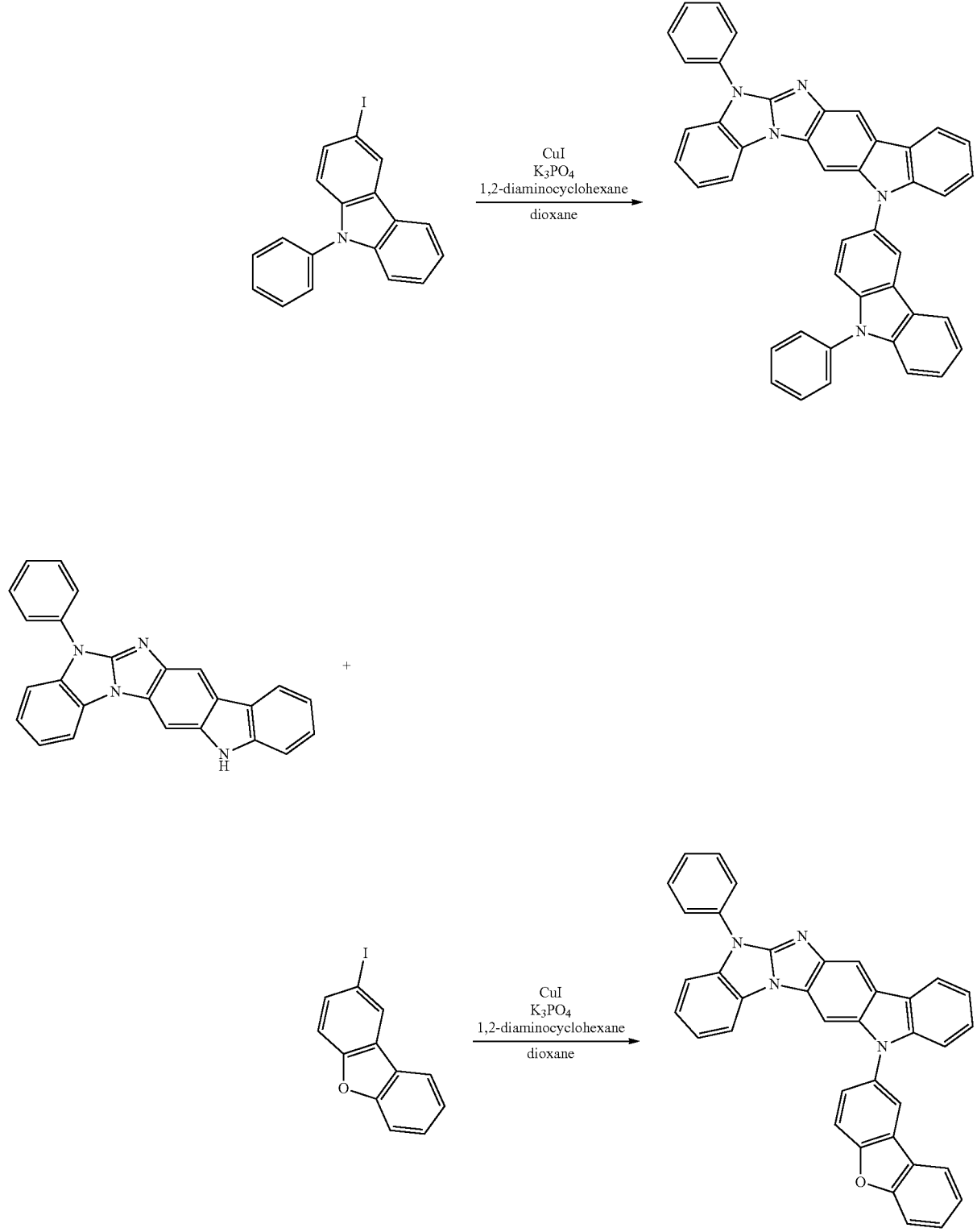

Specific conditions for the reaction steps shown in the schemes above are described for example in the example part and in Bulletin des Societes Chimiques Belges, 96(10), 787-92; 1987, Org. Lett. 2014, 16, 98-101, Journal of Molecular Catalysis A: Chemical 352 (2012) 110-127, European Polymer Journal 52 (2014) 181-192, WO12130709A1, Synlett, (1), 127-133; 2005, Organic Letters, 17(2), 346-349; 2015, WO2009148016 ($K_2CO_3$, NMP), and WO2009148062 ($K_2CO_3$, NMP).

iv) Synthesis scheme with reaction conditions for the preparation of a compound of formula (I), wherein $R^2$ and $R^3$ form together a ring system of formula IIc:

287 288
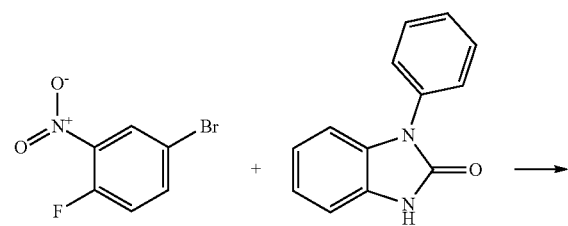
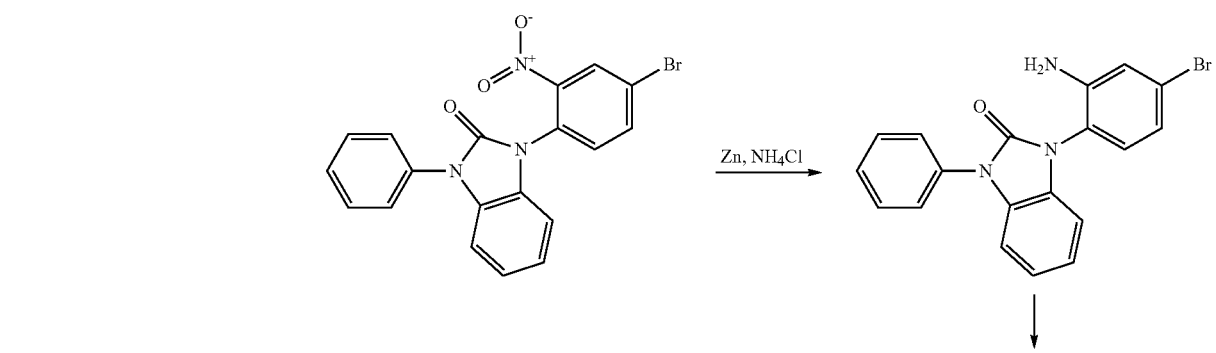
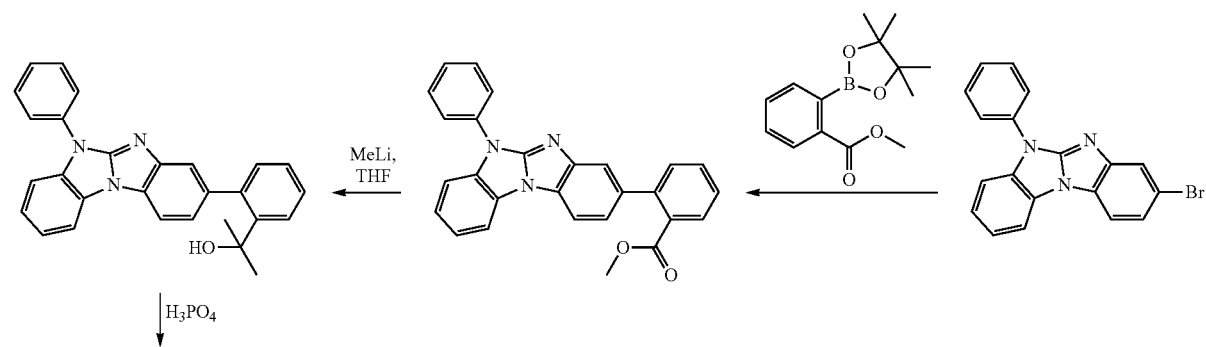
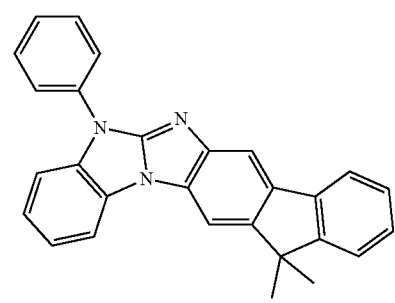

An analogous reaction is for example described in WO2011128017.

v) Synthesis scheme with reaction conditions for the preparation of a compound of formula (I), wherein $R^6$ and $R^7$ form together a ring system of formula IIc:

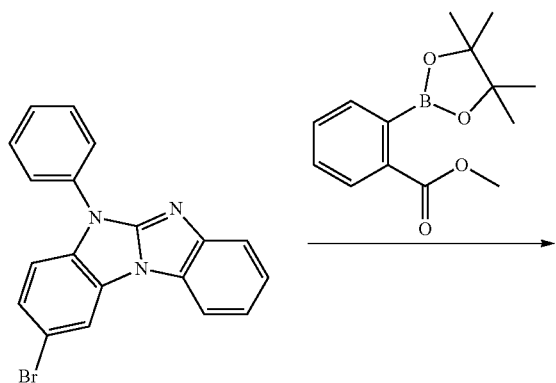

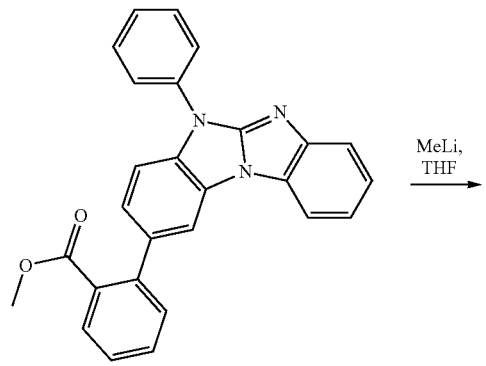

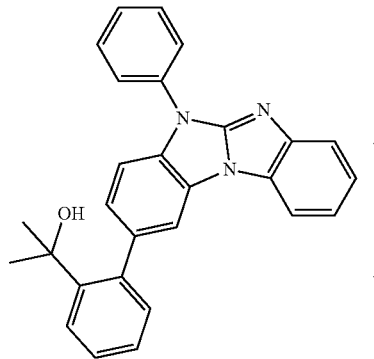

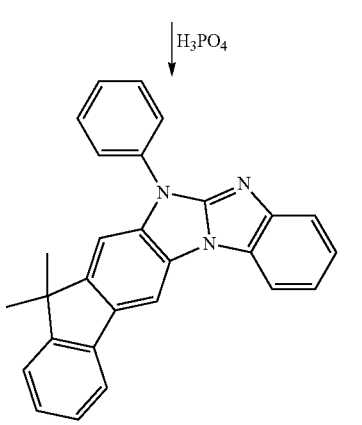

An analogous reaction is for example described in WO14009317.

vi) Synthesis scheme with reaction conditions for the preparation of a compound of formula (I), wherein $R^6$ and $R^7$ form together a ring system of formula IIc:

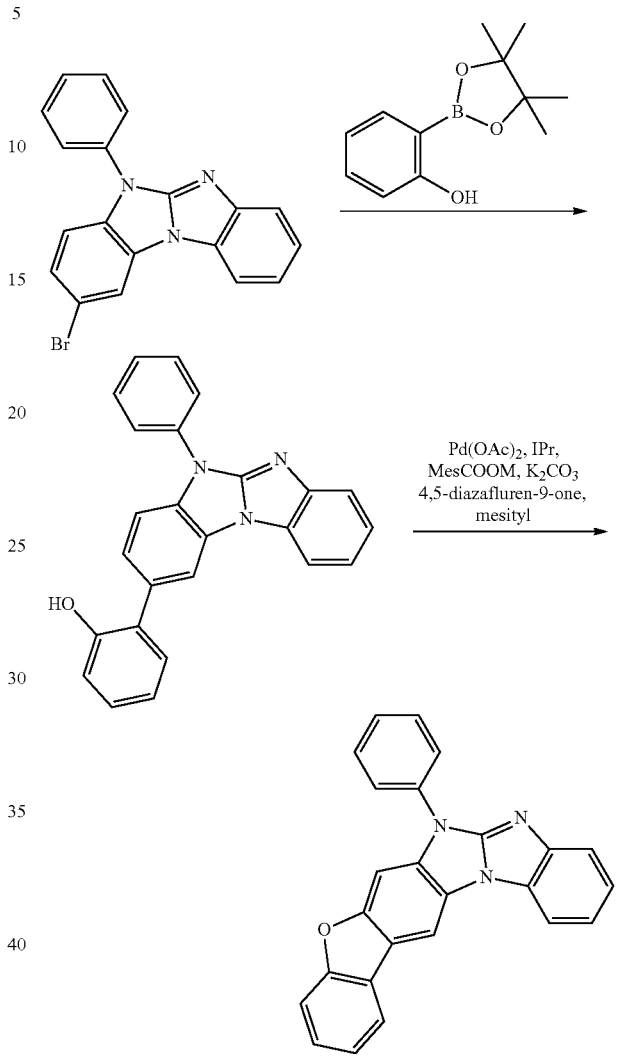

Analogous reactions are for example described in Org. Lett. 2011, 13, 20, 5504 (ring system); J. Am. Chem. Soc. 2011, 133, 9250-9253, Org. Lett. 2012, 14, 4, 1078 (dibenzofurane).

vii) Synthesis schemes with reaction conditions for the preparation of a compound of formula (I), wherein $R^6$ and $R^7$ form together a ring system of formula IIc:

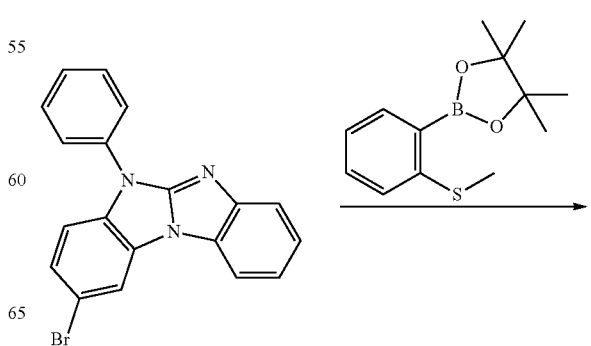

291
-continued

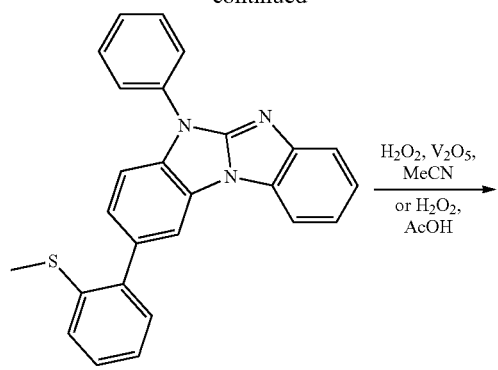

or

292

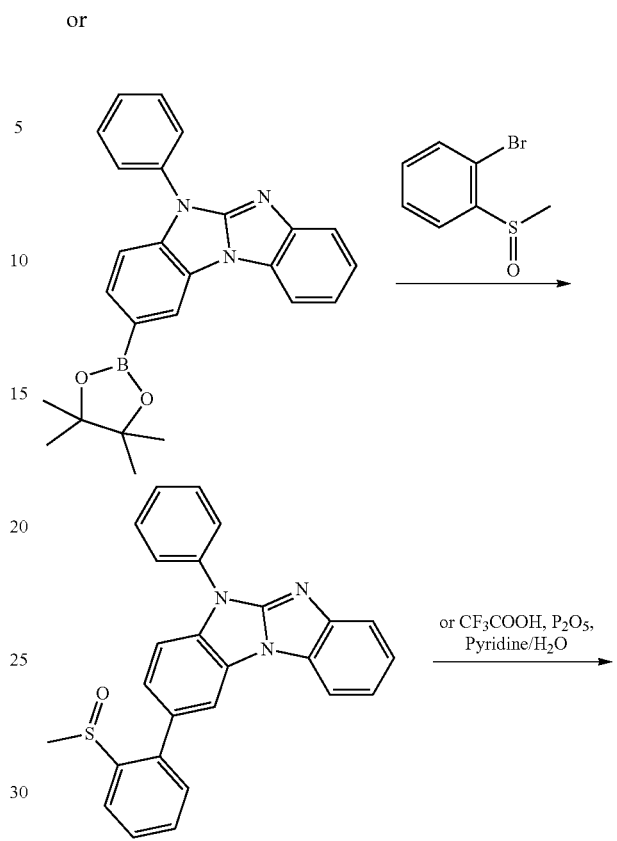

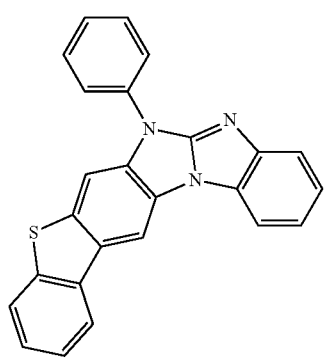

Analogous reactions are for example described in Synthetic Communications 1, 42: 497-505, 2012; Chem. Eur. J. 2009, 15, 8275-8282; (CF₃COOH, Pyridine/H₂O); Chemical Communications (Cambridge, United Kingdom), (13), 1548-1550; 2008; Organic Letters, 16(2), 342-345; 2014; Org. Lett. 2014, 16, 342-345; Organic Letters, 9(10), 1863-1866; 2007; Inorganic Chemistry, 53(23), 12532-12539; 2014; New Journal of Chemistry, 39(8), 6513-6521; 2015; Journal of Organic Chemistry, 73(23), 9207-9213; 2008; WO2010083873; WO2010083872 and WO2010131855.

Analogous reactions are for example described for example in New J. Chem. 2015, 39, 6513-6521.

293 is prepared as follows:

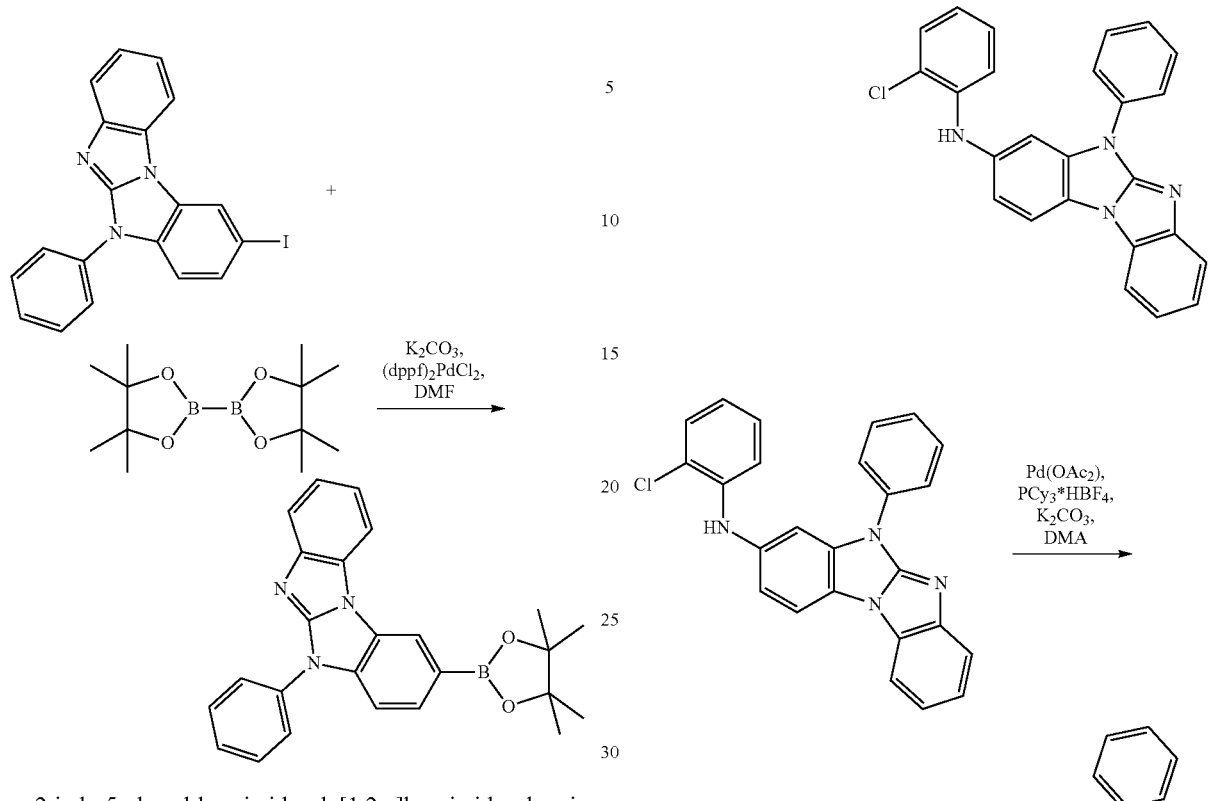

2-iodo-5-phenyl-benzimidazolo[1,2-a]benzimidazole is prepared as describe in WO 2014/009317.

In the following, reaction conditions for the preparation and functionalization of the base skeleton

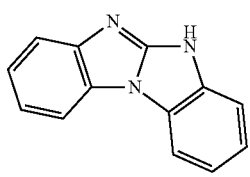 [SMILES: c1ccc2c(c1)nc1[nH]c3ccccc3n12]

are given.

viii) Synthesis scheme with reaction conditions for the preparation of a compound of formula (I), wherein R⁶ and R⁷ form together a ring system of formula IIc

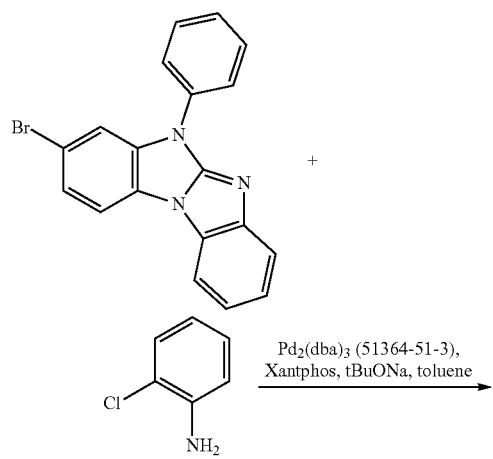

294

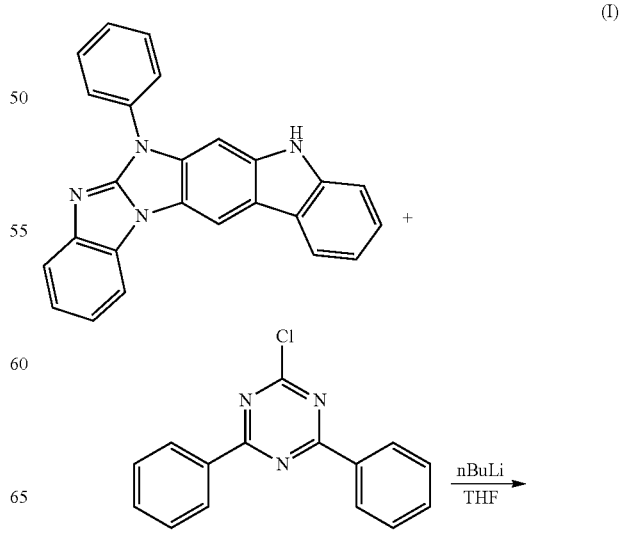

and functionalization of the NH group, for example by one of the following two alternatives:

ix) Synthesis scheme with reaction conditions for the preparation of a compound of formula (I), wherein $R^2$ and $R^3$ form together a ring system of formula IIc
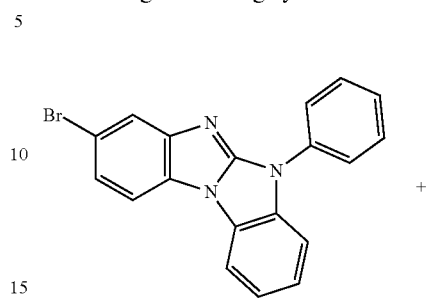
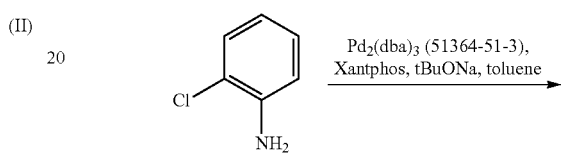
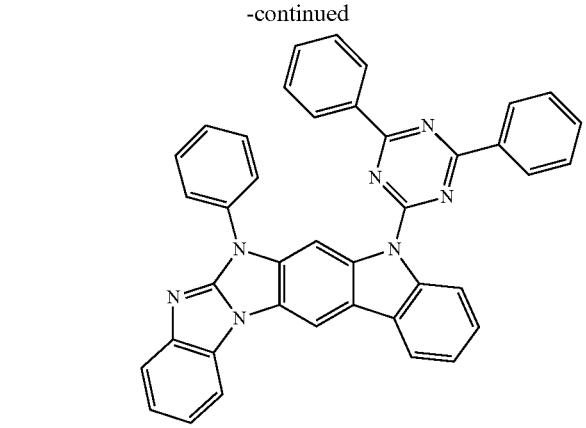
(II)
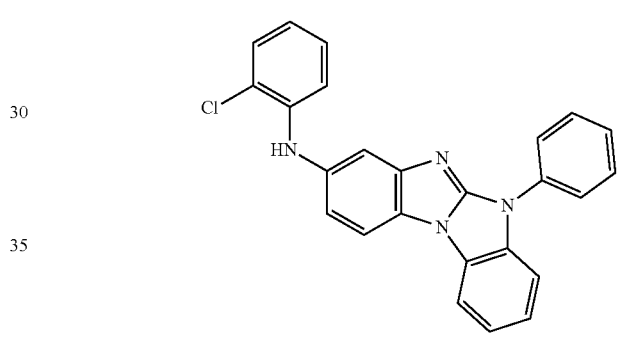
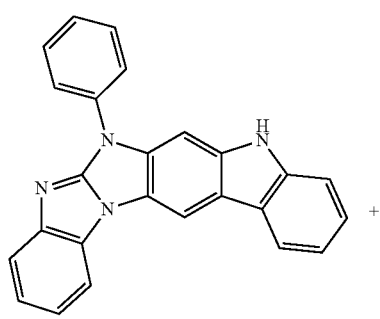
MW: 372.42
CHN: $C_{25}H_{16}N_4$
+
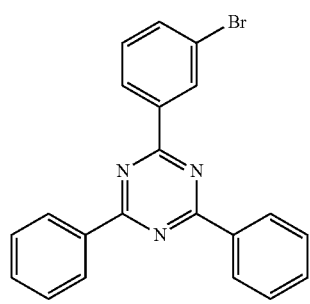
MW: 388.26
CHN: $C_{21}H_{14}BrN_3$
K$_3$PO$_4$
CuI
1,2-Diaminocyclohexan
Dioxan
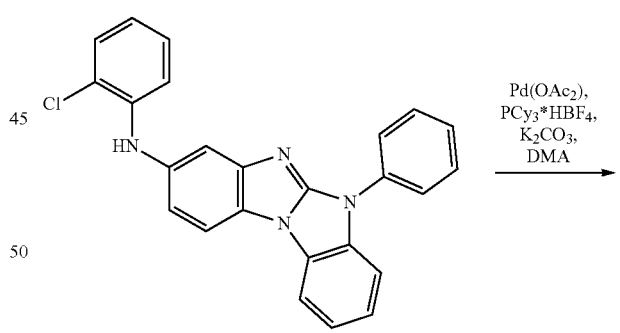
Pd(OAc)$_2$,
PCy$_3$*HBF$_4$,
K$_2$CO$_3$,
DMA
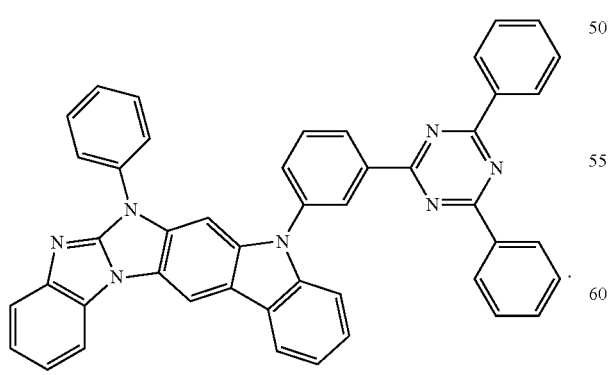
MW: 679.77
CHN: $C_{46}H_{29}N_7$
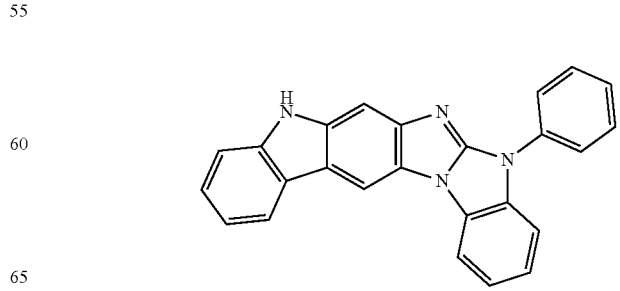

and functionalization of the NH group, for example by one of the following two alternatives:

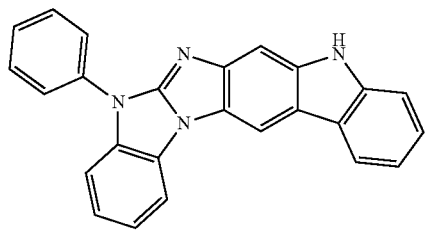
(I)

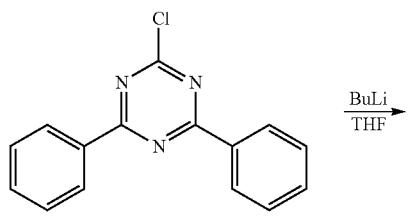

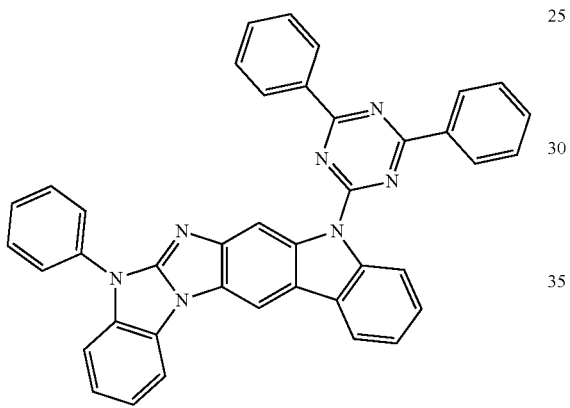
(II)

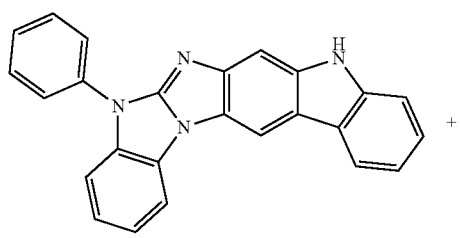
MW: 372.42
CHN: C$_{25}$H$_{16}$N$_4$

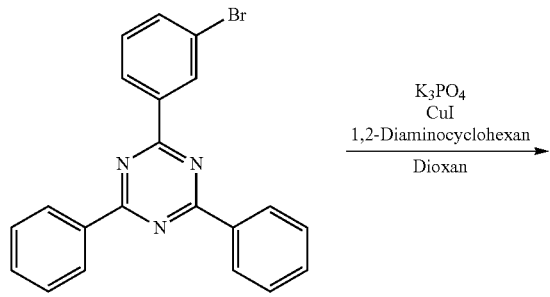
MW: 388.26
CHN: C$_{21}$H$_{14}$BrN$_3$

-continued

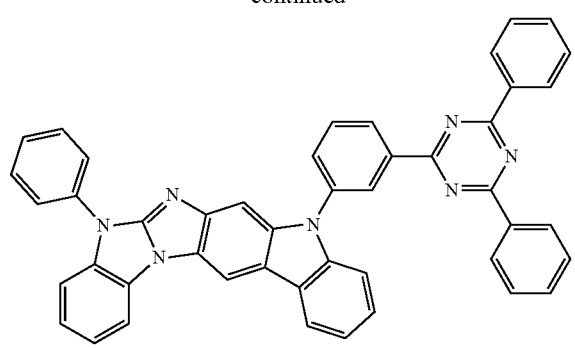
MW: 679.77
CHN: C$_{46}$H$_{29}$N$_7$

The compounds of formula (I), wherein two of the substituents R$^1$ and R$^2$, R$^2$ and R$^3$, R$^3$ and R$^4$, R$^5$ and R$^6$, R$^6$ and R$^7$, or R$^7$ and R$^8$ form together the following ring system

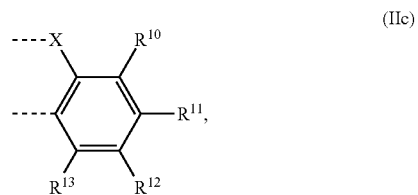
(IIc)

wherein X is NR$^{19}$, are prepared as shown in the following general reaction schemes:

I) R$^5$ and R$^6$, R$^6$ and R$^7$, or R$^7$ and R$^8$ form together a ring system of formula (Ic)

Reaction Step I-1

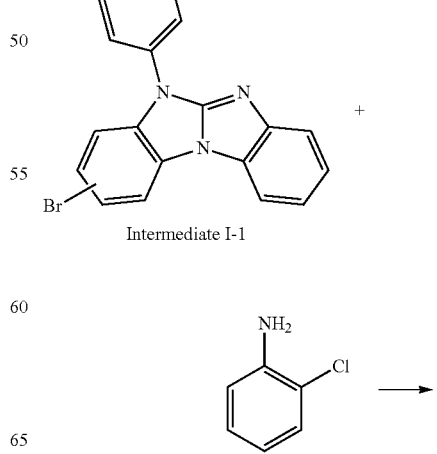
Intermediate I-1

-continued

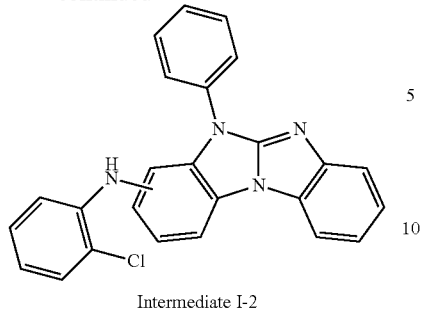

Intermediate I-2

Reaction Step I-2

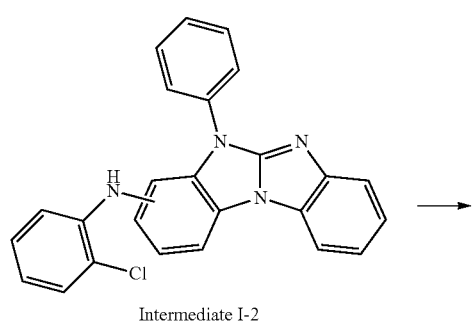

Intermediate I-2 →

-continued

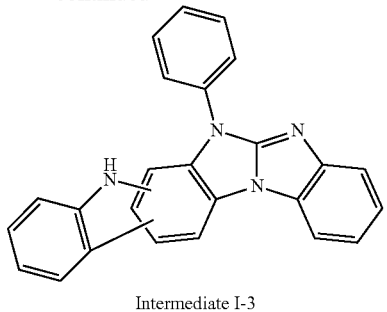

Intermediate I-3

Suitable reaction conditions for step I-1 are for example: $Pd_2(dba)_3$, Xantphos, tBuONa, toluene Suitable reaction conditions for step I-2 are for example: $Pd(OAc)_2$, $PCy_3*HBF_4$, $K_2CO_3$, DMA More detailed reaction conditions are mentioned below.

Specific examples for Intermediates I-1, I-2 and I-3 are shown in the following table:

| Nr. | Intermediate I-1 | Intermediate I-2 | Intermediate I-3 |
|---|---|---|---|
| I-A | | | |
| I-B | | | |

-continued
| Nr. | Intermediate I-1 | Intermediate I-2 | Intermediate I-3 |
|---|---|---|---|
| I-C | | | |
| I-D | | | |
Reaction Step I-3
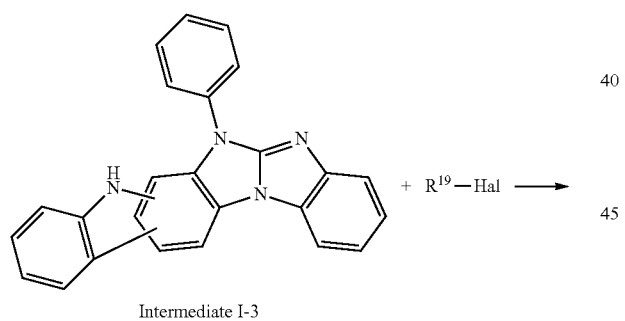
Intermediate I-3
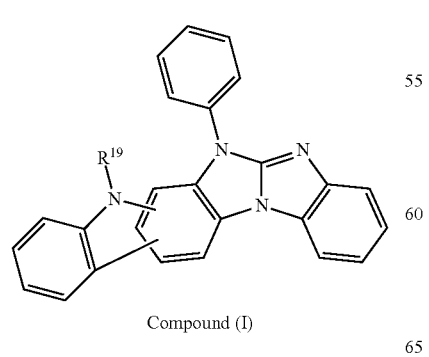
Compound (I)
wherein Hal is Cl or Br.

Detailed reaction conditions are mentioned below.

Specific examples for the reaction step I-3, wherein $R^{19}$-Hal is $R^{19}$—Cl, are shown in the following table:

| Nr. | Intermediate I-3 | $R^{19}$—Cl | Compound (I) |
|---|---|---|---|
| I-AA | | | |
| I-AB | | | |
| I-AC | | | |

-continued

| Nr. | Intermediate I-3 | R¹⁹—Cl | Compound (I) |
|---|---|---|---|
| I-AD | | | |

Specific examples for the reaction step I-3, wherein $R^{19}$-Hal is $R^{19}$—Br, are shown in the following table:

| Nr. | Intermediate I-3 | R¹⁹—Br | Compound (I) |
|---|---|---|---|
| I-AE | | | |
| I-AF | | | |

-continued

| Nr. | Intermediate I-3 | R[19]—Br | Compound (I) |
| --- | --- | --- | --- |
| I-AG | | | |
| I-AH | | | |

II) $R^1$ and $R^2$, $R^2$ and $R^3$, or $R^3$ and $R^4$ form together a ring system of formula (Ic)

Reaction Step I-1

Reaction Step I-2

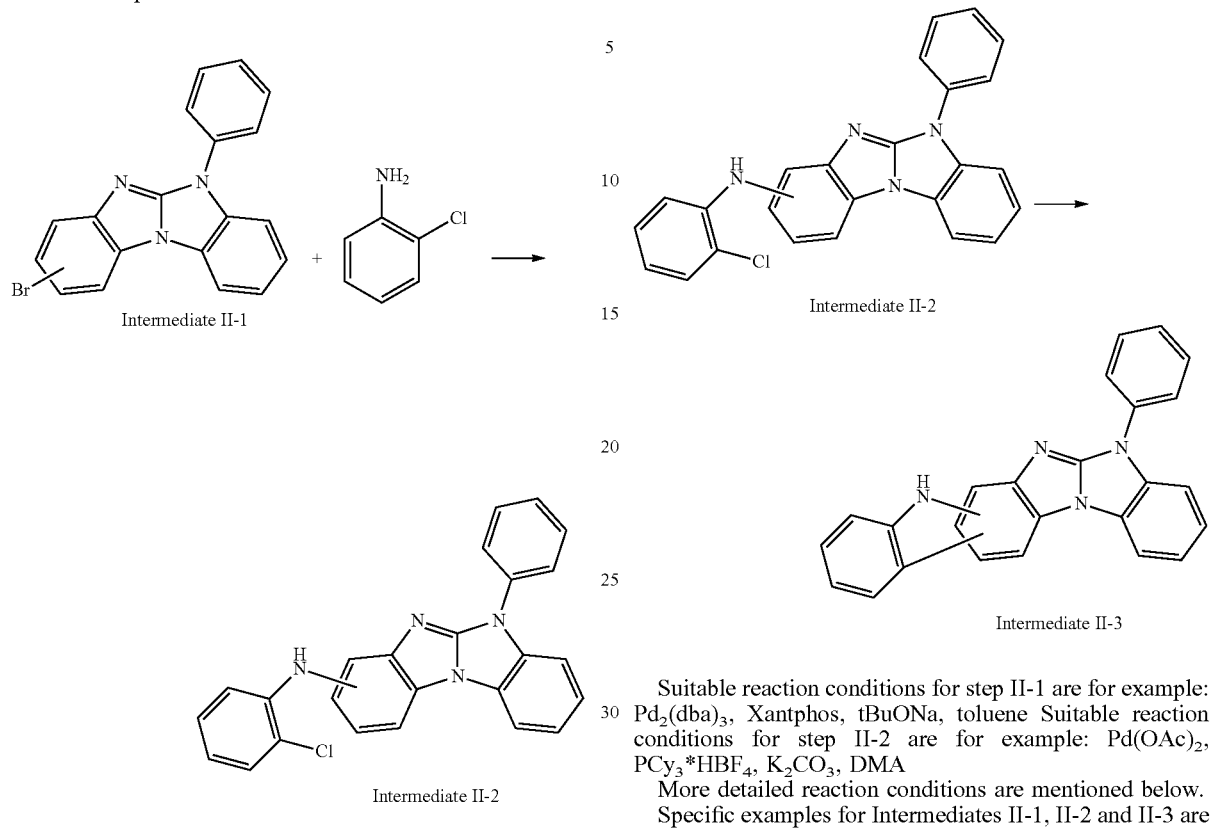

Suitable reaction conditions for step II-1 are for example: $Pd_2(dba)_3$, Xantphos, tBuONa, toluene Suitable reaction conditions for step II-2 are for example: $Pd(OAc)_2$, $PCy_3*HBF_4$, $K_2CO_3$, DMA More detailed reaction conditions are mentioned below.

Specific examples for Intermediates II-1, II-2 and II-3 are shown in the following table:

-continued
| Nr. | Intermediate II-1 | Intermediate II-2 | Intermediate II-3 |
|---|---|---|---|
| II-C | | | |
| II-D | | | |
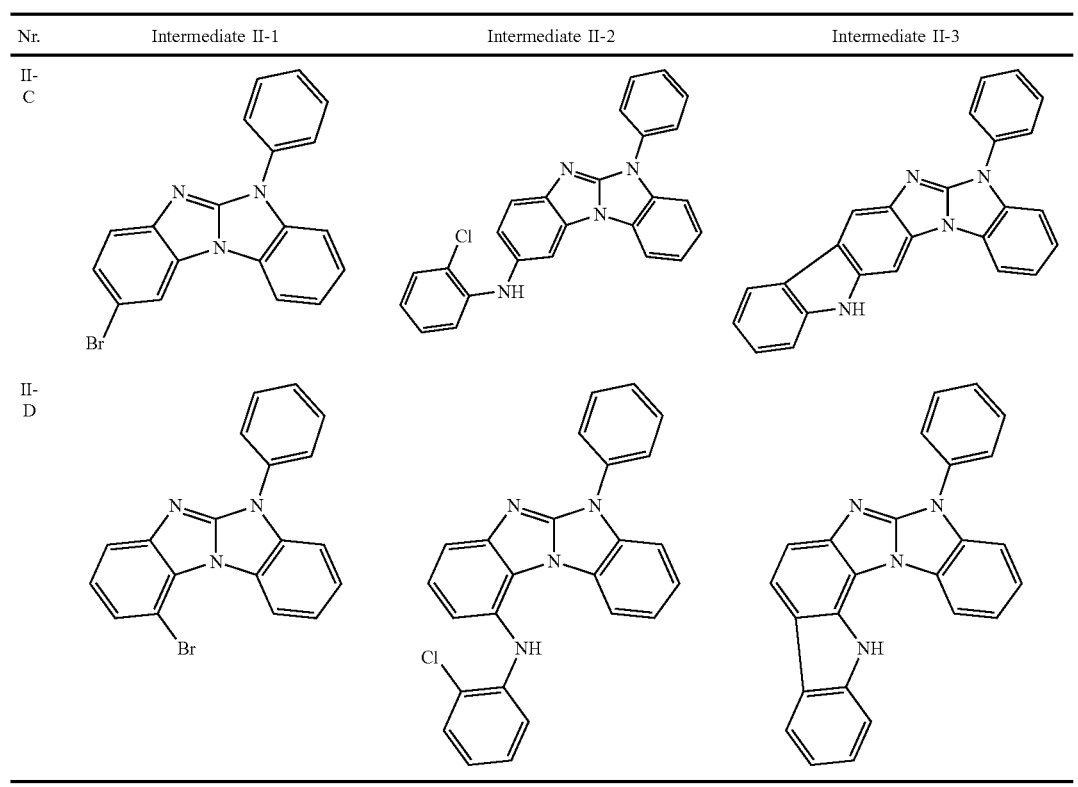
Reaction Step II-3
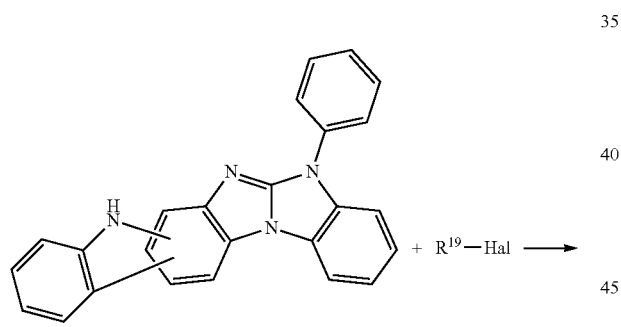
Intermediate II-3
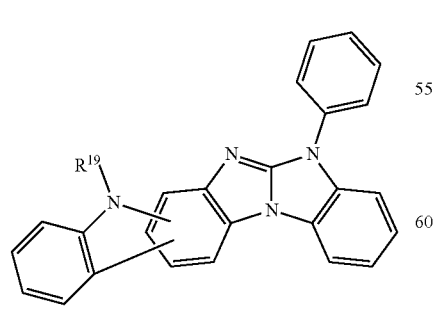
Compound (I)
wherein Hal is Cl or Br.

Detailed reaction conditions are mentioned below.

Specific examples for the reaction step II-3, wherein $R^{19}$-Hal is $R^{19}$—Cl, are shown in the following table:

| Nr. | Intermediate II-3 | $R^{19}$—Cl | Compound (I) |
|---|---|---|---|
| II-AA | | | |
| II-AB | | | |
| II-AC | | | |
| II-AD | | | |

Specific examples for the reaction step II-3, wherein $R^{19}$-Hal is $R^{19}$—Br, are shown in the following table:

| Nr. | Intermediate II-3 | $R^{19}$—Br | Compound (I) |
|---|---|---|---|
| II-AE | | | |
| II-AF | | | |
| II-AG | | | |
| II-AH | | | |

Suitable reaction conditions for step I-1 and step I-1:

The molar ratio between the intermediate I-1 respectively II-1 and 2-chloroanolone is usually 2:1 to 1:2.5, preferably 1.5:1 to 1:2, more preferably 1.3:1 to 1:1.5, most preferably 1.1:1 to 1:1.5 and further most preferably 1:1.5.

Suitable catalysts in the reaction step I-1 respectively II-1 mentioned above are preferably selected from the group consisting of $Pd_2(dba)_3$ and $Pd(OAc)_2$.

Suitable ligands in the reaction mentioned above are preferably selected from the group consisting of Xantphos, $tBu_3P*HBF_4$, $tBu_3P$, (+−)BINAP, BrettPhos, XPhos, $PCy_3*HBF_4$, $PCy_3$ preferably Xantphos. An overview of suitable ligands and catalysts are given in Chem. Sci., 2011, 2, 27.

Suitable bases in the reaction step I-1 respectively II-1 mentioned above are preferably selected from the group consisting of potassium phosphate tribasic ($K_3PO_4$), $K_2CO_3$, $Na_2CO_3$, $Cs_2CO_3$, NaOtBu and KOtBu, preferably NaOtBu. It is also possible to use a mixture of two or more bases.

The reaction step I-1 respectively II-1 mentioned above is preferably carried out in a solvent. Suitable solvents are for example toluene, xylene, dioxane, THF and tBuOH or mixtures of the solvents mentioned before, preferably toluene and xylene.

The reaction temperature in the reaction step I-1 respectively II-1 mentioned above is usually 20° C. to 220° C., preferably 50° C. to 200° C., more preferably 60° C. to 190° C., most preferably 60° C. to 180° C.

The reaction time in the reaction step I-1 respectively II-1 mentioned above is usually 10 minutes to 72 hours, preferably 30 minutes to 24 hours, more preferably 2 hours to 16 hours.

The reaction pressure is not critical and usually atmospheric pressure.

Suitable Reaction Conditions for Step I-2 and Step II-2:

Suitable catalysts in the reaction step I-2 respectively II-2 mentioned above are preferably selected from the group consisting of $Pd_2(dba)_3$ and $Pd(OAc)_2$.

Suitable ligands in the reaction step I-2 respectively II-2 mentioned above are preferably selected from the group consisting of $PCy_3*HBF_4$, $PCy_3$, Xantphos, $tBu_3P*HBF_4$, $tBu_3P$, (+−)BINAP, BrettPhos and XPhos, preferably $PCy_3*HBF_4$, $PCy_3$. An overview of suitable ligands and catalysts are given in Chem. Sci., 2011, 2, 27.

Suitable bases in the reaction step I-2 respectively II-2 mentioned above are preferably selected from the group consisting of potassium phosphate tribasic ($K_3PO_4$), $K_2CO_3$, $Na_2CO_3$, $Cs_2CO_3$, NaOtBu, KOtBu and DBU, preferably $K_2CO_3$. It is also possible to use a mixture of two or more bases.

The reaction mentioned above is preferably carried out in a solvent. Suitable solvents are for example toluene, xylene, dioxane, dimethyl acetamide (DMA), dimethyl formamide (DMF), dimethylsulfoxide (DMSO), N-methyl-2-pyrrolidone (NMP) and 1,3-dimethyl imidazolidone (DMI), or mixtures thereof, preferably DMA.

The reaction temperature in the reaction step I-2 respectively II-2 mentioned above is usually 20° C. to 220° C., preferably 50° C. to 200° C., more preferably 60° C. to 190° C., most preferably 60° C. to 180° C.

The reaction time in the reaction step I-2 respectively II-2 mentioned above is usually 10 minutes to 72 hours, preferably 30 minutes to 24 hours, more preferably 2 hours to 16 hours.

The reaction pressure is not critical and usually atmospheric pressure.

Suitable Reaction Conditions for Step I-3 and Step II-3, Wherein $R^{19}$-Hal is $R^{19}$ Cl:

The molar ratio between the compound of formula I-3 respectively II-3 and $R^{19}$—Cl is usually 2:1 to 1:2.5, preferably 1.5:1 to 1:2, more preferably 1.3:1 to 1:1.5, most preferably 1.1:1 to 1:1.5 and further most preferably 1:1.5.

Suitable bases in the reaction step I-3 respectively II-3 mentioned above are preferably selected from the group consisting of NaH, n-BuLi, t-BuLi and lithium hexamethyldisilazide. It is also possible to use a mixture of two or more bases.

The reaction step I-3 respectively II-3 mentioned above is preferably carried out in a solvent. Suitable solvents are for example THF, dioxane, dimethyl formamide (DMF), or mixtures thereof, preferably THF with n-BuLi as a base or DMF with NaH as a base.

The reaction temperature in the reaction step I-3 respectively II-3 mentioned above is usually −78° C. to 200° C., preferably −78° C. to 150° C., more preferably −78° C. to 120° C., most preferably −78° C. to 100° C.

The reaction time in the reaction step I-3 respectively II-3 mentioned above is usually 10 minutes to 72 hours, preferably 30 minutes to 24 hours, more preferably 2 hours to 16 hours.

The reaction pressure is not critical and usually atmospheric pressure.

Suitable Reaction Conditions for Step I-3 and Step II-3, Wherein $R^{19}$-Hal is $R^{19}$ Br:

The molar ratio between the compound of formula I-3 respectively II-3 and $R^{19}$—Br is usually 2:1 to 1:2.5, preferably 1.5:1 to 1:2, more preferably 1.3:1 to 1:1.5, most preferably 1.1:1 to 1:1.5 and further most preferably 1:1.5.

The reaction step I-3 respectively II-3 mentioned above is preferably carried out in a solvent. Suitable solvents are alcohols, for example tert. butanol, (polar) aprotic solvents, for example tertiary carboxylic acid amides like dimethyl acetamide (DMA), dimethyl formamide (DMF), di-methyl sulfoxide (DMSO), N-methyl-2-pyrrolidone (NMP), 1,3-dimethyl imidazolidone (DMI), nitrobenzene, or mixtures thereof.

The reaction step I-3 respectively II-3 mentioned above is preferably carried out in the presence of a catalyst. More preferably, a Cu catalyst is employed, for example Cu, CuI, $Cu_2O$, CuO, CuBr, or mixtures thereof. Preferably, the catalyst is CuI.

The catalyst is usually used in an amount of 1 mol % to 30 mol %, preferably 3 mol % to 27 mol %, more preferably 4 mol % to 25 mol %, most preferably 5 mol % to 20 mol %, based on the compound of formula I-3 respectively II-3.

In addition to the catalyst which is preferably present, at least one ligand is preferably present. Said ligand is preferably selected from the group consisting of

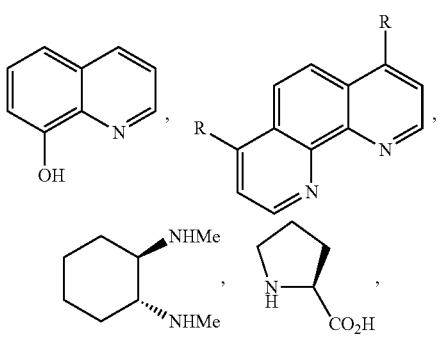

-continued

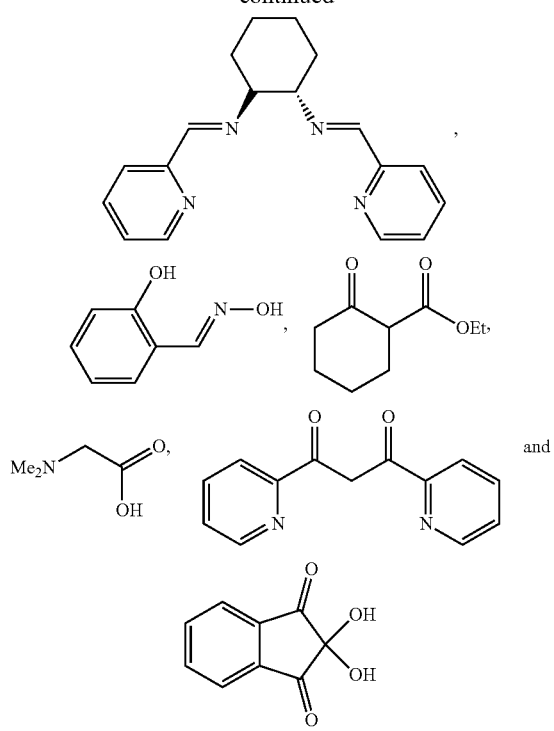

wherein R is for example OMe. The ligand is usually used in an amount of 5 mol % to 25 mol %, preferably 8 mol % to 20 mol %, more preferably 10 mol % to 17 mol %, most preferably 12 mol % to 16 mol %, based on the compound of formula I-3 respectively II-3. Preferably, the ligand is cis,trans-diaminocyclohexane.

The reaction is further preferably carried out in the presence of a base. Suitable bases are $K_3PO_4$, $K_2CO_3$, $Na_2CO_3$, $Cs_2CO_3$, NaH, NaOtBu, KOtBu, or mixtures thereof, preferably $K_3PO_4$, $K_2CO_3$, $Na_2CO_3$, $Cs_2CO_3$, or mixtures thereof. Preferably, the base is $K_3PO_4$.

The molar ratio of the base to $R^{19}$—Br is usually 2:1 to 1:3, preferably 1.5:1 to 1:2.5, more preferably 1.3:1 to 1:2, most preferably 1.1:1 to 1:1.8.

The reaction temperature in the reaction step I-3 respectively II-3 mentioned above is usually 20° C. to 190° C., preferably 30° C. to 180° C., more preferably 60° C. to 170° C.

The reaction time in the reaction step I-3 respectively II-3 mentioned above is usually 10 minutes to 72 hours, preferably 2 hours to 48 hours, more preferably 3 hours to 24 hours.

The reaction pressure is not critical and usually atmospheric pressure.

The intermediates I-1 and II-1 are for example prepared as described in the PCT application PCT/IB2016/055872.

Base Skeleton

The synthesis of the compounds of formula (I) can be carried out in analogy to the synthesis of benzimidazolo[1,2-a]benzimidazoles mentioned in the relevant art.

The synthesis of

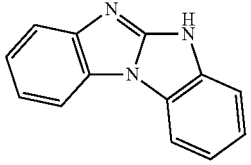 [SMILES: c1ccc2c(c1)nc1[nH]c3ccccc3n12]

is described, for example, in Achour, Reddouane; Zniber, Rachid, Bulletin des Sociétés Chimiques Belges 96 (1987) 787-92, WO12130709, Org. Lett. 2012, 14, 02, 452, *Eur. J. Org. Chem.* 2014, 5986-5997, and *RSC Advances* 2014, 4, 21904-21908

N-Arylation

The introduction of the group —$R^9$ (N-arylation) is generally carried out by reacting the base skeleton

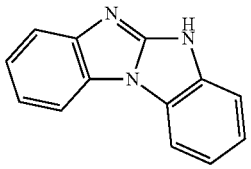 [SMILES: c1ccc2c(c1)nc1[nH]c3ccccc3n12]

with a group Hal-$R^9$, wherein Hal is F, Cl, Br or I, preferably F, Br or I. Suitable groups $R^9$ are mentioned before.

The nucleophilic aromatic substitution (N-arylation) of

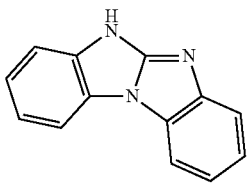 [SMILES: c1ccc2c(c1)nc1[nH]c3ccccc3n12]

with F—$R^9$ is generally performed in the presence of a base (Angew. Chem. 2012, 124, 8136-8140, Angew. Chem. Int. Ed. 2008, 47, 8104-8107). Suitable bases are known to those skilled in the art and are preferably selected from the group consisting of alkali metal alkali metal and alkaline earth metal hydroxides such as NaOH, KOH, Ca(OH)$_2$, alkali metal hydrides such as NaH, KH, alkali metal amides such as NaNH$_2$, alkali metal or alkaline earth metal carbonates such as $K_2CO_3$ or $Cs_2CO_3$, alkaline metal phosphates such as $K_3PO_4$ alkaline metal fluorides such as KF, CsF and alkali metal alkoxides such as NaOMe, NaOEt. In addition, mixtures of the aforementioned bases are suitable. $K_2CO_3$ or $Cs_2CO_3$, $K_3PO_4$ are preferred.

The nucleophilic aromatic substitution (N-arylation) can be performed in solvent or in a melt. Preferably, the reaction is carried out in a solvent. Suitable solvents are, for example, (polar) aprotic solvents such as dimethyl sulfoxide (DMSO), dimethylformamide (DMF), N-methyl-2-pyrrolidone (NMP) or dimethylacetamide (DMA).

The reaction temperature is strongly dependent on the reactivity of the aryl fluoride. The reaction (N-arylation) is preferably carried out at a temperature of –10 to 220° C., more preferably 60 to 150° C.

Ullmann reaction (N-arylation) of

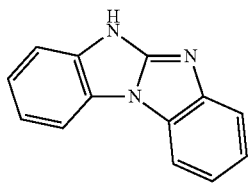 [SMILES: c1ccc2c(c1)nc1[nH]c3ccccc3n12]

with Y—R$^1$ (Y is Cl, Br, or I) generally performed in the presence of a base and a catalyst.

Reaction conditions for Ullmann reactions are, for example, described in Angew Chem Int Ed Engl., 48 (2009) 6954-71 WO14009317, WO12130709, J. Am. Chem. Soc. 131 (2009) 2009-2251, J. Org. Chem, 70 (2005) 5165.

Typically the Ullmann coupling of the compound of formula

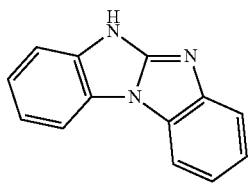 [SMILES: c1ccc2c(c1)nc1[nH]c3ccccc3n12]

with a compound of formula Y—R$^1$ (Y is Cl, Br, or I, especially Br, I very especially I) is done in the presence of copper, or a copper salt, such as, for example, CuI, CuBr, Cu$_2$O, or CuO, and a ligand, such as, for example, L-proline, trans-cyclohexane-1,2-diamine (DACH), 1,10-phenanthroline in a solvent, such as, for example, dimethylsulfoxide (DMSO), dimethylformamide (DMF), dimethylacetamide (DMA), N-methylpyrrolidone (NMP) and dioxane, or a solvent mixture. The reaction temperature is dependent on the reactivity of the starting materials, but is generally in the range of 25 to 200° C. If copper salt are used without a ligand the reaction temperatures are higher.

The N-arylation is, for example, disclosed in H. Gilman and D. A. Shirley, J. Am. Chem. Soc. 66 (1944) 888; D. Li et al., Dyes and Pigments 49 (2001) 181-186 and Eur. J. Org. Chem. (2007) 2147-2151.

Suitable base skeletons of the formula

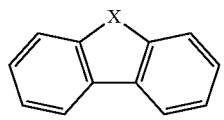

are either commercially available (especially in the cases when X is S, O, NH), or can be obtained by processes known to those skilled in the art. Reference is made to WO2010079051 and EP1885818.

The halogenation of said base skeletons

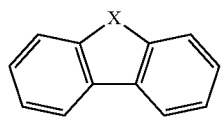

(carbazole, dibenzofuran or dibe-zothiophene, which is unsubstituted or substituted) can be performed by methods known to those skilled in the art. Preference is given to brominating or iodinating in the 3 and 6 positions (dibromination, diiodation or mixed bromination/iodation) or in the 3 or 6 positions (monobromination, monoiodation) of the base skeleton in the case of carbazole, respectively in the 2 and 8 positions (dibromination, diiodation) or in the 2 or 8 positions (monobromination, monoiodation) of the base skeleton in the case of dibenzofuran and dibenzothiophene.

Optionally substituted dibenzofurans, dibenzothiophenes and carbazoles can be dibrominated in the 2,8 positions (dibenzofuran and dibenzothiophene) or 3,6 positions (carbazole) with bromine or NBS in glacial acetic acid or in chloroform. For example, the bromination with Br$_2$ can be effected in glacial acetic acid or chloroform at low temperatures, e.g. 0° C. Suitable processes are described, for example, in M. Park, J. R. Buck, C. J. Rizzo, Tetrahedron, 54 (1998) 12707-12714 for X=NPh, and in W. Yang et al., J. Mater. Chem. 13 (2003) 1351 for X=S. In addition, 3,6-dibromocarbazole, 3,6-dibromo-9-phenylcarbazole, 2,8-dibromodibenzothiophene, 2,8-dibromodibenzofuran, 2-bromocarbazole, 3-bromodibenzothiophene, 3-bromodibenzofuran, 3-bromocarbazole, 2-bromodibenzothiophene and 2-bromodibenzofuran are commercially available.

Monobromination in the 4 position of dibenzofuran (and analogously for dibenzothiophene) is described, for example, in J. Am. Chem. Soc. 1984, 106, 7150. Dibenzofuran (dibenzothiophene) can be monobrominated in the 3 position by a sequence known to those skilled in the art, comprising a nitration, reduction and subsequent Sandmeyer reaction.

Monobromination in the 2 position of dibenzofuran or dibenzothiophene and monobromination in the 3 position of carbazole are effected analogously to the dibromination, with the exception that only one equivalent of bromine or NBS is added.

For the nucleophilic substitution, C$_1$— or F-substituted dibenzofurans, dibenzothiophenes and carbazoles are preferred. The chlorination is described, inter alia, in J. Heterocyclic Chemistry, 34 (1997) 891-900, Org. Lett., 6 (2004) 3501-3504; J. Chem. Soc. [Section] C: Organic, 16 (1971) 2775-7, Tetrahedron Lett. 25 (1984) 5363-6, J. Org. Chem. 69 (2004) 8177-8182. The fluorination is described in J. Org. Chem. 63 (1998) 878-880 and J. Chem. Soc., Perkin Trans. 2, 5 (2002) 953-957.

Introduction of the

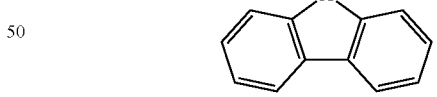

skeleton

The introduction of the

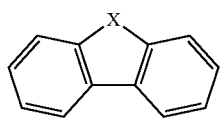

skeleton, can be affected, for example, by copper-catalyzed coupling (Ullmann reaction). Suitable reaction components and reaction conditions for carrying out the Ullmann reaction are mentioned above.

Alternatively, the introduction of the

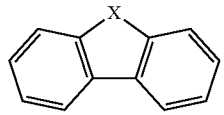

skeleton, especially in cases, wherein the

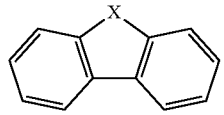

skeleton is substituted, e.g. by a group

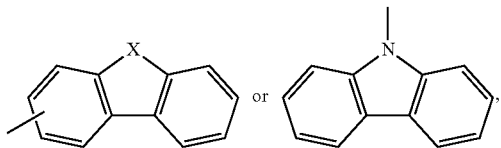

can be affected, for example, by Pd catalyzed coupling of diboronic acid or diboronate group containing dibenzofurans, dibenzothiophenes or carbazoles with halogenated aromatic groups, wherein the halogen is preferably I (Suzuki coupling).

An Example for a Suzuki coupling is shown in the example part of the present application:

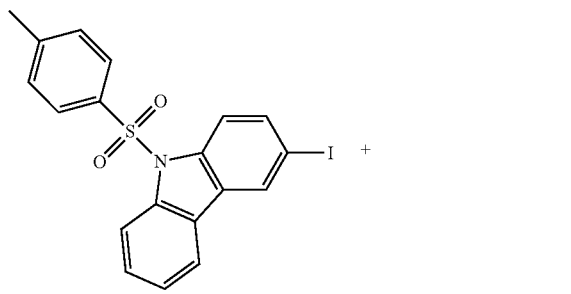

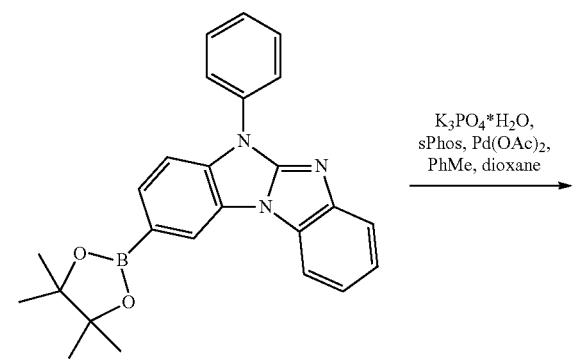 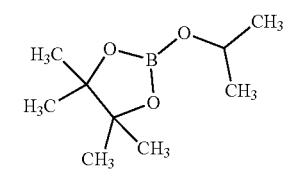

K₃PO₄*H₂O, sPhos, Pd(OAc)₂, PhMe, dioxane →

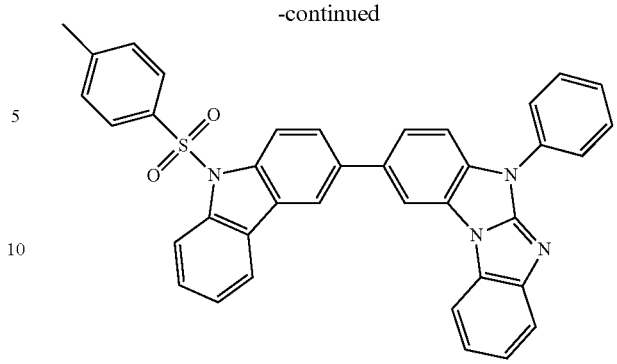

Diboronic acid or diboronate group containing dibenzofurans, dibenzothiophenes and carbazoles can be readily prepared by an increasing number of routes. An overview of the synthetic routes is, for example, given in Angew. Chem. Int. Ed. 48 (2009) 9240-9261.

By one common route diboronic acid or diboronate group containing dibenzofurans, dibenzothiophenes, and carbazoles can be obtained by reacting halogenated dibenzofurans dibenzothiophenes and carbazoles with $(Y^1O)_2B$—$B(OY^1)_2$,

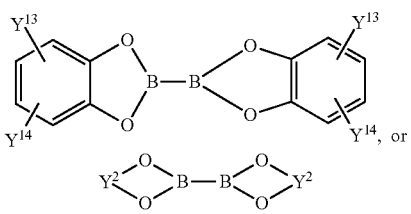

in the presence of a catalyst, such as, for example, [1,1'-bis(diphenylphosphino)ferrocene]dichloropalladium(II), complex (Pd(Cl)₂(dppf)), and a base, such as, for example, potassium acetate, in a solvent, such as, for example, dimethyl formamide, dimethyl sulfoxide, dioxane and/or toluene (cf. Prasad Appukkuttan et al., Synlett 8 (2003) 1204), wherein $Y^1$ is independently in each occurrence a $C_1$-$C_{18}$alkylgroup and $Y^2$ is independently in each occurrence a $C_2$-$C_{10}$alkylene group, such as —$CY^3Y^4$—$CY^5Y^6$—, or —$CY^7Y^8$—$CY^9Y^{10}$— $CY^{11}Y^{12}$—, wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen, or a $C_1$-$C_{18}$alkylgroup, especially —$C(CH_3)_2C(CH_3)_2$—, —$C(CH_3)_2CH_2C(CH_3)_2$—, or —$CH_2C(CH_3)_2CH_2$—, and $Y^{13}$ and $Y^{14}$ are independently of each other hydrogen, or a $C_1$-$C_{18}$alkylgroup.

Diboronic acid or diboronate group containing dibenzofurans, dibenzothiophenes and carbazoles can also be prepared by reacting halogenated dibenzofurans, dibenzothiophenes and carbazoles with alkyl lithium reagents, such as, for example, n-butyl lithium, or t-buthyl lithium, followed by reaction with boronic esters, such as, for example, B(isopropoxy)₃, B(methoxy)₃, or

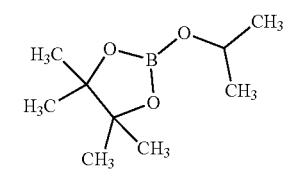

(cf. Synthesis (2000), 442-446).

Diboronic acid or diboronate group containing dibenzofurans, dibenzothiophenes and carbazoles can also be prepared by reacting dibenzofurans, dibenzothiophenes and carbazoles with lithium amides, such as, for example, lithium diisopropylamide (LDA) followed by reaction with boronic esters such as, for example, B(isopropoxy)$_3$, B(methoxy)$_3$, or

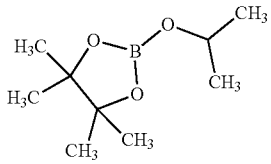

(J. Org. Chem. 73 (2008) 2176-2181).

In a further embodiment, the present invention concerns the following compounds, which are intermediates in the preparation of the compounds of formula (I):

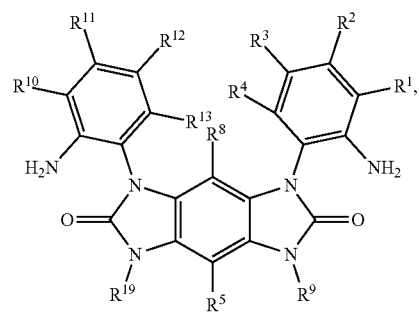
(IIIa)

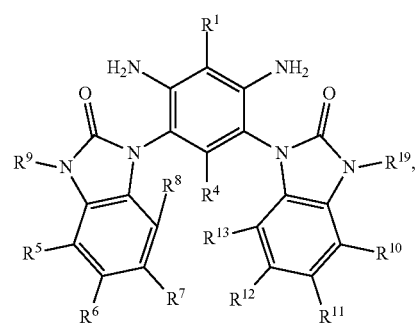
(IIIb)

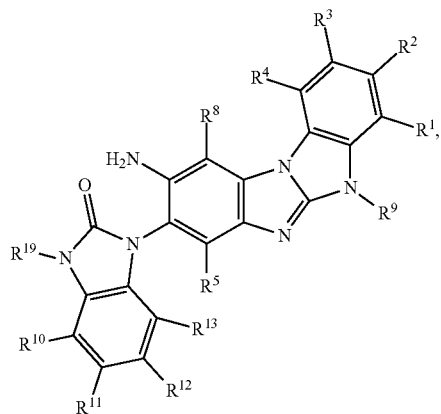
(IIIb′)

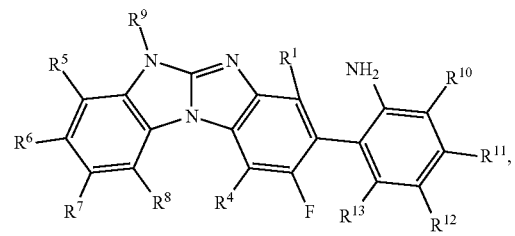
(IIIc)

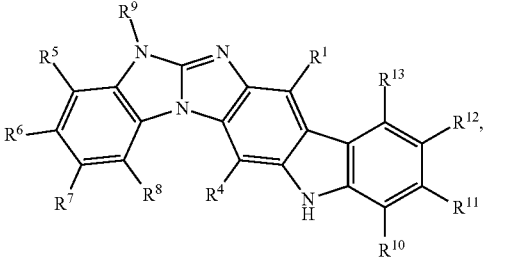
(IIId)

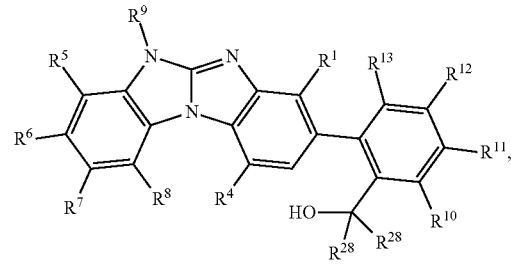
(IIIe)

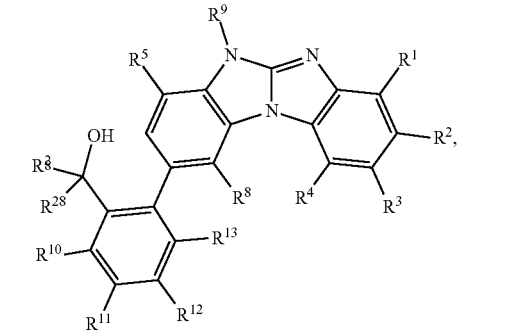
(IIIf)

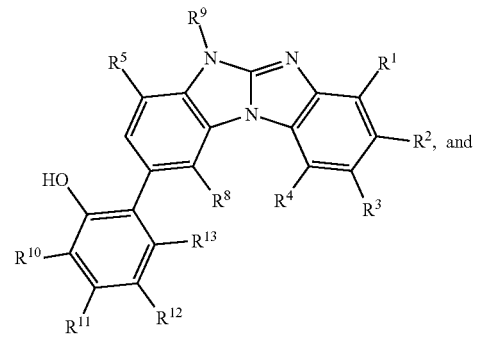
(IIIg)

-continued

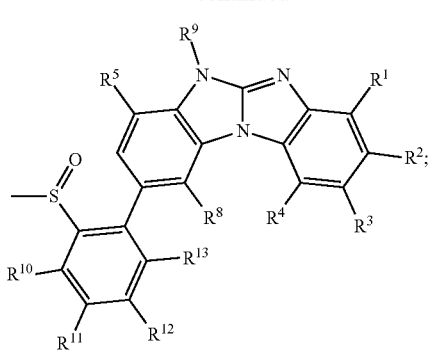

(IIIh)

as well as

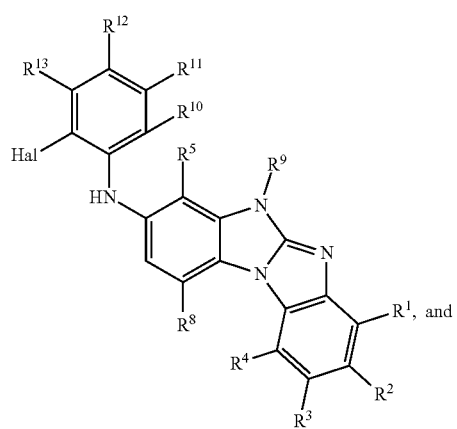

(IIIi)

and

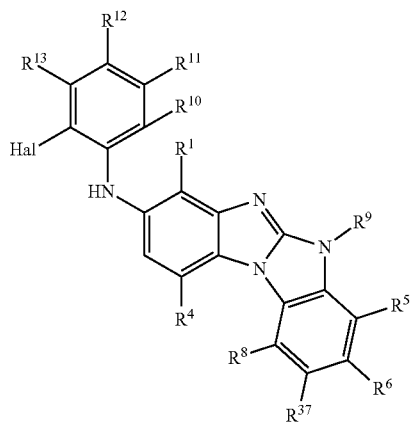

(IIIk)

wherein the residues $R^1$, $R^2$, $R^3$, $R^4$, $R^5$, $R^6$, $R^7$, $R^8$, $R^9$, $R^{10}$, $R^{11}$, $R^{12}$ and $R^{13}$ are described above.

Compounds of Formula (I) in Organic Electronics Applications

It has been found that the compounds of the formula (I) are particularly suitable for use in applications in which charge carrier conductivity is required, especially for use in organic electronics applications, for example selected from switching elements such as organic transistors, e.g. organic FETs and organic TFTs, organic solar cells and organic light-emitting diodes (OLEDs).

The organic transistor generally includes a semiconductor layer formed from an organic layer with charge transport capacity; a gate electrode formed from a conductive layer; and an insulating layer introduced between the semiconductor layer and the conductive layer. A source electrode and a drain electrode are mounted on this arrangement in order thus to produce the transistor element. In addition, further layers known to those skilled in the art may be present in the organic transistor. The layers with charge transport capacity may comprise the compounds of formula (I).

The organic solar cell (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes. When, however, plate-type electrodes arranged in parallel are used, at least one electrode is preferably formed from a transparent electrode, for example an ITO electrode or a fluorine-doped tin oxide electrode. The organic layer is formed from two sublayers, i.e. a layer with p-type semiconductor properties or hole transport capacity, and a layer formed with n-type semiconductor properties or charge transport capacity. In addition, it is possible for further layers known to those skilled in the art to be present in the organic solar cell. The layers with charge transport capacity may comprise the compounds of formula (I).

The compounds of the formula (I) being particularly suitable in OLEDs for use as matrix material in a light-emitting layer and/or as charge and/or exciton blocker material, i.e.as electron/exciton blocker material or as hole/exciton blocker material, and/or charge transport material, i.e. hole transport material or electron transport material, especially in combination with a phosphorescence emitter.

In the case of use of the inventive compounds of the formula (I) in OLEDs, OLEDs which have good efficiencies and a long lifetime and which can be operated especially at a low use and operating voltage are obtained. The inventive compounds of the formula (I) are suitable especially for use as matrix and/or charge transport, i.e. hole or electron transport, and/or charge blocker material, i.e. hole or electron blocker material, for green, red and yellow, preferably green and red, more preferably green emitters. Furthermore, the compounds of the formula (I) can be used as conductor/complementary materials in organic electronics applications selected from switching elements and organic solar cells. (In the sense of the present application, the terms matrix and host are used interchangeable).

In the emission layer or one of the emission layers of an OLED, it is also possible to combine an emitter material with at least one matrix material of the compound of the formula (I) and one or more, preferably one, further matrix materials (co-host). This may achieve a high quantum efficiency, low driving voltage and/or long lifetime of this device.

It is likewise possible that the compounds of the formula (I) are present in two or three of the following layers: in the light-emitting layer (preferably as matrix material), in the blocking layer (as charge blocker material) and/or in the charge transport layer (as charge transport material).

When a compound of the formula (I) is used as matrix (host) material in an emission layer and additionally as charge blocking material and/or as charge transport material, owing to the chemical identity or similarity of the materials, an improved interface between the emission layer and the adjacent material, which can lead to a decrease in the voltage with equal luminance and to an extension of the lifetime of the OLED. Moreover, the use of the same material as charge transport material and/or as charge blocker material and as matrix of an emission layer allows the production process of an OLED to be simplified, since the same source can be used for the vapor deposition process of the material of one of the compounds of the formula the compound of the formula (I).

Suitable structures of organic electronic devices, especially organic light-emitting diodes (OLED), are known to those skilled in the art and are specified below.

The present invention further provides an organic light-emitting diode (OLED) comprising an anode (a) and a cathode (i) and a light-emitting layer (e) arranged between the anode (a) and the cathode (i), and if appropriate at least one further layer selected from the group consisting of at least one blocking layer for holes/excitons, at least one blocking layer for electrons/excitons, at least one hole injection layer, at least one hole transport layer, at least one electron injection layer and at least one electron transport layer, wherein the at least one compound of the formula (I) is present in the light-emitting layer (e) and/or in at least one of the further layers. The at least one compound of the formula the compound of the formula (I) is preferably present in the light-emitting layer and/or the charge blocking layer and/or the charge transport layer.

In a preferred embodiment of the present invention, at least one compound of the formula the compound of the formula (I) is used as charge transport, i.e. electron transport or hole transport material. Examples of preferred compounds of the formula (I) are shown above.

In another preferred embodiment of the present invention, at least one compound of the formula the compound of the formula (I) is used as charge/exciton blocker material, i.e. as hole/exciton blocker material or electron/exciton blocker material. Examples of preferred compounds of the formula (I) are shown above.

The present application further relates to a light-emitting layer comprising at least one compound of the formula (I), preferably as host material or co-host material. Examples of preferred compounds of the formula (I) are shown above.

Structure of the Inventive OLED

The inventive organic light-emitting diode (OLED) thus generally has the following structure: an anode (a) and a cathode (i) and a light-emitting layer (e) arranged between the anode (a) and the cathode (i).

The inventive OLED may, for example—in a preferred embodiment—be formed from the following layers:
1. Anode (a)
2. Hole transport layer (c)
3. Light-emitting layer (e)
4. Blocking layer for holes/excitons (f)
5. Electron transport layer (g)
6. Cathode (i)

Layer sequences different than the aforementioned structure are also possible, and are known to those skilled in the art. For example, it is possible that the OLED does not have all of the layers mentioned; for example, an OLED with layers (a) (anode), (e) (light-emitting layer) and (i) (cathode) is likewise suitable, in which case the functions of the layers (c) (hole transport layer) and (f) (blocking layer for holes/excitons) and (g) (electron transport layer) are assumed by the adjacent layers. OLEDs which have layers (a), (c), (e) and (i), or layers (a), (e), (f), (g) and (i), are likewise suitable. In addition, the OLEDs may have a blocking layer for electrons/excitons (d) between the hole transport layer (c) and the Light-emitting layer (e).

It is additionally possible that a plurality of the aforementioned functions (electron/exciton blocker, hole/exciton blocker, hole injection, hole conduction, electron injection, electron conduction) are combined in one layer and are assumed, for example, by a single material present in this layer. For example, a material used in the hole transport layer, in one embodiment, may simul-taneously block excitons and/or electrons.

Furthermore, the individual layers of the OLED among those specified above may in turn be formed from two or more layers. For example, the hole transport layer may be formed from a layer into which holes are injected from the electrode, and a layer which transports the holes away from the hole-injecting layer into the light-emitting layer. The electron transport layer may likewise consist of a plurality of layers, for example a layer in which electrons are injected by the electrode, and a layer which receives electrons from the electron injection layer and transports them into the light-emitting layer. These layers mentioned are each selected according to fac-tors such as energy level, thermal resistance and charge carrier mobility, and also energy difference of the layers specified with the organic layers or the metal electrodes. The person skilled in the art is capable of selecting the structure of the OLEDs such that it is matched opti-mally to the organic compounds used in accordance with the invention.

In a preferred embodiment the OLED according to the present invention comprises in this order: (a) an anode,
(b) optionally a hole injection layer,
(c) optionally a hole transport layer,
(d) optionally an exciton blocking layer
(e) an emitting layer,
(f) optionally a hole/exciton blocking layer
(g) optionally an electron transport layer,
(h) optionally an electron injection layer, and
(i) a cathode.

In a particularly preferred embodiment the OLED according to the present invention comprises in this order:
(a) an anode,
(b) optionally a hole injection layer,
(c) a hole transport layer,
(d) an exciton blocking layer
(e) an emitting layer,
(f) a hole/exciton blocking layer
(g) an electron transport layer, and
(h) optionally an electron injection layer, and
(i) a cathode.

The properties and functions of these various layers, as well as example materials are known from the art and are described in more detail below on basis of preferred embodiments.

Anode (a):

The anode is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals comprise the metals of groups 11, 4, 5 and 6 of the Periodic Table of the Elements, and also the transition metals of groups 8 to 10. When the anode is to be transparent, mixed metal oxides of groups 12, 13 and 14 of the Periodic Table of the Elements are generally used, for example indium tin oxide (ITO). It is likewise possible that the anode (a) comprises an organic material, for example polyaniline, as described, for example, in Nature, Vol. 357, pages 477 to 479 (Jun. 11, 1992). Preferred anode materials include conductive metal oxides, such as indium tin oxide (ITO) and indium zinc oxide (IZO), aluminum zinc oxide (AlZnO), and metals. Anode (and substrate) may be sufficiently transparent to create a bottom-emitting device. A preferred transparent substrate and anode combination is commercially available ITO (anode) deposited on glass or plastic (substrate). A reflective anode may be preferred for some top-emitting devices, to increase the amount of light emitted from the top of the device. At least either the anode or the cathode should be at least partly transparent in order to be able to emit the light formed. Other anode materials and structures may be used.

Hole Injection Layer (b):

Generally, injection layers are comprised of a material that may improve the injection of charge carriers from one layer, such as an electrode or a charge generating layer, into an adjacent organic layer. Injection layers may also perform a charge transport function. The hole injection layer may be any layer that improves the injection of holes from anode into an adjacent organic layer. A hole injection layer may comprise a solution deposited material, such as a spin-coated polymer, or it may be a vapor deposited small molecule material, such as, for example, CuPc or MTDATA. Polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxy-ethoxy)ethoxy]-2,5-diyl) (Plexcore® OC Conducting Inks commercially available from Plextronics), and copolymers such as poly(3,4-ethylenedioxythiophene)/poly(4-styrene-sulfonate) also called PEDOT/PSS.

An example for a suitable hole injection material is:

(see also hole-transporting molecules).

Hole Transport Layer (c):

Either hole-transporting molecules or polymers may be used as the hole transport material. Suitable hole transport materials for layer (c) of the inventive OLED are disclosed, for example, in Kirk-Othmer Encyclopedia of Chemical Technology, 4th Edition, Vol. 18, pages 837 to 860, 1996, US20070278938, US2008/0106190, US2011/0163302 (triarylamines with (di)benzothiophen/(di)benzofuran; Nan-Xing Hu et al. Synth. Met. 111 (2000) 421 (indolocarbazoles), WO2010002850 (substituted phenylamine compounds) and WO2012/16601 (in particular the hole transport materials mentioned on pages 16 and 17 of WO2012/16601). Combination of different hole transport material may be used. Reference is made, for example, to WO2013/022419, wherein

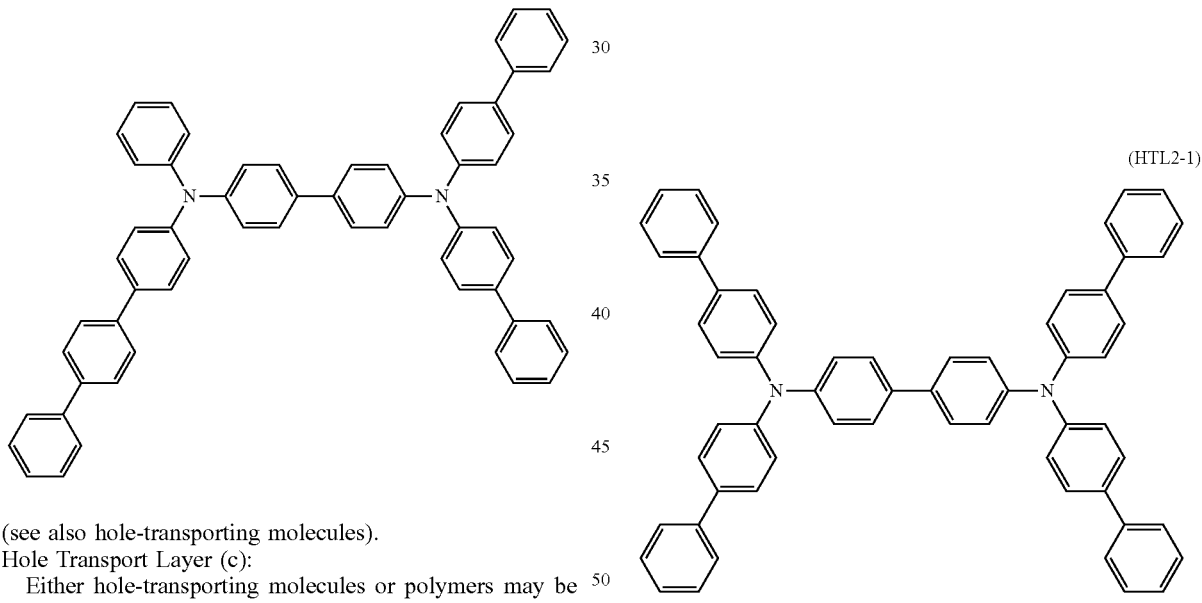

constitute the hole transport layer.

Customarily used hole-transporting molecules are selected from the group consisting of

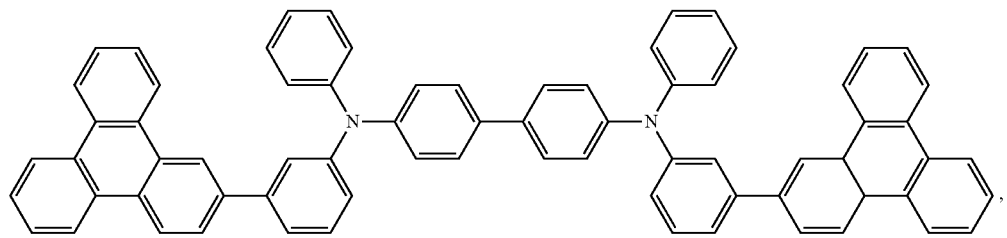

-continued
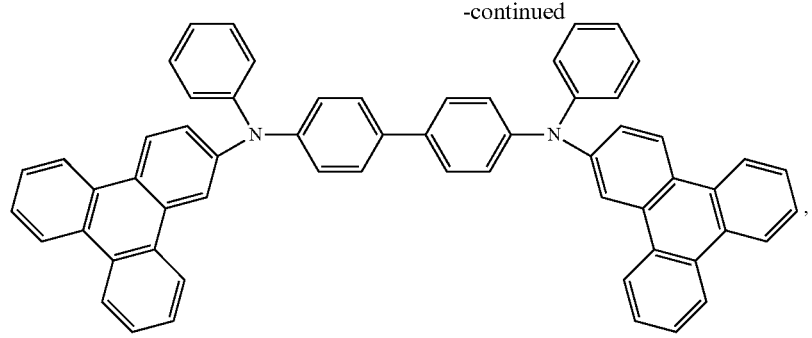
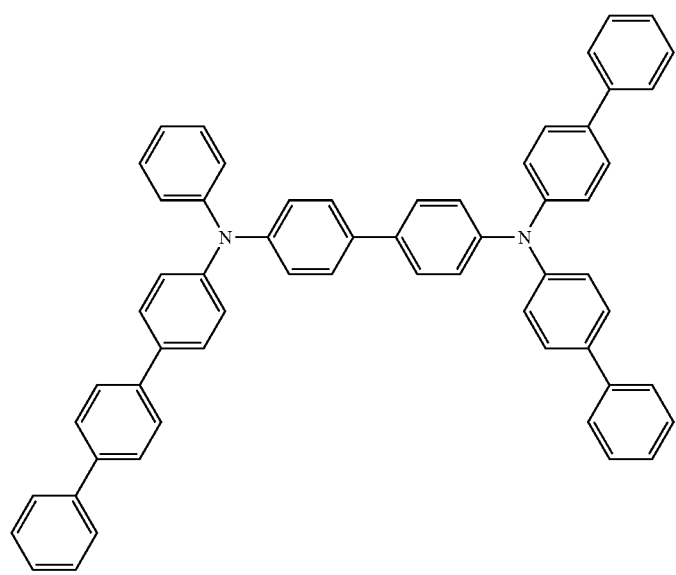
(4-phenyl-N-(4-phenylphenyl)-N-[4-[4-(N-[4-(4-phenyl-phenyl)phenyl]anilino)phenyl]phenyl]aniline),
(4-phenyl-N-(4-phenylphenyl)-N-[4-[4-(4-phenyl-N-(4-phenylphenyl)anilino)phenyl]phenyl]aniline),
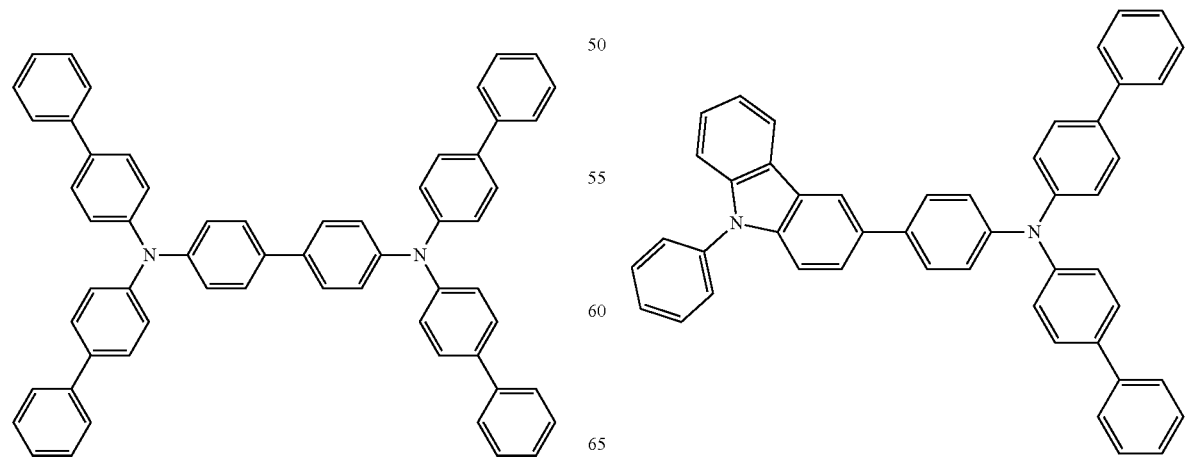

(4-phenyl-N-[4-(9-phenylcarbazol-3-yl)phenyl]-N-(4-phenylphenyl)aniline),

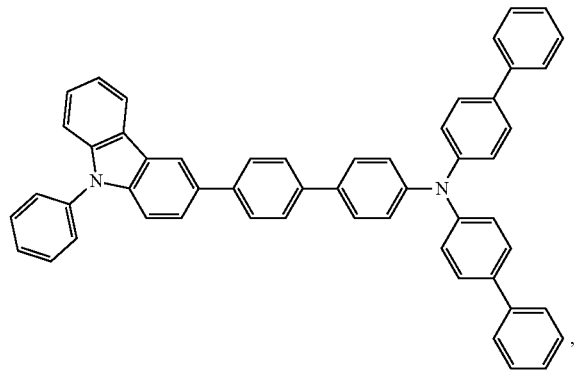

(1,1',3,3'-tetraphenylspiro[1,3,2-benzodiazasilole-2,2'-3a,7a-dihydro-1,3,2-benzodiazasilole]),

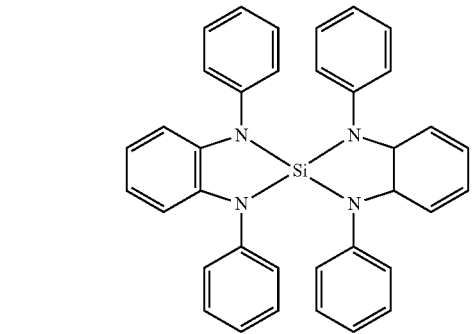

(N2,N2,N2',N2',N7,N7,N7',N7'-octakis(p-tolyl)-9,9'-spirobi[fluorene]-2,2',7,7'-tetramine), 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), tri-phenylamine (TPA), bis[4-(N,N-diethylamino)$_2$-methylphenyl](4-methylphenyl)methane (MPMP), 1-phenyl-3-[p-(diethylamino)styryl]5-[p-(diethylamino)phenyl]pyrazoline (PPR or DEASP), 1,2-trans-bis(9H-carbazol9-yl)-cyclobutane (DCZB), N,N,N',N'-tetrakis(4-methylphenyl)-(1,1'-biphenyl)-4,4'-diamine (TTB), fluorine compounds such as 2,2',7,7'-tetra(N,N-ditolyl)amino9,9-spirobifluorene (spiro-TTB), N,N'-bis(naphthalen-1-yl)-N,N'-bis(phenyl)$_{9,9}$-spirobifluorene (spiro-NPB) and 9,9-bis(4-(N,N-bis-biphenyl-4-yl-amino)phenyl-9Hfluorene, benzidine compounds such as N,N'-bis(naphthalen-1-yl)-N,N'-bis(phenyl)benzidine and porphyrin compounds such as copper phthalocyanines. In addition, polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS. Preferred examples of a material of the hole injecting layer are a porphyrin compound, an aromatic tertiary amine compound, or a styrylamine compound. Particularly preferable examples include an aromatic tertiary amine compound such as hexacyanohexaazatriphenylene (HAT).

The hole-transporting layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, 2003, 359 (p-doped organic layers); A. G. Werner, F. Li, K. Harada, M. Pfeiffer, T. Fritz, K. Leo, Appl. Phys. Lett., Vol. 82, No. 25, 2003, 4495 and Pfeiffer et al., Organic Electronics 2003, 4, 89-103 and K. Walzer, B. Maennig, M. Pfeiffer, K. Leo, Chem. Soc. Rev. 2007, 107, 1233. For example it is possible to use mixtures in the hole-transporting layer, in particular mixtures which lead to electrical p-doping of the hole-transporting layer. p-Doping is achieved by the addition of oxidizing materials. These mixtures may, for example, be the following mixtures: mixtures of the abovementioned hole transport materials with at least one metal oxide, for example $MoO_2$, $MoO_3$, $WO_E$, $ReO_3$ and/or $V_2O5$, preferably $MoO_3$ and/or $ReO_3$, more preferably $MoO_3$, or mixtures comprising the aforementioned hole transport materials and one or more compounds selected from 7,7,8,8-tetracyanoquinodimethane (TCNQ), 2,3,5,6-tetrafluoro-7,7,8,8-tetracyanoquinodimethane ($F_4$-TCNQ), 2,5-bis(2-hydroxyethoxy)-7,7,8,8-tetracyanoquinodimethane, bis(tetra-n-butylammonium)tetracyanodiphenoquinodimethane, 2,5-dimethyl-7,7,8,8-tetracyanoquinodimethane, tetracyanoethylene, 11,11,12,12-tetracyanonaphtho2,6-quinodimethane, 2-fluoro-7,7,8,8-tetracyanoquino-dimethane, 2,5-difluoro-7,7,8,8etracyanoquinodimethane, di-cyanomethylene-1,3,4,5,7,8-hexafluoro-6Hnaphthalen-2-ylidene)malononitrile ($F_6$-TNAP), Mo(tfd)$_3$ (from Kahn et al., J. Am. Chem. Soc. 2009, 131 (35), 12530-12531), compounds as described in EP1988587, US2008265216, EP2180029, US20100102709, WO2010-132236, EP2180029 and quinone compounds as mentioned in EP2401254.

In addition to the materials mentioned above or as an alternative, the compound of formula (I) may be used as hole transport material.

Electron/Exciton Blocking Layer (d):

Blocking layers may be used to reduce the number of charge carriers (electrons or holes) and/or excitons that leave the emissive layer. An electron/exciton blocking layer (d) may be disposed between the first emitting layer (e) and the hole transport layer (c), to block electrons from emitting layer (e) in the direction of hole transport layer (c). Blocking layers may also be used to block excitons from diffusing out of the emissive layer.

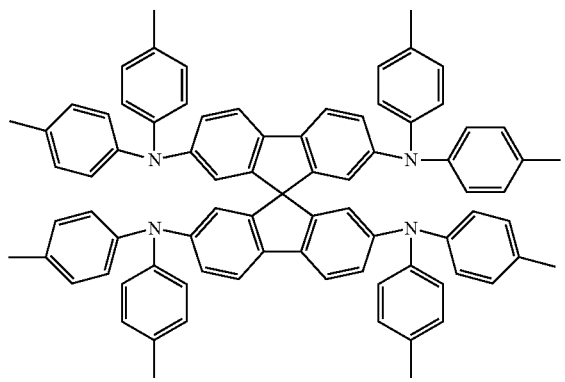

Suitable metal complexes for use as electron/exciton blocker material are, for example, carbene complexes as described in WO2005/019373A2, WO2006/056418A2, WO2005/113704, WO2007/115970, WO2007/115981, WO2008/000727 and PCT/EP2014/055520. Explicit reference is made here to the disclosure of the WO applications cited, and these disclosures shall be considered to be incorporated into the content of the present application.

In addition to the materials mentioned above or as an alternative, the compound of formula (I) may be used as exciton/electron blocker material.

Emitting Layer (e)

The light emitting layer is an organic layer having a light emitting function and is formed from one or more layers, wherein one of the layers comprises the host material and the light emitting material as described below.

Preferably, the light emitting layer of the inventive OLED comprises at least one compound of formula (I) as host material.

When the light emitting layer is composed of two or more layers, the light emitting layer or layers other than that mentioned above contains or contain a host material and a dopant material when a doping system is employed. The major function of the host material is to promote the recombination of electrons and holes and confine excitons in the light emitting layer. The dopant material causes the excitons generated by recombination to emit light efficiently.

In case of a phosphorescent device, the major function of the host material is to confine the excitons generated on the dopant in the light emitting layer.

The light emitting layer may be made into a double dopant layer, in which two or more kinds of dopant materials having high quantum yield are combinedly used and each dopant material emits light with its own color. For example, to obtain a yellow emission, a light emitting layer formed by co-depositing a host, a red-emitting dopant and a green-emitting dopant is used.

In a laminate of two or more light emitting layers, electrons and holes are accumulated in the interface between the light emitting layers, and therefore, the recombination region is localized in the interface between the light emitting layers, to improve the quantum efficiency.

The light emitting layer may be different in the hole injection ability and the electron injection ability, and also in the hole transporting ability and the electron transporting ability each being expressed by mobility.

The light emitting layer is formed, for example, by a known method, such as a vapor deposition method, a spin coating method, and LB method. Alternatively, the light emitting layer may be formed by making a solution of a binder, such as resin, and the material for the light emitting layer in a solvent into a thin film by a method such as spin coating.

The light emitting layer is preferably a molecular deposit film. The molecular deposit film is a thin film formed by depositing a vaporized material or a film formed by solidifying a material in the state of solution or liquid. The molecular deposit film can be distinguished from a thin film formed by LB method (molecular build-up film) by the differences in the assembly structures and higher order structures and the functional difference due to the structural differences.

The light-emitting layer (e) comprises at least one emitter material. In principle, it may be a fluo-rescence or phosphorescence emitter, suitable emitter materials being known to those skilled in the art. The at least one emitter material is preferably a phosphorescence emitter.

The emission wavelength of the phosphorescent dopant used in the light emitting layer is not particularly limited. In a preferred embodiment, at least one of the phosphorescent dopants used in the light emitting layer has the peak of emission wavelength of in general 430 nm or longer and 780 nm or shorter, preferably 490 nm or longer and 700 nm or shorter and more preferably 490 nm or longer and 650 nm or shorter. Most preferred are green emitter materials (490 nm to 570 nm).

The phosphorescent dopant (phosphorescent emitter material) is a compound which emits light by releasing the energy of excited triplet state and preferably a organometallic complex comprising at least one metal selected from Ir, Pt, Pd, Os, Au, Cu, Re, Rh and Ru and a ligand, alt-hough not particularly limited thereto as long as emitting light by releasing the energy of excited triplet state. A ligand having an ortho metal bond is preferred. In view of obtaining a high phosphorescent quantum yield and further improving the external quantum efficiency of electroluminescence device, a metal complex comprising a metal selected from Ir, Os, and Pt is preferred, with iridium complex, osmium complex, and platinum, particularly an ortho metallated complex thereof being more preferred, iridium complex and platinum complex being still more preferred, and an ortho metallated iridium complex being particularly preferred.

The compounds of the formula (I) can be used as the matrix in the light-emitting layer.

Suitable metal complexes for use in the inventive OLEDs, preferably as emitter material, are described, for example, in documents WO 02/60910 A1, US 2001/0015432 A1, US 2001/0019782 A1, US 2002/0055014 A1, US 2002/0024293 A1, US 2002/0048689 A1, EP 1 191 612 A2, EP 1 191 613 A2, EP 1 211 257 A2, US 2002/0094453 A1, WO 02/02714 A2, WO 00/70655 A2, WO 01/41512 A1, WO 02/15645 A1, WO 2005/019373 A2, WO 2005/113704 A2, WO 2006/115301 A1, WO 2006/067074 A1, WO 2006/056418, WO 2006121811 A1, WO 2007095118 A2, WO 2007/115970, WO 2007/115981, WO 2008/000727, WO2010129323, WO2010056669, WO10086089, US2011/0057559, WO2011/106344, US2011/0233528, WO2012/048266 and WO2012/172482.

Further suitable metal complexes are the commercially available metal complexes tris(2-phenylpyridine)iridium (III), iridium(III) tris(2-(4-tolyl)pyridinato-N,C$^{2'}$), bis(2-phenylpyridine)(acetylacetonato)iridium(III), iridium(III) tris(1-phenylisoquinoline), iridium(III) bis(2,2'-benzothienyl)pyridinato-N,C$^{3'}$)(acetylacetonate), tris(2-phenylquinoline)iridium(III), iridium(III) bis(2-(4,6-difluorophenyl)pyridinato-N,C$^2$)picolinate, iridium(III) bis(1-phenylisoquinoline)(acetylacetonate), bis(2-phenylquinoline)(acetylacetonato)iridium(III), iridium(III) bis(di-benzo[f,h]quinoxaline)(acetylacetonate), iridium(III) bis(2-methyldi-benzo[f,h]quinoxaline)(acetylacetonate) and tris(3-methyl-1-phenyl-4-trimethylacetyl-5-pyrazolino)terbium(III), bis[1-(9,9-dimethyl-9H-fluoren-2-yl)isoquinoline](acetyl-acetonato)iridium(III), bis(2-phenylbenzothiazolato)(acetylacetonato)iridium(III), bis(2-(9,9-dihexylfluorenyl)-1-pyridine)(acetylacetonato)iridium(III), bis(2-benzo[b]thiophen-2-yl-pyridine)(acetylacetonato)iridium(l II).

In addition, the following commercially available materials are suitable: tris(dibenzoylacetonato)mono(phena- nthroline)europium(III), tris(dibenzoylmethane)-mono(phenanthroline)europium(III), tris(dibenzoylmethane)mono(5-aminophenanthroline)-europium(III), tris(di-2-naphthoylmethane)mono(phenanthroline)europium(III), tris(4-bromobenzoylmethane)mono(phenanthroline)europium(III), tris(di(biphenyl)methane)-mono(phenanthroline)europium (III), tris(dibenzoylmethane)mono(4,7-diphenyl-phenanthroline)europium(III), tris(dibenzoylmethane)mono(4,7-di-methyl-phenanthroline)europium(III), tris(dibenzoylmethane)mono(4,7-dimethylphenanthrolinedisulfonic acid) europium(III) disodium salt, tris[di(4-(2-(2-ethoxyethoxy) ethoxy)benzoylmethane)]mono-(phenanthroline)europium (III) and tris[di[4-(2-(2-ethoxyethoxy)ethoxy)benzoylmethane)]mono(5-aminophenanthroline)europium(III), osmium(II) bis(3-(trifluoromethyl)-5-(4-tert-butylpyridyl)-1,2,4-triazolato)diphenylmethylphosphine, osmium(III) bis (3-(trifluoromethyl)-5-(2-pyridyl)-1,2,4-triazole)dimethylphenylphosphine, osmium(III) bis(3-(trifluoromethyl)-5-(4-tert-butylpyridyl)-1,2,4-triazolato)dimethylphenylphosphine, osmium(II) bis(3-(trifluoromethyl)-5-(2-pyridyl)-pyrazolato)dimethylphenylphosphine, tris[4,4'-di-tert-butyl (2,2')-bipyridine]ruthenium(IIII), osmi-um(lII) bis(2-(9,9-dibutylfluorenyl)-1-isoquinoline(acetylacetonate).

Particularly suitable metal complexes are described in US2012223295, US2014367667, US2013234119, US2014001446, US2014231794, US2014008633, WO2012108388 and WO2012108389. The emitters mentioned in US2013234119, paragraph [0222], are exemplified. Selected emitters, especially red emitters, of said emitters mentioned in US2013234119, paragraph [0222], are:

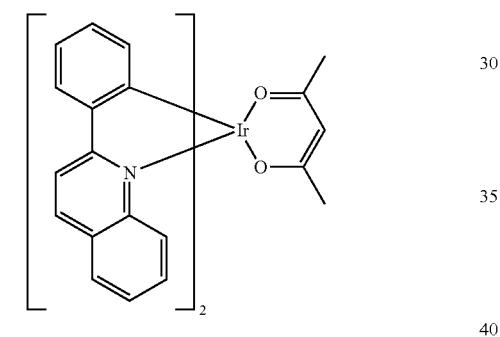

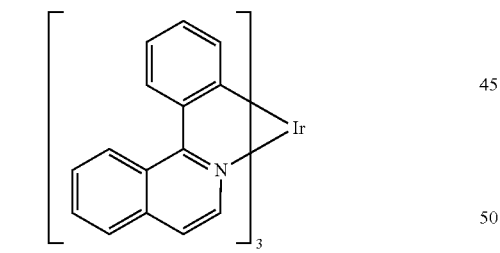

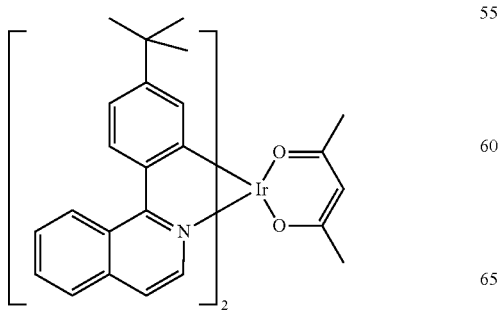

-continued

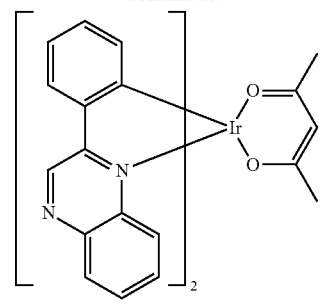

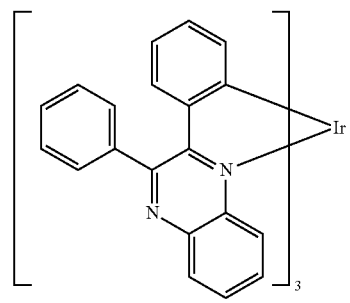

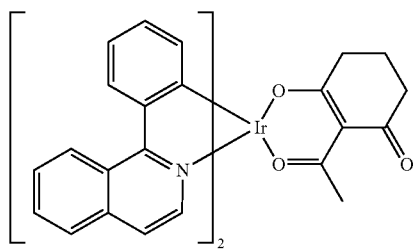

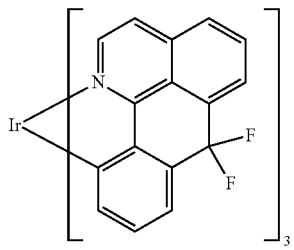

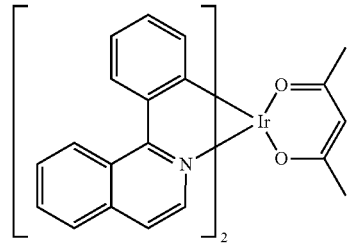

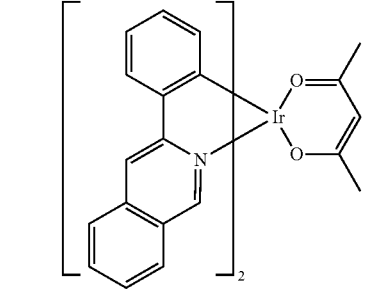

341
-continued
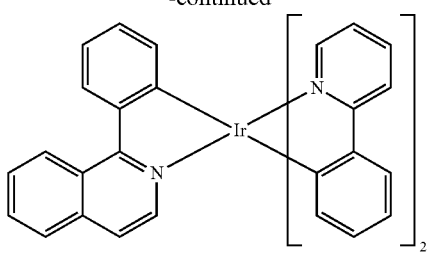
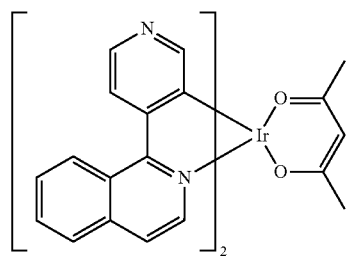
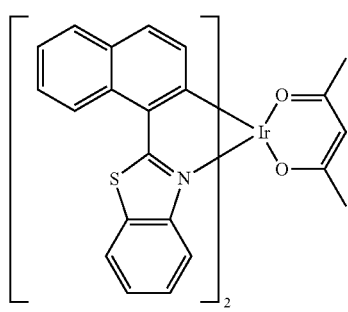
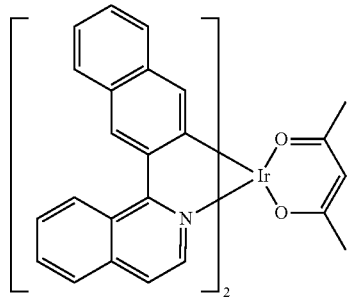
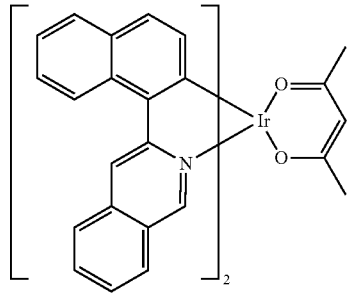
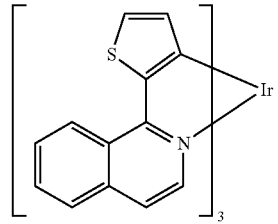
342
-continued
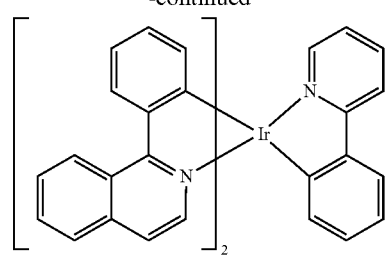
Further suitable Emitters are mentioned in: MRS Bulletin, 2007, 32, 694:
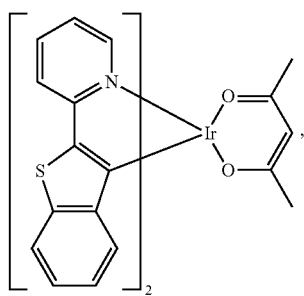
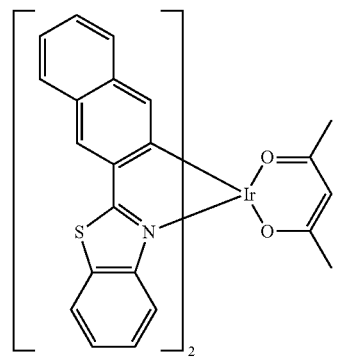
Further suitable Emitters are mentioned in: WO2009100991:
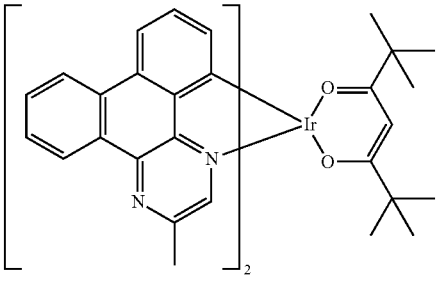

Further suitable Emitters are mentioned in: WO2008101842:
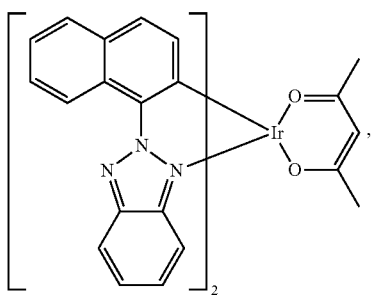
Further suitable Emitters are mentioned in: US 20140048784, especially in paragraph [0159]:
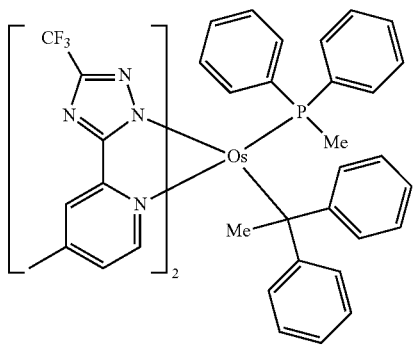
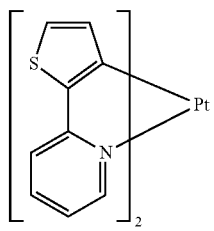
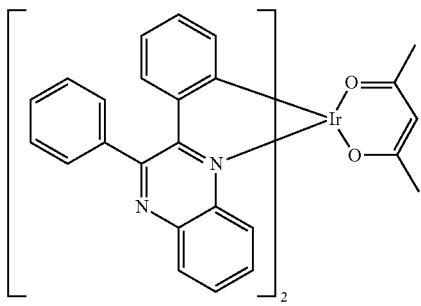
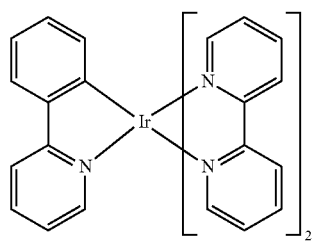
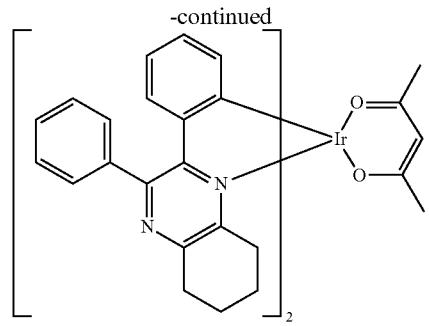
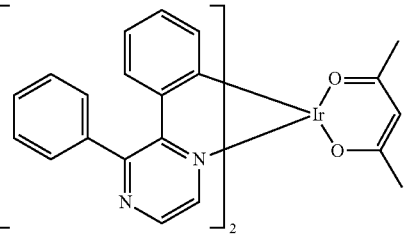
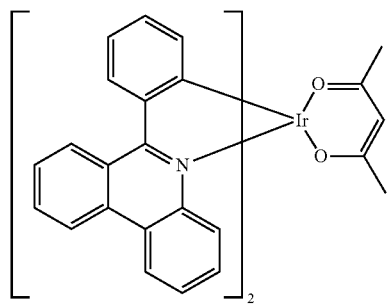
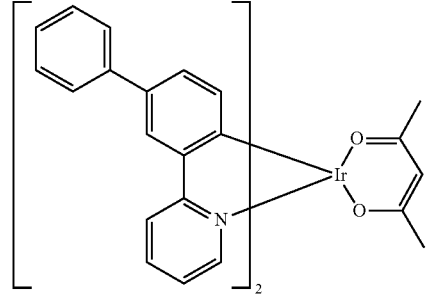
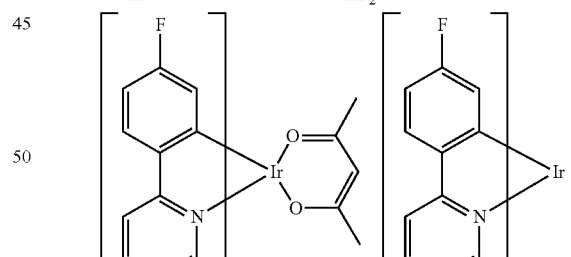
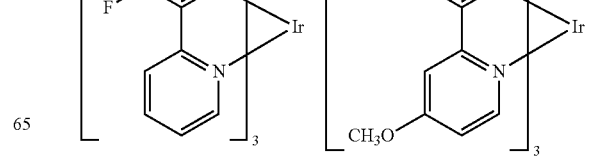

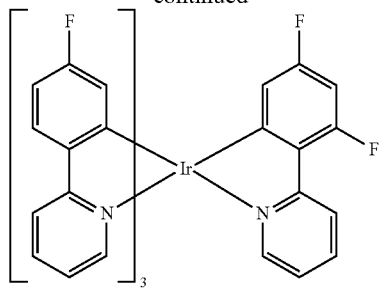
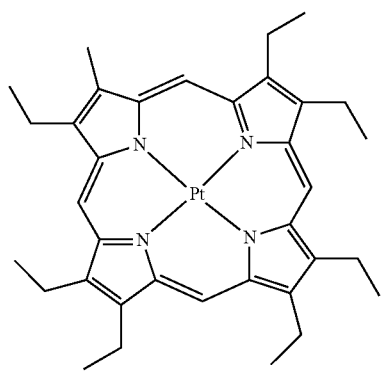
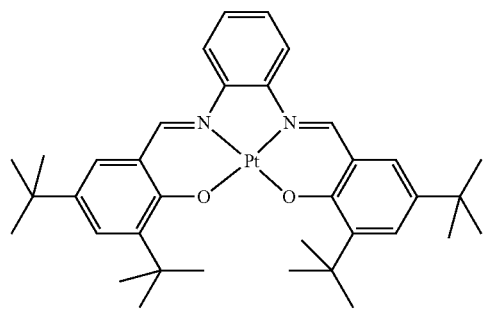
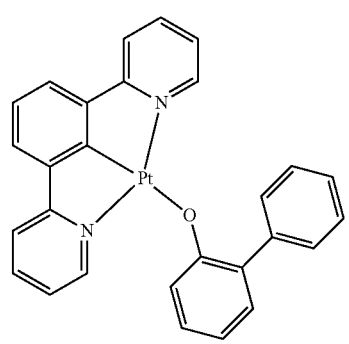
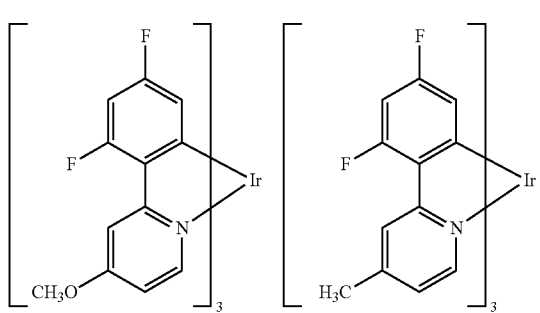
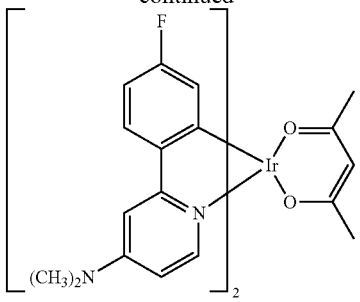
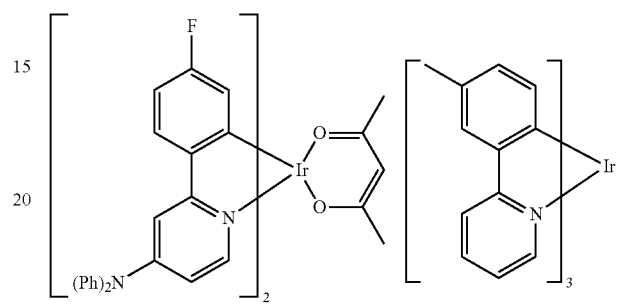
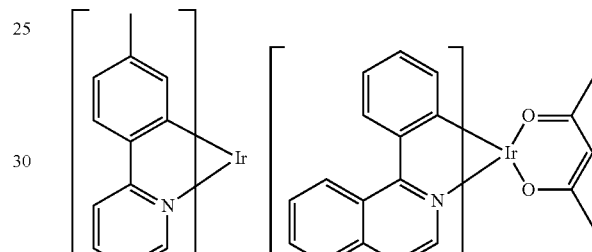
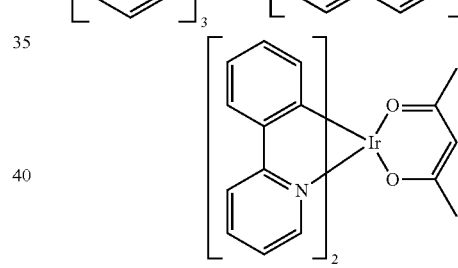
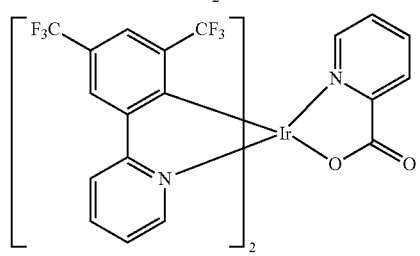
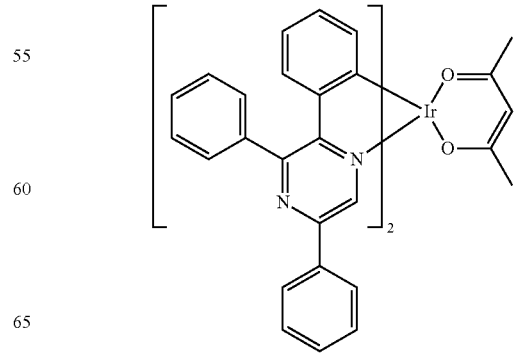

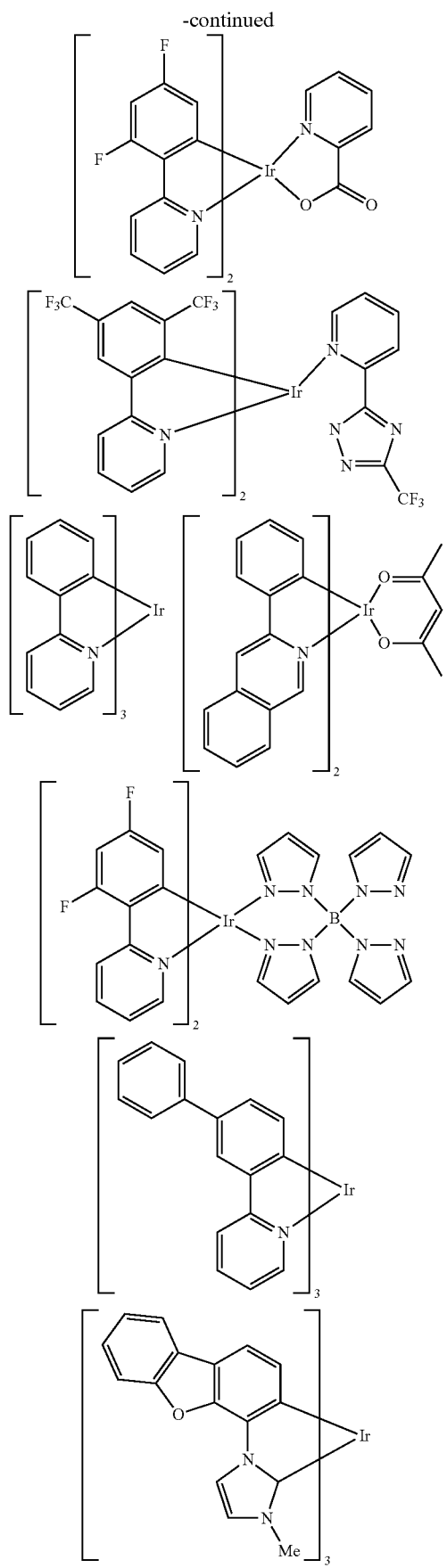
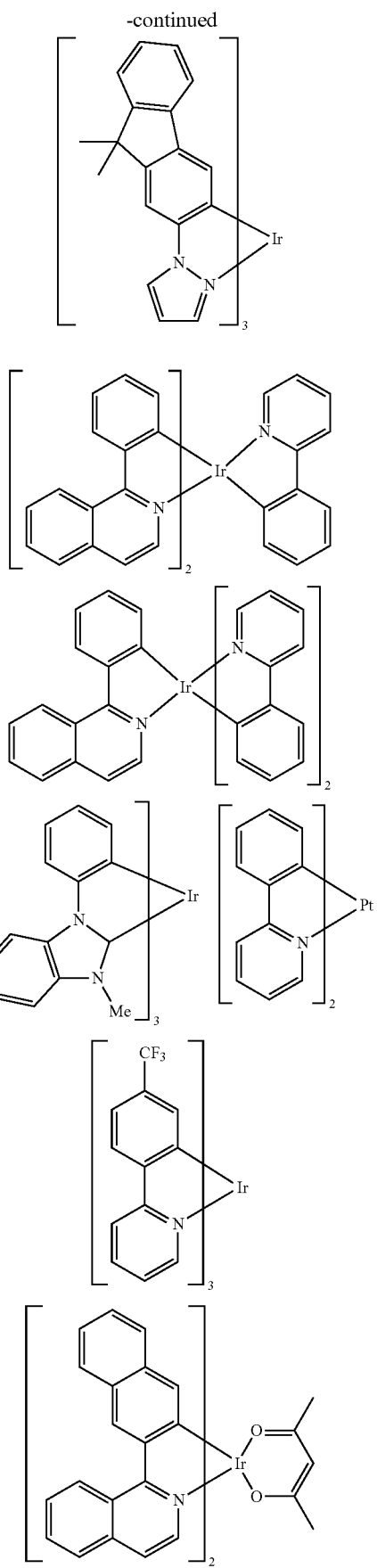

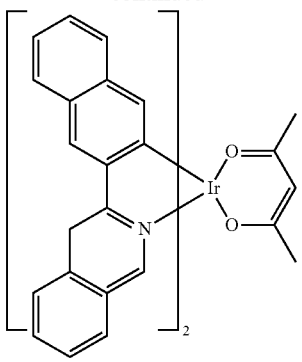
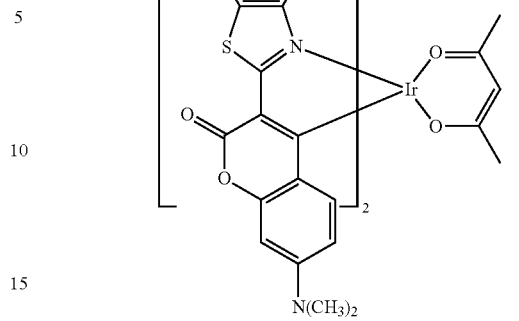
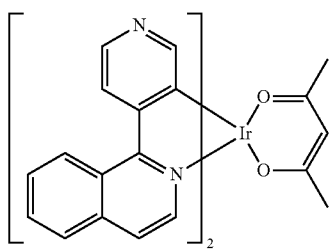
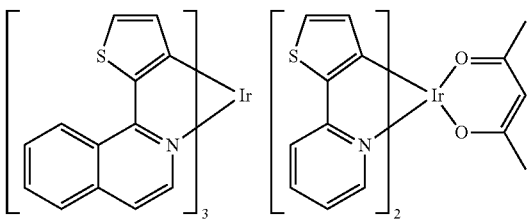
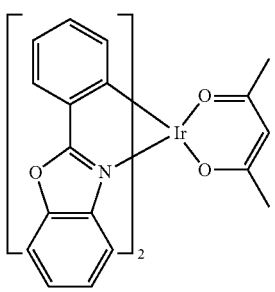
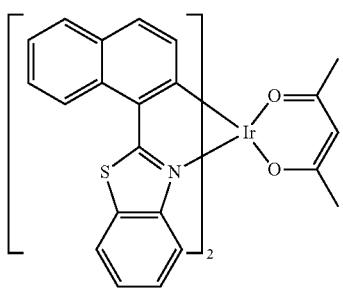

Suitable phosphorescent blue emitters are specified in the following publications: WO2006/056418A2, WO2005/113704, WO2007/115970, WO2007/115981, WO2008/000727, WO2009050281, WO2009050290, WO2011051404, US2011/057559 WO2011/073149, WO2012/121936A2, US2012/0305894A1, WO2012/170571, WO2012/170461, WO2012/170463, WO2006/121811, WO2007/095118, WO2008/156879, WO2008/156879, WO2010/068876, US2011/0057559, WO2011/106344, US2011/0233528, WO2012/048266, WO2012/172482, PCT/EP2014/064054 and PCT/EP2014/066272.

The light emitting layer (e) comprises for example at least one carbene complex as phosphorescence emitter. Suitable carbene complexes are, for example, compounds of the formula

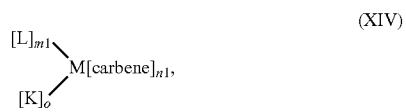

(XIV)

which are described in WO 2005/019373 A2, wherein the symbols have the following meanings:

M is a metal atom selected from the group consisting of Co, Rh, Ir, Nb, Pd, Pt, Fe, Ru, Os, Cr, Mo, W, Mn, Tc, Re, Cu, Ag and Au in any oxidation state possible for the respective metal atom; carbene is a carbene ligand which may be uncharged or monoanionic and monodentate, bidentate or tridentate, with the carbene ligand also being able to be a biscarbene or triscarbene ligand;

L is a monoanionic or dianionic ligand, which may be monodentate or bidentate;

K is an uncharged monodentate or bidentate ligand, preferably selected from the group consisting of phosphines; phosphonates and derivatives thereof, arsenates and derivatives thereof; phosphites; CO; pyridines; nitriles and conjugated dienes which form a π complex with $M^1$;

n1 is the number of carbene ligands, where n1 is at least 1 and when n1>1 the carbene ligands in the complex of the formula I can be identical or different;

m1 is the number of ligands L, where m1 can be 0 or ≥1 and when m1>1 the ligands L can be identical or different;

o is the number of ligands K, where o can be 0 or ≥1 and when o>1 the ligands K can be identical or different;

where the sum n1+m1+o is dependent on the oxidation state and coordination number of the metal atom and on the denticity of the ligands carbene, L and K and also on the charge on the ligands, carbene and L, with the proviso that n1 is at least 1.

More preferred are metal-carbene complexes of the general formula

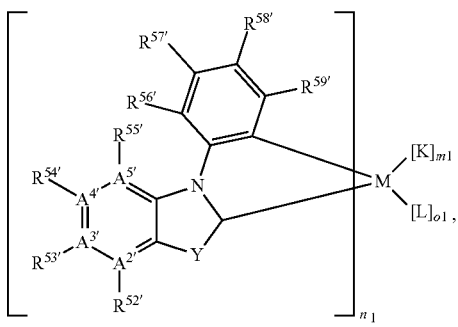

(XIVa)

which are described in WO2011/073149, where M is Ir, or Pt, n1 is an integer selected from 1, 2 and 3, Y is $NR^{51'}$, O, S or $C(R^{25'})_2$, $A^{2'}$, $A^{3'}$, $A^{4'}$, and $A^{5'}$ are each independently N or C, where 2 A'=nitrogen atoms and at least one carbon atom is present between two nitrogen atoms in the ring, $R^{51'}$ is a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, $R^{52'}$, $R^{53'}$, $R^{54'}$ and $R^{55'}$ are each, if $A^{2'}$, $A^{3'}$, $A^{4'}$ and/or $A^{5'}$ is N, a free electron pair, or, if $A^{2'}$, $A^{3'}$, $A^{4'}$ and/or $A^{5'}$ is C, each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or $R^{53'}$ and $R^{54'}$ together with $A^{3'}$ and $A^{4'}$ form an optionally substituted, unsaturated ring optionally interrupted by at least one further heteroatom and having a total of 5 to 18 carbon atoms and/or heteroatoms, $R^{56'}$, $R^{57'}$, $R^{58'}$ and $R^{59'}$ are each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, cyclo-heteroalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or $R^{56'}$ and $R^{57'}$, $R^{57'}$ and $R^{58'}$ or $R^{58'}$ and $R^{59'}$, together with the carbon atoms to which they are bonded, form a saturated, unsaturated or aromatic, optionally substituted ring optionally interrupted by at least one heteroatom and having a total of 5 to 18 carbon atoms and/or heteroatoms, and/or if $A^{5'}$ is C, $R^{55'}$ and $R^{56'}$ together form a saturated or unsaturated, linear or branched bridge optionally comprising heteroatoms, an aromatic unit, heteroaromatic unit and/or functional groups and having a total of 1 to 30 carbon atoms and/or heteroatoms, to which is optionally fused a substituted or unsubstituted, five- to eight-membered ring comprising carbon atoms and/or heteroatoms, $R^{25'}$ is independently a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, K is an uncharged mono- or bidentate ligand, L is a mono- or dianionic ligand, preferably monoanionic ligand, which may be mono- or bidentate, m1 is 0, 1 or 2, where, when m1 is 2, the K ligands may be the same or different, o1 is 0, 1 or 2, where, when o1 is 2, the L ligands may be the same or different.

The compound of formula XIV is preferably a compound of the formula:

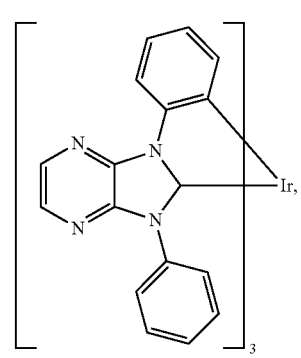

(BE-1)

(BE-2) 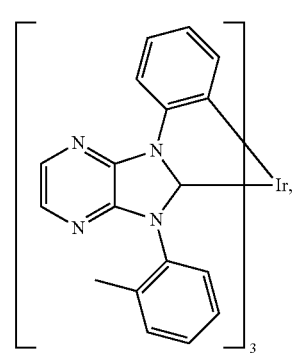
(BE-3) 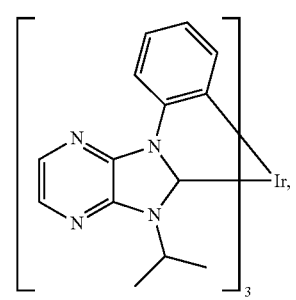
(BE-4) 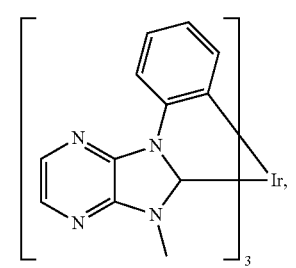
(BE-5) 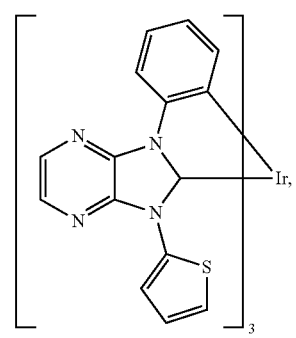
(BE-6) 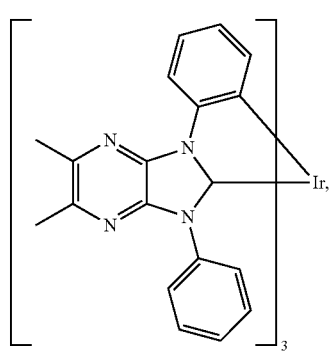
(BE-7) 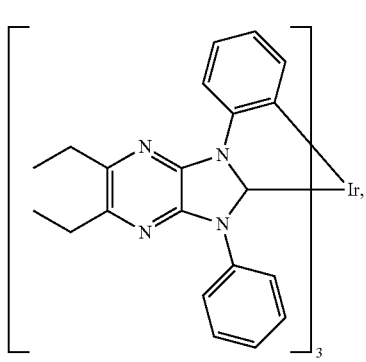
(BE-8) 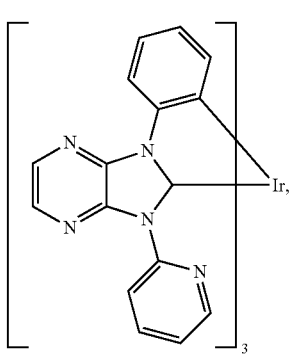
(BE-9) 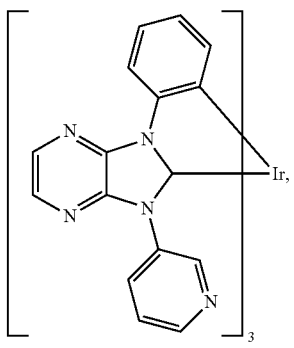
(BE-10) 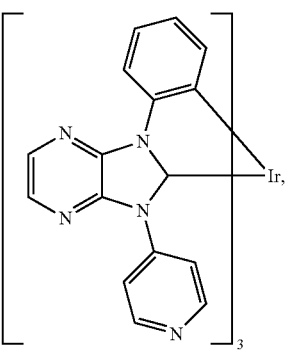

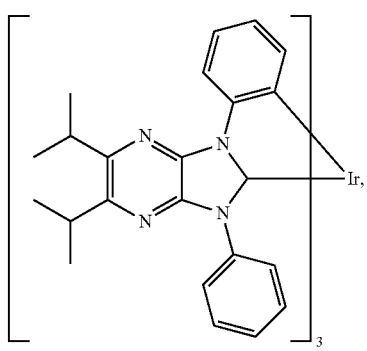 (BE-11)
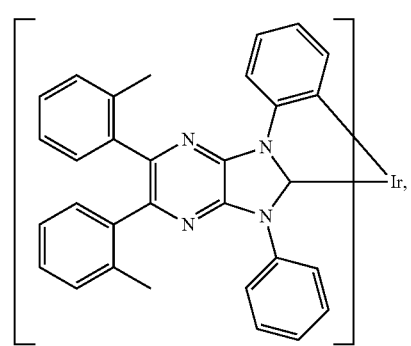 (BE-15)
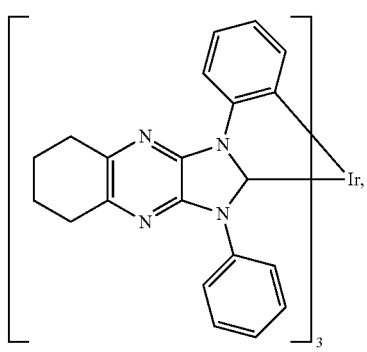 (BE-12)
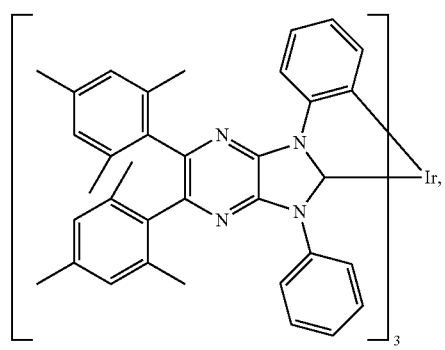 (BE-16)
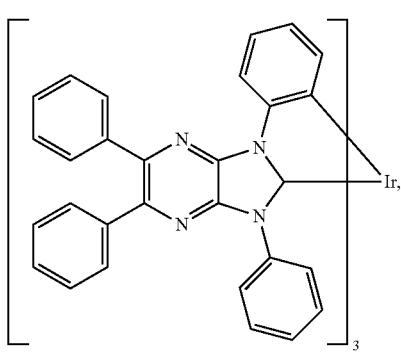 (BE-13)
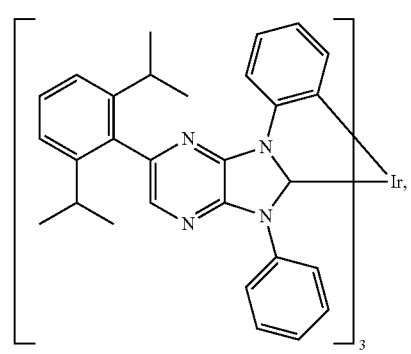 (BE-17)
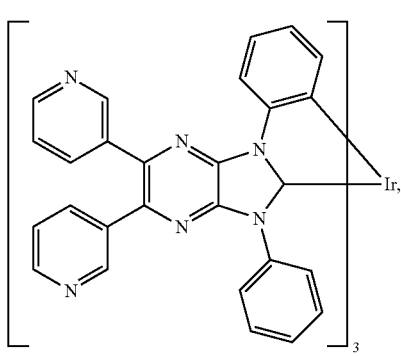 (BE-14)
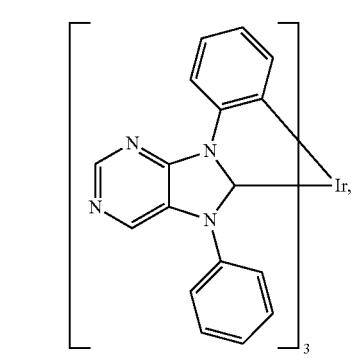 (BE-18)

(BE-19)
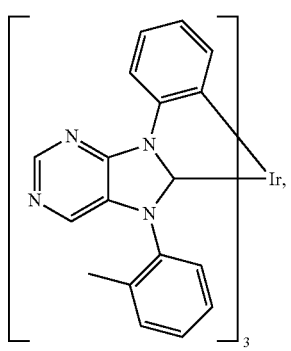
(BE-20)
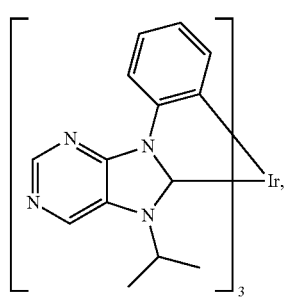
(BE-21)
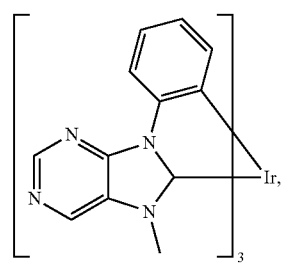
(BE-22)
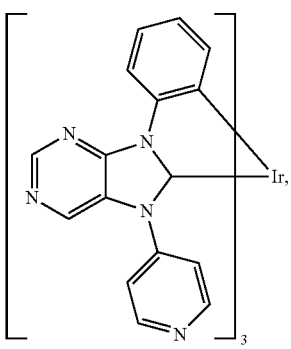
(BE-23)
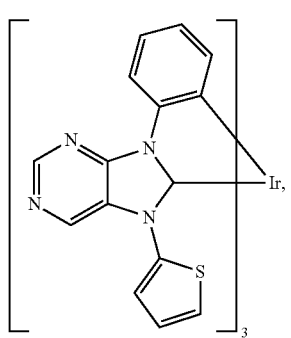
(BE-24)
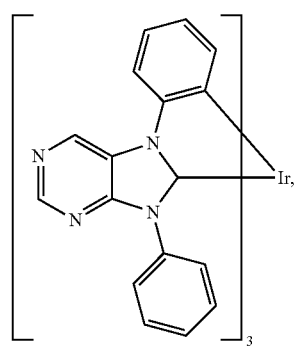
(BE-25)
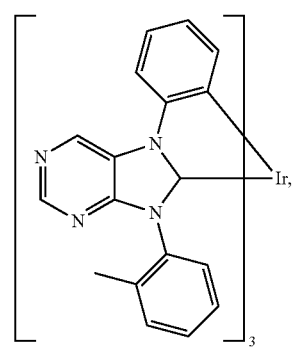
(BE-26)
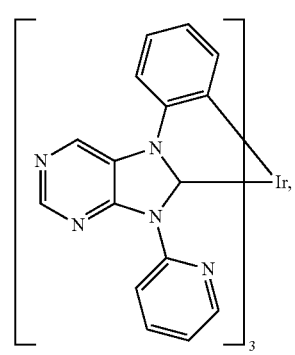
(BE-27)
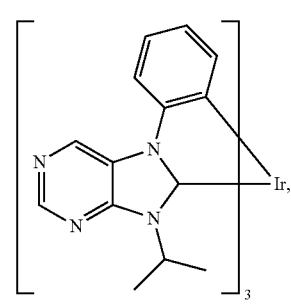
(BE-28)
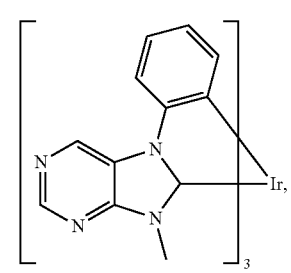

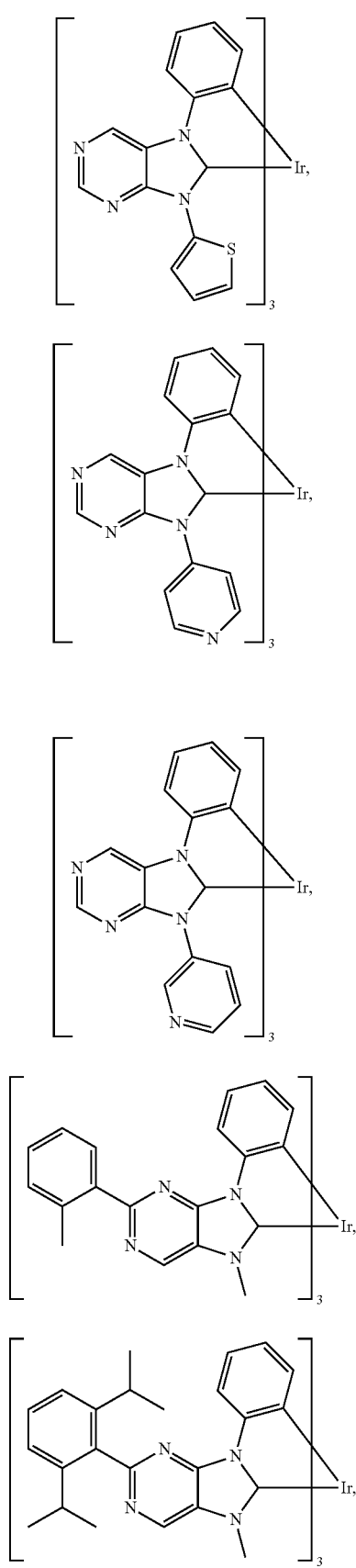
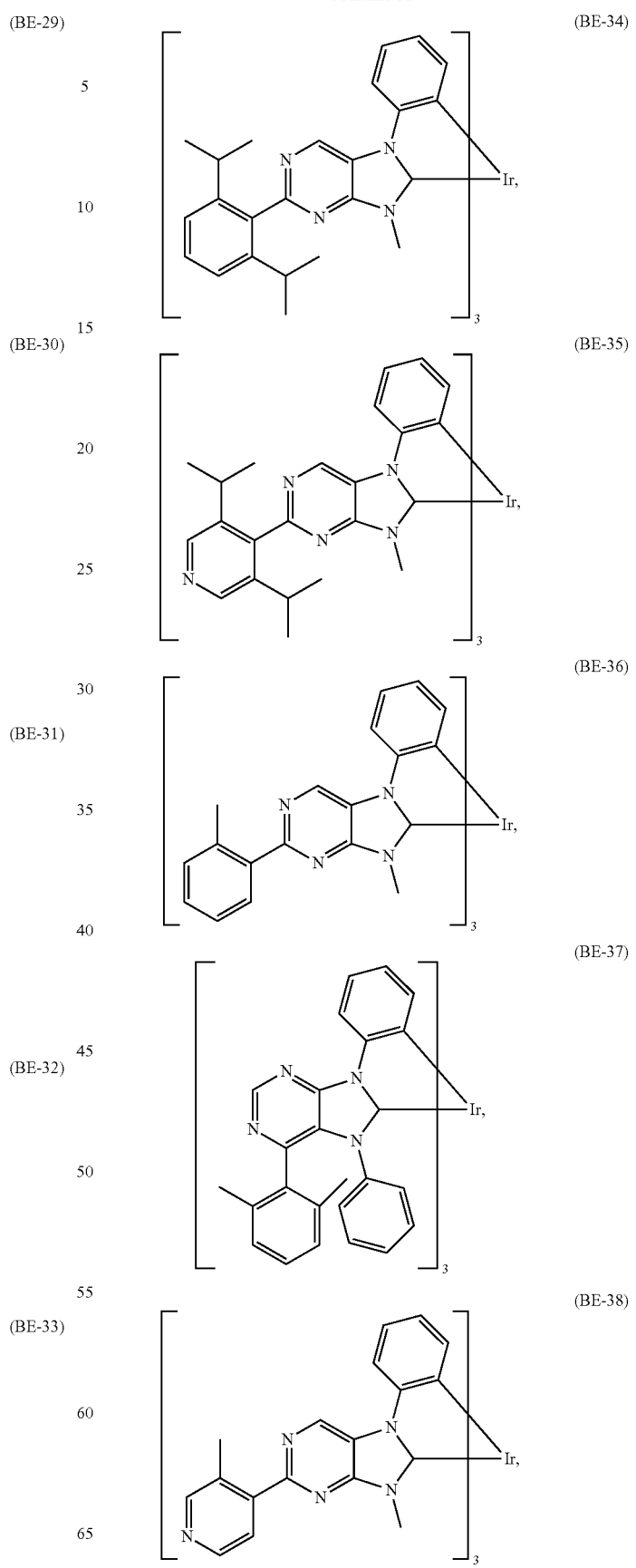

(BE-39)
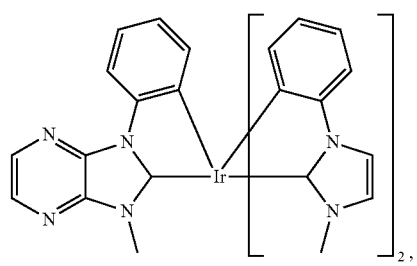
(BE-40)
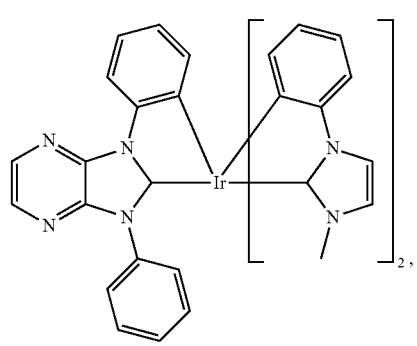
(BE-41)
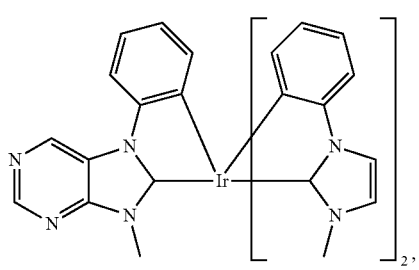
(BE-42)
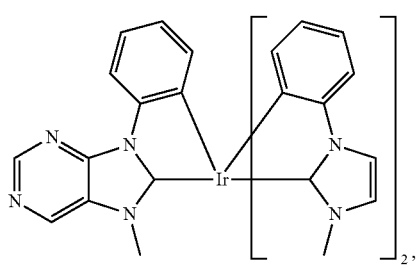
(BE-43)
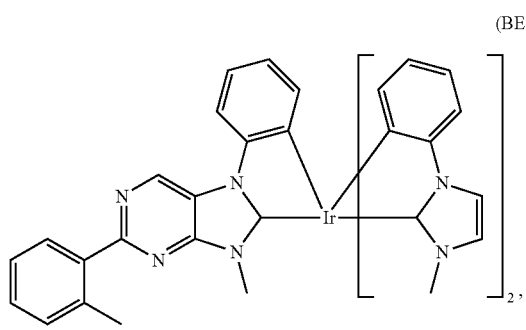
(BE-44)
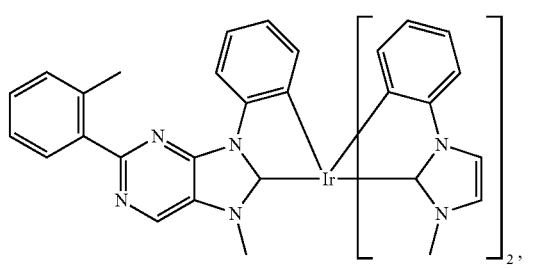
(BE-45)
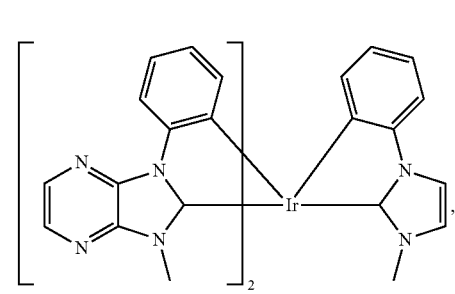
(BE-46)
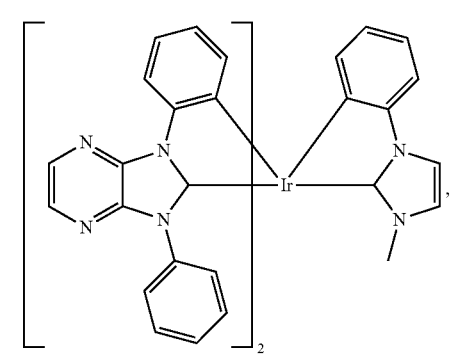
(BE-47)
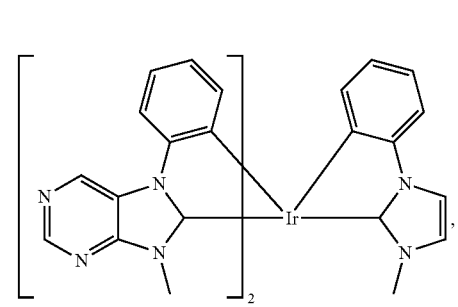
(BE-48)
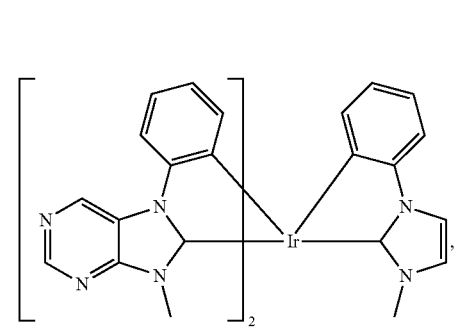

(BE-49)
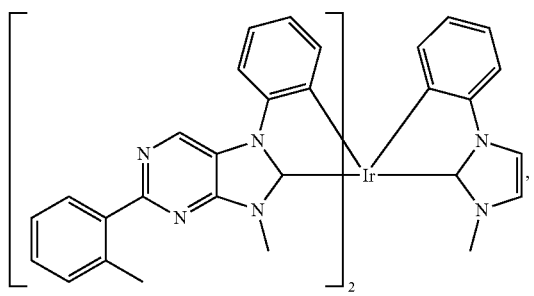
(BE-53)
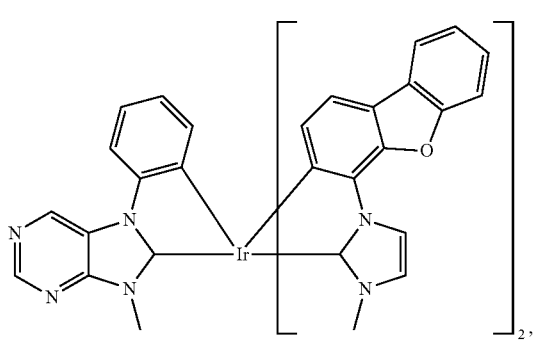
(BE-50)
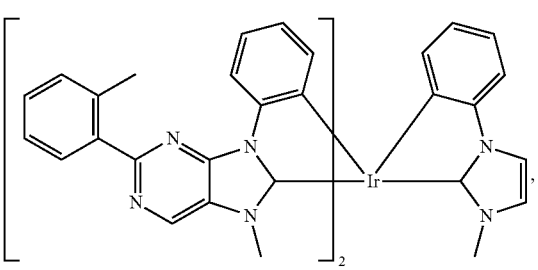
(BE-54)
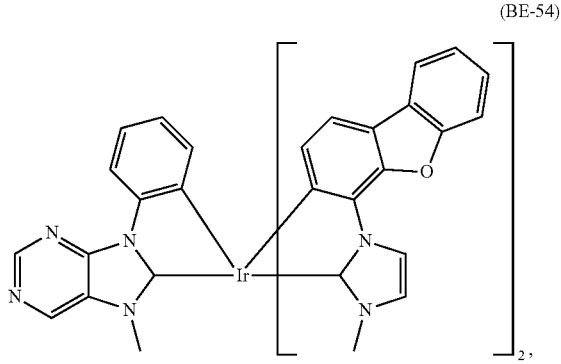
(BE-51)
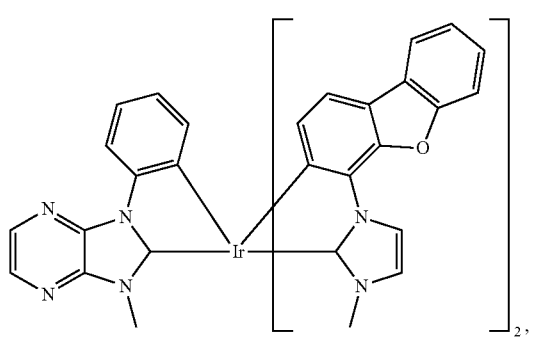
(BE-55)
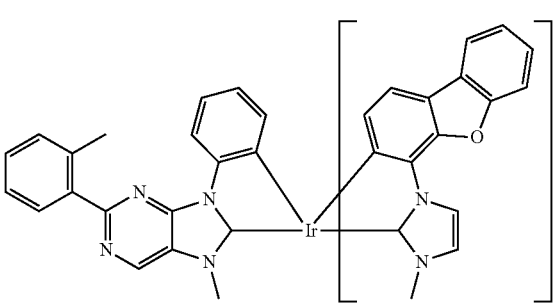
(BE-52)
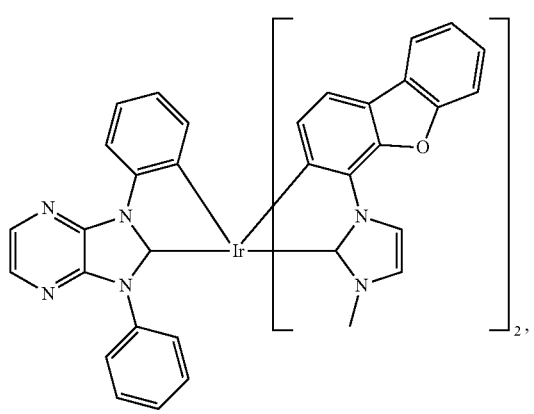
(BE-56)
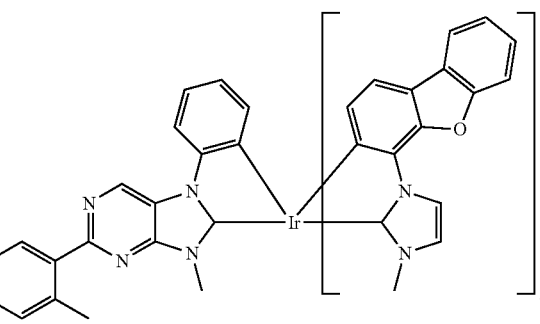

(BE-57)
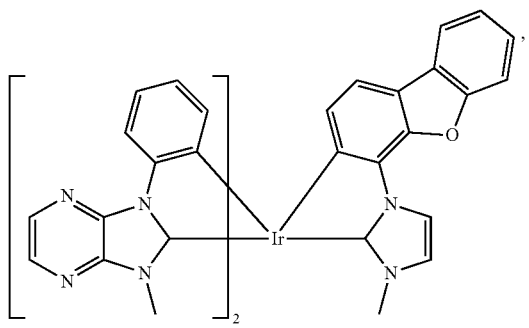
(BE-61)
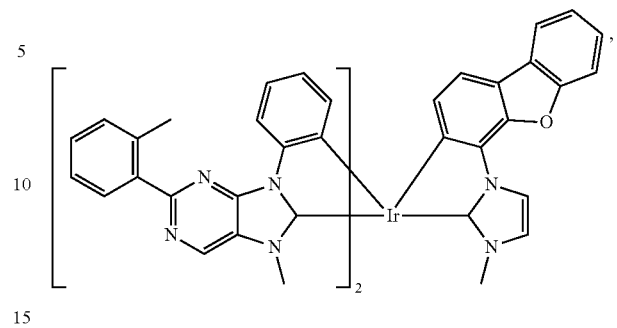
(BE-58)
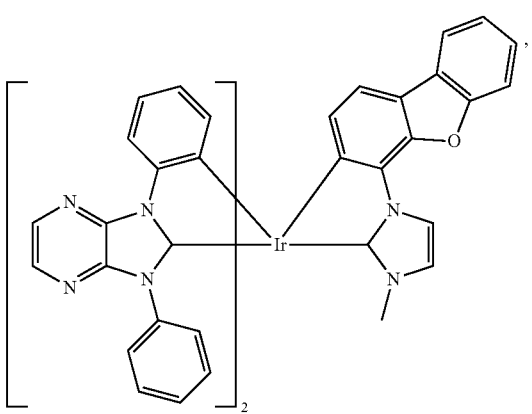
(BE-62)
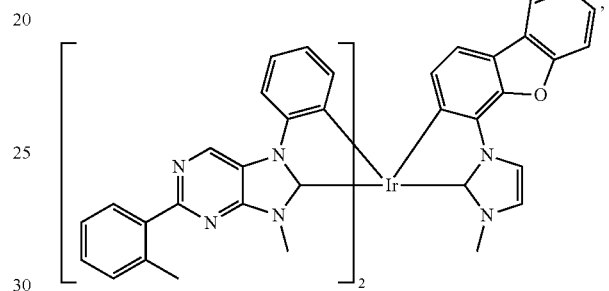
(BE-63)
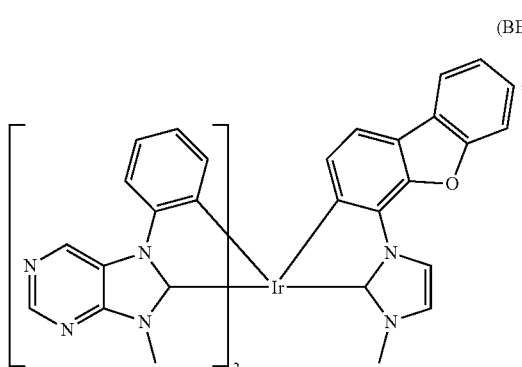
(BE-59)
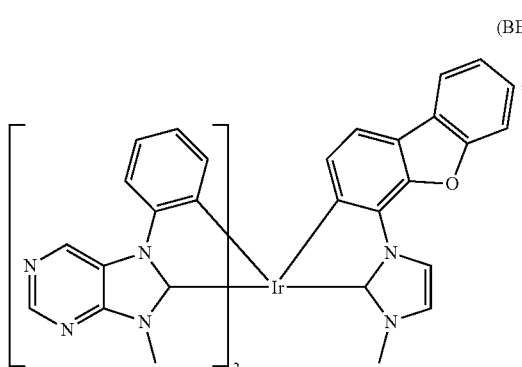
(BE-60)
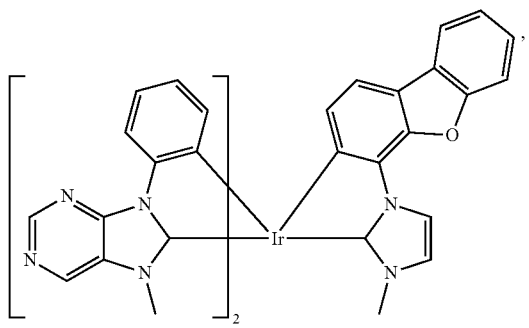
(BE-64)
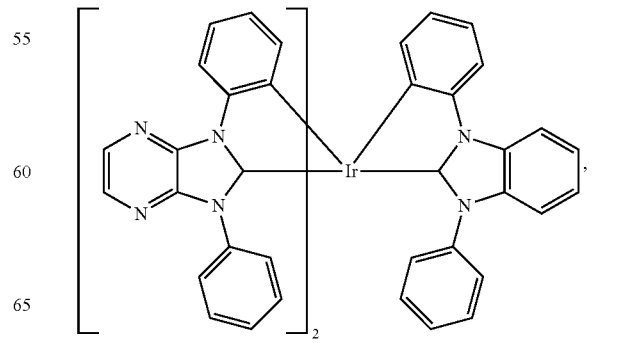

(BE-65)
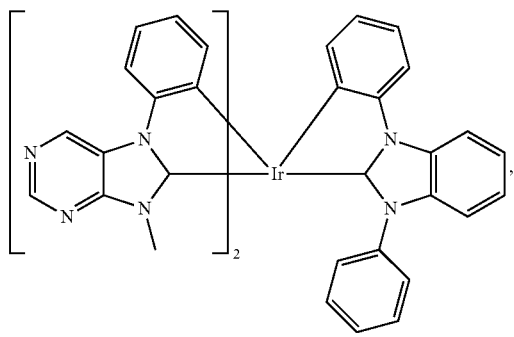
(BE-66)
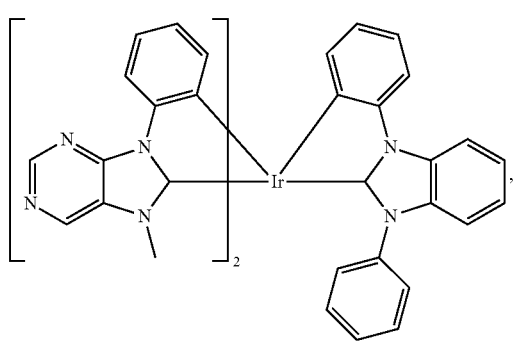
(BE-67)
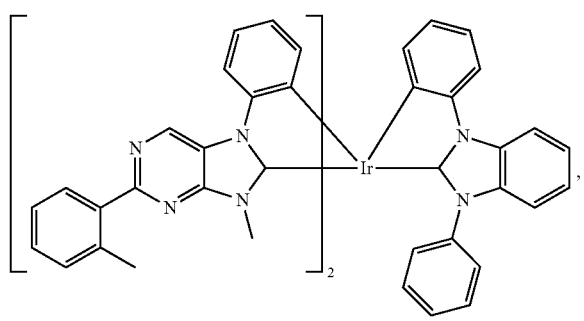
(BE-68)
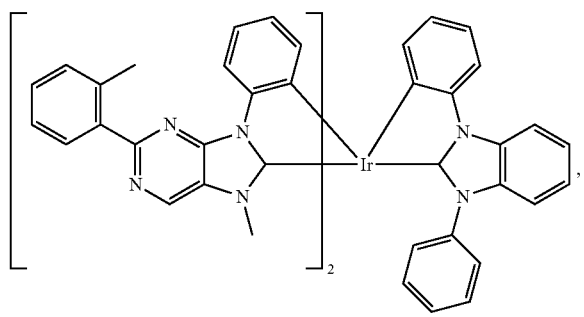
(BE-69)
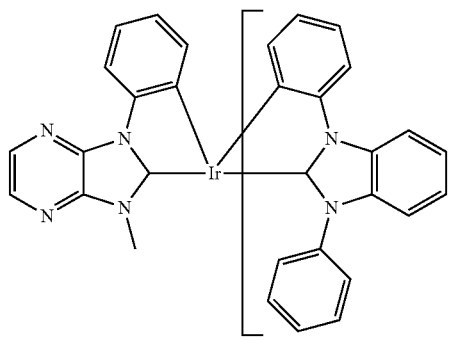
(BE-70)
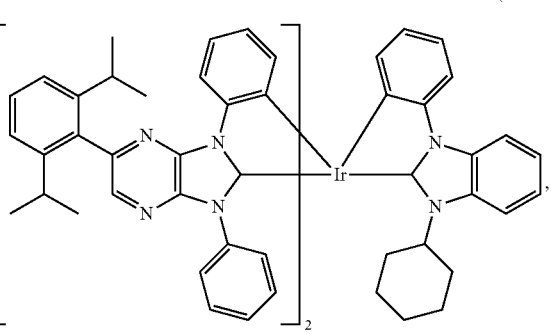
(BE-71)
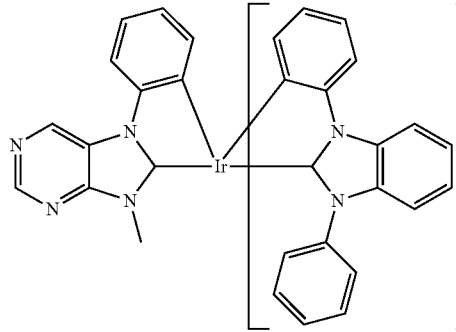
(BE-72)
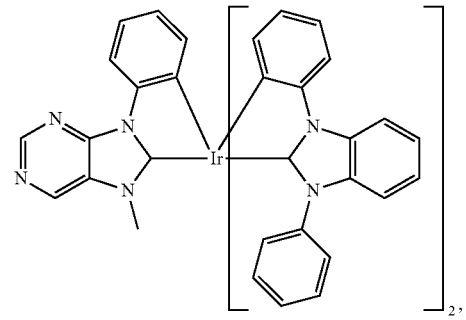

(BE-73)
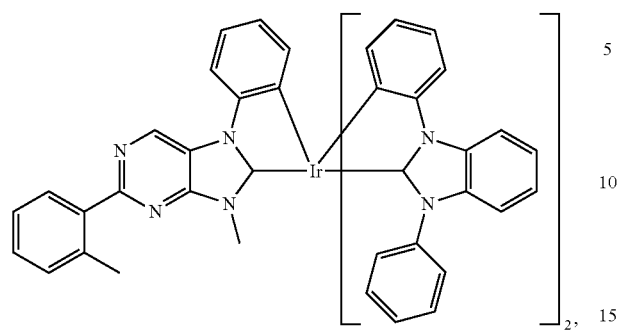
(BE-77)
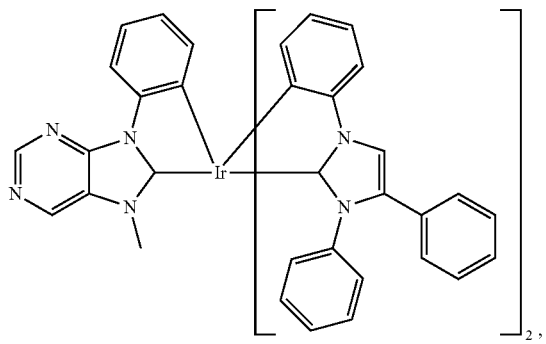
(BE-74)
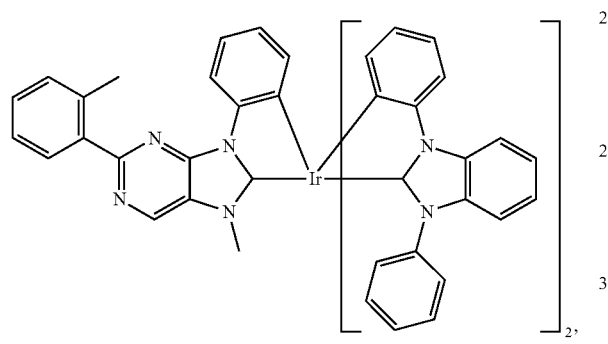
(BE-78)
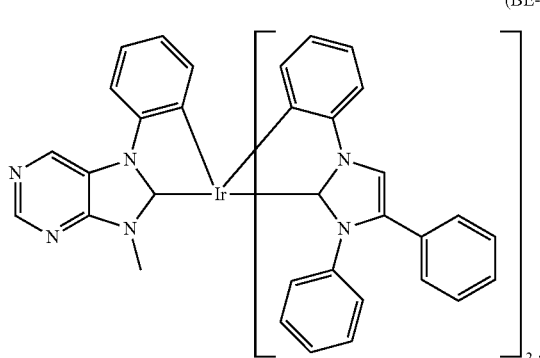
(BE-75)
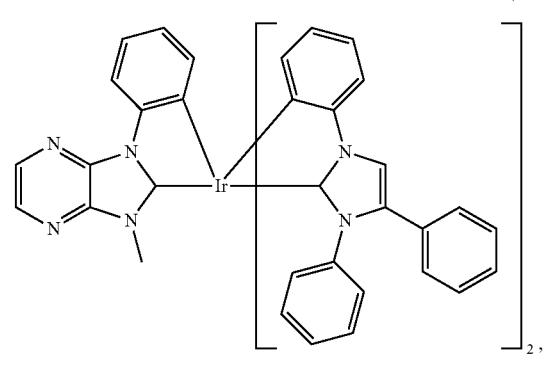
(BE-79)
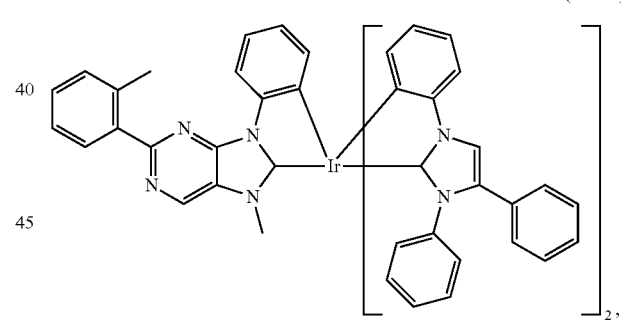
(BE-76)
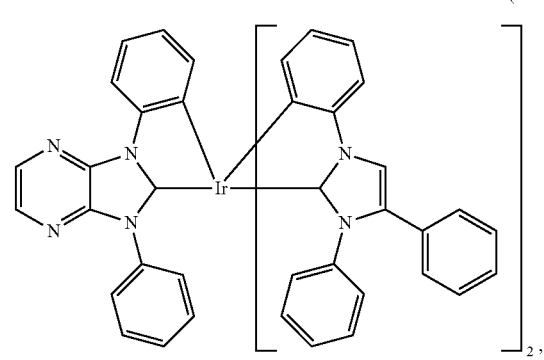
(BE-80)
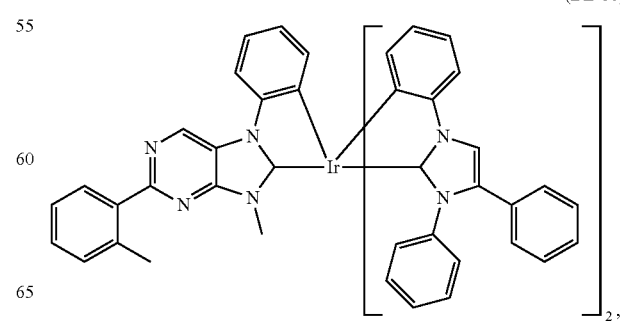

(BE-81)
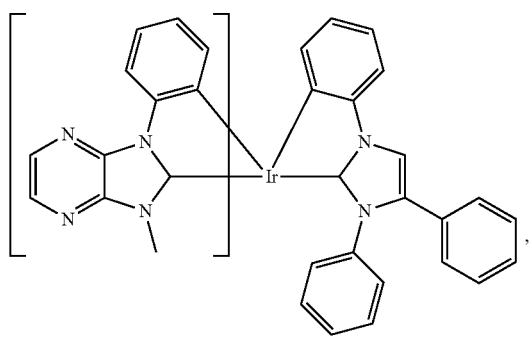
(BE-85)
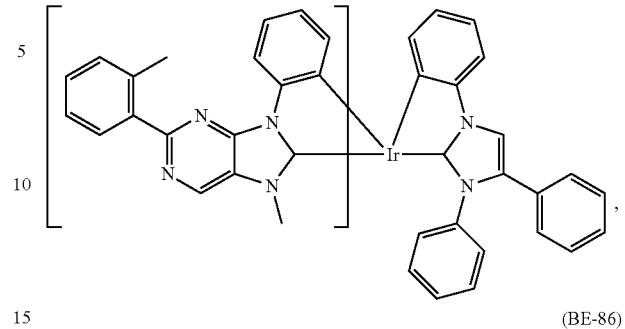
(BE-82)
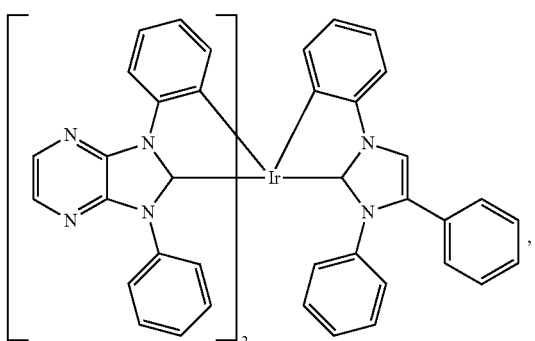
(BE-86)
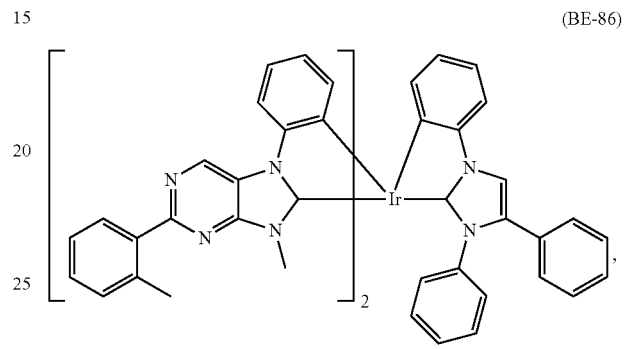
(BE-83)
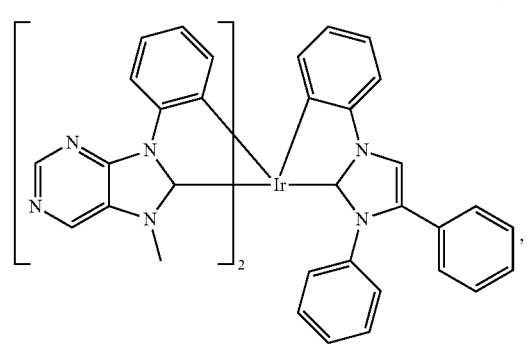
(BE-87)
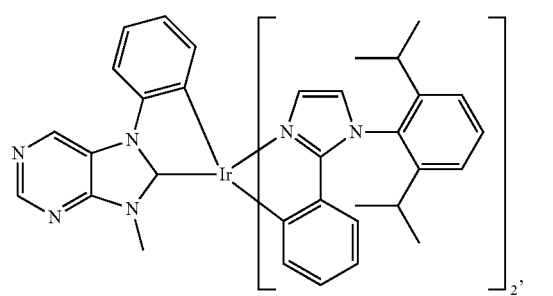
(BE-87)
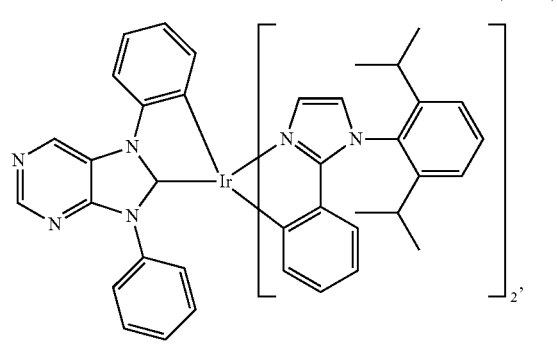
(BE-84)
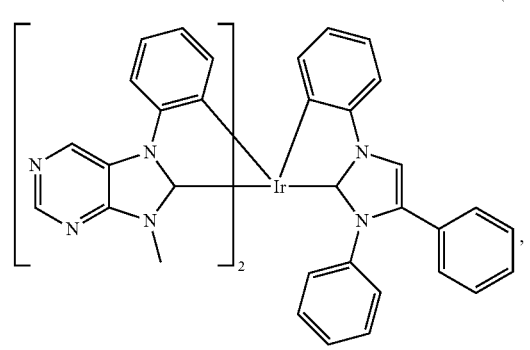
(BE-88)

(BE-89)
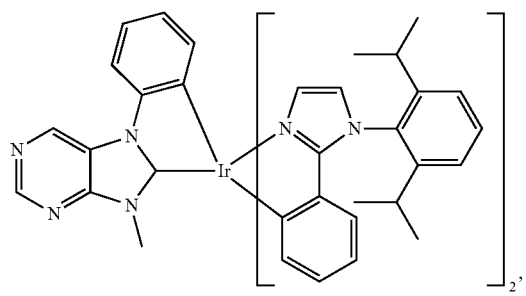
(BE-94)
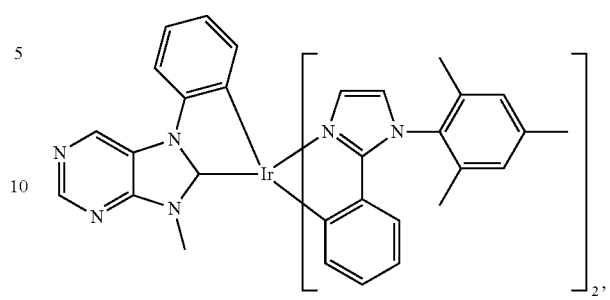
(BE-90)
(BE-95)
(BE-91)
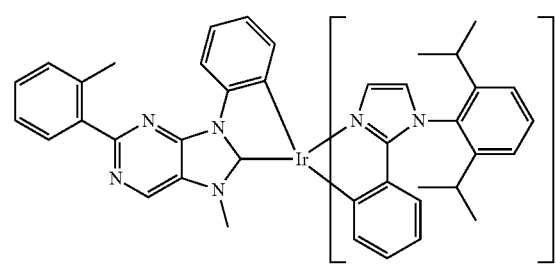
(BE-96)
(BE-92)
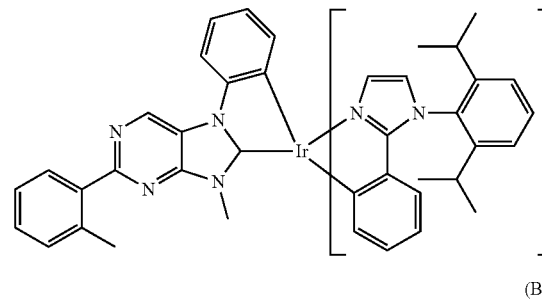
(BE-97)
(BE-93)
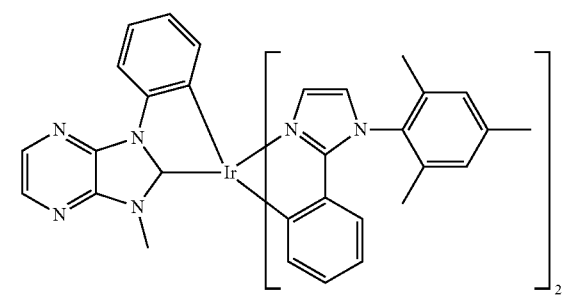
(BE-98)
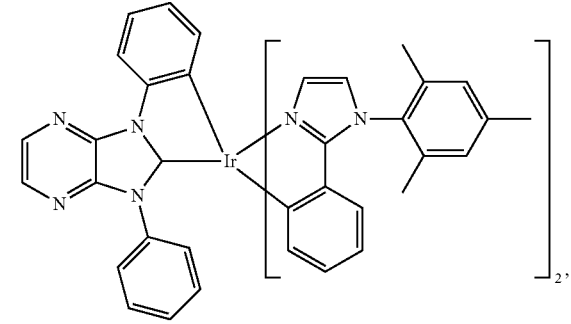

(BE-99)
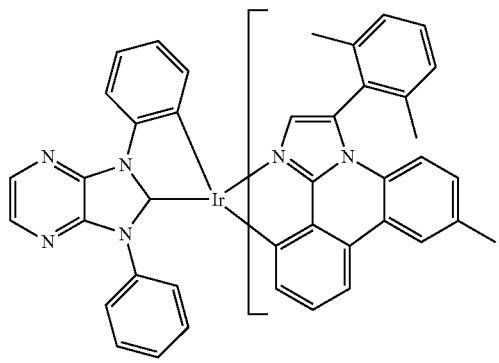
(BE-103)
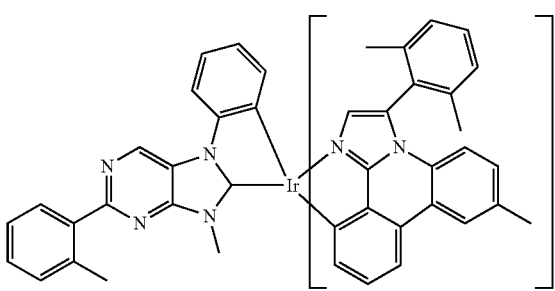
Further suitable non-carbene emitter materials are mentioned below:
(BE-100)
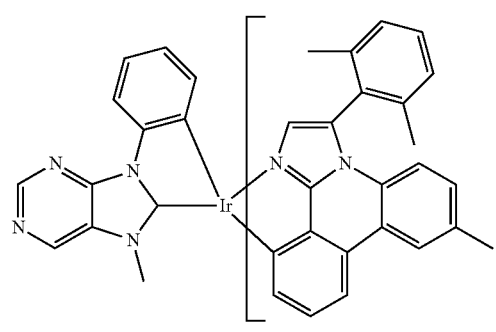
(BE-104)
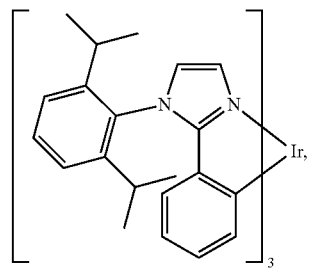
(BE-101)
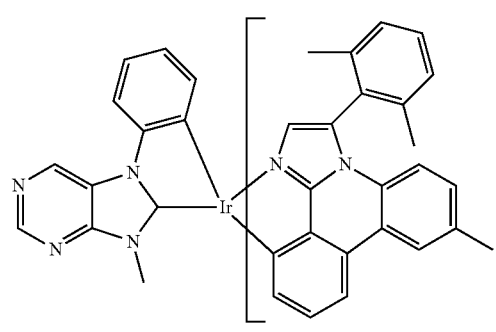
(BE-105)
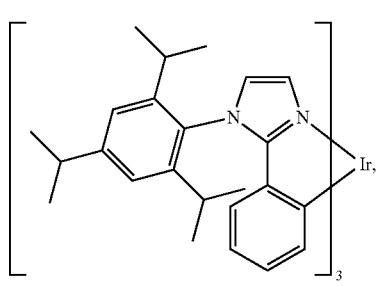
(BE-106)
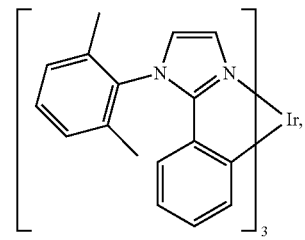
(BE-102)
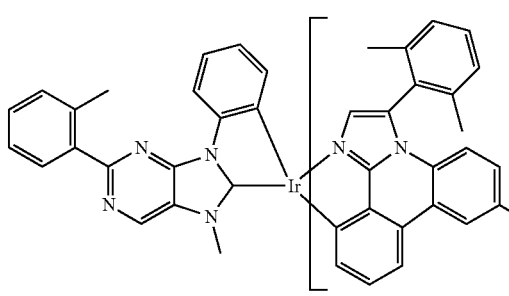
(BE-107)
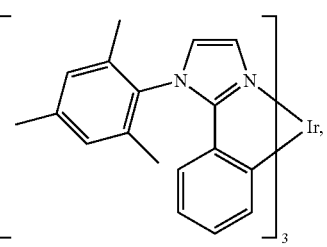

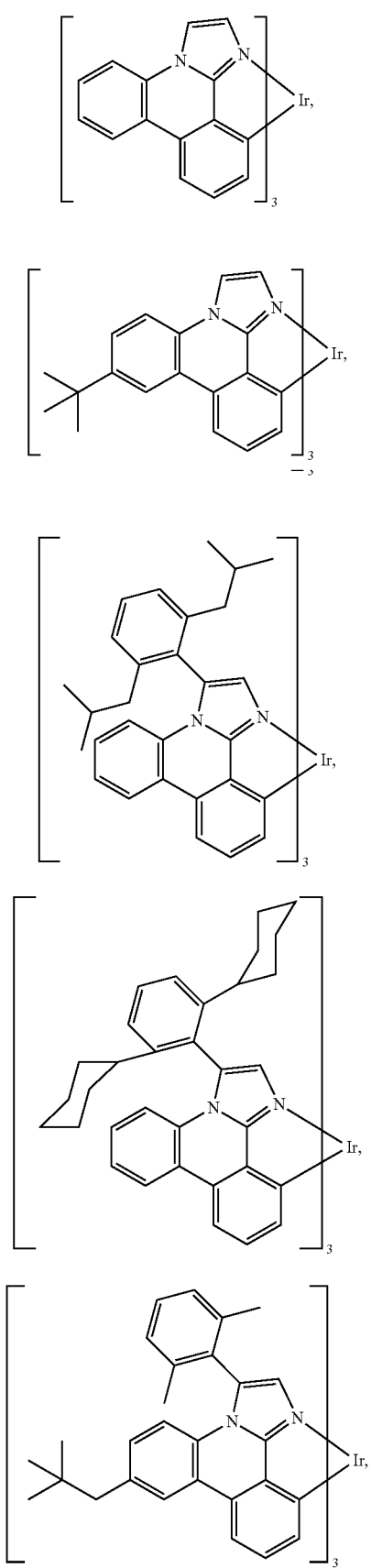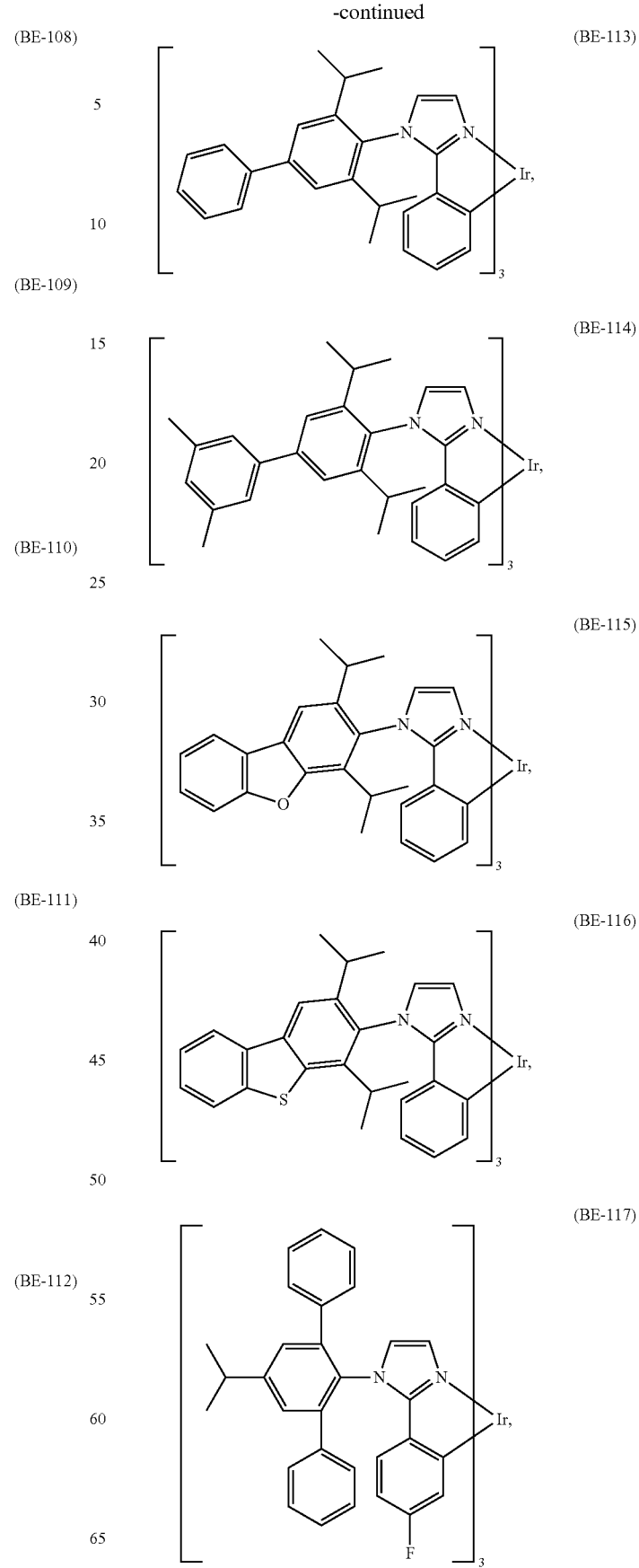

-continued (BE-118)
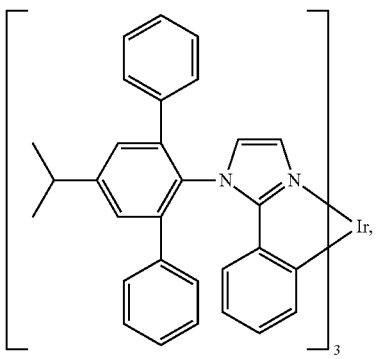

(BE-119)
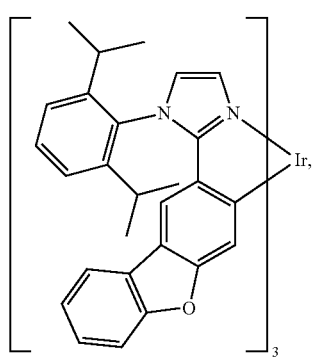

(BE-120)
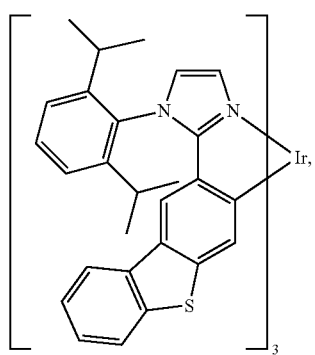

(BE-121)
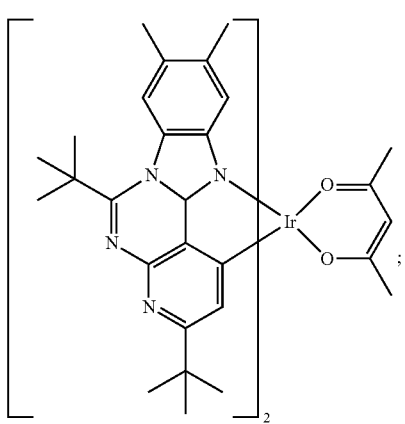

-continued (BE-122)
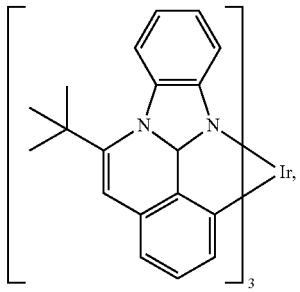

(BE-123)
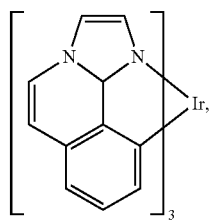

(BE-124)
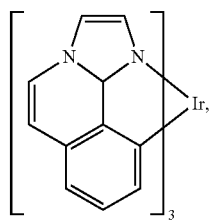

(BE-125)
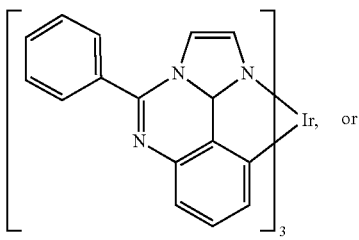

(BE-126)
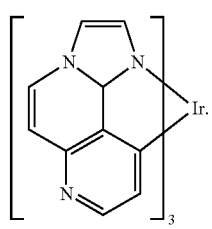

The compound of formula XIV is more preferably a compound (BE-1), (BE-2), (BE-7), (BE-12), (BE-16), (BE-64), or (BE-70). The most preferred phosphorescent blue emitters are compounds (BE-1) and (BE-12).

The homoleptic metal-carbene complexes may be present in the form of facial or meridional isomers or mixtures thereof, preference being given to the facial isomers.

Suitable carbene complexes of formula (XIV) and their preparation process are, for example, described in WO2011/073149.

The compounds of formula (I) the present invention can also be used as host for phosphorescent green emitters. Suitable phosphorescent green emitters are, for example, specified in the following publications: WO2006014599, WO20080220265, WO2009073245, WO2010027583, WO2010028151, US20110227049, WO2011090535, WO2012/08881, WO20100056669, WO20100118029, WO20100244004, WO2011109042, WO2012166608, US20120292600, EP2551933A1; U.S. Pat. No. 6,687,266, US20070190359, US20070190359, US20060008670; WO2006098460, US20110210316, WO2012053627; U.S. Pat. No. 6,921,915, US20090039776; JP2007123392 and European patent application no. 14180422.9.
Examples of suitable phosphorescent green emitters are shown below:
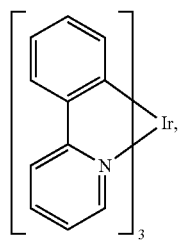
(GE-1)
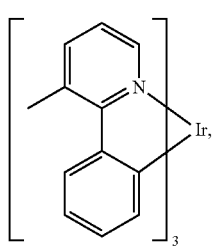
(GE-2)
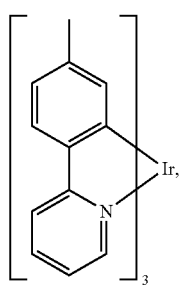
(GE-3)
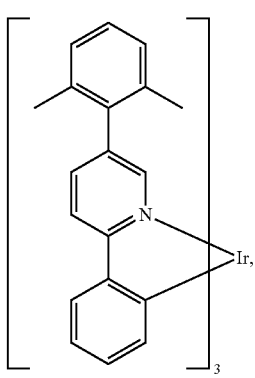
(GE-4)
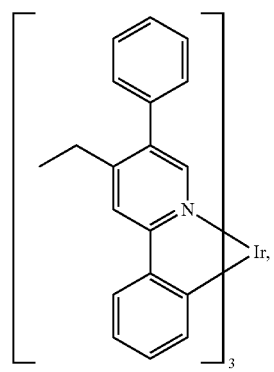
(GE-5)
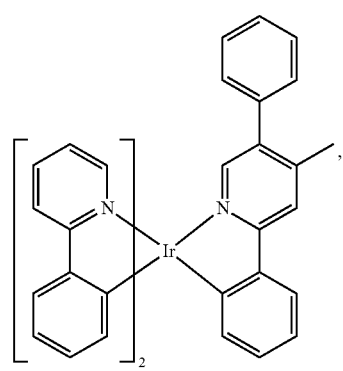
(GE-6)
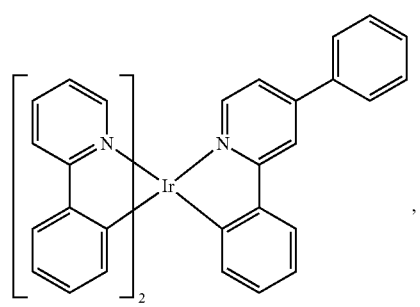
(GE-7)
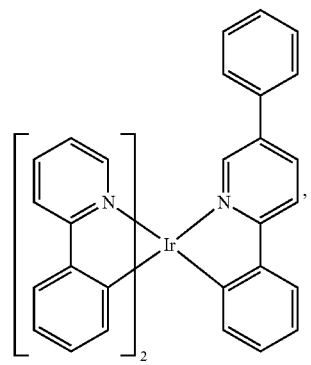
(GE-8)

(GE-9)
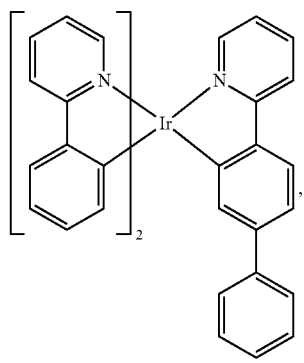
(GE-10)
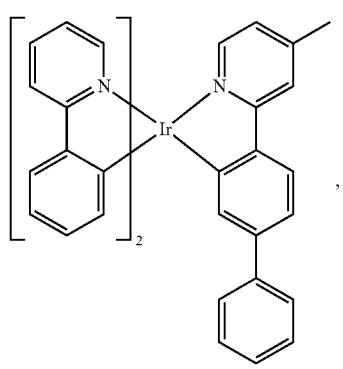
(GE-11)
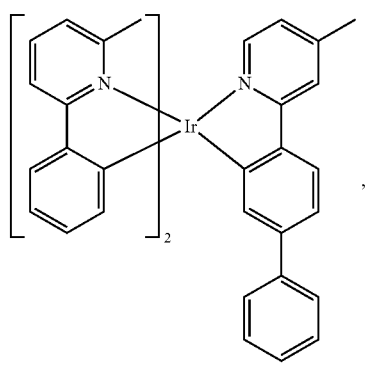
(GE-12)
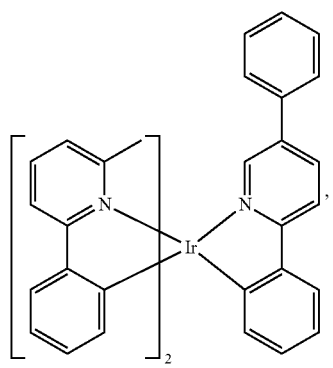
(GE-13)
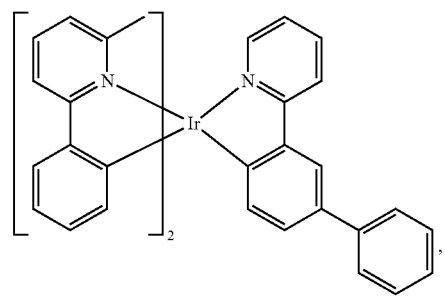
(GE-14)
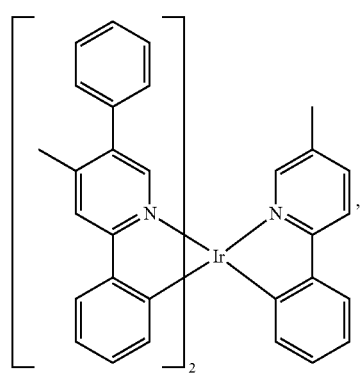
(GE-15)
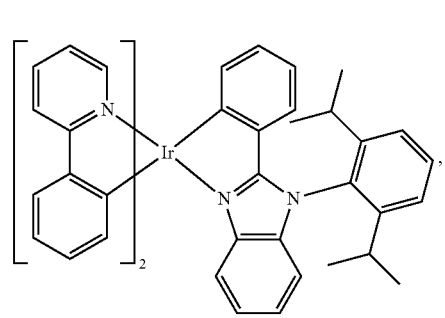
(GE-16)
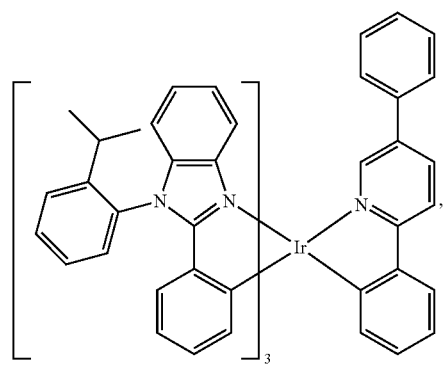

-continued
(GE-17)
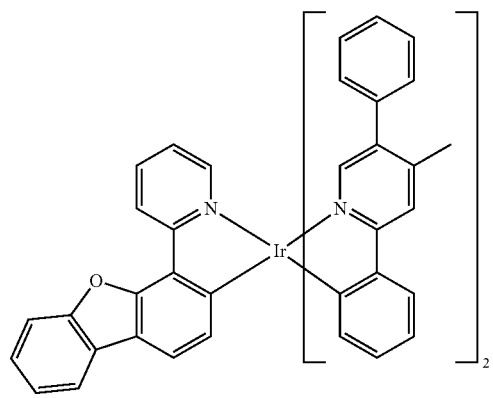
(GE-18)
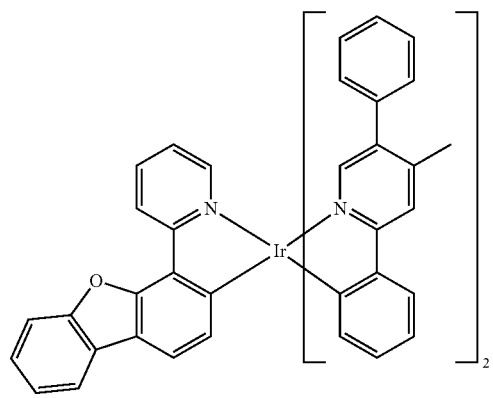
(GE-19)
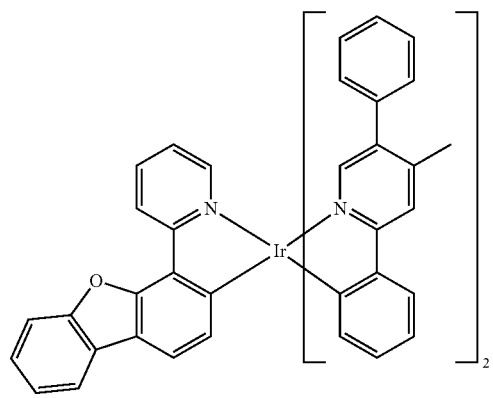
(GE-20)
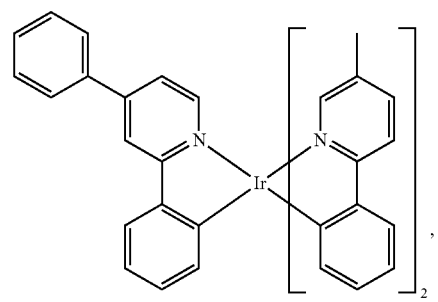
-continued
(GE-21)
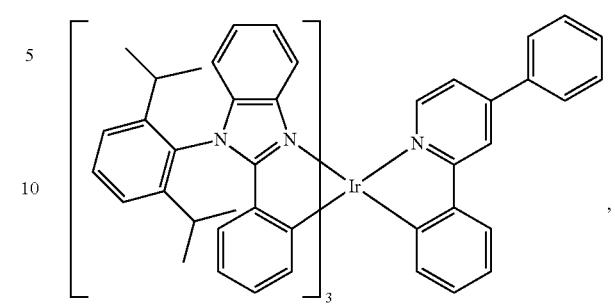
(GE-22)
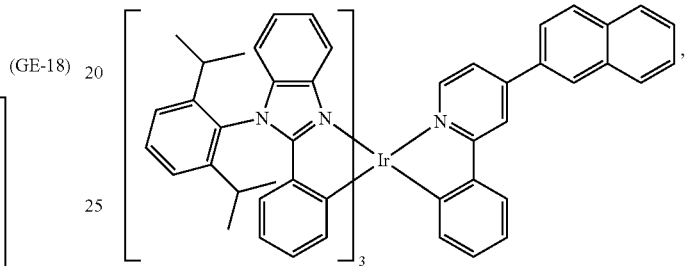
(GE-23)
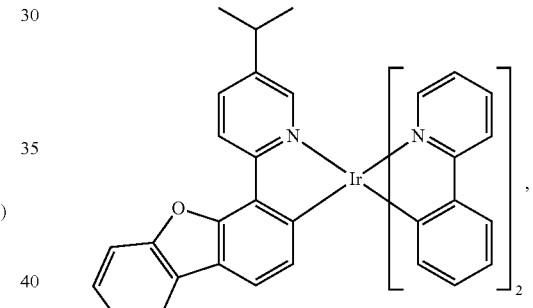
(GE-24)
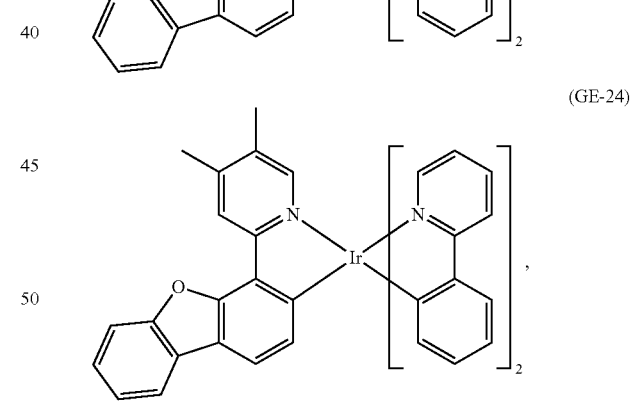
(GE-25)
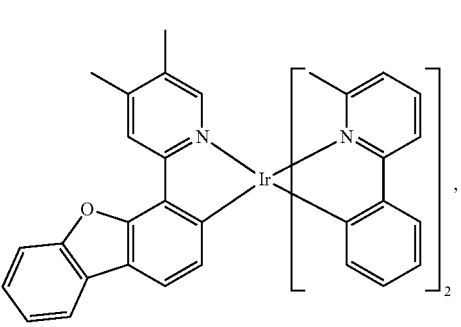

(GE-26)
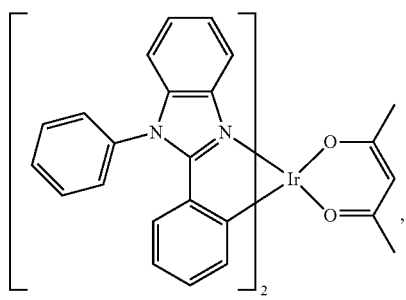
(GE-27)
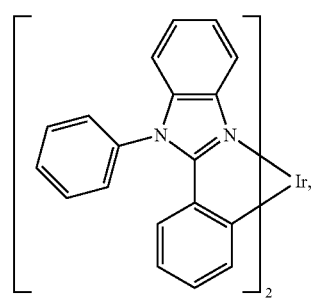
(GE-28)
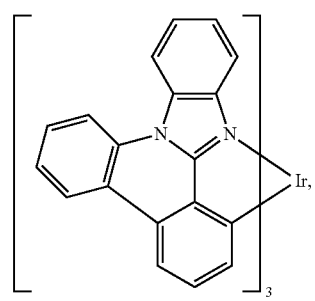
(GE-29)
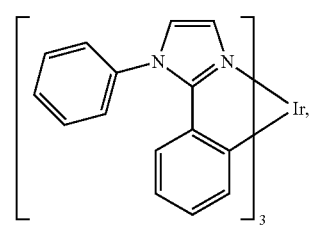
(GE-30)
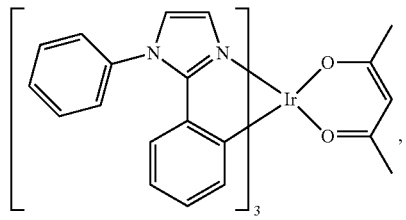
(GE-31)
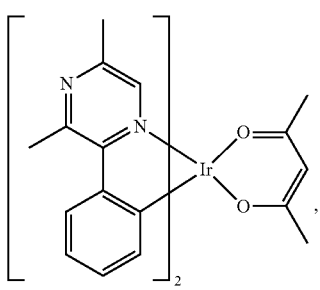
(GE-32)
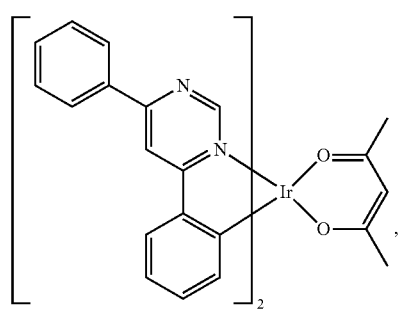
(GE-33)
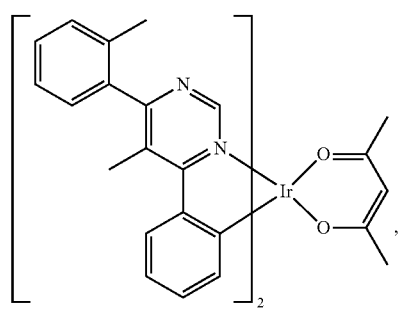
(GE-34)
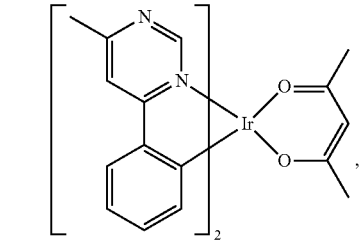
(GE-35)
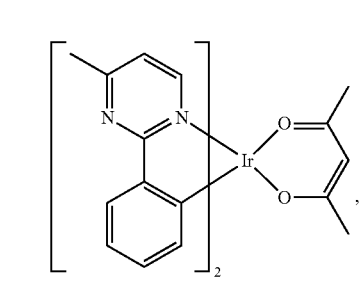
(GE-36)
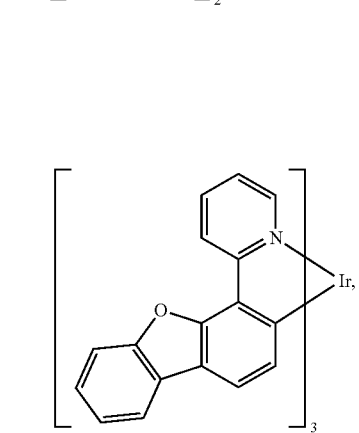

(GE-37)

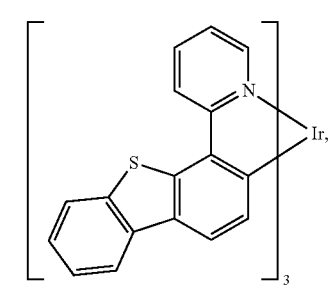

(GE-38)

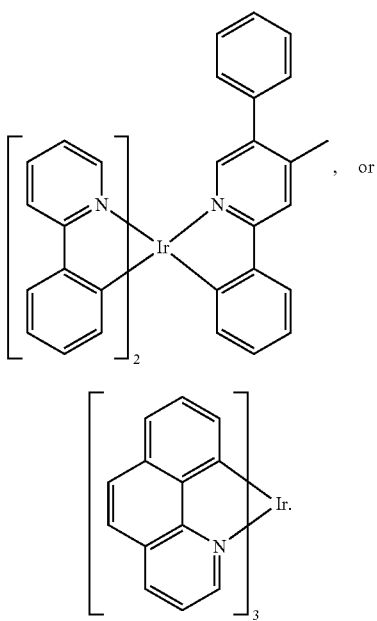

, or (GE-39)

The emitter materials (dopants), preferably the phosphorescent emitter materials, may be used alone or in combination of two or more.

The content of the emitter materials (dopants), preferably the phosphorescent emitter materials, in the light emitting layer is not particularly limited and selected according to the use of the device, and preferably 0.1 to 70% by mass, and more preferably 1 to 30% by mass. If being 0.1% by mass or more, the amount of light emission is sufficient. If being 70% by mass or less, the concentration quenching can be avoided. The further component in the emitting layer is usually one or more host material, which is preferably present in an amount of 30 to 99.9% by mass, more preferably 70 to 99% by mass, wherein the sum of the emitter material(s) and the host material(s) is 100% by mass.

Host (Matrix) Materials

The light-emitting layer may comprise further components in addition to the emitter material. For example, a fluorescent dye may be present in the light-emitting layer in order to alter the emission color of the emitter material. In addition—in a preferred embodiment—a matrix material can be used. This matrix material may be a polymer, for example poly(N-vinylcarbazole) or polysilane. The matrix material may, however, be a small molecule, for example 4,4'-N,N'-dicarbazolebiphenyl (CDP=CBP) or tertiary aromatic amines, for example TCTA.

In the case that one or more phosphorescent emitter materials are used in the light emitting layer, one or more phosphorescent hosts are employed as host material. The phosphorescent host is a compound which confines the triplet energy of the phosphorescent dopant efficiently in the light emitting layer to cause the phosphorescent dopant to emit light efficiently.

In a preferred embodiment, the light-emitting layer is formed of at least one emitter material and of at least one of the matrix materials mentioned below—in one embodiment at least one compound of the formula (I) is used as matrix (host) material. In one embodiment, the light-emitting layer comprises at least one emitter material and at least two matrix materials, wherein one of the matrix materials is a compound of the formula (I) and the other matrix material(s) is/are used as co-host(s). Suitable other host materials than the compound of formula (I) (co-hosts) are mentioned below.

The compounds of the formula (I) are suitable as single host material as well as host material, together with one or more further host materials (co-host). Suitable further host materials are mentioned below. "Further host materials" means in the sense of the present application, host materials different from the compounds of formula (I). However, it is also possible to use two or more different compounds of formula (I) as host material in the light-emitting layer in an OLED of the present application.

In another preferred embodiment of the present invention, at least one compound of the formula (I) is used as host material. Examples of preferred compounds of formula (I) useful as host material are shown above.

In a more preferred embodiment, the light-emitting layer is formed from 0.1 to 70% by weight, preferably 1 to 30% by weight, of at least one of the aforementioned emitter materials and 30 to 99.9% by weight, preferably 70 to 99% by weight, of at least one of the matrix materials mentioned in the specification—in one embodiment at least one compound of the formula (I)—where the sum total of the emitter material and of the matrix material adds up to 100% by weight.

In a further more preferred embodiment, the light-emitting layer comprises a compound of formula (I) as matrix material, one further matrix material (co-host) and at least one emitter material. In said embodiment, the light-emitting layer is formed from 0.1 to 70% by weight, preferably 1 to 30% by weight, of the at least one emitter material and 30 to 99.9% by weight, preferably 70 to 99% by weight, of a compound of the formula (I) and the further matrix material, where the sum total of the at least one emitter material, the further matrix material and of the compound of formula (I) adds up to 100% by weight.

The content ratio of the compound of the formula (I) as first host material and the further matrix material as co-host in the light emitting layer is not particularly limited and may be selected accordingly, and the ratio of first host material: second host material (co-host) is preferably 1:99 to 99:1, more preferably 10:90 to 90:10, each based on mass.

Further suitable host materials, which may be small molecules or (co)polymers of the small molecules mentioned, are specified in the following publications: WO2007108459 (H-1 to H-37), preferably H-20 to H-22 and H-32 to H-37, most preferably H-20, H-32, H-36, H-37, WO2008035571 A1 (Host 1 to Host 6), JP2010135467 (compounds 1 to 46 and Host-1 to Host-39 and Host-43), WO2009008100 compounds No. 1 to No. 67, preferably No. 3, No. 4, No. 7 to No. 12, No. 55, No. 59, No. 63 to No. 67, more preferably No. 4, No. 8 to No. 12, No. 55, No. 59, No. 64, No. 65, and No. 67, WO2009008099 compounds No. 1 to No. 110, WO2008140114 compounds 1-1 to 1-50, WO2008090912 compounds OC-7 to OC-36 and the polymers of Mo-42 to Mo-51, JP2008084913H-1 to H-70, WO2007077810 compounds 1 to 44, preferably 1, 2, 4-6, 8, 19-22, 26, 28-30, 32, 36, 39-44, WO201001830 the polymers of monomers 1-1 to 1-9, preferably of 1-3, 1-7, and 1-9, WO2008029729 the (polymers of) compounds 1-1 to 1-36, WO20100443342 HS-1 to HS-101 and BH-1 to BH-17, preferably BH-1 to BH-17, JP2009182298 the (co)polymers based on the monomers 1 to 75, JP2009170764, JP2009135183 the (co)polymers based on the monomers 1-14, WO2009063757 preferably the (co)polymers based on the monomers 1-1 to 1-26, WO2008146838 the compounds a-1 to a-43 and 1-1 to 1-46, JP2008207520 the (co)polymers based on the monomers 1-1 to 1-26, JP2008066569 the (co)polymers based on the monomers 1-1 to 1-16, WO2008029652 the (co)polymers based on the monomers 1-1 to 1-52, WO2007114244 the (co)polymers based on the monomers 1-1 to 1-18, JP2010040830 the compounds HA-1 to HA-20, HB-1 to HB-16, HC-1 to HC-23 and the (co)polymers based on the monomers HD-1 to HD-12, JP2009021336, WO2010090077 the compounds 1 to 55, WO2010079678 the compounds H1 to H42, WO2010067746, WO2010044342 the compounds HS-1 to HS-101 and Poly-1 to Poly-4, JP2010114180 the compounds PH-1 to PH-36, US2009284138 the compounds 1 to 111 and H1 to H71, WO2008072596 the compounds 1 to 45, JP2010021336 the compounds H-1 to H-38, preferably H-1, WO2010004877 the compounds H-1 to H-60, JP2009267255 the compounds 1-1 to 1-105, WO2009104488 the compounds 1-1 to 1-38, WO2009086028, US2009153034, US2009134784, WO2009084413 the compounds 2-1 to 2-56, JP2009114369 the compounds 2-1 to 2-40, JP2009114370 the compounds 1 to 67, WO2009060742 the compounds 2-1 to 2-56, WO2009060757 the compounds 1-1 to 1-76, WO2009060780 the compounds 1-1 to 1-70, WO2009060779 the compounds 1-1 to 1-42, WO2008156105 the compounds 1 to 54, JP2009059767 the compounds 1 to 20, JP2008074939 the compounds 1 to 256, JP2008021687 the compounds 1 to 50, WO2007119816 the compounds 1 to 37, WO2010087222 the compounds H-1 to H-31, WO2010095564 the compounds HOST-1 to HOST-61, WO2007108362, WO2009003898, WO2009003919, WO2010040777, US2007224446, WO06128800, WO2012014621, WO2012105310, WO2012/130709 and European patent applications EP12175635.7, EP12185230.5 and EP12191408.9 (in particular page 25 to 29 of EP12191408.9).

The above-mentioned small molecules are more preferred than the above-mentioned (co)polymers of the small molecules.

Further suitable host materials, are described in WO2011137072 (for example,

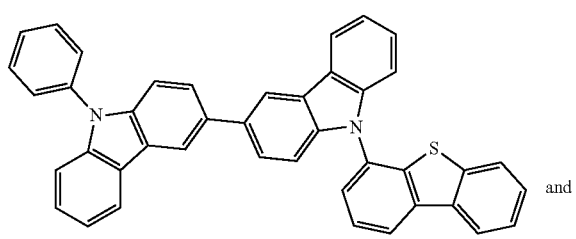

and

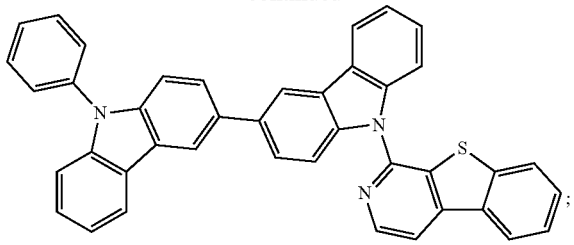

best results are achieved if said compounds are combined with

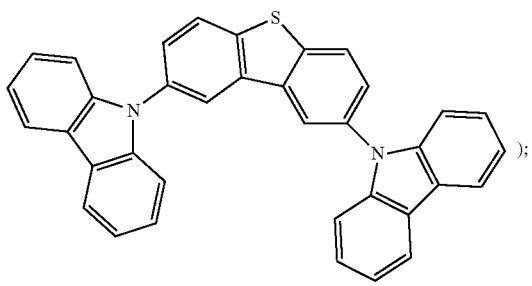 [SMILES: c1ccc2c(c1)c1ccccc1n2-c1ccc2sc3ccc(-n4c5ccccc5c5ccccc54)cc3c2c1]

WO2012048266 (for example,

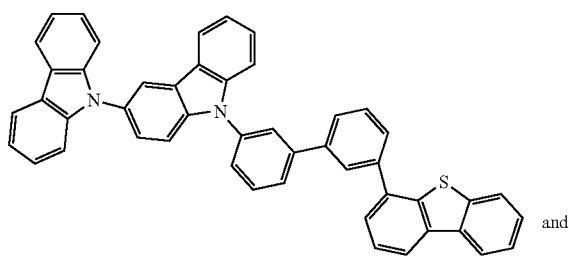

and

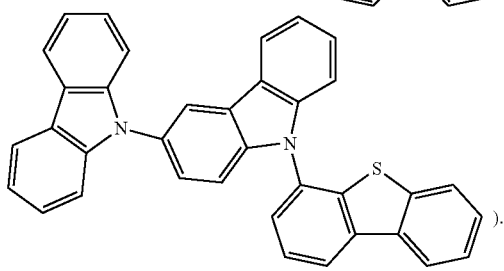

).

The host materials mentioned above may be used in the OLED of the present invention a alone or in combination with the compound of formula (I) as host material. In this case, the compound of formula (I) is the host and the host materials mentioned above are the co-hosts.

Further examples of the compounds which are suitable as phosphorescent host, alone or in combination with the compound of formula (I) as host material, include a carbazole derivative, a triazole derivative, a oxazole derivative, an oxadiazole derivative, an imidazole derivative, a po-lyarylalkane derivative, a pyrazoline derivative, a pyrazolone derivative, a phenylenediamine derivative, an arylamine derivative, an amino-substituted chalcone derivative, a styrylanthra-cene derivative, a fluorenone derivative, a hydrazone derivative, a stilbene derivative, a silazane derivative, an aromatic tertiary amine compound, a styrylamine compound, an aromatic methyl-idene compound, a porphyrin compound, an anthraquinodimethane derivative, an anthrone derivative, a diphenylquinone derivative, a thiopyran dioxide derivative, a carbodiimide derivative, a fluorenylidenemethane derivative, a distyrylpyrazine derivative, a tetracarboxylic anhydride of fused ring such as naphthalene and perylene, a phthalocyanine derivative, a metal complex of 8-quinolinol derivative, metal phthalocyanine, metal complexes having a ligand such as benzoxazole and benzothiazole, an electroconductive oligomer, such as a polysilane compound, a poly(N-vinylcarbazole) derivative, an aniline copolymer, thiophene oligomer, and a polythiophene, and a polymer such as a polythiophene derivative, a polyphenylene derivative, a poly-phenylenevinylene derivative, and a polyfluorene derivative. These phosphorescent hosts may be used alone or in combination of two or more. Specific examples thereof are shown below:

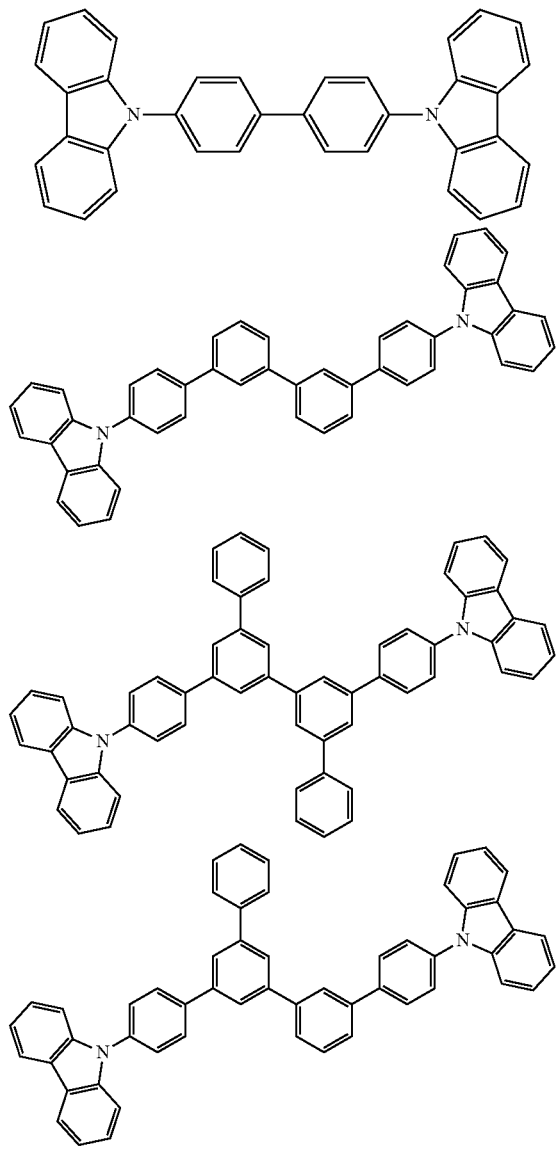

Further suitable hosts, which are especially useful as co-host together with at least one compound of formula (I) are the hosts described in US2012223295, US2014367667, US2013234119, US2014001446, US2014231794, US2014008633, WO2012108388, WO2014009317 and WO2012108389, as well as the compounds of formula (I) described in the two EP applications filed at the same day as the present application, i.e. Sep. 30, 2015, with the title "Benzimidazolo[1,2-a]benzimidazole carrying triazine groups for Organic Light Emitting Diodes" and "Benzimidazolo[1,2-a]benzimidazole carrying benzofurane or benzothiophene groups for Organic Light Emitting Diodes".

Especially preferred are the first and second host materials mentioned in US2013234119 and the compounds of formula (I) described in the two EP applications filed at the same day as the present application, i.e. Sep. 30, 2015, with the title "Benzimidazolo[1,2-a]benzimidazole carrying triazine groups for Organic Light Emitting Diodes" and "Benzimidazolo[1,2-a]benzimidazole carrying benzofurane or benzothiophene groups for Organic Light Emitting Diodes".

The first host material mentioned in US2013234119 which is preferably used as co-host together with at least one compound of formula (I) in the light emitting layer of an OLED according to the present invention is represented by formula (A). The lifetime of an OLED is increased by combinedly using as a first host material at least one compound of formula (I) and as co-host the host material represented by formula (A) in the light emitting layer.

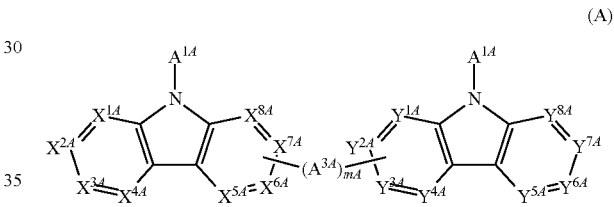

(A)

wherein
each of $A^{1A}$ and $A^{2A}$ independently represents an aryl group having 6 to 30 ring carbon atoms, which may be unsubstituted or substituted; or a heterocyclic group having 5 to 30 ring atoms, which may be unsubstituted or substituted;

$A^{3A}$ represents a divalent aryl group having 6 to 30 ring carbon atoms, which may be unsubstituted or substituted; or a divalent heterocyclic group having 5 to 30 ring atoms, which may be unsubstituted or substituted;

mA represents an integer of 0 to 3;

each of $X^{1A}$ to $X^{8A}$ and $Y^{1A}$ to $Y^{8A}$ independently represents N or $CR^a$;

each of $R^a$ independently represents a hydrogen atom, an aryl group having 6 to 30 ring carbon atoms, which may be unsubstituted or substituted; a heterocyclic group having 5 to 30 ring atoms, which may be unsubstituted or substituted; an alkyl group having 1 to 30 carbon atoms, which may be unsubstituted or substituted for example by E; a silyl group, which may be unsubstituted or substituted; a halogen atom, or a cyano group, provided that when two or more $R^a$ groups exist, the $R^a$ groups may be the same or different and one of $X^{5A}$ to $X^{8A}$ and one of $Y^{1A}$ to $Y^{4A}$ are bonded to each other via $A^{3A}$; and the formula (A) satisfies at least one of the flowing requirements (i) to (v):

(i) at least one of $A^{1A}$ and $A^{2A}$ represents a cyano-substituted aromatic hydrocarbon group having 6 to 30 ring carbon atoms or a cyano-substituted heterocyclic group having 5 to 30 ring atoms;

(ii) at least one of $X^{1A}$ to $X^{4A}$ and $Y^{5A}$ to $Y^{8A}$ represents $CR^a$, and at least one of $R^a$ in $X^{1A}$ to $X^{4A}$ and $Y^{5A}$ to $Y^{8A}$ represents a cyano-substituted aromatic hydrocarbon group having 6 to 30 ring carbon atoms or a cyano-substituted heterocyclic group having 5 to 30 ring atoms;

(iii) mA represents an integer of 1 to 3 and at least one of $A^3$ represents a cyano-substituted divalent aromatic hydrocarbon group having 6 to 30 ring carbon atoms or a cyano-substituted divalent heterocyclic group having 5 to 30 ring atoms;

(iv) at least one of $X^{5A}$ to $X^{8A}$ and $Y^{1A}$ to $Y^{4A}$ represents $CR^a$, and at least one of $R^a$ in $X^{5A}$ to $X^{8A}$ and $Y^{1A}$ to $Y^{4A}$ represents a cyano-substituted aromatic hydrocarbon group having 6 to 30 ring carbon atoms or a cyano-substituted heterocyclic group having 5 to 30 ring atoms; and (v) at least one of $X^{1A}$ to X8A and $Y^{1A}$ to $Y^{8A}$ represents C—CN.

The cyano-substituted aromatic hydrocarbon group having 6 to 30 ring carbon atoms and the cyano-substituted heterocyclic group having 5 to 30 ring atoms may be further substituted by a group other than the cyano group.

The subscript mA is preferably 0 to 2 and more preferably 0 or 1. When mA is 0, one of $X^{5A}$ to $X^{8A}$ and one of $Y^{1A}$ to $Y^{4A}$ are bonded to each other via a single bond.

In formula (A), the groups mentioned above have the following meanings:

The aromatic hydrocarbon group having 6 to 30 ring carbon atoms represented by $A^{1A}$, $A^{2A}$ and $R^a$ may be a non-condensed aromatic hydrocarbon group or a condensed aromatic hydrocarbon group. Specific examples thereof include phenyl group, naphthyl group, phenanthryl group, biphenyl group, terphenyl group, quaterphenyl group, fluoranthenyl group, triphenylenyl group, phenanthrenyl group, fluorenyl group, spirofluorenyl group, 9,9-diphenylfluorenyl group, 9,9'-spirobi[9H-fluorene]-2-yl group, 9,9-dimethylfluorenyl group, benzo[c]phenanthrenyl group, benzo[a]triphenylenyl group, naphtho[1,2-c]phenanthrenyl group, naphtho[1,2-a]triphenylenyl group, dibenzo[a,c]triphenylenyl group, and benzo[b]fluoranthenyl group, with phenyl group, naphthyl group, biphenyl group, terphenyl group, phenanthryl group, triphenylenyl group, fluorenyl group, spirobifluorenyl group, and fluoranthenyl group being preferred, and phenyl group, 1-naphthyl group, 2-naphthyl group, biphenyl-2-yl group, biphenyl-3-yl group, biphenyl-4-yl group, phenanthrene-9-yl group, phenanthrene-3-yl group, phenanthrene-2-yl group, triphenylene-2-yl group, 9,9-dimethylfluorene-2-yl group, fluoranthene-3-yl group being more preferred.

Examples of the divalent aromatic hydrocarbon group having 6 to 30 ring carbon atoms represented by $A^{3A}$ include divalent residues of the above aromatic hydrocarbon groups having 6 to 30 ring carbon atoms.

The heterocyclic group having 5 to 30 ring atoms represented by $A^{1A}$, $A^{2A}$ and $R^a$ may be a non-condensed heterocyclic group or a condensed heterocyclic group. Specific examples thereof include the residues of pyrrole ring, isoindole ring, benzofuran ring, isobenzofuran ring, dibenzothiophene ring, isoquinoline ring, quinoxaline ring, phenanthridine ring, phenanthroline ring, pyridine ring, pyrazine ring, pyrimidine ring, pyridazine ring, triazine ring, indole ring, quinoline ring, acridine ring, pyrrolidine ring, dioxane ring, piperidine ring, morpholine ring, piperazine ring, carbazole ring, furan ring, thiophene ring, oxazole ring, oxadiazole ring, benzoxazole ring, thia-zole ring, thiadiazole ring, benzothiazole ring, triazole ring, imidazole ring, benzimidazole ring, pyran ring, dibenzofuran ring, and benzo[c]dibenzofuran ring, and the residues of derivatives of these rings, with the residues of dibenzofuran ring, carbazole ring, dibenzothiophene ring, and derivatives of these rings being preferred, and the residues of dibenzofuran-2-yl group, dibenzofuran-4-yl group, 9-phenylcarbazole-3-yl group, 9-phenylcarbazole-2-yl group, dibenzothiophene-2-yl group, and dibenzothiophene-4-yl group being more preferred.

Examples of the divalent heterocyclic group having 5 to 30 ring atoms represented by $A^{3A}$ include divalent residues of the above heterocyclic group having 5 to 30 ring atoms.

Examples of the alkyl group having 1 to 30 carbon atoms represented by $R^a$ include methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, cyclopropyl group, cyclobutyl group, cyclopentyl group, cyclohexyl group, cyclooctyl group, and adamantyl group, with methyl group, ethyl group, n-propyl group, iso-propyl group, n-butyl group, s-butyl group, isobutyl group, t-butyl group, cyclopentyl group, and cyclohexyl group being preferred.

Examples of the silyl group, which may be unsubstituted or substituted; represented by $R^a$ include trimethylsilyl group, triethylsilyl group, tributylsilyl group, dimethylethylsilyl group, t-butyldimethylsilyl group, vinyldimethylsilyl group, propyldimethylsilyl group, dimethylisopropylsilyl group, dimethylpropylsilyl group, dimethylbutylsilyl group, dimethyltertiarybutylsilyl group, diethylisopropylsilyl group, phenyldimethylsilyl group, diphenylmethylsilyl group, diphenyltertiarybutylsilyl group, and triphenylsilyl group, with trimethylsilyl group, triethylsilyl group, t-butyldimethylsilyl group, vinyldimethylsilyl group, and propyldimethylsilyl group being preferred.

Examples of the halogen atom represented by $R^a$ include fluorine, chlorine, bromine, and iodine, with fluorine being preferred.

Also preferred as $R^a$ is a hydrogen atom or an aryl group having 6 to 30 ring carbon atoms, which may be unsubstituted or substituted.

Examples of the optional substituent indicated by "substituted or unsubstituted" and "may be substituted" referred to above or hereinafter include a halogen atom (fluorine, chlorine, bromine, iodine), a cyano group, an alkyl group having 1 to 20, preferably 1 to 6 carbon atoms, a cycloalkyl group having 3 to 20, preferably 5 to 12 carbon atoms, an alkoxyl group having 1 to 20, preferably 1 to 5 carbon atoms, a haloalkyl group having 1 to 20, preferably 1 to 5 carbon atoms, a haloalkoxyl group having 1 to 20, preferably 1 to 5 carbon atoms, an alkylsilyl group having 1 to 10, preferably 1 to 5 carbon atoms, an aromatic hydrocarbon group having 6 to 30, preferably 6 to 18 ring carbon atoms, an aryloxy group having 6 to 30, preferably 6 to 18 ring carbon atoms, an arylsilyl group having 6 to 30, preferably 6 to 18 carbon atoms, an aralkyl group having 7 to 30, preferably 7 to 20 carbon atoms, and a heteroaryl group having 5 to 30, preferably 5 to 18 ring atoms.

The optional substituent mentioned above may be further substituted by the optional group mentioned above.

Examples of the optional alkyl group having 1 to 20 carbon atoms include methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, and 1-methylpentyl group.

Examples of the optional cycloalkyl group having 3 to 20 carbon atoms include cyclopropyl group, cyclobutyl group, cyclopentyl group, cyclohexyl group, cyclooctyl group, and adamantyl group.

Examples of the optional alkoxyl group having 1 to 20 carbon atoms include those having an alkyl portion selected from the alkyl groups mentioned above.

Examples of the optional haloalkyl group having 1 to 20 carbon atoms include the alkyl groups mentioned above wherein the hydrogen atoms thereof are partly or entirely substituted by halogen atoms.

Examples of the optional haloalkoxyl group having 1 to 20 carbon atoms include the alkoxyl group mentioned above wherein the hydrogen atoms thereof are partly or entirely substituted by halogen atoms.

Examples of the optional alkylsilyl group having 1 to 10 carbon atoms include trimethylsilyl group, triethylsilyl group, tributylsilyl group, dimethylethylsilyl group, t-butyldimethylsilyl group, vinyldimethylsilyl group, propyldimethylsilyl group, dimethylisopropylsilyl group, dimethylpropylsilyl group, dimethylbutylsilyl group, dimethyltertiarybutylsilyl group, and diethylisopropylsilyl group.

Examples of the optional aryl group having 6 to 30 ring carbon atoms include those selected from the aryl groups mentioned above with respect to $A^{1A}$, $A^{2A}$ and $R^a$.

Examples of the optional aryloxy group having 6 to 30 ring carbon atoms include those having an aryl portion selected from the aromatic hydrocarbon groups mentioned above.

Examples of the optional arylsilyl group having 6 to 30 carbon atoms include phenyldimethylsilyl group, diphenylmethylsilyl group, diphenyltertiarybutylsilyl group, and triphenylsilyl group.

Examples of the optional aralkyl group having 7 to 30 carbon atoms include benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro-2-phenylisopropyl group.

Examples of the optional heteroaryl group having 5 to 30 ring atoms include those selected from the heterocyclic groups mentioned above with respect to $A^{1A}$, $A^{2A}$ and $R^a$.

The "carbon number of a to b" in the expression of "substituted or unsubstituted X group having carbon number of a to b" is the carbon number of the unsubstituted X group and does not include the carbon atom of the optional substituent.

The hydrogen atom referred to herein includes isotopes different from neutron numbers, i.e., light hydrogen (protium), heavy hydrogen (deuterium) and tritium.

In the host material represented by formula (A), the groups represented by formulae (a) and (b) are bonded to each other via $-(A^3)_{mA}-$ at one of $X^{5A}$ to $X^{8A}$ and one of $Y^{1A}$ to $Y^{4A}$. Specific examples of the bonding manner between formulae (a) and (b) are represented by $X^{6A}(A^{3A})_{mA}-Y^{3A}$, $X^{6A}(A^{3A})_{mA}-Y^{2A}$, $X^{6A}(A^{3A})_{mA}-Y^{4A}$, $X^{6A}(A^{3A})_{mA}-Y^{1A}$, $X^{7A}-(A^{3A})_{mA}-Y^{3A}$, $X^{5A}-(A^{3A})_{mA}-Y^{3A}$, $X^{8A}-(A^{3A})_{mA}-Y^{3A}$, $X^{7A}-(A^{3A})_{mA}-Y^{2A}$, $X^{7A}-(A^{3A})_{mA}-Y^{4A}$, $X^{7A}-(A^{3A})_{mA}-Y^{1A}$, $X^{5A}-(A^{3A})_{mA}-Y^{2A}$, $X^{8A}-(A^{3A})_{mA}-Y^{2A}$, $X^{8A}-(A^{3A})_{mA}-Y^{4A}$, $X^{8A}-(A^{3A})_{mA}-Y^{1A}$, $X^{5A}-(A^{3A})_{mA}-Y^{1A}$, and $X^{5A}-(A^{3A})_{mA}-Y^{4A}$.

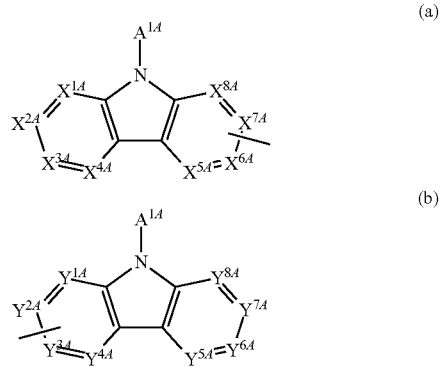

In preferred embodiments of the host material represented by formula (A), the bonding manner between formulae (a) and (b) are represented by $X^{6A}-(A^{3A})_{mA}-Y^{3A}$, $X^{6A}-(A^{3A})_{mA}-Y^{2A}$, or $X^{7A}-(A^{3A})_{mA}-Y^{3A}$, namely the material for organic electroluminescence device is preferably represented by formula (II), (III), or (IV):

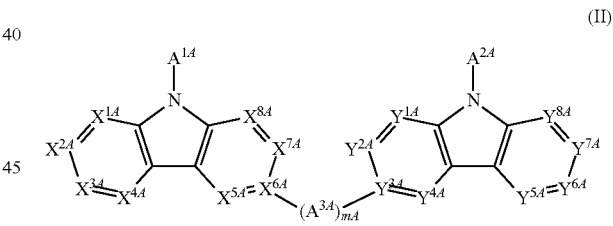

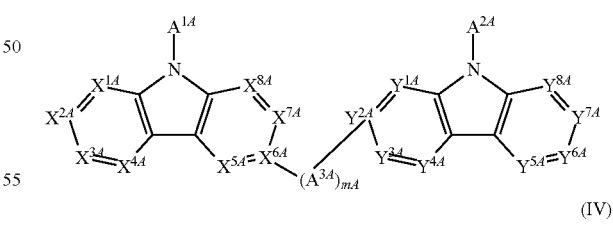

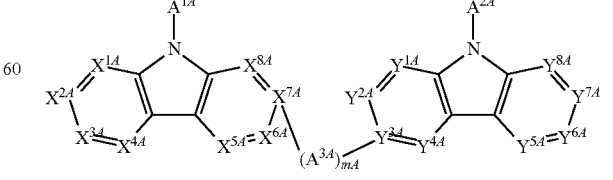

wherein $X^{1A}$ to $X^{8A}$, $Y^{1A}$ to $Y^{8A}$, $A^{1A}$ to $A^{3A}$, and mA are the same as $X^{1A}$ to $X^{8A}$, $Y^{1A}$ to $Y^{8A}$, $A^{1A}$ to $A^{3A}$, mA in formula (A), and each of formulae (II), (III), and (IV) satisfies at least one of the requirements (i) to (v) as specified in the definition of formula (A).

The host material represented by formula (A) satisfies at least one of the requirements (i) to (v), namely, the host material is a cyano group-introduced biscarbazole derivative having a group represented by formula (a) and a group represented by formula (b) which are linked to each other.

$A^{3-4}$ of formula (A) preferably represents a single bond, a substituted or unsubstituted divalent monocyclic hydrocarbon group having 6 or less ring carbon atoms, or a substituted or unsubstituted divalent monocyclic heterocyclic group having 6 or less ring atoms.

Examples of the monocyclic hydrocarbon group having 6 or less ring carbon atoms represented by $A^{3-4}$ include phenylene group, cyclopentenylene group, cyclopentadienylene group, cyclo-hexylene group, and cyclopentylene group, with phenylene group being preferred.

Examples of the monocyclic heterocyclic group having 6 or less ring atoms represented by $A^{3-4}$ include pyrrolylene group, pyrazinylene group, pyridinylene group, furylene group, and thio-phenylene group.

In a preferred embodiment of formulae (A), (II), (III), and (IV), mA is 0 and one of $X^{5-4}$ to $X^{8-4}$ and one of $Y^{1-4}$ to $Y^{4-4}$ are bonded to each other via a single bond; or $A^{3-4}$ represents the substituted or unsubstituted monocyclic hydrocarbon group having 6 or less ring carbon atoms or the substituted or unsubstituted monocyclic heterocyclic group having 6 or less ring atoms. In more preferred embodiment, mA is 0 and one of $X^{5-4}$ to $X^{8-4}$ and one of $Y^{1-4}$ to $Y^{4-4}$ are bonded to each other via a single bond; or $A^{3-4}$ represents a substituted or unsubstituted phenylene group.

The host material of formula (A) satisfies preferably at least one of the requirements (i) and (ii);

(i) at least one of $A^{1-4}$ and $A^{2-4}$ represents a cyano-substituted aromatic hydrocarbon group having 6 to 30 ring carbon atoms or a cyano-substituted heterocyclic group having 5 to 30 ring atoms; and (ii) at least one of $X^{1-4}$ to $X^{4-4}$ and $Y^{5-4}$ to $Y^{8-4}$ represents $CR^a$, and at least one of $R^a$ in $X^{1-4}$ to $X^{4-4}$ and $Y^{5-4}$ to $Y^{8-4}$ represents a cyano-substituted aromatic hydrocarbon group having 6 to 30 ring carbon atoms or a cyano-substituted heterocyclic group having 5 to 30 ring atoms.

Namely, the host material of formula (A) is preferably any one of the compounds;

(1) satisfying the requirement (i), but not satisfying the requirements (ii) to (v);

(2) satisfying the requirement (ii), but not satisfying the requirements (i) and (iii) to (v); and (3) satisfying both the requirements (i) and (ii), but not satisfying the requirements (iii) to (v).

The host material of formula (A) satisfying the requirement (i) and/or (ii) has a structure wherein the cyano group-containing aromatic hydrocarbon group or the cyano group-containing heterocyclic group is introduced to the terminal end of the central skeleton comprising the groups represented by formulae (a) and (b).

When the host material of formula (A) satisfies the requirement (i), at least one of $A^{1-4}$ and $A^{2-4}$ is preferably a cyano-substituted phenyl group, a cyano-substituted naphthyl group, a cyano-substituted phenanthryl group, a cyano-substituted dibenzofuranyl group, a cyano-substituted dibenzothiophenyl group, a cyano-substituted biphenyl group, a cyano-substituted terphenyl group, a cyano-substituted 9,9-diphenylfluorenyl group, a cyano-substituted 9,9'-spirobi[9H-fluorene]-2-yl group, a cyano-substituted 9,9'-dimethylfluorenyl group, or a cyano-substituted triphenylenyl group, and more preferably 3'-cyanobiphenyl-2-yl group, 3'-cyanobiphenyl-3-yl group, 3'-cyanobiphenyl-4-yl group, 4'-cyanobiphenyl-3-yl group, 4'-cyanobiphenyl-4-yl group, 4'-cyanobiphenyl-2-yl group, 6-cyanonaphthalene-2-yl group, 4-cyanonaphthalene-1-yl group, 7-cyanonaphthalene-2-yl group, 8-cyanodibenzofuran-2-yl group, 6-cyanodibenzofuran-4-yl group, 8-cyanodibenzothiophene-2-yl group, 6-cyanodibenzothiophene-4-yl group, 7-cyano-9-phenylcarbazole-2-yl group, 6-cyano-9-phenylcarbazole-3-yl group, 7-cyano-9,9-dimethylfluorene-2-yl group, or 7-cyanotriphenylene-2-yl group.

The host material of formula (A) wherein $A^{1-4}$ is substituted by a cyano group and $A^{2-4}$ is not substituted by a cyano group is preferred. In this case, the first host material which does not satisfy the requirement (ii) is more preferred.

When the host material of formula (A) satisfies the requirement (ii), at least one of $X^{1-4}$ to $X^{4-4}$ and $Y^{5-4}$ to $Y^{8-4}$ is preferably $CR^a$, and one of $R^a$ in $X^{1-4}$ to $X^{4-4}$ and $Y^{5-4}$ to $Y^{8-4}$ is preferably a cy-ano-substituted phenyl group, a cyano-substituted naphthyl group, a cyano-substituted phenanthryl group, a cyano-substituted dibenzofuranyl group, a cyano-substituted dibenzothiophenyl group, a cyano-substituted biphenyl group, a cyano-substituted terphenyl group, a cyano-substituted 9,9-diphenylfluorenyl group, a cyano-substituted 9,9'-spirobi[9H-fluorene]-2-yl group, a cyano-substituted 9,9'-dimethylfluorenyl group, or a cyano-substituted triphenylenyl group, and more preferably 3'-cyanobiphenyl-2-yl group, 3'-cyanobiphenyl-3-yl group, 3'-cyanobiphenyl-4-yl group, 4'-cyanobiphenyl-3-yl group, 4'-cyanobiphenyl-4-yl group, 4'-cyanobiphenyl-2-yl group, 6-cyanonaphthalene-2-yl group, 4-cyanonaphthalene-1-yl group, 7-cyanonaphthalene-2-yl group, 8-cyanodibenzofuran-2-yl group, 6-cyanodibenzofuran-4-yl group, 8-cyanodibenzothiophene-2-yl group, 6-cyanodibenzothiophene-4-yl group, 7-cyano-9-phenylcarbazole-2-yl group, 6-cyano-9-phenylcarbazole-3-yl group, 7-cyano-9,9-dimethylfluorene-2-yl group, or 7-cyanotriphenylene-2-yl group.

It is preferred for the host material of formula (A) to satisfy the requirement (ii), but not satisfy the requirement (i).

In formulae (A) and (II) to (IV), $A^{1-4}$ and $A^{2-4}$ are preferably different from each other, and more preferably, $A^{1-4}$ is substituted by a cyano group but $A^{2-4}$ is not substituted by a cyano group. Namely, the host material of formula (A) is preferably structurally asymmetric.

The production method of the first host material is not particularly limited and it is produced according to a known method, for example, by a coupling reaction of a carbazole derivative and an aromatic halogenated compound in the presence of a copper catalyst described in Tetrahedron 40 (1984) 1435 to 1456 or a palladium catalyst described in Journal of American Chemical Society 123 (2001) 7727 to 7729.

Examples of the host material of formula (A) are mentioned in [0145] in US2013234119.

Examples for preferred host materials used as co-hosts mentioned in US2013234119 WO2012108388 and WO2014009317 are:

401
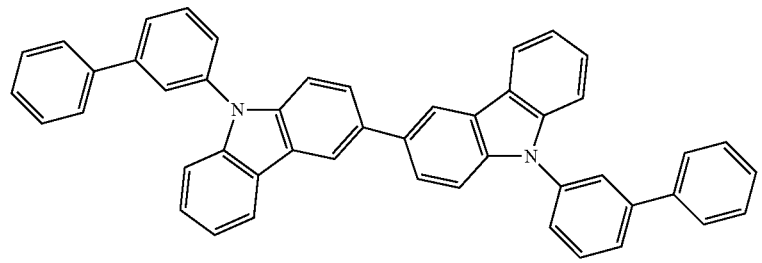
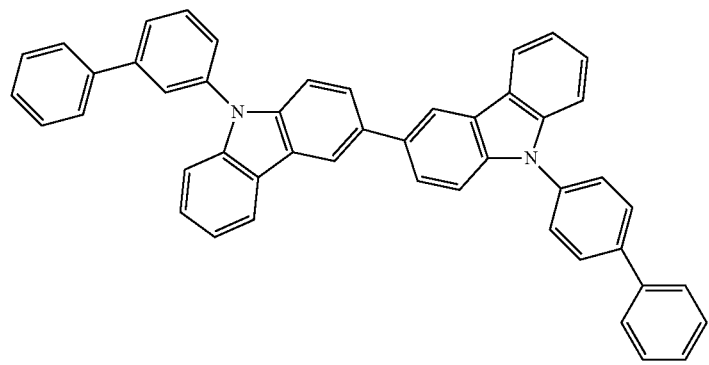
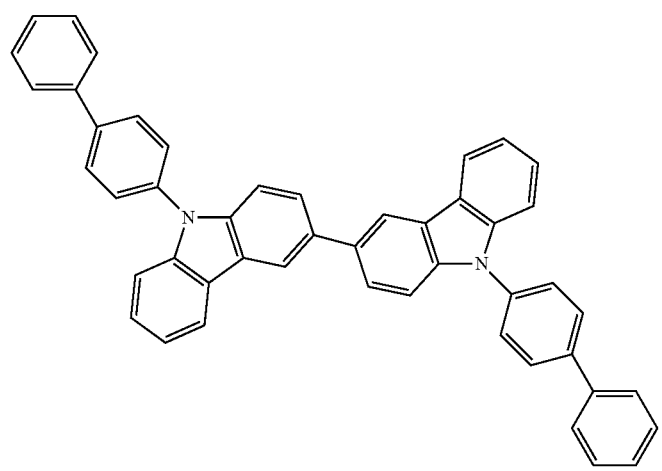
402
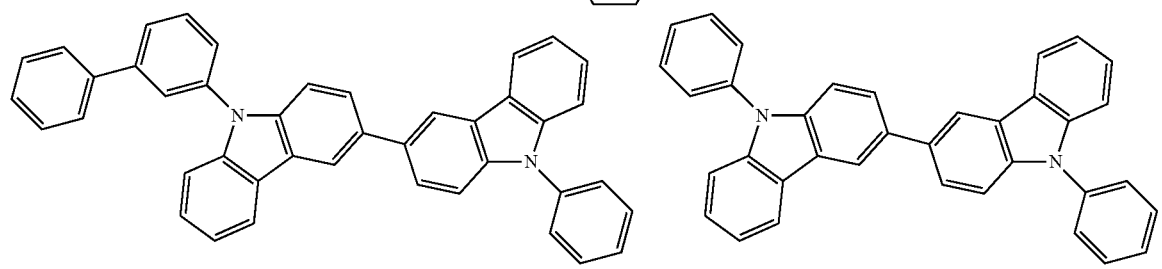
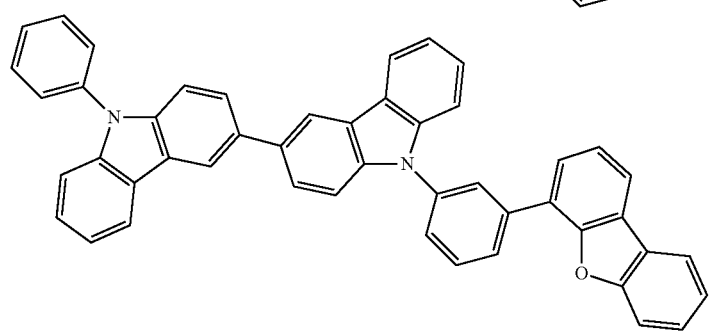

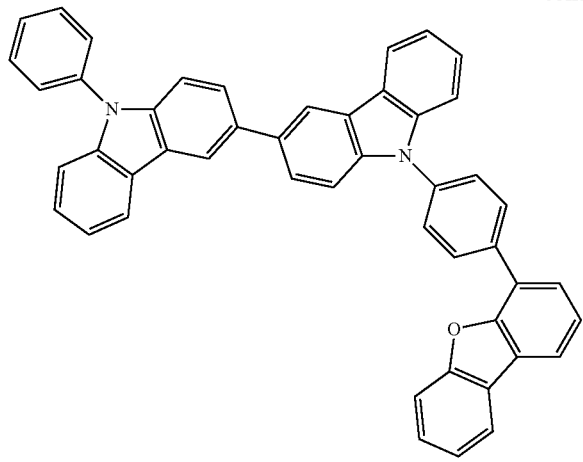
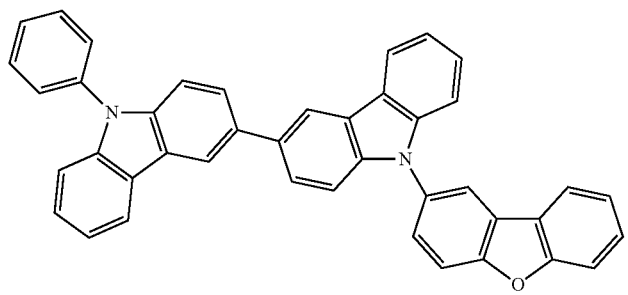
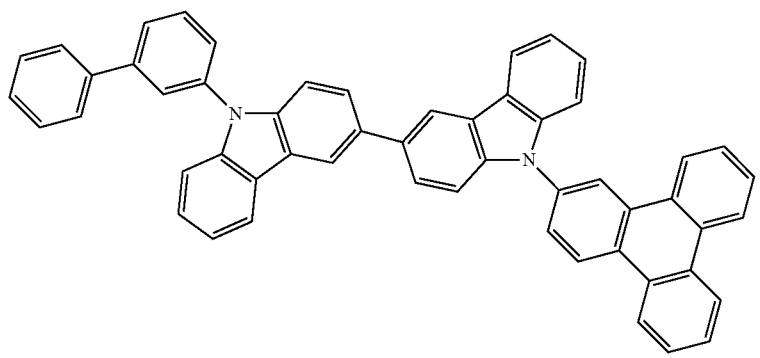
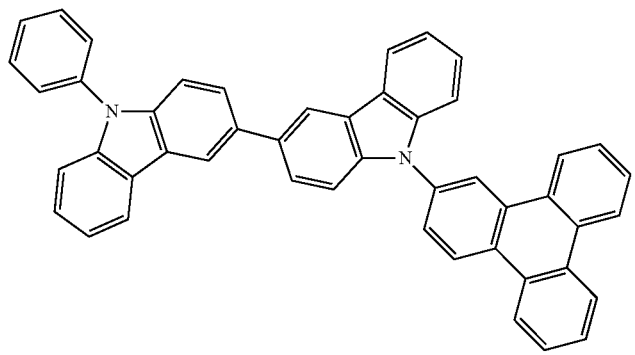

405
406
-continued
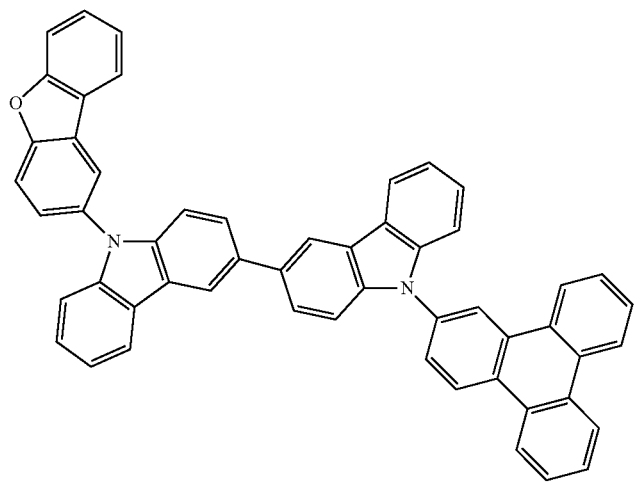
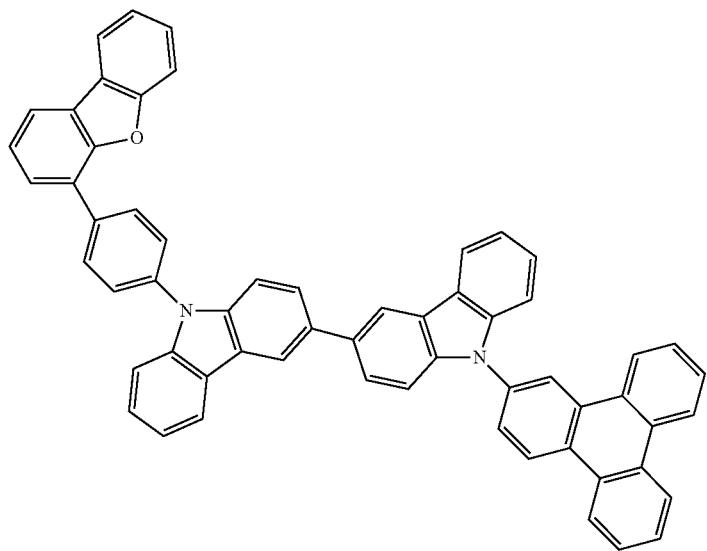
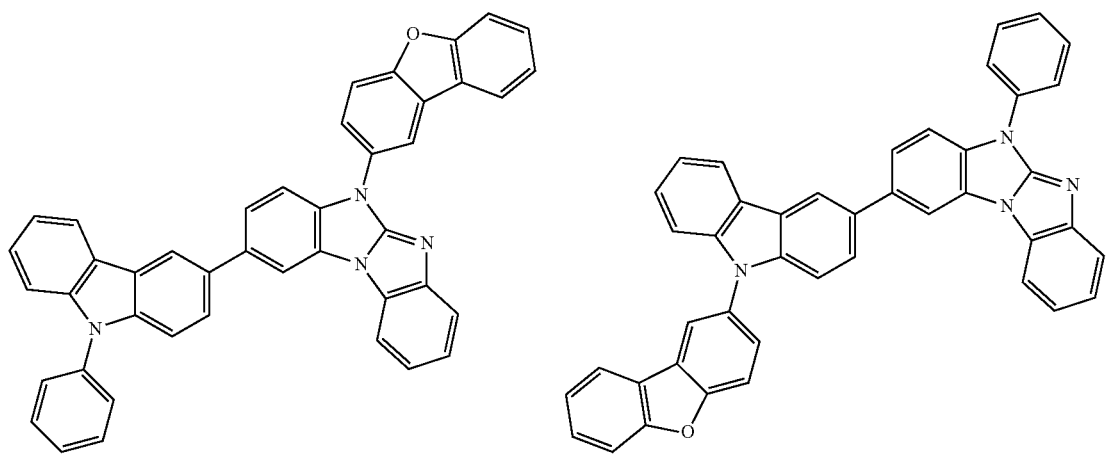

-continued
407 408
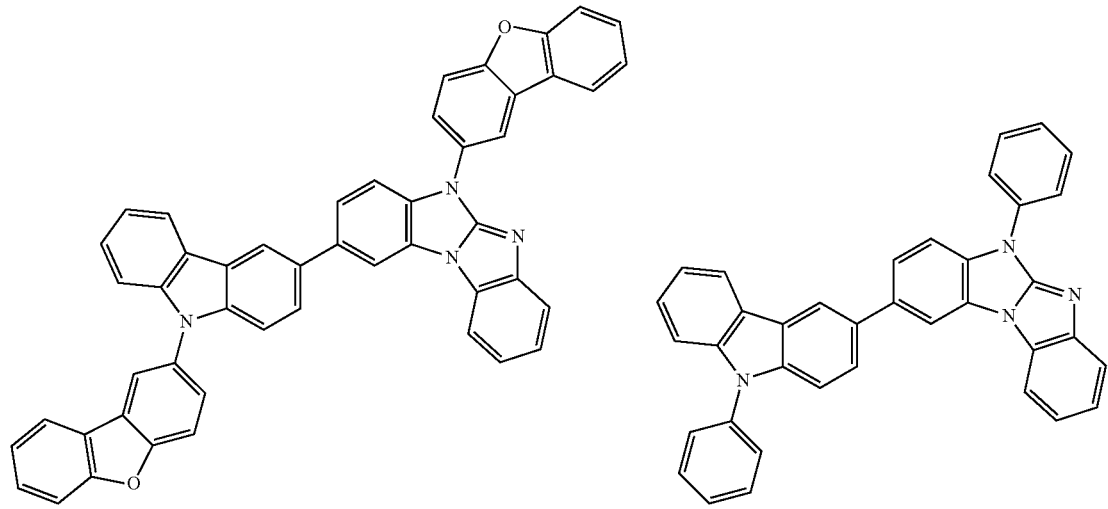
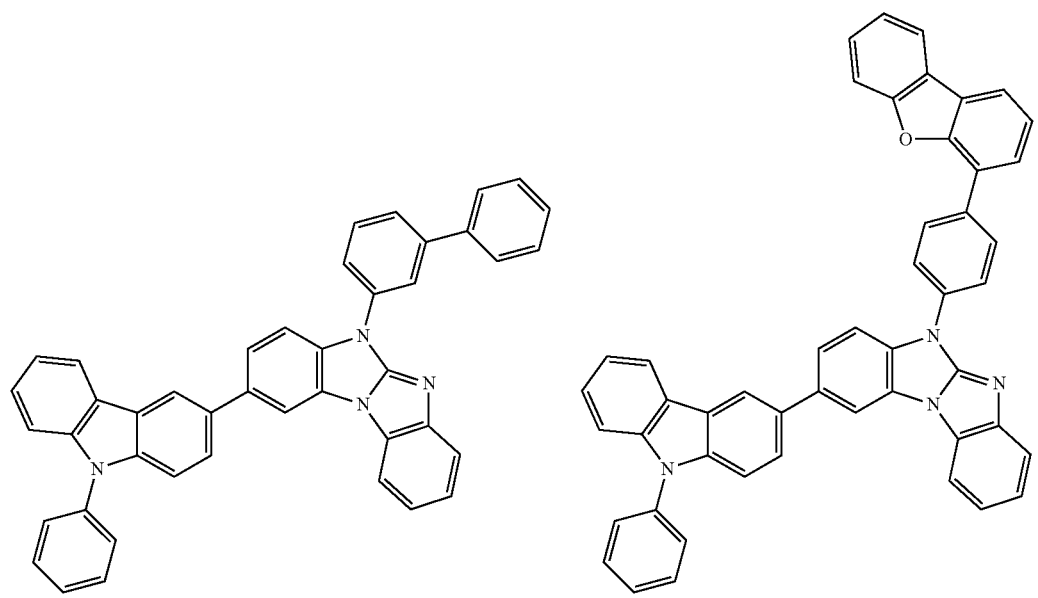
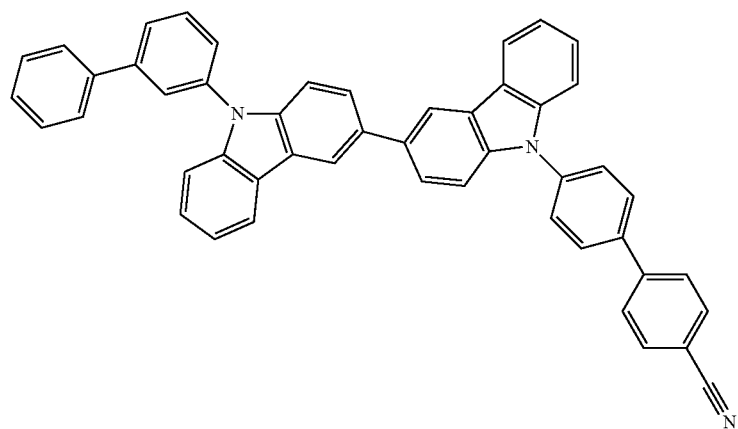

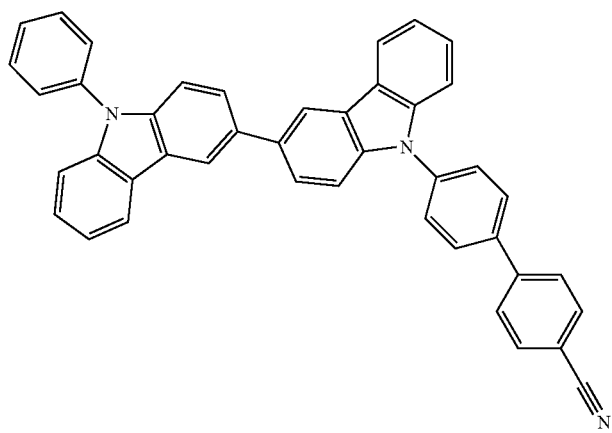
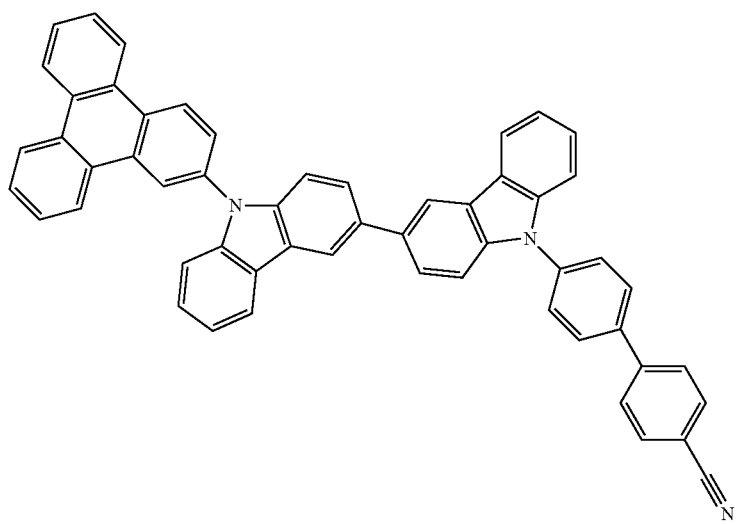
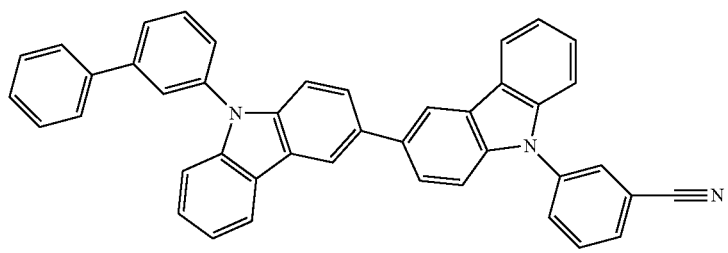
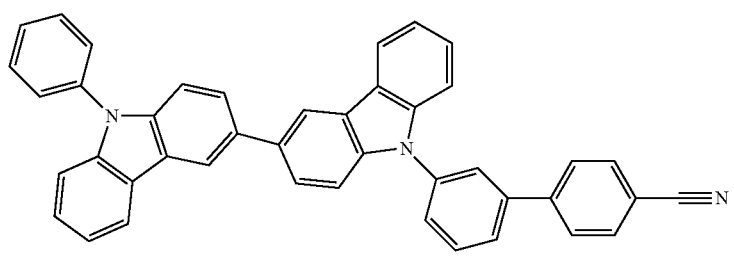

-continued

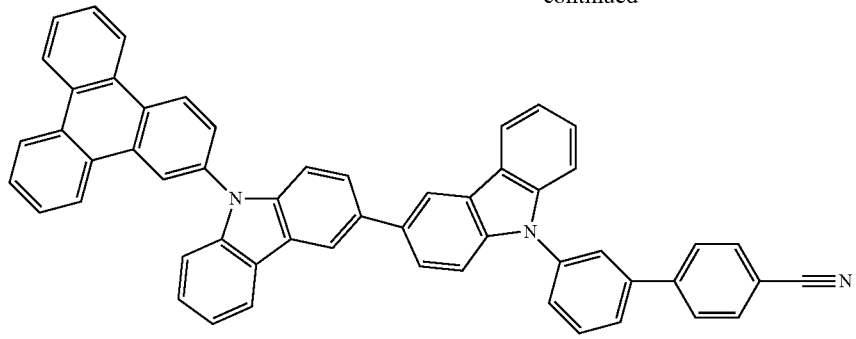

It is further possible to employ the compound of formula (I) to the present invention as host material in an OLED, preferably in the light emitting layer, together with at least one second host material described in US 2013234119, especially in paragraphs [0146] to [0195] in US 2013234119.

The second host material mentioned in US2013234119 which is preferably used as used co-host together with at least one compound of formula (I) in the light emitting layer of an OLED according to the present invention is represented by formula (KoH1).

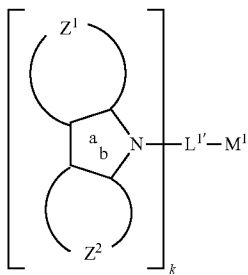

(KoH1)

$Z^1$ represents a ring structure fused to the side a and represented by formula (KoH1-1) or (KoH 1-2), and $Z^2$ represents a ring structure fused to the side b and represented by formula (KoH1-1) or (KoH1-2), provided that at least one of $Z^1$ and $Z^2$ is represented by formula (KoH 1-1);

$M^1$ represents a nitrogen-containing heteroaryl group having 5 to 30 ring atoms, which may be unsubstituted or substituted for example by G;

$L^{1'}$ represents a single bond, a divalent aromatic hydrocarbon group having 6 to 30 ring carbon atoms which may be unsubstituted or substituted for example by G, a divalent heterocyclic group having 5 to 30 ring atoms which may be unsubstituted or substituted for example by G, a cycloalkylene group having 5 to 30 ring atoms, or a group in which the preceding groups are directly linked to each other; and k represents 1 or 2.

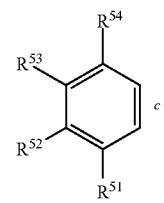
KoH1-1

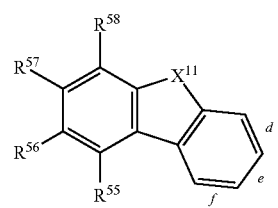
KoH1-2

In formula (KoH1-1), a side c is fused to the side a or b of formula (KoH1).

In formula (KoH1-2), any one of sides d, e and f is fused to the side a or b of formula (KoH1).

In formulae (KoH1-1) and (KoH 1-2):

$X^{11}$ represents a sulfur atom, an oxygen atom, $NR^{77}$, or $C(R^{78})(R^{79})$; and each of $R^{51}$ to $R^{54}$ and $R^{55}$ to $R^{58}$ independently represents a hydrogen atom, a heavy hydrogen atom, a halogen atom, a cyano group, an aryl group having 6 to 30 ring carbon atoms, which may be unsubstituted or substituted for example by G, a cycloalkylene group having 5 to 30 ring atoms, a heterocyclic group having 5 to 30 ring atoms, which may be unsubstituted or substituted for example by G, an alkyl group having 1 to 30 carbon atoms, which may be unsubstituted or substituted for example by E, an alkenyl group having 2 to 30 carbon atoms, which may be unsubstituted or substituted for example by E, an alkynyl group having 2 to 30 carbon atoms, which may be unsubstituted or substituted for example by G, an alkylsilyl group having 3 to 30 carbon atoms, which may be unsubstituted or substituted for example by E, an arylsilyl group having 6 to 30 ring carbon atoms, which may be unsubstituted or substituted for example by G, an alkoxy group having 1 to 30 carbon atoms, which may be unsubstituted or substituted for example by E, an aralkyl group having 6 to 30 ring carbon atoms, which may be unsubstituted or substituted for example by G, or an aryloxy group having 6 to 30 ring carbon atoms, which may be unsubstituted or substituted for example by G, provided that adjacent groups of $R^{51}$ to $R^{54}$ and $R^{55}$ to $R^{58}$ may be bonded to each other to form a ring;

$R^{77}$ is a $C_6$-$C_{24}$aryl group, which can optionally be substituted by G, or a $C_1$-$C_{24}$heteroaryl group, which can optionally be substituted by G;

$R^{78}$, $R^{79}$ is a $C_1$-$C_{25}$alkyl group, which can optionally be substituted by E and or interrupted by D; a $C_6$-$C_{24}$aryl group, which can optionally be substituted by G, or a $C_1$-$C_{24}$heteroaryl group, which can optionally be substituted by G;

E is —$OR^{69}$, —$SR^{69}$, —$NR^{65}R^{66}$, —$COR^{68}$, —$COOR^{67}$, —$CONR^{65}R^{66}$, —CN, —$Si(R^{70})_3$ or halogen. E is preferably —$OR^{69}$; —$SR^{69}$; —$NR^{65}R^{66}$; —$COR^{68}$; —$COOR^{67}$; —$CON^{65}R^{66}$; or —CN; wherein $R^{65}$, $R^{66}$, $R^{67}$, $R^{68}$ and $R^{69}$ are preferably independently of each other $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, tolyl, naphthyl, triphenylyl or biphenylyl;

G is E, or a $C_1$-$C_{24}$alkyl group, a $C_6$-$C_{30}$aryl group, a $C_6$-$C_{30}$aryl group, which is substituted by F, $C_1$-$C_{24}$alkyl, or $C_1$-$C_{24}$alkyl which is interrupted by O; a $C_2$-$C_{60}$heteroaryl group, or a $C_2$-$C_{60}$heteroaryl group, which is substituted by F, $C_1$-$C_{18}$alkyl, or $C_1$-$C_{18}$alkyl which is interrupted by O. G is preferably —$OR^{69}$, —$SR^{69}$, —$NR^{65}R^{66}$; a $C_1$-$C_{18}$alkyl group, a $C_6$-$C_{18}$aryl group, a $C_6$-$C_{18}$aryl group, which is substituted by F, or $C_1$-$C_{18}$alkyl; a $C_2$-$C_{24}$heteroaryl group, or a $C_2$-$C_{24}$heteroaryl group, which is substituted by F, or $C_1$-$C_{18}$alkyl; wherein $R^{65}$, $R^{66}$ and $R^{69}$ are independently of each other $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, tolyl, naphthyl, or biphenylyl. More preferably, G is a $C_6$-$C_{18}$aryl group like phenyl, tolyl, triphenylyl or biphenylyl, or a $C_6$-$C_{24}$heteroaryl group like dibenzothiophenylyl, dibenzofuranyl, pyridyl, triazinyl, pyrimidinyl, azatriphenylyl, azadibenzofuryl, azadibenzothiophenyl, azacarbazolyl, quinolonyl, isoquinolinyl, quinoxalinyl, quinazolinyl, phenanthrolinyl, phenanthridinyl, benzo[h]quinolonyl, benz[h]isoquinolinyl, benzo[f]isoquinolinyl, benzo[f]quinolinyl, benzo[h]quinazolinyl, benzo[f]quinazolinyl, dibenzo[f,h]quinolonyl, dibenzo[f,h]isoquinolonyl, dibenzo[f,h]quinoxalinyl or dibenzo[f,h]quinazolinyl.

Examples for preferred second host materials used as co-hosts mentioned in US2013234119 are:

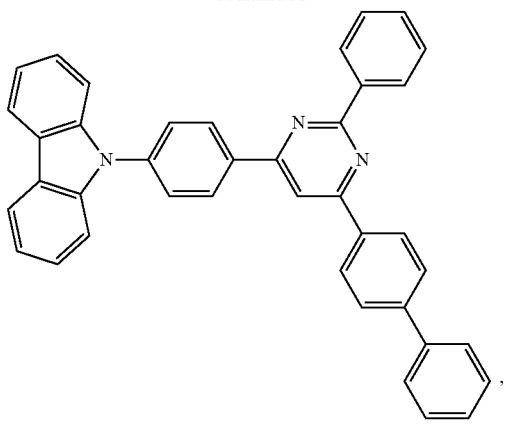,

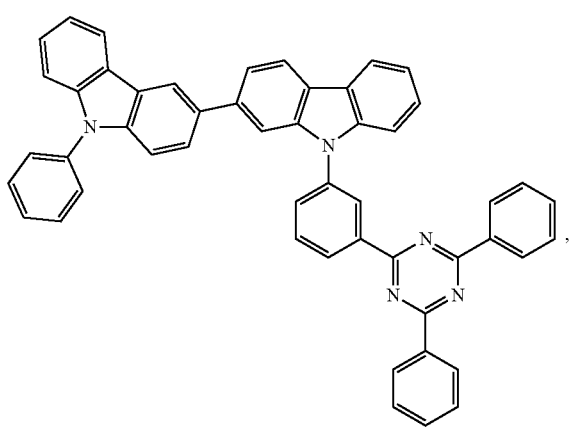,

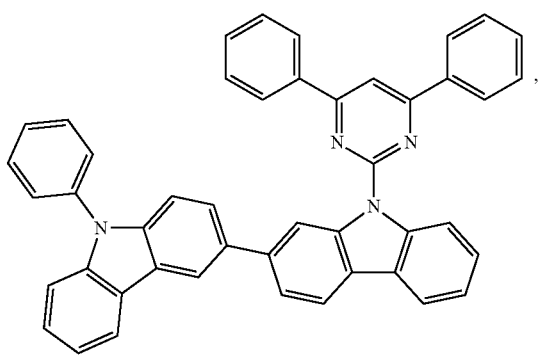,

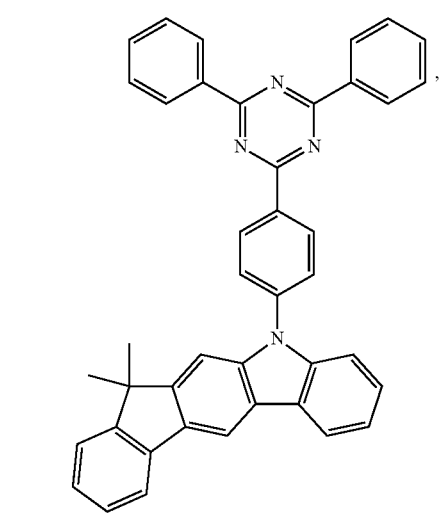

-continued

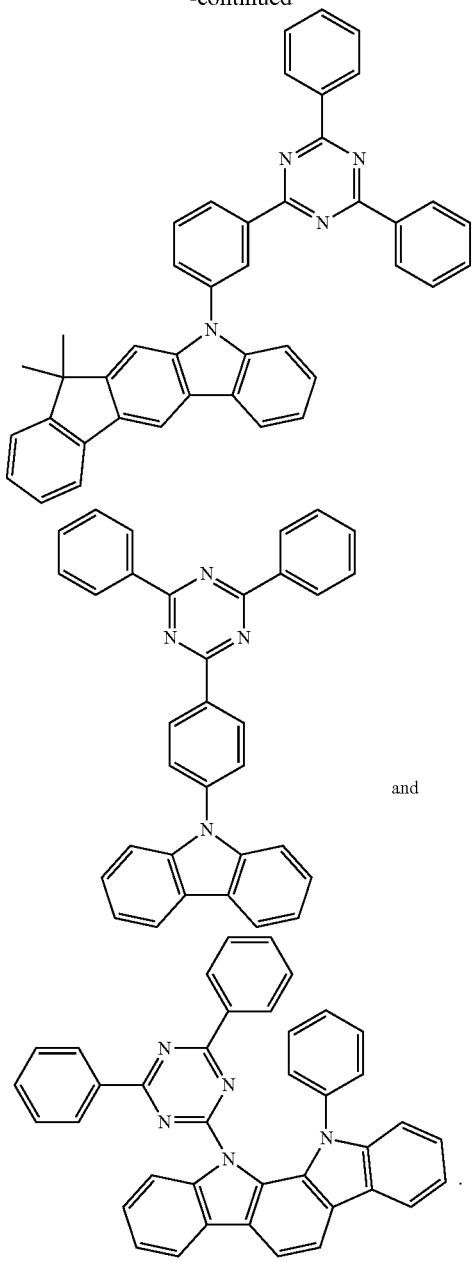

and

Hole/Exciton Blocking Layer (f):

Blocking layers may be used to reduce the number of charge carriers (electrons or holes) and/or excitons that leave the emissive layer. The hole blocking layer may be disposed between the emitting layer (e) and electron transport layer (g), to block holes from leaving layer (e) in the direction of electron transport layer (g). Blocking layers may also be used to block excitons from diffusing out of the emissive layer.

Additional hole blocker materials typically used in OLEDs are 2,6-bis(N-carbazolyl)pyridine (mCPy), 2,9-dimethyl-4,7-diphenyl-1,10-phenanthroline (bathocuproin, (BCP)), bis(2-methyl-8-quinolinato)-4-phenylphenylato) aluminum(III) (BAlq), phenothiazine S,S-dioxide derivates and 1,3,5-tris(N-phenyl-2-benzylimidazolyl)benzene) (TPBI), TPBI also being suitable as electron-transport material. Further suitable hole blockers and/or electron conductor materials are 2,2',2"-(1,3,5-benzenetriyl)tris(1-phenyl-1-H-benzimidazole), 2-(4-biphenylyl)-5-(4-tert-butylphenyl)-1,3,4-oxadiazole, 8-hydroxyquinolinolatolithium, 4-(naphthalen-1-yl)-3,5-diphenyl-4H-1,2,4-triazole, 1,3-bis[2-(2,2'-bipyridin-6-yl)-1,3,4-oxadiazo-5-yl]benzene, 4,7-diphenyl-1,10-phenanthroline, 3-(4-biphenylyl)-4-phenyl-5-tert-butylphenyl-1,2,4-triazole, 6,6'-bis[5-(biphenyl-4-yl)-1,3,4-oxadiazo-2-yl]-2,2'-bipyridyl, 2-phenyl-9,10-di(naphthalene-2-yl)anthracene, 2,7-bis[2-(2,2'-bipyridin-6-yl)-1,3,4-oxadiazo-5-yl]-9,9-dimethylfluorene, 1,3-bis[2-(4-tert-butylphenyl)-1,3,4-oxadiazo-5-yl]benzene, 2-(naphthalene-2-yl)-4,7-diphenyl-1,10-phenanthroline, tris(2,4,6-trimethyl-3-(pyridin-3-yl)phenyl)borane, 2,9-bis(naphthalene-2-yl)-4,7-diphenyl-1,10-phenanthroline, 1-methyl-2-(4-(naphthalene-2-yl)phenyl)-1H-imidazo[4,5-f][1,10]-phenanthroline. In a further embodiment, it is possible to use compounds which comprise aromatic or heteroaromatic rings joined via groups comprising carbonyl groups, as disclosed in WO2006/100298, disilyl compounds selected from the group consisting of disilylcarbazoles, disilylbenzofurans, disilylbenzothiophenes, disilylbenzophospholes, disilylbenzothiophene S-oxides and disilylbenzothiophene S,S-dioxides, as specified, for example, in PCT applications WO2009/003919 and WO2009003898 and disilyl compounds as disclosed in WO2008/034758, as a blocking layer for holes/excitons (f).

In another preferred embodiment compounds (SH-1), (SH-2), (SH-3), SH-4, SH-5, SH-6, (SH-7), (SH-8), (SH-9), (SH-10) and (SH-11) may be used as hole/exciton blocking materials.

In addition to the materials mentioned above or as an alternative, the compound of formula (I) may be used as hole/exciton blocker material.

Electron Transport Layer (g):

Electron transport layer may include a material capable of transporting electrons. Electron transport layer may be intrinsic (undoped), or doped. Doping may be used to enhance conductivity.

The compound of the formula (I) is suitable as electron transport material, either alone or in combination with one or more of the electron transport materials mentioned below.

Further suitable electron-transporting materials for layer (g) of the inventive OLEDs, which may be used in combination with the compound of formula (I) or in absence of the compound of formula (I) as electron transport material, comprise metals chelated with oxinoid compounds, such as tris(8-hydroxyquinolato)aluminum (Alq$_3$), compounds based on phenanthroline such as 2,9-dimethyl-4,7-diphenyl-1,10-phenanthroline (DDPA=BCP), 4,7-diphenyl-1,10-phenanthroline (Bphen), 2,4,7,9-tetraphenyl-1,10-phenanthroline, 4,7-diphenyl-1,10-phenanthroline (DPA) or phenanthroline derivatives disclosed in EP1786050, in EP1970371, or in EP1097981, and azole compounds such as 2-(4-biphenylyl)-5-(4-t-butylphenyl)-1,3,4-oxadiazole (PBD) and 3-(4-biphenylyl)-4phenyl-5-(4-t-butylphenyl)-1,2,4-triazole (TAZ).

Further suitable electron transport materials, which may be used in combination with the compound of formula (I) or in absence of the compound of formula (I) as electron transport material, are mentioned in Abhishek P. Kulkarni, Christopher J. Tonzola, Amit Babel, and Samson A. Jenekhe, *Chem. Mater.* 2004, 16, 4556-4573; G. Hughes, M. R. Bryce, *J. Mater. Chem.* 2005, 15, 94-107 and Yasuhiko Shirota and Hiroshi Kageyama, *Chem. Rev.* 2007, 107, 953-1010 (ETM, HTM).

It is likewise possible to use mixtures of at least two materials in the electron-transporting layer, in which case at least one material is electron-conducting. Preferably, in such mixed electron-transport layers, at least one phenanthroline compound is used, preferably BCP, or at least one pyridine compound according to the formula (XVI) below, preferably a compound of the formula (XVIa) below. More preferably, in mixed electron-transport layers, in addition to at least one phenanthroline compound, alkaline earth metal or alkali metal hydroxyquinolate complexes, for example Liq, are used. Suitable alkaline earth metal or alkali metal hydroxyquinolate complexes are specified below (formula XVII). Reference is made to WO2011/157779.

The electron-transport layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo, Appl. Phys. Lett., Vol. 82, No. 25, 23 Jun. 2003 and Pfeiffer et al., Organic Electronics 2003, 4, 89-103 and K. Walzer, B. Maennig, M. Pfeiffer, K. Leo, Chem. Soc. Rev. 2007, 107, 1233. For example, it is possible to use mixtures which lead to electrical n-doping of the electron-transport layer. n-Doping is achieved by the addition of reducing materials. These mixtures may, for example, be mixtures of the abovementioned electron transport materials with alkali/alkaline earth metals or alkali/alkaline earth metal salts, for example Li, Cs, Ca, Sr, $Cs_2CO_3$, with alkali metal complexes, for example 8-hydroxyquinolatolithium (Liq), and with Y, Ce, Sm, Gd, Tb, Er, Tm, Yb, $Li_3N$, $Rb_2CO_3$, dipotassi-um phthalate, $W(hpp)_4$ from EP1786050, or with compounds described in EP1837926B1, EP1837927, EP2246862 and WO2010132236.

In a preferred embodiment, the electron-transport layer comprises at least one compound of the general formula (XVII)

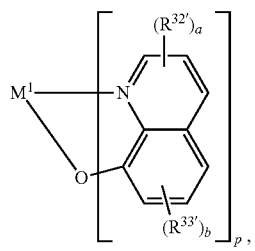

in which $R^{32'}$ and $R^{33'}$ are each independently F, $C_1$-$C_8$-alkyl, or $C_6$-$C_{14}$-aryl, which is optionally substituted by one or more $C_1$-$C_8$-alkyl groups, or two $R^{32'}$ and/or $R^{33'}$ substituents together form a fused benzene ring which is optionally substituted by one or more $C_1$-$C_8$-alkyl groups;

a and b are each independently 0, or 1, 2 or 3, $M^1$ is an alkaline metal atom or alkaline earth metal atom, p is 1 when $M^1$ is an alkali metal atom, p is 2 when $M^1$ is an earth alkali metal atom.

A very particularly preferred compound of the formula (XVII) is

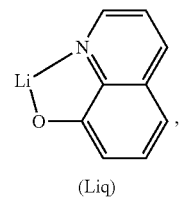

which may be present as a single species, or in other forms such as $Li_gQ_g$ in which g is an integer, for example $Li_6Q_6$. Q is an 8-hydroxyquinolate ligand or an 8-hydroxyquinolate derivative.

In a further preferred embodiment, the electron-transport layer comprises at least one compound of the formula (XVI),

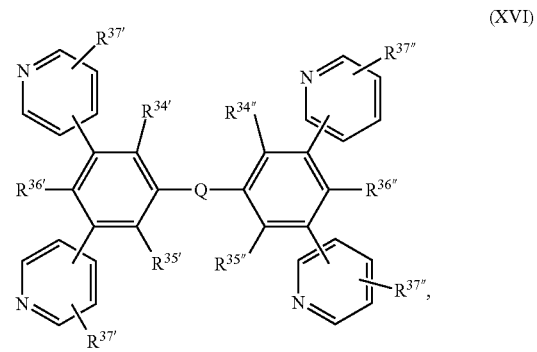

in which $R^{34"}$, $R^{35"}$, $R^{36"}$, $R^{37"}$, $R^{34'}$, $R^{35'}$, $R^{36'}$ and $R^{37'}$ are each independently H, $C_1$-$C_{18}$-alkyl, $C_1$-$C_{18}$-alkyl which is substituted by E' and/or interrupted by D', $C_6$-$C_{24}$-aryl, $C_6$-$C_{24}$-aryl which is substituted by G', $C_2$-$C_{20}$-heteroaryl or $C_2$-$C_{20}$-heteroaryl which is substituted by G', Q is an arylene or heteroarylene group, each of which is optionally substituted by G';

D' is —CO—; —COO—; —S—; —SO—; —$SO_2$—; —O—; —$NR^{40'}$—; —$SiR^{45'}$ $R^{46'}$—; —$POR^{47'}$—; —$CR^{38'}$=$CR^{39'}$—; or —C≡C—;

E' is —$OR^{44'}$; —$SR^{44'}$; —$NR^{40'}R^{41'}$; —$COR^{43'}$; —$COOR^{42'}$; —$CONR^{40'}R^{41'}$; —CN; or F;

G' is E', $C_1$-$C_{18}$-alkyl, $C_1$-$C_{18}$-alkyl which is interrupted by D', $C_1$-$C_{18}$-perfluoroalkyl, $C_1$-$C_{18}$-alkoxy, or $C_1$-$C_{18}$-alkoxy which is substituted by E' and/or interrupted by D', in which $R^{38'}$ and $R^{39'}$ are each independently H, $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—;

$R^{40'}$ and $R^{41'}$ are each independently $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—; or $R^{40'}$ and $R^{41'}$ together form a 6-membered ring;

$R^{42'}$ and $R^{43'}$ are each independently $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—;

$R^{44'}$ is $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—, $R^{45'}$ and $R^{46'}$ are each independently $C_1$-$C_{18}$-alkyl, $C_6$-$C_{18}$-aryl or $C_6$-$C_{18}$-aryl which is substituted by $C_1$-$C_{18}$-alkyl, $R^{47'}$ is $C_1$-$C_{18}$-alkyl, $C_6$-$C_{18}$-aryl or $C_6$-$C_{18}$-aryl which is substituted by $C_1$-$C_{18}$-alkyl.

Preferred compounds of the formula (XVI) are compounds of the formula (XVIa)

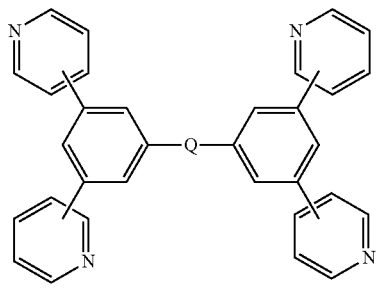
(XVIa)

in which Q is:

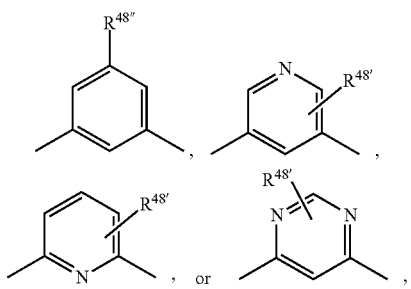

$R^{48'}$ is H or $C_1$-$C_{18}$-alkyl and
$R^{48''}$ is H, $C_1$-$C_{18}$-alkyl or

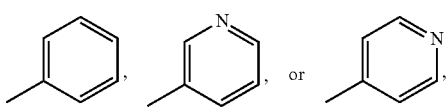

Particular preference is given to a compound of the formula

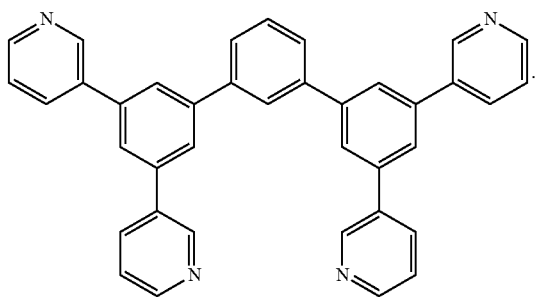
(ETM-2)

In a further, very particularly preferred embodiment, the electron-transport layer comprises a compound Liq and a compound ETM-2.

In a preferred embodiment, the electron-transport layer comprises at least one compound of the formula (XVII) in an amount of 99 to 1% by weight, preferably 75 to 25% by weight, more preferably about 50% by weight, and at least one compound of the formula (XVI) in an amount of 1 to 99% by weight, preferably 25 to 75% by weight, more preferably about 50% by weight, where the amount of the compounds of the formulae (XVII) and the amount of the compounds of the formulae (XVI) adds up to a total of 100% by weight.

The preparation of the compounds of the formula (XVI) is described in J. Kido et al., Chem. Commun. (2008) 5821-5823, J. Kido et al., Chem. Mater. 20 (2008) 5951-5953 and JP2008/127326, or the compounds can be prepared analogously to the processes disclosed in the aforementioned documents.

It is likewise possible to use mixtures of alkali metal hydroxyquinolate complexes, preferably Liq, and dibenzofuran compounds in the electron-transport layer. Reference is made to WO2011/157790. Dibenzofuran compounds A-1 to A-36 and B-1 to B-22 described in WO2011/157790 are preferred, wherein dibenzofuran compound

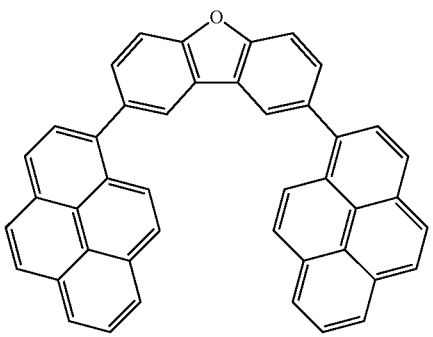 [SMILES: c1cc2ccc3ccc(-c4ccc5oc6ccc(-c7ccc8ccc9cccc%10ccc7c8c9%10)cc6c5c4)c4ccc(c1)c2c34]

(A-10; =ETM-1) is most preferred.

In a preferred embodiment, the electron-transport layer comprises Liq in an amount of 99 to 1% by weight, preferably 75 to 25% by weight, more preferably about 50% by weight, and at least one dibenzofuran compound in an amount of 1 to 99% by weight, preferably 25 to 75% by weight, more preferably about 50% by weight, where the amount of Liq and the amount of the dibenzofuran compound(s), especially ETM-1, adds up to a total of 100% by weight.

In a preferred embodiment, the electron-transport layer comprises at least one phenanthroline derivative and/or pyridine derivative.

In a further preferred embodiment, the electron-transport layer comprises at least one phenanthroline derivative and/or pyridine derivative and at least one alkali metal hydroxyquinolate complex.

In a further preferred embodiment, the electron-transport layer comprises at least one of the dibenzofuran compounds A-1 to A-36 and B-1 to B-22 described in WO2011/157790, especially ETM-1.

In a further preferred embodiment, the electron-transport layer comprises a compound described in WO2012/111462, WO2012/147397, WO2012014621, such as, for example, a compound of formula (ETM-3)

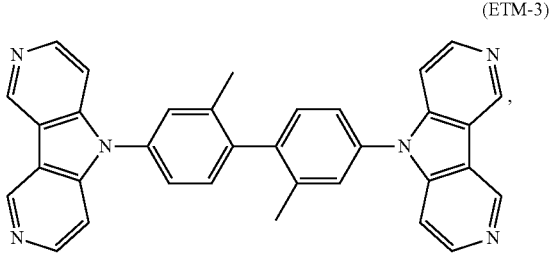 [SMILES: Cc1cc(-n2c3ccncc3c3cnccc32)ccc1-c1ccc(-n2c3ccncc3c3cnccc32)cc1C]

US2012/0261654, such as, for example, a compound of formula (ETM-4)

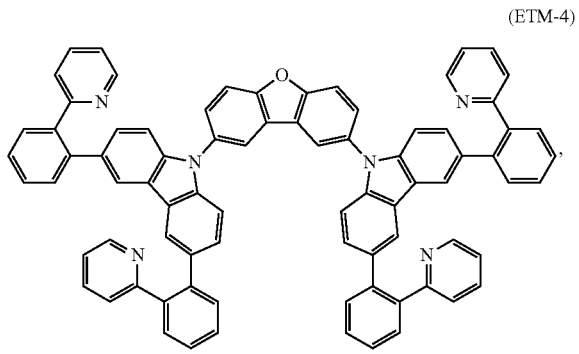 [SMILES: c1ccc(-c2ccccc2-c2ccc3c(c2)c2cc(-c4ccccc4-c4ccccn4)ccc2n3-c2ccc3oc4ccc(-n5c6ccc(-c7ccccc7-c7ccccn7)cc6c6cc(-c7ccccc7-c7ccccn7)ccc65)cc4c3c2)nc1]

and WO2012/115034, such as for example, such as, for example, a compound of formula (ETM-5)

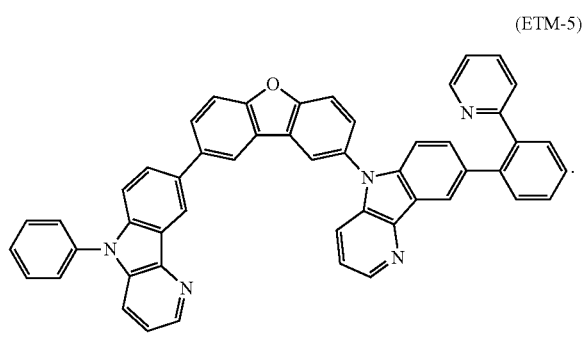 [SMILES: c1ccc(-n2c3ccc(-c4ccc5oc6ccc(-n7c8ccc(-c9ccccc9-c9ccccn9)cc8c8ncccc87)cc6c5c4)cc3c3ncccc32)cc1]

A further suitable electron transport material is:

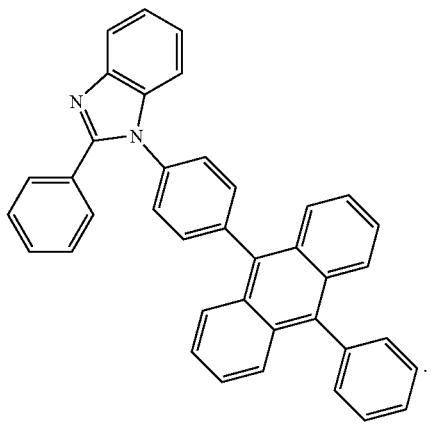 [SMILES: c1ccc(-c2c3ccccc3c(-c3ccc(-n4c(-c5ccccc5)nc5ccccc54)cc3)c3ccccc23)cc1]

Electron Injection Layer (h):

The electron injection layer may be any layer that improves the injection of electrons into an adjacent organic layer.

The compound of the formula (I) is suitable as electron injection material, either alone or in combination with one or more of the electron injection materials mentioned below.

Further lithium-comprising organometallic compounds such as 8-hydroxyquinolatolithium (Liq), CsF, NaF, KF, $Cs_2CO_3$ or LiF may be applied between the electron transport layer (g) and the cathode (i) as an electron injection layer (h) in order to reduce the operating voltage.

Cathode (i):

The cathode (i) is an electrode which serves to introduce electrons or negative charge carriers. The cathode may be any metal or nonmetal which has a lower work function than the anode. Suitable materials for the cathode are selected from the group consisting of alkali metals of group 1, for example Li, Cs, alkaline earth metals of group 2, metals of group 12 of the Periodic Table of the Elements, comprising the rare earth metals and the lanthanides and actinides. In addition, metals such as aluminum, indium, calcium, barium, samarium and magnesium, and combinations thereof, may be used.

In general, the different layers, if present, have the following thicknesses:

anode (a): 500 to 5000 Å (ångström), preferably 1000 to 2000 Å;

hole injection layer (b): 50 to 1000 Å, preferably 200 to 800 Å, hole-transport layer (c): 50 to 1000 Å, preferably 100 to 800 Å, exciton blocking layer (d): 10 to 500 Å, preferably 50 to 100 Å, light-emitting layer (e): 10 to 1000 Å, preferably 50 to 600 Å, hole/exciton blocking layer (f): 10 to 500 Å, preferably 50 to 100 Å, electron-transport layer (g): 50 to 1000 Å, preferably 200 to 800 Å, electron injection layer (h): 10 to 500 Å, preferably 20 to 100 Å, cathode (i): 200 to 10 000 Å, preferably 300 to 5000 Å.

The person skilled in the art is aware (for example on the basis of electrochemical studies) of how suitable materials have to be selected. Suitable materials for the individual layers are known to those skilled in the art and are disclosed, for example, in WO 00/70655.

In addition, it is possible that some of the layers used in the inventive OLED have been surface-treated in order to increase the efficiency of charge carrier transport. The selection of the materials for each of the layers mentioned is preferably determined by obtaining an OLED with a high efficiency and lifetime.

The inventive OLED can be produced by methods known to those skilled in the art. In general, the inventive OLED is produced by successive vapor deposition of the individual layers onto a suitable substrate. Suitable substrates are, for example, glass, inorganic semiconductors or polymer films. For vapor deposition, it is possible to use customary techniques, such as thermal evaporation, chemical vapor deposition (CVD), physical vapor deposition (PVD) and others. In an alternative process, the organic layers of the OLED can be applied from solutions or disper-sions in suitable solvents, employing coating techniques known to those skilled in the art.

Use of the compounds of the formula (I) in at least one layer of the OLED, preferably in the light-emitting layer (preferably as a matrix material), in a charge transport layer, i.e. electron transport layer or hole transport layer, preferably electron transport layer and/or in the electron injection layer makes it possible to obtain OLEDs with high efficiency and with low use and operating voltage. Frequently, the OLEDs obtained by the use of the compounds of the formula (I) additionally have high lifetimes. The efficiency of the OLEDs can additionally be improved by optimizing the other layers of the OLEDs. For example, high-efficiency cathodes such as Ca or Ba, if appropriate in combination with an intermediate layer of LiF, can be used. Moreover, additional layers may be present in the OLEDs in order to adjust the energy level of the different layers and to facilitate electroluminescence.

The OLEDs may further comprise at least one second light-emitting layer. The overall emission of the OLEDs may be composed of the emission of the at least two light-emitting layers and may also comprise white light.

The OLEDs can be used in all apparatus in which electroluminescence is useful. Suitable devices are preferably selected from stationary and mobile visual display units and illumination units. Stationary visual display units are, for example, visual display units of computers, televisions, visual display units in printers, kitchen appliances and advertising panels, illuminations and information panels. Mobile visual display units are, for example, visual display units in cellphones, tablet PCs, laptops, digital cameras, MP3 players, vehicles and destination displays on buses and trains. Further devices in which the inventive OLEDs can be used are, for example, keyboards; items of clothing; furniture; wallpaper. In addition, the present invention relates to a device selected from the group consisting of stationary visual display units such as visual display units of computers, televisions, visual display units in printers, kitchen appliances and advertising panels, illuminations, information panels, and mobile visual display units such as visual display units in cellphones, tablet PCs, laptops, digital cameras, MP3 players, vehicles and destination displays on buses and trains; illumination units; keyboards; items of clothing; furniture; wallpaper, comprising at least one inventive organic light-emitting diode or at least one inventive light-emitting layer.

The following examples are included for illustrative purposes only and do not limit the scope of the claims. Unless otherwise stated, all parts and percentages are by weight.

EXAMPLES 1,4-difluoro-2,5-dinitrobenzene was synthesized according known literature procedure (US20130237725). 3-phenyl-1H-benzimidazol-2-one was synthesized according known literature procedure (reaction of 1,10-carbonyldiimidazole with N2-phenylbenzene-1,2-diamine; Bioorganic and Medicinal Chemistry Letters, 2008, 18, 6067).

Example 1

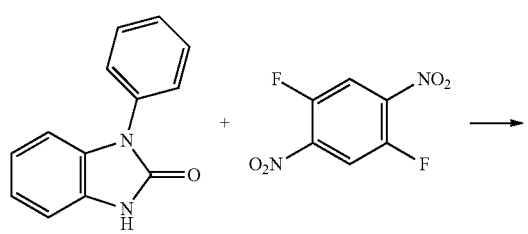

1-1

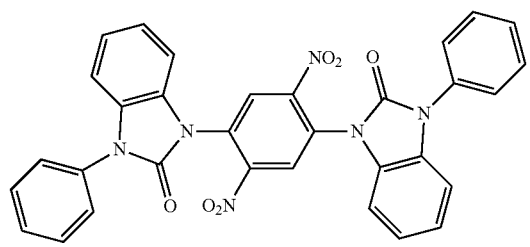

a.) 7.36 g (35.0 mmol) of 3-phenyl-1H-benzimidazol-2-one and 1.40 g (35 mmol) of NaH were mixed together in DMF (110 mL) at 0° C. for 10 min. Then, 3.57 g (17.5 mmol) of 1,4-difluoro-2,5-dinitrobenzene were added by portion. The mixture was stirred 2 h at 0° C., precipitated in water and filtrated to yield 9.12 g of 1-1 as a yellow powder [Purity=94% (HPLC)] which was used directly as it is for the next step.

Mass [M+1]=584.4

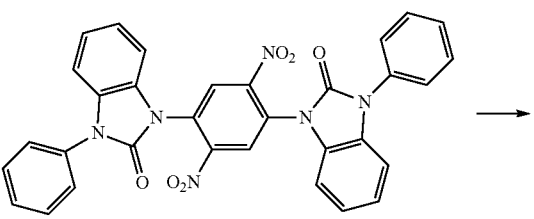

1-2

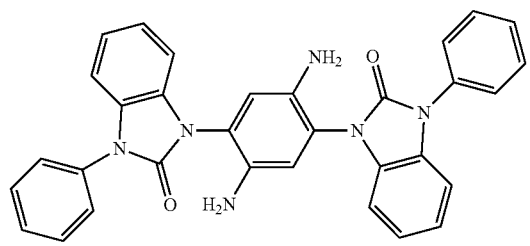

b.) 8.76 g (15.0 mmol) of 1-1 and 1.00 g of Pd/C 10% were mixed in 125 mL of 5:1 THF:EtOH at 50° C. under 5 bar of dihydrogen for 12 h. The mixture was then filtrated, the solvent evaporated and the resulting powder was recrystallized several times from THF to yield 5.58 g of 1-2 [Purity=98.0% (HPLC)] as a yellow powder.

Mass [M+1]=525.2

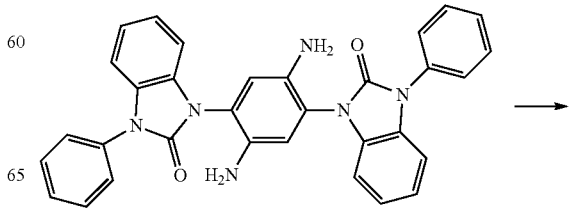

1

425
-continued

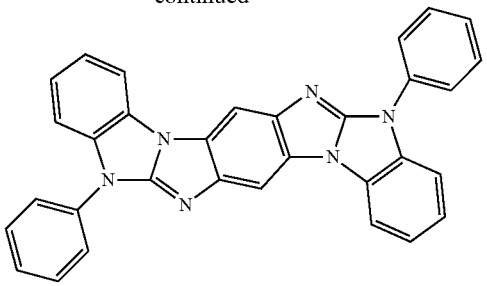

c.) 5.30 g (10.1 mmol) of 1-2 and 35 g of polyphosphoric acid were mixed together at 240° C. for 6 h. The dark brown mixture was then poured into 400 mL of water, filtrated and washed several times with water and MeOH. The product was recrystallized in DMSO then NMP and sublimed 3 times to yield 1.69 g of 1 [Purity=99.79% (HPLC)] as a slightly yellow crystal.

Mass [M+1]=489.4

Example 2

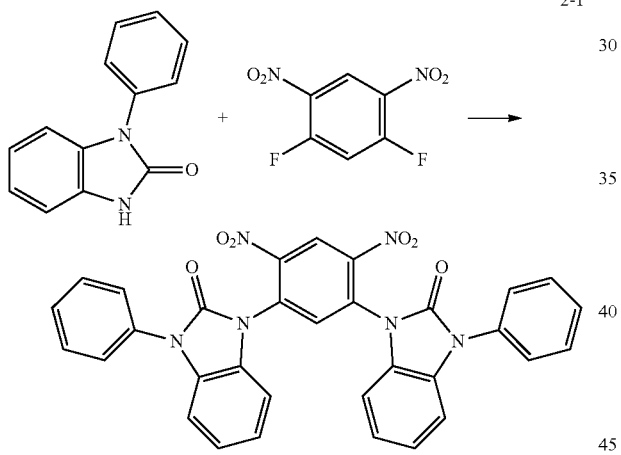

a.) 15.72 g (74.8 mmol) of 3-phenyl-1H-benzimidazol-2-one, 6.94 g (34.0 mmol) of 1,3-difluoro-4,6-dinitrobenzene and 28.87 g (136 mmol) of $K_3PO_4$ were mixed together in NMP (200 mL) at 0° C. for 2 h. The mixture was then stirred 2 h at room temperature and precipitated in water filtrated to yield 19.44 g of 2-1 as a yellow powder [Purity=85% (HPLC)] which was used directly as it is for the next step.

Mass [M+1]=584.2

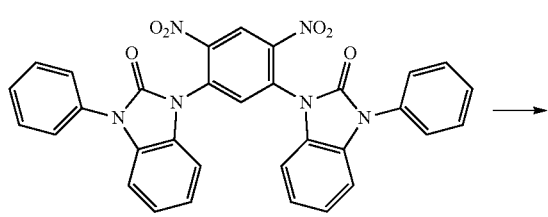

426
-continued

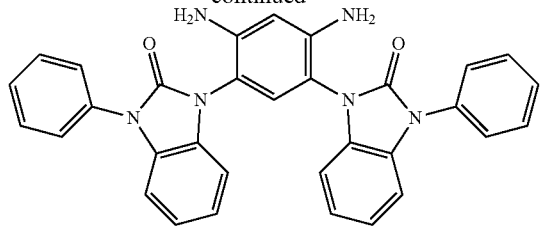

b.) 4.38 g (7.5 mmol) of 2-1 and 500 mg of Pd/C 10% were mixed in 60 mL of 3:1 THF:EtOH at 50° C. under 5 bar of dihydrogen for 2 h. The mixture was then filtrated, the solvent is evaporated and the resulting powder was purified by chromatography ($SiO_2$, gradient: toluene/THF) to yield 2.12 g of 2-2 [Purity=99.0% (HPLC)] as a white powder.

Mass [M+1]=525.3 c.) 9.11 g (17.4 mmol) of 2-2 and 75 g of polyphosphoric acid were mixed together at 230° C. for 6 h. The dark brown mixture was then poured into 650 mL of water, filtrated and washed several times with water and MeOH. The product was recrystallized twice in DMSO, washed with MeOH and sublimed twice. It was again recrystallized in DMSO and sublimed to yield 2.97 g of 2 [Purity 25=99.91% (HPLC)] as a white crystal.

Mass [M+1]=489.4

$^1$H NMR (400 MHz, DMSO): δ 9.04 (s, 1H), 8.60 (d, 2H), 7.97 (m, 4H), 7.83 (s, 1H), 7.65-7.75 (m, 6H), 7.52 (m, 4H), 7.43 (m, 2H).

Example 3

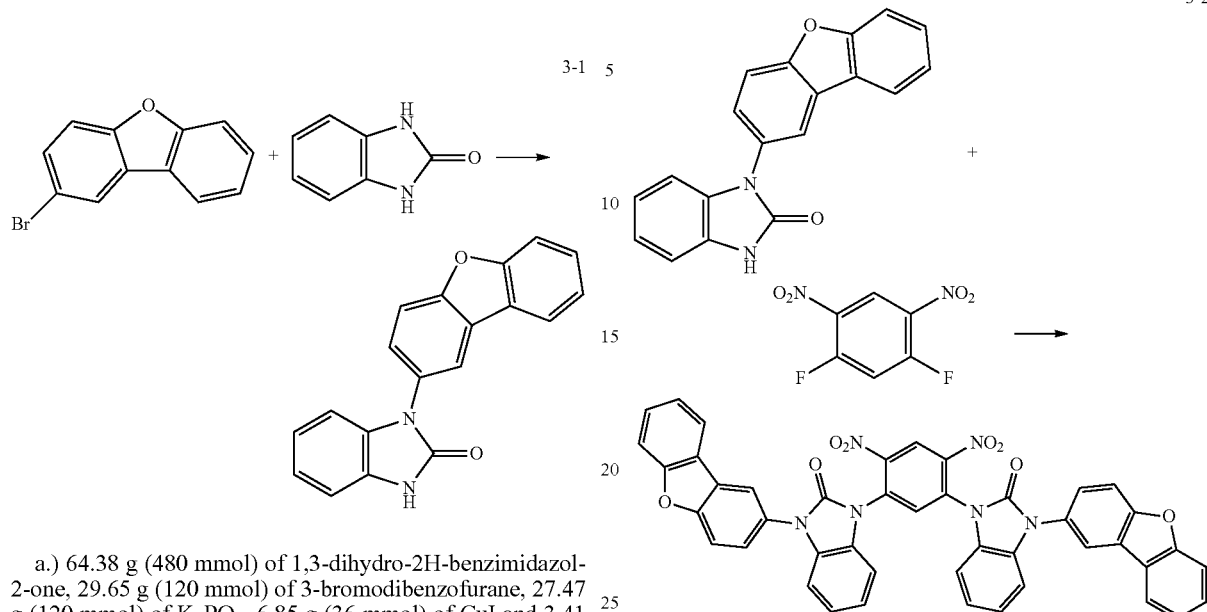

a.) 64.38 g (480 mmol) of 1,3-dihydro-2H-benzimidazol-2-one, 29.65 g (120 mmol) of 3-bromodibenzofurane, 27.47 g (120 mmol) of $K_3PO_4$, 6.85 g (36 mmol) of CuI and 3.41 g (24 mmol) of NN'-dimethylcyclohexanediamine were mixed together in dioxane (750 mL) at reflux under inert condition for 16 h. Dioxane was then evaporated and after work-up, the product was dissolved in $CHCl_3$, mixed with 80 g of $SiO_2$ and purified by chromatography ($SiO_2$, gradient:/MeOH) to yield 17.45 g of 3-dibenzofuran-2-yl-1H-benzimidazol-2-one, 3-1 [Purity=99.8% (HPLC)] as a white powder.

Mass [M+1]=301.3

$^1$H NMR (400 MHz, DMSO): δ 11.2 (s, 1H), 8.34 (d, 1H), 8.22 (dd, 1H), 7.88 (d, 1H), 7.76 (d, 1H), 7.64 (dd, 1H), 7.58 (m, 1H), 7.44 (m, 1H), 7.11 (m, 2H), 7.00 (m, 2H).

b.) 5.04 g (16.8 mmol) of 3-dibenzofuran-2-yl-1H-benzimidazol-2-one, 3-1, 1.63 g (8.0 mmol) of 1,3-difluoro-4,6-dinitrobenzene and 6.79 g (32 mmol) of $K_3PO_4$ were mixed together in NMP (80 mL) at 0° C. for 2 h. The mixture was then stirred 2 h at room temperature and precipitated in water filtrated to yield 6.43 g of 3-2 as yellow powder [Purity=90% (HPLC)] which was used directly as it is for the next step.

Mass [M+1]=765.2

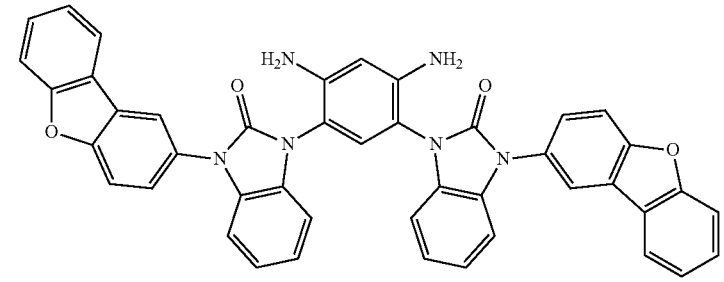

c.) 6.18 g (8.0 mmol) of 3-2 and 600 mg of Pd/C 10% were mixed in 200 mL of 3:1 THF:EtOH at 50° C. under 5 bar of hydrogen for 2 h. The mixture was then filtrated, the solvent is evaporated and the resulting powder was purified by chromatography (SiO$_2$, gradient: toluene/THF) to yield 5.39 g of 3-3 [Purity=99.1% (HPLC)] as a white powder.

Mass [M+1]=705.3

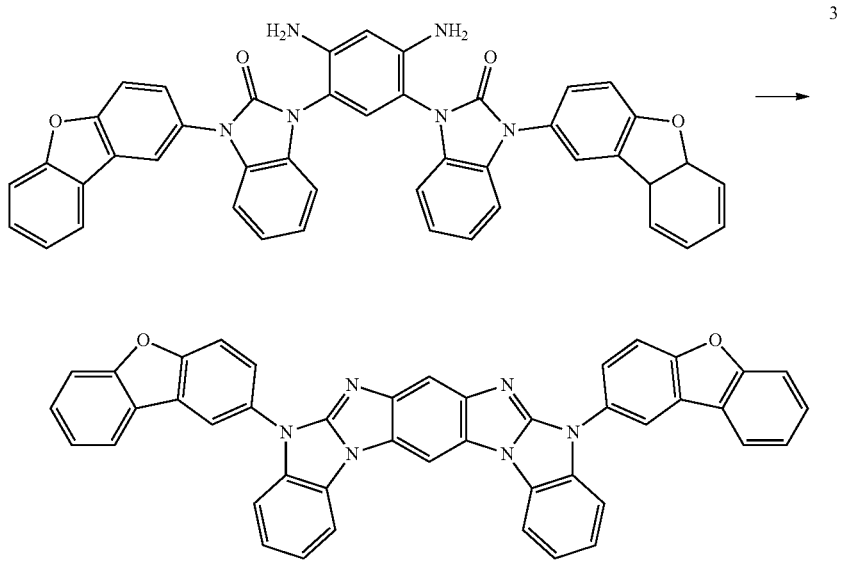

3 d.) 3.87 g (5.5 mmol) of 3-3 and 1.77 g (9.4 mmol) of p-toluensulfonic acid were mixed together in 40 mL of methylnaphthalene at 230° C. for 12 h. The dark brown mixture was cooled at 100° C., mixed with 40 g of SiO$_2$ and purified by chromatography (SiO$_2$, gradient: CHCl3/MeOH), recrystallized twice in acetic acid and sublimed to yield 1.47 g of 3 [Purity=99.97% (HPLC)] as a white crystal.

Mass [M+1]=669.2

$^1$H NMR (400 MHz, TFA): δ 9.29 (s, 1H), 8.72 (d, 2H), 8.59 (d, 2H), 8.44 (s, 1H), 8.25 (d, 2H), 8.19 (d, 2H), 8.13 (m, 2H), 8.04 (m, 4H), 7.95 (m, 4H), 7.85 (m, 2H), 7.69 (m, 2H).

Example 4

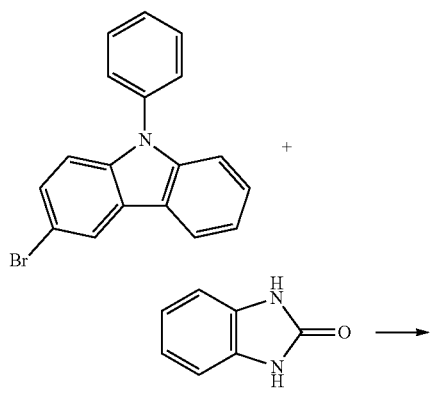

4-1

-continued

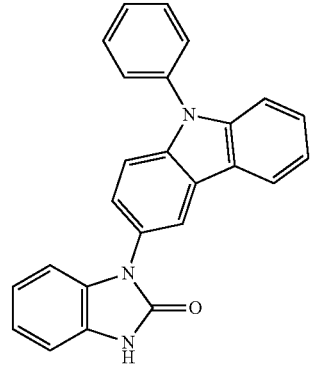

a.) 33.31 g (248 mmol) of 1,3-dihydro-2H-benzimidazol-2-one, 20.00 g (62.1 mmol) of 3-bromo-9-phenylcarbazol, 26.35 g (124.2 mmol) of K$_3$PO$_4$, 5.91 g (31.0 mmol) of CuI and 4.42 g (31.0 mmol) of NN'-dimethylcyclohexanediamine were mixed together in N,N-dimethylacetamide (350 mL) at 185° C. under inert condition for 24 h. After work-up, the product was dissolved in CHCl$_3$, mixed with 70 g of SiO$_2$ and purified by chromatography (SiO$_2$, gradient: CHCl$_3$/MeOH) to yield 15.52 g of 3-(9-phenylcarbazol-3-yl)-1H-benzimidazol-2-one, 4-1 [Purity=98% (HPLC)] as beige crystal.

Mass [M+1]=376.5

$^1$H NMR (400 MHz, DMSO): δ 11.13 (s, 1H), 8.42 (m, 1H), 8.33 (m, 1H), 7.72 (m, 4H), 7.59 (m, 1H), 7.45-7.56 (m, 3H), 7.42 (m, 1H), 7.33 (m, 1H), 7.10 (m, 2H), 7.02 (m, 1H), 6.97 (m, 1H),

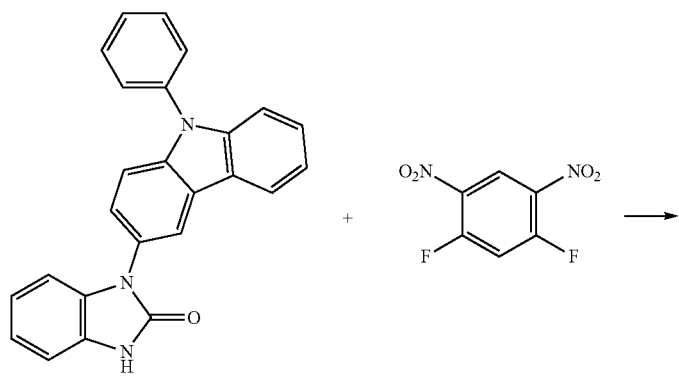

4-2

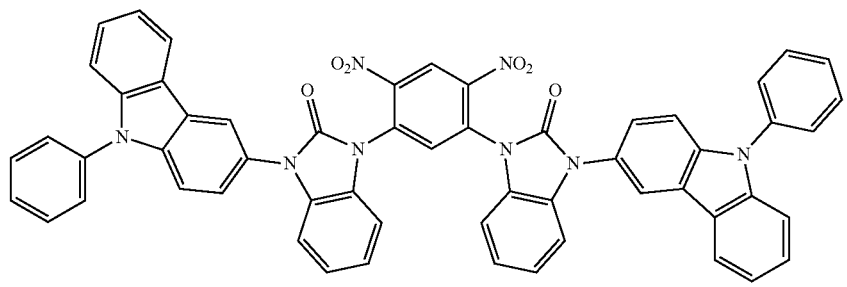

b.) 5.00 g (13.3 mmol) of 3-(9-phenylcarbazol-3-yl)-1H-benzimidazol-2-one, 4-1, 1.40 g (6.7 mmol) of 1,3-difluoro-4,6-dinitrobenzene and 5.65 g (26.6 mmol) of $K_3PO_4$ were mixed together in NMP (80 mL) at 0° C. for 2 h. The mixture was then stirred 2 h at room temperature and precipitated in water filtrated to yield 9.09 g of 4-2 as yellow powder [Purity=92% (HPLC)] which was used directly as it is for the next step.

Mass [M+1]=914.3 c.) 5.52 g (6.0 mmol) of 4-2 and 550 mg of Pd/C 10% were mixed in 70 mL of 3:1 THF:EtOH at 50° C. under 5 bar of hydrogen for 2 h. The mixture was then filtrated, the solvent was evaporated and the resulting powder was purified by chromatography ($SiO_2$, gradient: toluene/THF) to yield 4.6 g of 4-3 [Purity=99.0% (HPLC)] as a white powder.

Mass [M+1]=854.3

4-3

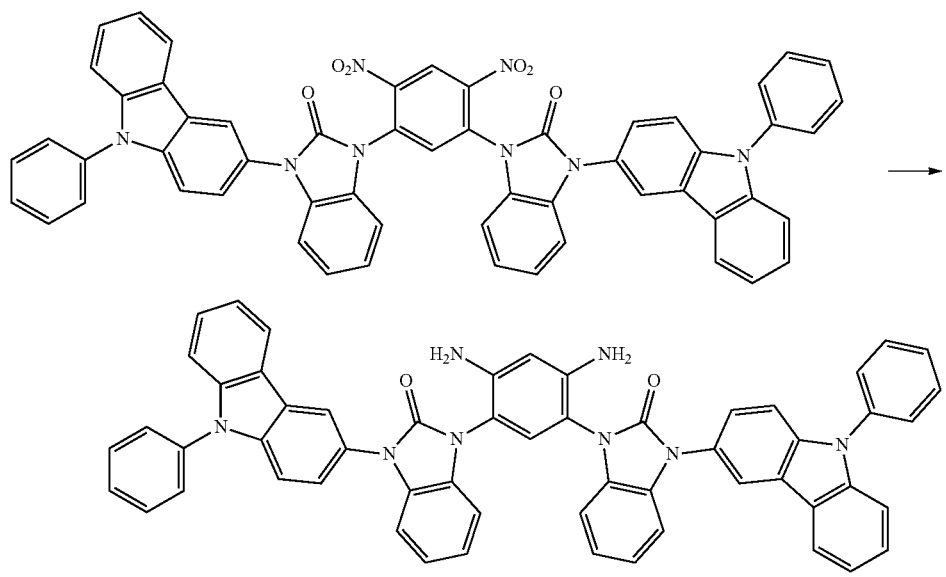

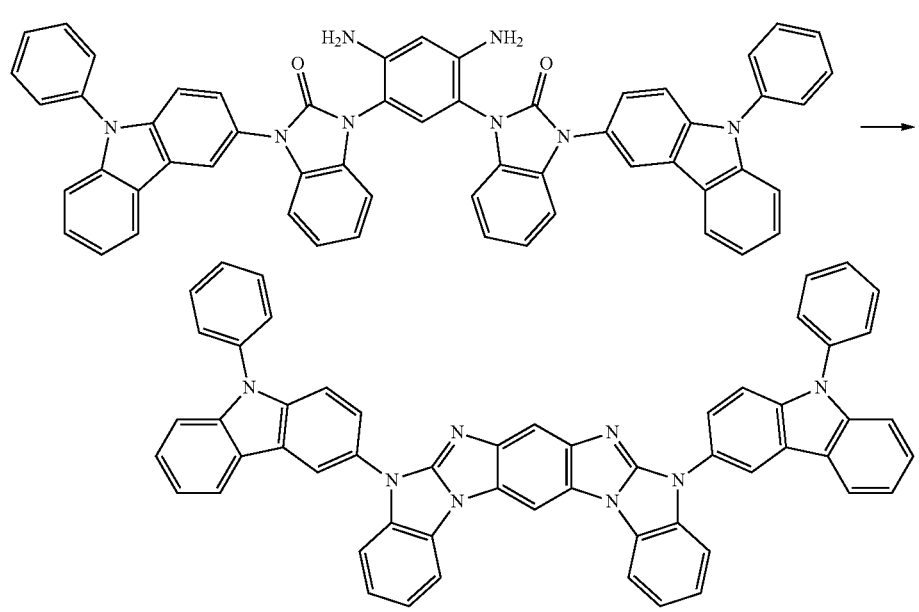

d.) 3.63 g (3.6 mmol) of 4-3 and 1.17 g (2.1 mmol) of p-toluensulfonic acid were mixed together in 30 mL of methylnaphthalene at 230° C. for 12 h. The dark brown mixture was cooled at 60° C. and mixed with 30 g of $SiO_2$. It was purified by chromatography ($SiO_2$, gradient: CHCl3/MeOH), recrystallized twice in acetic acid and sublimed to yield 0.84 g of 4 [Purity=99.81% (H PLC)] as a white crystal.

Mass [M+1]=818.2

$^1$H NMR (400 MHz, $CDCl_3$): δ 8.54 (d, 2H), 8.31 (s, 1H), 8.19 (m, 3H), 8.06 (d, 2H), 7.85 (dd, 2H), 7.60-7.72 (m, 10H), 7.44-58 (m, 10H), 7.31-7.42 (m, 4H).

Example 5 a.) N-(2-nitrophenyl)-2-phenyl-aniline, 5-1, was prepared according to Synthesis 1980, 3, 215. 7.06 g (50.0 mmol) 1-fluoro-2-nitro-benzene and 9.31 g (55 mmol) 2-phenylaniline were stirred under nitrogen. 11.6 g (200 mmol) potassium fluoride was added. The reaction mixture was stirred at 220° C. under nitrogen for 24 h.

The reaction mixture was poured in water and was extracted with dichloromethane. The organic phase was dried with magnesium sulfate. The solvent was removed in vacuum.

Column chromatography on silica gel with hexane/toluene 15/85 gave the red product. Yield 10.3 g (71%)

$^1$H NMR (400 MHz, CDCl3): δ 9.35 (s, 1H), 8.14 (dd, 1H), 7.32-7.48 (m, 10H), 7.18 (dd, 1H), 6.74 (td, 1H),

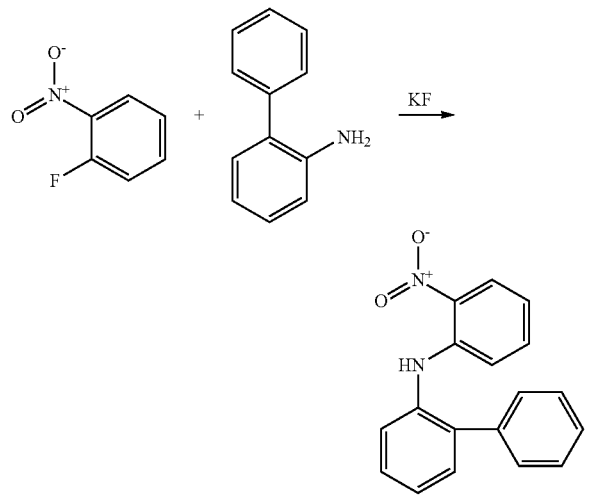

5-1

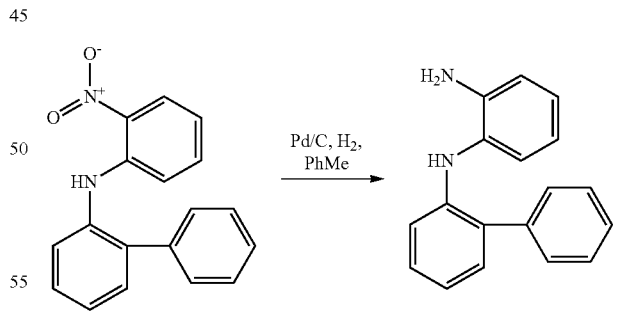

5-2 b.) To 10.2 g (35.0 mmol)N-(2-nitrophenyl)-2-phenyl-aniline, 5-1, in 120 ml toluene 950 mg Pd on carbon (5%) was added. The reaction mixture was stirred under 5 bar hydrogen for 3 h. The catalyst was filtered of and the solvent was removed in vacuum. Yield of 5-2: quantitative $^1$H NMR (400 MHz, CDCl3): δ 7.48-7.58 (m, 4H), 7.41 (tt, 1H), 7.19-7.29 (m, 2H), 7.12 (dd, 1H), 7.06 (td, 1H), 6.93 (td, 1H), 6.74-6.83 (m, 3H), 5.34 (s, 1H), 3.78 (s, 2H).

e.) 1-[2,4-diamino-5-[2-oxo-3-(2-phenylphenyl)benzimidazol-1-yl]phenyl]-3-(2-phenylphenyl)benzimidazol-2-one, 5-5, was prepared according to example 1b

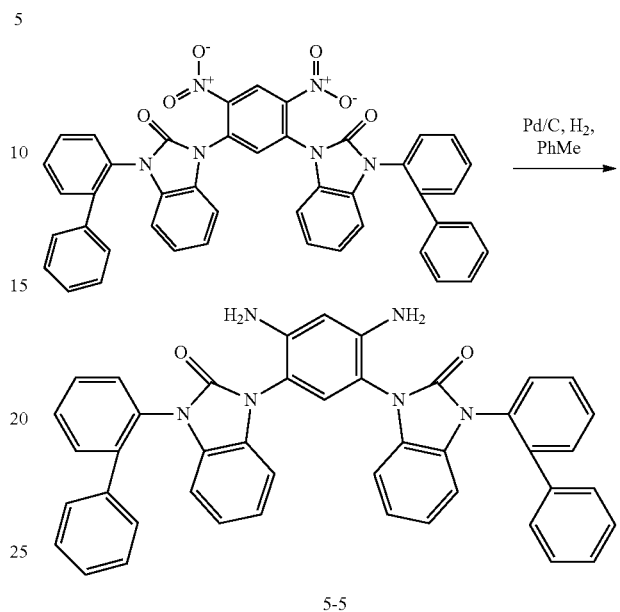

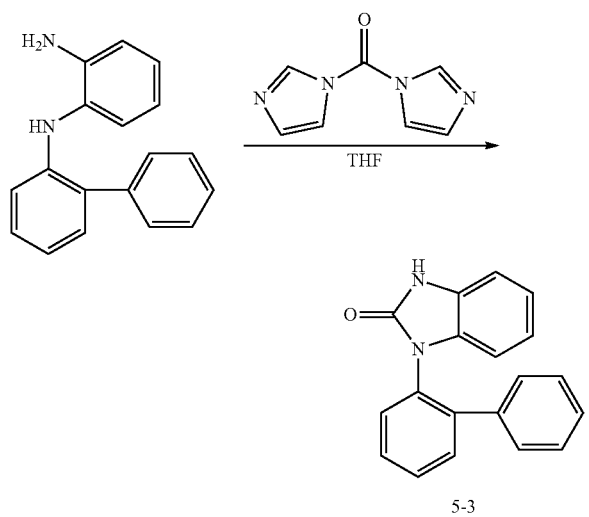

c.) 833 mg (3.20 mmol) N2-(2-phenylphenyl)benzene-1,2-diamine, 5-2, and 623 mg (3.84 mmol) di(imidazol-1-yl)methanone in 8 ml THF were stirred at 25° C. under nitrogen for 3 h.

The reaction mixture was poured in water and was extracted with dichloromethane. The organic phase was dried with magnesium sulfate. The solvent was removed in vacuum.

Column chromatography on silica gel with toluene/ethyl acetate 2/1 gave the product, 5-3. Yield 10.3 g (71%)

$^1$H NMR (400 MHz, CDCl3): δ 9.81 (s, 1H), 7.50-7.61 (m, 4H), 7.27-7.31 (m, 2H), 7.13-7.23 (m, 3H), 6.97-7.03 (m, 2H), 6.89-6.94 (m 1H), 6.63 (d, 1H).

d.) 1-[2,4-dinitro-5-[2-oxo-3-(2-phenylphenyl)benzimidazol-1-yl]phenyl]-3-(2-phenylphenyl)benzimidazol-2-one, 5-4, was prepared according to example 1a f.) 5 was prepared according to example 1 c

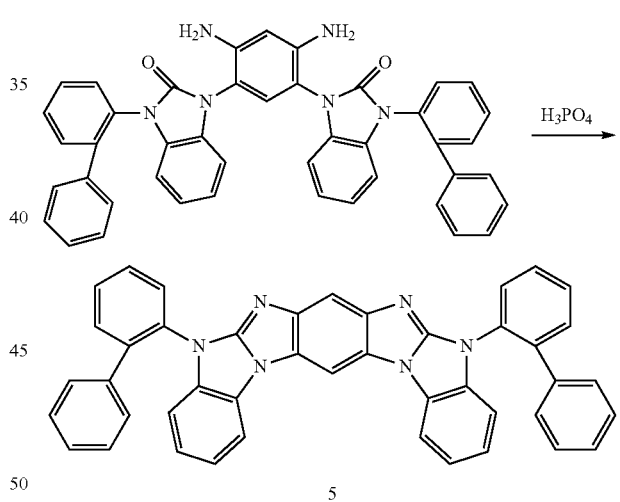

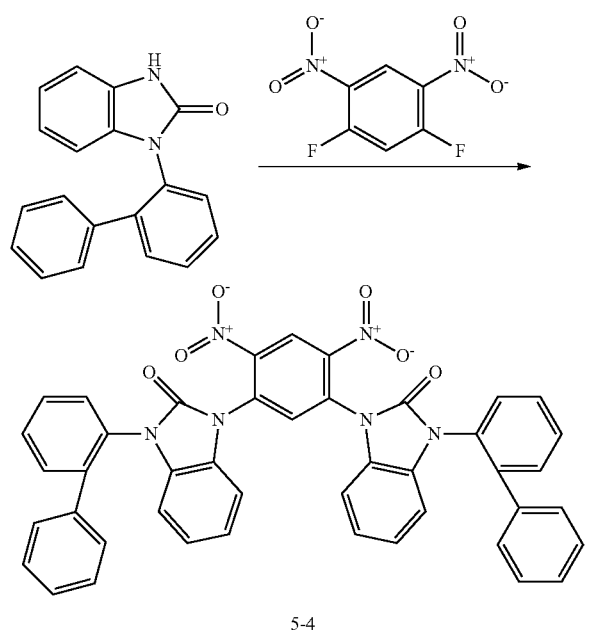

Example 6

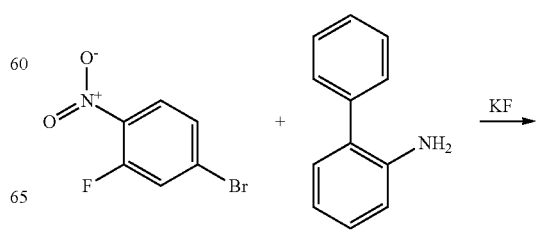

-continued

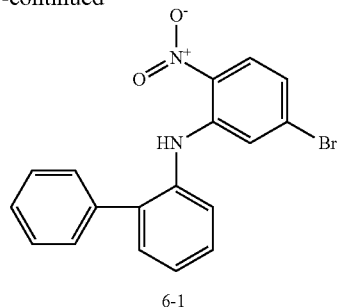

6-1 a.) 1.10 g (5.00 mmol) 4-bromo-2-fluoro-1-nitro-benzene and 931 mg (5.50 mmol) 2-phenylaniline were stirred under nitrogen. 1.16 g (20.0 mmol) potassium fluoride was added. The reaction mixture was stirred at 220° C. under nitrogen for 24 h.

The reaction mixture was poured in water and was extracted with dichloromethane. The organic phase was dried with magnesium sulfate. The solvent was removed in vacuum.

Column chromatography on silica gel with hexane/toluene 15/85 gave the red product, 6-1.

$^1$H NMR (400 MHz, CDCl3): δ 9.41 (s, 1H), 7.98 (d, 1H), 7.28-7.51 (m, 9H), 7.24 (d, 1H), 8.81 (dd, 1H).

Example 7

Example 7a

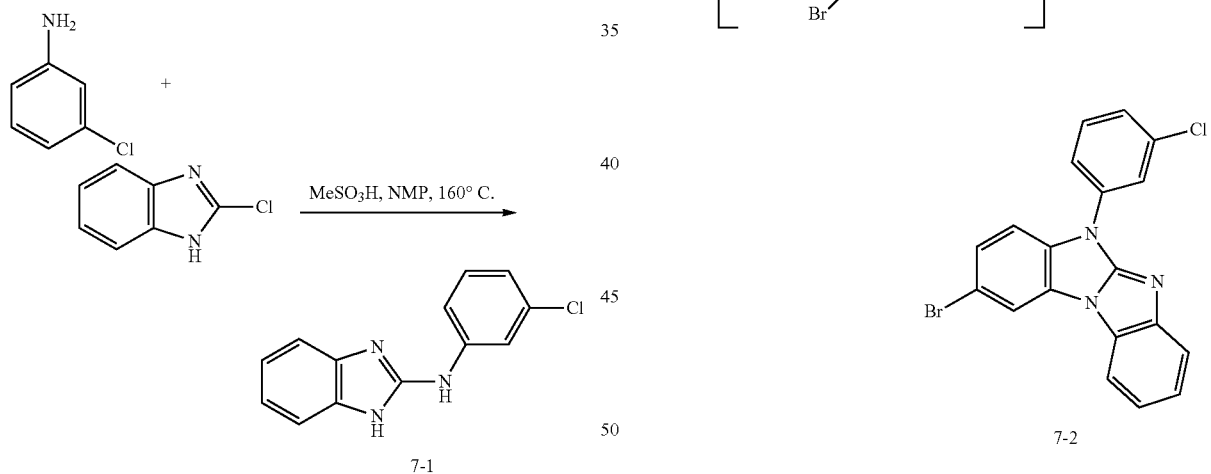

7-1

To 30.5 g (0.200 mol) 2-chlorobenzimidazole and 28.1 g (0.220 mol) 2-chloroaniline in 50 ml NMP 19.22 g (0.200 mmol) methane sulphonic acid was added. The reaction mixture was stirred at 100° C. for 18 h under nitrogen. The reaction mixture was poured on a saturated solution of sodium hydrogen carbonate in water. The water phase was extracted with ethyl acetate. The organic phase was 3 times washed with water and the organic phase was dried with magnesium sulfate. The solvent was removed in vacuum. The product was decocted in 100 ml dichloromethane.

Yield 44.8 g (92%)

$^1$H NMR (400 MHz, DMSO-d6): δ=11.0 (s, 1H), 9.66 (s, 1H), 8.09 (t, 1H). 7.56-7.59 (m, 1H), 7.30-7.40 (m, 3H), 6.95-7.05 (m, 3H)

Example 7b

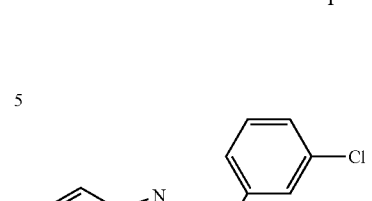

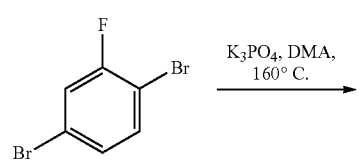

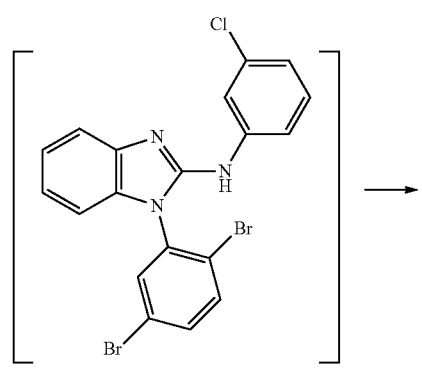

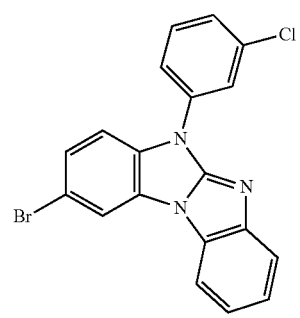

7-2

25.4 g (0.100 mol) 1,4-dibromo-2-fluorobezene, 24.4 g (0.100 mol)N-(3-chlorophenyl)-1H-benzimidazol-2-amine and 63.7 g (0.300 mol) potassium phosphate tribasic in 130 ml DMA were stirred at 160° C. for 3 h under nitrogen. The reaction mixture was cooled to 25° C. The Product was filtered off and was washed with water. The product was decocted in ethanol.

Yield 34.5 g (87%).

$^1$H NMR (400 MHz, CDCl3): δ=7.99 (d, 1H), 7.77-7.86 (m, 4H), 7.59 (t, 1H), 7.34-7.51 (m, 5H).

Example 7c

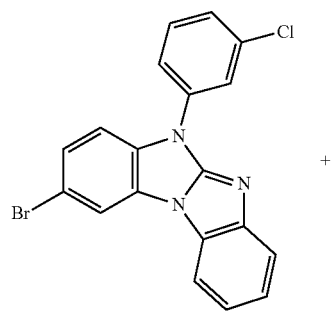

+

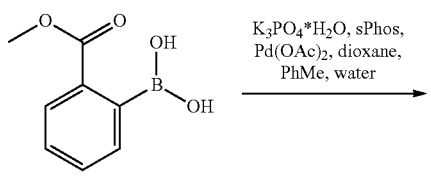

→

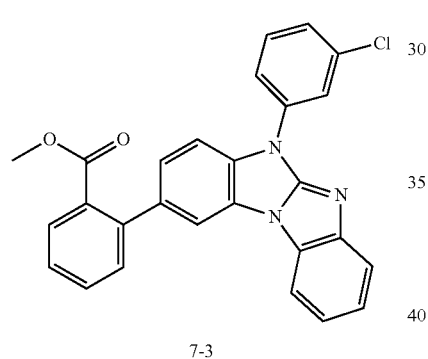

7-3

19.8 g (50 mmol) 2-bromo-5-(3-chlorophenyl)benzimidazolo[1,2-a]benzimidazole, 9.00 g (50 mmol) (2-methoxycarbonylphenyl)boronic acid and 53.1 g (0.250 mol) potassium phosphate tribasic in 200 ml DMF were degassed with argon. 2.46 g (6.00 mmol) 2-Dicyclohexylphosphino-2',6'-di-methoxybiphenyl (sPhos) and 224 mg (1.00 mmol) palladium (11) acetate were added. The reaction mixture was degassed with argon. The reaction mixture was stirred for 19 h at 100° C. under argon.

The reaction mixture was poured on water and the product was filtered off. The product was decocted with 200 ml ethanol.

Yield 15.5 g.

$^1$H NMR (400 MHz, CDCl3): δ=7.81-7.97 (m, 6H), 7.58-7.66 (m, 3H), 7.50-7.54 (m, 2H), 7.45-7.48 (m, 1H), 7.38-7.42 (m, 1H), 7.30-7.34 (m, 2H), 3.73 (s, 3H)

Example 7d

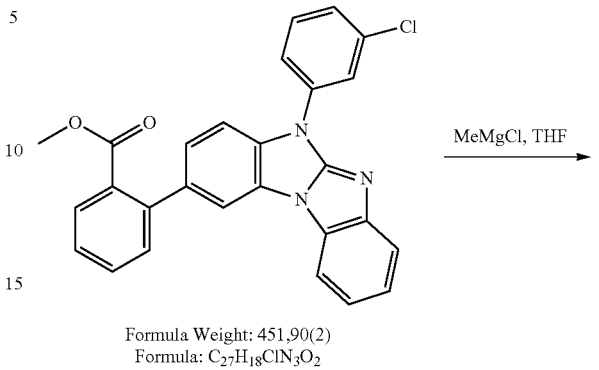

Formula Weight: 451,90(2)
Formula: $C_{27}H_{18}ClN_3O_2$

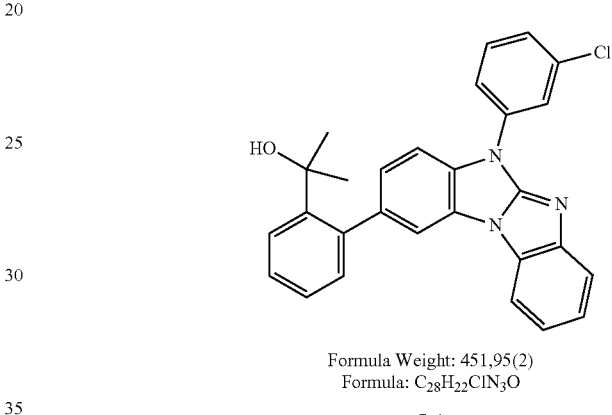

Formula Weight: 451,95(2)
Formula: $C_{28}H_{22}ClN_3O$ 7-4

To 0.904 g (2.00 mmol) methyl 2-[5-(3-chlorophenyl)benzimidazolo[1,2-a]benzimidazol-2-yl]benzoate in 20 ml waterfree THF, 3.13 ml (5.00 mmol) of a 1.6 M solution of methyl lithium in ether was added under argon at −78° C. The reaction mixture was warmed to 0° C. and was stirred at 0° C. for 3 h. The reaction mixture was poured on ice. A 10% solution of tartaric acid was added and the reaction mixture was extracted with dichloromethane. The organic phase was dried with magnesium sulfate. Column chromatography with toluene/ethyl acetate 10/1 gave the product.

In an alternative process, compound 7-4 was prepared as follows:

To 14.9 g (33.0 mmol) methyl 2-[5-(3-chlorophenyl)benzimidazolo[1,2-a]benzimidazol-2-yl]benzoate in 160 ml waterfree THF, 55 ml (0.165 mol) of a 3 M solution of methyl magnesium-chloride in THF was added under argon at 0° C. The reaction mixture was stirred at 50° C. for 3 h. The reaction mixture was poured on ice. A 10% solution of tartaric acid was added and the reaction mixture was extracted with dichloromethane. The organic phase was dried with magnesium sulfate. Column chromatography with toluene/ethyl acetate 10/1 gave the product.

$^1$H NMR (400 MHz, CDCl3): δ=7.94 (t, 1H), 7.86-7.89 (m, 1H), 7.72-7.82 (m, 4H), 7.60 (t, 2H), 7.20-7.48 (m, 8 h), 1.57 (s, 6H).

Example 7e

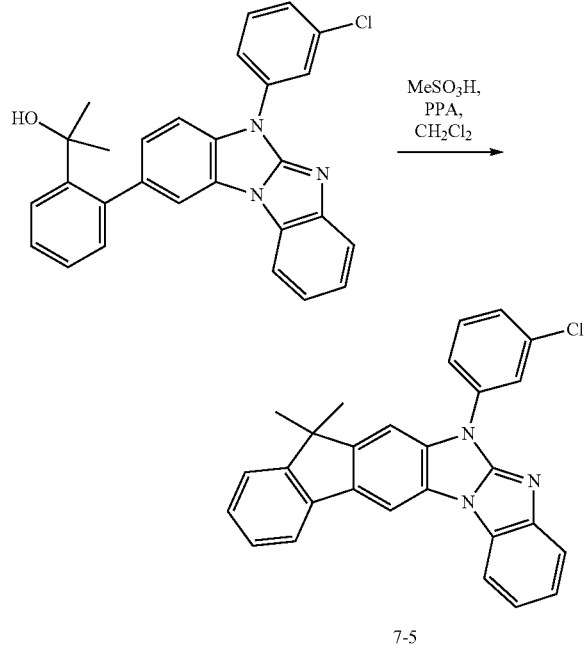

To 30.0 g PPA (polyphosphoric acid) and 22.5 g methane sulfonic acid 4.30 g (9.53 mmol) 2-[2-[5-(3-chlorophenyl)benzimidazolo[1,2-a]benzimidazol-2-yl]phenyl]propan-2-ol in in 60 ml dichloromethane was added at 0° C. The reaction mixture was stirred at 25° C. for 2 h.

The reaction mixture was poured on ice, neutralized with sodium hydrogen carbonate. The water phase was extracted with dichloromethane. The organic phase was dried with magnesium sulfate.

$^1$H NMR (400 MHz, CDCl3): δ=8.11 (s, 1H), 7.98-7.80 (m, 5H), 7.62 (t, 1H), 7.54 (s, 1H), 7.35-7.51 (m, 6 h), 1.58 (s, 6H).

Example 7f

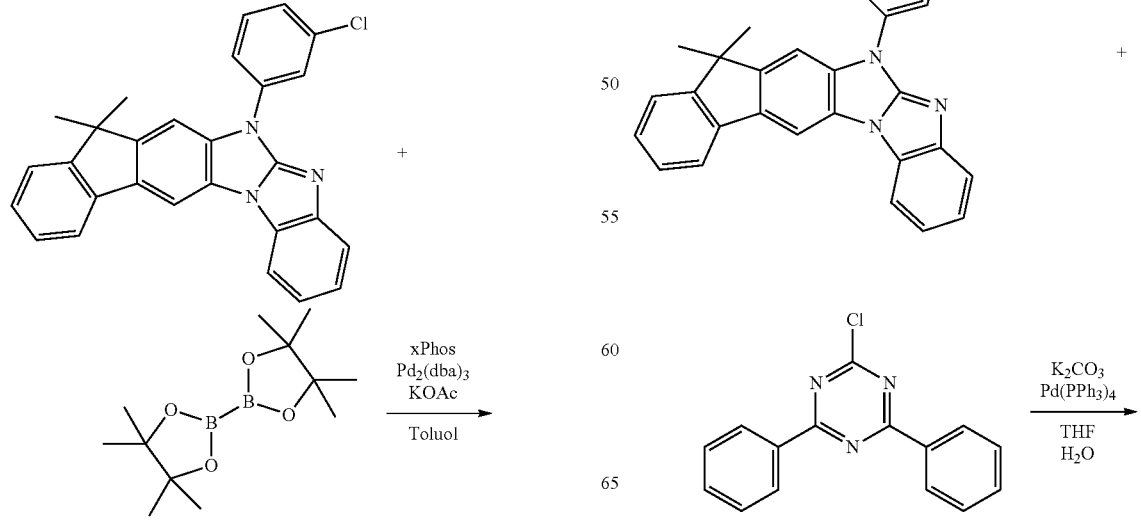

0.77 mg (1.77 mmol) of the product of example 7e, 470 mg (1.86 mmol) 4,4,5,5-tetramethyl-2-(4,4,5,5-tetramethyl-1,3,2-dioxaborolan-2-yl)-1,3,2-, dioxaborolane and 520 mg (5.30 mmol) potassium acetate in 20 ml waterfree toluene were degassed with argon. 254 mg (0.532 mmol) 2-dicyclohexylphosphino-2',4',6'-triisoproxylbiphenyl (xPhos) and 81 mg (0.089 mmol) tris (dibenzylidene-acetone) palladium (0) (Pd$_2$(dba)$_3$) was added. The reaction mixture was degassed with argon. The reaction mixture was stirred for 25 h at 130° C. under argon. 1 ml water and 100 mg sodium cyanide were added. The reaction mixture was stirred at 100° C. for 1 h. The reaction mixture was poured on water and was extracted with diethyl ether. The organic phase was dried with magnesium sulfate. The product was used without purification for the next reaction.

Example 7g

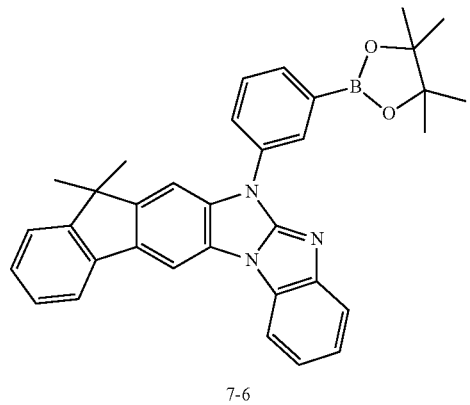

443

-continued

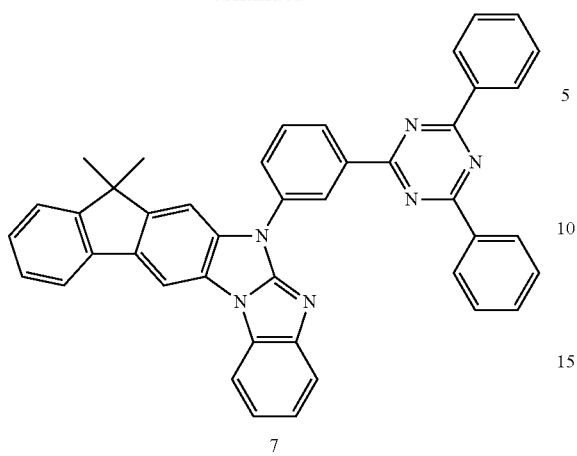

7

930 mg (1.77 mmol) of the product of example 7f, 570 mg (2.12 mmol) 2-chloro-4,6-diphenyl-1,3,5-triazine and 490 mg (3.54 mmol) potassium carbonate in a mixture of 15 ml THF, 15 ml toluene and 5 ml water were degassed with argon. 102 mg (0.089 mmol) tetrakis(triphenylphosphine) palladium(0) (Pd(Ph$_3$)$_4$) were added. The reaction mixture was degassed with argon. The reaction mixture was stirred for 11 h at 90° C. under argon. 10 ml of a 1% solution of sodium cyanide in water was added and the reaction mixture was stirred at 100° C. for 1 h. The product was poured on ethanol and the product was filtered off.

Column chromatography on silica gel with toluene/ethyl acetate 20/1 gave the product.

$^1$H NMR (400 MHz, CDCl3): δ=8.29-8.30 (m, 1H), 8.91-8.94 (m, 1H), 8.81-8.84 (m, 4H), 8.33-8.36 (m, 1H), 8.20 (s, 1H), 8.02-8.04 (m, 1H), 7.82-7.85 (m, 4H), 7.36-7.66 (m, 11H), 1.61 (s, 6H).

Example 8

Example 8a

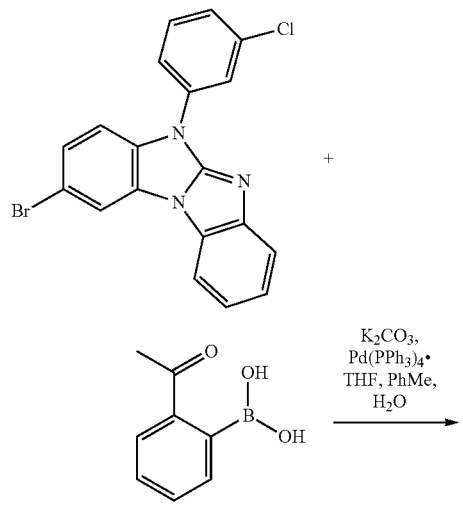

444

-continued

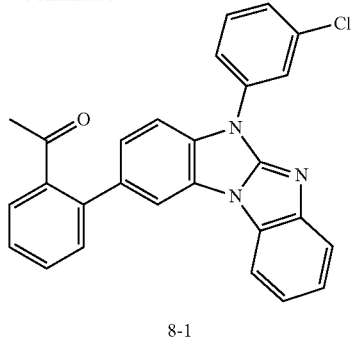

8-1

3.97 mg (10 mmol) 2-bromo-5-(3-chlorophenyl)benzimidazolo[1,2-a]benzimidazole (compound 7-2, example 7b), 1.64 g mg (10 mmol) (2-acetylphenyl)boronic acid and 2.76 g (20.0 mmol) potassium carbonate in a mixture of 30 THF, 30 ml toluene and 10 ml water were degassed with argon. 580 mg (0.50 mmol) tetrakis(triphenylphosphine)palladium (0) (Pd(Ph$_3$)$_4$) were added. The reaction mixture was degassed with argon. The reaction mixture was stirred for 6 h at 100° C. under argon.

The reaction mixture was poured on water and the organic phase was extracted with ethyl acetate. The organic phase was dried with magnesium sulfate. The solvent was removed in vacuum. The product was decocted with ethanol.

$^1$H NMR (400 MHz, CDCl3): δ=7.93-7.92 (m, 1H), 7.81-7.87 (m, 4H), 7.31-7.68 (10H), 2.18 (s, 3H).

Example 8b

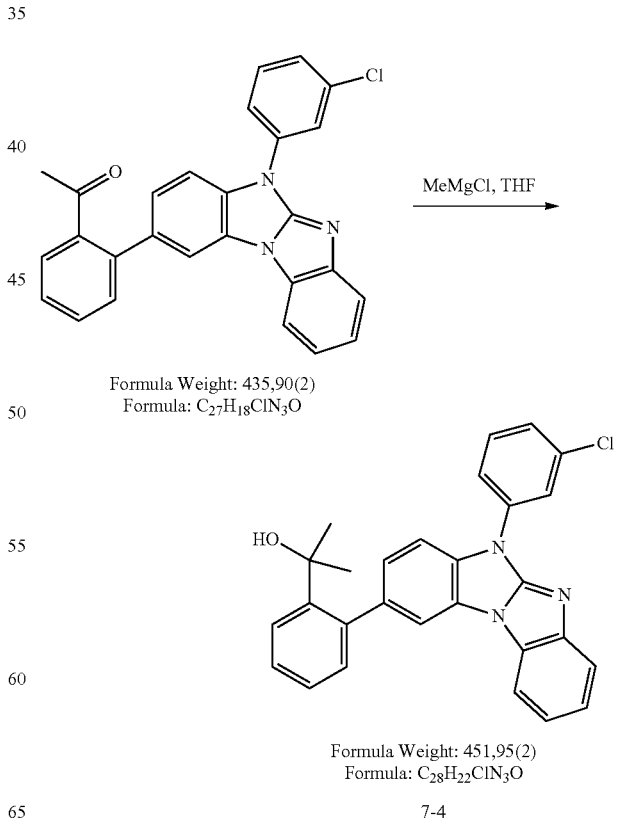

7-4

To 1.09 g (2.50 mmol) 1-[2-[5-(3-chlorophenyl)benzimidazolo[1,2-a]benzimidazol-2-yl]phenyl]ethanone in 50 ml waterfree THF 4.2 ml (12.5 mmol) of a 3 M solution of methyl magnesium chloride in THF was added under argon at 0° C. The reaction mixture was stirred under argon for 1 h.

The reaction mixture was poured on ice. ammonium chloride was added and the reaction mixture was extracted with ethyl acetate. The organic phase was dried with magnesium sulfate.

Column chromatography with toluene/ethyl acetate 10/1 gave the product.

Example 8c

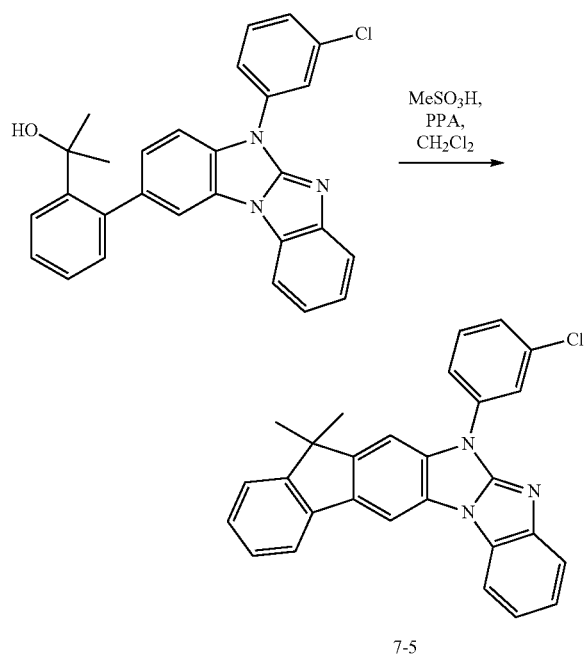

Compound 7-5 was prepared as described in example 7e.

Example 8d

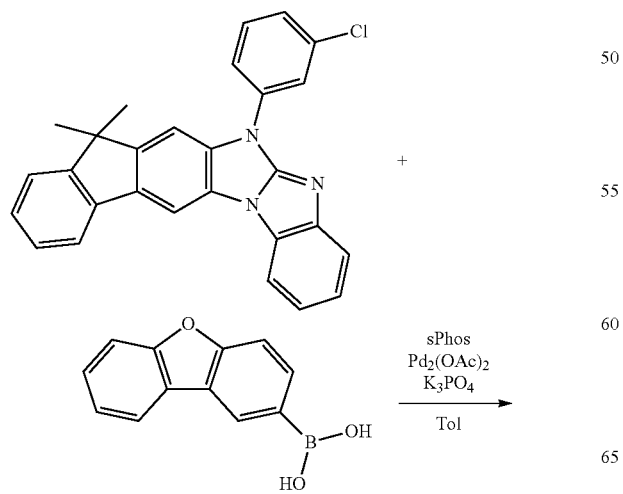

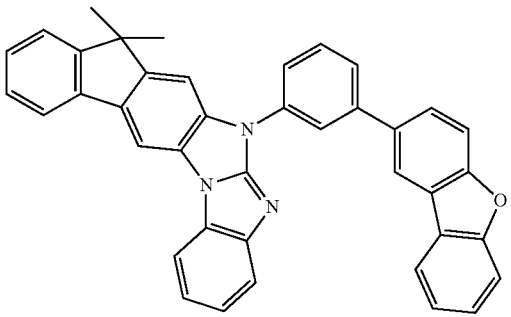

1.00 g (2.30 mmol) of the product 7-5 of example 7e, 733 mg (3.46 mmol) dibenzofuran-2-ylboronic acid and 1.96 g (9.22 mmol) potassium phosphate tribasic in 20 ml dioxane, 50 ml toluene and 20 ml water were degassed with argon. 57 mg (0.84 mmol) 2-Dicyclohexylphosphino-2',6'-dimethoxybiphenyl (sPhos) and 5.2 mg (0.14 mmol) palladium (II) acetate were added. The reaction mixture was degassed with argon. The reaction mixture was stirred for 4 h at 90° C. under argon.

40 ml of a 1% solution of sodium cyanide in water was added and the reaction mixture was stirred at 100° C. for 1 h. The water phase was extracted with toluene and the organic phase was dried with magnesium sulfate. The product was removed in vacuum. Column chromatography on siliga gel with dichloromethane/heptane 1/1 and then dichloromethane gave the product.

$^1$H NMR (400 MHz, CDCl3): δ=8.28 (d, 1H), 8.19-9.20 (m, 1H), 8.16 (s, 1H), 7.99-8.03 (m, 2H), 7.86-7.90 (m, 2H), 7.79-7.85 (m, 4H), 7.70 (d, 1H), 7.61-7.64 (m, 2H), 7.36-7.53 (m, 7H), 1.58 (s, 6H).

Example 9

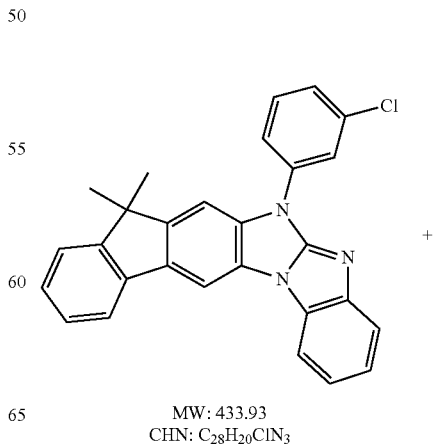

MW: 433.93
CHN: C$_{28}$H$_{20}$ClN$_3$

-continued

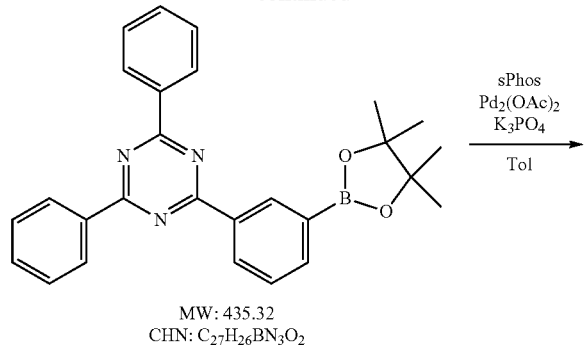

MW: 435.32
CHN: C₂₇H₂₆BN₃O₂

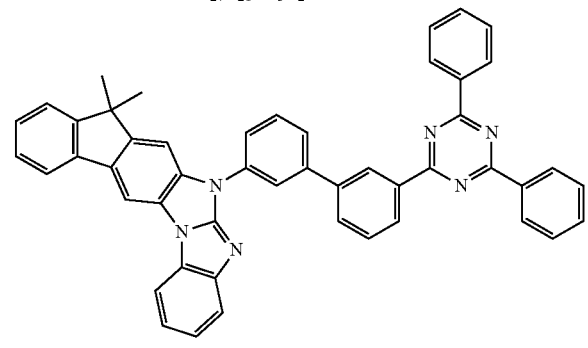

MW: 706.83
CHN: C₄₉H₃₄N₆

9

The product was prepared as described in example 8d, whereby dibenzofuran-2-ylboronic acid was replaced by

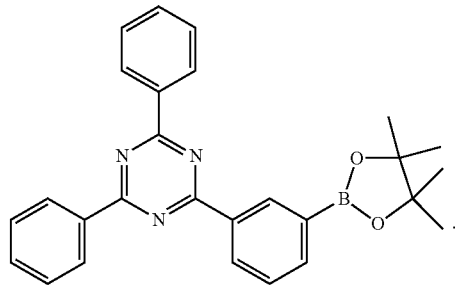 [SMILES: CC1(C)OB(c2cccc(-c3nc(-c4ccccc4)nc(-c4ccccc4)n3)c2)OC1(C)C]

¹H NMR (400 MHz, CDCl₃): δ=9.08-9-09 (m, 1H), 8.80-8.86 (m, 5H), 8.23-8.24 (m, 1H), 8.16 (s, 1H), 7.81-8.02 (m, 7H), 7.73 (t, 1H), 7.57-7.66 (m, 7H), 7.35-7.48 (m, 5H), 1.54 (s, 6H).

Example 10

Example 10a

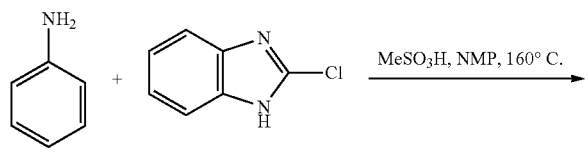

-continued

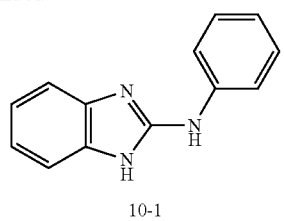

10-1

To 38.1 g (0.250 mol) 2-chlorobenzimidazole, 25.6 g 0.275 mol) aniline in 250 ml NMP 26.4 g (0.275 mmol) methane sulphonic acid were added. The reaction mixture was stirred at 100° C. for 3 h under nitrogen. The reaction mixture was poured on a saturated solution of sodium hydrogen carbonate in water. The water phase was extracted with ethyl acetate. The organic phase was 3 times washed with water and the organic phase was dried with magnesium sulfate. The solvent was removed in vacuum. The product was decocted in 100 ml dichloromethane.

Yield 43.6 g (83%)

¹H NMR (400 MHz, DMSO-d6): δ=10.9 (s, 1H), 9.38 (s, 1H), 7.29-7.36 (d, 2H), 2.29-7.36 (m, 4H), 6.96-7.02 (m, 2H), 6.91-6.94 (m, 1H).

Example 10b

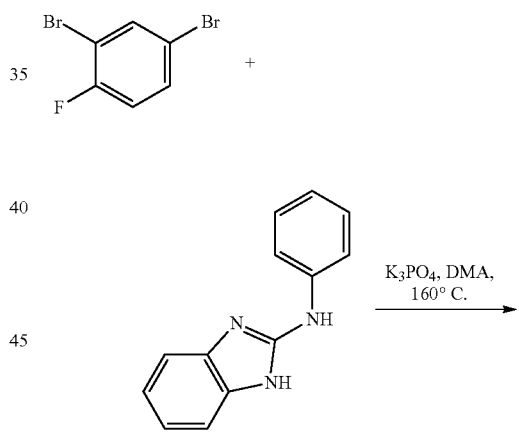

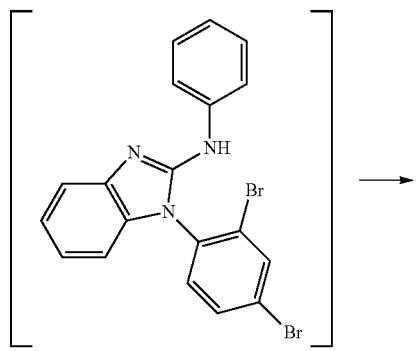

-continued

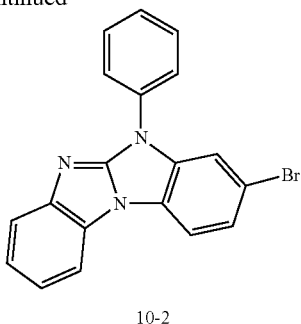

10-2

28.5 g (0.112 mol) 1,3-dibromo-4-fluorobezene, 23.5 g (0.112 mol)N-phenyl-1H-benzimidazol-2-amine and 59.6 g (0.281 mol) potassium phosphate tribasic in 250 ml DMA were stirred at 160° C. for 20 h under nitrogen. The reaction mixture was poured on water. The product was filtered off washed with water and ethanol.

Yield 38.9 g (97.6%).

$^1$H NMR (400 MHz, CDCl3): δ=7.78-7.83 (m, 4H), 7.64-7.70 (m, 4H), 7.48-7.52 (m, 2H), 7.40 (dt, 1H), 7.33 (dt, 1H).

Example 10c

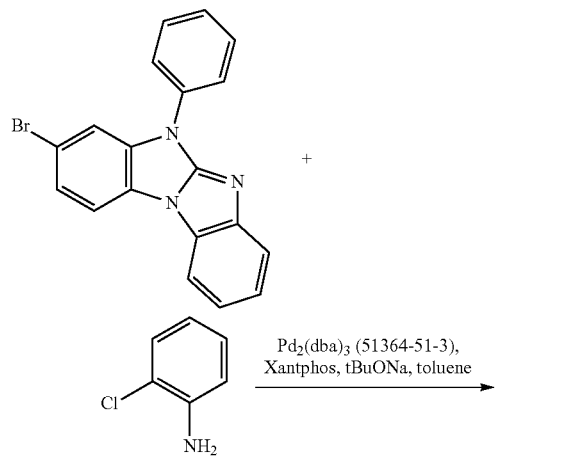

10-3

10.9 g (30.0 mmol) of 3-bromo-5-phenyl-benzimidazolo[1,2-a]benzimidazole, 5.74 g (45.0 mmol) 2-chloroaniline and 5.77 g (60.0 mmol) potassium t-butoxide in 90 ml toluene were degassed with argon. 550 mg (0.600 mmol) Tris(dibenzylideneacetone)dipalladium(0) and 520 mg (0.900 mmol) 4,5-Bis(diphenylphosphino)-9,9-dimethyl-xanthene (Xanphos) were added. The reaction mixture was degassed with argon. The reaction mixture was stirred for 3 h at 90° C. under argon.

The reaction mixture was poured on water and the organic phase was extracted with dichloromethane. The organic phase was dried with magnesium sulfate. The product was filtered on silica gel and was decocted with ethanol.

$^1$H NMR (400 MHz, CDCl3): δ=7.76, 7.85 (m, 5H), 7.63 (t, 1H), 7.46 (t, 1H), 7.29-7.40 (m, 4H), 7.1-7.23 (m, 3H), 6.81-6.85 (m, 1H), 6.21 (s, 1H)

Example 10d

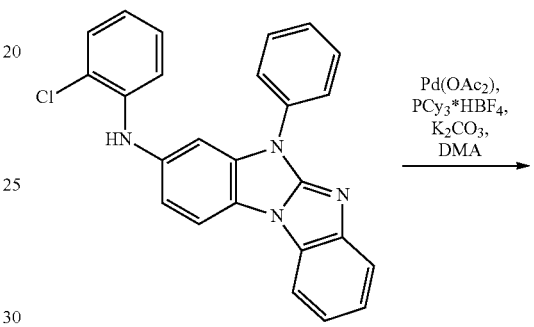

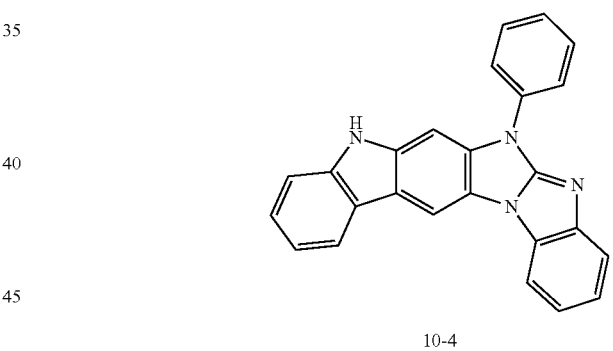

10-4

11.1 g (27.1 mmol)N-(2-chlorophenyl)-5-phenyl-benzimidazolo[1,2-a]benzimidazol-3-amine and 11.3 g (81.4 mmol) potassium carbonate in 80 ml waterfree DMA were degassed with argon. 305 mg (1.36 mmol) palladium (II) acetate and 1.00 g (2.72 mmol) tricyclohexylphosphine tetra-fluoroborate was added. The reaction mixture was degassed with argon. The reaction was stirred at 100° C. for 19 h.

100 ml 0.5% sodium cyanide solution was added and the reaction mixture was refluxed for 2 h. The product was filtered off and washed with water and ethanol. Column chromatography on silica gel with dichloromethane/ethyl acetate 95/5 gave the product. 5.70 g (56%)

$^1$H NMR (400 MHz, CDCl$_3$): δ=8.41 (s, 1H), 8.32 (s, 1H), 8.21 (d, 1H), 7.98-8.02 (m, 1H), 7.89-7.92 (m, 2H), 7.80-7.84 (m, 1H), 7.62, 7.67 (m, 2H), 7.52 (s, 1H), 7.44-7.49 (m, 3H), 7.32-7.42 (m, 3H).

Example 10e

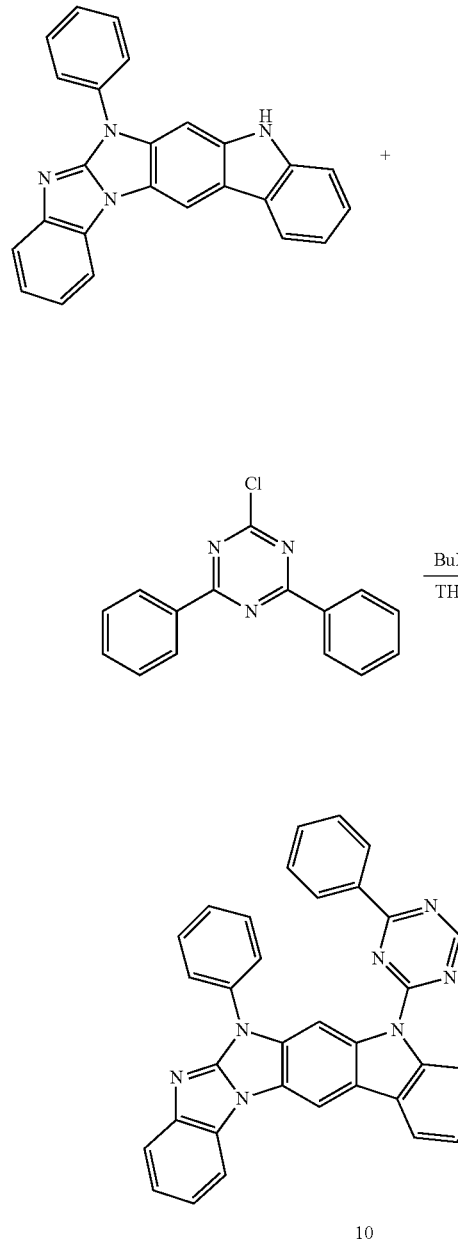

To 3.00 g (8.06 mmol) of the product 10-4 of example 10d in 60 ml waterfree THF 3.87 ml (9.67 mmol)N-butyl lithium 2.5 M in hexane were added at −78° C. under argon. The reaction was stirred at −78° C. for 1 h and 2.37 g (8.86 mmol) 2-chloro-4,6-diphenyl-1,3,5-triazine in 20 ml waterfree THF were added. The reaction mixture was stirred at −78° C. for 2 h and was then refluxed for 26 h.

The product was filtered off and was washed with ethanol, water and again with ethanol. The product was decocted in ethanol. Yield 1.18 g (24%)

$^1$H NMR (400 MHz, TFA-d1): δ=9.68 (s, 1H), 9.35 (d, 1H), 8.97 (s, 1H), 8.60 (sb, 2H), 8.43-8.47 (m, 2H), 8.22 (sb, 2H), 7.62-7.82 (m, 16H).

Example 11

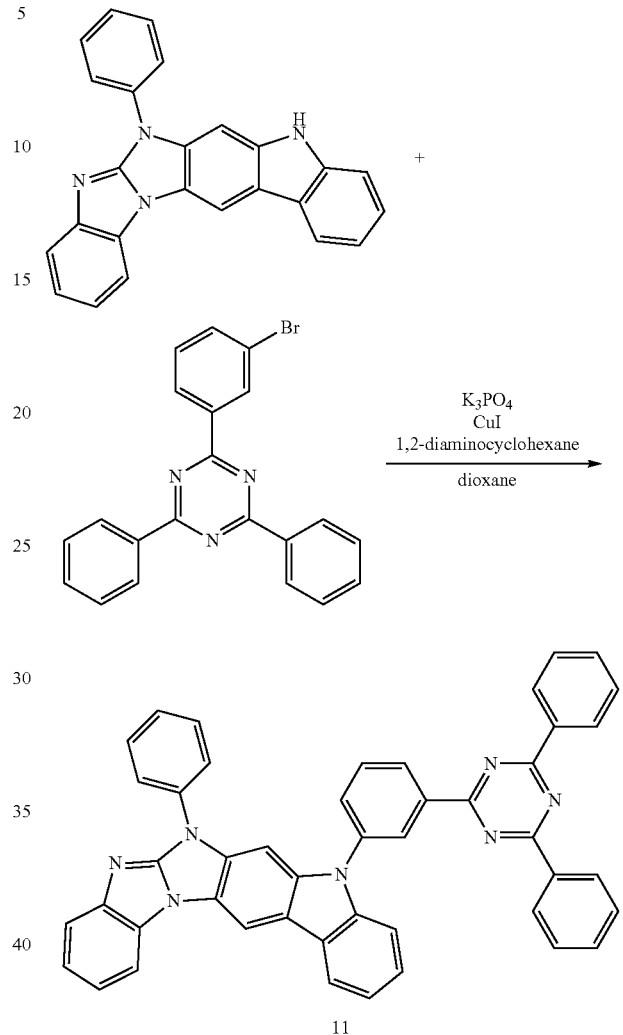

To 2.59 g (6.71 mmol) of the product 10-4 of example 10d, 2.48 g (6.38 mmol) 2-(3-bromophenyl)-4,6-diphenyl-1,3,5-triazine 4.27 g (20.1 mmol) potassium phosphate and 510 mg (2.69 mmol) copper(I)iodide were added in 100 ml dioxane. It was stirred under nitrogen at 100° C. 7.67 g (67.3 mmol) cis,trans diaminocyclohexane was added, and the reaction mixture was stirred for 15 h. The reaction temperature was increased to 120° C., and the reaction mixture was stirred for 3.5 days.

The reaction mixture was poured on methanol and the product was filtered off. The product was washed with ethanol, water and again with ethanol. Yield 3.15 g (69%).

$^1$H NMR (400 MHz, CDCl$_3$): δ=9.05 (s, 1H), 8.88-8.93 (m, 1H), 7.78 (d, 4H), 8.53 (s, 1H), 8.32 (d, 1H), 8.04-8.09 (m, 1H), 7.81-7.86 (m, 5H), 7.39-7.65 (m, 14H), 7.32-7.30 (m, (under CDCl$_3$)).

$^1$H NMR (400 MHz, THF-d8): δ=8.18 (t, 1H), 8.98 (dt, 1H), 8.83-8.86 (m, 5H), 8.38-8.41 (m, 1H), 8.19-8.21 (m, 1H), 7.98-8.01 (m, 3H), 7.93 (t, 1H), 7.78 (s, 1H), 7.55-7.70 (m, 8H), 7.31-7.48 (m, 6H), 7.26 (dt, 1H).

Example 12

Example 12a

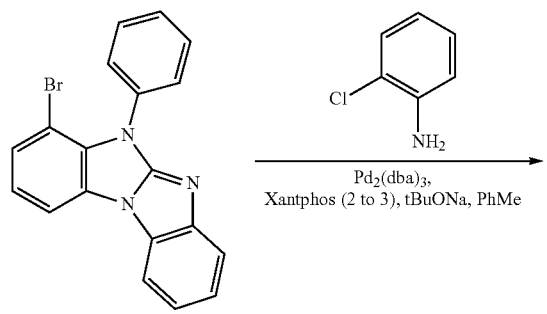

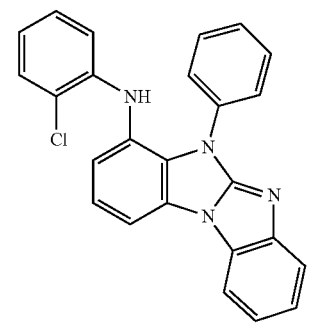

12-3

Compound 12-3 was prepared in analogy to compound 10-3 (example 1 Oc), whereby 3-bromo-5-phenyl-benzimidazolo[1,2-a]benzimidazole was replaced by 4-bromo-5-phenyl-benzimidazolo[1,2-a]benzimidazole.

$^1$H-NMR (400 MHz, CDCl$_3$): δ=7.86-7.88 (m, 1H), 7.75-7.78 (m, 1H), 7.66 (dd, 1H), 7.27-7.51 (m, 9H), 7.18 (dd, 1H), 7.06 (dt, 1H), 6.95 (dd, 1H), 6.75 (dt, 1H), 5.66 (sb, 1H).

Example 12b

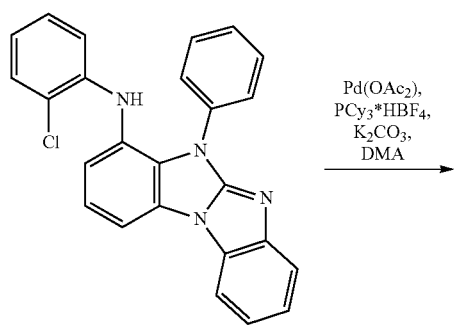

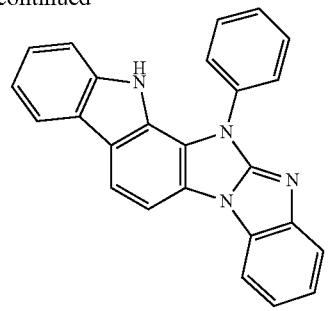

12-4

Compound 12-4 was prepared in analogy to compound 10-4 (example 10d).

$^1$H-NMR (400 MHz, CDCl$_3$): δ=8.13-8.17 (m, 2H), 7.97, 7.99 (m, 1H), 7.90-7.93 (m, 2H), 7.81-7.84 (m, 2H), 7.74-7.79 (m, 2H), 7.73 (sb, 1H), 7.60-7.65 (m, 1H), 7.31-7.47 (m, 5H).

APPLICATION EXAMPLES

Application Example 1

A glass substrate with 120 nm-thick indium-tin-oxide (ITO) transparent electrode (manufactured by Geomatec Co., Ltd.) used as an anode was first cleaned with isopropanol in an ultrasonic bath for 10 min. To eliminate any possible organic residues, the substrate was exposed to an ultraviolet light and ozone for further 30 min. This treatment also improves the hole injection properties of the ITO. The cleaned substrate was mounted on a substrate holder and loaded into a vacuum chamber. Thereafter, the organic materials specified below were applied by vapor deposition to the ITO substrate at a rate of approx. 0.2-1 Å/sec at about $10^{-6}$-$10^{-8}$ mbar. As a hole injection layer, 40 nm-thick of compound A was applied. Then 20 nm-thick of compound B was applied as a hole transporting layer. Subsequently, a mixture of 20% by weight of an emitter compound, (Ir(Phppy)$_3$), 40% by weight of a $1^{st}$ host (compound C) and 40% by weight of a $2^{nd}$ host (compound 2) were applied to form a 40 nm-thick phosphorescent-emitting layer. On the emitting layer, 30 nm-thick compound D was applied as an electron transport layer. Finally, 1 nm-thick LiF was deposited as an electron injection layer and 80 nm-thick Al was then deposited as a cathode to complete the device. The device was sealed with a glass lid and a getter in an inert nitrogen atmosphere with less than 1 ppm of water and oxygen.

Compound A

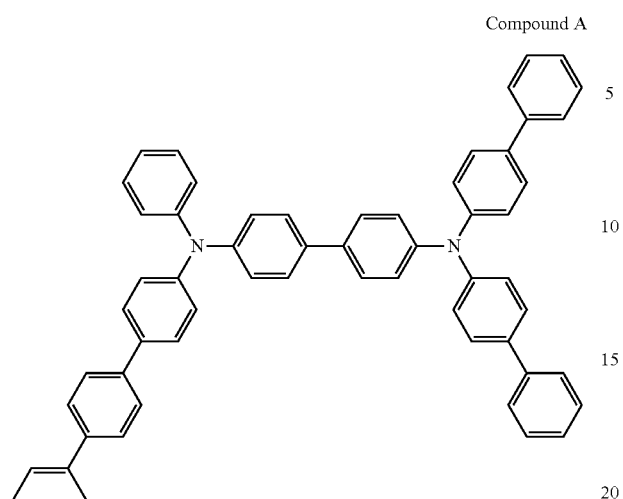

Compound B

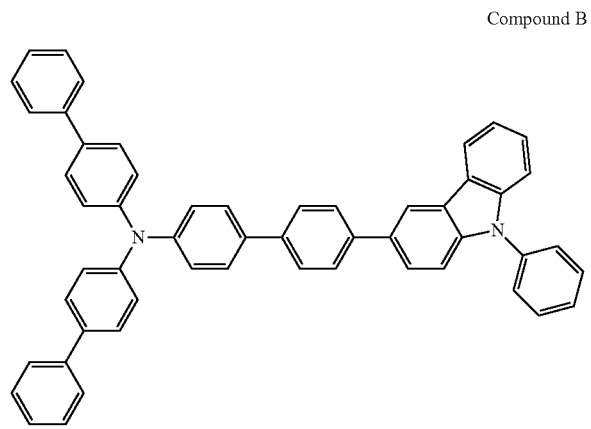

Compound C

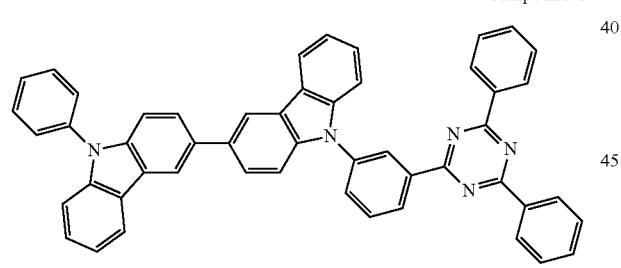

Compound D

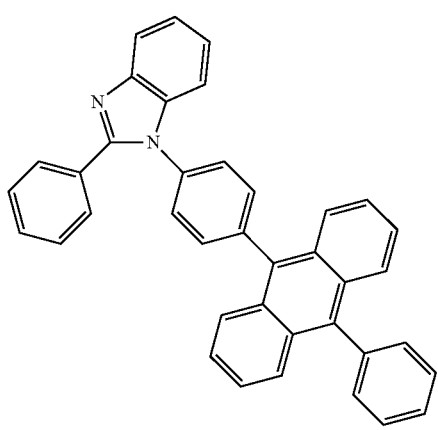

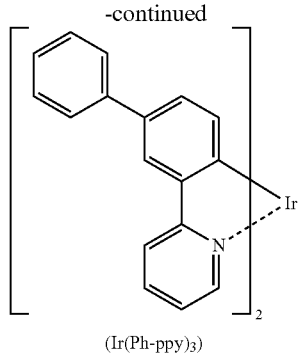

(Ir(Ph-ppy)₃)

Compound 2

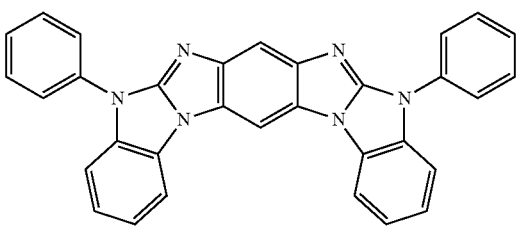

(example 2)

Application Example 2

Application Example 1 was repeated except that the host (compound 2) was replaced by compound 1. The device results are shown in Table 1.

Compound 1

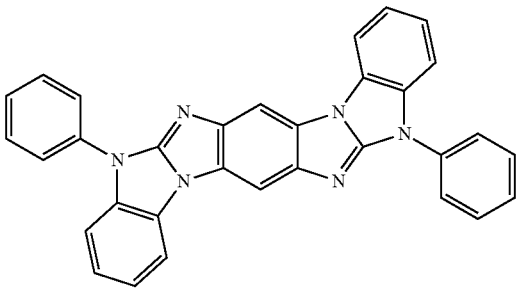

(example 1)

OLED Characterization

To characterize the OLED, electroluminescence spectra were recorded at various currents and voltages. In addition, the current-voltage characteristic was measured in combination with the luminance to determine luminous efficiency and external quantum efficiency (EQE). Driving voltage U, EQE and Commission Internationale de l'Éclairage (CIE) coordinate are given at 10 mA/cm² except otherwise stated.

TABLE 1

| Appl. Ex. | 2$^{nd}$ Host | U (V) | EQE (%) | CIE, x/y |
|---|---|---|---|---|
| Appl. Ex. 1 | Compound 2 | 4.8 | 15.9 | 0.33/0.62 |
| Appl. Ex. 2 | Compound 1 | 4.8 | 15.5 | 0.34/0.61 |

The results shown in Table 1 demonstrate that the compound 2 and 1 can be used as host material in an OLED together with a green emitter.

Also, compounds 3, 4 and 5 can be used as host material in an OLED with the same structure as mentioned in application example 1 together with a green emitter. Said OLED emits green light.

Comparative Application Example 1

A glass substrate with 120 nm-thick indium-tin-oxide (ITO) transparent electrode (manufactured by Geomatec Co., Ltd.) used as an anode was first cleaned with isopropanol in an ultrasonic bath for 10 min. To eliminate any possible organic residues, the substrate was exposed to an ultraviolet light and ozone for further 30 min. This treatment also improves the hole injection properties of the ITO. The cleaned substrate was mounted on a substrate holder and loaded into a vacuum chamber. Thereafter, the organic materials specified below were applied by vapor deposition to the ITO substrate at a rate of approx. 0.2-1 Å/sec at about $10^{-6}$-$10^{-8}$ mbar. As a hole injection layer, 5 nm-thick of compound A' was applied. Then 100 nm-thick of compound B' and 60 nm-thick compound C' were applied as hole transporting layer 1 and hole transporting layer 2, respectively. Subsequently, a mixture of 5% by weight of an emitter compound (Ir(ppy)$_3$), 47.5% by weight of a host (comparative compound 1) and 47.5% by weight of compound E were applied to form a 40 nm-thick phosphorescent-emitting layer. On the emitting layer, 30 nm-thick compound D was applied as an electron transport layer. Finally, 1 nm-thick LiF was deposited as an electron injection layer and 80 nm-thick Al was then deposited as a cathode to complete the device. The device was sealed with a glass lid and a getter in an inert nitrogen atmosphere with less than 1 ppm of water and oxygen.

Compound A'

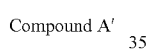

Compound B'

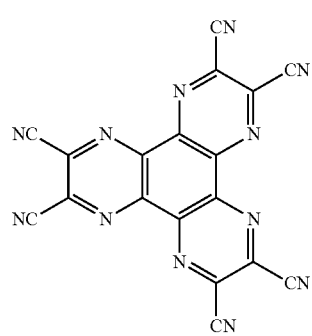

-continued

Compound C'

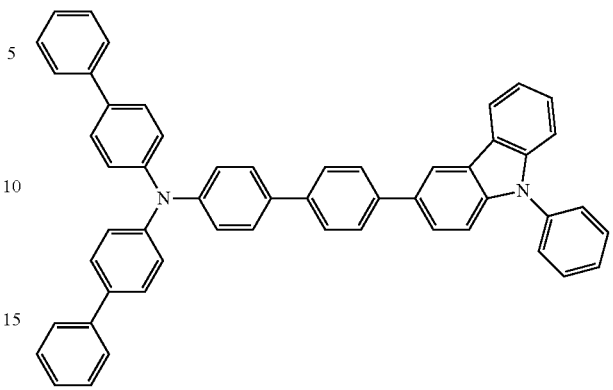

Compound D

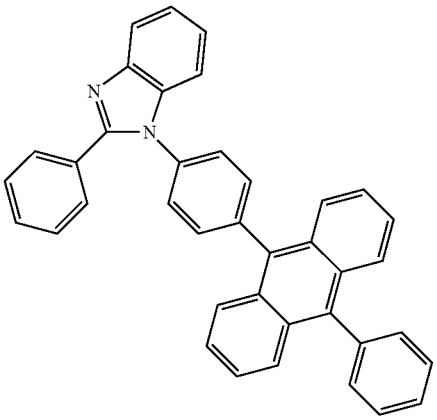

Compound E

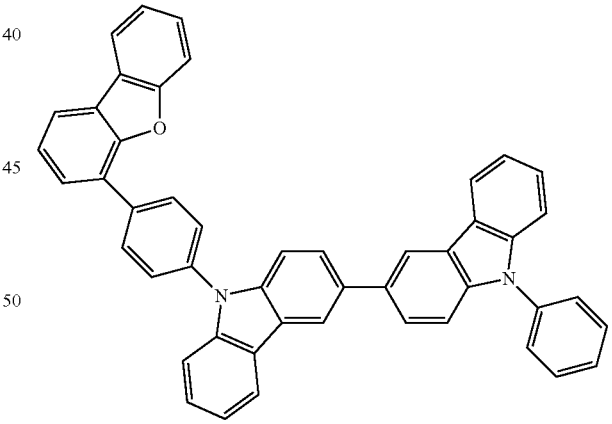

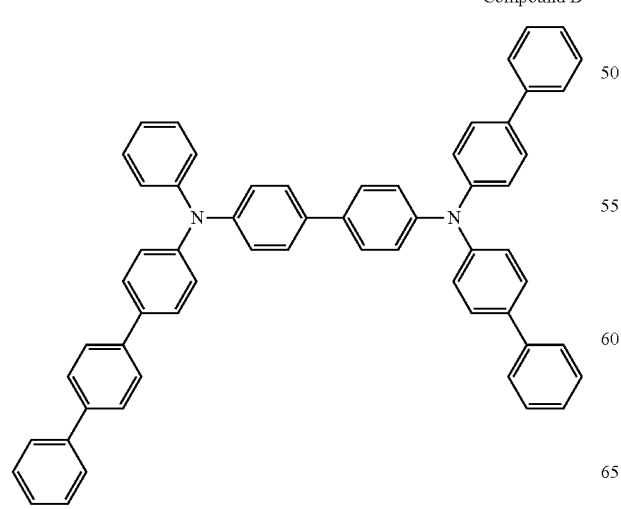

(Ir(ppy)$_3$)

Comparative compound 1

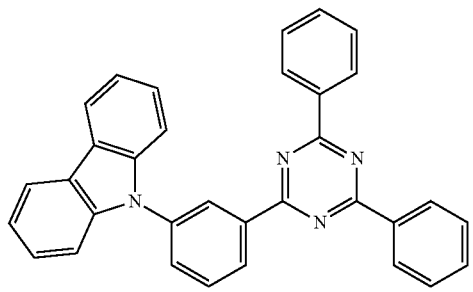

OLED Characterization

To characterize the OLED, electroluminescence spectra were recorded at various currents and voltages. In addition, the current-voltage characteristic was measured in combination with the luminance to determine luminous efficiency and external quantum efficiency (EQE). Driving voltage U and EQE are given at a current density of 10 mA/cm², and 80% lifetime (LT80), the time spent until the initial luminance at 50 mA/cm² was reduced to 80%, was recorded. The device results are shown in Table 2.

Comparative Application Example 2

Comparative Application Example 1 was repeated except that the host (comparative compound 1) was replaced by comparative compound 2. The device results are shown in Table 2.

Comparative compound 2

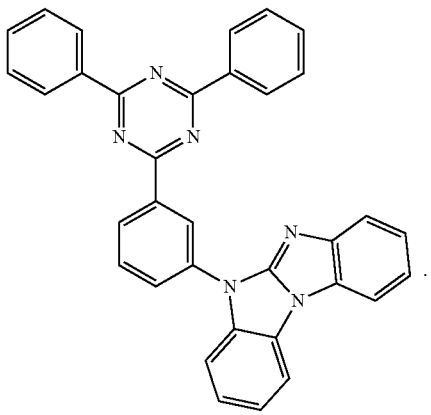

Application Example 3

Comparative Application Example 1 was repeated except that the host (comparative compound 1) was replaced by compound 11. The device results are shown in Table 2.

Compound 11

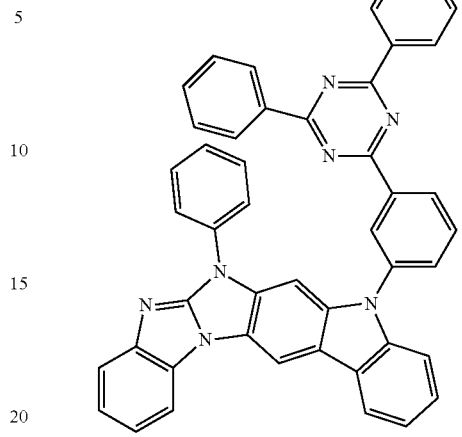

Application Example 4

Comparative Application Example 1 was repeated except that the host (comparative compound 1) was replaced by compound 10. The device results are shown in Table 2.

Compound 10

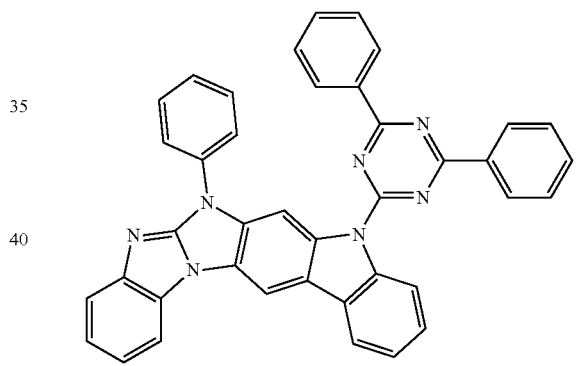

TABLE 2

| Appl. Ex. | Host | U [V] | LT80 [hrs] | CIE(x, y) |
| --- | --- | --- | --- | --- |
| Comp. Appl. Ex. 1 | Comparative Compound 1 | 5.55 | 57.6 | 0.32/0.63 |
| Comp. Appl. Ex. 2 | Comparative Compound 2 | 5.32 | 40.2 | 0.32/0.63 |
| Appl. Ex. 3 | Compound 11 | 5.24 | 72.0 | 0.31/0.63 |
| Appl. Ex. 4 | Compound 10 | 5.10 | 86.6 | 0.31/0.63 |

The results shown in Table 2 demonstrate that the lifetime and voltage are improved in the case that inventive compounds 11 and 10 are used as green hosts together with a co-host compound E in an OLED.

Comparative Application Example 3

Comparative Application Example 1 was repeated except that the host (comparative compound 1) was replaced by comparative compound 3. The device results are shown in Table 3.

Comparative compund 3

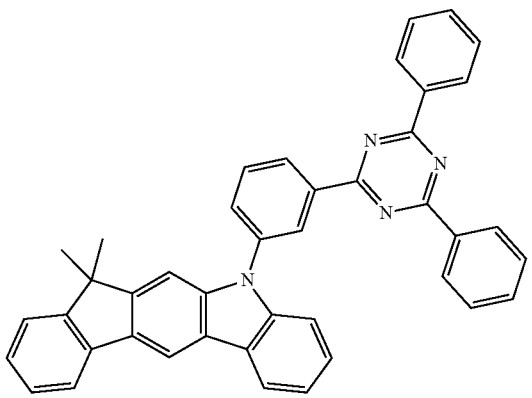

Application Example 5

Comparative Application Example 1 was repeated except that the host (comparative compound 1) was replaced by compound 3. The device results are shown in Table 3.

Compound 7

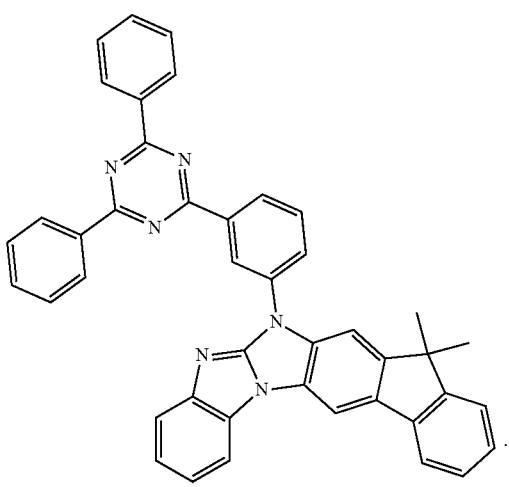

TABLE 3

| Appl. Ex. | Hosts | U [V] | LT80 [hrs] | CIE(x, y) |
|---|---|---|---|---|
| Comp. Appl. Ex. 3 | Comparative Compound 3 | 5.16 | 135 | 0.31/0.63 |
| Appl. Ex. 5 | Compound 7 | 4.86 | 187 | 0.32/0.63 |

The results shown in Table 3 demonstrate that the lifetime and voltage are improved in the case that an inventive compound 3 is used as a green host together with a co-host Compound E in an OLED.

The invention claimed is:

1. A compound of formula (I):

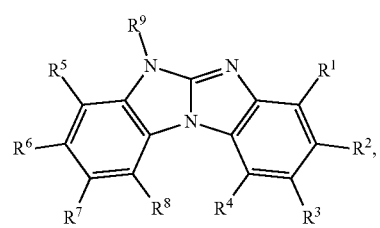

wherein:
at least one selected from the group consisting of a pair of $R^1$ and $R^2$, a pair of $R^2$ and $R^3$, a pair of $R^3$ and $R^4$, a pair of $R^5$ and $R^6$, a pair of $R^6$ and $R^7$, and a pair of $R^7$ and $R^8$ together forms one of the ring systems:

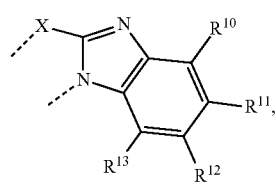

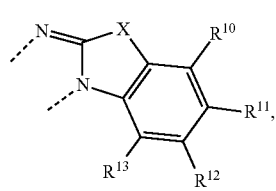

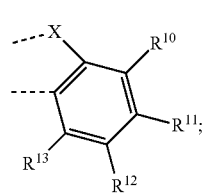

wherein X is $NR^{19}$, O, S, $C(R^{28})_2$, or $Si(R^{28})_2$;
each of $R^9$ and $R^{19}$ is independently;
  $R^{20}$, or
  $A^1{}_o$, $A^2{}_p$, $A^3{}_q$, $A^4{}_r$, or CN wherein each of o, p, q and r is independently 0 or 1, with the proviso that at least one of o, p, q and r is 1,
wherein $R^{20}$ is
  a $C_6$-$C_{30}$ aryl group which is unsubstituted or substituted by G,
  a $C_2$-$C_{60}$ heteroaryl group which is unsubstituted or substituted by G,
  a $C_1$-$C_{25}$ alkyl group;
  a $C_1$-$C_{25}$ alkyl group which is substituted by E,
  a $C_1$-$C_{25}$ alkyl group which is interrupted by D, or
  a $C_1$-$C_{25}$ alkyl group which is substituted by E and interrupted by D; and
each of $A^1$, $A^2$, $A^3$, and $A^4$ is independently:
  a $C_6$-$C_{24}$ arylene group which is unsubstituted or substituted by G, or
  a $C_2$-$C_{24}$ heteroarylene group which is unsubstituted or substituted by G;
$R^1$, $R^2$, $R^3$, $R^4$, $R^5$, $R^6$, $R^7$ and $R^8$, which do not form the ring system of formula (IIa), (IIb) or (IIc), are each independently: H, CN, $A^{1'}{}_{o'}$, $A^{2'}{}_{p'}$, $A^{3'}{}_{q'}$, $A^{4'}{}_{r'}$, or $R^{20}$ or E, or among $R^1$, $R^2$, $R^3$, $R^4$, $R^5$, $R^6$, $R^7$ and $R^8$, which do not form the ring system of formula (IIa), (IIb) or (IIc), at least one selected from the group consisting of a pair of $R^1$ and $R^2$, a pair of $R^2$ and $R^3$, a pair of $R^3$ and $R^4$, a pair of $R^5$ and $R^6$, a pair of $R^6$ and $R^7$, and a pair of $R^7$ and $R^8$ together forms a ring structure;

each of $R^{10}$, $R^{11}$, $R^{12}$ and $R^{13}$ is independently H, CN, $A^{1'}_{o'}$, $A^{2'}_{p'}$, $A^{3'}_{q'}$, $A^{4'}_{r'}$, or $R^{20'}$ or E, or at least one selected from the group consisting of a pair of $R^{10}$ and $R^{11}$, a pair of $R^{11}$ and $R^{12}$ and a pair of $R^{12}$ and $R^{13}$ together forms a ring structure;

o' is 0 or 1;
p' is 0 or 1;
q' is 0 or 1;
r' is 0 or 1;

each of $A^{1'}$, $A^{2'}$, $A^{3'}$ and $A^{4'}$ is independently:
- a $C_6$-$C_{24}$ arylene group which is unsubstituted or substituted by G, or
- a $C_2$-$C_{24}$ heteroarylene group which is unsubstituted or substituted by G;

$R^{20'}$ is:
- H,
- CN,
- a $C_6$-$C_{30}$ aryl group which is unsubstituted or substituted by G,
- a $C_2$-$C_{60}$ heteroaryl group which is unsubstituted or substituted by G,
- a $C_1$-$C_{25}$ alkyl group,
- a $C_1$-$C_{25}$ alkyl group which is substituted by E,
- a $C_1$-$C_{25}$ alkyl group which is interrupted by D, or
- a $C_1$-$C_{25}$ alkyl group which is substituted by E and interrupted by D;

$R^{28}$ in $C(R^{28})_2$, or $Si(R^{28})_2$ are each independently:
- a $C_6$-$C_{18}$ aryl group,
- a $C_6$-$C_{18}$ aryl group which is substituted by a $C_1$-$C_{18}$ alkyl group or by a $C_1$-$C_{18}$ alkoxy group,
- a $C_1$-$C_{18}$ alkyl group which is interrupted by —O—, or
- a $C_1$-$C_{18}$ alkyl group which is interrupted by —O— and substituted by E, or two $R^{28}$ in $C(R^{28})_2$, or $Si(R^{28})_2$ form, together with the carbon atom or Si atom to which they are bonded, a ring structure;

D is —CO—, —COO—, —S—, —SO—, —SO$_2$—, —O—, —CR$^{63}$=CR$^{64}$—, —NR$^{65}$—, —SiR$^{70}$R$^{71}$—, —POR$^{72}$—, or —C≡C—;

E is —OR$^{69}$, —SR$^{69}$, —NR$^{65}$R$^{66}$, —COR$^{68}$, —COOR$^{67}$, —CONR$^{65}$R$^{66}$, —CN, —Si(R$^{70}$)$_3$ or halogen;

G is:
- E,
- a $C_1$-$C_{24}$ alkyl group,
- a $C_6$-$C_{24}$ aryl group,
- a $C_6$-$C_{24}$ aryl group which is substituted by F, by a $C_1$-$C_{24}$ alkyl group, or by a $C_1$-$C_{24}$ alkyl group which is interrupted by O,
- a $C_2$-$C_{30}$ heteroaryl group, or
- a $C_2$-$C_{30}$ heteroaryl group which is substituted by F, by a $C_1$-$C_{24}$ alkyl group, or by a $C_1$-$C_{24}$ alkyl group which is interrupted by O;

each of $R^{63}$ and $R^{64}$ is independently:
- a $C_6$-$C_{18}$ aryl group,
- a $C_6$-$C_{18}$ aryl group which is substituted by a $C_1$-$C_{18}$ alkyl group or by a $C_1$-$C_{18}$ alkyl group,
- a $C_1$-$C_{18}$ alkyl group, or
- a $C_1$-$C_{18}$ alkyl group which is interrupted by —O—;

each of $R^{65}$ and $R^{66}$ is independently:
- a $C_6$-$C_{18}$ aryl group,
- a $C_6$-$C_{18}$ aryl group which is substituted by a $C_1$-$C_{18}$ alkyl group or by a $C_1$-$C_{18}$ alkoxy group,
- a $C_1$-$C_{18}$ alkyl group, or
- a $C_1$-$C_{18}$ alkyl group which is interrupted by —O—, or $R^{65}$ and $R^{66}$ together form a five or six membered ring;

$R^{67}$ is:
- a $C_6$-$C_{18}$ aryl group,
- a $C_6$-$C_{18}$ aryl group which is substituted by a $C_1$-$C_{18}$ alkyl group, or by a $C_1$-$C_{18}$ alkoxy group,
- a $C_1$-$C_{18}$ alkyl group or
- a $C_1$-$C_{18}$ alkyl group which is interrupted by —O—;

$R^{68}$ is:
- H,
- a $C_6$-$C_{18}$ aryl group,
- a $C_6$-$C_{18}$ aryl group which is substituted by a $C_1$-$C_{18}$ alkyl group or by a $C_1$-$C_{18}$ alkoxy group,
- a $C_1$-$C_{18}$ alkyl group, or
- a $C_1$-$C_{18}$ alkyl group which is interrupted by —O—;

$R^{69}$ is:
- a $C_6$-$C_{18}$ aryl group,
- a $C_6$-$C_{18}$ aryl group which is substituted by a $C_1$-$C_{18}$ alkyl group or by a $C_1$-$C_{18}$ alkoxy group,
- a $C_1$-$C_{18}$ alkyl group, or
- a $C_1$-$C_{18}$ alkyl group which is interrupted by —O—;

each of $R^{70}$ and $R^{71}$ is independently:
- a $C_1$-$C_{18}$ alkyl group,
- a $C_6$-$C_{18}$ aryl group, or
- a $C_6$-$C_{18}$ aryl group which is substituted by a $C_1$-$C_{18}$ alkyl group;

$R^{72}$ is:
- a $C_1$-$C_{18}$ alkyl group,
- a $C_6$-$C_{18}$ aryl group, or
- a $C_6$-$C_{18}$ aryl group which is substituted by a $C_1$-$C_{18}$ alkyl group; and wherein the dotted lines are bonding sites.

2. The compound of formula (I) as claimed in claim 1, wherein X is NR$^{19}$ or C(R$^{28}$)$_2$.

3. The compound of formula (I) as claimed in claim 1, wherein exactly one selected from the group consisting of the pair of $R^1$ and $R^2$, the pair of $R^2$ and $R^3$, the pair of $R^3$ and $R^4$, the pair of $R^5$ and $R^6$, the pair of $R^6$ and $R^7$, and the pair of $R^7$ and $R^8$ together forms the ring system of formula (IIa), (IIb) or (IIc).

4. The compound of formula (I) as claimed in claim 1, wherein:
- at least one selected from the group consisting of the pair of $R^1$ and $R^2$, the pair of $R^2$ and $R^3$, the pair of $R^3$ and $R^4$, and the pair of $R^6$ and $R^7$ together forms the ring system of formula (IIa), (IIb) or (IIc); or
- at least one selected from the group consisting of the pair of $R^1$ and $R^2$, the pair of $R^2$ and $R^3$, the pair of $R^3$ and $R^4$, the pair of $R^5$ and $R^6$, the pair of $R^6$ and $R^7$, and the pair of $R^7$ and $R^8$ together forms a ring system of formula (IIc).

5. The compound of formula (I) as claimed in claim 4, having the formula (I-IIb), (I-IIb'), (I'-II'c), (I'-II'c'), (I-IIc), (I-IIc'), (I'-II'ca), (I'-II'c'a), (I-IIca), (I-IIc'a), (I''-IIcb), (I-IIc''b), (I''-II''cb), (I''-II'''c''b), (I'''-IIcb), (I-IIc'''b), (I'''-II'''cb), (I'''-II'''c'''b), (I''-II''ca), (I-IIc''a), (I''-II''c''a), (I'''-II'''ca), (I-IIc'''a), (I'''-II'''ca) or (I'''-II'''c'''a):

-continued
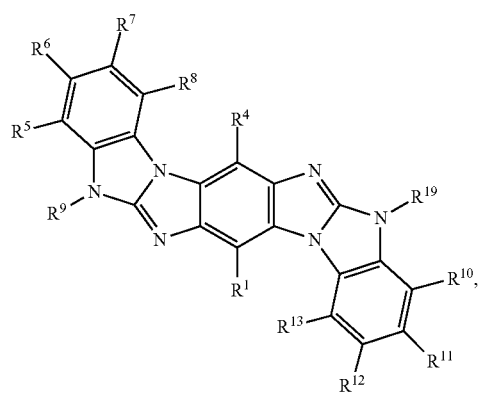
(I-IIb)
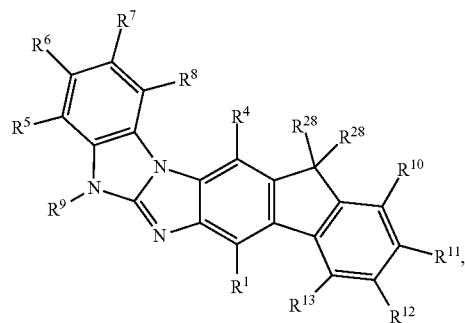
(I-IIc)
(I-IIb′)
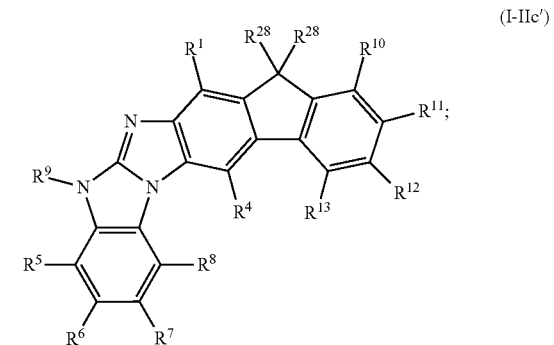
(I-IIc′)
(I′-II′c)
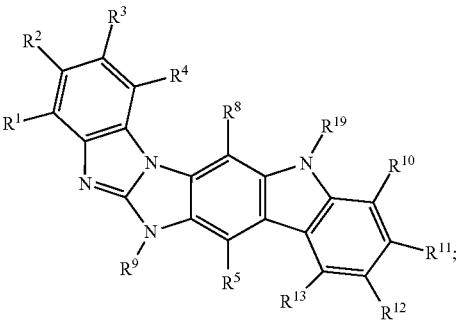
(I′-II′ca)
(I′-II′c′)
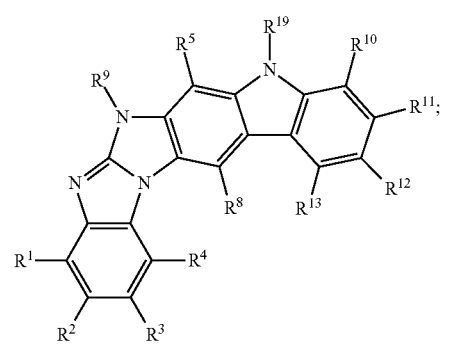
(I′-II′c′a)

-continued
(I-IIca)
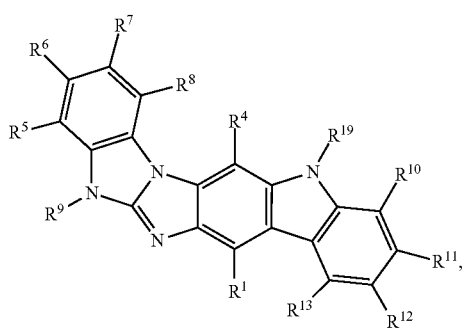
(I-IIc′a)
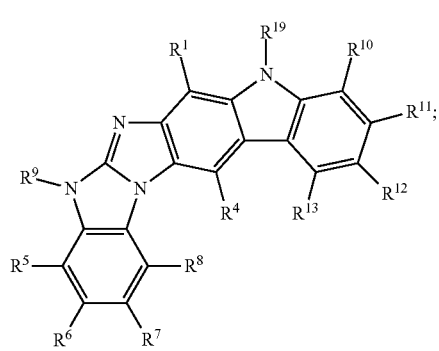
(I″-IIcb)
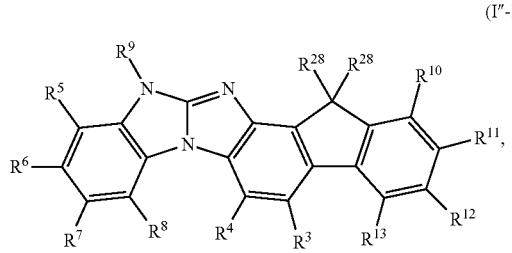
(I-IIc″b)
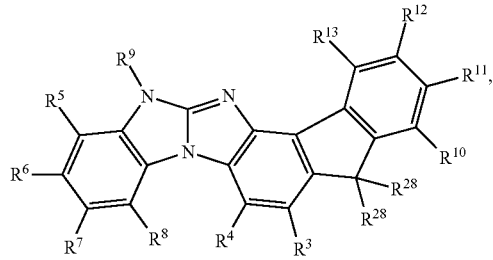
(I″-II″cb)
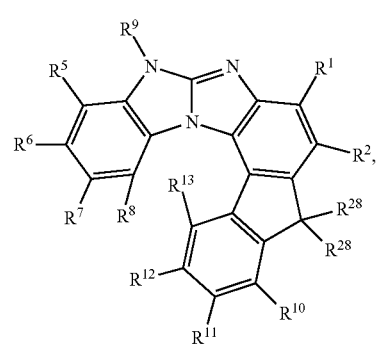
(I″-II″c″b)
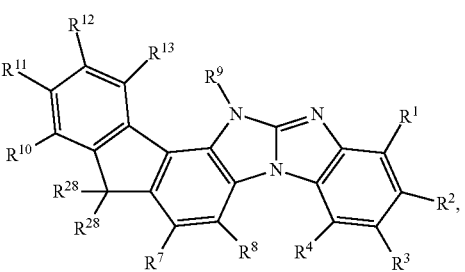
(I‴-IIcb)
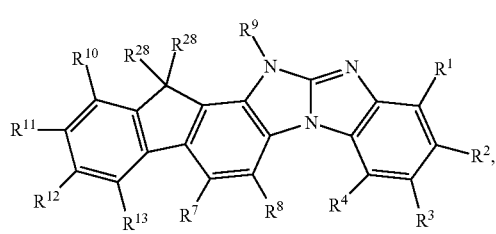
(I-IIc‴b)
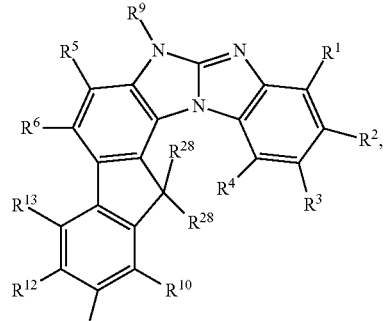
(I‴-II‴cb)
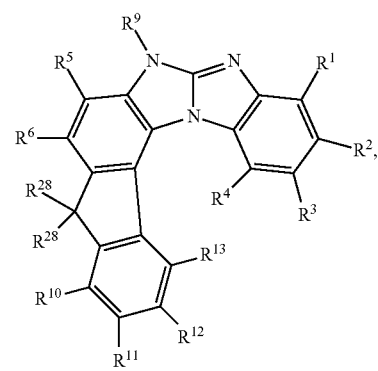
(I‴-II‴c‴b)

6. The compound of formula (I) as claimed in claim 1, wherein $R^1$, $R^2$, $R^3$, $R^4$, $R^5$, $R^6$, $R^7$ and $R^R$, which do not form the ring system of formula (IIa), (IIb) or (IIc), are H, or
one of $R^5$, $R^6$, $R^7$ and $R^8$ is:
   CN,
   a $C_6$-$C_{18}$ aryl group which is unsubstituted or substituted by G,
   a $C_2$-$C_{18}$ heteroaryl group which is unsubstituted or substituted by G,
   a $C_1$-$C_{25}$ alkyl group,
   a $C_1$-$C_{25}$ alkyl which is substituted by E,
   a $C_1$-$C_{25}$ alkyl which is interrupted by D, or
   a $C_1$-$C_{25}$ alkyl which is substituted by E and interrupted by D, and
all other $R^1$, $R^2$, $R^3$, $R^4$, $R^5$, $R^6$, $R^7$ and $R^8$ are H;
or
wherein $R^1$, $R^2$, $R^3$, $R^4$, $R^5$, $R^6$, $R^7$ and $R^8$, which do not form the ring system of formula (IIa), (IIb) or (IIc), are each independently H or CN, or
one of $R^1$, $R^2$, $R^3$ and $R^4$ is;
   a $C_6$-$C_{18}$ aryl group which is unsubstituted or substituted by G,
   a $C_2$-$C_{18}$ heteroaryl group which is unsubstituted or substituted by G,
   a $C_1$-$C_{25}$ alkyl group,
   a $C_1$-$C_{25}$ alkyl group which is substituted by E,
   a $C_1$-$C_{25}$ alkyl group which is interrupted by D, or
   a $C_1$-$C_{25}$ alkyl group which is substituted by E and interrupted by D, and
all other $R^1$, $R^2$, $R^3$, $R^4$, $R^5$, $R^6$, $R^7$ and $R^8$ are H.

7. The compound of formula (I) as claimed in claim 1, wherein $R^{10}$, $R^{11}$, $R^{12}$ and $R^{13}$ are H, or
one of $R^{10}$, $R^{11}$, $R^{12}$ and $R^{13}$ is:
   CN,
   a $C_6$-$C_{18}$ aryl group which is unsubstituted or substituted by G,
   a $C_2$-$C_{18}$ heteroaryl group which is unsubstituted or substituted by G,
   a $C_1$-$C_{25}$ alkyl group,
   a $C_1$-$C_{25}$ alkyl group which is substituted by E,
   a $C_1$-$C_2$ alkyl group which is interrupted by D, or
   a $C_1$-$C_{25}$ alkyl group which is substituted by E and interrupted by D, and
all other $R^{10}$, $R^{11}$, $R^{12}$ and $R^{13}$ are H.

8. The compound of formula (I) as claimed in claim 1, wherein each of $A^1$, $A^2$, $A^3$, $A^4$, $A^{1'}$, $A^{2'}$, $A^{3'}$ and $A^{4'}$ is independently one of formula:

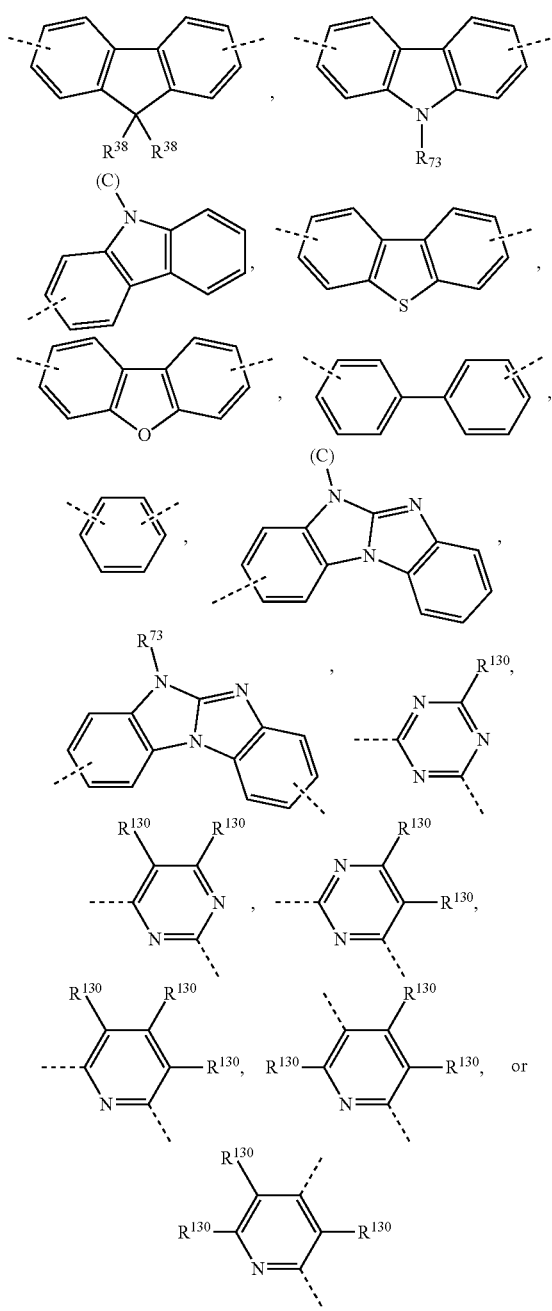

which is unsubstituted or substituted by G;
wherein R$^{73}$ is:
- C$_6$-C$_{18}$ aryl group,
- a C$_6$-C$_{18}$ aryl which is substituted by a C$_1$-C$_{18}$ alkyl group or by a C$_1$-C$_{18}$ alkoxy group,
- a C$_1$-C$_{18}$ alkyl group, or
- a C$_1$-C$_{18}$ alkyl group which is interrupted by —O;

R$^{38}$ is:
- a C$_1$-C$_{25}$ alkyl group,
- a C$_1$-C$_{25}$ alkyl group which is substituted by E,
- a C$_1$-C$_{25}$ alkyl group which is interrupted by D, or
- a C$_1$-C$_{25}$ alkyl group which is substituted by E and interrupted by D;
- a C$_6$-C$_{24}$ aryl group which is optionally substituted by G, or a C$_1$-C$_{24}$ heteroaryl group, which is optionally substituted by G; or two R$^{38}$ form, together with the atom to which they are bonded, a ring structure, which is optionally substituted by G;

each R$^{130}$ is independently;
- H,
- a C$_6$-C$_{24}$ arylene group which is optionally substituted by G, or
- a C$_2$-C$_{30}$ heteroarylene group which is optionally substituted by G;

wherein the dotted lines are bonding sites in -(A$^1$)$_o$-(A$^2$)$_p$-(A$^3$)$_q$-(A$^4$)$_r$-CN, or -(A$^{1'}$)$_o$-(A$^{2'}$)$_p$-(A$^{3'}$)$_q$-(A$^{4'}$)$_r$-R$^{20'}$;
wherein (C)- has the meaning that the bonding site of A$^1$, A$^2$, A$^3$, A$^4$, A$^{1'}$, A$^{2'}$, A$^{3'}$ and A$^{4'}$ is linked to a C-atom.

9. The compound of formula (I) as claimed in claim 1, wherein
when at least one of R$^1$, R$^2$, R$^3$, R$^4$, R$^5$, R$^6$, R$^7$ and R$^8$ is A$^{1'}_o$, A$^{2'}_p$, A$^{3'}_q$, A$^{4'}_r$, or R$^{20'}$,
R$^{20'}$ is H, CN or one of a group of formulae (2)-(15),
when at least one of R$^{10}$, R$^{11}$, R$^{12}$, and R$^{13}$ is A$^{1'}_o$, A$^{2'}_p$, A$^{3'}_q$, A$^{4'}_r$, or R$^{20'}$,
R$^{20'}$ is H, CN or one of the group of formulae (2)-(15):
or
when at least one of R$^9$ and R$^{19}$ is R$^{20}$,
R$^{20}$ is, independently of R$^{20'}$, one of the group of formulae (2)-(15):

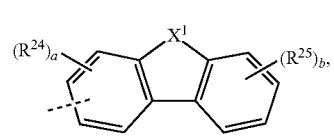

(2)

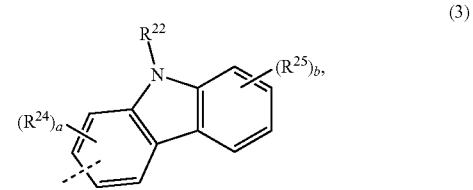

(3)

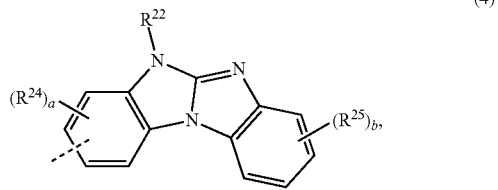

(4)

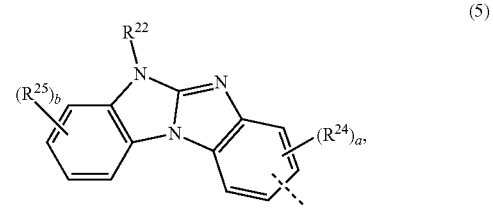

(5)

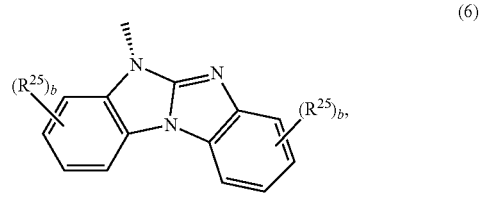

(6)

-continued (7)

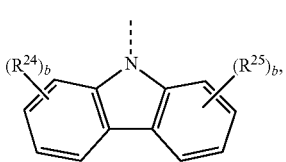

wherein:
$X^1$ is S, O, $C(R^{21})_2$, or $NR^{23}$;
$R^{22}$ is:
  a $C_6$-$C_{18}$ aryl group which is unsubstituted or substituted by G, or
  a $C_2$-$C_{18}$ heteroaryl group which is unsubstituted or substituted by G:
$R^{23}$ is:
  H,
  a $C_6$-$C_{18}$ aryl group which is unsubstituted or substituted by G, or
  a $C_2$-$C_{18}$ heteroaryl group which is unsubstituted or substituted by G;
each of $R^{24}$ and $R^{25}$ is independently:
  H,
  a $C_6$-$C_{18}$ aryl group which is unsubstituted or substituted by G,
  a $C_2$-$C_{18}$ heteroaryl group which is unsubstituted or substituted by G,
  a $C_1$-$C_{25}$ alky group,
  a $C_1$-$C_{25}$ alkyl group which is substituted by E,
  $C_1$-$C_{25}$ alkyl group which is interrupted by D,
  a $C_1$-$C_{25}$ alkyl group which is substituted by E and interrupted by D, or
  —CN;
a is 0, 1, 2 or 3;
b is 0, 1, 2, 3 or 4; and
the dotted line is a bonding site of $R^{20}$ or $R^{20'}$;

(8)

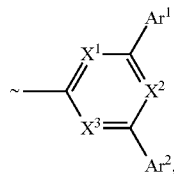

(9)

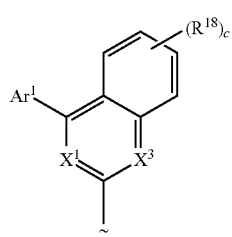

(10)

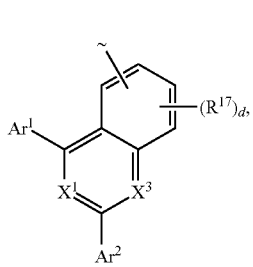

wherein:
each of $X^1$, $X^2$ and $X^3$ is independently $CR^{16}$ or N, wherein in formula (8) at least one of $X^1$ to $X^3$ is N, and wherein in formulae (9) and (10) at least one of $X^1$ and $X^3$ is N;
each of $Ar^1$ and $Ar^2$ is independently:
  a $C_6$-$C_{24}$ aryl group which is optionally substituted by G, or
  a $C_1$-$C_{24}$ heteroaryl group which is optionally substituted by G;
each of $R^{16}$, $R^{17}$ and $R^{18}$ is independently:
  H,
  a $C_6$-$C_{24}$ aryl group which is optionally substituted by G,
  a $C_1$-$C_{24}$ heteroaryl group which is optionally substituted by G, or
  a $C_1$-$C_{25}$ alkyl group,
  a $C_1$-$C_{25}$ alkyl group which is substituted by E,
  a $C_1$-$C_{25}$ alkyl group which is interrupted by D, or
  a $C_1$-$C_{25}$ alkyl group which is substituted by E and interrupted by D; and
wherein ~is a bonding site of $R^{20}$ or $R^{20'}$, and (11)

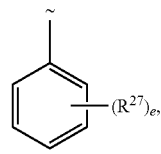

(12)

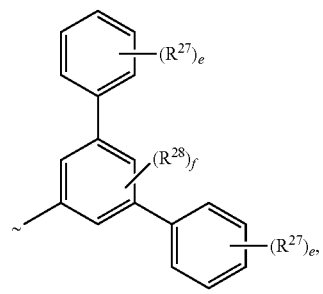

(13a)

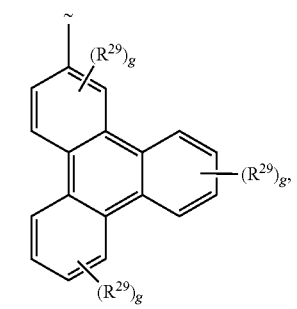

(13b)

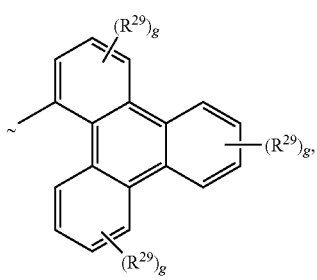

-continued

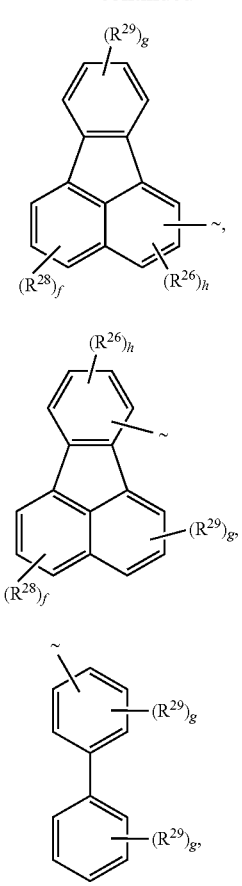

(14a)

(14b)

(15)

wherein:
$R^{26}$, $R^{27}$, $R^{28}$ and $R^{29}$ are each independently:
H,
a $C_6$-$C_{24}$ aryl group which is optionally substituted by G,
a $C_1$-$C_{24}$heteroaryl group which is optionally substituted by G,
a $C_1$-$C_{25}$ alkyl group,
a $C_1$-$C_{25}$ alkyl group which is substituted by E,
a $C_1$-$C_{25}$ alkyl group which is And/e interrupted by D,
a $C_1$-$C_{25}$ alkyl group which is substituted by E and interrupted by D or
E;
e is 0, 1, 2, 3, 4 or 5;
f is 0, 1, 2 or 3;
g is 0, 1, 2, 3 or 4; and
h is 0, 1 or 2;
or
two adjacent groups selected from the group consisting of $R^{26}$, $R^{27}$ $R^{28}$ and $R^{29}$ in formula (11), (12), (13a), (13b), (14a), (14b) or (15) together form a ring structure which is optionally substituted by G, And
wherein ~is a bonding site of $R^{20}$ or $R^{20'}$.

10. An organic electronic device, comprising the compound according to claim 1.

11. The organic electronic device according to claim 10, which is an organic electroluminescent device, wherein the organic electroluminescent device comprises an organic thin film layer between a cathode and an anode, wherein the organic thin film layer comprises one or more layers and comprises a light emitting layer, and at least one layer of the organic thin film layer comprises the compound of formula (I).

12. The organic electronic device according to claim 11, wherein the light emitting layer comprises the compound of formula (I).

13. The organic electronic device according to claim 11, wherein the light emitting layer comprises a phosphorescent material, which is an ortho-metallated complex comprising a metal atom selected from the group consisting of iridium (Ir), osmium (Os) and platinum (Pt).

14. A charge transport layer, charge/exciton blocking layer, or an emitting layer comprising the compound according to claim 1.

15. The emitting layer according to claim 14, comprising the compound of formula (I) as host material in combination with a phosphorescent emitter.

16. An apparatus selected from the group consisting of stationary visual display units; mobile visual display units; illumination units; keyboards; items of clothing; furniture; wallpaper, the apparatus comprising the organic electronic device according to claim 10.

17. A device, comprising the compound of claim 1, wherein the device is selected from the group consisting of organic electroluminescent devices, electrophotographic photoreceptors, photoelectric converters, organic solar cells, switching elements, organic light emitting field effect transistors, image sensors and dye lasers.

18. The compound of formula (I) as claimed in claim 1, wherein:
at least one selected from the group consisting of a pair of $R^1$ and $R^2$, a pair of $R^2$ and $R^3$, a pair of $R^3$ and $R^4$, a pair of $R^5$ and $R^6$, a pair of $R^6$ and $R^7$, and a pair of $R^7$ and $R^8$ together forms the ring system of formula (IIa) or (IIb).

19. The compound of formula (I) as claimed in claim 1, wherein:
at least one selected from the group consisting of a pair of $R^1$ and $R^2$, a pair of $R^2$ and $R^3$, a pair of $R^3$ and $R^4$, a pair of $R^5$ and $R^6$, a pair of $R^6$ and $R^7$, and a pair of $R^7$ and $R^8$ together forms the ring system of formula (IIb).

20. The compound of formula (I) as claimed in claim 4, wherein:
exactly one selected from the group consisting of the pair of $R^1$ and $R^2$, the pair of $R^2$ and $R^3$, the pair of $R^3$ and $R^4$, and the pair of $R^6$ and $R^7$ together forms the ring system of formula (IIa), (IIb) or (IIc);
or
one selected from the group consisting of the pair of $R^1$ and $R^2$, the pair of $R^2$ and $R^3$, the pair of $R^3$ and $R^4$, the pair of $R^5$ and $R^6$, the pair of $R^6$ and $R^7$, and the pair of $R^7$ and $R^8$ together forms the ring system of formula (IIc).

21. The compound of formula (I) as claimed in claim 4, wherein:
exactly one selected from the group consisting of the pair of $R^1$ and $R^2$, the pair of $R^2$ and $R^3$, the pair of $R^3$ and $R^4$, and the pair of $R^6$ and $R^7$ together forms the ring system of formula (IIa) or (IIb).

22. The compound of formula (I) as claimed in claim 4, wherein:
exactly one selected from the group consisting of the pair of $R^1$ and $R^2$, the pair of $R^2$ and $R^3$, the pair of $R^3$ and $R^4$, and the pair of $R^6$ and $R^7$ together forms the ring system of formula (IIb).

23. A process for preparing the compound of claim 1, the process comprising one of i)-ix):
  i) preparing the compound of formula (I), wherein $R^6$ and $R^7$ together form a ring system of formula (IIa), comprising:
    ia) preparing an intermediate of formula (IIIa):

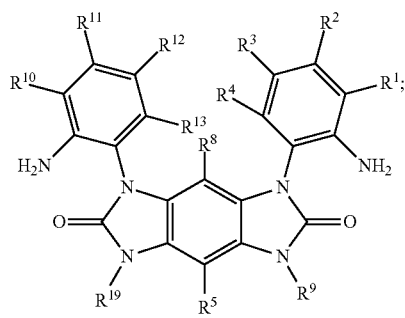

(IIIa)

ib) cyclizing the intermediate to form the compound of formula (I);
  ii) preparing the compound of formula (I), wherein $R^2$ and $R^3$ together form a ring system of formula (IIb), comprising:
    iia) preparing an intermediate of formula (IIIb) or (IIIb'):

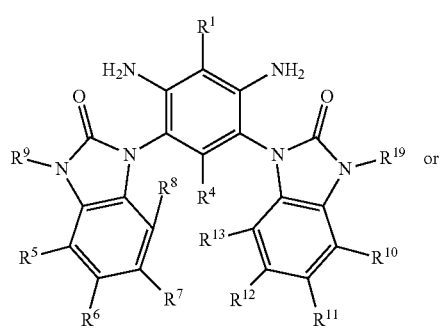

(IIIb)

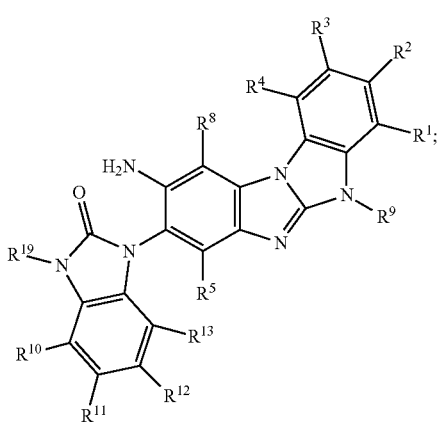

(IIIb')

and
    iib) cyclizing the intermediate to form the compound of formula (I);
  iii) preparing the compound of formula (I), wherein $R^2$ and $R^3$ together form a ring system of formula (IIc), comprising:
    iiia) preparing an intermediate of formula (IIIc):

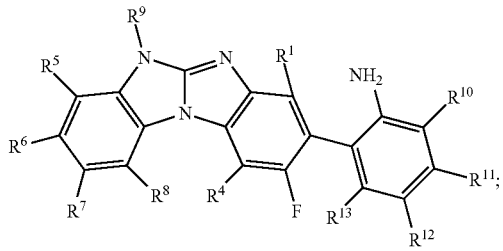

(IIIc)

and
    iiib) cyclizing the intermediate to form the compound of formula (IIId):

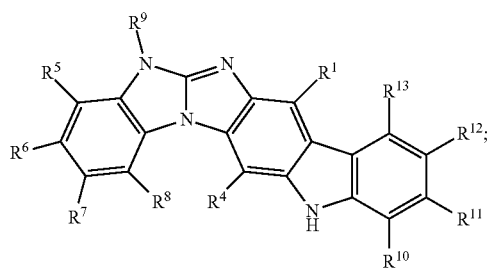

(IIId)

and
    iiic) functionalizing the NH group to form the compound of formula (I);
  iv) preparing the compound of formula (I), wherein $R^2$ and $R^3$ together form a ring system of formula (IIc), comprising:
    iva) preparing an intermediate of formula (IIIe):

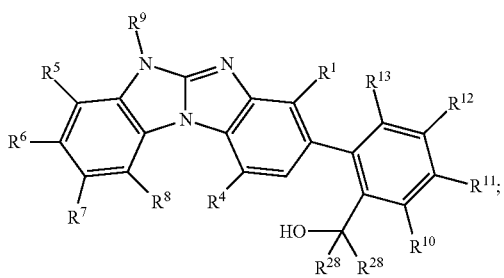

(IIIe)

and
    ivb) cyclizing the intermediate to form the compound of formula (I);
  v) preparing the compound of formula (I), wherein $R^6$ and $R^7$ together form a ring system of formula (IIc), comprising:

va) preparing an intermediate of formula (IIIf):

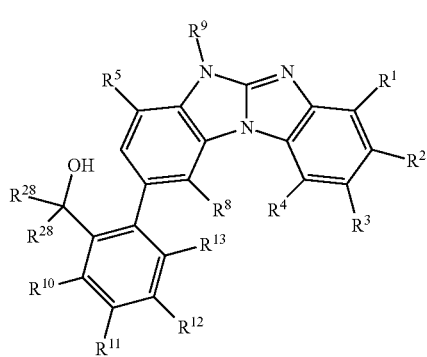

(IIIf)

; and
vb) cyclizing the intermediate to form the compound of formula (I);
vi) preparing the compound of formula (I), wherein $R^6$ and $R^7$ together form a ring system of formula (IIc), comprising:
via) preparing an intermediate of formula (IIIg):

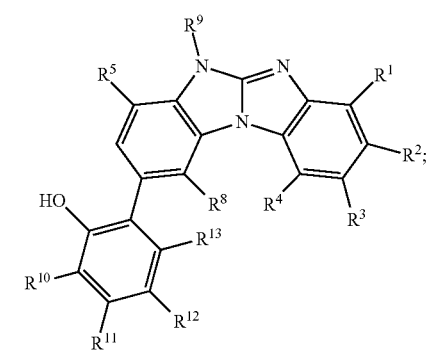

(IIIg)

and
vib) cyclizing the intermediate to form the compound of formula (I);
vii) preparing the compound of formula (I), wherein $R^6$ and $R^7$ together form a ring system of formula (IIc), comprising:
viia) preparing an intermediate of formula (IIIh):

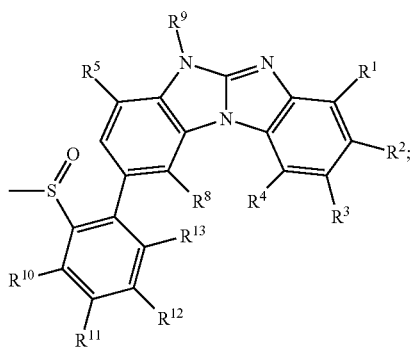

(IIIh)

and
viib) cyclizing the intermediate to form the compound of formula (I);

viii) preparing the compound of formula (I), wherein $R^6$ and $R^7$ together form a ring system of formula (IIc), comprising:
viiia) preparing an intermediate of formula (IIIi):

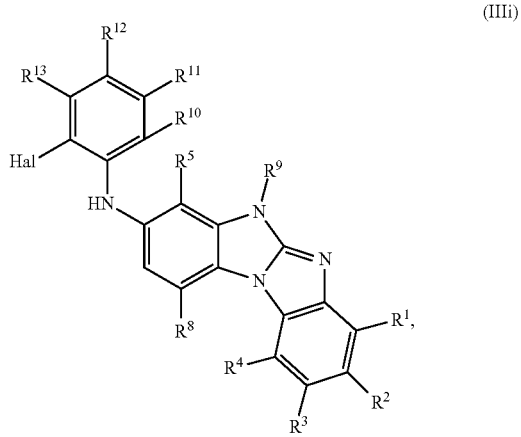

(IIIi)

wherein Hal is halogen;
viiib) cyclizing the intermediate to form a compound of formula (IIIj):

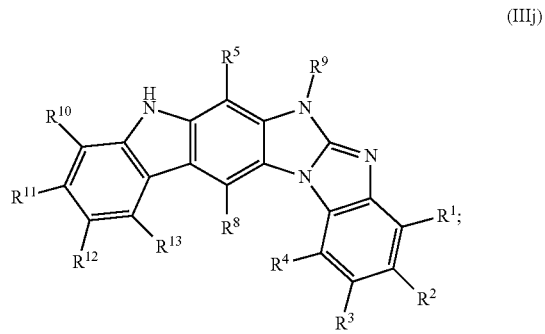

(IIIj)

and
viiic) functionalizing the NH group to form the compound of formula (I); and
ix) preparing the compound of formula (I), wherein $R^2$ and $R^3$ together form a ring system of formula (IIc), comprising:
ixa) preparing an intermediate of formula (IIIk):

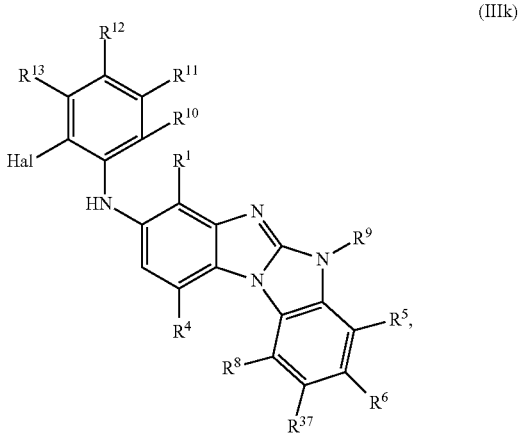

(IIIk)

wherein Hal is halogen:
ixb) cyclizing the intermediate to form a compound of formula (IIIl):

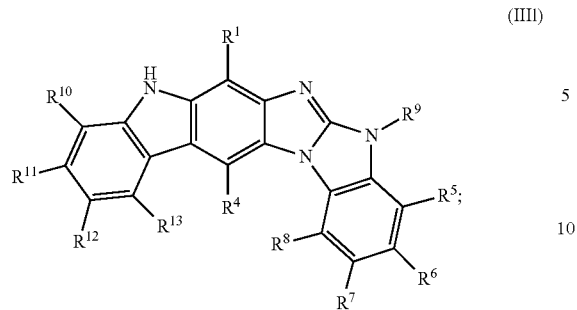
(IIII)
ixc) functionalizing the NH group to form the compound of formula (I); wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{19}$, $R^{28}$ and $R^{29}$ are as defined in claim 1.
* * * * *